US011479822B2

(12) United States Patent
Kondou et al.

(10) Patent No.: US 11,479,822 B2
(45) Date of Patent: Oct. 25, 2022

(54) BREAST CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Satoshi Kondou, Kamakura (JP); Hitoshi Nobumasa, Kamakura (JP); Satoko Kozono, Kamakura (JP); Hiroko Sudo, Kamakura (JP); Junpei Kawauchi, Kamakura (JP); Takahiro Ochiya, Tokyo (JP); Nobuyoshi Kosaka, Tokyo (JP); Makiko Ono, Tokyo (JP); Kenji Tamura, Tokyo (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 142 days.

(21) Appl. No.: 16/797,625

(22) Filed: Feb. 21, 2020

(65) Prior Publication Data

US 2020/0255910 A1    Aug. 13, 2020

Related U.S. Application Data

(62) Division of application No. 15/318,328, filed as application No. PCT/JP2015/066986 on Jun. 12, 2015, now Pat. No. 10,597,726.

(30) Foreign Application Priority Data

Jun. 13, 2014  (JP) .............................. JP2014-122672
Mar. 30, 2015  (JP) .............................. JP2015-069321

(51) Int. Cl.
 C12Q 1/68      (2018.01)
 C12P 19/34     (2006.01)
 C12Q 1/6886    (2018.01)
 C12M 1/00      (2006.01)
 C12N 15/09     (2006.01)

(52) U.S. Cl.
 CPC .............. *C12Q 1/6886* (2013.01); *C12M 1/00* (2013.01); *C12Q 1/68* (2013.01); *C12N 15/09* (2013.01); *C12Q 2600/158* (2013.01); *C12Q 2600/16* (2013.01); *C12Q 2600/178* (2013.01)

(58) Field of Classification Search
 CPC .. C12Q 1/68; C12Q 1/6886; C12Q 2600/158; C12Q 2600/178
 See application file for complete search history.

(56) References Cited

U.S. PATENT DOCUMENTS 8,603,744 B2    12/2013  Croce et al.
2001/0053519 A1 12/2001  Fodor et al.
2008/0076674 A1  3/2008  Litman et al.
2011/0028332 A1  2/2011  Kuroda et al.
2012/0115139 A1  5/2012  Kuroda et al.

FOREIGN PATENT DOCUMENTS

| CN | 101921760 A | 12/2010 |
| CN | 101988061 A | 3/2011 |
| CN | 101988064 A | 3/2011 |
| JP | 2008-500837 A | 1/2008 |
| JP | 2012-507300 A | 3/2012 |
| WO | WO 2005/118806 A2 | 12/2005 |
| WO | WO 2009/119809 A1 | 10/2009 |
| WO | WO 2010/062706 A2 | 6/2010 |
| WO | WO 2010/123043 A1 | 10/2010 |
| WO | WO 2013/190091 A1 | 12/2013 |
| WO | WO 2014/048441 A1 | 4/2014 |
| WO | WO 2014/081507 A1 | 5/2014 |

OTHER PUBLICATIONS

Carlos Pérez-Sánchez, et al., "Clinical Utility of microRNAs in Exhaled Breath Condensate as Biomarkers for Lung Cancer", J. Pers. Med. 2021, 11, 111. (Year: 2021).*
Qiagen Product Description "miScript™ miRNA PCR Array (384-well, 384HC) Human miRBase Profiler HC Plate 5", document 1073798, Aug. 2012, from https://b2b.qiagen.com/~/media/genetable/mi/hs/34/mihs-3405z (Year: 2012).*
Fu et al., "miRNA Biomarkers in Breast Cancer Detection and Management," Journal of Cancer (2011), vol. 2, pp. 116-122.
Office Action dated Sep. 24, 2021, in Republic of Korea Patent Application No. 10-2017-7000876.
Kojima et al., MicroRNA markers for the diagnosis of pancreatic and biliary-tract cancers, PLOS One (2015), vol. 10, No. 2, e0118220 (pp. 1-22).
Office Action dated Jun. 29, 2021, in Japanese Patent Application No. 2020-079623.
American Cancer Society, "Breast Cancer", pp. 6-9, 13, 27-28, 41-46, 52-54, 63-64, and 106 (2013).
Berillo et al., "Binding of intronic miRNAs to the mRNAs of host genes encoding intronic miRNAs and proteins that participate in tumourigenesis," Computers in Biology and Medicine (2013), vol. 43, pp. 1374-1381.
Cheung, V. G. et al., "Natural variation in human gene expression assessed in lymphoblastoid cells," Nature Genetics (2003), vol. 33, pp. 422-425.

(Continued)

*Primary Examiner* — Stephen T Kapushoc
(74) *Attorney, Agent, or Firm* — Birch, Stewart, Kolasch & Birch, LLP

(57) ABSTRACT

It is intended to provide a kit or a device for the detection of breast cancer and a method for detecting breast cancer. The present invention provides a kit or a device for the detection of breast cancer, comprising nucleic acid(s) capable of specifically binding to a miRNA in a sample of a subject, and a method for detecting breast cancer, comprising measuring the miRNA in vitro.

6 Claims, 4 Drawing Sheets

Specification includes a Sequence Listing.

(56) References Cited

OTHER PUBLICATIONS

Cobb et al., "Sepsis gene expression profiling: Murine splendic compared with hepatic responses determined by using complementary DNA microarrays," Crit. Care Med. (2002), vol. 30, No. 12, pp. 2711-2721.
Communication Pursuant to Rule 164(1) EPC dated Jan. 2, 2018, in European Patent Application No. 15805922.0.
Cookson et al., "Circulating microRNA profiles reflect the presence of breast tumours but not the profiles of microRNAs within the tumours," Cellular Oncology (2012), vol. 35, No. 4, pp. 301-308.
Cuk et al., "Circulating microRNAs in plasma as early detection markers for breast cancer," Int. J. Cancer (2013), vol. 132, No. 7, pp. 1602-1612.
Cuk et al., "Plasma microRNA panel for minimally invasive detection of breast cancer," Plos One (2013), vol. 8, No. 10, e76729, 10 pages.
Eto et al. "Prospect of microRNA toward laboratory medicine Gastrointestinal Cancer and microRNA," Clinical Chemistry (2014), vol. 43, 99-105.
Godfrey et al., "Serum microRNA expression as an early marker for breast cancer risk in prospectively collected samples from the Sister Study cohort," Breast Cancer Research (2013), vol. 15, No. 3, 10 pages.
Guadagni et al., "A Re-Evaluation of Carcinoembryonic Antigen (CEA) as a Serum Marker for Breast Cancer: A Prospective Longitudinal Study," Clinical Cancer Research (2001), vol. 7, p. 2357-2362.
Hoshikawa et al., "Hypoxia induces different genes in the lungs of rats compared with mice," Physiol. Genomics (2003), vol. 12, pp. 209-219.
Inazawa, "Gan ni Okeru Morateki miRNA Kaiseki to Shindan Chiryo eno Oyo", Journal of Clinical and Experimental Medicine (2014), vol. 249, No. 10, pp. 1119-1124.
International Search Report for PCT/JP2015/066986 (PCT/ISA/210) dated Sep. 1, 2015.
Leidner et al., "Dampening Enthusiasm for Circulating MicroRNA in Breast Cancer," PloS One (2013), vol. 8, No. 3, e57841, 11 pages.
MiScript™ miRNA PCR Array (384-well, 384HC) Human miRBase Profiler HC Plate 4 from Qiagen, from https://b2b.quiagen.com/-/media/genetable/mi/hs/34/mihs-3404z (2012).
Mitchell et al., "Circulating microRNAs as stable blood-based markers for cancer detection.", Proc. Natl. Acad. Sci. USA (2008), vol. 105, No. 30, pp. 10513-10518.
Ng et al., "Circulating microRNAs as specific biomarkers for breast cancer detection," Plos One (2013), vol. 8, No. 1, e53141, 10 pages.
Ono et al., E-2022 "Circulating microRNA markers for detection of breast cancer," Digital Abstract for The 73rd Annual Meeting of the Japanese Cancer Association, Published (online) Sep. 19, 2014.
Ono et al., E-2022 "Circulating microRNA markers for detection of breast cancer," English Oral Session for The 73rd Annual Meeting of the Japanese Cancer Association, Published (online) Sep. 26, 2014.
Persson et al., "Identification of new microRNAs in paired normal and tumor breast tissue suggests a dual role for the ERBB2/Her2 gene," Cancer Res. (2011), vol. 71, No. 1, pp. 78-86.
Sato, "microRNA chip nl yoru Biomarker Kaihatsu," Molecular Targeted Therapy for Cancer (2015), vol. 12, No. 4, pp. 456-465.
Schrauder et al., "Circulating Micro-RNAs as Potential Blood-Based Markers for Early Stage Breast Cancer Detection," PloS One, vol. 7, No. 1, e29770, 2012, 9 pages.
Sobin et al., "TNM Classification of Malignant Tumours," 7th edition , 2010, pp. 171-181.
Song et al., "Bioinformatic Prediction of SNPs within miRNA Binding Sites of Inflammatory Genes Associated with Gastric Cancer," Asian Pac. J. Cancer Prev. (2014), vol. 15, pp. 937-943.
Tamaki et al., "The Challenge to Reduce Breast Cancer Mortality in Okinawa: Consensus of the first Okinawa Breast Oncology Meeting," Japanese Journal of Clinical Oncology, vol. 43, No. 2, 2013, pp. 208-213.
Wang et al., "Plasma miR-601 and miR-760 are novel biomarkers for the early detection of colorectal cancer," Plos One, vol. 7, No. 9, e44398, 2012, 8 pages.
Written Opinion ofthe International Searching Authority for PCT/JP2015/066986 (PCT/ISA/237) dated Sep. 1, 2015.

\* cited by examiner

BREAST CANCER DETECTION KIT OR DEVICE, AND DETECTION METHOD

CROSS-REFERENCE TO RELATED APPLICATIONS

This application is a Divisional of copending U.S. application Ser. No. 15/318,328, filed on Dec. 12, 2016, which is the National Phase under 35 U.S.C. § 371 of International Application No. PCT/JP2015/066986 filed on Jun. 12, 2015, which claims the benefit under under 35 U.S.C. § 119(a) to Japanese Patent Application Nos. 2014-122672 filed Jun. 13, 2014, and 2015-069321 filed Mar. 30, 2015, all of which are hereby expressly incorporated by reference into the present application.

TECHNICAL FIELD

The present invention relates to a kit or a device for the detection of breast cancer, comprising nucleic acid(s) capable of specifically binding to a particular miRNA, which is used for examining the presence or absence of breast cancer in a subject, and a method for detecting breast cancer, comprising measuring an expression level of the miRNA using the nucleic acid.

BACKGROUND ART

The breast is constituted by a mammary gland which produces mother milk, lobules which arise from the mammary gland, mammary ducts which arise from the lobules and deliver milk, and fat which supports these constituents, etc. Approximately 90% of breast cancer cases originate in the mammary ducts, while approximately 5 to 10% of the breast cancer cases originate in the lobules (Non-Patent Literature 1). According to the 2011 statistics of cancer type-specific mortality in Japan disclosed by the Center for Cancer Control and Information Services, National Cancer Center, the number of breast cancer deaths climbed to 12,731 people. It is estimated that one out of 14 Japanese females will experience breast cancer. The number of incidences of this cancer in females takes the 1st place by cancer type. It is estimated that one out of 8 American females will experience breast cancer. The estimated number of American individuals affected by breast cancer climbed to 232,670 people in 2014, among which approximately 40,000 people reportedly died (Non-Patent Literature 1).

The stages of breast cancer progression are defined in Non-Patent Literature 2 and classified into stages 0, IA, IB, IIA, IIB, IIIA, IIIB, IIIC, and IV according to tumor size, infiltration, lymph node metastasis, distant metastasis, etc. The 5-year relative survival rate of breast cancer largely depends on the stages of cancer progression and is reportedly 100% for stage 0 and stage I, 93% for stage II, 72% for stage III, and 22% for stage IV (Non-Patent Literature 1). Thus, the early detection of breast cancer leads to improvement in the survival rate. Therefore, an approach that permits the early detection is strongly desired.

The treatment of breast cancer is basically surgical treatment, which is used in combination with drug therapy or radiotherapy depending on the progressed stage, metastasis, general health conditions, and breast cancer classification. Particularly, for early breast cancer of stage 1 or 2, breast conservation therapy may be selected with a combined use with radiotherapy (Non-Patent Literature 1).

According to Non-Patent Literature 1, initial diagnostic tests of breast cancer include inspection and palpation as well as imaging tests such as mammography, which is breast-dedicated X-ray examination, and ultrasonography (echo examination). When there are findings on suspected breast cancer by the initial test, pathological examination which involves inserting a needle into a lesion and collecting cells or tissues to be examined under a microscope, is carried out as a secondary test. If necessary, imaging tests such as CT, MRI, abdominal ultrasonography, bone scintigraphy, and PET are also carried out in order to examine the state or spread of the lesion.

For example, CEA, CA-15-3, and CA27-29 are known as tumor markers for the detection of breast cancer. These tumor markers in blood have been reported to elevate when breast cancer has metastasized to other organs such as the bone or the liver. However, these tumor markers do not elevate in some patients and may thus be limited by their usefulness (Non-Patent Literature 1).

As shown in Patent Literatures 1 to 4, there are reports, albeit at a research stage, on the detection of breast cancer using the expression levels of microRNAs (miRNAs) or combinations of the expression levels of miRNAs and the expression levels of additional protein markers in biological samples including blood.

Specifically, Patent Literature 1 discloses a method for detecting prostate cancer or other cancers including breast cancer by combining hsa-miR-602 or hsa-miR-135a-3p with known protein markers in blood.

Patent Literature 2 discloses a method for detecting various cancers including breast cancer by combining hsa-miR-23b-3p or hsa-miR-135a-3p with 5 or more other miRNAs in blood or tissues.

Patent Literature 3 discloses a method for detecting breast cancer using hsa-miR-92a-3p, hsa-miR-92a-2-5p, hsa-miR-92b-5p, and the like in blood cells.

Patent Literature 4 discloses a method for detecting breast cancer using hsa-miR-451a, hsa-miR-296-5p, hsa-miR-16-5p, and the like in tissues.

Non-Patent Literature 3 discloses that hsa-miR-760 and the like in blood are significantly expressed in breast cancer patients.

Non-Patent Literature 4 discloses that hsa-miR-423-5p, hsa-miR-486-5p, and the like in blood are decreased after surgery of breast cancer.

Non-Patent Literature 5 discloses that hsa-miR-4257, hsa-miR-1915-3p, hsa-miR-718, and the like in blood are significantly expressed in breast cancer patients.

Non-Patent Literature 6 discloses that hsa-miR-940 and the like in blood are significantly expressed in breast cancer patients.

CITATION LIST

Patent Literature

Patent Literature 1: JP Patent Publication (Kohyo) No. 2012-507300 A (2012)
Patent Literature 2: JP Patent Publication (Kohyo) No. 2008-500837 A (2008)
Patent Literature 3: International Publication No. WO 10/123043
Patent Literature 4: Published U.S. Patent Application No. 2008/0076674

Non-Patent Literature

Non-Patent Literature 1: American Cancer Society, "Breast Cancer", 2013, p. 6-9, 13, 27-28, 41-46, 52-54, 63-64, and 106

Non-Patent Literature 2: Sobin, L. et al., "TNM Classification of Malignant Tumours, the 7th edition", 2010, p. 171 to 181

Non-Patent Literature 3: Godfrey, A C. et al., 2013, Breast Cancer Research, Vol. 15 (3), p. R42

Non-Patent Literature 4: Cookson, V J. et al., 2012, Cellular Oncology, Vol. 35 (4), p. 301-8

Non-Patent Literature 5: Schrauder, M G. et al., 2012, PLoS One, Vol. 7 (1), p. e29770

Non-Patent Literature 6: Leidner, R S. et al., 2013, PLoS One, Vol. 8 (3), p. e57841

Non-Patent Literature 7: Tamaki, K. et al., 2013, Japanese Journal of Clinical Oncology, Vol. 43 (2), p. 208-213

Non-Patent Literature 8: Guadagni, F. et al., 2001, Clinical Cancer Research, Vol. 7, p. 2357 to 2362

SUMMARY OF INVENTION

Problem to be Solved by Invention

An object of the present invention is to find novel tumor markers for breast cancer and to provide a method that can effectively detect breast cancer using nucleic acid(s) capable of specifically binding to the markers. As described in Non-Patent Literature 1, initial diagnostic tests of breast cancer include inspection and palpation as well as imaging tests such as mammography, which is breast-dedicated X-ray examination, and ultrasonography. The mammography is reportedly effective as breast cancer examination targeting women aged 40 or older, and the American Cancer Society recommends that women in this age range take mammography every year (Non-Patent Literature 1). The mammography, however, has been reported to have limitations in the visualization of breast cancer present in the dense breast before menopause or a very small tumor of early breast cancer (Non-Patent Literature 1). In Japan, the mammography rate was only 24.3% in 2010, and a challenge to improvement in breast cancer survival rate will be to increase this mammography rate (Non-Patent Literature 7).

For example, CEA, CA-15-3, and CA27-29 mentioned above are known as tumor markers for the detection of breast cancer. These tumor markers, however, are helpful in confirming therapeutic effects on recurrent breast cancer, but rarely elevate in early breast cancer. Therefore, the tumor markers may not be useful for the purpose of breast cancer examination (Non-Patent Literature 1). According to Non-Patent Literature 8, the specific sensitivity of CEA and CA15-3 is uselessly 6.4% and 12.2%, respectively, for stage 1 and is only 25.0% and 62.5%, respectively, even for stage 4. Thus, the tumor marker measurement is less significant as a preoperative test. Since these blood tumor markers may elevate for reasons other than breast cancer, the presence or absence of breast cancer is difficult to determine. The false diagnosis of other cancers as breast cancer wastes appropriate therapeutic opportunity or places unnecessary economical and physical burdens on patients due to the application of wrong medicine.

As described below, there are reports, albeit at a research stage, on the determination of breast cancer using the expression levels of microRNAs (miRNAs) in biological samples including blood, none of which, however, have yet been brought into practical use.

Patent Literature 1 discloses a method for detecting prostate cancer or other cancers including breast cancer by combining hsa-miR-602 or hsa-miR-135a-3p with known protein markers in blood. The measurement of both miRNA and protein markers, however, brings about increase in examination costs and a complicated process and is therefore not favorable. This detection method does not describe specific detection performance such as accuracy, sensitivity, or specificity for determining breast cancer and is thus industrially less practical.

Patent Literature 2 discloses a method for detecting various cancers including breast cancer by combining hsa-miR-23b-3p or hsa-miR-135a-3p with 5 or more other miRNAs in blood or tissues. This detection method does not describe specific detection performance such as accuracy, sensitivity, or specificity for determining breast cancer and is thus industrially less practical.

Patent Literature 3 describes a method for detecting breast cancer using hsa-miR-92a-3p, hsa-miR-92a-2-5p, hsa-miR-92b-5p, and the like. This detection method does not describe specific detection performance such as accuracy, sensitivity, or specificity for determining breast cancer and is thus industrially less practical. In addition, these miRNA markers were not validated in an independent sample group and are therefore less reliable.

Patent Literature 4 discloses a method for detecting breast cancer using hsa-miR-451a, hsa-miR-296-5p, hsa-miR-16-5p, and the like in tissues. For this detection method, however, tissue resection by surgical operation is essential for obtaining samples, and this step places a heavy physical burden on patients. Therefore, this method is not favorable as an examination method. In addition, this detection method does not describe specific detection performance such as accuracy, sensitivity, or specificity for determining breast cancer and is thus industrially less practical.

Non-Patent Literature 3 discloses that hsa-miR-760 and the like in blood are significantly expressed in breast cancer patients. This literature, however, neither describes detection performance such as accuracy, sensitivity, or specificity for determining breast cancer nor describes a specific method for detecting breast cancer. Therefore, this approach is industrially less practical.

Non-Patent Literature 4 discloses that hsa-miR-423-5p, hsa-miR-486-5p, and the like in blood are decreased after surgery of breast cancer. This literature, however, neither describes detection performance such as accuracy, sensitivity, or specificity for determining breast cancer nor describes a specific method for detecting breast cancer. Therefore, this approach is industrially less practical.

Non-Patent Literature 5 discloses that hsa-miR-4257, hsa-miR-1915-3p, hsa-miR-718, and the like in blood are significantly expressed in breast cancer patients. This approach, however, employed as many as 240 miRNAs for detecting breast cancer and might cause increase in examination cost and complicated discriminant algorithms. Thus, this approach is not industrially practical.

Non-Patent Literature 6 discloses that hsa-miR-940 and the like in blood are significantly expressed in breast cancer patients. The authors, however, concluded that this marker is less reproducible, and finally abandoned the marker in the study. In addition, this literature neither describes detection performance such as accuracy, sensitivity, or specificity for determining breast cancer nor describes a specific method for detecting breast cancer. Therefore, this approach is industrially less practical.

As mentioned above, the existing tumor markers exhibit low performance in the detection of breast cancer, or neither performance nor detection methods are specifically shown as to the markers at a research stage. Therefore, use of these markers might impose implementation of needless extra examination due to the false detection of healthy subjects as being breast cancer patients, or might waste therapeutic opportunity because of overlooking breast cancer patients. In addition, the measurement of dozens of miRNAs increases examination cost and is therefore difficult to use in large-scale screening such as medical checkup. Furthermore, the collection of breast tissues for measuring the tumor markers is highly invasive to patients and is not favorable. Hence, there is a demand for a highly accurate breast cancer marker that is detectable from blood, which can be collected with limitedly invasiveness, and is capable of correctly determining a breast cancer patient as a breast cancer patient and a healthy subject as a healthy subject. Particularly, the early detection and treatment of breast cancer can drastically reduce the risk of recurrence and also permit breast conservation therapy. Therefore, a highly sensitive breast cancer marker capable of detecting breast cancer even at a low progressed stage is desired. Moreover, the mammography rate is presumably increased by providing a more convenient initial screening of breast cancer.

Solution to Problem

The present inventors have conducted diligent studies to attain the object and consequently completed the present invention by finding several genes usable as markers for the detection of breast cancer from blood, which can be collected with limitedly invasiveness, and finding that breast cancer can be significantly detected by using nucleic acids capable of specifically binding to any of these markers.

SUMMARY OF INVENTION

The present invention has the following features:
(1) A kit for the detection of breast cancer, comprising nucleic acid(s) capable of specifically binding to at least one polynucleotide selected from the group consisting of the following breast cancer markers: miR-4783-3p, miR-4730, miR-1307-3p, miR-4634, miR-663a, miR-4532, miR-7704, miR-3178, miR-6729-5p, miR-6090, miR-4732-5p, miR-3184-5p, miR-6727-5p, miR-6088, miR-4674, miR-8073, miR-4787-5p, miR-1469, miR-125a-3p, miR-1233-5p, miR-885-3p, miR-6802-5p, miR-328-5p, miR-6787-5p, miR-8069, miR-6875-5p, miR-1246, miR-4734, miR-6757-5p, miR-6756-5p, miR-3665, miR-6836-3p, miR-6821-5p, miR-6805-5p, miR-4728-5p, miR-6726-5p, miR-197-5p, miR-149-3p, miR-6850-5p, miR-4476, miR-6858-5p, miR-564, miR-4763-3p, miR-575, miR-6771-5p, miR-1231, miR-1908-3p, miR-150-3p, miR-3937, miR-887-3p, miR-3940-5p, miR-4741, miR-6808-5p, miR-6869-5p, miR-5090, miR-615-5p, miR-8072, miR-128-1-5p, miR-1238-5p, miR-365a-5p, miR-204-3p, miR-4492, miR-6785-5p, miR-6511a-5p, miR-4525, miR-1915-5p, miR-3180, miR-6879-5p, miR-1199-5p, miR-6746-5p, miR-711, miR-663b, miR-4707-3p, miR-6893-5p, miR-4675, miR-4638-5p, miR-4651, miR-6087, miR-4665-5p, miR-4758-5p, miR-6887-5p, miR-3620-5p, miR-1909-3p, miR-7641, miR-6724-5p, miR-1343-3p, miR-6780b-5p, miR-4484, miR-4690-5p, miR-4429, miR-1227-5p, miR-4725-3p, miR-6861-5p, miR-6812-5p, miR-3197, miR-8059, miR-3185, miR-4706, miR-4497, miR-3131, miR-6806-5p, miR-187-5p, miR-3180-3p, miR-6848-5p, miR-6820-5p, miR-6800-5p, miR-6717-5p, miR-6795-5p, miR-4632-5p, miR-665, miR-6778-5p, miR-3663-3p, miR-4689, miR-211-3p, miR-6511b-5p, miR-4750-5p, miR-6126, miR-614, miR-7110-5p, miR-744-5p, miR-6769a-5p, miR-4792, miR-5787, miR-6798-5p, miR-6781-5p, miR-4419b, miR-4446-3p, miR-4259, miR-5572, miR-6075, miR-296-3p, miR-6891-5p, miR-4745-5p, miR-6775-5p, miR-6870-5p, miR-920, miR-4530, miR-6819-5p, miR-6825-5p, miR-7847-3p, miR-6131, miR-4433-3p, miR-1228-5p, miR-6743-5p, miR-1268a, miR-3917, miR-6786-5p, miR-3154, miR-638, miR-6741-5p, miR-6889-5p, miR-6840-3p, miR-6510-5p, miR-3188, miR-551b-5p, miR-5001-5p, miR-1268b, miR-7107-5p, miR-6824-5p, miR-6732-5p, miR-371a-5p, miR-6794-5p, miR-6779-5p, miR-4271, miR-5195-3p, miR-6762-5p, miR-939-5p, miR-1247-3p, miR-6777-5p, miR-6722-3p, miR-3656, miR-4688, miR-3195, miR-6766-5p, miR-4447, miR-4656, miR-7108-5p, miR-3191-3p, miR-1273g-3p, miR-4463, miR-2861, miR-3196, miR-6877-5p, miR-3679-5p, miR-4442, miR-6789-5p, miR-6782-5p, miR-486-3p, miR-6085, miR-4746-3p, miR-619-5p, miR-937-5p, miR-6803-5p, miR-4298, miR-4454, miR-4459, miR-7150, miR-6880-5p, miR-4449, miR-8063, miR-4695-5p, miR-6132, miR-6829-5p, miR-4486, miR-6805-3p, miR-6826-5p, miR-4508, miR-1343-5p, miR-7114-5p, miR-3622a-5p, miR-6765-5p, miR-7845-5p, miR-3960, miR-6749-5p, miR-1260b, miR-6799-5p, miR-4723-5p, miR-6784-5p, miR-5100, miR-6769b-5p, miR-1207-5p, miR-642a-3p, miR-4505, miR-4270, miR-6721-5p, miR-7111-5p, miR-6791-5p, miR-7109-5p, miR-4258, miR-6515-3p, miR-6851-5p, miR-6125, miR-4749-5p, miR-4726-5p, miR-4513, miR-6089, miR-6816-5p, miR-4466, miR-4488, miR-6752-5p and miR-4739.

(2) The kit according to (1), wherein miR-4783-3p is hsa-miR-4783-3p, miR-4730 is hsa-miR-4730, miR-1307-3p is hsa-miR-1307-3p, miR-4634 is hsa-miR-4634, miR-663a is hsa-miR-663a, miR-4532 is hsa-miR-4532, miR-7704 is hsa-miR-7704, miR-3178 is hsa-miR-3178, miR-6729-5p is hsa-miR-6729-5p, miR-6090 is hsa-miR-6090, miR-4732-5p is hsa-miR-4732-5p, miR-3184-5p is hsa-miR-3184-5p, miR-6727-5p is hsa-miR-6727-5p, miR-6088 is hsa-miR-6088, miR-4674 is hsa-miR-4674, miR-8073 is hsa-miR-8073, miR-4787-5p is hsa-miR-4787-5p, miR-1469 is hsa-miR-1469, miR-125a-3p is hsa-miR-125a-3p, miR-1233-5p is hsa-miR-1233-5p, miR-885-3p is hsa-miR-885-3p, miR-6802-5p is hsa-miR-6802-5p, miR-328-5p is hsa-miR-328-5p, miR-6787-5p is hsa-miR-6787-5p, miR-8069 is hsa-miR-8069, miR-6875-5p is hsa-miR-6875-5p, miR-1246 is hsa-miR-1246, miR-4734 is hsa-miR-4734, miR-6757-5p is hsa-miR-6757-5p, miR-6756-5p is hsa-miR-6756-5p, miR-3665 is hsa-miR-3665, miR-6836-3p is hsa-miR-6836-3p, miR-6821-5p is hsa-miR-6821-5p, miR-6805-5p is hsa-miR-6805-5p, miR-4728-5p is hsa-miR-4728-5p, miR-6726-5p is hsa-miR-6726-5p, miR-197-5p is hsa-miR-197-5p, miR-149-3p is hsa-miR-149-3p, miR-6850-5p is hsa-miR-6850-5p, miR-4476 is hsa-miR-4476, miR-6858-5p is hsa-miR-6858-5p, miR-564 is hsa-miR-564, miR-4763-3p is hsa-miR-4763-3p, miR-575 is hsa-miR-575, miR-6771-5p is hsa-miR-6771-5p, miR-1231 is hsa-miR-1231, miR-1908-3p is hsa-miR-1908-3p, miR-150-3p is hsa-miR-150-3p, miR-3937 is hsa-miR-3937, miR-887-3p is hsa-miR-887-3p, miR-3940-5p is hsa-miR-3940-5p, miR-4741 is hsa-miR-4741, miR-6808-5p is hsa-miR-6808-5p, miR-6869-5p is hsa-miR-6869-5p, miR-5090 is hsa-miR-5090, miR-615-5p is hsa-miR-615-5p, miR-8072 is hsa-miR-8072, miR-128-1-5p is hsa-miR-128-1-5p, miR-1238-5p is hsa-miR-1238-5p, miR-365a-5p is hsa-miR-365a-5p, miR-204-3p is hsa-miR-204-3p, miR-4492 is hsa-miR-4492, miR-6785-5p is hsa-miR-6785-5p, miR-6511a-5p is hsa-miR-6511a-5p, miR-4525 is hsa-miR-4525, miR-1915-5p is hsa-miR-1915-5p, miR-3180 is hsa-miR-3180, miR-6879-5p is hsa-miR-6879-5p, miR-1199-5p is hsa-miR-1199-5p, miR-6746-5p is hsa-miR-6746-5p, miR-711 is hsa-miR-711, miR-663b is hsa-miR-663b, miR-4707-

3p is hsa-miR-4707-3p, miR-6893-5p is hsa-miR-6893-5p, miR-4675 is hsa-miR-4675, miR-4638-5p is hsa-miR-4638-5p, miR-4651 is hsa-miR-4651, miR-6087 is hsa-miR-6087, miR-4665-5p is hsa-miR-4665-5p, miR-4758-5p is hsa-miR-4758-5p, miR-6887-5p is hsa-miR-6887-5p, miR-3620-5p is hsa-miR-3620-5p, miR-1909-3p is hsa-miR-1909-3p, miR-7641 is hsa-miR-7641, miR-6724-5p is hsa-miR-6724-5p, miR-1343-3p is hsa-miR-1343-3p, miR-6780b-5p is hsa-miR-6780b-5p, miR-4484 is hsa-miR-4484, miR-4690-5p is hsa-miR-4690-5p, miR-4429 is hsa-miR-4429, miR-1227-5p is hsa-miR-1227-5p, miR-4725-3p is hsa-miR-4725-3p, miR-6861-5p is hsa-miR-6861-5p, miR-6812-5p is hsa-miR-6812-5p, miR-3197 is hsa-miR-3197, miR-8059 is hsa-miR-8059, miR-3185 is hsa-miR-3185, miR-4706 is hsa-miR-4706, miR-4497 is hsa-miR-4497, miR-3131 is hsa-miR-3131, miR-6806-5p is hsa-miR-6806-5p, miR-187-5p is hsa-miR-187-5p, miR-3180-3p is hsa-miR-3180-3p, miR-6848-5p is hsa-miR-6848-5p, miR-6820-5p is hsa-miR-6820-5p, miR-6800-5p is hsa-miR-6800-5p, miR-6717-5p is hsa-miR-6717-5p, miR-6795-5p is hsa-miR-6795-5p, miR-4632-5p is hsa-miR-4632-5p, miR-665 is hsa-miR-665, miR-6778-5p is hsa-miR-6778-5p, miR-3663-3p is hsa-miR-3663-3p, miR-4689 is hsa-miR-4689, miR-211-3p is hsa-miR-211-3p, miR-6511b-5p is hsa-miR-6511b-5p, miR-4750-5p is hsa-miR-4750-5p, miR-6126 is hsa-miR-6126, miR-614 is hsa-miR-614, miR-7110-5p is hsa-miR-7110-5p, miR-744-5p is hsa-miR-744-5p, miR-6769a-5p is hsa-miR-6769a-5p, miR-4792 is hsa-miR-4792, miR-5787 is hsa-miR-5787, miR-6798-5p is hsa-miR-6798-5p, miR-6781-5p is hsa-miR-6781-5p, miR-4419b is hsa-miR-4419b, miR-4446-3p is hsa-miR-4446-3p, miR-4259 is hsa-miR-4259, miR-5572 is hsa-miR-5572, miR-6075 is hsa-miR-6075, miR-296-3p is hsa-miR-296-3p, miR-6891-5p is hsa-miR-6891-5p, miR-4745-5p is hsa-miR-4745-5p, miR-6775-5p is hsa-miR-6775-5p, miR-6870-5p is hsa-miR-6870-5p, miR-920 is hsa-miR-920, miR-4530 is hsa-miR-4530, miR-6819-5p is hsa-miR-6819-5p, miR-6825-5p is hsa-miR-6825-5p, miR-7847-3p is hsa-miR-7847-3p, miR-6131 is hsa-miR-6131, miR-4433-3p is hsa-miR-4433-3p, miR-1228-5p is hsa-miR-1228-5p, miR-6743-5p is hsa-miR-6743-5p, miR-1268a is hsa-miR-1268a, miR-3917 is hsa-miR-3917, miR-6786-5p is hsa-miR-6786-5p, miR-3154 is hsa-miR-3154, miR-638 is hsa-miR-638, miR-6741-5p is hsa-miR-6741-5p, miR-6889-5p is hsa-miR-6889-5p, miR-6840-3p is hsa-miR-6840-3p, miR-6510-5p is hsa-miR-6510-5p, miR-3188 is hsa-miR-3188, miR-551b-5p is hsa-miR-551b-5p, miR-5001-5p is hsa-miR-5001-5p, miR-1268b is hsa-miR-1268b, miR-7107-5p is hsa-miR-7107-5p, miR-6824-5p is hsa-miR-6824-5p, miR-6732-5p is hsa-miR-6732-5p, miR-371a-5p is hsa-miR-371a-5p, miR-6794-5p is hsa-miR-6794-5p, miR-6779-5p is hsa-miR-6779-5p, miR-4271 is hsa-miR-4271, miR-5195-3p is hsa-miR-5195-3p, miR-6762-5p is hsa-miR-6762-5p, miR-939-5p is hsa-miR-939-5p, miR-1247-3p is hsa-miR-1247-3p, miR-6777-5p is hsa-miR-6777-5p, miR-6722-3p is hsa-miR-6722-3p, miR-3656 is hsa-miR-3656, miR-4688 is hsa-miR-4688, miR-3195 is hsa-miR-3195, miR-6766-5p is hsa-miR-6766-5p, miR-4447 is hsa-miR-4447, miR-4656 is hsa-miR-4656, miR-7108-5p is hsa-miR-7108-5p, miR-3191-3p is hsa-miR-3191-3p, miR-1273g-3p is hsa-miR-1273g-3p, miR-4463 is hsa-miR-4463, miR-2861 is hsa-miR-2861, miR-3196 is hsa-miR-3196, miR-6877-5p is hsa-miR-6877-5p, miR-3679-5p is hsa-miR-3679-5p, miR-4442 is hsa-miR-4442, miR-6789-5p is hsa-miR-6789-5p, miR-6782-5p is hsa-miR-6782-5p, miR-486-3p is hsa-miR-486-3p, miR-6085 is hsa-miR-6085, miR-4746-3p is hsa-miR-4746-3p, miR-619-5p is hsa-miR-619-5p, miR-937-5p is hsa-miR-937-5p, miR-6803-5p is hsa-miR-6803-5p, miR-4298 is hsa-miR-4298, miR-4454 is hsa-miR-4454, miR-4459 is hsa-miR-4459, miR-7150 is hsa-miR-7150, miR-6880-5p is hsa-miR-6880-5p, miR-4449 is hsa-miR-4449, miR-8063 is hsa-miR-8063, miR-4695-5p is hsa-miR-4695-5p, miR-6132 is hsa-miR-6132, miR-6829-5p is hsa-miR-6829-5p, miR-4486 is hsa-miR-4486, miR-6805-3p is hsa-miR-6805-3p, miR-6826-5p is hsa-miR-6826-5p, miR-4508 is hsa-miR-4508, miR-1343-5p is hsa-miR-1343-5p, miR-7114-5p is hsa-miR-7114-5p, miR-3622a-5p is hsa-miR-3622a-5p, miR-6765-5p is hsa-miR-6765-5p, miR-7845-5p is hsa-miR-7845-5p, miR-3960 is hsa-miR-3960, miR-6749-5p is hsa-miR-6749-5p, miR-1260b is hsa-miR-1260b, miR-6799-5p is hsa-miR-6799-5p, miR-4723-5p is hsa-miR-4723-5p, miR-6784-5p is hsa-miR-6784-5p, miR-5100 is hsa-miR-5100, miR-6769b-5p is hsa-miR-6769b-5p, miR-1207-5p is hsa-miR-1207-5p, miR-642a-3p is hsa-miR-642a-3p, miR-4505 is hsa-miR-4505, miR-4270 is hsa-miR-4270, miR-6721-5p is hsa-miR-6721-5p, miR-7111-5p is hsa-miR-7111-5p, miR-6791-5p is hsa-miR-6791-5p, miR-7109-5p is hsa-miR-7109-5p, miR-4258 is hsa-miR-4258, miR-6515-3p is hsa-miR-6515-3p, miR-6851-5p is hsa-miR-6851-5p, miR-6125 is hsa-miR-6125, miR-4749-5p is hsa-miR-4749-5p, miR-4726-5p is hsa-miR-4726-5p, miR-4513 is hsa-miR-4513, miR-6089 is hsa-miR-6089, miR-6816-5p is hsa-miR-6816-5p, miR-4466 is hsa-miR-4466, miR-4488 is hsa-miR-4488, miR-6752-5p is hsa-miR-6752-5p, and miR-4739 is hsa-miR-4739.

(3) The kit according to (1) or (2), wherein the nucleic acid is a polynucleotide selected from the group consisting of the following polynucleotides (a) to (e):
(a) a polynucleotide consisting of a nucleotide sequence represented by any of SEQ ID NOs: 1 to 235 and 851 to 856 or a nucleotide sequence derived from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 235 and 851 to 856 or a nucleotide sequence derived from the nucleotide sequence by the replacement of u with t,
(c) a polynucleotide consisting of a nucleotide sequence complementary to a nucleotide sequence represented by any of SEQ ID NOs: 1 to 235 and 851 to 856 or a nucleotide sequence derived from the nucleotide sequence by the replacement of u with t, a variant thereof, a derivative thereof, or a fragment thereof comprising 15 or more consecutive nucleotides,
(d) a polynucleotide comprising a nucleotide sequence complementary to a nucleotide sequence represented by any of SEQ ID NOs: 1 to 235 and 851 to 856 or a nucleotide sequence derived from the nucleotide sequence by the replacement of u with t, and
(e) a polynucleotide hybridizing under stringent conditions to any of the polynucleotides (a) to (d).

(4) The kit according to any of (1) to (3), wherein the kit further comprises nucleic acid(s) capable of specifically binding to at least one polynucleotide selected from the group consisting of other breast cancer markers miR-760, miR-602, miR-423-5p, miR-92a-2-5p, miR-16-5p, miR-451a, miR-135a-3p, miR-486-5p, miR-4257, miR-92b-5p, miR-1915-3p, miR-718, miR-940, miR-296-5p, miR-23b-3p and miR-92a-3p.

(5) The kit according to (4), wherein miR-760 is hsa-miR-760, miR-602 is hsa-miR-602, miR-423-5p is hsa-miR-423-5p, miR-92a-2-5p is hsa-miR-92a-2-5p, miR-16-5p is hsa-miR-16-5p, miR-451a is hsa-miR-451a, miR-135a-3p is hsa-miR-135a-3p, miR-486-5p is hsa-miR-486-5p, miR-4257 is hsa-miR-4257, miR-92b-5p is hsa-miR-92b-5p, miR-1915-3p is hsa-miR-1915-3p, miR-718 is hsa-miR-718, miR-940 is hsa-miR-940, miR-296-5p is hsa-miR-296-5p, miR-23b-3p is hsa-miR-23b-3p, and miR-92a-3p is hsa-miR-92a-3p.

(6) The kit according to (4) or (5), wherein the nucleic acid is a polynucleotide selected from the group consisting of the following polynucleotides (f) to (j):

(f) a polynucleotide consisting of a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 236 to 251, (h) a polynucleotide consisting of a nucleotide sequence complementary to a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 236 to 251 or a nucleotide sequence derived from the nucleotide sequence by the replacement of u with t, and (j) a polynucleotide hybridizing under stringent conditions to any of the polynucleotides (f) to (i).

(7) The kit according to any of (1) to (6), wherein the kit further comprises nucleic acid(s) capable of specifically binding to at least one polynucleotide selected from the group consisting of other breast cancer markers miR-658, miR-6842-5p, miR-6124, miR-6765-3p, miR-7106-5p, miR-4534, miR-92b-3p, miR-3135b, miR-4687-3p, miR-762, miR-3619-3p, miR-4467, miR-557, miR-1237-5p, miR-1908-5p, miR-4286, miR-6885-5p and miR-6763-5p.

(8) The kit according to (7), wherein miR-658 is hsa-miR-658, miR-6842-5p is hsa-miR-6842-5p, miR-6124 is hsa-miR-6124, miR-6765-3p is hsa-miR-6765-3p, miR-7106-5p is hsa-miR-7106-5p, miR-4534 is hsa-miR-4534, miR-92b-3p is hsa-miR-92b-3p, miR-3135b is hsa-miR-3135b, miR-4687-3p is hsa-miR-4687-3p, miR-762 is hsa-miR-762, miR-3619-3p is hsa-miR-3619-3p, miR-4467 is hsa-miR-4467, miR-557 is hsa-miR-557, miR-1237-5p is hsa-miR-1237-5p, miR-1908-5p is hsa-miR-1908-5p, miR-4286 is hsa-miR-4286, miR-6885-5p is hsa-miR-6885-5p, and miR-6763-5p is hsa-miR-6763-5p.

(9) The kit according to (7) or (8), wherein the nucleic acid is a polynucleotide selected from the group consisting of the following polynucleotides (k) to (o):

(k) a polynucleotide consisting of a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 252 to 269, (m) a polynucleotide consisting of a nucleotide sequence complementary to a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 252 to 269 or a nucleotide sequence derived from the nucleotide sequence by the replacement of u with t, and (o) a polynucleotide hybridizing under stringent conditions to any of the polynucleotides (k) to (n).

(10) The kit according to any of (1) to (9), wherein the kit comprises at least two nucleic acids capable of specifically binding to at least two polynucleotides, respectively, selected from the group consisting of all of the breast cancer markers according to (1) or (2).

(11) A device for the detection of breast cancer, comprising nucleic acid(s) capable of specifically binding to at least one polynucleotide selected from the group consisting of the following breast cancer markers: miR-4783-3p, miR-4730, miR-1307-3p, miR-4634, miR-663a, miR-4532, miR-7704, miR-3178, miR-6729-5p, miR-6090, miR-4732-5p, miR-3184-5p, miR-6727-5p, miR-6088, miR-4674, miR-8073, miR-4787-5p, miR-1469, miR-125a-3p, miR-1233-5p, miR-885-3p, miR-6802-5p, miR-328-5p, miR-6787-5p, miR-8069, miR-6875-5p, miR-1246, miR-4734, miR-6757-5p, miR-6756-5p, miR-3665, miR-6836-3p, miR-6821-5p, miR-6805-5p, miR-4728-5p, miR-6726-5p, miR-197-5p, miR-149-3p, miR-6850-5p, miR-4476, miR-6858-5p, miR-564, miR-4763-3p, miR-575, miR-6771-5p, miR-1231, miR-1908-3p, miR-150-3p, miR-3937, miR-887-3p, miR-3940-5p, miR-4741, miR-6808-5p, miR-6869-5p, miR-5090, miR-615-5p, miR-8072, miR-128-1-5p, miR-1238-5p, miR-365a-5p, miR-204-3p, miR-4492, miR-6785-5p, miR-6511a-5p, miR-4525, miR-1915-5p, miR-3180, miR-6879-5p, miR-1199-5p, miR-6746-5p, miR-711, miR-663b, miR-4707-3p, miR-6893-5p, miR-4675, miR-4638-5p, miR-4651, miR-6087, miR-4665-5p, miR-4758-5p, miR-6887-5p, miR-3620-5p, miR-1909-3p, miR-7641, miR-6724-5p, miR-1343-3p, miR-6780b-5p, miR-4484, miR-4690-5p, miR-4429, miR-1227-5p, miR-4725-3p, miR-6861-5p, miR-6812-5p, miR-3197, miR-8059, miR-3185, miR-4706, miR-4497, miR-3131, miR-6806-5p, miR-187-5p, miR-3180-3p, miR-6848-5p, miR-6820-5p, miR-6800-5p, miR-6717-5p, miR-6795-5p, miR-4632-5p, miR-665, miR-6778-5p, miR-3663-3p, miR-4689, miR-211-3p, miR-6511b-5p, miR-4750-5p, miR-6126, miR-614, miR-7110-5p, miR-744-5p, miR-6769a-5p, miR-4792, miR-5787, miR-6798-5p, miR-6781-5p, miR-4419b, miR-4446-3p, miR-4259, miR-5572, miR-6075, miR-296-3p, miR-6891-5p, miR-4745-5p, miR-6775-5p, miR-6870-5p, miR-920, miR-4530, miR-6819-5p, miR-6825-5p, miR-7847-3p, miR-6131, miR-4433-3p, miR-1228-5p, miR-6743-5p, miR-1268a, miR-3917, miR-6786-5p, miR-3154, miR-638, miR-6741-5p, miR-6889-5p, miR-6840-3p, miR-6510-5p, miR-3188, miR-551b-5p, miR-5001-5p, miR-1268b, miR-7107-5p, miR-6824-5p, miR-6732-5p, miR-371a-5p, miR-6794-5p, miR-6779-5p, miR-4271, miR-5195-3p, miR-6762-5p, miR-939-5p, miR-1247-3p, miR-6777-5p, miR-6722-3p, miR-3656, miR-4688, miR-3195, miR-6766-5p, miR-4447, miR-4656, miR-7108-5p, miR-3191-3p, miR-1273g-3p, miR-4463, miR-2861, miR-3196, miR-6877-5p, miR-3679-5p, miR-4442, miR-6789-5p, miR-6782-5p, miR-486-3p, miR-6085, miR-4746-3p, miR-619-5p, miR-937-5p, miR-6803-5p, miR-4298, miR-4454, miR-4459, miR-7150, miR-6880-5p, miR-4449, miR-8063, miR-4695-5p, miR-6132, miR-6829-5p, miR-4486, miR-6805-3p, miR-6826-5p, miR-4508, miR-1343-5p, miR-7114-5p, miR-3622a-5p, miR-6765-5p, miR-7845-5p, miR-3960, miR-6749-5p, miR-1260b, miR-6799-5p, miR-4723-5p, miR-6784-5p, miR-5100, miR-6769b-5p, miR-1207-5p, miR-642a-3p, miR-4505, miR-4270, miR-6721-5p, miR-7111-5p, miR-6791-5p, miR-7109-5p, miR-4258, miR-6515-3p, miR-6851-5p, miR-6125, miR-4749-5p, miR-4726-5p, miR-4513, miR-6089, miR-6816-5p, miR-4466, miR-4488, miR-6752-5p and miR-4739.

(12) The device according to (11), wherein miR-4783-3p is hsa-miR-4783-3p, miR-4730 is hsa-miR-4730, miR-1307-3p is hsa-miR-1307-3p, miR-4634 is hsa-miR-4634, miR-663a is hsa-miR-663a, miR-4532 is hsa-miR-4532, miR-7704 is hsa-miR-7704, miR-3178 is hsa-miR-3178, miR-6729-5p is hsa-miR-6729-5p, miR-6090 is hsa-miR-6090, miR-4732-5p is hsa-miR-4732-5p, miR-3184-5p is hsa-miR-3184-5p, miR-6727-5p is hsa-miR-6727-5p, miR-6088 is hsa-miR-6088, miR-4674 is hsa-miR-4674, miR-8073 is hsa-miR-8073, miR-4787-5p is hsa-miR-4787-5p, miR-1469 is hsa-miR-1469, miR-125a-3p is hsa-miR-125a-3p, miR-1233-5p is hsa-miR-1233-5p, miR-885-3p is hsa-miR-885-3p, miR-6802-5p is hsa-miR-6802-5p, miR-328-5p is hsa-miR-328-5p, miR-6787-5p is hsa-miR-6787-5p, miR-8069 is hsa-miR-8069, miR-6875-5p is hsa-miR-6875-5p, miR-1246 is hsa-miR-1246, miR-4734 is hsa-miR-4734, miR-6757-5p is hsa-miR-6757-5p, miR-6756-5p is hsa-miR-6756-5p, miR-3665 is hsa-miR-3665, miR-6836-3p is hsa-miR-6836-3p, miR-6821-5p is hsa-miR-6821-5p, miR-6805-5p is hsa-miR-6805-5p, miR-4728-5p is hsa-miR-4728-5p, miR-6726-5p is hsa-miR-6726-5p, miR-197-5p is hsa-miR-197-5p, miR-149-3p is hsa-miR-149-3p, miR-6850-5p is hsa-miR-6850-5p, miR-4476 is hsa-miR-4476, miR-6858-5p is hsa-miR-6858-5p, miR-564 is hsa-miR-564, miR-4763-3p is hsa-miR-4763-3p, miR-575 is hsa-miR-575, miR-6771-5p is hsa-miR-6771-5p, miR-1231 is hsa-miR-1231, miR-1908-3p is hsa-miR-1908-3p, miR-150-3p is hsa-miR-150-3p, miR-3937 is hsa-miR-3937, miR-887-3p is hsa-miR-887-3p, miR-3940-5p is hsa-miR-3940-5p, miR-4741 is hsa-miR-4741, miR-6808-5p is hsa-miR-6808-5p, miR-6869-5p is hsa-miR-6869-5p, miR-5090 is hsa-miR-5090, miR-615-5p is hsa-miR-615-5p, miR-8072 is hsa-miR-8072, miR-128-1-5p is hsa-miR-128-1-5p, miR-1238-5p is hsa-miR-1238-5p, miR-365a-5p is hsa-miR-365a-5p, miR-204-3p is hsa-miR-204-3p, miR-4492 is hsa-miR-4492, miR-6785-5p is hsa-miR-6785-5p, miR-6511a-5p is hsa-miR-6511a-5p, miR-4525 is hsa-miR-4525, miR-1915-5p is hsa-miR-1915-5p, miR-3180 is hsa-miR-3180, miR-6879-5p is hsa-miR-6879-5p, miR-1199-5p is hsa-miR-1199-5p, miR-6746-5p is hsa-miR-6746-5p, miR-711 is hsa-miR-711, miR-663b is hsa-miR-663b, miR-4707-3p is hsa-miR-4707-3p, miR-6893-5p is hsa-miR-6893-5p, miR-4675 is hsa-miR-4675, miR-4638-5p is hsa-miR-4638-5p, miR-4651 is hsa-miR-4651, miR-6087 is hsa-miR-6087, miR-4665-5p is hsa-miR-4665-5p, miR-4758-5p is hsa-miR-4758-5p, miR-6887-5p is hsa-miR-6887-5p, miR-3620-5p is hsa-miR-3620-5p, miR-1909-3p is hsa-miR-1909-3p, miR-7641 is hsa-miR-7641, miR-6724-5p is hsa-miR-6724-5p, miR-1343-3p is hsa-miR-1343-3p, miR-6780b-5p is hsa-miR-6780b-5p, miR-4484 is hsa-miR-4484, miR-4690-5p is hsa-miR-4690-5p, miR-4429 is hsa-miR-4429, miR-1227-5p is hsa-miR-1227-5p, miR-4725-3p is hsa-miR-4725-3p, miR-6861-5p is hsa-miR-6861-5p, miR-6812-5p is hsa-miR-6812-5p, miR-3197 is hsa-miR-3197, miR-8059 is hsa-miR-8059, miR-3185 is hsa-miR-3185, miR-4706 is hsa-miR-4706, miR-4497 is hsa-miR-4497, miR-3131 is hsa-miR-3131, miR-6806-5p is hsa-miR-6806-5p, miR-187-5p is hsa-miR-187-5p, miR-3180-3p is hsa-miR-3180-3p, miR-6848-5p is hsa-miR-6848-5p, miR-6820-5p is hsa-miR-6820-5p, miR-6800-5p is hsa-miR-6800-5p, miR-6717-5p is hsa-miR-6717-5p, miR-6795-5p is hsa-miR-6795-5p, miR-4632-5p is hsa-miR-4632-5p, miR-665 is hsa-miR-665, miR-6778-5p is hsa-miR-6778-5p, miR-3663-3p is hsa-miR-3663-3p, miR-4689 is hsa-miR-4689, miR-211-3p is hsa-miR-211-3p, miR-6511b-5p is hsa-miR-6511b-5p, miR-4750-5p is hsa-miR-4750-5p, miR-6126 is hsa-miR-6126, miR-614 is hsa-miR-614, miR-7110-5p is hsa-miR-7110-5p, miR-744-5p is hsa-miR-744-5p, miR-6769a-5p is hsa-miR-6769a-5p, miR-4792 is hsa-miR-4792, miR-5787 is hsa-miR-5787, miR-6798-5p is hsa-miR-6798-5p, miR-6781-5p is hsa-miR-6781-5p, miR-4419b is hsa-miR-4419b, miR-4446-3p is hsa-miR-4446-3p, miR-4259 is hsa-miR-4259, miR-5572 is hsa-miR-5572, miR-6075 is hsa-miR-6075, miR-296-3p is hsa-miR-296-3p, miR-6891-5p is hsa-miR-6891-5p, miR-4745-5p is hsa-miR-4745-5p, miR-6775-5p is hsa-miR-6775-5p, miR-6870-5p is hsa-miR-6870-5p, miR-920 is hsa-miR-920, miR-4530 is hsa-miR-4530, miR-6819-5p is hsa-miR-6819-5p, miR-6825-5p is hsa-miR-6825-5p, miR-7847-3p is hsa-miR-7847-3p, miR-6131 is hsa-miR-6131, miR-4433-3p is hsa-miR-4433-3p, miR-1228-5p is hsa-miR-1228-5p, miR-6743-5p is hsa-miR-6743-5p, miR-1268a is hsa-miR-1268a, miR-3917 is hsa-miR-3917, miR-6786-5p is hsa-miR-6786-5p, miR-3154 is hsa-miR-3154, miR-638 is hsa-miR-638, miR-6741-5p is hsa-miR-6741-5p, miR-6889-5p is hsa-miR-6889-5p, miR-6840-3p is hsa-miR-6840-3p, miR-6510-5p is hsa-miR-6510-5p, miR-3188 is hsa-miR-3188, miR-551b-5p is hsa-miR-551b-5p, miR-5001-5p is hsa-miR-5001-5p, miR-1268b is hsa-miR-1268b, miR-7107-5p is hsa-miR-7107-5p, miR-6824-5p is hsa-miR-6824-5p, miR-6732-5p is hsa-miR-6732-5p, miR-371a-5p is hsa-miR-371a-5p, miR-6794-5p is hsa-miR-6794-5p, miR-6779-5p is hsa-miR-6779-5p, miR-4271 is hsa-miR-4271, miR-5195-3p is hsa-miR-5195-3p, miR-6762-5p is hsa-miR-6762-5p, miR-939-5p is hsa-miR-939-5p, miR-1247-3p is hsa-miR-1247-3p, miR-6777-5p is hsa-miR-6777-5p, miR-6722-3p is hsa-miR-6722-3p, miR-3656 is hsa-miR-3656, miR-4688 is hsa-miR-4688, miR-3195 is hsa-miR-3195, miR-6766-5p is hsa-miR-6766-5p, miR-4447 is hsa-miR-4447, miR-4656 is hsa-miR-4656, miR-7108-5p is hsa-miR-7108-5p, miR-3191-3p is hsa-miR-3191-3p, miR-1273g-3p is hsa-miR-1273g-3p, miR-4463 is hsa-miR-4463, miR-2861 is hsa-miR-2861, miR-3196 is hsa-miR-3196, miR-6877-5p is hsa-miR-6877-5p, miR-3679-5p is hsa-miR-3679-5p, miR-4442 is hsa-miR-4442, miR-6789-5p is hsa-miR-6789-5p, miR-6782-5p is hsa-miR-6782-5p, miR-486-3p is hsa-miR-486-3p, miR-6085 is hsa-miR-6085, miR-4746-3p is hsa-miR-4746-3p, miR-619-5p is hsa-miR-619-5p, miR-937-5p is hsa-miR-937-5p, miR-6803-5p is hsa-miR-6803-5p, miR-4298 is hsa-miR-4298, miR-4454 is hsa-miR-4454, miR-4459 is hsa-miR-4459, miR-7150 is hsa-miR-7150, miR-6880-5p is hsa-miR-6880-5p, miR-4449 is hsa-miR-4449, miR-8063 is hsa-miR-8063, miR-4695-5p is hsa-miR-4695-5p, miR-6132 is hsa-miR-6132, miR-6829-5p is hsa-miR-6829-5p, miR-4486 is hsa-miR-4486, miR-6805-3p is hsa-miR-6805-3p, miR-6826-5p is hsa-miR-6826-5p, miR-4508 is hsa-miR-4508, miR-1343-5p is hsa-miR-1343-5p, miR-7114-5p is hsa-miR-7114-5p, miR-3622a-5p is hsa-miR-3622a-5p, miR-6765-5p is hsa-miR-6765-5p, miR-7845-5p is hsa-miR-7845-5p, miR-3960 is hsa-miR-3960, miR-6749-5p is hsa-miR-6749-5p, miR-1260b is hsa-miR-1260b, miR-6799-5p is hsa-miR-6799-5p, miR-4723-5p is hsa-miR-4723-5p, miR-6784-5p is hsa-miR-6784-5p, miR-5100 is hsa-miR-5100, miR-6769b-5p is hsa-miR-6769b-5p, miR-1207-5p is hsa-miR-1207-5p, miR-642a-3p is hsa-miR-642a-3p, miR-4505 is hsa-miR-4505, miR-4270 is hsa-miR-4270, miR-6721-5p is hsa-miR-6721-5p, miR-7111-5p is hsa-miR-7111-5p, miR-6791-5p is hsa-miR-6791-5p, miR-7109-5p is hsa-miR-7109-5p, miR- 4258 is hsa-miR-4258, miR-6515-3p is hsa-miR-6515-3p, miR-6851-5p is hsa-miR-6851-5p, miR-6125 is hsa-miR-6125, miR-4749-5p is hsa-miR-4749-5p, miR-4726-5p is hsa-miR-4726-5p, miR-4513 is hsa-miR-4513, miR-6089 is hsa-miR-6089, miR-6816-5p is hsa-miR-6816-5p, miR-4466 is hsa-miR-4466, miR-4488 is hsa-miR-4488, miR-6752-5p is hsa-miR-6752-5p, and miR-4739 is hsa-miR-4739.

(13) The device according to (11) or (12), wherein the nucleic acid is a polynucleotide selected from the group consisting of the following polynucleotides (a) to (e):
(a) a polynucleotide consisting of a nucleotide sequence represented by any of SEQ ID NOs: 1 to 235 and 851 to 856 or a nucleotide sequence derived from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 235 and 851 to 856 or a nucleotide sequence derived from the nucleotide sequence by the replacement of u with t,
(c) a polynucleotide consisting of a nucleotide sequence complementary to a nucleotide sequence represented by any of SEQ ID NOs: 1 to 235 and 851 to 856 or a nucleotide sequence derived from the nucleotide sequence by the replacement of u with t, a variant thereof, a derivative thereof, or a fragment thereof comprising 15 or more consecutive nucleotides,
(d) a polynucleotide comprising a nucleotide sequence complementary to a nucleotide sequence represented by any of SEQ ID NOs: 1 to 235 and 851 to 856 or a nucleotide sequence derived from the nucleotide sequence by the replacement of u with t, and
(e) a polynucleotide hybridizing under stringent conditions to any of the polynucleotides (a) to (d).

(14) The device according to any of (11) to (13), wherein the device further comprises nucleic acid(s) capable of specifically binding to at least one polynucleotide selected from the group consisting of other breast cancer markers miR-760, miR-602, miR-423-5p, miR-92a-2-5p, miR-16-5p, miR-451a, miR-135a-3p, miR-486-5p, miR-4257, miR-92b-5p, miR-1915-3p, miR-718, miR-940, miR-296-5p, miR-23b-3p and miR-92a-3p.

(15) The device according to (14), wherein miR-760 is hsa-miR-760, miR-602 is hsa-miR-602, miR-423-5p is hsa-miR-423-5p, miR-92a-2-5p is hsa-miR-92a-2-5p, miR-16-5p is hsa-miR-16-5p, miR-451a is hsa-miR-451a, miR-135a-3p is hsa-miR-135a-3p, miR-486-5p is hsa-miR-486-5p, miR-4257 is hsa-miR-4257, miR-92b-5p is hsa-miR-92b-5p, miR-1915-3p is hsa-miR-1915-3p, miR-718 is hsa-miR-718, miR-940 is hsa-miR-940, miR-296-5p is hsa-miR-296-5p, miR-23b-3p is hsa-miR-23b-3p, and miR-92a-3p is hsa-miR-92a-3p.

(16) The device according to (14) or (15), wherein the nucleic acid is a polynucleotide selected from the group consisting of the following polynucleotides (f) to (j):
(f) a polynucleotide consisting of a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides,
(g) a polynucleotide comprising a nucleotide sequence represented by any of SEQ ID NOs: 236 to 251,
(h) a polynucleotide consisting of a nucleotide sequence complementary to a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides,
(i) a polynucleotide comprising a nucleotide sequence complementary to a nucleotide sequence represented by any of SEQ ID NOs: 236 to 251 or a nucleotide sequence derived from the nucleotide sequence by the replacement of u with t, and
(j) a polynucleotide hybridizing under stringent conditions to any of the polynucleotides (f) to (i).

(17) The device according to any of (11) to (16), wherein the device further comprises nucleic acid(s) capable of specifically binding to at least one polynucleotide selected from the group consisting of other breast cancer markers miR-658, miR-6842-5p, miR-6124, miR-6765-3p, miR-7106-5p, miR-4534, miR-92b-3p, miR-3135b, miR-4687-3p, miR-762, miR-3619-3p, miR-4467, miR-557, miR-1237-5p, miR-1908-5p, miR-4286, miR-6885-5p and miR-6763-5p.

(18) The device according to (17), wherein miR-658 is hsa-miR-658, miR-6842-5p is hsa-miR-6842-5p, miR-6124 is hsa-miR-6124, miR-6765-3p is hsa-miR-6765-3p, miR-7106-5p is hsa-miR-7106-5p, miR-4534 is hsa-miR-4534, miR-92b-3p is hsa-miR-92b-3p, miR-3135b is hsa-miR-3135b, miR-4687-3p is hsa-miR-4687-3p, miR-762 is hsa-miR-762, miR-3619-3p is hsa-miR-3619-3p, miR-4467 is hsa-miR-4467, miR-557 is hsa-miR-557, miR-1237-5p is hsa-miR-1237-5p, miR-1908-5p is hsa-miR-1908-5p, miR-4286 is hsa-miR-4286, miR-6885-5p is hsa-miR-6885-5p, and miR-6763-5p is hsa-miR-6763-5p.

(19) The device according to (17) or (18), wherein the nucleic acid is a polynucleotide selected from the group consisting of the following polynucleotides (k) to (o):
(k) a polynucleotide consisting of a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides,
(l) a polynucleotide comprising a nucleotide sequence represented by any of SEQ ID NOs: 252 to 269,
(m) a polynucleotide consisting of a nucleotide sequence complementary to a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides,
(n) a polynucleotide comprising a nucleotide sequence complementary to a nucleotide sequence represented by any of SEQ ID NOs: 252 to 269 or a nucleotide sequence derived from the nucleotide sequence by the replacement of u with t, and
(o) a polynucleotide hybridizing under stringent conditions to any of the polynucleotides (k) to (n).

(20) The device according to any one of (11) to (19), wherein the device is for measurement based on a hybridization technique.

(21) The device according to (20), wherein the hybridization technique is a nucleic acid array technique.

(22) The device according to any one of (11) to (21), wherein the device comprises at least two nucleic acids capable of specifically binding to at least two polynucleotides, respectively, selected from all of the breast cancer markers according to (11) or (12).

(23) A method for detecting breast cancer, comprising measuring an expression level(s) of a target nucleic acid(s) in a sample from a subject using a kit according to any one of (1) to (10) or a device according to any one of (11) to (22), and evaluating in vitro whether or not the subject has breast cancer using both of the measured expression level(s) and a control expression level(s) in a sample from a healthy subject measured in the same way.

(24) The method according to (23), wherein the subject is a human.

(25) The method according to (23) or (24), wherein the sample is blood, serum, or plasma.

Definition of Terms

The terms used herein are defined as described below.

Abbreviations or terms such as nucleotide, polynucleotide, DNA, and RNA used herein abide by "Guidelines for the preparation of specification which contain nucleotide and/or amino acid sequences" (edited by Japan Patent Office) and common use in the art.

The term "polynucleotide" used herein refers to a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA and synthetic RNA. The "synthetic DNA" and the "synthetic RNA" used herein refer to DNA and RNA artificially prepared using, for example, an automatic nucleic acid synthesizer, on the basis of predetermined nucleotide sequences (which may be any of natural and non-natural sequences). The "non-natural sequence" used herein is intended to be used in a broad sense and includes, for example, a sequence comprising substitution, deletion, insertion, and/or addition of one or more nucleotide(s) (i.e., a variant sequence) and a sequence comprising one or more modified nucleotide(s) (i.e., a modified sequence), which are different from the natural sequence. The term "polynucleotide" used herein is used interchangeably with the term "nucleic acid".

The term "fragment" used herein refers to a polynucleotide (including oligonucleotides) having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus strand (or a sense strand) or a complementary strand (or an antisense strand) constituting the duplex. The gene is not particularly limited by its length. Thus, The "gene" used herein includes any of double-stranded DNA including human genomic DNA, single-stranded DNA (plus strand), single-stranded DNA having a sequence complementary to the plus strand (complementary strand) including cDNA, microRNA (miRNA), and their fragments, and their transcripts, unless otherwise specified. The "gene" includes not only a "gene" represented by a particular nucleotide sequence (or SEQ ID NO) but also "nucleic acids" encoding RNAs having biological functions equivalent to an RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 871 or a nucleotide sequence derived from the nucleotide sequence by the replacement of u with t. Regardless whether or not there is a difference in functional region, the "gene(s)" can comprise, for example, expression regulatory region(s), coding region(s), exon(s), or intron(s). The "gene" may be contained in a cell or may exist alone after being released into the outside of a cell. Alternatively, the "gene" may be in a state enclosed in a vesicle called exosome.

The term "exosome" used herein refers to a vesicle that is encapsulated by a lipid bilayer and secreted from a cell. The exosome is derived from a multivesicular endosome and may incorporate biomaterials such as "gene(s)" (e.g., RNA or DNA) or protein(s) when released into an extracellular environment. The exosome is known to be contained in a body fluid such as blood, serum, plasma, or lymph.

The term "transcript" used herein refers to RNA synthesized with the DNA sequence of a gene as a template. RNA polymerase binds to a site called a promoter located upstream of the gene and adds ribonucleotides complementary to the nucleotide sequence of the DNA to the 3' end to synthesize an RNA. This RNA contains not only the gene itself but also the whole sequence from a transcription initiation site to the end of a polyA sequence, including expression regulatory region(s), coding region(s), exon(s), or intron(s).

Unless otherwise specified, the term "microRNA (miRNA)" used herein is intended to mean a 15- to 25-nucleotide non-coding RNA that is transcribed as an RNA precursor which has a hairpin-like structure, cleaved by a dsRNA-cleaving enzyme which has RNase III cleavage activity, and integrated into a protein complex called RISC, and is involved in the suppression of translation of mRNA. The term "miRNA" used herein includes not only a "miRNA" represented by a particular nucleotide sequence (or SEQ ID NO) but also a precursor of the "miRNA" (pre-miRNA or pri-miRNA), and miRNAs that have biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 871. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting an RNA resulting from the expression of a gene or a polynucleotide derived from the RNA, and/or a polynucleotide complementary thereto.

The term "primer" used herein includes a polynucleotide that specifically recognizes and amplifies RNA resulting from the expression of a gene or a polynucleotide derived from the RNA, and/or a polynucleotide complementary thereto. In this context, the "complementary polynucleotide (complementary strand or reverse strand)" means a polynucleotide in a complementary relationship of A:T (U) and G:C base pairs with the full-length sequence of a polynucleotide consisting of a nucleotide sequence defined by any of SEQ ID NOs: 1 to 871 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence complementary 100% to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1 or 2 or more nucleotides in a nucleotide sequence represented by any of SEQ ID NOs: 1 to 871 or a nucleotide sequence derived from the nucleotide sequence by the replacement of u with t, or a partial sequence thereof; a variant that exhibits percent (%) identity of approximately 90% or higher, approximately 95% or higher, approximately 97% or higher, approximately 98% or higher, approximately 99% or higher to each of these nucleotide sequences or the partial sequence thereof; or a nucleic acid hybridizing under the stringent conditions defined above to a polynucleotide or an oligonucleotide comprising each of these nucleotide sequences or the partial sequence thereof.

The term "multiple" used herein means an integer of approximately 10, 9, 8, 7, 6, 5, 4, 3, or 2.

The "variant" used herein can be prepared by use of a well-known technique such as site-directed mutagenesis or PCR-based mutagenesis.

The term "percent (%) identity" used herein can be determined with or without an introduced gap, using a protein or gene search system based on BLAST or FASTA described above (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A, Vol. 85, p. 2444-2448).

The term "derivative" used herein is meant to include a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) without any limitation.

The "nucleic acid" used herein capable of specifically binding to a polynucleotide selected from the breast cancer marker miRNAs described above is a synthesized or prepared nucleic acid and specifically includes a "nucleic acid probe" or a "primer". The "nucleic acid" is utilized directly or indirectly for detecting the presence or absence of breast cancer in a subject, for diagnosing the presence or absence of breast cancer, or the severity of breast cancer, the presence or absence of amelioration of breast cancer, or the degree of amelioration of breast cancer, or the therapeutic sensitivity of breast cancer, or for screening for a candidate substance useful in the prevention, amelioration, or treatment of breast cancer. The "nucleic acid" includes a nucleotide, an oligonucleotide, and a polynucleotide capable of specifically recognizing and binding to a transcript represented by any of SEQ ID NOs: 1 to 871 or a synthetic cDNA nucleic acid thereof in vivo, particularly, in a sample such as a body fluid (e.g., blood or urine), in relation to the development of breast cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", or "detection or decision support". The term "evaluation" used herein is meant to include diagnosing or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "P" or "P value" used herein refers to a probability at which a more extreme statistic than that is actually calculated from data under a null hypothesis is observed in a statistical test. Thus, smaller "P" or "P value" is regarded as being a more significant difference between subjects to be compared.

The term "sensitivity" used herein means a value of (the number of true positives)/(the number of true positives+the number of false negatives). High sensitivity allows breast cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects who might have been misjudged as being breast cancer patients, leading to reduction in burden on patients and reduction in medical expense.

The term "accuracy" used herein means a value of (the number of true positives+the number of true negatives)/(the total number of cases). The accuracy indicates the ratio of samples that are identified correctly to all samples, and serves as a primary index for evaluating detection performance.

The "sample" used herein, that is subjected to determination, detection, or diagnosis refers to a tissue and a biological material in which the expression of the gene of the present invention varies as breast cancer develops, as breast cancer progresses, or as therapeutic effects on breast cancer are exerted. Specifically, the "sample" refers to a breast tissue, a perimammary vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-4783-3p gene" or "hsa-miR-4783-3p" used herein includes the hsa-miR-4783-3p gene (miRBase Accession No. MIMAT0019947) described in SEQ ID NO: 1, a homolog or an ortholog of a different organism species, and the like. The hsa-miR-4783-3p gene can be obtained by a method described in Persson H et al., 2011, Cancer Res, Vol. 71, p. 78-86. Also, "hsa-mir-4783" (miRBase Accession No. MI0017428, SEQ ID NO: 270) having a hairpin-like structure is known as a precursor of "hsa-miR-4783-3p".

The term "hsa-miR-4730 gene" or "hsa-miR-4730" used herein includes the hsa-miR-4730 gene (miRBase Accession No. MIMAT0019852) described in SEQ ID NO: 2, a homolog or an ortholog of a different organism species, and the like. The hsa-miR-4730 gene can be obtained by a method described in Persson H et al., 2011, Cancer Res, Vol. 71, p. 78-86. Also, "hsa-mir-4730" (miRBase Accession No. MI0017367, SEQ ID NO: 271) having a hairpin-like structure is known as a precursor of "hsa-miR-4730".

The term "hsa-miR-1307-3p gene" or "hsa-miR-1307-3p" used herein includes the hsa-miR-1307-3p gene (miRBase Accession No. MIMAT0005951) described in SEQ ID NO: 3, a homolog or an ortholog of a different organism species, and the like. The hsa-miR-1307-3p gene can be obtained by a method described in Morin R D et al., 2008, Genome Res, Vol. 18, p. 610-621. Also, "hsa-mir-1307" (miRBase Accession No. MI0006444, SEQ ID NO: 272) having a hairpin-like structure is known as a precursor of "hsa-miR-1307-3p".

The term "hsa-miR-4634 gene" or "hsa-miR-4634" used herein includes the hsa-miR-4634 gene (miRBase Accession No. MIMAT0019691) described in SEQ ID NO: 4, a homolog or an ortholog of a different organism species, and the like. The hsa-miR-4634 gene can be obtained by a method described in Persson H et al., 2011, Cancer Res, Vol. 71, p. 78-86. Also, "hsa-mir-4634" (miRBase Accession No. MI0017261, SEQ ID NO: 273) having a hairpin-like structure is known as a precursor of "hsa-miR-4634".

The term "hsa-miR-663a gene" or "hsa-miR-663a" used herein includes the hsa-miR-663a gene (miRBase Accession No. MIMAT0003326) described in SEQ ID NO: 5, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 274) having a hairpin-like structure is known as a precursor of "hsa-miR-663a".

The term "hsa-miR-4532 gene" or "hsa-miR-4532" used herein includes the hsa-miR-4532 gene (miRBase Accession No. MIMAT0019071) described in SEQ ID NO: 6, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. MI0016899, SEQ ID NO: 275) having a hairpin-like structure is known as a precursor of "hsa-miR-4532".

The term "hsa-miR-7704 gene" or "hsa-miR-7704" used herein includes the hsa-miR-7704 gene (miRBase Accession No. MIMAT0030019) described in SEQ ID NO: 7, a homolog or an ortholog of a different organism species, and the like. The hsa-miR-7704 gene can be obtained by a method described in Swaminathan S et al., 2013, Biochem Biophys Res Commun, Vol. 434, p. 228-234. Also, "hsa-mir-7704" (miRBase Accession No. MI0025240, SEQ ID NO: 276) having a hairpin-like structure is known as a precursor of "hsa-miR-7704".

The term "hsa-miR-3178 gene" or "hsa-miR-3178" used herein includes the hsa-miR-3178 gene (miRBase Accession No. MIMAT0015055) described in SEQ ID NO: 8, a homolog or an ortholog of a different organism species, and the like. The hsa-miR-3178 gene can be obtained by a method described in Stark M S et al., 2010, PLoS One, Vol. 5, e9685. Also, "hsa-mir-3178" (miRBase Accession No. MI0014212, SEQ ID NO: 277) having a hairpin-like structure is known as a precursor of "hsa-miR-3178".

The term "hsa-miR-6729-5p gene" or "hsa-miR-6729-5p" used herein includes the hsa-miR-6729-5p gene (miRBase Accession No. MIMAT0027359) described in SEQ ID NO: 9, a homolog or an ortholog of a different organism species, and the like. The hsa-miR-6729-5p gene can be obtained by a method described in Ladewig E et al., 2012, Genome Res, Vol. 22, p. 1634-1645. Also, "hsa-mir-6729" (miRBase Accession No. MI0022574, SEQ ID NO: 278) having a hairpin-like structure is known as a precursor of "hsa-miR-6729-5p".

The term "hsa-miR-6090 gene" or "hsa-miR-6090" used in herein includes the hsa-miR-6090 gene (miRBase Accession No. MIMAT0023715) described in SEQ ID NO: 10, a homolog or an ortholog of a different organism species, and the like. The hsa-miR-6090 gene can be obtained by a method described in Yoo J K et al., 2012, Stem Cells Dev, Vol. 21, p. 2049-2057. Also, "hsa-mir-6090" (miRBase Accession No. MI0020367, SEQ ID NO: 279) having a hairpin-like structure is known as a precursor of "hsa-miR-6090".

The term "hsa-miR-4732-5p gene" or "hsa-miR-4732-5p" used in herein includes the hsa-miR-4732-5p gene (miRBase Accession No. MIMAT0019855) described in SEQ ID NO: 11, a homolog or an ortholog of a different organism species, and the like. The hsa-miR-4732-5p gene can be obtained by a method described in Persson H et al., 2011, Cancer Res, Vol. 71, p. 78-86. Also, "hsa-mir-4732" (miRBase Accession No. MI0017369, SEQ ID NO: 280) having a hairpin-like structure is known as a precursor of "hsa-miR-4732-5p".

The term "hsa-miR-3184-5p gene" or "hsa-miR-3184-5p" used herein includes the hsa-miR-3184-5p gene (miRBase Accession No. MIMAT0015064) described in SEQ ID NO: 12, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 281) having a hairpin-like structure is known as a precursor of "hsa-miR-3184-5p".

The term "hsa-miR-6727-5p gene" or "hsa-miR-6727-5p" used herein includes the hsa-miR-6727-5p gene (miRBase Accession No. MIMAT0027355) described in SEQ ID NO: 13, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. MI0022572, SEQ ID NO: 282) having a hairpin-like structure is known as a precursor of "hsa-miR-6727-5p".

The term "hsa-miR-6088 gene" or "hsa-miR-6088" used herein includes the hsa-miR-6088 gene (miRBase Accession No. MIMAT0023713) described in SEQ ID NO: 14, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 283) having a hairpin-like structure is known as a precursor of "hsa-miR-6088".

The term "hsa-miR-4674 gene" or "hsa-miR-4674" used herein includes the hsa-miR-4674 gene (miRBase Accession No. MIMAT0019756) described in SEQ ID NO: 15, a homolog or an ortholog of a different organism species, and the like. The hsa-miR-4674 gene can be obtained by a method described in Persson H et al., 2011, Cancer Res, Vol. 71, p. 78-86. Also, "hsa-mir-4674" (miRBase Accession No. MI0017305, SEQ ID NO: 284) having a hairpin-like structure is known as a precursor of "hsa-miR-4674".

The term "hsa-miR-8073 gene" or "hsa-miR-8073" used herein includes the hsa-miR-8073 gene (miRBase Accession No. MIMAT0031000) described in SEQ ID NO: 16, a homolog or an ortholog of a different organism species, and the like. The hsa-miR-8073 gene can be obtained by a method described in Wang H J et al., 2013, Shock, Vol. 39, p. 480-487. Also, "hsa-mir-8073" (miRBase Accession No. MI0025909, SEQ ID NO: 285) having a hairpin-like structure is known as a precursor of "hsa-miR-8073".

The term "hsa-miR-4787-5p gene" or "hsa-miR-4787-5p" used herein includes the hsa-miR-4787-5p gene (miRBase Accession No. MIMAT0019956) described in SEQ ID NO: 17, a homolog or an ortholog of a different organism species, and the like. The hsa-miR-4787-5p gene can be obtained by a method described in Persson H et al., 2011, Cancer Res, Vol. 71, p. 78-86. Also, "hsa-mir-4787" (miRBase Accession No. MI0017434, SEQ ID NO: 286) having a hairpin-like structure is known as a precursor of "hsa-miR-4787-5p".

The term "hsa-miR-1469 gene" or "hsa-miR-1469" used herein includes the hsa-miR-1469 gene (miRBase Accession No. MIMAT0007347) described in SEQ ID NO: 18, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 287) having a hairpin-like structure is known as a precursor of "hsa-miR-1469".

The term "hsa-miR-125a-3p gene" or "hsa-miR-125a-3p" used herein includes the hsa-miR-125a-3p gene (miRBase Accession No. MIMAT0004602) described in SEQ ID NO: 19, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. MI0000469, SEQ ID NO: 288) having a hairpin-like structure is known as a precursor of "hsa-miR-125a-3p".

The term "hsa-miR-1233-5p gene" or "hsa-miR-1233-5p" used herein includes the hsa-miR-1233-5p gene (miRBase Accession No. MIMAT0022943) described in SEQ ID NO: 20, a homolog or an ortholog of a different organism species, and the like. The hsa-miR-1233-5p gene can be obtained by a method described in Berezikov E et al., 2007, Mol Cell, Vol. 28, p. 328-336. Also, "hsa-mir-1233-1 and hsa-mir-1233-2" (miRBase Accession Nos. MI0006323 and MI0015973, SEQ ID NOs: 289 and 290) having a hairpin-like structure are known as precursors of "hsa-miR-1233-5p".

The term "hsa-miR-885-3p gene" or "hsa-miR-885-3p" used herein includes the hsa-miR-885-3p gene (miRBase Accession No. MIMAT0004948) described in SEQ ID NO: 21, a homolog or an ortholog of a different organism species, and the like. The hsa-miR-885-3p gene can be obtained by a method described in Berezikov E et al., 2006, Genome Res, Vol. 16, p. 1289-1298. Also, "hsa-mir-885" (miRBase Accession No. MI0005560, SEQ ID NO: 291) having a hairpin-like structure is known as a precursor of "hsa-miR-885-3p".

The term "hsa-miR-6802-5p gene" or "hsa-miR-6802-5p" used herein includes the hsa-miR-6802-5p gene (miRBase Accession No. MIMAT0027504) described in SEQ ID NO: 22, a homolog or an ortholog of a different organism species, and the like. The hsa-miR-6802-5p gene can be obtained by a method described in Ladewig E et al., 2012, Genome Res, Vol. 22, p. 1634-1645. Also, "hsa-mir-6802" (miRBase Accession No. MI0022647, SEQ ID NO: 292) having a hairpin-like structure is known as a precursor of "hsa-miR-6802-5p".

The term "hsa-miR-328-5p gene" or "hsa-miR-328-5p" used herein includes the hsa-miR-328-5p gene (miRBase Accession No. MIMAT0026486) described in SEQ ID NO: 23, a homolog or an ortholog of a different organism species, and the like. The hsa-miR-328-5p gene can be obtained by a method described in Kim J et al., 2004, Proc Natl Acad Sci USA, Vol. 101, p. 360-365. Also, "hsa-mir-328" (miRBase Accession No. MI0000804, SEQ ID NO: 293) having a hairpin-like structure is known as a precursor of "hsa-miR-328-5p".

The term "hsa-miR-6787-5p gene" or "hsa-miR-6787-5p" used herein includes the hsa-miR-6787-5p gene (miRBase Accession No. MIMAT0027474) described in SEQ ID NO: 24, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632, SEQ ID NO: 294) having a hairpin-like structure is known as a precursor of "hsa-miR-6787-5p".

The term "hsa-miR-8069 gene" or "hsa-miR-8069" used herein includes the hsa-miR-8069 gene (miRBase Accession No. MIMAT0030996) described in SEQ ID NO: 25, a homolog or an ortholog of a different organism species, and the like. The hsa-miR-8069 gene can be obtained by a method described in Wang H J et al., 2013, Shock, Vol. 39, p. 480-487. Also, "hsa-mir-8069" (miRBase Accession No. MI0025905, SEQ ID NO: 295) having a hairpin-like structure is known as a precursor of "hsa-miR-8069".

The term "hsa-miR-6875-5p gene" or "hsa-miR-6875-5p" used herein includes the hsa-miR-6875-5p gene (miRBase Accession No. MIMAT0027650) described in SEQ ID NO: 26, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875" (miRBase Accession No. MI0022722, SEQ ID NO: 296) having a hairpin-like structure is known as a precursor of "hsa-miR-6875-5p".

The term "hsa-miR-1246 gene" or "hsa-miR-1246" used herein includes the hsa-miR-1246 gene (miRBase Accession No. MIMAT0005898) described in SEQ ID NO: 27, a homolog or an ortholog of a different organism species, and the like. The hsa-miR-1246 gene can be obtained by a method described in Morin R D et al., 2008, Genome Res, Vol. 18, p. 610-621. Also, "hsa-mir-1246" (miRBase Accession No. MI0006381, SEQ ID NO: 297) having a hairpin-like structure is known as a precursor of "hsa-miR-1246".

The term "hsa-miR-4734 gene" or "hsa-miR-4734" used herein includes the hsa-miR-4734 gene (miRBase Accession No. MIMAT0019859) described in SEQ ID NO: 28, a homolog or an ortholog of a different organism species, and the like. The hsa-miR-4734 gene can be obtained by a method described in Persson H et al., 2011, Cancer Res, Vol.

71, p. 78-86. Also, "hsa-mir-4734" (miRBase Accession No. MI0017371, SEQ ID NO: 298) having a hairpin-like structure is known as a precursor of "hsa-miR-4734".

The term "hsa-miR-6757-5p gene" or "hsa-miR-6757-5p" used herein includes the hsa-miR-6757-5p gene (miRBase Accession No. MIMAT0027414) described in SEQ ID NO: 29, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. MI0022602, SEQ ID NO: 299) having a hairpin-like structure is known as a precursor of "hsa-miR-6757-5p".

The term "hsa-miR-6756-5p gene" or "hsa-miR-6756-5p" used herein includes the hsa-miR-6756-5p gene (miRBase Accession No. MIMAT0027412) described in SEQ ID NO: 30, a homolog or an ortholog of a different organism species, and the like. The hsa-miR-6756-5p gene can be obtained by a method described in Ladewig E et al., 2012, Genome Res, Vol. 22, p. 1634-1645. Also, "hsa-mir-6756" (miRBase Accession No. MI0022601, SEQ ID NO: 300) having a hairpin-like structure is known as a precursor of "hsa-miR-6756-5p".

The term "hsa-miR-3665 gene" or "hsa-miR-3665" used herein includes the hsa-miR-3665 gene (miRBase Accession No. MIMAT0018087) described in SEQ ID NO: 31, a homolog or an ortholog of a different organism species, and the like. The hsa-miR-3665 gene can be obtained by a method described in Xie X et al., 2005, Nature, Vol. 434, p. 338-345. Also, "hsa-mir-3665" (miRBase Accession No. MI0016066, SEQ ID NO: 301) having a hairpin-like structure is known as a precursor of "hsa-miR-3665".

The term "hsa-miR-6836-3p gene" or "hsa-miR-6836-3p" used herein includes the hsa-miR-6836-3p gene (miRBase Accession No. MIMAT0027575) described in SEQ ID NO: 32, a homolog or an ortholog of a different organism species, and the like. The hsa-miR-6836-3p gene can be obtained by a method described in Ladewig E et al., 2012, Genome Res, Vol. 22, p. 1634-1645. Also, "hsa-mir-6836" (miRBase Accession No. MI0022682, SEQ ID NO: 302) having a hairpin-like structure is known as a precursor of "hsa-miR-6836-3p".

The term "hsa-miR-6821-5p gene" or "hsa-miR-6821-5p" used herein includes the hsa-miR-6821-5p gene (miRBase Accession No. MIMAT0027542) described in SEQ ID NO: 33, a homolog or an ortholog of a different organism species, and the like. The hsa-miR-6821-5p gene can be obtained by a method described in Ladewig E et al., 2012, Genome Res, Vol. 22, p. 1634-1645. Also, "hsa-mir-6821" (miRBase Accession No. MI0022666, SEQ ID NO: 303) having a hairpin-like structure is known as a precursor of "hsa-miR-6821-5p".

The term "hsa-miR-6805-5p gene" or "hsa-miR-6805-5p" used herein includes the hsa-miR-6805-5p gene (miRBase Accession No. MIMAT0027510) described in SEQ ID NO: 34, a homolog or an ortholog of a different organism species, and the like. The hsa-miR-6805-5p gene can be obtained by a method described in Ladewig E et al., 2012, Genome Res, Vol. 22, p. 1634-1645. Also, "hsa-mir-6805" (miRBase Accession No. MI0022650, SEQ ID NO: 304) having a hairpin-like structure is known as a precursor of "hsa-miR-6805-5p".

The term "hsa-miR-4728-5p gene" or "hsa-miR-4728-5p" used herein includes the hsa-miR-4728-5p gene (miRBase Accession No. MIMAT0019849) described in SEQ ID NO: 35, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI0017365, SEQ ID NO: 305) having a hairpin-like structure is known as a precursor of "hsa-miR-4728-5p".

The term "hsa-miR-6726-5p gene" or "hsa-miR-6726-5p" used herein includes the hsa-miR-6726-5p gene (miRBase Accession No. MIMAT0027353) described in SEQ ID NO: 36, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 306) having a hairpin-like structure is known as a precursor of "hsa-miR-6726-5p".

The term "hsa-miR-197-5p gene" or "hsa-miR-197-5p" used herein includes the hsa-miR-197-5p gene (miRBase Accession No. MIMAT0022691) described in SEQ ID NO: 37, a homolog or an ortholog of a different organism species, and the like. The hsa-miR-197-5p gene can be obtained by a method described in Lagos-Quintana M et al., 2003, RNA, Vol. 9, p. 175-179. Also, "hsa-mir-197" (miRBase Accession No. MI0000239, SEQ ID NO: 307) having a hairpin-like structure is known as a precursor of "hsa-miR-197-5p".

The term "hsa-miR-149-3p gene" or "hsa-miR-149-3p" used herein includes the hsa-miR-149-3p gene (miRBase Accession No. MIMAT0004609) described in SEQ ID NO: 38, a homolog or an ortholog of a different organism species, and the like. The hsa-miR-149-3p gene can be obtained by a method described in Lagos-Quintana M et al., 2002, Curr Biol, Vol. 12, p. 735-739. Also, "hsa-mir-149" (miRBase Accession No. MI0000478, SEQ ID NO: 308) having a hairpin-like structure is known as a precursor of "hsa-miR-149-3p".

The term "hsa-miR-6850-5p gene" or "hsa-miR-6850-5p" used herein includes the hsa-miR-6850-5p gene (miRBase Accession No. MIMAT0027600) described in SEQ ID NO: 39, a homolog or an ortholog of a different organism species, and the like. The hsa-miR-6850-5p gene can be obtained by a method described in Ladewig E et al., 2012, Genome Res, Vol. 22, p. 1634-1645. Also, "hsa-mir-6850" (miRBase Accession No. MI0022696, SEQ ID NO: 309) having a hairpin-like structure is known as a precursor of "hsa-miR-6850-5p".

The term "hsa-miR-4476 gene" or "hsa-miR-4476" used herein includes the hsa-miR-4476 gene (miRBase Accession No. MIMAT0019003) described in SEQ ID NO: 40, a homolog or an ortholog of a different organism species, and the like. The hsa-miR-4476 gene can be obtained by a method described in Jima D D et al., 2010, Blood, Vol. 116, e118-e127. Also, "hsa-mir-4476" (miRBase Accession No. MI0016828, SEQ ID NO: 310) having a hairpin-like structure is known as a precursor of "hsa-miR-4476".

The term "hsa-miR-6858-5p gene" or "hsa-miR-6858-5p" used herein includes the hsa-miR-6858-5p gene (miRBase Accession No. MIMAT0027616) described in SEQ ID NO: 41, a homolog or an ortholog of a different organism species, and the like. The hsa-miR-6858-5p gene can be obtained by a method described in Ladewig E et al., 2012, Genome Res, Vol. 22, p. 1634-1645. Also, "hsa-mir-6858" (miRBase Accession No. MI0022704, SEQ ID NO: 311) having a hairpin-like structure is known as a precursor of "hsa-miR-6858-5p".

The term "hsa-miR-564 gene" or "hsa-miR-564" used herein includes the hsa-miR-564 gene (miRBase Accession No. MIMAT0003228) described in SEQ ID NO: 42, a homolog or an ortholog of a different organism species, and the like. The hsa-miR-564 gene can be obtained by a method described in Cummins J M et al., 2006, Proc Natl Acad Sci USA, Vol. 103, p. 3687-3692. Also, "hsa-mir-564" (miRBase Accession No. MI0003570, SEQ ID NO: 312) having a hairpin-like structure is known as a precursor of "hsa-miR-564".

The term "hsa-miR-4763-3p gene" or "hsa-miR-4763-3p" used herein includes the hsa-miR-4763-3p gene (miRBase Accession No. MIMAT0019913) described in SEQ ID NO: 43, a homolog or an ortholog of a different organism species, and the like. The hsa-miR-4763-3p gene can be obtained by a method described in Persson H et al., 2011, Cancer Res, Vol. 71, p. 78-86. Also, "hsa-mir-4763" (miRBase Accession No. MI0017404, SEQ ID NO: 313) having a hairpin-like structure is known as a precursor of "hsa-miR-4763-3p".

The term "hsa-miR-575 gene" or "hsa-miR-575" used herein includes the hsa-miR-575 gene (miRBase Accession No. MIMAT0003240) described in SEQ ID NO: 44, a homolog or an ortholog of a different organism species, and the like. The hsa-miR-575 gene can be obtained by a method described in Cummins J M et al., 2006, Proc Natl Acad Sci USA, Vol. 103, p. 3687-3692. Also, "hsa-mir-575" (miRBase Accession No. MI0003582, SEQ ID NO: 314) having a hairpin-like structure is known as a precursor of "hsa-miR-575".

The term "hsa-miR-6771-5p gene" or "hsa-miR-6771-5p" used herein includes the hsa-miR-6771-5p gene (miRBase Accession No. MIMAT0027442) described in SEQ ID NO: 45, a homolog or an ortholog of a different organism species, and the like. The hsa-miR-6771-5p gene can be obtained by a method described in Ladewig E et al., 2012, Genome Res, Vol. 22, p. 1634-1645. Also, "hsa-mir-6771" (miRBase Accession No. MI0022616, SEQ ID NO: 315) having a hairpin-like structure is known as a precursor of "hsa-miR-6771-5p".

The term "hsa-miR-1231 gene" or "hsa-miR-1231" used herein includes the hsa-miR-1231 gene (miRBase Accession No. MIMAT0005586) described in SEQ ID NO: 46, a homolog or an ortholog of a different organism species, and the like. The hsa-miR-1231 gene can be obtained by a method described in Berezikov E et al., 2007, Mol Cell, Vol. 28, p. 328-336. Also, "hsa-mir-1231" (miRBase Accession No. MI0006321, SEQ ID NO: 316) having a hairpin-like structure is known as a precursor of "hsa-miR-1231".

The term "hsa-miR-1908-3p gene" or "hsa-miR-1908-3p" used herein includes the hsa-miR-1908-3p gene (miRBase Accession No. MIMAT0026916) described in SEQ ID NO: 47, a homolog or an ortholog of a different organism species, and the like. The hsa-miR-1908-3p gene can be obtained by a method described in Bar M et al., 2008, Stem Cells, Vol. 26, p. 2496-2505. Also, "hsa-mir-1908" (miRBase Accession No. MI0008329, SEQ ID NO: 317) having a hairpin-like structure is known as a precursor of "hsa-miR-1908-3p".

The term "hsa-miR-150-3p gene" or "hsa-miR-150-3p" used herein includes the hsa-miR-150-3p gene (miRBase Accession No. MIMAT0004610) described in SEQ ID NO: 48, a homolog or an ortholog of a different organism species, and the like. The hsa-miR-150-3p gene can be obtained by a method described in Lagos-Quintana M et al., 2002, Curr Biol, Vol. 12, p. 735-739. Also, "hsa-mir-150" (miRBase Accession No. MI0000479, SEQ ID NO: 318) having a hairpin-like structure is known as a precursor of "hsa-miR-150-3p".

The term "hsa-miR-3937 gene" or "hsa-miR-3937" used herein includes the hsa-miR-3937 gene (miRBase Accession No. MIMAT0018352) described in SEQ ID NO: 49, a homolog or an ortholog of a different organism species, and the like. The hsa-miR-3937 gene can be obtained by a method described in Liao J Y et al., 2010, PLoS One, Vol. 5, e10563. Also, "hsa-mir-3937" (miRBase Accession No. MI0016593, SEQ ID NO: 319) having a hairpin-like structure is known as a precursor of "hsa-miR-3937".

The term "hsa-miR-887-3p gene" or "hsa-miR-887-3p" used herein includes the hsa-miR-887-3p gene (miRBase Accession No. MIMAT0004951) described in SEQ ID NO: 50, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 320) having a hairpin-like structure is known as a precursor of "hsa-miR-887-3p".

The term "hsa-miR-3940-5p gene" or "hsa-miR-3940-5p" used herein includes the hsa-miR-3940-5p gene (miRBase Accession No. MIMAT0019229) described in SEQ ID NO: 51, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 321) having a hairpin-like structure is known as a precursor of "hsa-miR-3940-5p".

The term "hsa-miR-4741 gene" or "hsa-miR-4741" used herein includes the hsa-miR-4741 gene (miRBase Accession No. MIMAT0019871) described in SEQ ID NO: 52, a homolog or an ortholog of a different organism species, and the like. The hsa-miR-4741 gene can be obtained by a method described in Persson H et al., 2011, Cancer Res, Vol. 71, p. 78-86. Also, "hsa-mir-4741" (miRBase Accession No. MI0017379, SEQ ID NO: 322) having a hairpin-like structure is known as a precursor of "hsa-miR-4741".

The term "hsa-miR-6808-5p gene" or "hsa-miR-6808-5p" used herein includes the hsa-miR-6808-5p gene (miRBase Accession No. MIMAT0027516) described in SEQ ID NO: 53, a homolog or an ortholog of a different organism species, and the like. The hsa-miR-6808-5p gene can be obtained by a method described in Ladewig E et al., 2012, Genome Res, Vol. 22, p. 1634-1645. Also, "hsa-mir-6808" (miRBase Accession No. MI0022653, SEQ ID NO: 323) having a hairpin-like structure is known as a precursor of "hsa-miR-6808-5p".

The term "hsa-miR-6869-5p gene" or "hsa-miR-6869-5p" used herein includes the hsa-miR-6869-5p gene (miRBase Accession No. MIMAT0027638) described in SEQ ID NO: 54, a homolog or an ortholog of a different organism species, and the like. The hsa-miR-6869-5p gene can be obtained by a method described in Ladewig E et al., 2012, Genome Res, Vol. 22, p. 1634-1645. Also, "hsa-mir-6869" (miRBase Accession No. MI0022716, SEQ ID NO: 324) having a hairpin-like structure is known as a precursor of "hsa-miR-6869-5p".

The term "hsa-miR-5090 gene" or "hsa-miR-5090" used herein includes the hsa-miR-5090 gene (miRBase Accession No. MIMAT0021082) described in SEQ ID NO: 55, a homolog or an ortholog of a different organism species, and the like. The hsa-miR-5090 gene can be obtained by a method described in Ding N et al., 2011, J Radiat Res, Vol. 52, p. 425-432. Also, "hsa-mir-5090" (miRBase Accession No. MI0017979, SEQ ID NO: 325) having a hairpin-like structure is known as a precursor of "hsa-miR-5090".

The term "hsa-miR-615-5p gene" or "hsa-miR-615-5p" used herein includes the hsa-miR-615-5p gene (miRBase Accession No. MIMAT0004804) described in SEQ ID NO: 56, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 326) having a hairpin-like structure is known as a precursor of "hsa-miR-615-5p".

The term "hsa-miR-8072 gene" or "hsa-miR-8072" used herein includes the hsa-miR-8072 gene (miRBase Accession No. MIMAT0030999) described in SEQ ID NO: 57, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 327) having a hairpin-like structure is known as a precursor of "hsa-miR-8072".

The term "hsa-miR-128-1-5p gene" or "hsa-miR-128-1-5p" used herein includes the hsa-miR-128-1-5p gene (miRBase Accession No. MIMAT0026477) described in SEQ ID NO: 58, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 328) having a hairpin-like structure is known as a precursor of "hsa-miR-128-1-5p".

The term "hsa-miR-1238-5p gene" or "hsa-miR-1238-5p" used herein includes the hsa-miR-1238-5p gene (miRBase Accession No. MIMAT0022947) described in SEQ ID NO: 59, a homolog or an ortholog of a different organism species, and the like. The hsa-miR-1238-5p gene can be obtained by a method described in Berezikov E et al., 2007, Mol Cell, Vol. 28, p. 328-336. Also, "hsa-mir-1238" (miRBase Accession No. MI0006328, SEQ ID NO: 329) having a hairpin-like structure is known as a precursor of "hsa-miR-1238-5p".

The term "hsa-miR-365a-5p gene" or "hsa-miR-365a-5p" used herein includes the hsa-miR-365a-5p gene (miRBase Accession No. MIMAT0009199) described in SEQ ID NO: 60, a homolog or an ortholog of a different organism species, and the like. The hsa-miR-365a-5p gene can be obtained by a method described in Xie X et al., 2005, Nature, Vol. 434, p. 338-345. Also, "hsa-mir-365a" (miRBase Accession No. MI0000767, SEQ ID NO: 330) having a hairpin-like structure is known as a precursor of "hsa-miR-365a-5p".

The term "hsa-miR-204-3p gene" or "hsa-miR-204-3p" used herein includes the hsa-miR-204-3p gene (miRBase Accession No. MIMAT0022693) described in SEQ ID NO: 61, a homolog or an ortholog of a different organism species, and the like. The hsa-miR-204-3p gene can be obtained by a method described in Lim L P et al., 2003, Science, Vol. 299, p. 1540. Also, "hsa-mir-204" (miRBase Accession No. MI0000284, SEQ ID NO: 331) having a hairpin-like structure is known as a precursor of "hsa-miR-204-3p".

The term "hsa-miR-4492 gene" or "hsa-miR-4492" used herein includes the hsa-miR-4492 gene (miRBase Accession No. MIMAT0019027) described in SEQ ID NO: 62, a homolog or an ortholog of a different organism species, and the like. The hsa-miR-4492 gene can be obtained by a method described in Jima D D et al., 2010, Blood, Vol. 116, e118-e127. Also, "hsa-mir-4492" (miRBase Accession No. MI0016854, SEQ ID NO: 332) having a hairpin-like structure is known as a precursor of "hsa-miR-4492".

The term "hsa-miR-6785-5p gene" or "hsa-miR-6785-5p" used herein includes the hsa-miR-6785-5p gene (miRBase Accession No. MIMAT0027470) described in SEQ ID NO: 63, a homolog or an ortholog of a different organism species, and the like. The hsa-miR-6785-5p gene can be obtained by a method described in Ladewig E et al., 2012, Genome Res, Vol. 22, p. 1634-1645. Also, "hsa-mir-6785" (miRBase Accession No. MI0022630, SEQ ID NO: 333) having a hairpin-like structure is known as a precursor of "hsa-miR-6785-5p".

The term "hsa-miR-6511a-5p gene" or "hsa-miR-6511a-5p" used herein includes the hsa-miR-6511a-5p gene (miRBase Accession No. MIMAT0025478) described in SEQ ID NO: 64, a homolog or an ortholog of a different organism species, and the like. The hsa-miR-6511a-5p gene can be obtained by a method described in Joyce C E et al., 2011, Hum Mol Genet, Vol. 20, p. 4025-4040. Also, "hsa-mir-6511a-1, hsa-mir-6511a-2, hsa-mir-6511a-3, and hsa-mir-6511a-4" (miRBase Accession Nos. MI0022223, MI0023564, MI0023565, and MI0023566, SEQ ID NOs: 334, 335, 336, and 337) having a hairpin-like structure are known as precursors of "hsa-miR-6511a-5p".

The term "hsa-miR-4525 gene" or "hsa-miR-4525" used herein includes the hsa-miR-4525 gene (miRBase Accession No. MIMAT0019064) described in SEQ ID NO: 65, a homolog or an ortholog of a different organism species, and the like. The hsa-miR-4525 gene can be obtained by a method described in Jima D D et al., 2010, Blood, Vol. 116, e118-e127. Also, "hsa-miR-4525" (miRBase Accession No. MI0016892, SEQ ID NO: 338) having a hairpin-like structure is known as a precursor of "hsa-miR-4525".

The term "hsa-miR-1915-5p gene" or "hsa-miR-1915-5p" used herein includes the hsa-miR-1915-5p gene (miRBase Accession No. MIMAT0007891) described in SEQ ID NO: 66, a homolog or an ortholog of a different organism species, and the like. The hsa-miR-1915-5p gene can be obtained by a method described in Bar M et al., 2008, Stem Cells, Vol. 26, p. 2496-2505. Also, "hsa-mir-1915" (miRBase Accession No. MI0008336, SEQ ID NO: 339) having a hairpin-like structure is known as a precursor of "hsa-miR-1915-5p".

The term "hsa-miR-3180 gene" or "hsa-miR-3180" used herein includes the hsa-miR-3180 gene (miRBase Accession No. MIMAT0018178) described in SEQ ID NO: 67, a homolog or an ortholog of a different organism species, and the like. The hsa-miR-3180 gene can be obtained by a method described in Creighton C J et al., 2010, PLoS One, Vol. 5, e9637. Also, "hsa-mir-3180-4 and hsa-mir-3180-5" (miRBase Accession Nos. MI0016408 and MI0016409, SEQ ID NOs: 340 and 341) having a hairpin-like structure are known as precursors of "hsa-miR-3180".

The term "hsa-miR-6879-5p gene" or "hsa-miR-6879-5p" used herein includes the hsa-miR-6879-5p gene (miRBase Accession No. MIMAT0027658) described in SEQ ID NO: 68, a homolog or an ortholog of a different organism species, and the like. The hsa-miR-6879-5p gene can be obtained by a method described in Ladewig E et al., 2012, Genome Res, Vol. 22, p. 1634-1645. Also, "hsa-mir-6879" (miRBase Accession No. MI0022726, SEQ ID NO: 342) having a hairpin-like structure is known as a precursor of "hsa-miR-6879-5p".

The term "hsa-miR-1199-5p gene" or "hsa-miR-1199-5p" used herein includes the hsa-miR-1199-5p gene (miRBase Accession No. MIMAT0031119) described in SEQ ID NO: 69, a homolog or an ortholog of a different organism species, and the like. The hsa-miR-1199-5p gene can be obtained by a method described in Salvi A et al., 2013, Int J Oncol, Vol. 42, p. 391-402. Also, "hsa-mir-1199" (miRBase Accession No. MI0020340, SEQ ID NO: 343) having a hairpin-like structure is known as a precursor of "hsa-miR-1199-5p".

The term "hsa-miR-6746-5p gene" or "hsa-miR-6746-5p" used herein includes the hsa-miR-6746-5p gene (miRBase Accession No. MIMAT0027392) described in SEQ ID NO:

70, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. MI0022591, SEQ ID NO: 344) having a hairpin-like structure is known as a precursor of "hsa-miR-6746-5p".

The term "hsa-miR-711 gene" or "hsa-miR-711" used herein includes the hsa-miR-711 gene (miRBase Accession No. MIMAT0012734) described in SEQ ID NO: 71, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. MI0012488, SEQ ID NO: 345) having a hairpin-like structure is known as a precursor of "hsa-miR-711".

The term "hsa-miR-663b" or "hsa-miR-663b" used herein includes the hsa-miR-663b gene (miRBase Accession No. MIMAT0005867) described in SEQ ID NO: 72, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 346) having a hairpin-like structure is known as a precursor of "hsa-miR-663b".

The term "hsa-miR-4707-3p gene" or "hsa-miR-4707-3p" used herein includes the hsa-miR-4707-3p gene (miRBase Accession No. MIMAT0019808) described in SEQ ID NO: 73, a homolog or an ortholog of a different organism species, and the like. The hsa-miR-4707-3p gene can be obtained by a method described in Persson H et al., 2011, Cancer Res, Vol. 71, p. 78-86. Also, "hsa-mir-4707" (miRBase Accession No. MI0017340, SEQ ID NO: 347) having a hairpin-like structure is known as a precursor of "hsa-miR-4707-3p".

The term "hsa-miR-6893-5p gene" or "hsa-miR-6893-5p" used herein includes the hsa-miR-6893-5p gene (miRBase Accession No. MIMAT0027686) described in SEQ ID NO: 74, a homolog or an ortholog of a different organism species, and the like. The hsa-miR-6893-5p gene can be obtained by a method described in Ladewig E et al., 2012, Genome Res, Vol. 22, p. 1634-1645. Also, "hsa-mir-6893" (miRBase Accession No. MI0022740, SEQ ID NO: 348) having a hairpin-like structure is known as a precursor of "hsa-miR-6893-5p".

The term "hsa-miR-4675 gene" or "hsa-miR-4675" used herein includes the hsa-miR-4675 gene (miRBase Accession No. MIMAT0019757) described in SEQ ID NO: 75, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 349) having a hairpin-like structure is known as a precursor of "hsa-miR-4675".

The term "hsa-miR-4638-5p gene" or "hsa-miR-4638-5p" used herein includes the hsa-miR-4638-5p gene (miRBase Accession No. MIMAT0019695) described in SEQ ID NO: 76, a homolog or an ortholog of a different organism species, and the like. The hsa-miR-4638-5p gene can be obtained by a method described in Persson H et al., 2011, Cancer Res, Vol. 71, p. 78-86. Also, "hsa-mir-4638" (miRBase Accession No. MI0017265, SEQ ID NO: 350) having a hairpin-like structure is known as a precursor of "hsa-miR-4638-5p".

The term "hsa-miR-4651 gene" or "hsa-miR-4651" used herein includes the hsa-miR-4651 gene (miRBase Accession No. MIMAT0019715) described in SEQ ID NO: 77, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 351) having a hairpin-like structure is known as a precursor of "hsa-miR-4651".

The term "hsa-miR-6087 gene" or "hsa-miR-6087" used herein includes the hsa-miR-6087 gene (miRBase Accession No. MIMAT0023712) described in SEQ ID NO: 78, a homolog or an ortholog of a different organism species, and the like. The hsa-miR-6087 gene can be obtained by a method described in Yoo J K et al., 2012, Stem Cells Dev, Vol. 21, p. 2049-2057. Also, "hsa-mir-6087" (miRBase Accession No. MI0020364, SEQ ID NO: 352) having a hairpin-like structure is known as a precursor of "hsa-miR-6087".

The term "hsa-miR-4665-5p gene" or "hsa-miR-4665-5p" used herein includes the hsa-miR-4665-5p gene (miRBase Accession No. MIMAT0019739) described in SEQ ID NO: 79, a homolog or an ortholog of a different organism species, and the like. The hsa-miR-4665-5p gene can be obtained by a method described in Persson H et al., 2011, Cancer Res, Vol. 71, p. 78-86. Also, "hsa-mir-4665" (miRBase Accession No. MI0017295, SEQ ID NO: 353) having a hairpin-like structure is known as a precursor of "hsa-miR-4665-5p".

The term "hsa-miR-4758-5p gene" or "hsa-miR-4758-5p" used herein includes the hsa-miR-4758-5p gene (miRBase Accession No. MIMAT0019903) described in SEQ ID NO: 80, a homolog or an ortholog of a different organism species, and the like. The hsa-miR-4758-5p gene can be obtained by a method described in Persson H et al., 2011, Cancer Res, Vol. 71, p. 78-86. Also, "hsa-mir-4758" (miRBase Accession No. MI0017399, SEQ ID NO: 354) having a hairpin-like structure is known as a precursor of "hsa-miR-4758-5p".

The term "hsa-miR-6887-5p gene" or "hsa-miR-6887-5p" used herein includes the hsa-miR-6887-5p gene (miRBase Accession No. MIMAT0027674) described in SEQ ID NO: 81, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 355) having a hairpin-like structure is known as a precursor of "hsa-miR-6887-5p".

The term "hsa-miR-3620-5p gene" or "hsa-miR-3620-5p" used herein includes the hsa-miR-3620-5p gene (miRBase Accession No. MIMAT0022967) described in SEQ ID NO: 82, a homolog or an ortholog of a different organism species, and the like. The hsa-miR-3620-5p gene can be obtained by a method described in Witten D et al., 2010, BMC Biol, Vol. 8, p. 58. Also, "hsa-mir-3620" (miRBase Accession No. MI0016011, SEQ ID NO: 356) having a hairpin-like structure is known as a precursor of "hsa-miR-3620-5p".

The term "hsa-miR-1909-3p gene" or "hsa-miR-1909-3p" used herein includes the hsa-miR-1909-3p gene (miRBase Accession No. MIMAT0007883) described in SEQ ID NO: 83, a homolog or an ortholog of a different organism species, and the like. The hsa-miR-1909-3p gene can be obtained by a method described in Bar M et al., 2008, Stem Cells, Vol. 26, p. 2496-2505. Also, "hsa-mir-1909" (miRBase Accession No. MI0008330, SEQ ID NO: 357) having a hairpin-like structure is known as a precursor of "hsa-miR-1909-3p".

The term "hsa-miR-7641 gene" or "hsa-miR-7641" used herein includes the hsa-miR-7641 gene (miRBase Accession No. MIMAT0029782) described in SEQ ID NO: 84, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1 and hsa-mir-7641-2" (miRBase Accession Nos. MI0024975 and MI0024976, SEQ ID NOs: 358 and 359) having a hairpin-like structure are known as precursors of "hsa-miR-7641".

The term "hsa-miR-6724-5p gene" or "hsa-miR-6724-5p" used herein includes the hsa-miR-6724-5p gene (miRBase Accession No. MIMAT0025856) described in SEQ ID NO: 85, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 360) having a hairpin-like structure is known as a precursor of "hsa-miR-6724-5p".

The term "hsa-miR-1343-3p gene" or "hsa-miR-1343-3p" used herein includes the hsa-miR-1343-3p gene (miRBase Accession No. MIMAT0019776) described in SEQ ID NO: 86, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 361) having a hairpin-like structure is known as a precursor of "hsa-miR-1343-3p".

The term "hsa-miR-6780b-5p gene" or "hsa-miR-6780b-5p" used herein includes the hsa-miR-6780b-5p gene (miRBase Accession No. MIMAT0027572) described in SEQ ID NO: 87, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. MI0022681, SEQ ID NO: 362) having a hairpin-like structure is known as a precursor of "hsa-miR-6780b-5p".

The term "hsa-miR-4484 gene" or "hsa-miR-4484" used herein includes the hsa-miR-4484 gene (miRBase Accession No. MIMAT0019018) described in SEQ ID NO: 88, a homolog or an ortholog of a different organism species, and the like. The hsa-miR-4484 gene can be obtained by a method described in Jima D D et al., 2010, Blood, Vol. 116, e118-e127. Also, "hsa-mir-4484" (miRBase Accession No. MI0016845, SEQ ID NO: 363) having a hairpin-like structure is known as a precursor of "hsa-miR-4484".

The term "hsa-miR-4690-5p gene" or "hsa-miR-4690-5p" used herein includes the hsa-miR-4690-5p gene (miRBase Accession No. MIMAT0019779) described in SEQ ID NO: 89, a homolog or an ortholog of a different organism species, and the like. The hsa-miR-4690-5p gene can be obtained by a method described in Persson H et al., 2011, Cancer Res, Vol. 71, p. 78-86. Also, "hsa-mir-4690" (miRBase Accession No. MI0017323, SEQ ID NO: 364) having a hairpin-like structure is known as a precursor of "hsa-miR-4690-5p".

The term "hsa-miR-4429 gene" or "hsa-miR-4429" used herein includes the hsa-miR-4429 gene (miRBase Accession No. MIMAT0018944) described in SEQ ID NO: 90, a homolog or an ortholog of a different organism species, and the like. The hsa-miR-4429 gene can be obtained by a method described in Jima D D et al., 2010, Blood, Vol. 116, e118-e127. Also, "hsa-mir-4429" (miRBase Accession No. MI0016768, SEQ ID NO: 365) having a hairpin-like structure is known as a precursor of "hsa-miR-4429".

The term "hsa-miR-1227-5p gene" or "hsa-miR-1227-5p" used herein includes the hsa-miR-1227-5p gene (miRBase Accession No. MIMAT0022941) described in SEQ ID NO: 91, a homolog or an ortholog of a different organism species, and the like. The hsa-miR-1227-5p gene can be obtained by a method described in Berezikov E et al., 2007, Mol Cell, Vol. 28, p. 328-336. Also, "hsa-mir-1227" (miRBase Accession No. MI0006316, SEQ ID NO: 366) having a hairpin-like structure is known as a precursor of "hsa-miR-1227-5p".

The term "hsa-miR-4725-3p gene" or "hsa-miR-4725-3p" used herein includes the hsa-miR-4725-3p gene (miRBase Accession No. MIMAT0019844) described in SEQ ID NO: 92, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 367) having a hairpin-like structure is known as a precursor of "hsa-miR-4725-3p".

The term "hsa-miR-6861-5p gene" or "hsa-miR-6861-5p" used herein includes the hsa-miR-6861-5p gene (miRBase Accession No. MIMAT0027623) described in SEQ ID NO: 93, a homolog or an ortholog of a different organism species, and the like. The hsa-miR-6861-5p gene can be obtained by a method described in Ladewig E et al., 2012, Genome Res, Vol. 22, p. 1634-1645. Also, "hsa-mir-6861" (miRBase Accession No. MI0022708, SEQ ID NO: 368) having a hairpin-like structure is known as a precursor of "hsa-miR-6861-5p".

The term "hsa-miR-6812-5p gene" or "hsa-miR-6812-5p" used herein includes the hsa-miR-6812-5p gene (miRBase Accession No. MIMAT0027524) described in SEQ ID NO: 94, a homolog or an ortholog of a different organism species, and the like. The hsa-miR-6812-5p gene can be obtained by a method described in Ladewig E et al., 2012, Genome Res, Vol. 22, p. 1634-1645. Also, "hsa-mir-6812" (miRBase Accession No. MI0022657, SEQ ID NO: 369) having a hairpin-like structure is known as a precursor of "hsa-miR-6812-5p".

The term "hsa-miR-3197 gene" or "hsa-miR-3197" used herein includes the hsa-miR-3197 gene (miRBase Accession No. MIMAT0015082) described in SEQ ID NO: 95, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No. MI0014245, SEQ ID NO: 370) having a hairpin-like structure is known as a precursor of "hsa-miR-3197".

The term "hsa-miR-8059 gene" or "hsa-miR-8059" used herein includes the hsa-miR-8059 gene (miRBase Accession No. MIMAT0030986) described in SEQ ID NO: 96, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 371) having a hairpin-like structure is known as a precursor of "hsa-miR-8059".

The term "hsa-miR-3185 gene" or "hsa-miR-3185" used herein includes the hsa-miR-3185 gene (miRBase Accession No. MIMAT0015065) described in SEQ ID NO: 97, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 372) having a hairpin-like structure is known as a precursor of "hsa-miR-3185".

The term "hsa-miR-4706 gene" or "hsa-miR-4706" used herein includes the hsa-miR-4706 gene (miRBase Accession No. MIMAT0019806) described in SEQ ID NO: 98, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miRBase Accession No.

MI0017339, SEQ ID NO: 373) having a hairpin-like structure is known as a precursor of "hsa-miR-4706".

The term "hsa-miR-4497 gene" or "hsa-miR-4497" used herein includes the hsa-miR-4497 gene (miRBase Accession No. MIMAT0019032) described in SEQ ID NO: 99, a homolog or an ortholog of a different organism species, and the like. The hsa-miR-4497 gene can be obtained by a method described in Jima D D et al., 2010, Blood, Vol. 116, e118-e127. Also, "hsa-mir-4497" (miRBase Accession No. MI0016859, SEQ ID NO: 374) having a hairpin-like structure is known as a precursor of "hsa-miR-4497".

The term "hsa-miR-3131 gene" or "hsa-miR-3131" used herein includes the hsa-miR-3131 gene (miRBase Accession No. MIMAT0014996) described in SEQ ID NO: 100, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 375) having a hairpin-like structure is known as a precursor of "hsa-miR-3131".

The term "hsa-miR-6806-5p gene" or "hsa-miR-6806-5p" used herein includes the hsa-miR-6806-5p gene (miRBase Accession No. MIMAT0027512) described in SEQ ID NO: 101, a homolog or an ortholog of a different organism species, and the like. The hsa-miR-6806-5p gene can be obtained by a method described in Ladewig E et al., 2012, Genome Res, Vol. 22, p. 1634-1645. Also, "hsa-mir-6806" (miRBase Accession No. MI0022651, SEQ ID NO: 376) having a hairpin-like structure is known as a precursor of "hsa-miR-6806-5p".

The term "hsa-miR-187-5p gene" or "hsa-miR-187-5p" used herein includes the hsa-miR-187-5p gene (miRBase Accession No. MIMAT0004561) described in SEQ ID NO: 102, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 377) having a hairpin-like structure is known as a precursor of "hsa-miR-187-5p".

The term "hsa-miR-3180-3p gene" or "hsa-miR-3180-3p" used herein includes the hsa-miR-3180-3p gene (miRBase Accession No. MIMAT0015058) described in SEQ ID NO: 103, a homolog or an ortholog of a different organism species, and the like. The hsa-miR-3180-3p gene can be obtained by a method described in Creighton C J et al., 2010, PLoS One, Vol. 5, e9637. Also, "hsa-mir-3180-1, hsa-mir-3180-2, and hsa-mir-3180-3" (miRBase Accession Nos. MI0014214, MI0014215, and MI0014217, SEQ ID NOs: 378, 379, and 380) having a hairpin-like structure are known as precursors of "hsa-miR-3180-3p".

The term "hsa-miR-6848-5p gene" or "hsa-miR-6848-5p" used herein includes the hsa-miR-6848-5p gene (miRBase Accession No. MIMAT0027596) described in SEQ ID NO: 104, a homolog or an ortholog of a different organism species, and the like. The hsa-miR-6848-5p gene can be obtained by a method described in Ladewig E et al., 2012, Genome Res, Vol. 22, p. 1634-1645. Also, "hsa-mir-6848" (miRBase Accession No. MI0022694, SEQ ID NO: 381) having a hairpin-like structure is known as a precursor of "hsa-miR-6848-5p".

The term "hsa-miR-6820-5p gene" or "hsa-miR-6820-5p" used herein includes the hsa-miR-6820-5p gene (miRBase Accession No. MIMAT0027540) described in SEQ ID NO: 105, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 382) having a hairpin-like structure is known as a precursor of "hsa-miR-6820-5p".

The term "hsa-miR-6800-5p gene" or "hsa-miR-6800-5p" used herein includes the hsa-miR-6800-5p gene (miRBase Accession No. MIMAT0027500) described in SEQ ID NO: 106, a homolog or an ortholog of a different organism species, and the like. The hsa-miR-6800-5p gene can be obtained by a method described in Ladewig E et al., 2012, Genome Res, Vol. 22, p. 1634-1645. Also, "hsa-mir-6800" (miRBase Accession No. MI0022645, SEQ ID NO: 383) having a hairpin-like structure is known as a precursor of "hsa-miR-6800-5p".

The term "hsa-miR-6717-5p gene" or "hsa-miR-6717-5p" used herein includes the hsa-miR-6717-5p gene (miRBase Accession No. MIMAT0025846) described in SEQ ID NO: 107, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 384) having a hairpin-like structure is known as a precursor of "hsa-miR-6717-5p".

The term "hsa-miR-6795-5p gene" or "hsa-miR-6795-5p" used herein includes the hsa-miR-6795-5p gene (miRBase Accession No. MIMAT0027490) described in SEQ ID NO: 108, a homolog or an ortholog of a different organism species, and the like. The hsa-miR-6795-5p gene can be obtained by a method described in Ladewig E et al., 2012, Genome Res, Vol. 22, p. 1634-1645. Also, "hsa-mir-6795" (miRBase Accession No. MI0022640, SEQ ID NO: 385) having a hairpin-like structure is known as a precursor of "hsa-miR-6795-5p".

The term "hsa-miR-4632-5p gene" or "hsa-miR-4632-5p" used herein includes the hsa-miR-4632-5p gene (miRBase Accession No. MIMAT0022977) described in SEQ ID NO: 109, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miRBase Accession No. MI0017259, SEQ ID NO: 386) having a hairpin-like structure is known as a precursor of "hsa-miR-4632-5p".

The term "hsa-miR-665 gene" or "hsa-miR-665" used herein includes the hsa-miR-665 gene (miRBase Accession No. MIMAT0004952) described in SEQ ID NO: 110, a homolog or an ortholog of a different organism species, and the like. The hsa-miR-665 gene can be obtained by a method described in Berezikov E et al., 2006, Genome Res, Vol. 16, p. 1289-1298. Also, "hsa-mir-665" (miRBase Accession No. MI0005563, SEQ ID NO: 387) having a hairpin-like structure is known as a precursor of "hsa-miR-665".

The term "hsa-miR-6778-5p gene" or "hsa-miR-6778-5p" used herein includes the hsa-miR-6778-5p gene (miRBase Accession No. MIMAT0027456) described in SEQ ID NO: 111, a homolog or an ortholog of a different organism species, and the like. The hsa-miR-6778-5p gene can be obtained by a method described in Ladewig E et al., 2012, Genome Res, Vol. 22, p. 1634-1645. Also, "hsa-mir-6778" (miRBase Accession No. MI0022623, SEQ ID NO: 388) having a hairpin-like structure is known as a precursor of "hsa-miR-6778-5p".

The term "hsa-miR-3663-3p gene" or "hsa-miR-3663-3p" used herein includes the hsa-miR-3663-3p gene (miRBase Accession No. MIMAT0018085) described in SEQ ID NO: 112, a homolog or an ortholog of a different organism species, and the like. The hsa-miR-3663-3p gene can be obtained by a method described in Liao J Y et al., 2010, PLoS One, Vol. 5, e10563. Also, "hsa-mir-3663" (miRBase Accession No. MI0016064, SEQ ID NO: 389) having a hairpin-like structure is known as a precursor of "hsa-miR-3663-3p".

The term "hsa-miR-4689 gene" or "hsa-miR-4689" used herein includes the hsa-miR-4689 gene (miRBase Accession No. MIMAT0019778) described in SEQ ID NO: 113, a homolog or an ortholog of a different organism species, and the like. The hsa-miR-4689 gene can be obtained by a method described in Persson H et al., 2011, Cancer Res, Vol. 71, p. 78-86. Also, "hsa-mir-4689" (miRBase Accession No. MI0017322, SEQ ID NO: 390) having a hairpin-like structure is known as a precursor of "hsa-miR-4689".

The term "hsa-miR-211-3p gene" or "hsa-miR-211-3p" used herein includes the hsa-miR-211-3p gene (miRBase Accession No. MIMAT0022694) described in SEQ ID NO: 114, a homolog or an ortholog of a different organism species, and the like. The hsa-miR-211-3p gene can be obtained by a method described in Lim L P et al., 2003, Science, Vol. 299, p. 1540. Also, "hsa-mir-211" (miRBase Accession No. MI0000287, SEQ ID NO: 391) having a hairpin-like structure is known as a precursor of "hsa-miR-211-3p".

The term "hsa-miR-6511b-5p gene" or "hsa-miR-6511b-5p" used herein includes the hsa-miR-6511b-5p gene (miRBase Accession No. MIMAT0025847) described in SEQ ID NO: 115, a homolog or an ortholog of a different organism species, and the like. The hsa-miR-6511b-5p gene can be obtained by a method described in Li Y et al., 2012, Gene, Vol. 497, p. 330-335. Also, "hsa-mir-6511b-1 and hsa-mir-6511b-2" (miRBase Accession Nos. MI0022552 and MI0023431, SEQ ID NOs: 392 and 393) having a hairpin-like structure are known as precursors of "hsa-miR-6511b-5p".

The term "hsa-miR-4750-5p gene" or "hsa-miR-4750-5p" used herein includes the hsa-miR-4750-5p gene (miRBase Accession No. MIMAT0019887) described in SEQ ID NO: 116, a homolog or an ortholog of a different organism species, and the like. The hsa-miR-4750-5p gene can be obtained by a method described in Persson H et al., 2011, Cancer Res, Vol. 71, p. 78-86. Also, "hsa-mir-4750" (miRBase Accession No. MI0017389, SEQ ID NO: 394) having a hairpin-like structure is known as a precursor of "hsa-miR-4750-5p".

The term "hsa-miR-6126 gene" or "hsa-miR-6126" used herein includes the hsa-miR-6126 gene (miRBase Accession No. MIMAT0024599) described in SEQ ID NO: 117, a homolog or an ortholog of a different organism species, and the like. The hsa-miR-6126 gene can be obtained by a method described in Smith J L et al., 2012, J Virol, Vol. 86, p. 5278-5287. Also, "hsa-mir-6126" (miRBase Accession No. MI0021260, SEQ ID NO: 395) having a hairpin-like structure is known as a precursor of "hsa-miR-6126".

The term "hsa-miR-614 gene" or "hsa-miR-614" used herein includes the hsa-miR-614 gene (miRBase Accession No. MIMAT0003282) described in SEQ ID NO: 118, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 396) having a hairpin-like structure is known as a precursor of "hsa-miR-614".

The term "hsa-miR-7110-5p gene" or "hsa-miR-7110-5p" used herein includes the hsa-miR-7110-5p gene (miRBase Accession No. MIMAT0028117) described in SEQ ID NO: 119, a homolog or an ortholog of a different organism species, and the like. The hsa-miR-7110-5p gene can be obtained by a method described in Ladewig E et al., 2012, Genome Res, Vol. 22, p. 1634-1645. Also, "hsa-mir-7110" (miRBase Accession No. MI0022961, SEQ ID NO: 397) having a hairpin-like structure is known as a precursor of "hsa-miR-7110-5p".

The term "hsa-miR-744-5p gene" or "hsa-miR-744-5p" used herein includes the hsa-miR-744-5p gene (miRBase Accession No. MIMAT0004945) described in SEQ ID NO: 120, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 398) having a hairpin-like structure is known as a precursor of "hsa-miR-744-5p".

The term "hsa-miR-6769a-5p gene" or "hsa-miR-6769a-5p" used herein includes the hsa-miR-6769a-5p gene (miRBase Accession No. MIMAT0027438) described in SEQ ID NO: 121, a homolog or an ortholog of a different organism species, and the like. The hsa-miR-6769a-5p gene can be obtained by a method described in Ladewig E et al., 2012, Genome Res, Vol. 22, p. 1634-1645. Also, "hsa-mir-6769a" (miRBase Accession No. MI0022614, SEQ ID NO: 399) having a hairpin-like structure is known as a precursor of "hsa-miR-6769a-5p".

The term "hsa-miR-4792 gene" or "hsa-miR-4792" used herein includes the hsa-miR-4792 gene (miRBase Accession No. MIMAT0019964) described in SEQ ID NO: 122, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 400) having a hairpin-like structure is known as a precursor of "hsa-miR-4792".

The term "hsa-miR-5787 gene" or "hsa-miR-5787" used herein includes the hsa-miR-5787 gene (miRBase Accession No. MIMAT0023252) described in SEQ ID NO: 123, a homolog or an ortholog of a different organism species, and the like. The hsa-miR-5787 gene can be obtained by a method described in Yoo H et al., 2011, Biochem Biophys Res Commun, Vol. 415, p. 567-572. Also, "hsa-mir-5787" (miRBase Accession No. MI0019797, SEQ ID NO: 401) having a hairpin-like structure is known as a precursor of "hsa-miR-5787".

The term "hsa-miR-6798-5p gene" or "hsa-miR-6798-5p" used herein includes the hsa-miR-6798-5p gene (miRBase Accession No. MIMAT0027496) described in SEQ ID NO: 124, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 402) having a hairpin-like structure is known as a precursor of "hsa-miR-6798-5p".

The term "hsa-miR-6781-5p gene" or "hsa-miR-6781-5p" used herein includes the hsa-miR-6781-5p gene (miRBase Accession No. MIMAT0027462) described in SEQ ID NO: 125, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. MI0022626, SEQ ID NO: 403) having a hairpin-like structure is known as a precursor of "hsa-miR-6781-5p".

The term "hsa-miR-4419b gene" or "hsa-miR-4419b" used herein includes the hsa-miR-4419b gene (miRBase Accession No. MIMAT0019034) described in SEQ ID NO: 126, a homolog or an ortholog of a different organism species, and the like. The hsa-miR-4419b gene can be obtained by a method described in Jima D D et al., 2010, Blood, Vol. 116, e118-e127. Also, "hsa-mir-4419b" (miRBase Accession No. MI0016861, SEQ ID NO: 404) having a hairpin-like structure is known as a precursor of "hsa-miR-4419b".

The term "hsa-miR-4446-3p gene" or "hsa-miR-4446-3p" used herein includes the hsa-miR-4446-3p gene (miRBase Accession No. MIMAT0018965) described in SEQ ID NO: 127, a homolog or an ortholog of a different organism species, and the like. The hsa-miR-4446-3p gene can be obtained by a method described in Jima D D et al., 2010, Blood, Vol. 116, e118-e127. Also, "hsa-mir-4446" (miRBase Accession No. MI0016789, SEQ ID NO: 405) having a hairpin-like structure is known as a precursor of "hsa-miR-4446-3p".

The term "hsa-miR-4259 gene" or "hsa-miR-4259" used herein includes the hsa-miR-4259 gene (miRBase Accession No. MIMAT0016880) described in SEQ ID NO: 128, a homolog or an ortholog of a different organism species, and the like. The hsa-miR-4259 gene can be obtained by a method described in Goff L A et al., 2009, PLoS One, Vol. 4, e7192. Also, "hsa-mir-4259" (miRBase Accession No. MI0015858, SEQ ID NO: 406) having a hairpin-like structure is known as a precursor of "hsa-miR-4259".

The term "hsa-miR-5572 gene" or "hsa-miR-5572" used herein includes the hsa-miR-5572 gene (miRBase Accession No. MIMAT0022260) described in SEQ ID NO: 129, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 407) having a hairpin-like structure is known as a precursor of "hsa-miR-5572".

The term "hsa-miR-6075 gene" or "hsa-miR-6075" used herein includes the hsa-miR-6075 gene (miRBase Accession No. MIMAT0023700) described in SEQ ID NO: 130, a homolog or an ortholog of a different organism species, and the like. The hsa-miR-6075 gene can be obtained by a method described in Voellenkle C et al., 2012, RNA, Vol. 18, p. 472-484. Also, "hsa-mir-6075" (miRBase Accession No. MI0020352, SEQ ID NO: 408) having a hairpin-like structure is known as a precursor of "hsa-miR-6075".

The term "hsa-miR-296-3p gene" or "hsa-miR-296-3p" used herein includes the hsa-miR-296-3p gene (miRBase Accession No. MIMAT0004679) described in SEQ ID NO: 131, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 409) having a hairpin-like structure is known as a precursor of "hsa-miR-296-3p".

The term "hsa-miR-6891-5p gene" or "hsa-miR-6891-5p" used herein includes the hsa-miR-6891-5p gene (miRBase Accession No. MIMAT0027682) described in SEQ ID NO: 132, a homolog or an ortholog of a different organism species, and the like. The hsa-miR-6891-5p gene can be obtained by a method described in Ladewig E et al., 2012, Genome Res, Vol. 22, p. 1634-1645. Also, "hsa-mir-6891" (miRBase Accession No. MI0022738, SEQ ID NO: 410) having a hairpin-like structure is known as a precursor of "hsa-miR-6891-5p".

The term "hsa-miR-4745-5p gene" or "hsa-miR-4745-5p" used herein includes the hsa-miR-4745-5p gene (miRBase Accession No. MIMAT0019878) described in SEQ ID NO: 133, a homolog or an ortholog of a different organism species, and the like. The hsa-miR-4745-5p gene can be obtained by a method described in Persson H et al., 2011, Cancer Res, Vol. 71, p. 78-86. Also, "hsa-mir-4745" (miRBase Accession No. MI0017384, SEQ ID NO: 411) having a hairpin-like structure is known as a precursor of "hsa-miR-4745-5p".

The term "hsa-miR-6775-5p gene" or "hsa-miR-6775-5p" used herein includes the hsa-miR-6775-5p gene (miRBase Accession No. MIMAT0027450) described in SEQ ID NO: 134, a homolog or an ortholog of a different organism species, and the like. The hsa-miR-6775-5p gene can be obtained by a method described in Ladewig E et al., 2012, Genome Res, Vol. 22, p. 1634-1645. Also, "hsa-mir-6775" (miRBase Accession No. MI0022620, SEQ ID NO: 412) having a hairpin-like structure is known as a precursor of "hsa-miR-6775-5p".

The term "hsa-miR-6870-5p gene" or "hsa-miR-6870-5p" used herein includes the hsa-miR-6870-5p gene (miRBase Accession No. MIMAT0027640) described in SEQ ID NO: 135, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 413) having a hairpin-like structure is known as a precursor of "hsa-miR-6870-5p".

The term "hsa-miR-920 gene" or "hsa-miR-920" used herein includes the hsa-miR-920 gene (miRBase Accession No. MIMAT0004970) described in SEQ ID NO: 136, a homolog or an ortholog of a different organism species, and the like. The hsa-miR-920 gene can be obtained by a method described in Novotny G W et al., 2007, Int J Androl, Vol. 30, p. 316-326. Also, "hsa-mir-920" (miRBase Accession No. MI0005712, SEQ ID NO: 414) having a hairpin-like structure is known as a precursor of "hsa-miR-920".

The term "hsa-miR-4530 gene" or "hsa-miR-4530" used herein includes the hsa-miR-4530 gene (miRBase Accession No. MIMAT0019069) described in SEQ ID NO: 137, a homolog or an ortholog of a different organism species, and the like. The hsa-miR-4530 gene can be obtained by a method described in Jima D D et al., 2010, Blood, Vol. 116, e118-e127. Also, "hsa-mir-4530" (miRBase Accession No. MI0016897, SEQ ID NO: 415) having a hairpin-like structure is known as a precursor of "hsa-miR-4530".

The term "hsa-miR-6819-5p gene" or "hsa-miR-6819-5p" used herein includes the hsa-miR-6819-5p gene (miRBase Accession No. MIMAT0027538) described in SEQ ID NO: 138, a homolog or an ortholog of a different organism species, and the like. The hsa-miR-6819-5p gene can be obtained by a method described in Ladewig E et al., 2012, Genome Res, Vol. 22, p. 1634-1645. Also, "hsa-mir-6819" (miRBase Accession No. MI0022664, SEQ ID NO: 416) having a hairpin-like structure is known as a precursor of "hsa-miR-6819-5p".

The term "hsa-miR-6825-5p gene" or "hsa-miR-6825-5p" used herein includes the hsa-miR-6825-5p gene (miRBase Accession No. MIMAT0027550) described in SEQ ID NO: 139, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825"

(miRBase Accession No. MI0022670, SEQ ID NO: 417) having a hairpin-like structure is known as a precursor of "hsa-miR-6825-5p".

The term "hsa-miR-7847-3p gene" or "hsa-miR-7847-3p" used herein includes the hsa-miR-7847-3p gene (miRBase Accession No. MIMAT0030422) described in SEQ ID NO: 140, a homolog or an ortholog of a different organism species, and the like. The hsa-miR-7847-3p gene can be obtained by a method described in Plc H et al., 2012, PLoS One, Vol. 7, e50746. Also, "hsa-mir-7847" (miRBase Accession No. MI0025517, SEQ ID NO: 418) having a hairpin-like structure is known as a precursor of "hsa-miR-7847-3p".

The term "hsa-miR-6131 gene" or "hsa-miR-6131" used herein includes the hsa-miR-6131 gene (miRBase Accession No. MIMAT0024615) described in SEQ ID NO: 141, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. MI0021276, SEQ ID NO: 419) having a hairpin-like structure is known as a precursor of "hsa-miR-6131".

The term "hsa-miR-4433-3p gene" or "hsa-miR-4433-3p" used herein includes the hsa-miR-4433-3p gene (miRBase Accession No. MIMAT0018949) described in SEQ ID NO: 142, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. MI0016773, SEQ ID NO: 420) having a hairpin-like structure is known as a precursor of "hsa-miR-4433-3p".

The term "hsa-miR-1228-5p gene" or "hsa-miR-1228-5p" used herein includes the hsa-miR-1228-5p gene (miRBase Accession No. MIMAT0005582) described in SEQ ID NO: 143, a homolog or an ortholog of a different organism species, and the like. The hsa-miR-1228-5p gene can be obtained by a method described in Berezikov E et al., 2007, Mol Cell, Vol. 28, p. 328-336. Also, "hsa-mir-1228" (miRBase Accession No. MI0006318, SEQ ID NO: 421) having a hairpin-like structure is known as a precursor of "hsa-miR-1228-5p".

The term "hsa-miR-6743-5p gene" or "hsa-miR-6743-5p" used herein includes the hsa-miR-6743-5p gene (miRBase Accession No. MIMAT0027387) described in SEQ ID NO: 144, a homolog or an ortholog of a different organism species, and the like. The hsa-miR-6743-5p gene can be obtained by a method described in Ladewig E et al., 2012, Genome Res, Vol. 22, p. 1634-1645. Also, "hsa-mir-6743" (miRBase Accession No. MI0022588, SEQ ID NO: 422) having a hairpin-like structure is known as a precursor of "hsa-miR-6743-5p".

The term "hsa-miR-1268a gene" or "hsa-miR-1268a" used herein includes the hsa-miR-1268a gene (miRBase Accession No. MIMAT0005922) described in SEQ ID NO: 145, a homolog or an ortholog of a different organism species, and the like. The hsa-miR-1268a gene can be obtained by a method described in Morin R D et al., 2008, Genome Res, Vol. 18, p. 610-621. Also, "hsa-mir-1268a" (miRBase Accession No. MI0006405, SEQ ID NO: 423) having a hairpin-like structure is known as a precursor of "hsa-miR-1268a".

The term "hsa-miR-3917 gene" or "hsa-miR-3917" used herein includes the hsa-miR-3917 gene (miRBase Accession No. MIMAT0018191) described in SEQ ID NO: 146, a homolog or an ortholog of a different organism species, and the like. The hsa-miR-3917 gene can be obtained by a method described in Creighton C J et al., 2010, PLoS One, Vol. 5, e9637. Also, "hsa-mir-3917" (miRBase Accession No. MI0016423, SEQ ID NO: 424) having a hairpin-like structure is known as a precursor of "hsa-miR-3917".

The term "hsa-miR-6786-5p gene" or "hsa-miR-6786-5p" used herein includes the hsa-miR-6786-5p gene (miRBase Accession No. MIMAT0027472) described in SEQ ID NO: 147, a homolog or an ortholog of a different organism species, and the like. The hsa-miR-6786-5p gene can be obtained by a method described in Ladewig E et al., 2012, Genome Res, Vol. 22, p. 1634-1645. Also, "hsa-mir-6786" (miRBase Accession No. MI0022631, SEQ ID NO: 425) having a hairpin-like structure is known as a precursor of "hsa-miR-6786-5p".

The term "hsa-miR-3154 gene" or "hsa-miR-3154" used herein includes the hsa-miR-3154 gene (miRBase Accession No. MIMAT0015028) described in SEQ ID NO: 148, a homolog or an ortholog of a different organism species, and the like. The hsa-miR-3154 gene can be obtained by a method described in Berezikov E et al., 2006, Genome Res, Vol. 16, p. 1289-1298. Also, "hsa-mir-3154" (miRBase Accession No. MI0014182, SEQ ID NO: 426) having a hairpin-like structure is known as a precursor of "hsa-miR-3154".

The term "hsa-miR-638 gene" or "hsa-miR-638" used herein includes the hsa-miR-638 gene (miRBase Accession No. MIMAT0003308) described in SEQ ID NO: 149, a homolog or an ortholog of a different organism species, and the like. The hsa-miR-638 gene can be obtained by a method described in Cummins J M et al., 2006, Proc Natl Acad Sci USA, Vol. 103, p. 3687-3692. Also, "hsa-mir-638" (miRBase Accession No. MI0003653, SEQ ID NO: 427) having a hairpin-like structure is known as a precursor of "hsa-miR-638".

The term "hsa-miR-6741-5p gene" or "hsa-miR-6741-5p" used herein includes the hsa-miR-6741-5p gene (miRBase Accession No. MIMAT0027383) described in SEQ ID NO: 150, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 428) having a hairpin-like structure is known as a precursor of "hsa-miR-6741-5p".

The term "hsa-miR-6889-5p gene" or "hsa-miR-6889-5p" used herein includes the hsa-miR-6889-5p gene (miRBase Accession No. MIMAT0027678) described in SEQ ID NO: 151, a homolog or an ortholog of a different organism species, and the like. The hsa-miR-6889-5p gene can be obtained by a method described in Ladewig E et al., 2012, Genome Res, Vol. 22, p. 1634-1645. Also, "hsa-mir-6889" (miRBase Accession No. MI0022736, SEQ ID NO: 429) having a hairpin-like structure is known as a precursor of "hsa-miR-6889-5p".

The term "hsa-miR-6840-3p gene" or "hsa-miR-6840-3p" used herein includes the hsa-miR-6840-3p gene (miRBase Accession No. MIMAT0027583) described in SEQ ID NO: 152, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 430) having a hairpin-like structure is known as a precursor of "hsa-miR-6840-3p".

The term "hsa-miR-6510-5p gene" or "hsa-miR-6510-5p" used herein includes the hsa-miR-6510-5p gene (miRBase Accession No. MIMAT0025476) described in SEQ ID NO: 153, a homolog or an ortholog of a different organism species, and the like. The hsa-miR-6510-5p gene can be obtained by a method described in Joyce C E et al., 2011, Hum Mol Genet, Vol. 20, p. 4025-4040. Also, "hsa-mir-6510" (miRBase Accession No. MI0022222, SEQ ID NO: 431) having a hairpin-like structure is known as a precursor of "hsa-miR-6510-5p".

The term "hsa-miR-3188 gene" or "hsa-miR-3188" used herein includes the hsa-miR-3188 gene (miRBase Accession No. MIMAT0015070) described in SEQ ID NO: 154, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 432) having a hairpin-like structure is known as a precursor of "hsa-miR-3188".

The term "hsa-miR-551b-5p gene" or "hsa-miR-551b-5p" used herein includes the hsa-miR-551b-5p gene (miRBase Accession No. MIMAT0004794) described in SEQ ID NO: 155, a homolog or an ortholog of a different organism species, and the like. The hsa-miR-551b-5p gene can be obtained by a method described in Cummins J M et al., 2006, Proc Natl Acad Sci USA, Vol. 103, p. 3687-3692. Also, "hsa-mir-551b" (miRBase Accession No. MI0003575, SEQ ID NO: 433) having a hairpin-like structure is known as a precursor of "hsa-miR-551b-5p".

The term "hsa-miR-5001-5p gene" or "hsa-miR-5001-5p" used herein includes the hsa-miR-5001-5p gene (miRBase Accession No. MIMAT0021021) described in SEQ ID NO: 156, a homolog or an ortholog of a different organism species, and the like. The hsa-miR-5001-5p gene can be obtained by a method described in Hansen T B et al., 2011, RNA Biol, Vol. 8, p. 378-383. Also, "hsa-mir-5001" (miRBase Accession No. MI0017867, SEQ ID NO: 434) having a hairpin-like structure is known as a precursor of "hsa-miR-5001-5p".

The term "hsa-miR-1268b gene" or "hsa-miR-1268b" used herein includes the hsa-miR-1268b gene (miRBase Accession No. MIMAT0018925) described in SEQ ID NO: 157, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 435) having a hairpin-like structure is known as a precursor of "hsa-miR-1268b".

The term "hsa-miR-7107-5p gene" or "hsa-miR-7107-5p" used herein includes the hsa-miR-7107-5p gene (miRBase Accession No. MIMAT0028111) described in SEQ ID NO: 158, a homolog or an ortholog of a different organism species, and the like. The hsa-miR-7107-5p gene can be obtained by a method described in Ladewig E et al., 2012, Genome Res, Vol. 22, p. 1634-1645. Also, "hsa-mir-7107" (miRBase Accession No. MI0022958, SEQ ID NO: 436) having a hairpin-like structure is known as a precursor of "hsa-miR-7107-5p".

The term "hsa-miR-6824-5p gene" or "hsa-miR-6824-5p" used herein includes the hsa-miR-6824-5p gene (miRBase Accession No. MIMAT0027548) described in SEQ ID NO: 159, a homolog or an ortholog of a different organism species, and the like. The hsa-miR-6824-5p gene can be obtained by a method described in Ladewig E et al., 2012, Genome Res, Vol. 22, p. 1634-1645. Also, "hsa-mir-6824" (miRBase Accession No. MI0022669, SEQ ID NO: 437) having a hairpin-like structure is known as a precursor of "hsa-miR-6824-5p".

The term "hsa-miR-6732-5p gene" or "hsa-miR-6732-5p" used herein includes the hsa-miR-6732-5p gene (miRBase Accession No. MIMAT0027365) described in SEQ ID NO: 160, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. MI0022577, SEQ ID NO: 438) having a hairpin-like structure is known as a precursor of "hsa-miR-6732-5p".

The term "hsa-miR-371a-5p gene" or "hsa-miR-371a-5p" used herein includes the hsa-miR-371a-5p gene (miRBase Accession No. MIMAT0004687) described in SEQ ID NO: 161, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 439) having a hairpin-like structure is known as a precursor of "hsa-miR-371a-5p".

The term "hsa-miR-6794-5p gene" or "hsa-miR-6794-5p" used herein includes the hsa-miR-6794-5p gene (miRBase Accession No. MIMAT0027488) described in SEQ ID NO: 162, a homolog or an ortholog of a different organism species, and the like. The hsa-miR-6794-5p gene can be obtained by a method described in Ladewig E et al., 2012, Genome Res, Vol. 22, p. 1634-1645. Also, "hsa-mir-6794" (miRBase Accession No. MI0022639, SEQ ID NO: 440) having a hairpin-like structure is known as a precursor of "hsa-miR-6794-5p".

The term "hsa-miR-6779-5p gene" or "hsa-miR-6779-5p" used herein includes the hsa-miR-6779-5p gene (miRBase Accession No. MIMAT0027458) described in SEQ ID NO: 163, a homolog or an ortholog of a different organism species, and the like. The hsa-miR-6779-5p gene can be obtained by a method described in Ladewig E et al., 2012, Genome Res, Vol. 22, p. 1634-1645. Also, "hsa-mir-6779" (miRBase Accession No. MI0022624, SEQ ID NO: 441) having a hairpin-like structure is known as a precursor of "hsa-miR-6779-5p".

The term "hsa-miR-4271 gene" or "hsa-miR-4271" used herein includes the hsa-miR-4271 gene (miRBase Accession No. MIMAT0016901) described in SEQ ID NO: 164, a homolog or an ortholog of a different organism species, and the like. The hsa-miR-4271 gene can be obtained by a method described in Goff L A et al., 2009, PLoS One, Vol. 4, e7192. Also, "hsa-mir-4271" (miRBase Accession No. MI0015879, SEQ ID NO: 442) having a hairpin-like structure is known as a precursor of "hsa-miR-4271".

The term "hsa-miR-5195-3p gene" or "hsa-miR-5195-3p" used herein includes the hsa-miR-5195-3p gene (miRBase Accession No. MIMAT0021127) described in SEQ ID NO: 165, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 443) having a hairpin-like structure is known as a precursor of "hsa-miR-5195-3p".

The term "hsa-miR-6762-5p gene" or "hsa-miR-6762-5p" used herein includes the hsa-miR-6762-5p gene (miRBase Accession No. MIMAT0027424) described in SEQ ID NO: 166, a homolog or an ortholog of a different organism species, and the like. The hsa-miR-6762-5p gene can be obtained by a method described in Ladewig E et al., 2012, Genome Res, Vol. 22, p. 1634-1645. Also, "hsa-mir-6762"

(miRBase Accession No. MI0022607, SEQ ID NO: 444) having a hairpin-like structure is known as a precursor of "hsa-miR-6762-5p".

The term "hsa-miR-939-5p gene" or "hsa-miR-939-5p" used herein includes the hsa-miR-939-5p gene (miRBase Accession No. MIMAT0004982) described in SEQ ID NO: 167, a homolog or an ortholog of a different organism species, and the like. The hsa-miR-939-5p gene can be obtained by a method described in Lui W O et al., 2007, Cancer Res, Vol. 67, p. 6031-6043. Also, "hsa-mir-939" (miRBase Accession No. MI0005761, SEQ ID NO: 445) having a hairpin-like structure is known as a precursor of "hsa-miR-939-5p".

The term "hsa-miR-1247-3p gene" or "hsa-miR-1247-3p" used herein includes the hsa-miR-1247-3p gene (miRBase Accession No. MIMAT0022721) described in SEQ ID NO: 168, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 446) having a hairpin-like structure is known as a precursor of "hsa-miR-1247-3p".

The term "hsa-miR-6777-5p gene" or "hsa-miR-6777-5p" used herein includes the hsa-miR-6777-5p gene (miRBase Accession No. MIMAT0027454) described in SEQ ID NO: 169, a homolog or an ortholog of a different organism species, and the like. The hsa-miR-6777-5p gene can be obtained by a method described in Ladewig E et al., 2012, Genome Res, Vol. 22, p. 1634-1645. Also, "hsa-mir-6777" (miRBase Accession No. MI0022622, SEQ ID NO: 447) having a hairpin-like structure is known as a precursor of "hsa-miR-6777-5p".

The term "hsa-miR-6722-3p gene" or "hsa-miR-6722-3p" used herein includes the hsa-miR-6722-3p gene (miRBase Accession No. MIMAT0025854) described in SEQ ID NO: 170, a homolog or an ortholog of a different organism species, and the like. The hsa-miR-6722-3p gene can be obtained by a method described in Li Y et al., 2012, Gene, Vol. 497, p. 330-335. Also, "hsa-mir-6722" (miRBase Accession No. MI0022557, SEQ ID NO: 448) having a hairpin-like structure is known as a precursor of "hsa-miR-6722-3p".

The term "hsa-miR-3656 gene" or "hsa-miR-3656" used herein includes the hsa-miR-3656 gene (miRBase Accession No. MIMAT0018076) described in SEQ ID NO: 171, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 449) having a hairpin-like structure is known as a precursor of "hsa-miR-3656".

The term "hsa-miR-4688 gene" or "hsa-miR-4688" used herein includes the hsa-miR-4688 gene (miRBase Accession No. MIMAT0019777) described in SEQ ID NO: 172, a homolog or an ortholog of a different organism species, and the like. The hsa-miR-4688 gene can be obtained by a method described in Persson H et al., 2011, Cancer Res, Vol. 71, p. 78-86. Also, "hsa-mir-4688" (miRBase Accession No. MI0017321, SEQ ID NO: 450) having a hairpin-like structure is known as a precursor of "hsa-miR-4688".

The term "hsa-miR-3195 gene" or "hsa-miR-3195" used herein includes the hsa-miR-3195 gene (miRBase Accession No. MIMAT0015079) described in SEQ ID NO: 173, a homolog or an ortholog of a different organism species, and the like. The hsa-miR-3195 gene can be obtained by a method described in Stark M S et al., 2010, PLoS One, Vol. 5, e9685. Also, "hsa-mir-3195" (miRBase Accession No. MI0014240, SEQ ID NO: 451) having a hairpin-like structure is known as a precursor of "hsa-miR-3195".

The term "hsa-miR-6766-5p gene" or "hsa-miR-6766-5p" used herein includes the hsa-miR-6766-5p gene (miRBase Accession No. MIMAT0027432) described in SEQ ID NO: 174, a homolog or an ortholog of a different organism species, and the like. The hsa-miR-6766-5p gene can be obtained by a method described in Ladewig E et al., 2012, Genome Res, Vol. 22, p. 1634-1645. Also, "hsa-mir-6766" (miRBase Accession No. MI0022611, SEQ ID NO: 452) having a hairpin-like structure is known as a precursor of "hsa-miR-6766-5p".

The term "hsa-miR-4447 gene" or "hsa-miR-4447" used herein includes the hsa-miR-4447 gene (miRBase Accession No. MIMAT0018966) described in SEQ ID NO: 175, a homolog or an ortholog of a different organism species, and the like. The hsa-miR-4447 gene can be obtained by a method described in Jima D D et al., 2010, Blood, Vol. 116, e118-e127. Also, "hsa-mir-4447" (miRBase Accession No. MI0016790, SEQ ID NO: 453) having a hairpin-like structure is known as a precursor of "hsa-miR-4447".

The term "hsa-miR-4656 gene" or "hsa-miR-4656" used herein includes the hsa-miR-4656 gene (miRBase Accession No. MIMAT0019723) described in SEQ ID NO: 176, a homolog or an ortholog of a different organism species, and the like. The hsa-miR-4656 gene can be obtained by a method described in Persson H et al., 2011, Cancer Res, Vol. 71, p. 78-86. Also, "hsa-mir-4656" (miRBase Accession No. MI0017284, SEQ ID NO: 454) having a hairpin-like structure is known as a precursor of "hsa-miR-4656".

The term "hsa-miR-7108-5p gene" or "hsa-miR-7108-5p" used herein includes the hsa-miR-7108-5p gene (miRBase Accession No. MIMAT0028113) described in SEQ ID NO: 177, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 455) having a hairpin-like structure is known as a precursor of "hsa-miR-7108-5p".

The term "hsa-miR-3191-3p gene" or "hsa-miR-3191-3p" used herein includes the hsa-miR-3191-3p gene (miRBase Accession No. MIMAT0015075) described in SEQ ID NO: 178, a homolog or an ortholog of a different organism species, and the like. The hsa-miR-3191-3p gene can be obtained by a method described in Stark M S et al., 2010, PLoS One, Vol. 5, e9685. Also, "hsa-mir-3191" (miRBase Accession No. MI0014236, SEQ ID NO: 456) having a hairpin-like structure is known as a precursor of "hsa-miR-3191-3p".

The term "hsa-miR-1273g-3p gene" or "hsa-miR-1273g-3p" used herein includes the hsa-miR-1273g-3p gene (miRBase Accession No. MIMAT0022742) described in SEQ ID NO: 179, a homolog or an ortholog of a different organism species, and the like. The hsa-miR-1273g-3p gene can be obtained by a method described in Reshmi G et al., 2011, Genomics, Vol. 97, p. 333-340. Also, "hsa-mir-1273g" (miRBase Accession No. MI0018003, SEQ ID NO: 457) having a hairpin-like structure is known as a precursor of "hsa-miR-1273g-3p".

The term "hsa-miR-4463 gene" or "hsa-miR-4463" used herein includes the hsa-miR-4463 gene (miRBase Accession No. MIMAT0018987) described in SEQ ID NO: 180, a homolog or an ortholog of a different organism species, and the like. The hsa-miR-4463 gene can be obtained by a method described in Jima D D et al., 2010, Blood, Vol. 116, e118-e127. Also, "hsa-mir-4463" (miRBase Accession No. MI0016811, SEQ ID NO: 458) having a hairpin-like structure is known as a precursor of "hsa-miR-4463".

The term "hsa-miR-2861 gene" or "hsa-miR-2861" used herein includes the hsa-miR-2861 gene (miRBase Accession No. MIMAT0013802) described in SEQ ID NO: 181, a homolog or an ortholog of a different organism species, and the like. The hsa-miR-2861 gene can be obtained by a method described in Li H et al., 2009, 1 Clin Invest, Vol. 119, p. 3666-3677. Also, "hsa-mir-2861" (miRBase Accession No. MI0013006, SEQ ID NO: 459) having a hairpin-like structure is known as a precursor of "hsa-miR-2861".

The term "hsa-miR-3196 gene" or "hsa-miR-3196" used herein includes the hsa-miR-3196 gene (miRBase Accession No. MIMAT0015080) described in SEQ ID NO: 182, a homolog or an ortholog of a different organism species, and the like. The hsa-miR-3196 gene can be obtained by a method described in Stark M S et al., 2010, PLoS One, Vol. 5, e9685. Also, "hsa-mir-3196" (miRBase Accession No. MI0014241, SEQ ID NO: 460) having a hairpin-like structure is known as a precursor of "hsa-miR-3196".

The term "hsa-miR-6877-5p gene" or "hsa-miR-6877-5p" used herein includes the hsa-miR-6877-5p gene (miRBase Accession No. MIMAT0027654) described in SEQ ID NO: 183, a homolog or an ortholog of a different organism species, and the like. The hsa-miR-6877-5p gene can be obtained by a method described in Ladewig E et al., 2012, Genome Res, Vol. 22, p. 1634-1645. Also, "hsa-mir-6877" (miRBase Accession No. MI0022724, SEQ ID NO: 461) having a hairpin-like structure is known as a precursor of "hsa-miR-6877-5p".

The term "hsa-miR-3679-5p gene" or "hsa-miR-3679-5p" used herein includes the hsa-miR-3679-5p gene (miRBase Accession No. MIMAT0018104) described in SEQ ID NO: 184, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 462) having a hairpin-like structure is known as a precursor of "hsa-miR-3679-5p".

The term "hsa-miR-4442 gene" or "hsa-miR-4442" used herein includes the hsa-miR-4442 gene (miRBase Accession No. MIMAT0018960) described in SEQ ID NO: 185, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 463) having a hairpin-like structure is known as a precursor of "hsa-miR-4442".

The term "hsa-miR-6789-5p gene" or "hsa-miR-6789-5p" used herein includes the hsa-miR-6789-5p gene (miRBase Accession No. MIMAT0027478) described in SEQ ID NO: 186, a homolog or an ortholog of a different organism species, and the like. The hsa-miR-6789-5p gene can be obtained by a method described in Ladewig E et al., 2012, Genome Res, Vol. 22, p. 1634-1645. Also, "hsa-mir-6789" (miRBase Accession No. MI0022634, SEQ ID NO: 464) having a hairpin-like structure is known as a precursor of "hsa-miR-6789-5p".

The term "hsa-miR-6782-5p gene" or "hsa-miR-6782-5p" used herein includes the hsa-miR-6782-5p gene (miRBase Accession No. MIMAT0027464) described in SEQ ID NO: 187, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 465) having a hairpin-like structure is known as a precursor of "hsa-miR-6782-5p".

The term "hsa-miR-486-3p gene" or "hsa-miR-486-3p" used herein includes the hsa-miR-486-3p gene (miRBase Accession No. MIMAT0004762) described in SEQ ID NO: 188, a homolog or an ortholog of a different organism species, and the like. The hsa-miR-486-3p gene can be obtained by a method described in Fu H et al., 2005, FEBS Lett, Vol. 579, p. 3849-3854. Also, "hsa-mir-486 and hsa-mir-486-2" (miRBase Accession Nos. MI0002470 and MI0023622, SEQ ID NOs: 466 and 467) having a hairpin-like structure are known as precursors of "hsa-miR-486-3p".

The term "hsa-miR-6085 gene" or "hsa-miR-6085" used herein includes the hsa-miR-6085 gene (miRBase Accession No. MIMAT0023710) described in SEQ ID NO: 189, a homolog or an ortholog of a different organism species, and the like. The hsa-miR-6085 gene can be obtained by a method described in Voellenkle C et al., 2012, RNA, Vol. 18, p. 472-484. Also, "hsa-mir-6085" (miRBase Accession No. MI0020362, SEQ ID NO: 468) having a hairpin-like structure is known as a precursor of "hsa-miR-6085".

The term "hsa-miR-4746-3p gene" or "hsa-miR-4746-3p" used herein includes the hsa-miR-4746-3p gene (miRBase Accession No. MIMAT0019881) described in SEQ ID NO: 190, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 469) having a hairpin-like structure is known as a precursor of "hsa-miR-4746-3p".

The term "hsa-miR-619-5p gene" or "hsa-miR-619-5p" used herein includes the hsa-miR-619-5p gene (miRBase Accession No. MIMAT0026622) described in SEQ ID NO: 191, a homolog or an ortholog of a different organism species, and the like. The hsa-miR-619-5p gene can be obtained by a method described in Cummins J M et al., 2006, Proc Natl Acad Sci USA, Vol. 103, p. 3687-3692. Also, "hsa-mir-619" (miRBase Accession No. MI0003633, SEQ ID NO: 470) having a hairpin-like structure is known as a precursor of "hsa-miR-619-5p".

The term "hsa-miR-937-5p gene" or "hsa-miR-937-5p" used herein includes the hsa-miR-937-5p gene (miRBase Accession No. MIMAT0022938) described in SEQ ID NO: 192, a homolog or an ortholog of a different organism species, and the like. The hsa-miR-937-5p gene can be obtained by a method described in Lui W O et al., 2007, Cancer Res, Vol. 67, p. 6031-6043. Also, "hsa-mir-937" (miRBase Accession No. MI0005759, SEQ ID NO: 471) having a hairpin-like structure is known as a precursor of "hsa-miR-937-5p".

The term "hsa-miR-6803-5p gene" or "hsa-miR-6803-5p" used herein includes the hsa-miR-6803-5p gene (miRBase Accession No. MIMAT0027506) described in SEQ ID NO: 193, a homolog or an ortholog of a different organism species, and the like. The hsa-miR-6803-5p gene can be obtained by a method described in Ladewig E et al., 2012, Genome Res, Vol. 22, p. 1634-1645. Also, "hsa-mir-6803" (miRBase Accession No. MI0022648, SEQ ID NO: 472) having a hairpin-like structure is known as a precursor of "hsa-miR-6803-5p".

The term "hsa-miR-4298 gene" or "hsa-miR-4298" used herein includes the hsa-miR-4298 gene (miRBase Accession No. MIMAT0016852) described in SEQ ID NO: 194, a homolog or an ortholog of a different organism species, and the like. The hsa-miR-4298 gene can be obtained by a method described in Goff L A et al., 2009, PLoS One, Vol. 4, e7192. Also, "hsa-mir-4298" (miRBase Accession No. MI0015830, SEQ ID NO: 473) having a hairpin-like structure is known as a precursor of "hsa-miR-4298".

The term "hsa-miR-4454 gene" or "hsa-miR-4454" used herein includes the hsa-miR-4454 gene (miRBase Accession No. MIMAT0018976) described in SEQ ID NO: 195, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 474) having a hairpin-like structure is known as a precursor of "hsa-miR-4454".

The term "hsa-miR-4459 gene" or "hsa-miR-4459" used herein includes the hsa-miR-4459 gene (miRBase Accession No. MIMAT0018981) described in SEQ ID NO: 196, a homolog or an ortholog of a different organism species, and the like. The hsa-miR-4459 gene can be obtained by a method described in Jima D D et al., 2010, Blood, Vol. 116, e118-e127. Also, "hsa-mir-4459" (miRBase Accession No. MI0016805, SEQ ID NO: 475) having a hairpin-like structure is known as a precursor of "hsa-miR-4459".

The term "hsa-miR-7150 gene" or "hsa-miR-7150" used herein includes the hsa-miR-7150 gene (miRBase Accession No. MIMAT0028211) described in SEQ ID NO: 197, a homolog or an ortholog of a different organism species, and the like. The hsa-miR-7150 gene can be obtained by a method described in Oulas A et al., 2009, Nucleic Acids Res, Vol. 37, p. 3276-3287. Also, "hsa-mir-7150" (miRBase Accession No. MI0023610, SEQ ID NO: 476) having a hairpin-like structure is known as a precursor of "hsa-miR-7150".

The term "hsa-miR-6880-5p gene" or "hsa-miR-6880-5p" used herein includes the hsa-miR-6880-5p gene (miRBase Accession No. MIMAT0027660) described in SEQ ID NO: 198, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. MI0022727, SEQ ID NO: 477) having a hairpin-like structure is known as a precursor of "hsa-miR-6880-5p".

The term "hsa-miR-4449 gene" or "hsa-miR-4449" used herein includes the hsa-miR-4449 gene (miRBase Accession No. MIMAT0018968) described in SEQ ID NO: 199, a homolog or an ortholog of a different organism species, and the like. The hsa-miR-4449 gene can be obtained by a method described in Jima D D et al., 2010, Blood, Vol. 116, e118-e127. Also, "hsa-mir-4449" (miRBase Accession No. MI0016792, SEQ ID NO: 478) having a hairpin-like structure is known as a precursor of "hsa-miR-4449".

The term "hsa-miR-8063 gene" or "hsa-miR-8063" used herein includes the hsa-miR-8063 gene (miRBase Accession No. MIMAT0030990) described in SEQ ID NO: 200, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 479) having a hairpin-like structure is known as a precursor of "hsa-miR-8063".

The term "hsa-miR-4695-5p gene" or "hsa-miR-4695-5p" used herein includes the hsa-miR-4695-5p gene (miRBase Accession No. MIMAT0019788) described in SEQ ID NO: 201, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 480) having a hairpin-like structure is known as a precursor of "hsa-miR-4695-5p".

The term "hsa-miR-6132 gene" or "hsa-miR-6132" used herein includes the hsa-miR-6132 gene (miRBase Accession No. MIMAT0024616) described in SEQ ID NO: 202, a homolog or an ortholog of a different organism species, and the like. The hsa-miR-6132 gene can be obtained by a method described in Dannemann M et al., 2012, Genome Biol Evol, Vol. 4, p. 552-564. Also, "hsa-mir-6132" (miRBase Accession No. MI0021277, SEQ ID NO: 481) having a hairpin-like structure is known as a precursor of "hsa-miR-6132".

The term "hsa-miR-6829-5p gene" or "hsa-miR-6829-5p" used herein includes the hsa-miR-6829-5p gene (miRBase Accession No. MIMAT0027558) described in SEQ ID NO: 203, a homolog or an ortholog of a different organism species, and the like. The hsa-miR-6829-5p gene can be obtained by a method described in Ladewig E et al., 2012, Genome Res, Vol. 22, p. 1634-1645. Also, "hsa-mir-6829" (miRBase Accession No. MI0022674, SEQ ID NO: 482) having a hairpin-like structure is known as a precursor of "hsa-miR-6829-5p".

The term "hsa-miR-4486 gene" or "hsa-miR-4486" used herein includes the hsa-miR-4486 gene (miRBase Accession No. MIMAT0019020) described in SEQ ID NO: 204, a homolog or an ortholog of a different organism species, and the like. The hsa-miR-4486 gene can be obtained by a method described in Jima D D et al., 2010, Blood, Vol. 116, e118-e127. Also, "hsa-mir-4486" (miRBase Accession No. MI0016847, SEQ ID NO: 483) having a hairpin-like structure is known as a precursor of "hsa-miR-4486".

The term "hsa-miR-6805-3p gene" or "hsa-miR-6805-3p" used herein includes the hsa-miR-6805-3p gene (miRBase Accession No. MIMAT0027511) described in SEQ ID NO: 205, a homolog or an ortholog of a different organism species, and the like. The hsa-miR-6805-3p gene can be obtained by a method described in Ladewig E et al., 2012, Genome Res, Vol. 22, p. 1634-1645. Also, "hsa-mir-6805" (miRBase Accession No. MI0022650, SEQ ID NO: 304) having a hairpin-like structure is known as a precursor of "hsa-miR-6805-3p".

The term "hsa-miR-6826-5p gene" or "hsa-miR-6826-5p" used herein includes the hsa-miR-6826-5p gene (miRBase Accession No. MIMAT0027552) described in SEQ ID NO: 206, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. MI0022671, SEQ ID NO: 484) having a hairpin-like structure is known as a precursor of "hsa-miR-6826-5p".

The term "hsa-miR-4508 gene" or "hsa-miR-4508" used herein includes the hsa-miR-4508 gene (miRBase Accession No. MIMAT0019045) described in SEQ ID NO: 207, a homolog or an ortholog of a different organism species, and the like. The hsa-miR-4508 gene can be obtained by a method described in Jima D D et al., 2010, Blood, Vol. 116, e118-e127. Also, "hsa-mir-4508" (miRBase Accession No. MI0016872, SEQ ID NO: 485) having a hairpin-like structure is known as a precursor of "hsa-miR-4508".

The term "hsa-miR-1343-5p gene" or "hsa-miR-1343-5p" used herein includes the hsa-miR-1343-5p gene (miRBase Accession No. MIMAT0027038) described in SEQ ID NO: 208, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 361) having a hairpin-like structure is known as a precursor of "hsa-miR-1343-5p".

The term "hsa-miR-7114-5p gene" or "hsa-miR-7114-5p" used herein includes the hsa-miR-7114-5p gene (miRBase Accession No. MIMAT0028125) described in SEQ ID NO: 209, a homolog or an ortholog of a different organism species, and the like. The hsa-miR-7114-5p gene can be obtained by a method described in Ladewig E et al., 2012, Genome Res, Vol. 22, p. 1634-1645. Also, "hsa-mir-7114" (miRBase Accession No. MI0022965, SEQ ID NO: 486) having a hairpin-like structure is known as a precursor of "hsa-miR-7114-5p".

The term "hsa-miR-3622a-5p gene" or "hsa-miR-3622a-5p" used herein includes the hsa-miR-3622a-5p gene (miRBase Accession No. MIMAT0018003) described in SEQ ID NO: 210, a homolog or an ortholog of a different organism species, and the like. The hsa-miR-3622a-5p gene can be obtained by a method described in Witten D et al., 2010, BMC Biol, Vol. 8, p. 58. Also, "hsa-mir-3622a" (miRBase Accession No. MI0016013, SEQ ID NO: 487) having a hairpin-like structure is known as a precursor of "hsa-miR-3622a-5p".

The term "hsa-miR-6765-5p gene" or "hsa-miR-6765-5p" used herein includes the hsa-miR-6765-5p gene (miRBase Accession No. MIMAT0027430) described in SEQ ID NO: 211, a homolog or an ortholog of a different organism species, and the like. The hsa-miR-6765-5p gene can be obtained by a method described in Ladewig E et al., 2012, Genome Res, Vol. 22, p. 1634-1645. Also, "hsa-mir-6765" (miRBase Accession No. MI0022610, SEQ ID NO: 488) having a hairpin-like structure is known as a precursor of "hsa-miR-6765-5p".

The term "hsa-miR-7845-5p gene" or "hsa-miR-7845-5p" used herein includes the hsa-miR-7845-5p gene (miRBase Accession No. MIMAT0030420) described in SEQ ID NO: 212, a homolog or an ortholog of a different organism species, and the like. The hsa-miR-7845-5p gene can be obtained by a method described in Plc H et al., 2012, PLoS One, Vol. 7, e50746. Also, "hsa-mir-7845" (miRBase Accession No. MI0025515, SEQ ID NO: 489) having a hairpin-like structure is known as a precursor of "hsa-miR-7845-5p".

The term "hsa-miR-3960 gene" or "hsa-miR-3960" used herein includes the hsa-miR-3960 gene (miRBase Accession No. MIMAT0019337) described in SEQ ID NO: 213, a homolog or an ortholog of a different organism species, and the like. The hsa-miR-3960 gene can be obtained by a method described in Hu R et al., 2011, J Biol Chem, Vol. 286, p. 12328-12339. Also, "hsa-mir-3960" (miRBase Accession No. MI0016964, SEQ ID NO: 490) having a hairpin-like structure is known as a precursor of "hsa-miR-3960".

The term "hsa-miR-6749-5p gene" or "hsa-miR-6749-5p" used herein includes the hsa-miR-6749-5p gene (miRBase Accession No. MIMAT0027398) described in SEQ ID NO: 214, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594, SEQ ID NO: 491) having a hairpin-like structure is known as a precursor of "hsa-miR-6749-5p".

The term "hsa-miR-1260b gene" or "hsa-miR-1260b" used herein includes the hsa-miR-1260b gene (miRBase Accession No. MIMAT0015041) described in SEQ ID NO: 215, a homolog or an ortholog of a different organism species, and the like. The hsa-miR-1260b gene can be obtained by a method described in Stark M S et al., 2010, PLoS One, Vol. 5, e9685. Also, "hsa-mir-1260b" (miRBase Accession No. MI0014197, SEQ ID NO: 492) having a hairpin-like structure is known as a precursor of "hsa-miR-1260b".

The term "hsa-miR-6799-5p gene" or "hsa-miR-6799-5p" used herein includes the hsa-miR-6799-5p gene (miRBase Accession No. MIMAT0027498) described in SEQ ID NO: 216, a homolog or an ortholog of a different organism species, and the like. The hsa-miR-6799-5p gene can be obtained by a method described in Ladewig E et al., 2012, Genome Res, Vol. 22, p. 1634-1645. Also, "hsa-mir-6799" (miRBase Accession No. MI0022644, SEQ ID NO: 493) having a hairpin-like structure is known as a precursor of "hsa-miR-6799-5p".

The term "hsa-miR-4723-5p gene" or "hsa-miR-4723-5p" used herein includes the hsa-miR-4723-5p gene (miRBase Accession No. MIMAT0019838) described in SEQ ID NO: 217, a homolog or an ortholog of a different organism species, and the like. The hsa-miR-4723-5p gene can be obtained by a method described in Persson H et al., 2011, Cancer Res, Vol. 71, p. 78-86. Also, "hsa-mir-4723" (miRBase Accession No. MI0017359, SEQ ID NO: 494) having a hairpin-like structure is known as a precursor of "hsa-miR-4723-5p".

The term "hsa-miR-6784-5p gene" or "hsa-miR-6784-5p" used herein includes the hsa-miR-6784-5p gene (miRBase Accession No. MIMAT0027468) described in SEQ ID NO: 218, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 495) having a hairpin-like structure is known as a precursor of "hsa-miR-6784-5p".

The term "hsa-miR-5100 gene" or "hsa-miR-5100" used herein includes the hsa-miR-5100 gene (miRBase Accession No. MIMAT0022259) described in SEQ ID NO: 219, a homolog or an ortholog of a different organism species, and the like. The hsa-miR-5100 gene can be obtained by a method described in Tandon M et al., 2012, Oral Dis, Vol. 18, p. 127-131. Also, "hsa-mir-5100" (miRBase Accession No. MI0019116, SEQ ID NO: 496) having a hairpin-like structure is known as a precursor of "hsa-miR-5100".

The term "hsa-miR-6769b-5p gene" or "hsa-miR-6769b-5p" used herein includes the hsa-miR-6769b-5p gene (miRBase Accession No. MIMAT0027620) described in SEQ ID NO: 220, a homolog or an ortholog of a different organism species, and the like. The hsa-miR-6769b-5p gene can be obtained by a method described in Ladewig E et al., 2012, Genome Res, Vol. 22, p. 1634-1645. Also, "hsa-mir-6769b" (miRBase Accession No. MI0022706, SEQ ID NO: 497) having a hairpin-like structure is known as a precursor of "hsa-miR-6769b-5p".

The term "hsa-miR-1207-5p gene" or "hsa-miR-1207-5p" used herein includes the hsa-miR-1207-5p gene (miRBase Accession No. MIMAT0005871) described in SEQ ID NO: 221, a homolog or an ortholog of a different organism species, and the like. The hsa-miR-1207-5p gene can be obtained by a method described in Huppi K et al., 2008, Mol Cancer Res, Vol. 6, p. 212-221. Also, "hsa-mir-1207" (miRBase Accession No. MI0006340, SEQ ID NO: 498) having a hairpin-like structure is known as a precursor of "hsa-miR-1207-5p".

The term "hsa-miR-642a-3p gene" or "hsa-miR-642a-3p" used herein includes the hsa-miR-642a-3p gene (miRBase Accession No. MIMAT0020924) described in SEQ ID NO: 222, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692. Also, "hsa-mir-642a" (miRBase Accession No. MI0003657, SEQ ID NO: 499) having a hairpin-like structure is known as a precursor of "hsa-miR-642a-3p".

The term "hsa-miR-4505 gene" or "hsa-miR-4505" used herein includes the hsa-miR-4505 gene (miRBase Accession No. MIMAT0019041) described in SEQ ID NO: 223, a homolog or an ortholog of a different organism species, and the like. The hsa-miR-4505 gene can be obtained by a method described in Jima D D et al., 2010, Blood, Vol. 116, e118-e127. Also, "hsa-mir-4505" (miRBase Accession No. MI0016868, SEQ ID NO: 500) having a hairpin-like structure is known as a precursor of "hsa-miR-4505".

The term "hsa-miR-4270 gene" or "hsa-miR-4270" used herein includes the hsa-miR-4270 gene (miRBase Accession No. MIMAT0016900) described in SEQ ID NO: 224, a homolog or an ortholog of a different organism species, and the like. The hsa-miR-4270 gene can be obtained by a method described in Goff L A et al., 2009, PLoS One, Vol. 4, e7192. Also, "hsa-mir-4270" (miRBase Accession No. MI0015878, SEQ ID NO: 501) having a hairpin-like structure is known as a precursor of "hsa-miR-4270".

The term "hsa-miR-6721-5p gene" or "hsa-miR-6721-5p" used herein includes the hsa-miR-6721-5p gene (miRBase Accession No. MIMAT0025852) described in SEQ ID NO: 225, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 502) having a hairpin-like structure is known as a precursor of "hsa-miR-6721-5p".

The term "hsa-miR-7111-5p gene" or "hsa-miR-7111-5p" used herein includes the hsa-miR-7111-5p gene (miRBase Accession No. MIMAT0028119) described in SEQ ID NO: 226, a homolog or an ortholog of a different organism species, and the like. The hsa-miR-7111-5p gene can be obtained by a method described in Ladewig E et al., 2012, Genome Res, Vol. 22, p. 1634-1645. Also, "hsa-mir-7111" (miRBase Accession No. MI0022962, SEQ ID NO: 503) having a hairpin-like structure is known as a precursor of "hsa-miR-7111-5p".

The term "hsa-miR-6791-5p gene" or "hsa-miR-6791-5p" used herein includes the hsa-miR-6791-5p gene (miRBase Accession No. MIMAT0027482) described in SEQ ID NO: 227, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 504) having a hairpin-like structure is known as a precursor of "hsa-miR-6791-5p".

The term "hsa-miR-7109-5p gene" or "hsa-miR-7109-5p" used herein includes the hsa-miR-7109-5p gene (miRBase Accession No. MIMAT0028115) described in SEQ ID NO: 228, a homolog or an ortholog of a different organism species, and the like. The hsa-miR-7109-5p gene can be obtained by a method described in Ladewig E et al., 2012, Genome Res, Vol. 22, p. 1634-1645. Also, "hsa-mir-7109" (miRBase Accession No. MI0022960, SEQ ID NO: 505) having a hairpin-like structure is known as a precursor of "hsa-miR-7109-5p".

The term "hsa-miR-4258 gene" or "hsa-miR-4258" used herein includes the hsa-miR-4258 gene (miRBase Accession No. MIMAT0016879) described in SEQ ID NO: 229, a homolog or an ortholog of a different organism species, and the like. The hsa-miR-4258 gene can be obtained by a method described in Goff L A et al., 2009, PLoS One, Vol. 4, e7192. Also, "hsa-mir-4258" (miRBase Accession No. MI0015857, SEQ ID NO: 506) having a hairpin-like structure is known as a precursor of "hsa-miR-4258".

The term "hsa-miR-6515-3p gene" or "hsa-miR-6515-3p" used herein includes the hsa-miR-6515-3p gene (miRBase Accession No. MIMAT0025487) described in SEQ ID NO: 230, a homolog or an ortholog of a different organism species, and the like. The hsa-miR-6515-3p gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 507) having a hairpin-like structure is known as a precursor of "hsa-miR-6515-3p".

The term "hsa-miR-6851-5p gene" or "hsa-miR-6851-5p" used herein includes the hsa-miR-6851-5p gene (miRBase Accession No. MIMAT0027602) described in SEQ ID NO: 231, a homolog or an ortholog of a different organism species, and the like. The hsa-miR-6851-5p gene can be obtained by a method described in Ladewig E et al., 2012, Genome Res, Vol. 22, p. 1634-1645. Also, "hsa-mir-6851" (miRBase Accession No. MI0022697, SEQ ID NO: 508) having a hairpin-like structure is known as a precursor of "hsa-miR-6851-5p".

The term "hsa-miR-6125 gene" or "hsa-miR-6125" used herein includes the hsa-miR-6125 gene (miRBase Accession No. MIMAT0024598) described in SEQ ID NO: 232, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 509) having a hairpin-like structure is known as a precursor of "hsa-miR-6125".

The term "hsa-miR-4749-5p gene" or "hsa-miR-4749-5p" used herein includes the hsa-miR-4749-5p gene (miRBase Accession No. MIMAT0019885) described in SEQ ID NO: 233, a homolog or an ortholog of a different organism species, and the like. The hsa-miR-4749-5p gene can be obtained by a method described in Persson H et al., 2011, Cancer Res, Vol. 71, p. 78-86. Also, "hsa-mir-4749" (miRBase Accession No. MI0017388, SEQ ID NO: 510) having a hairpin-like structure is known as a precursor of "hsa-miR-4749-5p".

The term "hsa-miR-4726-5p gene" or "hsa-miR-4726-5p" used herein includes the hsa-miR-4726-5p gene (miRBase Accession No. MIMAT0019845) described in SEQ ID NO: 234, a homolog or an ortholog of a different organism species, and the like. The hsa-miR-4726-5p gene can be obtained by a method described in Persson H et al., 2011, Cancer Res, Vol. 71, p. 78-86. Also, "hsa-mir-4726" (miRBase Accession No. MI0017363, SEQ ID NO: 511) having a hairpin-like structure is known as a precursor of "hsa-miR-4726-5p".

The term "hsa-miR-4513 gene" or "hsa-miR-4513" used herein includes the hsa-miR-4513 gene (miRBase Accession No. MIMAT0019050) described in SEQ ID NO: 235, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 512) having a hairpin-like structure is known as a precursor of "hsa-miR-4513".

The term "hsa-miR-760 gene" or "hsa-miR-760" used herein includes the hsa-miR-760 gene (miRBase Accession No. MIMAT0004957) described in SEQ ID NO: 236, a homolog or an ortholog of a different organism species, and the like. The hsa-miR-760 gene can be obtained by a method described in Berezikov E et al., 2006, Genome Res, Vol. 16, p. 1289-1298. Also, "hsa-mir-760" (miRBase Accession No. MI0005567, SEQ ID NO: 513) having a hairpin-like structure is known as a precursor of "hsa-miR-760".

The term "hsa-miR-602 gene" or "hsa-miR-602" used herein includes the hsa-miR-602 gene (miRBase Accession No. MIMAT0003270) described in SEQ ID NO: 237, a homolog or an ortholog of a different organism species, and the like. The hsa-miR-602 gene can be obtained by a method described in Cummins J M et al., 2006, Proc Natl Acad Sci USA, Vol. 103, p. 3687-3692. Also, "hsa-mir-602" (miRBase Accession No. MI0003615, SEQ ID NO: 514) having a hairpin-like structure is known as a precursor of "hsa-miR-602".

The term "hsa-miR-423-5p gene" or "hsa-miR-423-5p" used herein includes the hsa-miR-423-5p gene (miRBase Accession No. MIMAT0004748) described in SEQ ID NO: 238, a homolog or an ortholog of a different organism species, and the like. The hsa-miR-423-5p gene can be obtained by a method described in Kasashima K et al., 2004, Biochem Biophys Res Commun, Vol. 322, p. 403-410. Also, "hsa-mir-423" (miRBase Accession No. MI0001445, SEQ ID NO: 515) having a hairpin-like structure is known as a precursor of "hsa-miR-423-5p".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 239, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 516) having a hairpin-like structure is known as a precursor of "hsa-miR-92a-2-5p".

The term "hsa-miR-16-5p gene" or "hsa-miR-16-5p" used herein includes the hsa-miR-16-5p gene (miRBase Accession No. MIMAT0000069) described in SEQ ID NO: 240, a homolog or an ortholog of a different organism species, and the like. The hsa-miR-16-5p gene can be obtained by a method described in Lagos-Quintana M et al., 2001, Science, Vol. 294, p. 853-858. Also, "hsa-mir-16-1 and hsa-mir-16-2" (miRBase Accession Nos. MI0000070 and MI0000115, SEQ ID NOs: 517 and 518) having a hairpin-like structure are known as precursors of "hsa-miR-16-5p".

The term "hsa-miR-451a gene" or "hsa-miR-451a" used herein includes the hsa-miR-451a gene (miRBase Accession No. MIMAT0001631) described in SEQ ID NO: 241, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 519) having a hairpin-like structure is known as a precursor of "hsa-miR-451a".

The term "hsa-miR-135a-3p gene" or "hsa-miR-135a-3p" used herein includes the hsa-miR-135a-3p gene (miRBase Accession No. MIMAT0004595) described in SEQ ID NO: 242, a homolog or an ortholog of a different organism species, and the like. The hsa-miR-135a-3p gene can be obtained by a method described in Lagos-Quintana M et al., 2002, Curr Biol, Vol. 12, p. 735-739. Also, "hsa-mir-135a" (miRBase Accession No. MI0000452, SEQ ID NO: 520) having a hairpin-like structure is known as a precursor of "hsa-miR-135a-3p".

The term "hsa-miR-486-5p gene" or "hsa-miR-486-5p" used herein includes the hsa-miR-486-5p gene (miRBase Accession No. MIMAT0002177) described in SEQ ID NO: 243, a homolog or an ortholog of a different organism species, and the like. The hsa-miR-486-5p gene can be obtained by a method described in Fu H et al., 2005, FEBS Lett, Vol. 579, p. 3849-3854. Also, "hsa-mir-486 and hsa-mir-486-2" (miRBase Accession Nos. MI0002470 and MI0023622, SEQ ID NOs: 466 and 467) having a hairpin-like structure are known as precursors of "hsa-miR-486-5p".

The term "hsa-miR-4257 gene" or "hsa-miR-4257" used herein includes the hsa-miR-4257 gene (miRBase Accession No. MIMAT0016878) described in SEQ ID NO: 244, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. MI0015856, SEQ ID NO: 521) having a hairpin-like structure is known as a precursor of "hsa-miR-4257".

The term "hsa-miR-92b-5p gene" or "hsa-miR-92b-5p" used herein includes the hsa-miR-92b-5p gene (miRBase Accession No. MIMAT0004792) described in SEQ ID NO: 245, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 522) having a hairpin-like structure is known as a precursor of "hsa-miR-92b-5p".

The term "hsa-miR-1915-3p gene" or "hsa-miR-1915-3p" used herein includes the hsa-miR-1915-3p gene (miRBase Accession No. MIMAT0007892) described in SEQ ID NO: 246, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 339) having a hairpin-like structure is known as a precursor of "hsa-miR-1915-3p".

The term "hsa-miR-718 gene" or "hsa-miR-718" used herein includes the hsa-miR-718 gene (miRBase Accession No. MIMAT0012735) described in SEQ ID NO: 247, a homolog or an ortholog of a different organism species, and the like. The hsa-miR-718 gene can be obtained by a method described in Artzi S et al., 2008, BMC Bioinformatics, Vol. 9, p. 39. Also, "hsa-mir-718" (miRBase Accession No. MI0012489, SEQ ID NO: 523) having a hairpin-like structure is known as a precursor of "hsa-miR-718".

The term "hsa-miR-940 gene" or "hsa-miR-940" used herein includes the hsa-miR-940 gene (miRBase Accession No. MIMAT0004983) described in SEQ ID NO: 248, a homolog or an ortholog of a different organism species, and the like. The hsa-miR-940 gene can be obtained by a method described in Lui W O et al., 2007, Cancer Res, Vol. 67, p. 6031-6043. Also, "hsa-mir-940" (miRBase Accession No. MI0005762, SEQ ID NO: 524) having a hairpin-like structure is known as a precursor of "hsa-miR-940".

The term "hsa-miR-296-5p gene" or "hsa-miR-296-5p" used herein includes the hsa-miR-296-5p gene (miRBase Accession No. MIMAT0000690) described in SEQ ID NO: 249, a homolog or an ortholog of a different organism species, and the like. The hsa-miR-296-5p gene can be obtained by a method described in Houbaviy H B et al., 2003, Dev Cell, Vol. 5, p. 351-358. Also, "hsa-mir-296" (miRBase Accession No. MI0000747, SEQ ID NO: 409) having a hairpin-like structure is known as a precursor of "hsa-miR-296-5p".

The term "hsa-miR-23b-3p gene" or "hsa-miR-23b-3p" used herein includes the hsa-miR-23b-3p gene (miRBase Accession No. MIMAT0000418) described in SEQ ID NO: 250, a homolog or an ortholog of a different organism species, and the like. The hsa-miR-23b-3p gene can be obtained by a method described in Lagos-Quintana M et al., 2002, Curr Biol, Vol. 12, p. 735-739. Also, "hsa-mir-23b" (miRBase Accession No. MI0000439, SEQ ID NO: 525) having a hairpin-like structure is known as a precursor of "hsa-miR-23b-3p".

The term "hsa-miR-92a-3p gene" or "hsa-miR-92a-3p" used herein includes the hsa-miR-92a-3p gene (miRBase Accession No. MIMAT0000092) described in SEQ ID NO: 251, a homolog or an ortholog of a different organism species, and the like. The hsa-miR-92a-3p gene can be obtained by a method described in Mourelatos Z et al., 2002, Genes Dev, Vol. 16, p. 720-728. Also, "hsa-mir-92a-1 and hsa-mir-92a-2" (miRBase Accession Nos. MI0000093 and MI0000094, SEQ ID NOs: 526 and 527) having a hairpin-like structure are known as precursors of "hsa-miR-92a-3p".

The term "hsa-miR-658 gene" or "hsa-miR-658" used herein includes the hsa-miR-658 gene (miRBase Accession No. MIMAT0003336) described in SEQ ID NO: 252, a homolog or an ortholog of a different organism species, and the like. The hsa-miR-658 gene can be obtained by a method described in Cummins J M et al., 2006, Proc Natl Acad Sci USA, Vol. 103, p. 3687-3692. Also, "hsa-mir-658" (miRBase Accession No. MI0003682, SEQ ID NO: 528) having a hairpin-like structure is known as a precursor of "hsa-miR-658".

The term "hsa-miR-6842-5p gene" or "hsa-miR-6842-5p" used herein includes the hsa-miR-6842-5p gene (miRBase Accession No. MIMAT0027586) described in SEQ ID NO: 253, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 529) having a hairpin-like structure is known as a precursor of "hsa-miR-6842-5p".

The term "hsa-miR-6124 gene" or "hsa-miR-6124" used herein includes the hsa-miR-6124 gene (miRBase Accession No. MIMAT0024597) described in SEQ ID NO: 254, a homolog or an ortholog of a different organism species, and the like. The hsa-miR-6124 gene can be obtained by a method described in Smith J L et al., 2012, J Virol, Vol. 86, p. 5278-5287. Also, "hsa-mir-6124" (miRBase Accession No. MI0021258, SEQ ID NO: 530) having a hairpin-like structure is known as a precursor of "hsa-miR-6124".

The term "hsa-miR-6765-3p gene" or "hsa-miR-6765-3p" used herein includes the hsa-miR-6765-3p gene (miRBase Accession No. MIMAT0027431) described in SEQ ID NO: 255, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 531) having a hairpin-like structure is known as a precursor of "hsa-miR-6765-3p".

The term "hsa-miR-7106-5p gene" or "hsa-miR-7106-5p" used herein includes the hsa-miR-7106-5p gene (miRBase Accession No. MIMAT0028109) described in SEQ ID NO: 256, a homolog or an ortholog of a different organism species, and the like. The hsa-miR-7106-5p gene can be obtained by a method described in Ladewig E et al., 2012, Genome Res, Vol. 22, p. 1634-1645. Also, "hsa-mir-7106" (miRBase Accession No. MI0022957, SEQ ID NO: 532) having a hairpin-like structure is known as a precursor of "hsa-miR-7106-5p".

The term "hsa-miR-4534 gene" or "hsa-miR-4534" used herein includes the hsa-miR-4534 gene (miRBase Accession No. MIMAT0019073) described in SEQ ID NO: 257, a homolog or an ortholog of a different organism species, and the like. The hsa-miR-4534 gene can be obtained by a method described in Jima D D et al., 2010, Blood, Vol. 116, e118-e127. Also, "hsa-mir-4534" (miRBase Accession No. MI0016901, SEQ ID NO: 533) having a hairpin-like structure is known as a precursor of "hsa-miR-4534".

The term "hsa-miR-92b-3p gene" or "hsa-miR-92b-3p" used herein includes the hsa-miR-92b-3p gene (miRBase Accession No. MIMAT0003218) described in SEQ ID NO: 258, a homolog or an ortholog of a different organism species, and the like. The hsa-miR-92b-3p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 522) having a hairpin-like structure is known as a precursor of "hsa-miR-92b-3p".

The term "hsa-miR-3135b gene" or "hsa-miR-3135b" used herein includes the hsa-miR-3135b gene (miRBase Accession No. MIMAT0018985) described in SEQ ID NO: 259, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 534) having a hairpin-like structure is known as a precursor of "hsa-miR-3135b".

The term "hsa-miR-4687-3p gene" or "hsa-miR-4687-3p" used herein includes the hsa-miR-4687-3p gene (miRBase Accession No. MIMAT0019775) described in SEQ ID NO: 260, a homolog or an ortholog of a different organism species, and the like. The hsa-miR-4687-3p gene can be obtained by a method described in Persson H et al., 2011, Cancer Res, Vol. 71, p. 78-86. Also, "hsa-mir-4687" (miRBase Accession No. MI0017319, SEQ ID NO: 535) having a hairpin-like structure is known as a precursor of "hsa-miR-4687-3p".

The term "hsa-miR-762 gene" or "hsa-miR-762" used herein includes the hsa-miR-762 gene (miRBase Accession No. MIMAT0010313) described in SEQ ID NO: 261, a homolog or an ortholog of a different organism species, and the like. The hsa-miR-762 gene can be obtained by a method described in Berezikov E et al., 2006, Genome Res, Vol. 16, p. 1289-1298. Also, "hsa-mir-762" (miRBase Accession No. MI0003892, SEQ ID NO: 536) having a hairpin-like structure is known as a precursor of "hsa-miR-762".

The term "hsa-miR-3619-3p gene" or "hsa-miR-3619-3p" used herein includes the hsa-miR-3619-3p gene (miRBase Accession No. MIMAT0019219) described in SEQ ID NO: 262, a homolog or an ortholog of a different organism species, and the like. The hsa-miR-3619-3p gene can be obtained by a method described in Witten D et al., 2010, BMC Biol, Vol. 8, p. 58. Also, "hsa-mir-3619" (miRBase Accession No. MI0016009, SEQ ID NO: 537) having a hairpin-like structure is known as a precursor of "hsa-miR-3619-3p".

The term "hsa-miR-4467 gene" or "hsa-miR-4467" used herein includes the hsa-miR-4467 gene (miRBase Accession No. MIMAT0018994) described in SEQ ID NO: 263, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 538) having a hairpin-like structure is known as a precursor of "hsa-miR-4467".

The term "hsa-miR-557 gene" or "hsa-miR-557" used herein includes the hsa-miR-557 gene (miRBase Accession No. MIMAT0003221) described in SEQ ID NO: 264, a homolog or an ortholog of a different organism species, and the like. The hsa-miR-557 gene can be obtained by a method described in Cummins J M et al., 2006, Proc Natl Acad Sci USA, Vol. 103, p. 3687-3692. Also, "hsa-mir-557" (miRBase Accession No. MI0003563, SEQ ID NO: 539) having a hairpin-like structure is known as a precursor of "hsa-miR-557".

The term "hsa-miR-1237-5p gene" or "hsa-miR-1237-5p" used herein includes the hsa-miR-1237-5p gene (miRBase Accession No. MIMAT0022946) described in SEQ ID NO: 265, a homolog or an ortholog of a different organism species, and the like. The hsa-miR-1237-5p gene can be obtained by a method described in Berezikov E et al., 2007, Mol Cell, Vol. 28, p. 328-336. Also, "hsa-mir-1237" (miRBase Accession No. MI0006327, SEQ ID NO: 540) having a hairpin-like structure is known as a precursor of "hsa-miR-1237-5p".

The term "hsa-miR-1908-5p gene" or "hsa-miR-1908-5p" used herein includes the hsa-miR-1908-5p gene (miRBase Accession No. MIMAT0007881) described in SEQ ID NO: 266, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 541) having a hairpin-like structure is known as a precursor of "hsa-miR-1908-5p".

The term "hsa-miR-4286 gene" or "hsa-miR-4286" used herein includes the hsa-miR-4286 gene (miRBase Accession No. MIMAT0016916) described in SEQ ID NO: 267, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 542) having a hairpin-like structure is known as a precursor of "hsa-miR-4286".

The term "hsa-miR-6885-5p gene" or "hsa-miR-6885-5p" used herein includes the hsa-miR-6885-5p gene (miRBase Accession No. MIMAT0027670) described in SEQ ID NO: 268, a homolog or an ortholog of a different organism species, and the like. The hsa-miR-6885-5p gene can be obtained by a method described in Ladewig E et al., 2012, Genome Res, Vol. 22, p. 1634-1645. Also, "hsa-mir-6885" (miRBase Accession No. MI0022732, SEQ ID NO: 543) having a hairpin-like structure is known as a precursor of "hsa-miR-6885-5p".

The term "hsa-miR-6763-5p gene" or "hsa-miR-6763-5p" used herein includes the hsa-miR-6763-5p gene (miRBase Accession No. MIMAT0027426) described in SEQ ID NO: 269, a homolog or an ortholog of a different organism species, and the like. The hsa-miR-6763-5p gene can be obtained by a method described in Ladewig E et al., 2012, Genome Res, Vol. 22, p. 1634-1645. Also, "hsa-mir-6763" (miRBase Accession No. MI0022608, SEQ ID NO: 544) having a hairpin-like structure is known as a precursor of "hsa-miR-6763-5p".

The term "hsa-miR-6089 gene" or "hsa-miR-6089" used herein includes the hsa-miR-6089 gene (miRBase Accession No. MIMAT0023714) described in SEQ ID NO: 851, a homolog or an ortholog of a different organism species, and the like. The hsa-miR-6089 gene can be obtained by a method described in Yoo J K et al., 2012, Stem Cells Dev, Vol. 21, p. 2049-2057. Also, "hsa-mir-6089-1 and hsa-mir-6089-2" (miRBase Accession Nos. MI0020366 and MI0023563, SEQ ID NOs: 857 and 858) having a hairpin-like structure are known as precursors of "hsa-miR-6089".

The term "hsa-miR-6816-5p gene" or "hsa-miR-6816-5p" used herein includes the hsa-miR-6816-5p gene (miRBase Accession No. MIMAT0027532) described in SEQ ID NO: 852, a homolog or an ortholog of a different organism species, and the like. The hsa-miR-6816-5p gene can be obtained by a method described in Ladewig E et al., 2012, Genome Res., Vol. 22, p. 1634-1645. Also, "hsa-mir-6816" (miRBase Accession No. MI0022661, SEQ ID NO: 859) having a hairpin-like structure is known as a precursor of "hsa-miR-6816-5p".

The term "hsa-miR-4466 gene" or "hsa-miR-4466" used herein includes the hsa-miR-4466 gene (miRBase Accession No. MIMAT0018993) described in SEQ ID NO: 853, a homolog or an ortholog of a different organism species, and the like. The hsa-miR-4466 gene can be obtained by a method described in Jima D D et al., 2010, Blood, Vol. 116, e118-e127. Also, "hsa-mir-4466" (miRBase Accession No. MI0016817, SEQ ID NO: 860) having a hairpin-like structure is known as a precursor of "hsa-miR-4466".

The term "hsa-miR-4488 gene" or "hsa-miR-4488" used herein includes the hsa-miR-4488 gene (miRBase Accession No. MIMAT0019022) described in SEQ ID NO: 854, a homolog or an ortholog of a different organism species, and the like. The hsa-miR-4488 gene can be obtained by a method described in Jima D D et al., 2010, Blood, Vol. 116, e118-e127. Also, "hsa-mir-4488" (miRBase Accession No. MI0016849, SEQ ID NO: 861) having a hairpin-like structure is known as a precursor of "hsa-miR-4488".

The term "hsa-miR-6752-5p gene" or "hsa-miR-6752-5p" used herein includes the hsa-miR-6752-5p gene (miRBase Accession No. MIMAT0027404) described in SEQ ID NO: 855, a homolog or an ortholog of a different organism species, and the like. The hsa-miR-6752-5p gene can be obtained by a method described in Ladewig E et al., 2012, Genome Res., Vol. 22, p. 1634-1645. Also, "hsa-mir-6752" (miRBase Accession No. MI0022597, SEQ ID NO: 862) having a hairpin-like structure is known as a precursor of "hsa-miR-6752-5p".

The term "hsa-miR-4739 gene" or "hsa-miR-4739" used herein includes the hsa-miR-4739 gene (miRBase Accession No. MIMAT0019868) described in SEQ ID NO: 856, a homolog or an ortholog of a different organism species, and the like. The hsa-miR-4739 gene can be obtained by a method described in Persson H et al., 2011, Cancer Res, Vol. 71, p. 78-86. Also, "hsa-mir-4739" (miRBase Accession No. MI0017377, SEQ ID NO: 863) having a hairpin-like structure is known as a precursor of "hsa-miR-4739".

A mature miRNA may become a variant due to the sequence cleaved shorter or longer by one to several upstream or downstream nucleotide(s) substitution when cleaved as the mature miRNA from its RNA precursor having a hairpin-like structure. This variant is called isomiR (Morin R D. et al., 2008, Genome Res., Vol. 18, p. 610-621). The miRBase Release 20 shows the nucleotide sequences represented by SEQ ID NOs: 1 to 269 and 851 to 856 as well as a large number of the nucleotide sequence variants and fragments represented by SEQ ID NOs: 545 to 850 and 864 to 871, called isomiRs. These variants can also be obtained as miRNAs that have a nucleotide sequence represented by any of SEQ ID NOs: 1 to 269 and 851 to 856. Specifically, among the variants of polynucleotides consisting of a nucleotide sequence represented by any of SEQ ID NOs: 1, 2, 3, 4, 5, 6, 8, 11, 14, 15, 19, 20, 21, 23, 27, 28, 31, 35, 37, 38, 40, 42, 43, 47, 48, 50, 51, 52, 55, 56, 58, 60, 61, 62, 64, 65, 66, 67, 71, 72, 73, 76, 77, 78, 79, 80, 82, 83, 85, 86, 88, 89, 90, 92, 95, 97, 98, 99, 100, 102, 103, 107, 109, 110, 113, 114, 115, 116, 117, 118, 120, 122, 123, 126, 127, 129, 131, 133, 137, 141, 142, 143, 145, 146, 148, 149, 153, 154, 155, 156, 157, 161, 164, 165, 167, 168, 171, 172, 173, 178, 179, 180, 181, 182, 184, 185, 188, 191, 192, 194, 195, 196, 199, 201, 202, 204, 207, 210, 213, 215, 217, 219, 222, 223, 225, 230, 232, 233, 234, 235, 236, 238, 239, 240, 241, 242, 243, 245, 246, 247, 248, 249, 250, 251, 252, 254, 258, 259, 260, 263, 265, 266, 267, 851, 853, 854 and 856, or a nucleotide sequence derived from the nucleotide sequence by the replacement of u with t according to the present invention, examples of the longest variants registered in miRBase Release 20 include polynucleotides represented by SEQ ID NOs: 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 607, 609, 611, 613, 615, 617, 619, 621, 623, 625, 627, 629, 631, 633, 635, 637, 639, 641, 643, 645, 647, 649, 651, 653, 655, 657, 659, 661, 663, 665, 667, 669, 671, 673, 675, 677, 679, 681, 683, 685, 687, 689, 691, 693, 695, 697, 699, 701, 703, 705, 707, 709, 711, 713, 715, 717, 719, 721, 723, 725, 727, 729, 731, 733, 735, 737, 739, 741, 743, 745, 747, 749, 751, 753, 755, 757, 759, 761, 763, 765, 767, 769, 771, 773, 775, 777, 779, 781, 783, 785, 787, 789, 791, 793, 795, 797, 799, 801, 803, 805, 807, 809, 811, 813, 815, 817, 819, 821, 823, 825, 827, 829, 831, 833, 835, 837, 839, 841, 843, 845, 847, 849, 864, 866, 868 and 870, respectively. Also, among the variants of polynucleotides consisting of a nucleotide sequence represented by any of SEQ ID NOs: 1, 2, 3, 4, 5, 6, 8, 11, 14, 15, 19, 20, 21, 23, 27, 28, 31, 35, 37, 38, 40, 42, 43, 47, 48, 50, 51, 52, 55, 56, 58, 60, 61, 62, 64, 65, 66, 67, 71, 72, 73, 76, 77, 78, 79, 80, 82, 83, 85, 86, 88, 89, 90, 92, 95, 97, 98, 99, 100, 102, 103, 107, 109, 110, 113, 114, 115, 116, 117, 118, 120, 122, 123, 126, 127, 129, 131, 133, 137, 141, 142, 143, 145, 146, 148, 149, 153, 154, 155, 156, 157, 161, 164, 165, 167, 168, 171, 172, 173, 178, 179, 180, 181, 182, 184, 185, 188, 191, 192, 194, 195, 196, 199, 201, 202, 204, 207, 210, 213, 215, 217, 219, 222, 223, 225, 230, 232, 233, 234, 235, 236, 238, 239, 240, 241, 242, 243, 245, 246, 247, 248, 249, 250, 251, 252, 254, 258, 259, 260, 263, 265, 266, 267, 851, 853, 854 and 856, or a nucleotide sequence derived from the nucleotide sequence by the replacement of u with t according to the present invention, examples of the shortest variants registered in miRBase Release 20 include polynucleotides having sequences represented by SEQ ID NOs: 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 865, 867, 869 and 871, respectively. In addition to these variants and fragments, examples thereof include a large number of isomiR polynucleotides of SEQ ID NOs: 1 to 269 and 851 to 856 registered in miRBase. Examples of the polynucleotide comprising a nucleotide sequence represented by any of SEQ ID NOs: 1 to 269 and 851 to 856 include a polynucleotide represented by any of SEQ ID NOs: 270 to 544, and 857 to 863, which are their respective precursors.

The names and miRBase Accession Nos. (registration numbers) of the genes represented by SEQ ID NOs: 1 to 871 are shown in Table 1.

The term "capable of specifically binding" used herein means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-4783-3p | MIMAT0019947 |
| 2 | hsa-miR-4730 | MIMAT0019852 |
| 3 | hsa-miR-1307-3p | MIMAT0005951 |
| 4 | hsa-miR-4634 | MIMAT0019691 |
| 5 | hsa-miR-663a | MIMAT0003326 |
| 6 | hsa-miR-4532 | MIMAT0019071 |
| 7 | hsa-miR-7704 | MIMAT0030019 |
| 8 | hsa-miR-3178 | MIMAT0015055 |
| 9 | hsa-miR-6729-5p | MIMAT0027359 |
| 10 | hsa-miR-6090 | MIMAT0023715 |
| 11 | hsa-miR-4732-5p | MIMAT0019855 |
| 12 | hsa-miR-3184-5p | MIMAT0015064 |
| 13 | hsa-miR-6727-5p | MIMAT0027355 |
| 14 | hsa-miR-6088 | MIMAT0023713 |
| 15 | hsa-miR-4674 | MIMAT0019756 |
| 16 | hsa-miR-8073 | MIMAT0031000 |
| 17 | hsa-miR-4787-5p | MIMAT0019956 |
| 18 | hsa-miR-1469 | MIMAT0007347 |
| 19 | hsa-miR-125a-3p | MIMAT0004602 |
| 20 | hsa-miR-1233-5p | MIMAT0022943 |
| 21 | hsa-miR-885-3p | MIMAT0004948 |
| 22 | hsa-miR-6802-5p | MIMAT0027504 |
| 23 | hsa-miR-328-5p | MIMAT0026486 |
| 24 | hsa-miR-6787-5p | MIMAT0027474 |
| 25 | hsa-miR-8069 | MIMAT0030996 |
| 26 | hsa-miR-6875-5p | MIMAT0027650 |
| 27 | hsa-miR-1246 | MIMAT0005898 |
| 28 | hsa-miR-4734 | MIMAT0019859 |
| 29 | hsa-miR-6757-5p | MIMAT0027414 |
| 30 | hsa-miR-6756-5p | MIMAT0027412 |
| 31 | hsa-miR-3665 | MIMAT0018087 |
| 32 | hsa-miR-6836-3p | MIMAT0027575 |
| 33 | hsa-miR-6821-5p | MIMAT0027542 |
| 34 | hsa-miR-6805-5p | MIMAT0027510 |
| 35 | hsa-miR-4728-5p | MIMAT0019849 |
| 36 | hsa-miR-6726-5p | MIMAT0027353 |
| 37 | hsa-miR-197-5p | MIMAT0022691 |
| 38 | hsa-miR-149-3p | MIMAT0004609 |
| 39 | hsa-miR-6850-5p | MIMAT0027600 |
| 40 | hsa-miR-4476 | MIMAT0019003 |
| 41 | hsa-miR-6858-5p | MIMAT0027616 |
| 42 | hsa-miR-564 | MIMAT0003228 |
| 43 | hsa-miR-4763-3p | MIMAT0019913 |
| 44 | hsa-miR-575 | MIMAT0003240 |
| 45 | hsa-miR-6771-5p | MIMAT0027442 |
| 46 | hsa-miR-1231 | MIMAT0005586 |
| 47 | hsa-miR-1908-3p | MIMAT0026916 |
| 48 | hsa-miR-150-3p | MIMAT0004610 |
| 49 | hsa-miR-3937 | MIMAT0018352 |
| 50 | hsa-miR-887-3p | MIMAT0004951 |
| 51 | hsa-miR-3940-5p | MIMAT0019229 |
| 52 | hsa-miR-4741 | MIMAT0019871 |
| 53 | hsa-miR-6808-5p | MIMAT0027516 |
| 54 | hsa-miR-6869-5p | MIMAT0027638 |

TABLE 1-continued

| SEQ ID NO: | Gene name | miRBase registration No. |
|---|---|---|
| 55 | hsa-miR-5090 | MIMAT0021082 |
| 56 | hsa-miR-615-5p | MIMAT0004804 |
| 57 | hsa-miR-8072 | MIMAT0030999 |
| 58 | hsa-miR-128-1-5p | MIMAT0026477 |
| 59 | hsa-miR-1238-5p | MIMAT0022947 |
| 60 | hsa-miR-365a-5p | MIMAT0009199 |
| 61 | hsa-miR-204-3p | MIMAT0022693 |
| 62 | hsa-miR-4492 | MIMAT0019027 |
| 63 | hsa-miR-6785-5p | MIMAT0027470 |
| 64 | hsa-miR-6511a-5p | MIMAT0025478 |
| 65 | hsa-miR-4525 | MIMAT0019064 |
| 66 | hsa-miR-1915-5p | MIMAT0007891 |
| 67 | hsa-miR-3180 | MIMAT0018178 |
| 68 | hsa-miR-6879-5p | MIMAT0027658 |
| 69 | hsa-miR-1199-5p | MIMAT0031119 |
| 70 | hsa-miR-6746-5p | MIMAT0027392 |
| 71 | hsa-miR-711 | MIMAT0012734 |
| 72 | hsa-miR-663b | MIMAT0005867 |
| 73 | hsa-miR-4707-3p | MIMAT0019808 |
| 74 | hsa-miR-6893-5p | MIMAT0027686 |
| 75 | hsa-miR-4675 | MIMAT0019757 |
| 76 | hsa-miR-4638-5p | MIMAT0019695 |
| 77 | hsa-miR-4651 | MIMAT0019715 |
| 78 | hsa-miR-6087 | MIMAT0023712 |
| 79 | hsa-miR-4665-5p | MIMAT0019739 |
| 80 | hsa-miR-4758-5p | MIMAT0019903 |
| 81 | hsa-miR-6887-5p | MIMAT0027674 |
| 82 | hsa-miR-3620-5p | MIMAT0022967 |
| 83 | hsa-miR-1909-3p | MIMAT0007883 |
| 84 | hsa-miR-7641 | MIMAT0029782 |
| 85 | hsa-miR-6724-5p | MIMAT0025856 |
| 86 | hsa-miR-1343-3p | MIMAT0019776 |
| 87 | hsa-miR-6780b-5p | MIMAT0027572 |
| 88 | hsa-miR-4484 | MIMAT0019018 |
| 89 | hsa-miR-4690-5p | MIMAT0019779 |
| 90 | hsa-miR-4429 | MIMAT0018944 |
| 91 | hsa-miR-1227-5p | MIMAT0022941 |
| 92 | hsa-miR-4725-3p | MIMAT0019844 |
| 93 | hsa-miR-6861-5p | MIMAT0027623 |
| 94 | hsa-miR-6812-5p | MIMAT0027524 |
| 95 | hsa-miR-3197 | MIMAT0015082 |
| 96 | hsa-miR-8059 | MIMAT0030986 |
| 97 | hsa-miR-3185 | MIMAT0015065 |
| 98 | hsa-miR-4706 | MIMAT0019806 |
| 99 | hsa-miR-4497 | MIMAT0019032 |
| 100 | hsa-miR-3131 | MIMAT0014996 |
| 101 | hsa-miR-6806-5p | MIMAT0027512 |
| 102 | hsa-miR-187-5p | MIMAT0004561 |
| 103 | hsa-miR-3180-3p | MIMAT0015058 |
| 104 | hsa-miR-6848-5p | MIMAT0027596 |
| 105 | hsa-miR-6820-5p | MIMAT0027540 |
| 106 | hsa-miR-6800-5p | MIMAT0027500 |
| 107 | hsa-miR-6717-5p | MIMAT0025846 |
| 108 | hsa-miR-6795-5p | MIMAT0027490 |
| 109 | hsa-miR-4632-5p | MIMAT0022977 |
| 110 | hsa-miR-665 | MIMAT0004952 |
| 111 | hsa-miR-6778-5p | MIMAT0027456 |
| 112 | hsa-miR-3663-3p | MIMAT0018085 |
| 113 | hsa-miR-4689 | MIMAT0019778 |
| 114 | hsa-miR-211-3p | MIMAT0022694 |
| 115 | hsa-miR-6511b-5p | MIMAT0025847 |
| 116 | hsa-miR-4750-5p | MIMAT0019887 |
| 117 | hsa-miR-6126 | MIMAT0024599 |
| 118 | hsa-miR-614 | MIMAT0003282 |
| 119 | hsa-miR-7110-5p | MIMAT0028117 |
| 120 | hsa-miR-744-5p | MIMAT0004945 |
| 121 | hsa-miR-6769a-5p | MIMAT0027438 |
| 122 | hsa-miR-4792 | MIMAT0019964 |
| 123 | hsa-miR-5787 | MIMAT0023252 |
| 124 | hsa-miR-6798-5p | MIMAT0027496 |
| 125 | hsa-miR-6781-5p | MIMAT0027462 |
| 126 | hsa-miR-4419b | MIMAT0019034 |
| 127 | hsa-miR-4446-3p | MIMAT0018965 |
| 128 | hsa-miR-4259 | MIMAT0016880 |
| 129 | hsa-miR-5572 | MIMAT0022260 |
| 130 | hsa-miR-6075 | MIMAT0023700 |
| 131 | hsa-miR-296-3p | MIMAT0004679 |
| 132 | hsa-miR-6891-5p | MIMAT0027682 |
| 133 | hsa-miR-4745-5p | MIMAT0019878 |
| 134 | hsa-miR-6775-5p | MIMAT0027450 |
| 135 | hsa-miR-6870-5p | MIMAT0027640 |
| 136 | hsa-miR-920 | MIMAT0004970 |
| 137 | hsa-miR-4530 | MIMAT0019069 |
| 138 | hsa-miR-6819-5p | MIMAT0027538 |
| 139 | hsa-miR-6825-5p | MIMAT0027550 |
| 140 | hsa-miR-7847-3p | MIMAT0030422 |
| 141 | hsa-miR-6131 | MIMAT0024615 |
| 142 | hsa-miR-4433-3p | MIMAT0018949 |
| 143 | hsa-miR-1228-5p | MIMAT0005582 |
| 144 | hsa-miR-6743-5p | MIMAT0027387 |
| 145 | hsa-miR-1268a | MIMAT0005922 |
| 146 | hsa-miR-3917 | MIMAT0018191 |
| 147 | hsa-miR-6786-5p | MIMAT0027472 |
| 148 | hsa-miR-3154 | MIMAT0015028 |
| 149 | hsa-miR-638 | MIMAT0003308 |
| 150 | hsa-miR-6741-5p | MIMAT0027383 |
| 151 | hsa-miR-6889-5p | MIMAT0027678 |
| 152 | hsa-miR-6840-3p | MIMAT0027583 |
| 153 | hsa-miR-6510-5p | MIMAT0025476 |
| 154 | hsa-miR-3188 | MIMAT0015070 |
| 155 | hsa-miR-551b-5p | MIMAT0004794 |
| 156 | hsa-miR-5001-5p | MIMAT0021021 |
| 157 | hsa-miR-1268b | MIMAT0018925 |
| 158 | hsa-miR-7107-5p | MIMAT0028111 |
| 159 | hsa-miR-6824-5p | MIMAT0027548 |
| 160 | hsa-miR-6732-5p | MIMAT0027365 |
| 161 | hsa-miR-371a-5p | MIMAT0004687 |
| 162 | hsa-miR-6794-5p | MIMAT0027488 |
| 163 | hsa-miR-6779-5p | MIMAT0027458 |
| 164 | hsa-miR-4271 | MIMAT0016901 |
| 165 | hsa-miR-5195-3p | MIMAT0021127 |
| 166 | hsa-miR-6762-5p | MIMAT0027424 |
| 167 | hsa-miR-939-5p | MIMAT0004982 |
| 168 | hsa-miR-1247-3p | MIMAT0022721 |
| 169 | hsa-miR-6777-5p | MIMAT0027454 |
| 170 | hsa-miR-6722-3p | MIMAT0025854 |
| 171 | hsa-miR-3656 | MIMAT0018076 |
| 172 | hsa-miR-4688 | MIMAT0019777 |
| 173 | hsa-miR-3195 | MIMAT0015079 |
| 174 | hsa-miR-6766-5p | MIMAT0027432 |
| 175 | hsa-miR-4447 | MIMAT0018966 |
| 176 | hsa-miR-4656 | MIMAT0019723 |
| 177 | hsa-miR-7108-5p | MIMAT0028113 |
| 178 | hsa-miR-3191-3p | MIMAT0015075 |
| 179 | hsa-miR-1273g-3p | MIMAT0022742 |
| 180 | hsa-miR-4463 | MIMAT0018987 |
| 181 | hsa-miR-2861 | MIMAT0013802 |
| 182 | hsa-miR-3196 | MIMAT0015080 |
| 183 | hsa-miR-6877-5p | MIMAT0027654 |
| 184 | hsa-miR-3679-5p | MIMAT0018104 |
| 185 | hsa-miR-4442 | MIMAT0018960 |
| 186 | hsa-miR-6789-5p | MIMAT0027478 |
| 187 | hsa-miR-6782-5p | MIMAT0027464 |
| 188 | hsa-miR-486-3p | MIMAT0004762 |
| 189 | hsa-miR-6085 | MIMAT0023710 |
| 190 | hsa-miR-4746-3p | MIMAT0019881 |
| 191 | hsa-miR-619-5p | MIMAT0026622 |
| 192 | hsa-miR-937-5p | MIMAT0022938 |
| 193 | hsa-miR-6803-5p | MIMAT0027506 |
| 194 | hsa-miR-4298 | MIMAT0016852 |
| 195 | hsa-miR-4454 | MIMAT0018976 |
| 196 | hsa-miR-4459 | MIMAT0018981 |
| 197 | hsa-miR-7150 | MIMAT0028211 |
| 198 | hsa-miR-6880-5p | MIMAT0027660 |
| 199 | hsa-miR-4449 | MIMAT0018968 |
| 200 | hsa-miR-8063 | MIMAT0030990 |
| 201 | hsa-miR-4695-5p | MIMAT0019788 |
| 202 | hsa-miR-6132 | MIMAT0024616 |
| 203 | hsa-miR-6829-5p | MIMAT0027558 |
| 204 | hsa-miR-4486 | MIMAT0019020 |
| 205 | hsa-miR-6805-3p | MIMAT0027511 |
| 206 | hsa-miR-6826-5p | MIMAT0027552 |
| 207 | hsa-miR-4508 | MIMAT0019045 |
| 208 | hsa-miR-1343-5p | MIMAT0027038 |

TABLE 1-continued

| SEQ ID NO: | Gene name | miRBase registration No. |
|---|---|---|
| 209 | hsa-miR-7114-5p | MIMAT0028125 |
| 210 | hsa-miR-3622a-5p | MIMAT0018003 |
| 211 | hsa-miR-6765-5p | MIMAT0027430 |
| 212 | hsa-miR-7845-5p | MIMAT0030420 |
| 213 | hsa-miR-3960 | MIMAT0019337 |
| 214 | hsa-miR-6749-5p | MIMAT0027398 |
| 215 | hsa-miR-1260b | MIMAT0015041 |
| 216 | hsa-miR-6799-5p | MIMAT0027498 |
| 217 | hsa-miR-4723-5p | MIMAT0019838 |
| 218 | hsa-miR-6784-5p | MIMAT0027468 |
| 219 | hsa-miR-5100 | MIMAT0022259 |
| 220 | hsa-miR-6769b-5p | MIMAT0027620 |
| 221 | hsa-miR-1207-5p | MIMAT0005871 |
| 222 | hsa-miR-642a-3p | MIMAT0020924 |
| 223 | hsa-miR-4505 | MIMAT0019041 |
| 224 | hsa-miR-4270 | MIMAT0016900 |
| 225 | hsa-miR-6721-5p | MIMAT0025852 |
| 226 | hsa-miR-7111-5p | MIMAT0028119 |
| 227 | hsa-miR-6791-5p | MIMAT0027482 |
| 228 | hsa-miR-7109-5p | MIMAT0028115 |
| 229 | hsa-miR-4258 | MIMAT0016879 |
| 230 | hsa-miR-6515-3p | MIMAT0025487 |
| 231 | hsa-miR-6851-5p | MIMAT0027602 |
| 232 | hsa-miR-6125 | MIMAT0024598 |
| 233 | hsa-miR-4749-5p | MIMAT0019885 |
| 234 | hsa-miR-4726-5p | MIMAT0019845 |
| 235 | hsa-miR-4513 | MIMAT0019050 |
| 236 | hsa-miR-760 | MIMAT0004957 |
| 237 | hsa-miR-602 | MIMAT0003270 |
| 238 | hsa-miR-423-5p | MIMAT0004748 |
| 239 | hsa-miR-92a-2-5p | MIMAT0004508 |
| 240 | hsa-miR-16-5p | MIMAT0000069 |
| 241 | hsa-miR-451a | MIMAT0001631 |
| 242 | hsa-miR-135a-3p | MIMAT0004595 |
| 243 | hsa-miR-486-5p | MIMAT0002177 |
| 244 | hsa-miR-4257 | MIMAT0016878 |
| 245 | hsa-miR-92b-5p | MIMAT0004792 |
| 246 | hsa-miR-1915-3p | MIMAT0007892 |
| 247 | hsa-miR-718 | MIMAT0012735 |
| 248 | hsa-miR-940 | MIMAT0004983 |
| 249 | hsa-miR-296-5p | MIMAT0000690 |
| 250 | hsa-miR-23b-3p | MIMAT0000418 |
| 251 | hsa-miR-92a-3p | MIMAT0000092 |
| 252 | hsa-miR-658 | MIMAT0003336 |
| 253 | hsa-miR-6842-5p | MIMAT0027586 |
| 254 | hsa-miR-6124 | MIMAT0024597 |
| 255 | hsa-miR-6765-3p | MIMAT0027431 |
| 256 | hsa-miR-7106-5p | MIMAT0028109 |
| 257 | hsa-miR-4534 | MIMAT0019073 |
| 258 | hsa-miR-92b-3p | MIMAT0003218 |
| 259 | hsa-miR-3135b | MIMAT0018985 |
| 260 | hsa-miR-4687-3p | MIMAT0019775 |
| 261 | hsa-miR-762 | MIMAT0010313 |
| 262 | hsa-miR-3619-3p | MIMAT0019219 |
| 263 | hsa-miR-4467 | MIMAT0018994 |
| 264 | hsa-miR-557 | MIMAT0003221 |
| 265 | hsa-miR-1237-5p | MIMAT0022946 |
| 266 | hsa-miR-1908-5p | MIMAT0007881 |
| 267 | hsa-miR-4286 | MIMAT0016916 |
| 268 | hsa-miR-6885-5p | MIMAT0027670 |
| 269 | hsa-miR-6763-5p | MIMAT0027426 |
| 270 | hsa-mir-4783 | MI0017428 |
| 271 | hsa-mir-4730 | MI0017367 |
| 272 | hsa-mir-1307 | MI0006444 |
| 273 | hsa-mir-4634 | MI0017261 |
| 274 | hsa-mir-663a | MI0003672 |
| 275 | hsa-mir-4532 | MI0016899 |
| 276 | hsa-mir-7704 | MI0025240 |
| 277 | hsa-mir-3178 | MI0014212 |
| 278 | hsa-mir-6729 | MI0022574 |
| 279 | hsa-mir-6090 | MI0020367 |
| 280 | hsa-mir-4732 | MI0017369 |
| 281 | hsa-mir-3184 | MI0014226 |
| 282 | hsa-mir-6727 | MI0022572 |
| 283 | hsa-mir-6088 | MI0020365 |
| 284 | hsa-mir-4674 | MI0017305 |
| 285 | hsa-mir-8073 | MI0025909 |
| 286 | hsa-mir-4787 | MI0017434 |
| 287 | hsa-mir-1469 | MI0007074 |
| 288 | hsa-mir-125a | MI0000469 |
| 289 | hsa-mir-1233-1 | MI0006323 |
| 290 | hsa-mir-1233-2 | MI0015973 |
| 291 | hsa-mir-885 | MI0005560 |
| 292 | hsa-mir-6802 | MI0022647 |
| 293 | hsa-mir-328 | MI0000804 |
| 294 | hsa-mir-6787 | MI0022632 |
| 295 | hsa-mir-8069 | MI0025905 |
| 296 | hsa-mir-6875 | MI0022722 |
| 297 | hsa-mir-1246 | MI0006381 |
| 298 | hsa-mir-4734 | MI0017371 |
| 299 | hsa-mir-6757 | MI0022602 |
| 300 | hsa-mir-6756 | MI0022601 |
| 301 | hsa-mir-3665 | MI0016066 |
| 302 | hsa-mir-6836 | MI0022682 |
| 303 | hsa-mir-6821 | MI0022666 |
| 304 | hsa-mir-6805 | MI0022650 |
| 305 | hsa-mir-4728 | MI0017365 |
| 306 | hsa-mir-6726 | MI0022571 |
| 307 | hsa-mir-197 | MI0000239 |
| 308 | hsa-mir-149 | MI0000478 |
| 309 | hsa-mir-6850 | MI0022696 |
| 310 | hsa-mir-4476 | MI0016828 |
| 311 | hsa-mir-6858 | MI0022704 |
| 312 | hsa-mir-564 | MI0003570 |
| 313 | hsa-mir-4763 | MI0017404 |
| 314 | hsa-mir-575 | MI0003582 |
| 315 | hsa-mir-6771 | MI0022616 |
| 316 | hsa-mir-1231 | MI0006321 |
| 317 | hsa-mir-1908 | MI0008329 |
| 318 | hsa-mir-150 | MI0000479 |
| 319 | hsa-mir-3937 | MI0016593 |
| 320 | hsa-mir-887 | MI0005562 |
| 321 | hsa-mir-3940 | MI0016597 |
| 322 | hsa-mir-4741 | MI0017379 |
| 323 | hsa-mir-6808 | MI0022653 |
| 324 | hsa-mir-6869 | MI0022716 |
| 325 | hsa-mir-5090 | MI0017979 |
| 326 | hsa-mir-615 | MI0003628 |
| 327 | hsa-mir-8072 | MI0025908 |
| 328 | hsa-mir-128-1 | MI0000447 |
| 329 | hsa-mir-1238 | MI0006328 |
| 330 | hsa-mir-365a | MI0000767 |
| 331 | hsa-mir-204 | MI0000284 |
| 332 | hsa-mir-4492 | MI0016854 |
| 333 | hsa-mir-6785 | MI0022630 |
| 334 | hsa-mir-6511a-1 | MI0022223 |
| 335 | hsa-mir-6511a-2 | MI0023564 |
| 336 | hsa-mir-6511a-3 | MI0023565 |
| 337 | hsa-mir-6511a-4 | MI0023566 |
| 338 | hsa-mir-4525 | MI0016892 |
| 339 | hsa-mir-1915 | MI0008336 |
| 340 | hsa-mir-3180-4 | MI0016408 |
| 341 | hsa-mir-3180-5 | MI0016409 |
| 342 | hsa-mir-6879 | MI0022726 |
| 343 | hsa-mir-1199 | MI0020340 |
| 344 | hsa-mir-6746 | MI0022591 |
| 345 | hsa-mir-711 | MI0012488 |
| 346 | hsa-mir-663b | MI0006336 |
| 347 | hsa-mir-4707 | MI0017340 |
| 348 | hsa-mir-6893 | MI0022740 |
| 349 | hsa-mir-4675 | MI0017306 |
| 350 | hsa-mir-4638 | MI0017265 |
| 351 | hsa-mir-4651 | MI0017279 |
| 352 | hsa-mir-6087 | MI0020364 |
| 353 | hsa-mir-4665 | MI0017295 |
| 354 | hsa-mir-4758 | MI0017399 |
| 355 | hsa-mir-6887 | MI0022734 |
| 356 | hsa-mir-3620 | MI0016011 |
| 357 | hsa-mir-1909 | MI0008330 |
| 358 | hsa-mir-7641-1 | MI0024975 |
| 359 | hsa-mir-7641-2 | MI0024976 |
| 360 | hsa-mir-6724 | MI0022559 |
| 361 | hsa-mir-1343 | MI0017320 |
| 362 | hsa-mir-6780b | MI0022681 |

TABLE 1-continued

| SEQ ID NO: | Gene name | miRBase registration No. |
|---|---|---|
| 363 | hsa-mir-4484 | MI0016845 |
| 364 | hsa-mir-4690 | MI0017323 |
| 365 | hsa-mir-4429 | MI0016768 |
| 366 | hsa-mir-1227 | MI0006316 |
| 367 | hsa-mir-4725 | MI0017362 |
| 368 | hsa-mir-6861 | MI0022708 |
| 369 | hsa-mir-6812 | MI0022657 |
| 370 | hsa-mir-3197 | MI0014245 |
| 371 | hsa-mir-8059 | MI0025895 |
| 372 | hsa-mir-3185 | MI0014227 |
| 373 | hsa-mir-4706 | MI0017339 |
| 374 | hsa-mir-4497 | MI0016859 |
| 375 | hsa-mir-3131 | MI0014151 |
| 376 | hsa-mir-6806 | MI0022651 |
| 377 | hsa-mir-187 | MI0000274 |
| 378 | hsa-mir-3180-1 | MI0014214 |
| 379 | hsa-mir-3180-2 | MI0014215 |
| 380 | hsa-mir-3180-3 | MI0014217 |
| 381 | hsa-mir-6848 | MI0022694 |
| 382 | hsa-mir-6820 | MI0022665 |
| 383 | hsa-mir-6800 | MI0022645 |
| 384 | hsa-mir-6717 | MI0022551 |
| 385 | hsa-mir-6795 | MI0022640 |
| 386 | hsa-mir-4632 | MI0017259 |
| 387 | hsa-mir-665 | MI0005563 |
| 388 | hsa-mir-6778 | MI0022623 |
| 389 | hsa-mir-3663 | MI0016064 |
| 390 | hsa-mir-4689 | MI0017322 |
| 391 | hsa-mir-211 | MI0000287 |
| 392 | hsa-mir-6511b-1 | MI0022552 |
| 393 | hsa-mir-6511b-2 | MI0023431 |
| 394 | hsa-mir-4750 | MI0017389 |
| 395 | hsa-mir-6126 | MI0021260 |
| 396 | hsa-mir-614 | MI0003627 |
| 397 | hsa-mir-7110 | MI0022961 |
| 398 | hsa-mir-744 | MI0005559 |
| 399 | hsa-mir-6769a | MI0022614 |
| 400 | hsa-mir-4792 | MI0017439 |
| 401 | hsa-mir-5787 | MI0019797 |
| 402 | hsa-mir-6798 | MI0022643 |
| 403 | hsa-mir-6781 | MI0022626 |
| 404 | hsa-mir-4419b | MI0016861 |
| 405 | hsa-mir-4446 | MI0016789 |
| 406 | hsa-mir-4259 | MI0015858 |
| 407 | hsa-mir-5572 | MI0019117 |
| 408 | hsa-mir-6075 | MI0020352 |
| 409 | hsa-mir-296 | MI0000747 |
| 410 | hsa-mir-6891 | MI0022738 |
| 411 | hsa-mir-4745 | MI0017384 |
| 412 | hsa-mir-6775 | MI0022620 |
| 413 | hsa-mir-6870 | MI0022717 |
| 414 | hsa-mir-920 | MI0005712 |
| 415 | hsa-mir-4530 | MI0016897 |
| 416 | hsa-mir-6819 | MI0022664 |
| 417 | hsa-mir-6825 | MI0022670 |
| 418 | hsa-mir-7847 | MI0025517 |
| 419 | hsa-mir-6131 | MI0021276 |
| 420 | hsa-mir-4433 | MI0016773 |
| 421 | hsa-mir-1228 | MI0006318 |
| 422 | hsa-mir-6743 | MI0022588 |
| 423 | hsa-mir-1268a | MI0006405 |
| 424 | hsa-mir-3917 | MI0016423 |
| 425 | hsa-mir-6786 | MI0022631 |
| 426 | hsa-mir-3154 | MI0014182 |
| 427 | hsa-mir-638 | MI0003653 |
| 428 | hsa-mir-6741 | MI0022586 |
| 429 | hsa-mir-6889 | MI0022736 |
| 430 | hsa-mir-6840 | MI0022686 |
| 431 | hsa-mir-6510 | MI0022222 |
| 432 | hsa-mir-3188 | MI0014232 |
| 433 | hsa-mir-551b | MI0003575 |
| 434 | hsa-mir-5001 | MI0017867 |
| 435 | hsa-mir-1268b | MI0016748 |
| 436 | hsa-mir-7107 | MI0022958 |
| 437 | hsa-mir-6824 | MI0022669 |
| 438 | hsa-mir-6732 | MI0022577 |
| 439 | hsa-mir-371a | MI0000779 |
| 440 | hsa-mir-6794 | MI0022639 |
| 441 | hsa-mir-6779 | MI0022624 |
| 442 | hsa-mir-4271 | MI0015879 |
| 443 | hsa-mir-5195 | MI0018174 |
| 444 | hsa-mir-6762 | MI0022607 |
| 445 | hsa-mir-939 | MI0005761 |
| 446 | hsa-mir-1247 | MI0006382 |
| 447 | hsa-mir-6777 | MI0022622 |
| 448 | hsa-mir-6722 | MI0022557 |
| 449 | hsa-mir-3656 | MI0016056 |
| 450 | hsa-mir-4688 | MI0017321 |
| 451 | hsa-mir-3195 | MI0014240 |
| 452 | hsa-mir-6766 | MI0022611 |
| 453 | hsa-mir-4447 | MI0016790 |
| 454 | hsa-mir-4656 | MI0017284 |
| 455 | hsa-mir-7108 | MI0022959 |
| 456 | hsa-mir-3191 | MI0014236 |
| 457 | hsa-mir-1273g | MI0018003 |
| 458 | hsa-mir-4463 | MI0016811 |
| 459 | hsa-mir-2861 | MI0013006 |
| 460 | hsa-mir-3196 | MI0014241 |
| 461 | hsa-mir-6877 | MI0022724 |
| 462 | hsa-mir-3679 | MI0016080 |
| 463 | hsa-mir-4442 | MI0016785 |
| 464 | hsa-mir-6789 | MI0022634 |
| 465 | hsa-mir-6782 | MI0022627 |
| 466 | hsa-mir-486 | MI0002470 |
| 467 | hsa-mir-486-2 | MI0023622 |
| 468 | hsa-mir-6085 | MI0020362 |
| 469 | hsa-mir-4746 | MI0017385 |
| 470 | hsa-mir-619 | MI0003633 |
| 471 | hsa-mir-937 | MI0005759 |
| 472 | hsa-mir-6803 | MI0022648 |
| 473 | hsa-mir-4298 | MI0015830 |
| 474 | hsa-mir-4454 | MI0016800 |
| 475 | hsa-mir-4459 | MI0016805 |
| 476 | hsa-mir-7150 | MI0023610 |
| 477 | hsa-mir-6880 | MI0022727 |
| 478 | hsa-mir-4449 | MI0016792 |
| 479 | hsa-mir-8063 | MI0025899 |
| 480 | hsa-mir-4695 | MI0017328 |
| 481 | hsa-mir-6132 | MI0021277 |
| 482 | hsa-mir-6829 | MI0022674 |
| 483 | hsa-mir-4486 | MI0016847 |
| 484 | hsa-mir-6826 | MI0022671 |
| 485 | hsa-mir-4508 | MI0016872 |
| 486 | hsa-mir-7114 | MI0022965 |
| 487 | hsa-mir-3622a | MI0016013 |
| 488 | hsa-mir-6765 | MI0022610 |
| 489 | hsa-mir-7845 | MI0025515 |
| 490 | hsa-mir-3960 | MI0016964 |
| 491 | hsa-mir-6749 | MI0022594 |
| 492 | hsa-mir-1260b | MI0014197 |
| 493 | hsa-mir-6799 | MI0022644 |
| 494 | hsa-mir-4723 | MI0017359 |
| 495 | hsa-mir-6784 | MI0022629 |
| 496 | hsa-mir-5100 | MI0019116 |
| 497 | hsa-mir-6769b | MI0022706 |
| 498 | hsa-mir-1207 | MI0006340 |
| 499 | hsa-mir-642a | MI0003657 |
| 500 | hsa-mir-4505 | MI0016868 |
| 501 | hsa-mir-4270 | MI0015878 |
| 502 | hsa-mir-6721 | MI0022556 |
| 503 | hsa-mir-7111 | MI0022962 |
| 504 | hsa-mir-6791 | MI0022636 |
| 505 | hsa-mir-7109 | MI0022960 |
| 506 | hsa-mir-4258 | MI0015857 |
| 507 | hsa-mir-6515 | MI0022227 |
| 508 | hsa-mir-6851 | MI0022697 |
| 509 | hsa-mir-6125 | MI0021259 |
| 510 | hsa-mir-4749 | MI0017388 |
| 511 | hsa-mir-4726 | MI0017363 |
| 512 | hsa-mir-4513 | MI0016879 |
| 513 | hsa-mir-760 | MI0005567 |
| 514 | hsa-mir-602 | MI0003615 |
| 515 | hsa-mir-423 | MI0001445 |
| 516 | hsa-mir-92a-2 | MI0000094 |

TABLE 1-continued

| SEQ ID NO: | Gene name | miRBase registration No. |
|---|---|---|
| 517 | hsa-mir-16-1 | MI0000070 |
| 518 | hsa-mir-16-2 | MI0000115 |
| 519 | hsa-mir-451a | MI0001729 |
| 520 | hsa-mir-135a | MI0000452 |
| 521 | hsa-mir-4257 | MI0015856 |
| 522 | hsa-mir-92b | MI0003560 |
| 523 | hsa-mir-718 | MI0012489 |
| 524 | hsa-mir-940 | MI0005762 |
| 525 | hsa-mir-23b | MI0000439 |
| 526 | hsa-mir-92a-1 | MI0000093 |
| 527 | hsa-mir-92a-2 | MI0000094 |
| 528 | hsa-mir-658 | MI0003682 |
| 529 | hsa-mir-6842 | MI0022688 |
| 530 | hsa-mir-6124 | MI0021258 |
| 531 | hsa-mir-6765 | MI0022610 |
| 532 | hsa-mir-7106 | MI0022957 |
| 533 | hsa-mir-4534 | MI0016901 |
| 534 | hsa-mir-3135b | MI0016809 |
| 535 | hsa-mir-4687 | MI0017319 |
| 536 | hsa-mir-762 | MI0003892 |
| 537 | hsa-mir-3619 | MI0016009 |
| 538 | hsa-mir-4467 | MI0016818 |
| 539 | hsa-mir-557 | MI0003563 |
| 540 | hsa-mir-1237 | MI0006327 |
| 541 | hsa-mir-1908 | MI0008329 |
| 542 | hsa-mir-4286 | MI0015894 |
| 543 | hsa-mir-6885 | MI0022732 |
| 544 | hsa-mir-6763 | MI0022608 |
| 545 | isomiR example 1 of SEQ ID NO: 1 | — |
| 546 | isomiR example 2 of SEQ ID NO: 1 | — |
| 547 | isomiR example 1 of SEQ ID NO: 2 | — |
| 548 | isomiR example 2 of SEQ ID NO: 2 | — |
| 549 | isomiR example 1 of SEQ ID NO: 3 | — |
| 550 | isomiR example 2 of SEQ ID NO: 3 | — |
| 551 | isomiR example 1 of SEQ ID NO: 4 | — |
| 552 | isomiR example 2 of SEQ ID NO: 4 | — |
| 553 | isomiR example 1 of SEQ ID NO: 5 | — |
| 554 | isomiR example 2 of SEQ ID NO: 5 | — |
| 555 | isomiR example 1 of SEQ ID NO: 6 | — |
| 556 | isomiR example 2 of SEQ ID NO: 6 | — |
| 557 | isomiR example 1 of SEQ ID NO: 8 | — |
| 558 | isomiR example 2 of SEQ ID NO: 8 | — |
| 559 | isomiR example 1 of SEQ ID NO: 11 | — |
| 560 | isomiR example 2 of SEQ ID NO: 11 | — |
| 561 | isomiR example 1 of SEQ ID NO: 14 | — |
| 562 | isomiR example 2 of SEQ ID NO: 14 | — |
| 563 | isomiR example 1 of SEQ ID NO: 15 | — |
| 564 | isomiR example 2 of SEQ ID NO: 15 | — |
| 565 | isomiR example 1 of SEQ ID NO: 19 | — |
| 566 | isomiR example 2 of SEQ ID NO: 19 | — |
| 567 | isomiR example 1 of SEQ ID NO: 20 | — |
| 568 | isomiR example 2 of SEQ ID NO: 20 | — |
| 569 | isomiR example 1 of SEQ ID NO: 21 | — |
| 570 | isomiR example 2 of SEQ ID NO: 21 | — |
| 571 | isomiR example 1 of SEQ ID NO: 23 | — |
| 572 | isomiR example 2 of SEQ ID NO: 23 | — |
| 573 | isomiR example 1 of SEQ ID NO: 27 | — |
| 574 | isomiR example 2 of SEQ ID NO: 27 | — |
| 575 | isomiR example 1 of SEQ ID NO: 28 | — |
| 576 | isomiR example 2 of SEQ ID NO: 28 | — |
| 577 | isomiR example 1 of SEQ ID NO: 31 | — |
| 578 | isomiR example 2 of SEQ ID NO: 31 | — |
| 579 | isomiR example 1 of SEQ ID NO: 35 | — |
| 580 | isomiR example 2 of SEQ ID NO: 35 | — |
| 581 | isomiR example 1 of SEQ ID NO: 37 | — |
| 582 | isomiR example 2 of SEQ ID NO: 37 | — |
| 583 | isomiR example 1 of SEQ ID NO: 38 | — |
| 584 | isomiR example 2 of SEQ ID NO: 38 | — |
| 585 | isomiR example 1 of SEQ ID NO: 40 | — |
| 586 | isomiR example 2 of SEQ ID NO: 40 | — |
| 587 | isomiR example 1 of SEQ ID NO: 42 | — |
| 588 | isomiR example 2 of SEQ ID NO: 42 | — |
| 589 | isomiR example 1 of SEQ ID NO: 43 | — |
| 590 | isomiR example 2 of SEQ ID NO: 43 | — |
| 591 | isomiR example 1 of SEQ ID NO: 47 | — |
| 592 | isomiR example 2 of SEQ ID NO: 47 | — |
| 593 | isomiR example 1 of SEQ ID NO: 48 | — |
| 594 | isomiR example 2 of SEQ ID NO: 48 | — |
| 595 | isomiR example 1 of SEQ ID NO: 50 | — |
| 596 | isomiR example 2 of SEQ ID NO: 50 | — |
| 597 | isomiR example 1 of SEQ ID NO: 51 | — |
| 598 | isomiR example 2 of SEQ ID NO: 51 | — |
| 599 | isomiR example 1 of SEQ ID NO: 52 | — |
| 600 | isomiR example 2 of SEQ ID NO: 52 | — |
| 601 | isomiR example 1 of SEQ ID NO: 55 | — |
| 602 | isomiR example 2 of SEQ ID NO: 55 | — |
| 603 | isomiR example 1 of SEQ ID NO: 56 | — |
| 604 | isomiR example 2 of SEQ ID NO: 56 | — |
| 605 | isomiR example 1 of SEQ ID NO: 58 | — |
| 606 | isomiR example 2 of SEQ ID NO: 58 | — |
| 607 | isomiR example 1 of SEQ ID NO: 60 | — |
| 608 | isomiR example 2 of SEQ ID NO: 60 | — |
| 609 | isomiR example 1 of SEQ ID NO: 61 | — |
| 610 | isomiR example 2 of SEQ ID NO: 61 | — |
| 611 | isomiR example 1 of SEQ ID NO: 62 | — |
| 612 | isomiR example 2 of SEQ ID NO: 62 | — |
| 613 | isomiR example 1 of SEQ ID NO: 64 | — |
| 614 | isomiR example 2 of SEQ ID NO: 64 | — |
| 615 | isomiR example 1 of SEQ ID NO: 65 | — |
| 616 | isomiR example 2 of SEQ ID NO: 65 | — |
| 617 | isomiR example 1 of SEQ ID NO: 66 | — |
| 618 | isomiR example 2 of SEQ ID NO: 66 | — |
| 619 | isomiR example 1 of SEQ ID NO: 67 | — |
| 620 | isomiR example 2 of SEQ ID NO: 67 | — |
| 621 | isomiR example 1 of SEQ ID NO: 71 | — |
| 622 | isomiR example 2 of SEQ ID NO: 71 | — |
| 623 | isomiR example 1 of SEQ ID NO: 72 | — |
| 624 | isomiR example 2 of SEQ ID NO: 72 | — |
| 625 | isomiR example 1 of SEQ ID NO: 73 | — |
| 626 | isomiR example 2 of SEQ ID NO: 73 | — |
| 627 | isomiR example 1 of SEQ ID NO: 76 | — |
| 628 | isomiR example 2 of SEQ ID NO: 76 | — |
| 629 | isomiR example 1 of SEQ ID NO: 77 | — |
| 630 | isomiR example 2 of SEQ ID NO: 77 | — |
| 631 | isomiR example 1 of SEQ ID NO: 78 | — |
| 632 | isomiR example 2 of SEQ ID NO: 78 | — |
| 633 | isomiR example 1 of SEQ ID NO: 79 | — |
| 634 | isomiR example 2 of SEQ ID NO: 79 | — |
| 635 | isomiR example 1 of SEQ ID NO: 80 | — |
| 636 | isomiR example 2 of SEQ ID NO: 80 | — |
| 637 | isomiR example 1 of SEQ ID NO: 82 | — |
| 638 | isomiR example 2 of SEQ ID NO: 82 | — |
| 639 | isomiR example 1 of SEQ ID NO: 83 | — |
| 640 | isomiR example 2 of SEQ ID NO: 83 | — |
| 641 | isomiR example 1 of SEQ ID NO: 85 | — |
| 642 | isomiR example 2 of SEQ ID NO: 85 | — |
| 643 | isomiR example 1 of SEQ ID NO: 86 | — |
| 644 | isomiR example 2 of SEQ ID NO: 86 | — |
| 645 | isomiR example 1 of SEQ ID NO: 88 | — |
| 646 | isomiR example 2 of SEQ ID NO: 88 | — |
| 647 | isomiR example 1 of SEQ ID NO: 89 | — |
| 648 | isomiR example 2 of SEQ ID NO: 89 | — |
| 649 | isomiR example 1 of SEQ ID NO: 90 | — |
| 650 | isomiR example 2 of SEQ ID NO: 90 | — |
| 651 | isomiR example 1 of SEQ ID NO: 92 | — |
| 652 | isomiR example 2 of SEQ ID NO: 92 | — |
| 653 | isomiR example 1 of SEQ ID NO: 95 | — |
| 654 | isomiR example 2 of SEQ ID NO: 95 | — |
| 655 | isomiR example 1 of SEQ ID NO: 97 | — |
| 656 | isomiR example 2 of SEQ ID NO: 97 | — |
| 657 | isomiR example 1 of SEQ ID NO: 98 | — |
| 658 | isomiR example 2 of SEQ ID NO: 98 | — |
| 659 | isomiR example 1 of SEQ ID NO: 99 | — |
| 660 | isomiR example 2 of SEQ ID NO: 99 | — |
| 661 | isomiR example 1 of SEQ ID NO: 100 | — |
| 662 | isomiR example 2 of SEQ ID NO: 100 | — |
| 663 | isomiR example 1 of SEQ ID NO: 102 | — |
| 664 | isomiR example 2 of SEQ ID NO: 102 | — |
| 665 | isomiR example 1 of SEQ ID NO: 103 | — |
| 666 | isomiR example 2 of SEQ ID NO: 103 | — |
| 667 | isomiR example 1 of SEQ ID NO: 107 | — |
| 668 | isomiR example 2 of SEQ ID NO: 107 | — |
| 669 | isomiR example 1 of SEQ ID NO: 109 | — |
| 670 | isomiR example 2 of SEQ ID NO: 109 | — |

TABLE 1-continued

| SEQ ID NO: | Gene name | miRBase registration No. |
|---|---|---|
| 671 | isomiR example 1 of SEQ ID NO: 110 | — |
| 672 | isomiR example 2 of SEQ ID NO: 110 | — |
| 673 | isomiR example 1 of SEQ ID NO: 113 | — |
| 674 | isomiR example 2 of SEQ ID NO: 113 | — |
| 675 | isomiR example 1 of SEQ ID NO: 114 | — |
| 676 | isomiR example 2 of SEQ ID NO: 114 | — |
| 677 | isomiR example 1 of SEQ ID NO: 115 | — |
| 678 | isomiR example 2 of SEQ ID NO: 115 | — |
| 679 | isomiR example 1 of SEQ ID NO: 116 | — |
| 680 | isomiR example 2 of SEQ ID NO: 116 | — |
| 681 | isomiR example 1 of SEQ ID NO: 117 | — |
| 682 | isomiR example 2 of SEQ ID NO: 117 | — |
| 683 | isomiR example 1 of SEQ ID NO: 118 | — |
| 684 | isomiR example 2 of SEQ ID NO: 118 | — |
| 685 | isomiR example 1 of SEQ ID NO: 120 | — |
| 686 | isomiR example 2 of SEQ ID NO: 120 | — |
| 687 | isomiR example 1 of SEQ ID NO: 122 | — |
| 688 | isomiR example 2 of SEQ ID NO: 122 | — |
| 689 | isomiR example 1 of SEQ ID NO: 123 | — |
| 690 | isomiR example 2 of SEQ ID NO: 123 | — |
| 691 | isomiR example 1 of SEQ ID NO: 126 | — |
| 692 | isomiR example 2 of SEQ ID NO: 126 | — |
| 693 | isomiR example 1 of SEQ ID NO: 127 | — |
| 694 | isomiR example 2 of SEQ ID NO: 127 | — |
| 695 | isomiR example 1 of SEQ ID NO: 129 | — |
| 696 | isomiR example 2 of SEQ ID NO: 129 | — |
| 697 | isomiR example 1 of SEQ ID NO: 131 | — |
| 698 | isomiR example 2 of SEQ ID NO: 131 | — |
| 699 | isomiR example 1 of SEQ ID NO: 133 | — |
| 700 | isomiR example 2 of SEQ ID NO: 133 | — |
| 701 | isomiR example 1 of SEQ ID NO: 137 | — |
| 702 | isomiR example 2 of SEQ ID NO: 137 | — |
| 703 | isomiR example 1 of SEQ ID NO: 141 | — |
| 704 | isomiR example 2 of SEQ ID NO: 141 | — |
| 705 | isomiR example 1 of SEQ ID NO: 142 | — |
| 706 | isomiR example 2 of SEQ ID NO: 142 | — |
| 707 | isomiR example 1 of SEQ ID NO: 143 | — |
| 708 | isomiR example 2 of SEQ ID NO: 143 | — |
| 709 | isomiR example 1 of SEQ ID NO: 145 | — |
| 710 | isomiR example 2 of SEQ ID NO: 145 | — |
| 711 | isomiR example 1 of SEQ ID NO: 146 | — |
| 712 | isomiR example 2 of SEQ ID NO: 146 | — |
| 713 | isomiR example 1 of SEQ ID NO: 148 | — |
| 714 | isomiR example 2 of SEQ ID NO: 148 | — |
| 715 | isomiR example 1 of SEQ ID NO: 149 | — |
| 716 | isomiR example 2 of SEQ ID NO: 149 | — |
| 717 | isomiR example 1 of SEQ ID NO: 153 | — |
| 718 | isomiR example 2 of SEQ ID NO: 153 | — |
| 719 | isomiR example 1 of SEQ ID NO: 154 | — |
| 720 | isomiR example 2 of SEQ ID NO: 154 | — |
| 721 | isomiR example 1 of SEQ ID NO: 155 | — |
| 722 | isomiR example 2 of SEQ ID NO: 155 | — |
| 723 | isomiR example 1 of SEQ ID NO: 156 | — |
| 724 | isomiR example 2 of SEQ ID NO: 156 | — |
| 725 | isomiR example 1 of SEQ ID NO: 157 | — |
| 726 | isomiR example 2 of SEQ ID NO: 157 | — |
| 727 | isomiR example 1 of SEQ ID NO: 161 | — |
| 728 | isomiR example 2 of SEQ ID NO: 161 | — |
| 729 | isomiR example 1 of SEQ ID NO: 164 | — |
| 730 | isomiR example 2 of SEQ ID NO: 164 | — |
| 731 | isomiR example 1 of SEQ ID NO: 165 | — |
| 732 | isomiR example 2 of SEQ ID NO: 165 | — |
| 733 | isomiR example 1 of SEQ ID NO: 167 | — |
| 734 | isomiR example 2 of SEQ ID NO: 167 | — |
| 735 | isomiR example 1 of SEQ ID NO: 168 | — |
| 736 | isomiR example 2 of SEQ ID NO: 168 | — |
| 737 | isomiR example 1 of SEQ ID NO: 171 | — |
| 738 | isomiR example 2 of SEQ ID NO: 171 | — |
| 739 | isomiR example 1 of SEQ ID NO: 172 | — |
| 740 | isomiR example 2 of SEQ ID NO: 172 | — |
| 741 | isomiR example 1 of SEQ ID NO: 173 | — |
| 742 | isomiR example 2 of SEQ ID NO: 173 | — |
| 743 | isomiR example 1 of SEQ ID NO: 178 | — |
| 744 | isomiR example 2 of SEQ ID NO: 178 | — |
| 745 | isomiR example 1 of SEQ ID NO: 179 | — |
| 746 | isomiR example 2 of SEQ ID NO: 179 | — |
| 747 | isomiR example 1 of SEQ ID NO: 180 | — |
| 748 | isomiR example 2 of SEQ ID NO: 180 | — |
| 749 | isomiR example 1 of SEQ ID NO: 181 | — |
| 750 | isomiR example 2 of SEQ ID NO: 181 | — |
| 751 | isomiR example 1 of SEQ ID NO: 182 | — |
| 752 | isomiR example 2 of SEQ ID NO: 182 | — |
| 753 | isomiR example 1 of SEQ ID NO: 184 | — |
| 754 | isomiR example 2 of SEQ ID NO: 184 | — |
| 755 | isomiR example 1 of SEQ ID NO: 185 | — |
| 756 | isomiR example 2 of SEQ ID NO: 185 | — |
| 757 | isomiR example 1 of SEQ ID NO: 188 | — |
| 758 | isomiR example 2 of SEQ ID NO: 188 | — |
| 759 | isomiR example 1 of SEQ ID NO: 191 | — |
| 760 | isomiR example 2 of SEQ ID NO: 191 | — |
| 761 | isomiR example 1 of SEQ ID NO: 192 | — |
| 762 | isomiR example 2 of SEQ ID NO: 192 | — |
| 763 | isomiR example 1 of SEQ ID NO: 194 | — |
| 764 | isomiR example 2 of SEQ ID NO: 194 | — |
| 765 | isomiR example 1 of SEQ ID NO: 195 | — |
| 766 | isomiR example 2 of SEQ ID NO: 195 | — |
| 767 | isomiR example 1 of SEQ ID NO: 196 | — |
| 768 | isomiR example 2 of SEQ ID NO: 196 | — |
| 769 | isomiR example 1 of SEQ ID NO: 199 | — |
| 770 | isomiR example 2 of SEQ ID NO: 199 | — |
| 771 | isomiR example 1 of SEQ ID NO: 201 | — |
| 772 | isomiR example 2 of SEQ ID NO: 201 | — |
| 773 | isomiR example 1 of SEQ ID NO: 202 | — |
| 774 | isomiR example 2 of SEQ ID NO: 202 | — |
| 775 | isomiR example 1 of SEQ ID NO: 204 | — |
| 776 | isomiR example 2 of SEQ ID NO: 204 | — |
| 777 | isomiR example 1 of SEQ ID NO: 207 | — |
| 778 | isomiR example 2 of SEQ ID NO: 207 | — |
| 779 | isomiR example 1 of SEQ ID NO: 210 | — |
| 780 | isomiR example 2 of SEQ ID NO: 210 | — |
| 781 | isomiR example 1 of SEQ ID NO: 213 | — |
| 782 | isomiR example 2 of SEQ ID NO: 213 | — |
| 783 | isomiR example 1 of SEQ ID NO: 215 | — |
| 784 | isomiR example 2 of SEQ ID NO: 215 | — |
| 785 | isomiR example 1 of SEQ ID NO: 217 | — |
| 786 | isomiR example 2 of SEQ ID NO: 217 | — |
| 787 | isomiR example 1 of SEQ ID NO: 219 | — |
| 788 | isomiR example 2 of SEQ ID NO: 219 | — |
| 789 | isomiR example 1 of SEQ ID NO: 222 | — |
| 790 | isomiR example 2 of SEQ ID NO: 222 | — |
| 791 | isomiR example 1 of SEQ ID NO: 223 | — |
| 792 | isomiR example 2 of SEQ ID NO: 223 | — |
| 793 | isomiR example 1 of SEQ ID NO: 225 | — |
| 794 | isomiR example 2 of SEQ ID NO: 225 | — |
| 795 | isomiR example 1 of SEQ ID NO: 230 | — |
| 796 | isomiR example 2 of SEQ ID NO: 230 | — |
| 797 | isomiR example 1 of SEQ ID NO: 232 | — |
| 798 | isomiR example 2 of SEQ ID NO: 232 | — |
| 799 | isomiR example 1 of SEQ ID NO: 233 | — |
| 800 | isomiR example 2 of SEQ ID NO: 233 | — |
| 801 | isomiR example 1 of SEQ ID NO: 234 | — |
| 802 | isomiR example 2 of SEQ ID NO: 234 | — |
| 803 | isomiR example 1 of SEQ ID NO: 235 | — |
| 804 | isomiR example 2 of SEQ ID NO: 235 | — |
| 805 | isomiR example 1 of SEQ ID NO: 236 | — |
| 806 | isomiR example 2 of SEQ ID NO: 236 | — |
| 807 | isomiR example 1 of SEQ ID NO: 238 | — |
| 808 | isomiR example 2 of SEQ ID NO: 238 | — |
| 809 | isomiR example 1 of SEQ ID NO: 239 | — |
| 810 | isomiR example 2 of SEQ ID NO: 239 | — |
| 811 | isomiR example 1 of SEQ ID NO: 240 | — |
| 812 | isomiR example 2 of SEQ ID NO: 240 | — |
| 813 | isomiR example 1 of SEQ ID NO: 241 | — |
| 814 | isomiR example 2 of SEQ ID NO: 241 | — |
| 815 | isomiR example 1 of SEQ ID NO: 242 | — |
| 816 | isomiR example 2 of SEQ ID NO: 242 | — |
| 817 | isomiR example 1 of SEQ ID NO: 243 | — |
| 818 | isomiR example 2 of SEQ ID NO: 243 | — |
| 819 | isomiR example 1 of SEQ ID NO: 245 | — |
| 820 | isomiR example 2 of SEQ ID NO: 245 | — |
| 821 | isomiR example 1 of SEQ ID NO: 246 | — |
| 822 | isomiR example 2 of SEQ ID NO: 246 | — |
| 823 | isomiR example 1 of SEQ ID NO: 247 | — |
| 824 | isomiR example 2 of SEQ ID NO: 247 | — |

TABLE 1-continued

| SEQ ID NO: | Gene name | miRBase registration No. |
|---|---|---|
| 825 | isomiR example 1 of SEQ ID NO: 248 | — |
| 826 | isomiR example 2 of SEQ ID NO: 248 | — |
| 827 | isomiR example 1 of SEQ ID NO: 249 | — |
| 828 | isomiR example 2 of SEQ ID NO: 249 | — |
| 829 | isomiR example 1 of SEQ ID NO: 250 | — |
| 830 | isomiR example 2 of SEQ ID NO: 250 | — |
| 831 | isomiR example 1 of SEQ ID NO: 251 | — |
| 832 | isomiR example 2 of SEQ ID NO: 251 | — |
| 833 | isomiR example 1 of SEQ ID NO: 252 | — |
| 834 | isomiR example 2 of SEQ ID NO: 252 | — |
| 835 | isomiR example 1 of SEQ ID NO: 254 | — |
| 836 | isomiR example 2 of SEQ ID NO: 254 | — |
| 837 | isomiR example 1 of SEQ ID NO: 258 | — |
| 838 | isomiR example 2 of SEQ ID NO: 258 | — |
| 839 | isomiR example 1 of SEQ ID NO: 259 | — |
| 840 | isomiR example 2 of SEQ ID NO: 259 | — |
| 841 | isomiR example 1 of SEQ ID NO: 260 | — |
| 842 | isomiR example 2 of SEQ ID NO: 260 | — |
| 843 | isomiR example 1 of SEQ ID NO: 263 | — |
| 844 | isomiR example 2 of SEQ ID NO: 263 | — |
| 845 | isomiR example 1 of SEQ ID NO: 265 | — |
| 846 | isomiR example 2 of SEQ ID NO: 265 | — |
| 847 | isomiR example 1 of SEQ ID NO: 266 | — |
| 848 | isomiR example 2 of SEQ ID NO: 266 | — |
| 849 | isomiR example 1 of SEQ ID NO: 267 | — |
| 850 | isomiR example 2 of SEQ ID NO: 267 | — |
| 851 | hsa-miR-6089 | MIMAT0023714 |
| 852 | hsa-miR-6816-5p | MIMAT0027532 |
| 853 | hsa-miR-4466 | MIMAT0018993 |
| 854 | hsa-miR-4488 | MIMAT0019022 |
| 855 | hsa-miR-6752-5p | MIMAT0027404 |
| 856 | hsa-miR-4739 | MIMAT0019868 |
| 857 | hsa-mir-6089-1 | MI0020366 |
| 858 | hsa-mir-6089-2 | MI0023563 |
| 859 | hsa-mir-6816 | MI0022661 |
| 860 | hsa-mir-4466 | MI0016817 |
| 861 | hsa-mir-4488 | MI0016849 |
| 862 | hsa-mir-6752 | MI0022597 |
| 863 | hsa-mir-4739 | MI0017377 |
| 864 | isomiR example 1 of SEQ ID NO: 851 | — |
| 865 | isomiR example 2 of SEQ ID NO: 851 | — |
| 866 | isomiR example 1 of SEQ ID NO: 853 | — |
| 867 | isomiR example 2 of SEQ ID NO: 853 | — |
| 868 | isomiR example 1 of SEQ ID NO: 854 | — |
| 869 | isomiR example 2 of SEQ ID NO: 854 | — |
| 870 | isomiR example 1 of SEQ ID NO: 856 | — |
| 871 | isomiR example 2 of SEQ ID NO: 856 | — |

The present specification encompasses the contents described in the specifications and/or drawings of Japanese Patent Application No. 2014-122672 and No. 2015-069321 from which the present application claims priorities.

Advantageous Effect of Invention

According to the present invention, breast cancer can be detected easily and in high accuracy. For example, the presence or absence of breast cancer in patients can be easily detected by using, as indicators, the measurement values of several miRNAs in bloods, sera, and/or plasmas of the patients, which can be collected with limitedly invasiveness.

DESCRIPTION OF EMBODIMENTS

Figure 1:
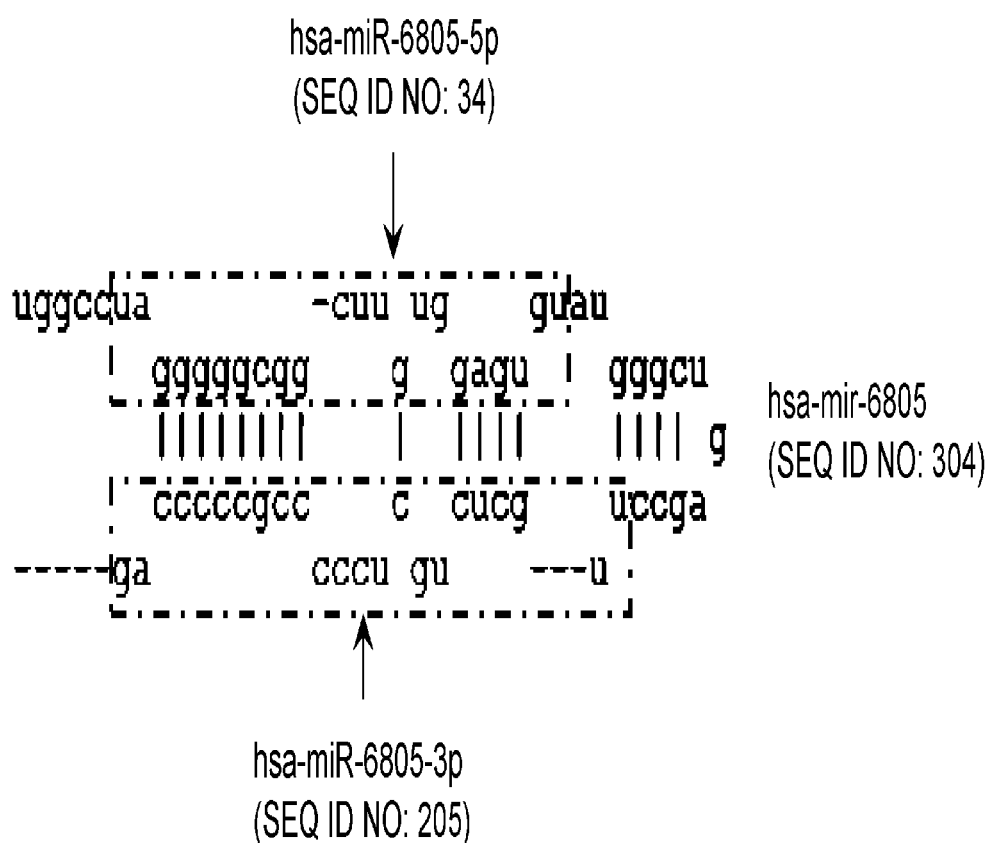
FIG. 1 This figure shows the relationship between the nucleotide sequences of hsa-miR-6805-5p represented by SEQ ID NO: 34 and hsa-miR-6805-3p represented by SEQ ID NO: 205, which are produced from a precursor hsa-mir-6805 represented by SEQ ID NO: 304.

Hereinafter, the present invention will be further described in detail.

1. Target Nucleic Acid for Breast Cancer

Primary target nucleic acids as breast cancer markers for detecting the presence and/or absence of breast cancer or breast cancer cells using the nucleic acid probes or the primers for the detection of breast cancer defined above according to the present invention, at least one miRNA selected from the group consisting of the following miR-NAs: hsa-miR-4783-3p, hsa-miR-4730, hsa-miR-1307-3p, hsa-miR-4634, hsa-miR-663a, hsa-miR-4532, hsa-miR-7704, hsa-miR-3178, hsa-miR-6729-5p, hsa-miR-6090, hsa-miR-4732-5p, hsa-miR-3184-5p, hsa-miR-6727-5p, hsamiR-6088, hsa-miR-4674, hsa-miR-8073, hsa-miR-4787-5p, hsa-miR-1469, hsa-miR-125a-3p, hsa-miR-1233-5p, hsa-miR-885-3p, hsa-miR-6802-5p, hsa-miR-328-5p, hsa-miR-6787-5p, hsa-miR-8069, hsa-miR-6875-5p, hsa-miR-1246, hsa-miR-4734, hsa-miR-6757-5p, hsa-miR-6756-5p, hsa-miR-3665, hsa-miR-6836-3p, hsa-miR-6821-5p, hsa-miR-6805-5p, hsa-miR-4728-5p, hsa-miR-6726-5p, hsa-miR-197-5p, hsa-miR-149-3p, hsa-miR-6850-5p, hsa-miR-4476, hsa-miR-6858-5p, hsa-miR-564, hsa-miR-4763-3p, hsa-miR-575, hsa-miR-6771-5p, hsa-miR-1231, hsa-miR-1908-3p, hsa-miR-150-3p, hsa-miR-3937, hsa-miR-887-3p, hsa-miR-3940-5p, hsa-miR-4741, hsa-miR-6808-5p, hsa-miR-6869-5p, hsa-miR-5090, hsa-miR-615-5p, hsa-miR-8072, hsa-miR-128-1-5p, hsa-miR-1238-5p, hsa-miR-365a-5p, hsa-miR-204-3p, hsa-miR-4492, hsa-miR-6785-5p, hsa-miR-6511a-5p, hsa-miR-4525, hsa-miR-1915-5p, hsa-miR-3180, hsa-miR-6879-5p, hsa-miR-1199-5p, hsa-miR-6746-5p, hsa-miR-711, hsa-miR-663b, hsa-miR-4707-3p, hsa-miR-6893-5p, hsa-miR-4675, hsa-miR-4638-5p, hsa-miR-4651, hsa-miR-6087, hsa-miR-4665-5p, hsa-miR-4758-5p, hsa-miR-6887-5p, hsa-miR-3620-5p, hsa-miR-1909-3p, hsa-miR-7641, hsa-miR-6724-5p, hsa-miR-1343-3p, hsa-miR-6780b-5p, hsa-miR-4484, hsa-miR-4690-5p, hsa-miR-4429, hsa-miR-1227-5p, hsa-miR-4725-3p, hsa-miR-6861-5p, hsa-miR-6812-5p, hsa-miR-3197, hsa-miR-8059, hsa-miR-3185, hsa-miR-4706, hsa-miR-4497, hsa-miR-3131, hsa-miR-6806-5p, hsa-miR-187-5p, hsa-miR-3180-3p, hsa-miR-6848-5p, hsa-miR-6820-5p, hsa-miR-6800-5p, hsa-miR-6717-5p, hsa-miR-6795-5p, hsa-miR-4632-5p, hsa-miR-665, hsa-miR-6778-5p, hsa-miR-3663-3p, hsa-miR-4689, hsa-miR-211-3p, hsa-miR-6511b-5p, hsa-miR-4750-5p, hsa-miR-6126, hsa-miR-614, hsa-miR-7110-5p, hsa-miR-744-5p, hsa-miR-6769a-5p, hsa-miR-4792, hsa-miR-5787, hsa-miR-6798-5p, hsa-miR-6781-5p, hsa-miR-4419b, hsa-miR-4446-3p, hsa-miR-4259, hsa-miR-5572, hsa-miR-6075, hsa-miR-296-3p, hsa-miR-6891-5p, hsa-miR-4745-5p, hsa-miR-6775-5p, hsa-miR-6870-5p, hsa-miR-920, hsa-miR-4530, hsa-miR-6819-5p, hsa-miR-6825-5p, hsa-miR-7847-3p, hsa-miR-6131, hsa-miR-4433-3p, hsa-miR-1228-5p, hsa-miR-6743-5p, hsa-miR-1268a, hsa-miR-3917, hsa-miR-6786-5p, hsa-miR-3154, hsa-miR-638, hsa-miR-6741-5p, hsa-miR-6889-5p, hsa-miR-6840-3p, hsa-miR-6510-5p, hsa-miR-3188, hsa-miR-551b-5p, hsa-miR-5001-5p, hsa-miR-1268b, hsa-miR-7107-5p, hsa-miR-6824-5p, hsa-miR-6732-5p, hsa-miR-371a-5p, hsa-miR-6794-5p, hsa-miR-6779-5p, hsa-miR-4271, hsa-miR-5195-3p, hsa-miR-6762-5p, hsa-miR-939-5p, hsa-miR-1247-3p, hsa-miR-6777-5p, hsa-miR-6722-3p, hsa-miR-3656, hsa-miR-4688, hsa-miR-3195, hsa-miR-6766-5p, hsa-miR-4447, hsa-miR-4656, hsa-miR-7108-5p, hsa-miR-3191-3p, hsa-miR-1273g-3p, hsa-miR-4463, hsa-miR-2861, hsa-miR-3196, hsa-miR-6877-5p, hsa-miR-3679-5p, hsa-miR-4442, hsa-miR-6789-5p, hsa-miR-6782-5p, hsa-miR-486-3p, hsa-miR-6085, hsa-miR-4746-3p, hsa-miR-619-5p, hsa-miR-937-5p, hsa-miR-6803-5p, hsa-miR-4298, hsa-miR-4454, hsa-miR-4459, hsa-miR-7150, hsa-miR-6880-5p, hsa-miR-4449, hsa-miR-8063, hsa-miR-4695-5p, hsa-miR-6132, hsa-miR-6829-5p, hsa-miR-4486, hsa-miR-6805-3p, hsa-miR-6826-5p, hsa-miR-4508, hsa-miR-1343-5p, hsa-miR-7114-5p, hsa-miR-3622a-5p, hsa-miR-6765-5p, hsa-miR-7845-5p, hsa-miR-3960, hsa-miR-6749-5p, hsa-miR-1260b, hsa-miR-6799-5p, hsa-miR-4723-5p, hsa-miR-6784-5p, hsa-miR-5100, hsa-miR-6769b-5p, hsa-miR-1207-5p, hsa-miR-642a-3p, hsa-miR-4505, hsa-miR-4270, hsa-miR-6721-5p, hsa-miR-7111-5p, hsa-miR-6791-5p, hsa-miR-7109-5p, hsa-miR-4258, hsa-miR-6515-3p, hsa-miR-6851-5p, hsa-miR-6125, hsa-miR-4749-5p, hsa-miR-4726-5p, hsa-miR-4513, hsa-miR-6089, hsa-miR-6816-5p, hsa-miR-4466, hsa-miR-4488, hsa-miR-6752-5p and hsa-miR-4739 can be used. Furthermore, at least one miRNA selected from the group consisting of the following other breast cancer markers that can be combined with these miRNAs, i.e., hsa-miR-760, hsa-miR-602, hsa-miR-423-5p, hsa-miR-92a-2-5p, hsa-miR-16-5p, hsa-miR-451a, hsa-miR-135a-3p, hsa-miR-486-5p, hsa-miR-4257, hsa-miR-92b-5p, hsa-miR-1915-3p, hsa-miR-718, hsa-miR-940, hsa-miR-296-5p, hsa-miR-23b-3p and hsa-miR-92a-3p can also be preferably used as a target nucleic acid. Moreover, at least one miRNA selected from the group consisting of the following other breast cancer markers that can be combined with these miRNAs, i.e., hsa-miR-658, hsa-miR-6842-5p, hsa-miR-6124, hsa-miR-6765-3p, hsa-miR-7106-5p, hsa-miR-4534, hsa-miR-92b-3p, hsa-miR-3135b, hsa-miR-4687-3p, hsa-miR-762, hsa-miR-3619-3p, hsa-miR-4467, hsa-miR-557, hsa-miR-1237-5p, hsa-miR-1908-5p, hsa-miR-4286, hsa-miR-6885-5p and hsa-miR-6763-5p can also be preferably used as target nucleic acids.

These miRNAs include, for example, a human gene comprising a nucleotide sequence represented by any of SEQ ID NOs: 1 to 269, and 851 to 856 (i.e., hsa-miR-4783-3p, hsa-miR-4730, hsa-miR-1307-3p, hsa-miR-4634, hsa-miR-663a, hsa-miR-4532, hsa-miR-7704, hsa-miR-3178, hsa-miR-6729-5p, hsa-miR-6090, hsa-miR-4732-5p, hsa-miR-3184-5p, hsa-miR-6727-5p, hsa-miR-6088, hsa-miR-4674, hsa-miR-8073, hsa-miR-4787-5p, hsa-miR-1469, hsa-miR-125a-3p, hsa-miR-1233-5p, hsa-miR-885-3p, hsa-miR-6802-5p, hsa-miR-328-5p, hsa-miR-6787-5p, hsa-miR-8069, hsa-miR-6875-5p, hsa-miR-1246, hsa-miR-4734, hsa-miR-6757-5p, hsa-miR-6756-5p, hsa-miR-3665, hsa-miR-6836-3p, hsa-miR-6821-5p, hsa-miR-6805-5p, hsa-miR-4728-5p, hsa-miR-6726-5p, hsa-miR-197-5p, hsa-miR-149-3p, hsa-miR-6850-5p, hsa-miR-4476, hsa-miR-6858-5p, hsa-miR-564, hsa-miR-4763-3p, hsa-miR-575, hsa-miR-6771-5p, hsa-miR-1231, hsa-miR-1908-3p, hsa-miR-150-3p, hsa-miR-3937, hsa-miR-887-3p, hsa-miR-3940-5p, hsa-miR-4741, hsa-miR-6808-5p, hsa-miR-6869-5p, hsa-miR-5090, hsa-miR-615-5p, hsa-miR-8072, hsa-miR-128-1-5p, hsa-miR-1238-5p, hsa-miR-365a-5p, hsa-miR-204-3p, hsa-miR-4492, hsa-miR-6785-5p, hsa-miR-6511a-5p, hsa-miR-4525, hsa-miR-1915-5p, hsa-miR-3180, hsa-miR-6879-5p, hsa-miR-1199-5p, hsa-miR-6746-5p, hsa-miR-711, hsa-miR-663b, hsa-miR-4707-3p, hsa-miR-6893-5p, hsa-miR-4675, hsa-miR-4638-5p, hsa-miR-4651, hsa-miR-6087, hsa-miR-4665-5p, hsa-miR-4758-5p, hsa-miR-6887-5p, hsa-miR-3620-5p, hsa-miR-1909-3p, hsa-miR-7641, hsa-miR-6724-5p, hsa-miR-1343-3p, hsa-miR-6780b-5p, hsa-miR-4484, hsa-miR-4690-5p, hsa-miR-4429, hsa-miR-1227-5p, hsa-miR-4725-3p, hsa-miR-6861-5p, hsa-miR-6812-5p, hsa-miR-3197, hsa-miR-8059, hsa-miR-3185, hsa-miR-4706, hsa-miR-4497, hsa-miR-3131, hsa-miR-6806-5p, hsa-miR-187-5p, hsa-miR-3180-3p, hsa-miR-6848-5p, hsa-miR-6820-5p, hsa-miR-6800-5p, hsa-miR-6717-5p, hsa-miR-6795-5p, hsa-miR-4632-5p, hsa-miR-665, hsa-miR-6778-5p, hsa-miR-3663-3p, hsa-miR-4689, hsa-miR-211-3p, hsa-miR-6511b-5p, hsa-miR-4750-5p, hsa-miR-6126, hsa-miR-614, hsa-miR-7110-5p, hsa-miR-744-5p, hsa-miR-6769a-5p, hsa-miR-4792, hsa-miR-5787, hsa-miR-6798-5p, hsa-miR-6781-5p, hsa-miR-4419b, hsa-miR-4446-3p, hsa-miR-4259, hsa-miR-5572, hsa-miR-6075, hsa-miR-296-3p, hsa-miR-6891-5p, hsa-miR-4745-5p, hsa-miR-6775-5p, hsa-miR-6870-5p, hsa-miR-920, hsa-miR-4530, hsa-miR-6819-5p, hsa-miR-6825-5p, hsa-miR-7847-3p, hsa-miR-6131, hsa-miR-4433-3p, hsa-miR-1228-5p, hsa-miR-6743-5p, hsa-miR-1268a, hsa-miR-3917, hsamiR-6786-5p, hsa-miR-3154, hsa-miR-638, hsa-miR-6741-5p, hsa-miR-6889-5p, hsa-miR-6840-3p, hsa-miR-6510-5p, hsa-miR-3188, hsa-miR-551b-5p, hsa-miR-5001-5p, hsa-miR-1268b, hsa-miR-7107-5p, hsa-miR-6824-5p, hsa-miR-6732-5p, hsa-miR-371a-5p, hsa-miR-6794-5p, hsa-miR-6779-5p, hsa-miR-4271, hsa-miR-5195-3p, hsa-miR-6762-5p, hsa-miR-939-5p, hsa-miR-1247-3p, hsa-miR-6777-5p, hsa-miR-6722-3p, hsa-miR-3656, hsa-miR-4688, hsa-miR-3195, hsa-miR-6766-5p, hsa-miR-4447, hsa-miR-4656, hsa-miR-7108-5p, hsa-miR-3191-3p, hsa-miR-1273g-3p, hsa-miR-4463, hsa-miR-2861, hsa-miR-3196, hsa-miR-6877-5p, hsa-miR-3679-5p, hsa-miR-4442, hsa-miR-6789-5p, hsa-miR-6782-5p, hsa-miR-486-3p, hsa-miR-6085, hsa-miR-4746-3p, hsa-miR-619-5p, hsa-miR-937-5p, hsa-miR-6803-5p, hsa-miR-4298, hsa-miR-4454, hsa-miR-4459, hsa-miR-7150, hsa-miR-6880-5p, hsa-miR-4449, hsa-miR-8063, hsa-miR-4695-5p, hsa-miR-6132, hsa-miR-6829-5p, hsa-miR-4486, hsa-miR-6805-3p, hsa-miR-6826-5p, hsa-miR-4508, hsa-miR-1343-5p, hsa-miR-7114-5p, hsa-miR-3622a-5p, hsa-miR-6765-5p, hsa-miR-7845-5p, hsa-miR-3960, hsa-miR-6749-5p, hsa-miR-1260b, hsa-miR-6799-5p, hsa-miR-4723-5p, hsa-miR-6784-5p, hsa-miR-5100, hsa-miR-6769b-5p, hsa-miR-1207-5p, hsa-miR-642a-3p, hsa-miR-4505, hsa-miR-4270, hsa-miR-6721-5p, hsa-miR-7111-5p, hsa-miR-6791-5p, hsa-miR-7109-5p, hsa-miR-4258, hsa-miR-6515-3p, hsa-miR-6851-5p, hsa-miR-6125, hsa-miR-4749-5p, hsa-miR-4726-5p, hsa-miR-4513, hsa-miR-6089, hsa-miR-6816-5p, hsa-miR-4466, hsa-miR-4488, hsa-miR-6752-5p, hsa-miR-4739, hsa-miR-760, hsa-miR-602, hsa-miR-423-5p, hsa-miR-92a-2-5p, hsa-miR-16-5p, hsa-miR-451a, hsa-miR-135a-3p, hsa-miR-486-5p, hsa-miR-4257, hsa-miR-92b-5p, hsa-miR-1915-3p, hsa-miR-718, hsa-miR-940, hsa-miR-296-5p, hsa-miR-23b-3p, hsa-miR-92a-3p, hsa-miR-658, hsa-miR-6842-5p, hsa-miR-6124, hsa-miR-6765-3p, hsa-miR-7106-5p, hsa-miR-4534, hsa-miR-92b-3p, hsa-miR-3135b, hsa-miR-4687-3p, hsa-miR-762, hsa-miR-3619-3p, hsa-miR-4467, hsa-miR-557, hsa-miR-1237-5p, hsa-miR-1908-5p, hsa-miR-4286, hsa-miR-6885-5p and hsa-miR-6763-5p, respectively), a congener thereof, a transcript thereof, or/and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 871 or a transcript thereof, more preferably the transcript, i.e., a miRNA or its precursor RNA (pri-miRNA or pre-miRNA).

The first target gene is the hsa-miR-4783-3p gene, a congener thereof, a transcript thereof, or a variant or a derivative thereof. None of the previously known reports show that change in the expression of the gene or the transcript thereof can serve as a marker for breast cancer.

The second target gene is the hsa-miR-4730 gene, a congener thereof, a transcript thereof, or a variant or a derivative thereof. None of the previously known reports show that change in the expression of the gene or the transcript thereof can serve as a marker for breast cancer.

The third target gene is the hsa-miR-1307-3p gene, a congener thereof, a transcript thereof, or a variant or a derivative thereof. None of the previously known reports show that change in the expression of the gene or the transcript thereof can serve as a marker for breast cancer.

The fourth target gene is the hsa-miR-4634 gene, a congener thereof, a transcript thereof, or a variant or a derivative thereof. None of the previously known reports show that change in the expression of the gene or the transcript thereof can serve as a marker for breast cancer.

The fifth target gene is the hsa-miR-663a gene, a congener thereof, a transcript thereof, or a variant or a derivative thereof. None of the previously known reports show that change in the expression of the gene or the transcript thereof can serve as a marker for breast cancer.

The sixth target gene is the hsa-miR-4532 gene, a congener thereof, a transcript thereof, or a variant or a derivative thereof. None of the previously known reports show that change in the expression of the gene or the transcript thereof can serve as a marker for breast cancer.

The seventh target gene is the hsa-miR-7704 gene, a congener thereof, a transcript thereof, or a variant or a derivative thereof. None of the previously known reports show that change in the expression of the gene or the transcript thereof can serve as a marker for breast cancer.

The eighth target gene is the hsa-miR-3178 gene, a congener thereof, a transcript thereof, or a variant or a derivative thereof. None of the previously known reports show that change in the expression of the gene or the transcript thereof can serve as a marker for breast cancer.

The ninth target gene is the hsa-miR-6729-5p gene, a congener thereof, a transcript thereof, or a variant or a derivative thereof. None of the previously known reports show that change in the expression of the gene or the transcript thereof can serve as a marker for breast cancer.

The 10th target gene is the hsa-miR-6090 gene, a congener thereof, a transcript thereof, or a variant or a derivative thereof. None of the previously known reports show that change in the expression of the gene or the transcript thereof can serve as a marker for breast cancer.

The 11th target gene is the hsa-miR-4732-5p gene, a congener thereof, a transcript thereof, or a variant or a derivative thereof. None of the previously known reports show that change in the expression of the gene or the transcript thereof can serve as a marker for breast cancer.

The 12th target gene is the hsa-miR-3184-5p gene, a congener thereof, a transcript thereof, or a variant or a derivative thereof. None of the previously known reports show that change in the expression of the gene or the transcript thereof can serve as a marker for breast cancer.

The 13th target gene is the hsa-miR-6727-5p gene, a congener thereof, a transcript thereof, or a variant or a derivative thereof. None of the previously known reports show that change in the expression of the gene or the transcript thereof can serve as a marker for breast cancer.

The 14th target gene is the hsa-miR-6088 gene, a congener thereof, a transcript thereof, or a variant or a derivative thereof. None of the previously known reports show that change in the expression of the gene or the transcript thereof can serve as a marker for breast cancer.

The 15th target gene is the hsa-miR-4674 gene, a congener thereof, a transcript thereof, or a variant or a derivative thereof. None of the previously known reports show that change in the expression of the gene or the transcript thereof can serve as a marker for breast cancer.

The 16th target gene is the hsa-miR-8073 gene, a congener thereof, a transcript thereof, or a variant or a derivative thereof. None of the previously known reports show that change in the expression of the gene or the transcript thereof can serve as a marker for breast cancer.

The 17th target gene is the hsa-miR-4787-5p gene, a congener thereof, a transcript thereof, or a variant or a derivative thereof. None of the previously known reports show that change in the expression of the gene or the transcript thereof can serve as a marker for breast cancer.

The 18th target gene is the hsa-miR-1469 gene, a congener thereof, a transcript thereof, or a variant or a derivative thereof. None of the previously known reports show that change in the expression of the gene or the transcript thereof can serve as a marker for breast cancer.

The 19th target gene is the hsa-miR-125a-3p gene, a congener thereof, a transcript thereof, or a variant or a derivative thereof. None of the previously known reports show that change in the expression of the gene or the transcript thereof can serve as a marker for breast cancer.

The 20th target gene is the hsa-miR-1233-5p gene, a congener thereof, a transcript thereof, or a variant or a derivative thereof. None of the previously known reports show that change in the expression of the gene or the transcript thereof can serve as a marker for breast cancer.

The 21st target gene is the hsa-miR-885-3p gene, a congener thereof, a transcript thereof, or a variant or a derivative thereof. None of the previously known reports show that change in the expression of the gene or the transcript thereof can serve as a marker for breast cancer.

The 22nd target gene is the hsa-miR-6802-5p gene, a congener thereof, a transcript thereof, or a variant or a derivative thereof. None of the previously known reports show that change in the expression of the gene or the transcript thereof can serve as a marker for breast cancer.

The 23rd target gene is the hsa-miR-328-5p gene, a congener thereof, a transcript thereof, or a variant or a derivative thereof. None of the previously known reports show that change in the expression of the gene or the transcript thereof can serve as a marker for breast cancer.

The 24th target gene is the hsa-miR-6787-5p gene, a congener thereof, a transcript thereof, or a variant or a derivative thereof. None of the previously known reports show that change in the expression of the gene or the transcript thereof can serve as a marker for breast cancer.

The 25th target gene is the hsa-miR-8069 gene, a congener thereof, a transcript thereof, or a variant or a derivative thereof. None of the previously known reports show that change in the expression of the gene or the transcript thereof can serve as a marker for breast cancer.

The 26th target gene is the hsa-miR-6875-5p gene, a congener thereof, a transcript thereof, or a variant or a derivative thereof. None of the previously known reports show that change in the expression of the gene or the transcript thereof can serve as a marker for breast cancer.

The 27th target gene is the hsa-miR-1246 gene, a congener thereof, a transcript thereof, or a variant or a derivative thereof. None of the previously known reports show that change in the expression of the gene or the transcript thereof can serve as a marker for breast cancer.

The 28th target gene is the hsa-miR-4734 gene, a congener thereof, a transcript thereof, or a variant or a derivative thereof. None of the previously known reports show that change in the expression of the gene or the transcript thereof can serve as a marker for breast cancer.

The 29th target gene is the hsa-miR-6757-5p gene, a congener thereof, a transcript thereof, or a variant or a derivative thereof. None of the previously known reports show that change in the expression of the gene or the transcript thereof can serve as a marker for breast cancer.

The 30th target gene is the hsa-miR-6756-5p gene, a congener thereof, a transcript thereof, or a variant or a derivative thereof. None of the previously known reports show that change in the expression of the gene or the transcript thereof can serve as a marker for breast cancer.

The 31st target gene is the hsa-miR-3665 gene, a congener thereof, a transcript thereof, or a variant or a derivative thereof. None of the previously known reports show that change in the expression of the gene or the transcript thereof can serve as a marker for breast cancer.

The 32nd target gene is the hsa-miR-6836-3p gene, a congener thereof, a transcript thereof, or a variant or a derivative thereof. None of the previously known reports show that change in the expression of the gene or the transcript thereof can serve as a marker for breast cancer.

The 33rd target gene is the hsa-miR-6821-5p gene, a congener thereof, a transcript thereof, or a variant or a derivative thereof. None of the previously known reports show that change in the expression of the gene or the transcript thereof can serve as a marker for breast cancer.

The 34th target gene is the hsa-miR-6805-5p gene, a congener thereof, a transcript thereof, or a variant or a derivative thereof. None of the previously known reports show that change in the expression of the gene or the transcript thereof can serve as a marker for breast cancer.

The 35th target gene is the hsa-miR-4728-5p gene, a congener thereof, a transcript thereof, or a variant or a derivative thereof. None of the previously known reports show that change in the expression of the gene or the transcript thereof can serve as a marker for breast cancer.

The 36th target gene is the hsa-miR-6726-5p gene, a congener thereof, a transcript thereof, or a variant or a derivative thereof. None of the previously known reports show that change in the expression of the gene or the transcript thereof can serve as a marker for breast cancer.

The 37th target gene is the hsa-miR-197-5p gene, a congener thereof, a transcript thereof, or a variant or a derivative thereof. None of the previously known reports show that change in the expression of the gene or the transcript thereof can serve as a marker for breast cancer.

The 38th target gene is the hsa-miR-149-3p gene, a congener thereof, a transcript thereof, or a variant or a derivative thereof. None of the previously known reports show that change in the expression of the gene or the transcript thereof can serve as a marker for breast cancer.

The 39th target gene is the hsa-miR-6850-5p gene, a congener thereof, a transcript thereof, or a variant or a derivative thereof. None of the previously known reports show that change in the expression of the gene or the transcript thereof can serve as a marker for breast cancer.

The 40th target gene is the hsa-miR-4476 gene, a congener thereof, a transcript thereof, or a variant or a derivative thereof. None of the previously known reports show that change in the expression of the gene or the transcript thereof can serve as a marker for breast cancer.

The 41st target gene is the hsa-miR-6858-5p gene, a congener thereof, a transcript thereof, or a variant or a derivative thereof. None of the previously known reports show that change in the expression of the gene or the transcript thereof can serve as a marker for breast cancer.

The 42nd target gene is the hsa-miR-564 gene, a congener thereof, a transcript thereof, or a variant or a derivative thereof. None of the previously known reports show that change in the expression of the gene or the transcript thereof can serve as a marker for breast cancer.

The 43rd target gene is the hsa-miR-4763-3p gene, a congener thereof, a transcript thereof, or a variant or a derivative thereof. None of the previously known reports show that change in the expression of the gene or the transcript thereof can serve as a marker for breast cancer.

The 44th target gene is the hsa-miR-575 gene, a congener thereof, a transcript thereof, or a variant or a derivative thereof. None of the previously known reports show that change in the expression of the gene or the transcript thereof can serve as a marker for breast cancer.

The 45th target gene is the hsa-miR-6771-5p gene, a congener thereof, a transcript thereof, or a variant or a derivative thereof. None of the previously known reports show that change in the expression of the gene or the transcript thereof can serve as a marker for breast cancer.

The 46th target gene is the hsa-miR-1231 gene, a congener thereof, a transcript thereof, or a variant or a derivative thereof. None of the previously known reports show that change in the expression of the gene or the transcript thereof can serve as a marker for breast cancer.

The 47th target gene is the hsa-miR-1908-3p gene, a congener thereof, a transcript thereof, or a variant or a derivative thereof. None of the previously known reports show that change in the expression of the gene or the transcript thereof can serve as a marker for breast cancer.

The 48th target gene is the hsa-miR-150-3p gene, a congener thereof, a transcript thereof, or a variant or a derivative thereof. None of the previously known reports show that change in the expression of the gene or the transcript thereof can serve as a marker for breast cancer.

The 49th target gene is the hsa-miR-3937 gene, a congener thereof, a transcript thereof, or a variant or a derivative thereof. None of the previously known reports show that change in the expression of the gene or the transcript thereof can serve as a marker for breast cancer.

The 50th target gene is the hsa-miR-887-3p gene, a congener thereof, a transcript thereof, or a variant or a derivative thereof. None of the previously known reports show that change in the expression of the gene or the transcript thereof can serve as a marker for breast cancer.

The 51st target gene is the hsa-miR-3940-5p gene, a congener thereof, a transcript thereof, or a variant or a derivative thereof. None of the previously known reports show that change in the expression of the gene or the transcript thereof can serve as a marker for breast cancer.

The 52nd target gene is the hsa-miR-4741 gene, a congener thereof, a transcript thereof, or a variant or a derivative thereof. None of the previously known reports show that change in the expression of the gene or the transcript thereof can serve as a marker for breast cancer.

The 53rd target gene is the hsa-miR-6808-5p gene, a congener thereof, a transcript thereof, or a variant or a derivative thereof. None of the previously known reports show that change in the expression of the gene or the transcript thereof can serve as a marker for breast cancer.

The 54th target gene is the hsa-miR-6869-5p gene, a congener thereof, a transcript thereof, or a variant or a derivative thereof. None of the previously known reports show that change in the expression of the gene or the transcript thereof can serve as a marker for breast cancer.

The 55th target gene is the hsa-miR-5090 gene, a congener thereof, a transcript thereof, or a variant or a derivative thereof. None of the previously known reports show that change in the expression of the gene or the transcript thereof can serve as a marker for breast cancer.

The 56th target gene is the hsa-miR-615-5p gene, a congener thereof, a transcript thereof, or a variant or a derivative thereof. None of the previously known reports show that change in the expression of the gene or the transcript thereof can serve as a marker for breast cancer.

The 57th target gene is the hsa-miR-8072 gene, a congener thereof, a transcript thereof, or a variant or a derivative thereof. None of the previously known reports show that change in the expression of the gene or the transcript thereof can serve as a marker for breast cancer.

The 58th target gene is the hsa-miR-128-1-5p gene, a congener thereof, a transcript thereof, or a variant or a derivative thereof. None of the previously known reports show that change in the expression of the gene or the transcript thereof can serve as a marker for breast cancer.

The 59th target gene is the hsa-miR-1238-5p gene, a congener thereof, a transcript thereof, or a variant or a derivative thereof. None of the previously known reports show that change in the expression of the gene or the transcript thereof can serve as a marker for breast cancer.

The 60th target gene is the hsa-miR-365a-5p gene, a congener thereof, a transcript thereof, or a variant or a derivative thereof. None of the previously known reports show that change in the expression of the gene or the transcript thereof can serve as a marker for breast cancer.

The 61st target gene is the hsa-miR-204-3p gene, a congener thereof, a transcript thereof, or a variant or a derivative thereof. None of the previously known reports show that change in the expression of the gene or the transcript thereof can serve as a marker for breast cancer.

The 62nd target gene is the hsa-miR-4492 gene, a congener thereof, a transcript thereof, or a variant or a derivative thereof. None of the previously known reports show that change in the expression of the gene or the transcript thereof can serve as a marker for breast cancer.

The 63rd target gene is the hsa-miR-6785-5p gene, a congener thereof, a transcript thereof, or a variant or a derivative thereof. None of the previously known reports show that change in the expression of the gene or the transcript thereof can serve as a marker for breast cancer.

The 64th target gene is the hsa-miR-6511a-5p gene, a congener thereof, a transcript thereof, or a variant or a derivative thereof. None of the previously known reports show that change in the expression of the gene or the transcript thereof can serve as a marker for breast cancer.

The 65th target gene is the hsa-miR-4525 gene, a congener thereof, a transcript thereof, or a variant or a derivative thereof. None of the previously known reports show that change in the expression of the gene or the transcript thereof can serve as a marker for breast cancer.

The 66th target gene is the hsa-miR-1915-5p gene, a congener thereof, a transcript thereof, or a variant or a derivative thereof. None of the previously known reports show that change in the expression of the gene or the transcript thereof can serve as a marker for breast cancer.

The 67th target gene is the hsa-miR-3180 gene, a congener thereof, a transcript thereof, or a variant or a derivative thereof. None of the previously known reports show that change in the expression of the gene or the transcript thereof can serve as a marker for breast cancer.

The 68th target gene is the hsa-miR-6879-5p gene, a congener thereof, a transcript thereof, or a variant or a derivative thereof. None of the previously known reports show that change in the expression of the gene or the transcript thereof can serve as a marker for breast cancer.

The 69th target gene is the hsa-miR-1199-5p gene, a congener thereof, a transcript thereof, or a variant or a derivative thereof. None of the previously known reports show that change in the expression of the gene or the transcript thereof can serve as a marker for breast cancer.

The 70th target gene is the hsa-miR-6746-5p gene, a congener thereof, a transcript thereof, or a variant or a derivative thereof. None of the previously known reports show that change in the expression of the gene or the transcript thereof can serve as a marker for breast cancer.

The 71st target gene is the hsa-miR-711 gene, a congener thereof, a transcript thereof, or a variant or a derivative thereof. None of the previously known reports show that change in the expression of the gene or the transcript thereof can serve as a marker for breast cancer.

The 72nd target gene is the hsa-miR-663b gene, a congener thereof, a transcript thereof, or a variant or a derivative thereof. None of the previously known reports show that change in the expression of the gene or the transcript thereof can serve as a marker for breast cancer.

The 73rd target gene is the hsa-miR-4707-3p gene, a congener thereof, a transcript thereof, or a variant or a derivative thereof. None of the previously known reports show that change in the expression of the gene or the transcript thereof can serve as a marker for breast cancer.

The 74th target gene is the hsa-miR-6893-5p gene, a congener thereof, a transcript thereof, or a variant or a derivative thereof. None of the previously known reports show that change in the expression of the gene or the transcript thereof can serve as a marker for breast cancer.

The 75th target gene is the hsa-miR-4675 gene, a congener thereof, a transcript thereof, or a variant or a derivative thereof. None of the previously known reports show that change in the expression of the gene or the transcript thereof can serve as a marker for breast cancer.

The 76th target gene is the hsa-miR-4638-5p gene, a congener thereof, a transcript thereof, or a variant or a derivative thereof. None of the previously known reports show that change in the expression of the gene or the transcript thereof can serve as a marker for breast cancer.

The 77th target gene is the hsa-miR-4651 gene, a congener thereof, a transcript thereof, or a variant or a derivative thereof. None of the previously known reports show that change in the expression of the gene or the transcript thereof can serve as a marker for breast cancer.

The 78th target gene is the hsa-miR-6087 gene, a congener thereof, a transcript thereof, or a variant or a derivative thereof. None of the previously known reports show that change in the expression of the gene or the transcript thereof can serve as a marker for breast cancer.

The 79th target gene is the hsa-miR-4665-5p gene, a congener thereof, a transcript thereof, or a variant or a derivative thereof. None of the previously known reports show that change in the expression of the gene or the transcript thereof can serve as a marker for breast cancer.

The 80th target gene is the hsa-miR-4758-5p gene, a congener thereof, a transcript thereof, or a variant or a derivative thereof. None of the previously known reports show that change in the expression of the gene or the transcript thereof can serve as a marker for breast cancer.

The 81st target gene is the hsa-miR-6887-5p gene, a congener thereof, a transcript thereof, or a variant or a derivative thereof. None of the previously known reports show that change in the expression of the gene or the transcript thereof can serve as a marker for breast cancer.

The 82nd target gene is the hsa-miR-3620-5p gene, a congener thereof, a transcript thereof, or a variant or a derivative thereof. None of the previously known reports show that change in the expression of the gene or the transcript thereof can serve as a marker for breast cancer.

The 83rd target gene is the hsa-miR-1909-3p gene, a congener thereof, a transcript thereof, or a variant or a derivative thereof. None of the previously known reports show that change in the expression of the gene or the transcript thereof can serve as a marker for breast cancer.

The 84th target gene is the hsa-miR-7641 gene, a congener thereof, a transcript thereof, or a variant or a derivative thereof. None of the previously known reports show that change in the expression of the gene or the transcript thereof can serve as a marker for breast cancer.

The 85th target gene is the hsa-miR-6724-5p gene, a congener thereof, a transcript thereof, or a variant or a derivative thereof. None of the previously known reports show that change in the expression of the gene or the transcript thereof can serve as a marker for breast cancer.

The 86th target gene is the hsa-miR-1343-3p gene, a congener thereof, a transcript thereof, or a variant or a derivative thereof. None of the previously known reports show that change in the expression of the gene or the transcript thereof can serve as a marker for breast cancer.

The 87th target gene is the hsa-miR-6780b-5p gene, a congener thereof, a transcript thereof, or a variant or a derivative thereof. None of the previously known reports show that change in the expression of the gene or the transcript thereof can serve as a marker for breast cancer.

The 88th target gene is the hsa-miR-4484 gene, a congener thereof, a transcript thereof, or a variant or a derivative thereof. None of the previously known reports show that change in the expression of the gene or the transcript thereof can serve as a marker for breast cancer.

The 89th target gene is the hsa-miR-4690-5p gene, a congener thereof, a transcript thereof, or a variant or a derivative thereof. None of the previously known reports show that change in the expression of the gene or the transcript thereof can serve as a marker for breast cancer.

The 90th target gene is the hsa-miR-4429 gene, a congener thereof, a transcript thereof, or a variant or a derivative thereof. None of the previously known reports show that change in the expression of the gene or the transcript thereof can serve as a marker for breast cancer.

The 91st target gene is the hsa-miR-1227-5p gene, a congener thereof, a transcript thereof, or a variant or a derivative thereof. None of the previously known reports show that change in the expression of the gene or the transcript thereof can serve as a marker for breast cancer.

The 92nd target gene is the hsa-miR-4725-3p gene, a congener thereof, a transcript thereof, or a variant or a derivative thereof. None of the previously known reports show that change in the expression of the gene or the transcript thereof can serve as a marker for breast cancer.

The 93rd target gene is the hsa-miR-6861-5p gene, a congener thereof, a transcript thereof, or a variant or a derivative thereof. None of the previously known reports show that change in the expression of the gene or the transcript thereof can serve as a marker for breast cancer.

The 94th target gene is the hsa-miR-6812-5p gene, a congener thereof, a transcript thereof, or a variant or a derivative thereof. None of the previously known reports show that change in the expression of the gene or the transcript thereof can serve as a marker for breast cancer.

The 95th target gene is the hsa-miR-3197 gene, a congener thereof, a transcript thereof, or a variant or a derivative thereof. None of the previously known reports show that change in the expression of the gene or the transcript thereof can serve as a marker for breast cancer.

The 96th target gene is the hsa-miR-8059 gene, a congener thereof, a transcript thereof, or a variant or a derivative thereof. None of the previously known reports show that change in the expression of the gene or the transcript thereof can serve as a marker for breast cancer.

The 97th target gene is the hsa-miR-3185 gene, a congener thereof, a transcript thereof, or a variant or a derivative thereof. None of the previously known reports show that change in the expression of the gene or the transcript thereof can serve as a marker for breast cancer.

The 98th target gene is the hsa-miR-4706 gene, a congener thereof, a transcript thereof, or a variant or a derivative thereof. None of the previously known reports show that change in the expression of the gene or the transcript thereof can serve as a marker for breast cancer.

The 99th target gene is the hsa-miR-4497 gene, a congener thereof, a transcript thereof, or a variant or a derivative thereof. None of the previously known reports show that change in the expression of the gene or the transcript thereof can serve as a marker for breast cancer.

The 100th target gene is the hsa-miR-3131 gene, a congener thereof, a transcript thereof, or a variant or a derivative thereof. None of the previously known reports show that change in the expression of the gene or the transcript thereof can serve as a marker for breast cancer.

The 101st target gene is the hsa-miR-6806-5p gene, a congener thereof, a transcript thereof, or a variant or a derivative thereof. None of the previously known reports show that change in the expression of the gene or the transcript thereof can serve as a marker for breast cancer.

The 102nd target gene is the hsa-miR-187-5p gene, a congener thereof, a transcript thereof, or a variant or a derivative thereof. None of the previously known reports show that change in the expression of the gene or the transcript thereof can serve as a marker for breast cancer.

The 103rd target gene is the hsa-miR-3180-3p gene, a congener thereof, a transcript thereof, or a variant or a derivative thereof. None of the previously known reports show that change in the expression of the gene or the transcript thereof can serve as a marker for breast cancer.

The 104th target gene is the hsa-miR-6848-5p gene, a congener thereof, a transcript thereof, or a variant or a derivative thereof. None of the previously known reports show that change in the expression of the gene or the transcript thereof can serve as a marker for breast cancer.

The 105th target gene is the hsa-miR-6820-5p gene, a congener thereof, a transcript thereof, or a variant or a derivative thereof. None of the previously known reports show that change in the expression of the gene or the transcript thereof can serve as a marker for breast cancer.

The 106th target gene is the hsa-miR-6800-5p gene, a congener thereof, a transcript thereof, or a variant or a derivative thereof. None of the previously known reports show that change in the expression of the gene or the transcript thereof can serve as a marker for breast cancer.

The 107th target gene is the hsa-miR-6717-5p gene, a congener thereof, a transcript thereof, or a variant or a derivative thereof. None of the previously known reports show that change in the expression of the gene or the transcript thereof can serve as a marker for breast cancer.

The 108th target gene is the hsa-miR-6795-5p gene, a congener thereof, a transcript thereof, or a variant or a derivative thereof. None of the previously known reports show that change in the expression of the gene or the transcript thereof can serve as a marker for breast cancer.

The 109th target gene is the hsa-miR-4632-5p gene, a congener thereof, a transcript thereof, or a variant or a derivative thereof. None of the previously known reports show that change in the expression of the gene or the transcript thereof can serve as a marker for breast cancer.

The 110th target gene is the hsa-miR-665 gene, a congener thereof, a transcript thereof, or a variant or a derivative thereof. None of the previously known reports show that change in the expression of the gene or the transcript thereof can serve as a marker for breast cancer.

The 111th target gene is the hsa-miR-6778-5p gene, a congener thereof, a transcript thereof, or a variant or a derivative thereof. None of the previously known reports show that change in the expression of the gene or the transcript thereof can serve as a marker for breast cancer.

The 112th target gene is the hsa-miR-3663-3p gene, a congener thereof, a transcript thereof, or a variant or a derivative thereof. None of the previously known reports show that change in the expression of the gene or the transcript thereof can serve as a marker for breast cancer.

The 113th target gene is the hsa-miR-4689 gene, a congener thereof, a transcript thereof, or a variant or a derivative thereof. None of the previously known reports show that change in the expression of the gene or the transcript thereof can serve as a marker for breast cancer.

The 114th target gene is the hsa-miR-211-3p gene, a congener thereof, a transcript thereof, or a variant or a derivative thereof. None of the previously known reports show that change in the expression of the gene or the transcript thereof can serve as a marker for breast cancer.

The 115th target gene is the hsa-miR-6511b-5p gene, a congener thereof, a transcript thereof, or a variant or a derivative thereof. None of the previously known reports show that change in the expression of the gene or the transcript thereof can serve as a marker for breast cancer.

The 116th target gene is the hsa-miR-4750-5p gene, a congener thereof, a transcript thereof, or a variant or a derivative thereof. None of the previously known reports show that change in the expression of the gene or the transcript thereof can serve as a marker for breast cancer.

The 117th target gene is the hsa-miR-6126 gene, a congener thereof, a transcript thereof, or a variant or a derivative thereof. None of the previously known reports show that change in the expression of the gene or the transcript thereof can serve as a marker for breast cancer.

The 118th target gene is the hsa-miR-614 gene, a congener thereof, a transcript thereof, or a variant or a derivative thereof. None of the previously known reports show that change in the expression of the gene or the transcript thereof can serve as a marker for breast cancer.

The 119th target gene is the hsa-miR-7110-5p gene, a congener thereof, a transcript thereof, or a variant or a derivative thereof. None of the previously known reports show that change in the expression of the gene or the transcript thereof can serve as a marker for breast cancer.

The 120th target gene is the hsa-miR-744-5p gene, a congener thereof, a transcript thereof, or a variant or a derivative thereof. None of the previously known reports show that change in the expression of the gene or the transcript thereof can serve as a marker for breast cancer.

The 121st target gene is the hsa-miR-6769a-5p gene, a congener thereof, a transcript thereof, or a variant or a derivative thereof. None of the previously known reports show that change in the expression of the gene or the transcript thereof can serve as a marker for breast cancer.

The 122nd target gene is the hsa-miR-4792 gene, a congener thereof, a transcript thereof, or a variant or a derivative thereof. None of the previously known reports show that change in the expression of the gene or the transcript thereof can serve as a marker for breast cancer.

The 123rd target gene is the hsa-miR-5787 gene, a congener thereof, a transcript thereof, or a variant or a derivative thereof. None of the previously known reports show that change in the expression of the gene or the transcript thereof can serve as a marker for breast cancer.

The 124th target gene is the hsa-miR-6798-5p gene, a congener thereof, a transcript thereof, or a variant or a derivative thereof. None of the previously known reports show that change in the expression of the gene or the transcript thereof can serve as a marker for breast cancer.

The 125th target gene is the hsa-miR-6781-5p gene, a congener thereof, a transcript thereof, or a variant or a derivative thereof. None of the previously known reports show that change in the expression of the gene or the transcript thereof can serve as a marker for breast cancer.

The 126th target gene is the hsa-miR-4419b gene, a congener thereof, a transcript thereof, or a variant or a derivative thereof. None of the previously known reports show that change in the expression of the gene or the transcript thereof can serve as a marker for breast cancer.

The 127th target gene is the hsa-miR-4446-3p gene, a congener thereof, a transcript thereof, or a variant or a derivative thereof. None of the previously known reports show that change in the expression of the gene or the transcript thereof can serve as a marker for breast cancer.

The 128th target gene is the hsa-miR-4259 gene, a congener thereof, a transcript thereof, or a variant or a derivative thereof. None of the previously known reports show that change in the expression of the gene or the transcript thereof can serve as a marker for breast cancer.

The 129th target gene is the hsa-miR-5572 gene, a congener thereof, a transcript thereof, or a variant or a derivative thereof. None of the previously known reports show that change in the expression of the gene or the transcript thereof can serve as a marker for breast cancer.

The 130th target gene is the hsa-miR-6075 gene, a congener thereof, a transcript thereof, or a variant or a derivative thereof. None of the previously known reports show that change in the expression of the gene or the transcript thereof can serve as a marker for breast cancer.

The 131st target gene is the hsa-miR-296-3p gene, a congener thereof, a transcript thereof, or a variant or a derivative thereof. None of the previously known reports show that change in the expression of the gene or the transcript thereof can serve as a marker for breast cancer.

The 132nd target gene is the hsa-miR-6891-5p gene, a congener thereof, a transcript thereof, or a variant or a derivative thereof. None of the previously known reports show that change in the expression of the gene or the transcript thereof can serve as a marker for breast cancer.

The 133rd target gene is the hsa-miR-4745-5p gene, a congener thereof, a transcript thereof, or a variant or a derivative thereof. None of the previously known reports show that change in the expression of the gene or the transcript thereof can serve as a marker for breast cancer.

The 134th target gene is the hsa-miR-6775-5p gene, a congener thereof, a transcript thereof, or a variant or a derivative thereof. None of the previously known reports show that change in the expression of the gene or the transcript thereof can serve as a marker for breast cancer.

The 135th target gene is the hsa-miR-6870-5p gene, a congener thereof, a transcript thereof, or a variant or a derivative thereof. None of the previously known reports show that change in the expression of the gene or the transcript thereof can serve as a marker for breast cancer.

The 136th target gene is the hsa-miR-920 gene, a congener thereof, a transcript thereof, or a variant or a derivative thereof. None of the previously known reports show that change in the expression of the gene or the transcript thereof can serve as a marker for breast cancer.

The 137th target gene is the hsa-miR-4530 gene, a congener thereof, a transcript thereof, or a variant or a derivative thereof. None of the previously known reports show that change in the expression of the gene or the transcript thereof can serve as a marker for breast cancer.

The 138th target gene is the hsa-miR-6819-5p gene, a congener thereof, a transcript thereof, or a variant or a derivative thereof. None of the previously known reports show that change in the expression of the gene or the transcript thereof can serve as a marker for breast cancer.

The 139th target gene is the hsa-miR-6825-5p gene, a congener thereof, a transcript thereof, or a variant or a derivative thereof. None of the previously known reports show that change in the expression of the gene or the transcript thereof can serve as a marker for breast cancer.

The 140th target gene is the hsa-miR-7847-3p gene, a congener thereof, a transcript thereof, or a variant or a derivative thereof. None of the previously known reports show that change in the expression of the gene or the transcript thereof can serve as a marker for breast cancer.

The 141st target gene is the hsa-miR-6131 gene, a congener thereof, a transcript thereof, or a variant or a derivative thereof. None of the previously known reports show that change in the expression of the gene or the transcript thereof can serve as a marker for breast cancer.

The 142nd target gene is the hsa-miR-4433-3p gene, a congener thereof, a transcript thereof, or a variant or a derivative thereof. None of the previously known reports show that change in the expression of the gene or the transcript thereof can serve as a marker for breast cancer.

The 143rd target gene is the hsa-miR-1228-5p gene, a congener thereof, a transcript thereof, or a variant or a derivative thereof. None of the previously known reports show that change in the expression of the gene or the transcript thereof can serve as a marker for breast cancer.

The 144th target gene is the hsa-miR-6743-5p gene, a congener thereof, a transcript thereof, or a variant or a derivative thereof. None of the previously known reports show that change in the expression of the gene or the transcript thereof can serve as a marker for breast cancer.

The 145th target gene is the hsa-miR-1268a gene, a congener thereof, a transcript thereof, or a variant or a derivative thereof. None of the previously known reports show that change in the expression of the gene or the transcript thereof can serve as a marker for breast cancer.

The 146th target gene is the hsa-miR-3917 gene, a congener thereof, a transcript thereof, or a variant or a derivative thereof. None of the previously known reports show that change in the expression of the gene or the transcript thereof can serve as a marker for breast cancer.

The 147th target gene is the hsa-miR-6786-5p gene, a congener thereof, a transcript thereof, or a variant or a derivative thereof. None of the previously known reports show that change in the expression of the gene or the transcript thereof can serve as a marker for breast cancer.

The 148th target gene is the hsa-miR-3154 gene, a congener thereof, a transcript thereof, or a variant or a derivative thereof. None of the previously known reports show that change in the expression of the gene or the transcript thereof can serve as a marker for breast cancer.

The 149th target gene is the hsa-miR-638 gene, a congener thereof, a transcript thereof, or a variant or a derivative thereof. None of the previously known reports show that change in the expression of the gene or the transcript thereof can serve as a marker for breast cancer.

The 150th target gene is the hsa-miR-6741-5p gene, a congener thereof, a transcript thereof, or a variant or a derivative thereof. None of the previously known reports show that change in the expression of the gene or the transcript thereof can serve as a marker for breast cancer.

The 151st target gene is the hsa-miR-6889-5p gene, a congener thereof, a transcript thereof, or a variant or a The 152nd target gene is the hsa-miR-6840-3p gene, a congener thereof, a transcript thereof, or a variant or a derivative thereof. None of the previously known reports show that change in the expression of the gene or the transcript thereof can serve as a marker for breast cancer.

The 153rd target gene is the hsa-miR-6510-5p gene, a congener thereof, a transcript thereof, or a variant or a derivative thereof. None of the previously known reports show that change in the expression of the gene or the transcript thereof can serve as a marker for breast cancer.

The 154th target gene is the hsa-miR-3188 gene, a congener thereof, a transcript thereof, or a variant or a derivative thereof. None of the previously known reports show that change in the expression of the gene or the transcript thereof can serve as a marker for breast cancer.

The 155th target gene is the hsa-miR-551b-5p gene, a congener thereof, a transcript thereof, or a variant or a derivative thereof. None of the previously known reports show that change in the expression of the gene or the transcript thereof can serve as a marker for breast cancer.

The 156th target gene is the hsa-miR-5001-5p gene, a congener thereof, a transcript thereof, or a variant or a derivative thereof. None of the previously known reports show that change in the expression of the gene or the transcript thereof can serve as a marker for breast cancer.

The 157th target gene is the hsa-miR-1268b gene, a congener thereof, a transcript thereof, or a variant or a derivative thereof. None of the previously known reports show that change in the expression of the gene or the transcript thereof can serve as a marker for breast cancer.

The 158th target gene is the hsa-miR-7107-5p gene, a congener thereof, a transcript thereof, or a variant or a derivative thereof. None of the previously known reports show that change in the expression of the gene or the transcript thereof can serve as a marker for breast cancer.

The 159th target gene is the hsa-miR-6824-5p gene, a congener thereof, a transcript thereof, or a variant or a derivative thereof. None of the previously known reports show that change in the expression of the gene or the transcript thereof can serve as a marker for breast cancer.

The 160th target gene is the hsa-miR-6732-5p gene, a congener thereof, a transcript thereof, or a variant or a derivative thereof. None of the previously known reports show that change in the expression of the gene or the transcript thereof can serve as a marker for breast cancer.

The 161st target gene is the hsa-miR-371a-5p gene, a congener thereof, a transcript thereof, or a variant or a derivative thereof. None of the previously known reports show that change in the expression of the gene or the transcript thereof can serve as a marker for breast cancer.

The 162nd target gene is the hsa-miR-6794-5p gene, a congener thereof, a transcript thereof, or a variant or a derivative thereof. None of the previously known reports show that change in the expression of the gene or the transcript thereof can serve as a marker for breast cancer.

The 163rd target gene is the hsa-miR-6779-5p gene, a congener thereof, a transcript thereof, or a variant or a derivative thereof. None of the previously known reports show that change in the expression of the gene or the transcript thereof can serve as a marker for breast cancer.

The 164th target gene is the hsa-miR-4271 gene, a congener thereof, a transcript thereof, or a variant or a derivative thereof. None of the previously known reports show that change in the expression of the gene or the transcript thereof can serve as a marker for breast cancer.

The 165th target gene is the hsa-miR-5195-3p gene, a congener thereof, a transcript thereof, or a variant or a derivative thereof. None of the previously known reports show that change in the expression of the gene or the transcript thereof can serve as a marker for breast cancer.

The 166th target gene is the hsa-miR-6762-5p gene, a congener thereof, a transcript thereof, or a variant or a derivative thereof. None of the previously known reports show that change in the expression of the gene or the transcript thereof can serve as a marker for breast cancer.

The 167th target gene is the hsa-miR-939-5p gene, a congener thereof, a transcript thereof, or a variant or a derivative thereof. None of the previously known reports show that change in the expression of the gene or the transcript thereof can serve as a marker for breast cancer.

The 168th target gene is the hsa-miR-1247-3p gene, a congener thereof, a transcript thereof, or a variant or a derivative thereof. None of the previously known reports show that change in the expression of the gene or the transcript thereof can serve as a marker for breast cancer.

The 169th target gene is the hsa-miR-6777-5p gene, a congener thereof, a transcript thereof, or a variant or a derivative thereof. None of the previously known reports show that change in the expression of the gene or the transcript thereof can serve as a marker for breast cancer.

The 170th target gene is the hsa-miR-6722-3p gene, a congener thereof, a transcript thereof, or a variant or a derivative thereof. None of the previously known reports show that change in the expression of the gene or the transcript thereof can serve as a marker for breast cancer.

The 171st target gene is the hsa-miR-3656 gene, a congener thereof, a transcript thereof, or a variant or a derivative thereof. None of the previously known reports show that change in the expression of the gene or the transcript thereof can serve as a marker for breast cancer.

The 172nd target gene is the hsa-miR-4688 gene, a congener thereof, a transcript thereof, or a variant or a derivative thereof. None of the previously known reports show that change in the expression of the gene or the transcript thereof can serve as a marker for breast cancer.

The 173rd target gene is the hsa-miR-3195 gene, a congener thereof, a transcript thereof, or a variant or a derivative thereof. None of the previously known reports show that change in the expression of the gene or the transcript thereof can serve as a marker for breast cancer.

The 174th target gene is the hsa-miR-6766-5p gene, a congener thereof, a transcript thereof, or a variant or a derivative thereof. None of the previously known reports show that change in the expression of the gene or the transcript thereof can serve as a marker for breast cancer.

The 175th target gene is the hsa-miR-4447 gene, a congener thereof, a transcript thereof, or a variant or a derivative thereof. None of the previously known reports show that change in the expression of the gene or the transcript thereof can serve as a marker for breast cancer.

The 176th target gene is the hsa-miR-4656 gene, a congener thereof, a transcript thereof, or a variant or a derivative thereof. None of the previously known reports show that change in the expression of the gene or the transcript thereof can serve as a marker for breast cancer.

The 177th target gene is the hsa-miR-7108-5p gene, a congener thereof, a transcript thereof, or a variant or a derivative thereof. None of the previously known reports show that change in the expression of the gene or the transcript thereof can serve as a marker for breast cancer.

The 178th target gene is the hsa-miR-3191-3p gene, a congener thereof, a transcript thereof, or a variant or a derivative thereof. None of the previously known reports show that change in the expression of the gene or the transcript thereof can serve as a marker for breast cancer.

The 179th target gene is the hsa-miR-1273g-3p gene, a congener thereof, a transcript thereof, or a variant or a derivative thereof. None of the previously known reports show that change in the expression of the gene or the transcript thereof can serve as a marker for breast cancer.

The 180th target gene is the hsa-miR-4463 gene, a congener thereof, a transcript thereof, or a variant or a derivative thereof. None of the previously known reports show that change in the expression of the gene or the transcript thereof can serve as a marker for breast cancer.

The 181st target gene is the hsa-miR-2861 gene, a congener thereof, a transcript thereof, or a variant or a derivative thereof. None of the previously known reports show that change in the expression of the gene or the transcript thereof can serve as a marker for breast cancer.

The 182nd target gene is the hsa-miR-3196 gene, a congener thereof, a transcript thereof, or a variant or a derivative thereof. None of the previously known reports show that change in the expression of the gene or the transcript thereof can serve as a marker for breast cancer.

The 183rd target gene is the hsa-miR-6877-5p gene, a congener thereof, a transcript thereof, or a variant or a derivative thereof. None of the previously known reports show that change in the expression of the gene or the transcript thereof can serve as a marker for breast cancer.

The 184th target gene is the hsa-miR-3679-5p gene, a congener thereof, a transcript thereof, or a variant or a derivative thereof. None of the previously known reports show that change in the expression of the gene or the transcript thereof can serve as a marker for breast cancer.

The 185th target gene is the hsa-miR-4442 gene, a congener thereof, a transcript thereof, or a variant or a derivative thereof. None of the previously known reports show that change in the expression of the gene or the transcript thereof can serve as a marker for breast cancer.

The 186th target gene is the hsa-miR-6789-5p gene, a congener thereof, a transcript thereof, or a variant or a derivative thereof. None of the previously known reports show that change in the expression of the gene or the transcript thereof can serve as a marker for breast cancer.

The 187th target gene is the hsa-miR-6782-5p gene, a congener thereof, a transcript thereof, or a variant or a derivative thereof. None of the previously known reports show that change in the expression of the gene or the transcript thereof can serve as a marker for breast cancer.

The 188th target gene is the hsa-miR-486-3p gene, a congener thereof, a transcript thereof, or a variant or a derivative thereof. None of the previously known reports show that change in the expression of the gene or the transcript thereof can serve as a marker for breast cancer.

The 189th target gene is the hsa-miR-6085 gene, a congener thereof, a transcript thereof, or a variant or a derivative thereof. None of the previously known reports show that change in the expression of the gene or the transcript thereof can serve as a marker for breast cancer.

The 190th target gene is the hsa-miR-4746-3p gene, a congener thereof, a transcript thereof, or a variant or a derivative thereof. None of the previously known reports show that change in the expression of the gene or the transcript thereof can serve as a marker for breast cancer.

The 191st target gene is the hsa-miR-619-5p gene, a congener thereof, a transcript thereof, or a variant or a derivative thereof. None of the previously known reports show that change in the expression of the gene or the transcript thereof can serve as a marker for breast cancer.

The 192nd target gene is the hsa-miR-937-5p gene, a congener thereof, a transcript thereof, or a variant or a derivative thereof. None of the previously known reports show that change in the expression of the gene or the transcript thereof can serve as a marker for breast cancer.

The 193rd target gene is the hsa-miR-6803-5p gene, a congener thereof, a transcript thereof, or a variant or a derivative thereof. None of the previously known reports show that change in the expression of the gene or the transcript thereof can serve as a marker for breast cancer.

The 194th target gene is the hsa-miR-4298 gene, a congener thereof, a transcript thereof, or a variant or a derivative thereof. None of the previously known reports show that change in the expression of the gene or the transcript thereof can serve as a marker for breast cancer.

The 195th target gene is the hsa-miR-4454 gene, a congener thereof, a transcript thereof, or a variant or a derivative thereof. None of the previously known reports show that change in the expression of the gene or the transcript thereof can serve as a marker for breast cancer.

The 196th target gene is the hsa-miR-4459 gene, a congener thereof, a transcript thereof, or a variant or a derivative thereof. None of the previously known reports show that change in the expression of the gene or the transcript thereof can serve as a marker for breast cancer.

The 197th target gene is the hsa-miR-7150 gene, a congener thereof, a transcript thereof, or a variant or a derivative thereof. None of the previously known reports show that change in the expression of the gene or the transcript thereof can serve as a marker for breast cancer.

The 198th target gene is the hsa-miR-6880-5p gene, a congener thereof, a transcript thereof, or a variant or a derivative thereof. None of the previously known reports show that change in the expression of the gene or the transcript thereof can serve as a marker for breast cancer.

The 199th target gene is the hsa-miR-4449 gene, a congener thereof, a transcript thereof, or a variant or a derivative thereof. None of the previously known reports show that change in the expression of the gene or the transcript thereof can serve as a marker for breast cancer.

The 200th target gene is the hsa-miR-8063 gene, a congener thereof, a transcript thereof, or a variant or a derivative thereof. None of the previously known reports show that change in the expression of the gene or the transcript thereof can serve as a marker for breast cancer.

The 201st target gene is the hsa-miR-4695-5p gene, a congener thereof, a transcript thereof, or a variant or a derivative thereof. None of the previously known reports show that change in the expression of the gene or the transcript thereof can serve as a marker for breast cancer.

The 202nd target gene is the hsa-miR-6132 gene, a congener thereof, a transcript thereof, or a variant or a derivative thereof. None of the previously known reports show that change in the expression of the gene or the transcript thereof can serve as a marker for breast cancer.

The 203rd target gene is the hsa-miR-6829-5p gene, a congener thereof, a transcript thereof, or a variant or a derivative thereof. None of the previously known reports show that change in the expression of the gene or the transcript thereof can serve as a marker for breast cancer.

The 204th target gene is the hsa-miR-4486 gene, a congener thereof, a transcript thereof, or a variant or a derivative thereof. None of the previously known reports show that change in the expression of the gene or the transcript thereof can serve as a marker for breast cancer.

The 205th target gene is the hsa-miR-6805-3p gene, a congener thereof, a transcript thereof, or a variant or a derivative thereof. None of the previously known reports show that change in the expression of the gene or the transcript thereof can serve as a marker for breast cancer.

The 206th target gene is the hsa-miR-6826-5p gene, a congener thereof, a transcript thereof, or a variant or a derivative thereof. None of the previously known reports show that change in the expression of the gene or the transcript thereof can serve as a marker for breast cancer.

The 207th target gene is the hsa-miR-4508 gene, a congener thereof, a transcript thereof, or a variant or a derivative thereof. None of the previously known reports show that change in the expression of the gene or the transcript thereof can serve as a marker for breast cancer.

The 208th target gene is the hsa-miR-1343-5p gene, a congener thereof, a transcript thereof, or a variant or a derivative thereof. None of the previously known reports show that change in the expression of the gene or the transcript thereof can serve as a marker for breast cancer.

The 209th target gene is the hsa-miR-7114-5p gene, a congener thereof, a transcript thereof, or a variant or a derivative thereof. None of the previously known reports show that change in the expression of the gene or the transcript thereof can serve as a marker for breast cancer.

The 210th target gene is the hsa-miR-3622a-5p gene, a congener thereof, a transcript thereof, or a variant or a derivative thereof. None of the previously known reports show that change in the expression of the gene or the transcript thereof can serve as a marker for breast cancer.

The 211th target gene is the hsa-miR-6765-5p gene, a congener thereof, a transcript thereof, or a variant or a derivative thereof. None of the previously known reports show that change in the expression of the gene or the transcript thereof can serve as a marker for breast cancer.

The 212th target gene is the hsa-miR-7845-5p gene, a congener thereof, a transcript thereof, or a variant or a derivative thereof. None of the previously known reports show that change in the expression of the gene or the transcript thereof can serve as a marker for breast cancer.

The 213th target gene is the hsa-miR-3960 gene, a congener thereof, a transcript thereof, or a variant or a derivative thereof. None of the previously known reports show that change in the expression of the gene or the transcript thereof can serve as a marker for breast cancer.

The 214th target gene is the hsa-miR-6749-5p gene, a congener thereof, a transcript thereof, or a variant or a derivative thereof. None of the previously known reports show that change in the expression of the gene or the transcript thereof can serve as a marker for breast cancer.

The 215th target gene is the hsa-miR-1260b gene, a congener thereof, a transcript thereof, or a variant or a derivative thereof. None of the previously known reports show that change in the expression of the gene or the transcript thereof can serve as a marker for breast cancer.

The 216th target gene is the hsa-miR-6799-5p gene, a congener thereof, a transcript thereof, or a variant or a derivative thereof. None of the previously known reports show that change in the expression of the gene or the transcript thereof can serve as a marker for breast cancer.

The 217th target gene is the hsa-miR-4723-5p gene, a congener thereof, a transcript thereof, or a variant or a derivative thereof. None of the previously known reports show that change in the expression of the gene or the transcript thereof can serve as a marker for breast cancer.

The 218th target gene is the hsa-miR-6784-5p gene, a congener thereof, a transcript thereof, or a variant or a derivative thereof. None of the previously known reports show that change in the expression of the gene or the transcript thereof can serve as a marker for breast cancer.

The 219th target gene is the hsa-miR-5100 gene, a congener thereof, a transcript thereof, or a variant or a derivative thereof. None of the previously known reports show that change in the expression of the gene or the transcript thereof can serve as a marker for breast cancer.

The 220th target gene is the hsa-miR-6769b-5p gene, a congener thereof, a transcript thereof, or a variant or a derivative thereof. None of the previously known reports show that change in the expression of the gene or the transcript thereof can serve as a marker for breast cancer.

The 221st target gene is the hsa-miR-1207-5p gene, a congener thereof, a transcript thereof, or a variant or a derivative thereof. None of the previously known reports show that change in the expression of the gene or the transcript thereof can serve as a marker for breast cancer.

The 222nd target gene is the hsa-miR-642a-3p gene, a congener thereof, a transcript thereof, or a variant or a derivative thereof. None of the previously known reports show that change in the expression of the gene or the transcript thereof can serve as a marker for breast cancer.

The 223rd target gene is the hsa-miR-4505 gene, a congener thereof, a transcript thereof, or a variant or a derivative thereof. None of the previously known reports show that change in the expression of the gene or the transcript thereof can serve as a marker for breast cancer.

The 224th target gene is the hsa-miR-4270 gene, a congener thereof, a transcript thereof, or a variant or a derivative thereof. None of the previously known reports show that change in the expression of the gene or the transcript thereof can serve as a marker for breast cancer.

The 225th target gene is the hsa-miR-6721-5p gene, a congener thereof, a transcript thereof, or a variant or a derivative thereof. None of the previously known reports show that change in the expression of the gene or the transcript thereof can serve as a marker for breast cancer.

The 226th target gene is the hsa-miR-7111-5p gene, a congener thereof, a transcript thereof, or a variant or a derivative thereof. None of the previously known reports show that change in the expression of the gene or the transcript thereof can serve as a marker for breast cancer.

The 227th target gene is the hsa-miR-6791-5p gene, a congener thereof, a transcript thereof, or a variant or a derivative thereof. None of the previously known reports show that change in the expression of the gene or the transcript thereof can serve as a marker for breast cancer.

The 228th target gene is the hsa-miR-7109-5p gene, a congener thereof, a transcript thereof, or a variant or a derivative thereof. None of the previously known reports show that change in the expression of the gene or the transcript thereof can serve as a marker for breast cancer.

The 229th target gene is the hsa-miR-4258 gene, a congener thereof, a transcript thereof, or a variant or a derivative thereof. None of the previously known reports show that change in the expression of the gene or the transcript thereof can serve as a marker for breast cancer.

The 230th target gene is the hsa-miR-6515-3p gene, a congener thereof, a transcript thereof, or a variant or a derivative thereof. None of the previously known reports show that change in the expression of the gene or the transcript thereof can serve as a marker for breast cancer.

The 231st target gene is the hsa-miR-6851-5p gene, a congener thereof, a transcript thereof, or a variant or a derivative thereof. None of the previously known reports show that change in the expression of the gene or the transcript thereof can serve as a marker for breast cancer.

The 232nd target gene is the hsa-miR-6125 gene, a congener thereof, a transcript thereof, or a variant or a derivative thereof. None of the previously known reports show that change in the expression of the gene or the transcript thereof can serve as a marker for breast cancer.

The 233rd target gene is the hsa-miR-4749-5p gene, a congener thereof, a transcript thereof, or a variant or a derivative thereof. None of the previously known reports show that change in the expression of the gene or the transcript thereof can serve as a marker for breast cancer.

The 234th target gene is the hsa-miR-4726-5p gene, a congener thereof, a transcript thereof, or a variant or a derivative thereof. None of the previously known reports show that change in the expression of the gene or the transcript thereof can serve as a marker for breast cancer.

The 235th target gene is the hsa-miR-4513 gene, a congener thereof, a transcript thereof, or a variant or a derivative thereof. None of the previously known reports show that change in the expression of the gene or the transcript thereof can serve as a marker for breast cancer.

The 236th target gene is the hsa-miR-760 gene, a congener thereof, a transcript thereof, or a variant or a derivative thereof. The previously known report shows that change in the expression of the gene or the transcript thereof can serve as a marker for breast cancer (Non-Patent Literature 3 described above).

The 237th target gene is the hsa-miR-602 gene, a congener thereof, a transcript thereof, or a variant or a derivative thereof. The previously known report shows that change in the expression of the gene or the transcript thereof can serve as a marker for breast cancer (Patent Literature 1 described above).

The 238th target gene is the hsa-miR-423-5p gene, a congener thereof, a transcript thereof, or a variant or a derivative thereof. The previously known report shows that change in the expression of the gene or the transcript thereof can serve as a marker for breast cancer (Non-Patent Literature 4 described above).

The 239th target gene is the hsa-miR-92a-2-5p gene, a congener thereof, a transcript thereof, or a variant or a derivative thereof. The previously known report shows that change in the expression of the gene or the transcript thereof can serve as a marker for breast cancer (Patent Literature 3 described above).

The 240th target gene is the hsa-miR-16-5p gene, a congener thereof, a transcript thereof, or a variant or a derivative thereof. The previously known report shows that change in the expression of the gene or the transcript thereof can serve as a marker for breast cancer (Patent Literature 4 described above).

The 241st target gene is the hsa-miR-451a gene, a congener thereof, a transcript thereof, or a variant or a derivative thereof. The previously known report shows that change in the expression of the gene or the transcript thereof can serve as a marker for breast cancer (Patent Literature 4 described above).

The 242nd target gene is the hsa-miR-135a-3p gene, a congener thereof, a transcript thereof, or a variant or a derivative thereof. The previously known report shows that change in the expression of the gene or the transcript thereof can serve as a marker for breast cancer (Patent Literatures 1 and 2 described above).

The 243rd target gene is the hsa-miR-486-5p gene, a congener thereof, a transcript thereof, or a variant or a derivative thereof. The previously known report shows that change in the expression of the gene or the transcript thereof can serve as a marker for breast cancer (Non-Patent Literature 4 described above).

The 244th target gene is the hsa-miR-4257 gene, a congener thereof, a transcript thereof, or a variant or a derivative thereof. The previously known report shows that change in the expression of the gene or the transcript thereof can serve as a marker for breast cancer (Non-Patent Literature 5 described above).

The 245th target gene is the hsa-miR-92b-5p gene, a congener thereof, a transcript thereof, or a variant or a derivative thereof. The previously known report shows that change in the expression of the gene or the transcript thereof can serve as a marker for breast cancer (Patent Literature 3 described above).

The 246th target gene is the hsa-miR-1915-3p gene, a congener thereof, a transcript thereof, or a variant or a derivative thereof. The previously known report shows that change in the expression of the gene or the transcript thereof can serve as a marker for breast cancer (Non-Patent Literature 5 described above).

The 247th target gene is the hsa-miR-718 gene, a congener thereof, a transcript thereof, or a variant or a derivative thereof. The previously known report shows that change in the expression of the gene or the transcript thereof can serve as a marker for breast cancer (Non-Patent Literature 5 described above).

The 248th target gene is the hsa-miR-940 gene, a congener thereof, a transcript thereof, or a variant or a derivative thereof. The previously known report shows that change in the expression of the gene or the transcript thereof can serve as a marker for breast cancer (Non-Patent Literature 6 described above).

The 249th target gene is the hsa-miR-296-5p gene, a congener thereof, a transcript thereof, or a variant or a derivative thereof. The previously known report shows that change in the expression of the gene or the transcript thereof can serve as a marker for breast cancer (Patent Literature 4 described above).

The 250th target gene is the hsa-miR-23b-3p gene, a congener thereof, a transcript thereof, or a variant or a derivative thereof. The previously known report shows that change in the expression of the gene or the transcript thereof can serve as a marker for breast cancer (Patent Literature 2 described above).

The 251st target gene is the hsa-miR-92a-3p gene, a congener thereof, a transcript thereof, or a variant or a derivative thereof. The previously known report shows that change in the expression of the gene or the transcript thereof can serve as a marker for breast cancer (Patent Literature 3 described above).

The 252nd target gene is the hsa-miR-658 gene, a congener thereof, a transcript thereof, or a variant or a derivative thereof. None of the previously known reports show that change in the expression of the gene or the transcript thereof can serve as a marker for breast cancer.

The 253rd target gene is the hsa-miR-6842-5p gene, a congener thereof, a transcript thereof, or a variant or a derivative thereof. None of the previously known reports show that change in the expression of the gene or the transcript thereof can serve as a marker for breast cancer.

The 254th target gene is the hsa-miR-6124 gene, a congener thereof, a transcript thereof, or a variant or a derivative thereof. None of the previously known reports show that change in the expression of the gene or the transcript thereof can serve as a marker for breast cancer.

The 255th target gene is the hsa-miR-6765-3p gene, a congener thereof, a transcript thereof, or a variant or a derivative thereof. None of the previously known reports show that change in the expression of the gene or the transcript thereof can serve as a marker for breast cancer.

The 256th target gene is the hsa-miR-7106-5p gene, a congener thereof, a transcript thereof, or a variant or a derivative thereof. None of the previously known reports show that change in the expression of the gene or the transcript thereof can serve as a marker for breast cancer.

The 257th target gene is the hsa-miR-4534 gene, a congener thereof, a transcript thereof, or a variant or a derivative thereof. None of the previously known reports show that change in the expression of the gene or the transcript thereof can serve as a marker for breast cancer.

The 258th target gene is the hsa-miR-92b-3p gene, a congener thereof, a transcript thereof, or a variant or a derivative thereof. None of the previously known reports show that change in the expression of the gene or the transcript thereof can serve as a marker for breast cancer.

The 259th target gene is the hsa-miR-3135b gene, a congener thereof, a transcript thereof, or a variant or a derivative thereof. None of the previously known reports show that change in the expression of the gene or the transcript thereof can serve as a marker for breast cancer.

The 260th target gene is the hsa-miR-4687-3p gene, a congener thereof, a transcript thereof, or a variant or a derivative thereof. None of the previously known reports show that change in the expression of the gene or the transcript thereof can serve as a marker for breast cancer.

The 261st target gene is the hsa-miR-762 gene, a congener thereof, a transcript thereof, or a variant or a derivative thereof. None of the previously known reports show that change in the expression of the gene or the transcript thereof can serve as a marker for breast cancer.

The 262nd target gene is the hsa-miR-3619-3p gene, a congener thereof, a transcript thereof, or a variant or a derivative thereof. None of the previously known reports show that change in the expression of the gene or the transcript thereof can serve as a marker for breast cancer.

The 263rd target gene is the hsa-miR-4467 gene, a congener thereof, a transcript thereof, or a variant or a derivative thereof. None of the previously known reports show that change in the expression of the gene or the transcript thereof can serve as a marker for breast cancer.

The 264th target gene is the hsa-miR-557 gene, a congener thereof, a transcript thereof, or a variant or a derivative thereof. None of the previously known reports show that change in the expression of the gene or the transcript thereof can serve as a marker for breast cancer.

The 265th target gene is the hsa-miR-1237-5p gene, a congener thereof, a transcript thereof, or a variant or a derivative thereof. None of the previously known reports show that change in the expression of the gene or the transcript thereof can serve as a marker for breast cancer.

The 266th target gene is the hsa-miR-1908-5p gene, a congener thereof, a transcript thereof, or a variant or a derivative thereof. None of the previously known reports show that change in the expression of the gene or the transcript thereof can serve as a marker for breast cancer.

The 267th target gene is the hsa-miR-4286 gene, a congener thereof, a transcript thereof, or a variant or a derivative thereof. None of the previously known reports show that change in the expression of the gene or the transcript thereof can serve as a marker for breast cancer.

The 268th target gene is the hsa-miR-6885-5p gene, a congener thereof, a transcript thereof, or a variant or a derivative thereof. None of the previously known reports show that change in the expression of the gene or the transcript thereof can serve as a marker for breast cancer.

The 269th target gene is the hsa-miR-6763-5p gene, a congener thereof, a transcript thereof, or a variant or a derivative thereof. None of the previously known reports show that change in the expression of the gene or the transcript thereof can serve as a marker for breast cancer.

The 270th target gene is the hsa-miR-6089 gene, a congener thereof, a transcript thereof, or a variant or a derivative thereof. None of the previously known reports show that change in the expression of the gene or the transcript thereof can serve as a marker for breast cancer.

The 271st target gene is the hsa-miR-6816-5p gene, a congener thereof, a transcript thereof, or a variant or a derivative thereof. None of the previously known reports show that change in the expression of the gene or the transcript thereof can serve as a marker for breast cancer.

The 272nd target gene is the hsa-miR-4466 gene, a congener thereof, a transcript thereof, or a variant or a derivative thereof. None of the previously known reports show that change in the expression of the gene or the transcript thereof can serve as a marker for breast cancer.

The 273rd target gene is the hsa-miR-4488 gene, a congener thereof, a transcript thereof, or a variant or a derivative thereof. None of the previously known reports show that change in the expression of the gene or the transcript thereof can serve as a marker for breast cancer.

The 274th target gene is the hsa-miR-6752-5p gene, a congener thereof, a transcript thereof, or a variant or a derivative thereof. None of the previously known reports show that change in the expression of the gene or the transcript thereof can serve as a marker for breast cancer.

The 275th target gene is the hsa-miR-4739 gene, a congener thereof, a transcript thereof, or a variant or a derivative thereof. None of the previously known reports show that change in the expression of the gene or the transcript thereof can serve as a marker for breast cancer.

2. Nucleic Acid Probe or Primer for Detection of Breast Cancer

In the present invention, nucleic acid(s) capable of specifically binding to any of the target nucleic acids as the breast cancer markers described above can be used as a nucleic acid, for example, a nucleic acid probe or a primer, for the detection or diagnosis of breast cancer.

In the present invention, the nucleic acid probes or the primers that can be used for detecting breast cancer or for diagnosing breast cancer enables qualitative and/or quantitative measurement of the presence, expression level, or existing amount (abundance) of any of the target nucleic acids as the breast cancer markers described above, for example, human-derived hsa-miR-4783-3p, hsa-miR-4730, hsa-miR-1307-3p, hsa-miR-4634, hsa-miR-663a, hsa-miR-4532, hsa-miR-7704, hsa-miR-3178, hsa-miR-6729-5p, hsa-miR-6090, hsa-miR-4732-5p, hsa-miR-3184-5p, hsa-miR-6727-5p, hsa-miR-6088, hsa-miR-4674, hsa-miR-8073, hsa-miR-4787-5p, hsa-miR-1469, hsa-miR-125a-3p, hsa-miR-1233-5p, hsa-miR-885-3p, hsa-miR-6802-5p, hsa-miR-328-5p, hsa-miR-6787-5p, hsa-miR-8069, hsa-miR-6875-5p, hsa-miR-1246, hsa-miR-4734, hsa-miR-6757-5p, hsa-miR-6756-5p, hsa-miR-3665, hsa-miR-6836-3p, hsa-miR-6821-5p, hsa-miR-6805-5p, hsa-miR-4728-5p, hsa-miR-6726-5p, hsa-miR-197-5p, hsa-miR-149-3p, hsa-miR-6850-5p, hsa-miR-4476, hsa-miR-6858-5p, hsa-miR-564, hsa-miR-4763-3p, hsa-miR-575, hsa-miR-6771-5p, hsa-miR-1231, hsa-miR-1908-3p, hsa-miR-150-3p, hsa-miR-3937, hsa-miR-887-3p, hsa-miR-3940-5p, hsa-miR-4741, hsa-miR-6808-

5p, hsa-miR-6869-5p, hsa-miR-5090, hsa-miR-615-5p, hsa-miR-8072, hsa-miR-128-1-5p, hsa-miR-1238-5p, hsa-miR-365a-5p, hsa-miR-204-3p, hsa-miR-4492, hsa-miR-6785-5p, hsa-miR-6511a-5p, hsa-miR-4525, hsa-miR-1915-5p, hsa-miR-3180, hsa-miR-6879-5p, hsa-miR-1199-5p, hsa-miR-6746-5p, hsa-miR-711, hsa-miR-663b, hsa-miR-4707-3p, hsa-miR-6893-5p, hsa-miR-4675, hsa-miR-4638-5p, hsa-miR-4651, hsa-miR-6087, hsa-miR-4665-5p, hsa-miR-4758-5p, hsa-miR-6887-5p, hsa-miR-3620-5p, hsa-miR-1909-3p, hsa-miR-7641, hsa-miR-6724-5p, hsa-miR-1343-3p, hsa-miR-6780b-5p, hsa-miR-4484, hsa-miR-4690-5p, hsa-miR-4429, hsa-miR-1227-5p, hsa-miR-4725-3p, hsa-miR-6861-5p, hsa-miR-6812-5p, hsa-miR-3197, hsa-miR-8059, hsa-miR-3185, hsa-miR-4706, hsa-miR-4497, hsa-miR-3131, hsa-miR-6806-5p, hsa-miR-187-5p, hsa-miR-3180-3p, hsa-miR-6848-5p, hsa-miR-6820-5p, hsa-miR-6800-5p, hsa-miR-6717-5p, hsa-miR-6795-5p, hsa-miR-4632-5p, hsa-miR-665, hsa-miR-6778-5p, hsa-miR-3663-3p, hsa-miR-4689, hsa-miR-211-3p, hsa-miR-6511b-5p, hsa-miR-4750-5p, hsa-miR-6126, hsa-miR-614, hsa-miR-7110-5p, hsa-miR-744-5p, hsa-miR-6769a-5p, hsa-miR-4792, hsa-miR-5787, hsa-miR-6798-5p, hsa-miR-6781-5p, hsa-miR-4419b, hsa-miR-4446-3p, hsa-miR-4259, hsa-miR-5572, hsa-miR-6075, hsa-miR-296-3p, hsa-miR-6891-5p, hsa-miR-4745-5p, hsa-miR-6775-5p, hsa-miR-6870-5p, hsa-miR-920, hsa-miR-4530, hsa-miR-6819-5p, hsa-miR-6825-5p, hsa-miR-7847-3p, hsa-miR-6131, hsa-miR-4433-3p, hsa-miR-1228-5p, hsa-miR-6743-5p, hsa-miR-1268a, hsa-miR-3917, hsa-miR-6786-5p, hsa-miR-3154, hsa-miR-638, hsa-miR-6741-5p, hsa-miR-6889-5p, hsa-miR-6840-3p, hsa-miR-6510-5p, hsa-miR-3188, hsa-miR-551b-5p, hsa-miR-5001-5p, hsa-miR-1268b, hsa-miR-7107-5p, hsa-miR-6824-5p, hsa-miR-6732-5p, hsa-miR-371a-5p, hsa-miR-6794-5p, hsa-miR-6779-5p, hsa-miR-4271, hsa-miR-5195-3p, hsa-miR-6762-5p, hsa-miR-939-5p, hsa-miR-1247-3p, hsa-miR-6777-5p, hsa-miR-6722-3p, hsa-miR-3656, hsa-miR-4688, hsa-miR-3195, hsa-miR-6766-5p, hsa-miR-4447, hsa-miR-4656, hsa-miR-7108-5p, hsa-miR-3191-3p, hsa-miR-1273g-3p, hsa-miR-4463, hsa-miR-2861, hsa-miR-3196, hsa-miR-6877-5p, hsa-miR-3679-5p, hsa-miR-4442, hsa-miR-6789-5p, hsa-miR-6782-5p, hsa-miR-486-3p, hsa-miR-6085, hsa-miR-4746-3p, hsa-miR-619-5p, hsa-miR-937-5p, hsa-miR-6803-5p, hsa-miR-4298, hsa-miR-4454, hsa-miR-4459, hsa-miR-7150, hsa-miR-6880-5p, hsa-miR-4449, hsa-miR-8063, hsa-miR-4695-5p, hsa-miR-6132, hsa-miR-6829-5p, hsa-miR-4486, hsa-miR-6805-3p, hsa-miR-6826-5p, hsa-miR-4508, hsa-miR-1343-5p, hsa-miR-7114-5p, hsa-miR-3622a-5p, hsa-miR-6765-5p, hsa-miR-7845-5p, hsa-miR-3960, hsa-miR-6749-5p, hsa-miR-1260b, hsa-miR-6799-5p, hsa-miR-4723-5p, hsa-miR-6784-5p, hsa-miR-5100, hsa-miR-6769b-5p, hsa-miR-1207-5p, hsa-miR-642a-3p, hsa-miR-4505, hsa-miR-4270, hsa-miR-6721-5p, hsa-miR-7111-5p, hsa-miR-6791-5p, hsa-miR-7109-5p, hsa-miR-4258, hsa-miR-6515-3p, hsa-miR-6851-5p, hsa-miR-6125, hsa-miR-4749-5p, hsa-miR-4726-5p, hsa-miR-4513, hsa-miR-6089, hsa-miR-6816-5p, hsa-miR-4466, hsa-miR-4488, hsa-miR-6752-5p and hsa-miR-4739 or a combination thereof, congeners thereof, transcripts thereof, or variants or derivatives thereof; and, optionally in combination therewith, hsa-miR-760, hsa-miR-602, hsa-miR-423-5p, hsa-miR-92a-2-5p, hsa-miR-16-5p, hsa-miR-451a, hsa-miR-135a-3p, hsa-miR-486-5p, hsa-miR-4257, hsa-miR-92b-5p, hsa-miR-1915-3p, hsa-miR-718, hsa-miR-940, hsa-miR-296-5p, hsa-miR-23b-3p and hsa-miR-92a-3p or a combination thereof, transcripts thereof, or variants or derivatives thereof; and, optionally in combination therewith, hsa-miR-658, hsa-miR-6842-5p, hsa-miR-6124, hsa-miR-6765-3p, hsa-miR-7106-5p, hsa-miR-4534, hsa-miR-92b-3p, hsa-miR-3135b, hsa-miR-4687-3p, hsa-miR-762, hsa-miR-3619-3p, hsa-miR-4467, hsa-miR-557, hsa-miR-1237-5p, hsa-miR-1908-5p, hsa-miR-4286, hsa-miR-6885-5p and hsa-miR-6763-5p or a combination thereof; congeners thereof; transcripts thereof; or variants or derivatives thereof.

The expression level of the target nucleic acids described above are increased or decreased (hereinafter, referred to as "increased/decreased") depending on the types of the target nucleic acids in subjects who have breast cancer, as compared with healthy subjects. Hence, the nucleic acid of the present invention can be effectively used for measuring expression levels of the target nucleic acids in body fluids derived from subjects (e.g., humans) suspected of having breast cancer and body fluids derived from healthy subjects and thereby detecting breast cancer through the comparison thereof.

The nucleic acid probe or the primer that can be used in the present invention is a nucleic acid probe capable of specifically binding to a polynucleotide consisting of a nucleotide sequence represented by at least one of SEQ ID NOs: 1 to 235 and 851 to 856, or a primer for amplifying a polynucleotide consisting of a nucleotide sequence represented by at least one of SEQ ID NOs: 1 to 235 and 851 to 856.

The nucleic acid probe or the primer that can be used in the present invention may further comprise a nucleic acid probe capable of specifically binding to a polynucleotide consisting of a nucleotide sequence represented by at least one of SEQ ID NOs: 236 to 251, or a primer for amplifying a polynucleotide consisting of a nucleotide sequence represented by at least one of SEQ ID NOs: 236 to 251.

The nucleic acid probe or the primer that can be used in the present invention may further comprise a nucleic acid probe capable of specifically binding to a polynucleotide that consists of a nucleotide sequence represented by at least one of SEQ ID NOs: 252 to 269, or a primer for amplifying a polynucleotide that consists of a nucleotide sequence represented by at least one of SEQ ID NOs: 252 to 269.

Specifically, these nucleic acid probes or primers comprise a combination of one or more polynucleotides selected from: a group of polynucleotides that comprise nucleotide sequences represented by any of SEQ ID NOs: 1 to 871 or nucleotide sequences derived from the nucleotide sequences by the replacement of u with t, and a group of complementary polynucleotides thereof, a group of polynucleotides that respectively hybridize under stringent conditions (mentioned later) to DNAs consisting of nucleotide sequences complementary to these nucleotide sequences; and a group of complementary polynucleotides thereof, and a group of polynucleotide comprising 15 or more, preferably 17 or more consecutive nucleotides in the nucleotide sequences of these polynucleotides. These polynucleotides can be used as nucleic acid probes and primers for detecting the breast cancer markers as target nucleic acids.

More specifically, examples of the nucleic acid probes or the primers that can be used in the present invention include one or more polynucleotides selected from the group consisting of the following polynucleotides (a) to (e):

(a) a polynucleotide consisting of a nucleotide sequence represented by any of SEQ ID NOs: 1 to 235, and 851 to 856 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence complementary to a nucleotide sequence represented by any of SEQ ID NOs: 1 to 235, and 851 to 856 or a nucleotide sequence derived from the nucleotide sequence by the replacement of u with t,
(c) a polynucleotide consisting of a nucleotide sequence complementary to a nucleotide sequence represented by any of SEQ ID NOs: 1 to 235, and 851 to 856 or a nucleotide sequence derived from the nucleotide sequence by the replacement of u with t, a variant thereof, a derivative thereof, or a fragment thereof comprising 15 or more consecutive nucleotides,
(d) a polynucleotide comprising a nucleotide sequence complementary to a nucleotide sequence represented by any of SEQ ID NOs: 1 to 235, and 851 to 856 or a nucleotide sequence derived from the nucleotide sequence by the replacement of u with t, and
(e) a polynucleotide hybridizing under stringent conditions to any of the polynucleotides (a) to (d).

In addition to at least one polynucleotide selected from the group consisting of the polynucleotides (a) to (e), the nucleic acid probes or the primers that can be used in the present invention may further comprise a polynucleotide selected from the group consisting of the following polynucleotides (f) to (j):
(f) a polynucleotide consisting of a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides,
(g) a polynucleotide comprising a nucleotide sequence represented by any of SEQ ID NOs: 236 to 251,
(h) a polynucleotide consisting of a nucleotide sequence complementary to a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides,
(i) a polynucleotide comprising a nucleotide sequence complementary to a nucleotide sequence represented by any of SEQ ID NOs: 236 to 251 or a nucleotide sequence derived from the nucleotide sequence by the replacement of u with t, and
(j) a polynucleotide hybridizing under stringent conditions to any of the polynucleotides (f) to (i).

In addition to at least one polynucleotide selected from the group consisting of (a) to (j) described above, the nucleic acid probes or the primers that can be used in the present invention may further comprise a polynucleotide selected from the group consisting of the following polynucleotides (k) to (o):
(k) a polynucleotide consisting of a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides,
(l) a polynucleotide comprising a nucleotide sequence represented by any of SEQ ID NOs: 252 to 269,
(m) a polynucleotide consisting of a nucleotide sequence complementary to a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides,
(n) a polynucleotide comprising a nucleotide sequence complementary to a nucleotide sequence represented by any of SEQ ID NOs: 252 to 269 or a nucleotide sequence derived from the nucleotide sequence by the replacement of u with t, and
(o) a polynucleotide hybridizing under stringent conditions to any of the polynucleotides (k) to (n).

For these polynucleotides, the "fragment thereof comprising 15 or more consecutive nucleotides" can comprise, but is not limited to, the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide.

These polynucleotides or fragments thereof used in the present invention may each be DNA or may each be RNA.

The polynucleotides that can be used in the present invention can each be prepared by use of a general technique such as a DNA recombination technique, a PCR method, or a method using an automatic DNA/RNA synthesizer.

The DNA recombination technique and the PCR method may employ techniques described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-4783-3p, hsa-miR-4730, hsa-miR-1307-3p, hsa-miR-4634, hsa-miR-663a, hsa-miR-4532, hsa-miR-7704, hsa-miR-3178, hsa-miR-6729-5p, hsa-miR-6090, hsa-miR-4732-5p, hsa-miR-3184-5p, hsa-miR-6727-5p, hsa-miR-6088, hsa-miR-4674, hsa-miR-8073, hsa-miR-4787-5p, hsa-miR-1469, hsa-miR-125a-3p, hsa-miR-1233-5p, hsa-miR-885-3p, hsa-miR-6802-5p, hsa-miR-328-5p, hsa-miR-6787-5p, hsa-miR-8069, hsa-miR-6875-5p, hsa-miR-1246, hsa-miR-4734, hsa-miR-6757-5p, hsa-miR-6756-5p, hsa-miR-3665, hsa-miR-6836-3p, hsa-miR-6821-5p, hsa-miR-6805-5p, hsa-miR-4728-5p, hsa-miR-6726-5p, hsa-miR-197-5p, hsa-miR-149-3p, hsa-miR-6850-5p, hsa-miR-4476, hsa-miR-6858-5p, hsa-miR-564, hsa-miR-4763-3p, hsa-miR-575, hsa-miR-6771-5p, hsa-miR-1231, hsa-miR-1908-3p, hsa-miR-150-3p, hsa-miR-3937, hsa-miR-887-3p, hsa-miR-3940-5p, hsa-miR-4741, hsa-miR-6808-5p, hsa-miR-6869-5p, hsa-miR-5090, hsa-miR-615-5p, hsa-miR-8072, hsa-miR-128-1-5p, hsa-miR-1238-5p, hsa-miR-365a-5p, hsa-miR-204-3p, hsa-miR-4492, hsa-miR-6785-5p, hsa-miR-6511a-5p, hsa-miR-4525, hsa-miR-1915-5p, hsa-miR-3180, hsa-miR-6879-5p, hsa-miR-1199-5p, hsa-miR-6746-5p, hsa-miR-711, hsa-miR-663b, hsa-miR-4707-3p, hsa-miR-6893-5p, hsa-miR-4675, hsa-miR-4638-5p, hsa-miR-4651, hsa-miR-6087, hsa-miR-4665-5p, hsa-miR-4758-5p, hsa-miR-6887-5p, hsa-miR-3620-5p, hsa-miR-1909-3p, hsa-miR-7641, hsa-miR-6724-5p, hsa-miR-1343-3p, hsa-miR-6780b-5p, hsa-miR-4484, hsa-miR-4690-5p, hsa-miR-4429, hsa-miR-1227-5p, hsa-miR-4725-3p, hsa-miR-6861-5p, hsa-miR-6812-5p, hsa-miR-3197, hsa-miR-8059, hsa-miR-3185, hsa-miR-4706, hsa-miR-4497, hsa-miR-3131, hsa-miR-6806-5p, hsa-miR-187-5p, hsa-miR-3180-3p, hsa-miR-6848-5p, hsa-miR-6820-5p, hsa-miR-6800-5p, hsa-miR-6717-5p, hsa-miR-6795-5p, hsa-miR-4632-5p, hsa-miR-665, hsa-miR-6778-5p, hsa-miR-3663-3p, hsa-miR-4689, hsa-miR-211-3p, hsa-miR-6511b-5p, hsa-miR-4750-5p, hsa-miR-6126, hsa-miR-614, hsa-miR-7110-5p, hsa-miR-744-5p, hsa-miR-6769a-5p, hsa-miR-4792, hsa-miR-5787, hsa-miR-6798-5p, hsa-miR-6781-5p, hsa-miR-4419b, hsa-miR-4446-3p, hsa-miR-4259, hsamiR-5572, hsa-miR-6075, hsa-miR-296-3p, hsa-miR-6891-5p, hsa-miR-4745-5p, hsa-miR-6775-5p, hsa-miR-6870-5p, hsa-miR-920, hsa-miR-4530, hsa-miR-6819-5p, hsa-miR-6825-5p, hsa-miR-7847-3p, hsa-miR-6131, hsa-miR-4433-3p, hsa-miR-1228-5p, hsa-miR-6743-5p, hsa-miR-1268a, hsa-miR-3917, hsa-miR-6786-5p, hsa-miR-3154, hsa-miR-638, hsa-miR-6741-5p, hsa-miR-6889-5p, hsa-miR-6840-3p, hsa-miR-6510-5p, hsa-miR-3188, hsa-miR-551b-5p, hsa-miR-5001-5p, hsa-miR-1268b, hsa-miR-7107-5p, hsa-miR-6824-5p, hsa-miR-6732-5p, hsa-miR-371a-5p, hsa-miR-6794-5p, hsa-miR-6779-5p, hsa-miR-4271, hsa-miR-5195-3p, hsa-miR-6762-5p, hsa-miR-939-5p, hsa-miR-1247-3p, hsa-miR-6777-5p, hsa-miR-6722-3p, hsa-miR-3656, hsa-miR-4688, hsa-miR-3195, hsa-miR-6766-5p, hsa-miR-4447, hsa-miR-4656, hsa-miR-7108-5p, hsa-miR-3191-3p, hsa-miR-1273g-3p, hsa-miR-4463, hsa-miR-2861, hsa-miR-3196, hsa-miR-6877-5p, hsa-miR-3679-5p, hsa-miR-4442, hsa-miR-6789-5p, hsa-miR-6782-5p, hsa-miR-486-3p, hsa-miR-6085, hsa-miR-4746-3p, hsa-miR-619-5p, hsa-miR-937-5p, hsa-miR-6803-5p, hsa-miR-4298, hsa-miR-4454, hsa-miR-4459, hsa-miR-7150, hsa-miR-6880-5p, hsa-miR-4449, hsa-miR-8063, hsa-miR-4695-5p, hsa-miR-6132, hsa-miR-6829-5p, hsa-miR-4486, hsa-miR-6805-3p, hsa-miR-6826-5p, hsa-miR-4508, hsa-miR-1343-5p, hsa-miR-7114-5p, hsa-miR-3622a-5p, hsa-miR-6765-5p, hsa-miR-7845-5p, hsa-miR-3960, hsa-miR-6749-5p, hsa-miR-1260b, hsa-miR-6799-5p, hsa-miR-4723-5p, hsa-miR-6784-5p, hsa-miR-5100, hsa-miR-6769b-5p, hsa-miR-1207-5p, hsa-miR-642a-3p, hsa-miR-4505, hsa-miR-4270, hsa-miR-6721-5p, hsa-miR-7111-5p, hsa-miR-6791-5p, hsa-miR-7109-5p, hsa-miR-4258, hsa-miR-6515-3p, hsa-miR-6851-5p, hsa-miR-6125, hsa-miR-4749-5p, hsa-miR-4726-5p, hsa-miR-4513, hsa-miR-6089, hsa-miR-6816-5p, hsa-miR-4466, hsa-miR-4488, hsa-miR-6752-5p, hsa-miR-4739, hsa-miR-760, hsa-miR-602, hsa-miR-423-5p, hsa-miR-92a-2-5p, hsa-miR-16-5p, hsa-miR-451a, hsa-miR-135a-3p, hsa-miR-486-5p, hsa-miR-4257, hsa-miR-92b-5p, hsa-miR-1915-3p, hsa-miR-718, hsa-miR-940, hsa-miR-296-5p, hsa-miR-23b-3p, hsa-miR-92a-3p, hsa-miR-658, hsa-miR-6842-5p, hsa-miR-6124, hsa-miR-6765-3p, hsa-miR-7106-5p, hsa-miR-4534, hsa-miR-92b-3p, hsa-miR-3135b, hsa-miR-4687-3p, hsa-miR-762, hsa-miR-3619-3p, hsa-miR-4467, hsa-miR-557, hsa-miR-1237-5p, hsa-miR-1908-5p, hsa-miR-4286, hsa-miR-6885-5p and hsa-miR-6763-5p represented by SEQ ID NOs: 1 to 269, and 851 to 856 are known in the art, and their acquisition methods are also known as mentioned above. Therefore, each polynucleotide that can be used as a nucleic acid probe or a primer in the present invention can be prepared by cloning the gene.

Such nucleic acid probes or primers can be chemically synthesized using an automatic DNA synthesizer. In general, the phosphoramidite method is used in this synthesis, and single-stranded DNA up to approximately 100 nucleotides can be automatically synthesized by this method. The automatic DNA synthesizer is commercially available from, for example, Polygen GmbH, ABI, or Applied Biosystems, Inc.

Alternatively, the polynucleotides of the present invention can also be prepared by a cDNA cloning methods. The cDNA cloning technique may employ, for example, microRNA Cloning Kit Wako.

In this context, the sequences of the nucleic acid probes and the primers for detecting the polynucleotide consisting of a nucleotide sequence represented by any of SEQ ID NOs: 1 to 269, and 851 to 856 do not exist as miRNAs or precursors thereof in the living body or in vivo. For example, the nucleotide sequences represented by SEQ ID NO: 34 and SEQ ID NO: 205 are produced from the precursor represented by SEQ ID NO: 304. This precursor has a hairpin-like structure as shown in FIG. 1, and the nucleotide sequences represented by SEQ ID NO: 34 and SEQ ID NO: 205 have mismatch sequences with each other. As such, a nucleotide sequence completely complementary to the nucleotide sequence represented by SEQ ID NO: 34 or SEQ ID NO: 205 is not naturally produced in vivo. Likewise, the nucleic acid probe and the primer for detecting the nucleotide sequence represented by any of SEQ ID NOs: 1 to 269, and 851 to 856 have artificial nucleotide sequences that do not exist in the living body or in vivo.

3. Kit or Device for Detection of Breast Cancer

The present invention also provides a kit or a device for the detection of breast cancer, comprising one or more polynucleotides (which may include a variant, a fragment, or a derivative thereof; hereinafter, also referred to as polynucleotide for detection) that can be used as nucleic acid probes or primers in the present invention for measuring target nucleic acids as breast cancer markers.

The target nucleic acid as a breast cancer marker according to the present invention is selected from the following group 1:

miR-4783-3p, miR-4730, miR-1307-3p, miR-4634, miR-663a, miR-4532, miR-7704, miR-3178, miR-6729-5p, miR-6090, miR-4732-5p, miR-3184-5p, miR-6727-5p, miR-6088, miR-4674, miR-8073, miR-4787-5p, miR-1469, miR-125a-3p, miR-1233-5p, miR-885-3p, miR-6802-5p, miR-328-5p, miR-6787-5p, miR-8069, miR-6875-5p, miR-1246, miR-4734, miR-6757-5p, miR-6756-5p, miR-3665, miR-6836-3p, miR-6821-5p, miR-6805-5p, miR-4728-5p, miR-6726-5p, miR-197-5p, miR-149-3p, miR-6850-5p, miR-4476, miR-6858-5p, miR-564, miR-4763-3p, miR-575, miR-6771-5p, miR-1231, miR-1908-3p, miR-150-3p, miR-3937, miR-887-3p, miR-3940-5p, miR-4741, miR-6808-5p, miR-6869-5p, miR-5090, miR-615-5p, miR-8072, miR-128-1-5p, miR-1238-5p, miR-365a-5p, miR-204-3p, miR-4492, miR-6785-5p, miR-6511a-5p, miR-4525, miR-1915-5p, miR-3180, miR-6879-5p, miR-1199-5p, miR-6746-5p, miR-711, miR-663b, miR-4707-3p, miR-6893-5p, miR-4675, miR-4638-5p, miR-4651, miR-6087, miR-4665-5p, miR-4758-5p, miR-6887-5p, miR-3620-5p, miR-1909-3p, miR-7641, miR-6724-5p, miR-1343-3p, miR-6780b-5p, miR-4484, miR-4690-5p, miR-4429, miR-1227-5p, miR-4725-3p, miR-6861-5p, miR-6812-5p, miR-3197, miR-8059, miR-3185, miR-4706, miR-4497, miR-3131, miR-6806-5p, miR-187-5p, miR-3180-3p, miR-6848-5p, miR-6820-5p, miR-6800-5p, miR-6717-5p, miR-6795-5p, miR-4632-5p, miR-665, miR-6778-5p, miR-3663-3p, miR-4689, miR-211-3p, miR-6511b-5p, miR-4750-5p, miR-6126, miR-614, miR-7110-5p, miR-744-5p, miR-6769a-5p, miR-4792, miR-5787, miR-6798-5p, miR-6781-5p, miR-4419b, miR-4446-3p, miR-4259, miR-5572, miR-6075, miR-296-3p, miR-6891-5p, miR-4745-5p, miR-6775-5p, miR-6870-5p, miR-920, miR-4530, miR-6819-5p, miR-6825-5p, miR-7847-3p, miR-6131, miR-4433-3p, miR-1228-5p, miR-6743-5p, miR-1268a, miR-3917, miR-6786-5p, miR-3154, miR-638, miR-6741-5p, miR-6889-5p, miR-6840-3p, miR-6510-5p, miR-3188, miR-551b-5p, miR-5001-5p, miR-1268b, miR-7107-5p, miR-6824-5p, miR-6732-5p, miR-371a-5p, miR-6794-5p, miR-6779-5p, miR-4271, miR-5195-3p, miR-6762-5p, miR-939-5p, miR-1247-3p, miR-6777-5p, miR-6722-3p, miR-3656, miR-4688, miR-3195, miR-6766-5p, miR-4447, miR-4656, miR-7108-5p, miR-3191-3p, miR-1273g-3p, miR-4463, miR-2861, miR-3196, miR-6877-5p, miR-3679-5p, miR-4442, miR-6789-5p, miR-6782-5p, miR-486-3p, miR-6085, miR-4746-3p, miR-619-5p, miR-937-5p, miR-6803-5p, miR-4298, miR-4454, miR-4459, miR-7150, miR-6880-5p, miR-4449, miR-8063, miR-4695-5p, miR-6132, miR-6829-5p, miR-4486, miR-6805-3p, miR-6826-5p, miR-4508, miR-1343-5p, miR-7114-5p, miR-3622a-5p, miR-6765-5p, miR-7845-5p, miR-3960, miR-6749-5p, miR-1260b, miR-6799-5p, miR-4723-5p, miR-6784-5p, miR-5100, miR-6769b-5p, miR-1207-5p, miR-642a-3p, miR-4505, miR-4270, miR-6721-5p, miR-7111-5p, miR-6791-5p, miR-7109-5p, miR-4258, miR-6515-3p, miR-6851-5p, miR-6125, miR-4749-5p, miR-4726-5p, miR-4513, miR-6089, miR-6816-5p, miR-4466, miR-4488, miR-6752-5p and miR-4739.

An additional target nucleic acid(s) that may be optionally used in the measurement is selected from the following group 2:

miR-760, miR-602, miR-423-5p, miR-92a-2-5p, miR-16-5p, miR-451a, miR-135a-3p, miR-486-5p, miR-4257, miR-92b-5p, miR-1915-3p, miR-718, miR-940, miR-296-5p, miR-23b-3p and miR-92a-3p.

An additional target nucleic acid(s) that may be optionally used in the measurement is further selected from the following group 3:

miR-658, miR-6842-5p, miR-6124, miR-6765-3p, miR-7106-5p, miR-4534, miR-92b-3p, miR-3135b, miR-4687-3p, miR-762, miR-3619-3p, miR-4467, miR-557, miR-1237-5p, miR-1908-5p, miR-4286, miR-6885-5p and miR-6763-5p.

The kit or the device of the present invention comprises nucleic acid(s) capable of specifically binding to any of the target nucleic acids as the breast cancer markers described above, preferably one or more polynucleotides selected from the nucleic acid probes or the primers described in the preceding Section 2, specifically, the polynucleotides described in the preceding Section 2, or variants thereof, etc.

Specifically, the kit or the device of the present invention can comprise at least one polynucleotides comprising (or consisting of) a nucleotide sequence represented by any of SEQ ID NOs: 1 to 235, and 851 to 856 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention can further comprise one or more polynucleotides comprising (or consisting of) a nucleotide sequence represented by any of SEQ ID NOs: 236 to 251 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The kit or the device of the present invention can further comprise one or more polynucleotide(s) comprising (or consisting of) a nucleotide sequence represented by any of SEQ ID NOs: 252 to 269 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment(s) that can be comprised in the kit or the device of the present invention is/are, for example, one or more polynucleotides, preferably two or more polynucleotides selected from the group consisting of the following polynucleotides (1) to (3):

(1) a polynucleotide comprising 15 or more consecutive nucleotides in a nucleotide sequence that is derived from a nucleotide sequence represented by any of SEQ ID NOs: 1 to 235, and 851 to 856 by the replacement of u with t, or a complementary sequence thereof;

(2) a polynucleotide comprising 15 or more consecutive nucleotides in a nucleotide sequence that is derived from a nucleotide sequence represented by any of SEQ ID NOs: 236 to 251 by the replacement of u with t, or a complementary sequence thereof; and (3) a polynucleotide comprising 15 or more consecutive nucleotides in a nucleotide sequence that is derived from a nucleotide sequence represented by any of SEQ ID NOs: 252 to 269 by the replacement of u with t, or a complementary sequence thereof.

In a preferred embodiment, the polynucleotide is a polynucleotide consisting of a nucleotide sequence represented by any of SEQ ID NOs: 1 to 235, and 851 to 856 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 236 to 251 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 252 to 269 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide.

Specific examples of the aforementioned polynucleotide combination that constitutes the kit or the device of the present invention can include combinations of 1, 2, 3, 4, 5, 6, 7, 8, 9, 10 or more of the polynucleotides consisting of the nucleotide sequences represented by SEQ ID NOs: 1 to 269 and 851 to 856 shown in Table 1 described above. However, these are given merely for illustrative purposes, and all of various other possible combinations are included in the present invention.

The aforementioned combination constituting the kit or the device for discriminating a breast cancer patient from a healthy subject according to the present invention is desirably, for example, a combination of two or more polynucleotides consisting of the nucleotide sequences represented by SEQ ID NOs shown in Table 1. Usually, a combination of two of these polynucleotides can produce adequate performance. Specifically, any two of the aforementioned polynucleotides that consist of the aforementioned nucleotide sequences represented by SEQ ID NOs: 1 to 269 and 851 to 856 may be combined. For such a combination, it is preferred to select at least one of the newly found polynucleotides consisting of the nucleotide sequences represented by SEQ ID NOs: 1 to 235 and 851 to 856. More specifically, the combination is more preferably a combination comprising at least one of polynucleotides consisting of the nucleotide sequences represented by SEQ ID NOs: 20, 24, 26, 27, 30, 33, 182, 194, 206, and 208, among the combinations of the polynucleotides consisting of the nucleotide sequences represented by SEQ ID NOs: 1 to 269 and 851 to 856.

The combination of polynucleotides with cancer type specificity capable of discriminating a breast cancer patient not only from a healthy subject but also from other cancer patients is preferably, for example, a combination of multiple polynucleotides comprising at least one polynucleotide selected from the group consisting of polynucleotides consisting of the nucleotide sequences represented by SEQ ID NOs: 1, 2, 3, 4, 5, 6, 7, 8, 9, 11, 12, 13, 14, 15, 16, 17, 20, 21, 22, 23, 24, 25, 26, 27, 29, 30, 31, 32, 33, 34, 35, 36, 37, 38, 39, 41, 43, 45, 46, 47, 49, 50, 51, 52, 53, 54, 55, 58, 59, 60, 62, 63, 64, 65, 67, 68, 69, 70, 71, 72, 73, 75, 77, 79, 80, 81, 82, 83, 86, 88, 89, 90, 92, 93, 94, 96, 98, 99, 100, 103, 104, 106, 107, 108, 110, 111, 113, 114, 115, 116, 118, 119, 121, 122, 124, 125, 126, 127, 128, 129, 130, 131, 132, 133, 135, 136, 139, 140, 143, 145, 146, 147, 149, 150, 155, 157, 160, 161, 165, 167, 171, 173, 174, 175, 177, 178, 181, 182, 186, 190, 193, 194, 199, 204, 205, 206, 208, 211, 218, 225, 232, 236, 237, 238, 239, 242, 243, 244, 246, 247, 252, 260, 265, 266, 851, 852, 853, 854, 855, 856 (hereinafter, this group is referred to as "cancer type-specific polynucleotide group 1"), with any of the polynucleotides consisting of nucleotide sequences represented by the other SEQ ID NOs.

The combination of polynucleotides with cancer type specificity capable of discriminating a breast cancer patient not only from a healthy subject but also from other cancer patients is more preferably a combination of multiple polynucleotides, any of which are selected from the cancer type-specific polynucleotide group 1 described above.

The combination of polynucleotides with cancer type specificity capable of discriminating a breast cancer patient not only from a healthy subject but also from other cancer patients is more preferably a combination comprising at least one polynucleotide selected from, particularly, the group consisting of polynucleotides of SEQ ID NOs: 1, 2, 3, 4, 5, 6, 7, 8, 9, 11, 12, 13, 14, 15, 16, 17, 20, 21, 22, 23, 24, 25, 26, 27, 29, 30, 31, 32, 33, 34, 35, 36, 37, 38, 39, 41, 43, 45, 46, 47, 49, 50, 51, 52, 54, 55, 58, 59, 60, 62, 63, 64, 65, 67, 68, 69, 71, 72, 73, 75, 77, 79, 80, 82, 83, 86, 88, 92, 93, 96, 99, 103, 104, 106, 110, 111, 114, 116, 118, 119, 122, 124, 125, 127, 130, 132, 133, 135, 139, 143, 145, 147, 149, 157, 160, 173, 177, 181, 182, 186, 211, 218, 232, 236, 237, 238, 239, 242, 243, 246, 247, 260, 266, 851, 852, 853, 854 (hereinafter, this group is referred to as "cancer type-specific polynucleotide group 2"), among the combinations of multiple polynucleotides selected from the cancer type-specific polynucleotide group 1 described above.

The number of the polynucleotides with cancer type specificity in the combination described above can be 1, 2, 3, 4, 5, 6, 7, 8, 9, 10 or more and is preferably 2 or more for the combination.

Non-limiting examples of the combination of two polynucleotides that consist of one polynucleotide that consists of a nucleotide sequence selected from the cancer type-specific polynucleotide group 2 or a complementary sequence thereof and one polynucleotide that consists of a nucleotide sequence selected from the cancer type-specific polynucleotide group 1 or a complementary sequence thereof are listed below.

(1-1) a combination of SEQ ID NOs: 2 and 1 (markers: hsa-miR-4730 and hsa-miR-4783-3p);
(1-2) a combination of SEQ ID NOs: 2 and 237 (markers: hsa-miR-4730 and hsa-miR-602);
(1-3) a combination of SEQ ID NOs: 2 and 4 (markers: hsa-miR-4730 and hsa-miR-4634);
(1-4) a combination of SEQ ID NOs: 2 and 3 (markers: hsa-miR-4730 and hsa-miR-1307-3p);
(1-5) a combination of SEQ ID NOs: 2 and 51 (markers: hsa-miR-4730 and hsa-miR-3940-5p);
(2-1) a combination of SEQ ID NOs: 1 and 237 (markers: hsa-miR-4783-3p and hsa-miR-602);
(2-2) a combination of SEQ ID NOs: 1 and 4 (markers: hsa-miR-4783-3p and hsa-miR-4634);
(2-3) a combination of SEQ ID NOs: 1 and 3 (markers: hsa-miR-4783-3p and hsa-miR-1307-3p);
(2-4) a combination of SEQ ID NOs: 1 and 51 (markers: hsa-miR-4783-3p and hsa-miR-3940-5p);
(2-5) a combination of SEQ ID NOs: 1 and 6 (markers: hsa-miR-4783-3p and hsa-miR-4532);
(3-1) a combination of SEQ ID NOs: 4 and 237 (markers: hsa-miR-4634 and hsa-miR-602);
(3-2) a combination of SEQ ID NOs: 3 and 237 (markers: hsa-miR-1307-3p and hsa-miR-602);
(3-3) a combination of SEQ ID NOs: 51 and 237 (markers: hsa-miR-3940-5p and hsa-miR-602);
(3-4) a combination of SEQ ID NOs: 237 and 6 (markers: hsa-miR-602 and hsa-miR-4532);
(3-5) a combination of SEQ ID NOs: 237 and 12 (markers: hsa-miR-602 and hsa-miR-3184-5p);
(4-1) a combination of SEQ ID NOs: 3 and 4 (markers: hsa-miR-1307-3p and hsa-miR-4634);
(4-2) a combination of SEQ ID NOs: 4 and 51 (markers: hsa-miR-4634 and hsa-miR-3940-5p);
(4-3) a combination of SEQ ID NOs: 4 and 6 (markers: hsa-miR-4634 and hsa-miR-4532);
(4-4) a combination of SEQ ID NOs: 4 and 12 (markers: hsa-miR-4634 and hsa-miR-3184-5p);
(4-5) a combination of SEQ ID NOs: 4 and 15 (markers: hsa-miR-4634 and hsa-miR-4674);
(5-1) a combination of SEQ ID NOs: 3 and 51 (markers: hsa-miR-1307-3p and hsa-miR-3940-5p);
(5-2) a combination of SEQ ID NOs: 3 and 6 (markers: hsa-miR-1307-3p and hsa-miR-4532);
(5-3) a combination of SEQ ID NOs: 3 and 12 (markers: hsa-miR-1307-3p and hsa-miR-3184-5p);
(5-4) a combination of SEQ ID NOs: 3 and 15 (markers: hsa-miR-1307-3p and hsa-miR-4674);
(5-5) a combination of SEQ ID NOs: 3 and 8 (markers: hsa-miR-1307-3p and hsa-miR-3178);
(6-1) a combination of SEQ ID NOs: 51 and 6 (markers: hsa-miR-3940-5p and hsa-miR-4532);
(6-2) a combination of SEQ ID NOs: 51 and 12 (markers: hsa-miR-3940-5p and hsa-miR-3184-5p);

(6-3) a combination of SEQ ID NOs: 51 and 15 (markers: hsa-miR-3940-5p and hsa-miR-4674);
(6-4) a combination of SEQ ID NOs: 51 and 8 (markers: hsa-miR-3940-5p and hsa-miR-3178);
(6-5) a combination of SEQ ID NOs: 51 and 34 (markers: hsa-miR-3940-5p and hsa-miR-6805-5p);
(7-1) a combination of SEQ ID NOs: 2 and 6 (markers: hsa-miR-4730 and hsa-miR-4532);
(7-2) a combination of SEQ ID NOs: 12 and 6 (markers: hsa-miR-3184-5p and hsa-miR-4532);
(7-3) a combination of SEQ ID NOs: 15 and 6 (markers: hsa-miR-4674 and hsa-miR-4532);
(7-4) a combination of SEQ ID NOs: 8 and 6 (markers: hsa-miR-3178 and hsa-miR-4532);
(7-5) a combination of SEQ ID NOs: 6 and 34 (markers: hsa-miR-4532 and hsa-miR-6805-5p);
(8-1) a combination of SEQ ID NOs: 2 and 12 (markers: hsa-miR-4730 and hsa-miR-3184-5p);
(8-2) a combination of SEQ ID NOs: 1 and 12 (markers: hsa-miR-4783-3p and hsa-miR-3184-5p);
(8-3) a combination of SEQ ID NOs: 12 and 15 (markers: hsa-miR-3184-5p and hsa-miR-4674);
(8-4) a combination of SEQ ID NOs: 8 and 12 (markers: hsa-miR-3178 and hsa-miR-3184-5p);
(8-5) a combination of SEQ ID NOs: 12 and 34 (markers: hsa-miR-3184-5p and hsa-miR-6805-5p);
(9-1) a combination of SEQ ID NOs: 2 and 15 (markers: hsa-miR-4730 and hsa-miR-4674);
(9-2) a combination of SEQ ID NOs: 1 and 15 (markers: hsa-miR-4783-3p and hsa-miR-4674);
(9-3) a combination of SEQ ID NOs: 237 and 15 (markers: hsa-miR-602 and hsa-miR-4674);
(9-4) a combination of SEQ ID NOs: 8 and 15 (markers: hsa-miR-3178 and hsa-miR-4674);
(9-5) a combination of SEQ ID NOs: 15 and 34 (markers: hsa-miR-4674 and hsa-miR-6805-5p);
(10-1) a combination of SEQ ID NOs: 2 and 8 (markers: hsa-miR-4730 and hsa-miR-3178);
(10-2) a combination of SEQ ID NOs: 1 and 8 (markers: hsa-miR-4783-3p and hsa-miR-3178);
(10-3) a combination of SEQ ID NOs: 237 and 8 (markers: hsa-miR-602 and hsa-miR-3178);
(10-4) a combination of SEQ ID NOs: 4 and 8 (markers: hsa-miR-4634 and hsa-miR-3178);
(10-5) a combination of SEQ ID NOs: 8 and 34 (markers: hsa-miR-3178 and hsa-miR-6805-5p);
(11-1) a combination of SEQ ID NOs: 2 and 34 (markers: hsa-miR-4730 and hsa-miR-6805-5p);
(11-2) a combination of SEQ ID NOs: 1 and 34 (markers: hsa-miR-4783-3p and hsa-miR-6805-5p);
(11-3) a combination of SEQ ID NOs: 237 and 34 (markers: hsa-miR-602 and hsa-miR-6805-5p);
(11-4) a combination of SEQ ID NOs: 4 and 34 (markers: hsa-miR-4634 and hsa-miR-6805-5p);
(11-5) a combination of SEQ ID NOs: 3 and 34 (markers: hsa-miR-1307-3p and hsa-miR-6805-5p);
(12-1) a combination of SEQ ID NOs: 2 and 9 (markers: hsa-miR-4730 and hsa-miR-6729-5p);
(12-2) a combination of SEQ ID NOs: 1 and 9 (markers: hsa-miR-4783-3p and hsa-miR-6729-5p);
(12-3) a combination of SEQ ID NOs: 9 and 237 (markers: hsa-miR-6729-5p and hsa-miR-602);
(12-4) a combination of SEQ ID NOs: 4 and 9 (markers: hsa-miR-4634 and hsa-miR-6729-5p);
(12-5) a combination of SEQ ID NOs: 3 and 9 (markers: hsa-miR-1307-3p and hsa-miR-6729-5p);
(13-1) a combination of SEQ ID NOs: 2 and 143 (markers: hsa-miR-4730 and hsa-miR-1228-5p);
(13-2) a combination of SEQ ID NOs: 1 and 143 (markers: hsa-miR-4783-3p and hsa-miR-1228-5p);
(13-3) a combination of SEQ ID NOs: 237 and 143 (markers: hsa-miR-602 and hsa-miR-1228-5p);
(13-4) a combination of SEQ ID NOs: 4 and 143 (markers: hsa-miR-4634 and hsa-miR-1228-5p);
(13-5) a combination of SEQ ID NOs: 3 and 143 (markers: hsa-miR-1307-3p and hsa-miR-1228-5p);
(14-1) a combination of SEQ ID NOs: 2 and 13 (markers: hsa-miR-4730 and hsa-miR-6727-5p);
(14-2) a combination of SEQ ID NOs: 1 and 13 (markers: hsa-miR-4783-3p and hsa-miR-6727-5p);
(14-3) a combination of SEQ ID NOs: 237 and 13 (markers: hsa-miR-602 and hsa-miR-6727-5p);
(14-4) a combination of SEQ ID NOs: 4 and 13 (markers: hsa-miR-4634 and hsa-miR-6727-5p);
(14-5) a combination of SEQ ID NOs: 3 and 13 (markers: hsa-miR-1307-3p and hsa-miR-6727-5p);
(15-1) a combination of SEQ ID NOs: 2 and 125 (markers: hsa-miR-4730 and hsa-miR-6781-5p);
(15-2) a combination of SEQ ID NOs: 1 and 125 (markers: hsa-miR-4783-3p and hsa-miR-6781-5p);
(15-3) a combination of SEQ ID NOs: 237 and 125 (markers: hsa-miR-602 and hsa-miR-6781-5p);
(15-4) a combination of SEQ ID NOs: 4 and 125 (markers: hsa-miR-4634 and hsa-miR-6781-5p);
(15-5) a combination of SEQ ID NOs: 3 and 125 (markers: hsa-miR-1307-3p and hsa-miR-6781-5p);
(16-1) a combination of SEQ ID NOs: 2 and 236 (markers: hsa-miR-4730 and hsa-miR-760);
(16-2) a combination of SEQ ID NOs: 1 and 236 (markers: hsa-miR-4783-3p and hsa-miR-760);
(16-3) a combination of SEQ ID NOs: 237 and 236 (markers: hsa-miR-602 and hsa-miR-760);
(16-4) a combination of SEQ ID NOs: 4 and 236 (markers: hsa-miR-4634 and hsa-miR-760);
(16-5) a combination of SEQ ID NOs: 3 and 236 (markers: hsa-miR-1307-3p and hsa-miR-760);
(17-1) a combination of SEQ ID NOs: 2 and 46 (markers: hsa-miR-4730 and hsa-miR-1231);
(17-2) a combination of SEQ ID NOs: 1 and 46 (markers: hsa-miR-4783-3p and hsa-miR-1231);
(17-3) a combination of SEQ ID NOs: 237 and 46 (markers: hsa-miR-602 and hsa-miR-1231);
(17-4) a combination of SEQ ID NOs: 4 and 46 (markers: hsa-miR-4634 and hsa-miR-1231);
(17-5) a combination of SEQ ID NOs: 3 and 46 (markers: hsa-miR-1307-3p and hsa-miR-1231);
(18-1) a combination of SEQ ID NOs: 2 and 32 (markers: hsa-miR-4730 and hsa-miR-6836-3p);
(18-2) a combination of SEQ ID NOs: 1 and 32 (markers: hsa-miR-4783-3p and hsa-miR-6836-3p);
(18-3) a combination of SEQ ID NOs: 237 and 32 (markers: hsa-miR-602 and hsa-miR-6836-3p);
(18-4) a combination of SEQ ID NOs: 4 and 32 (markers: hsa-miR-4634 and hsa-miR-6836-3p);
(18-5) a combination of SEQ ID NOs: 3 and 32 (markers: hsa-miR-1307-3p and hsa-miR-6836-3p);
(19-1) a combination of SEQ ID NOs: 2 and 62 (markers: hsa-miR-4730 and hsa-miR-4492);
(19-2) a combination of SEQ ID NOs: 1 and 62 (markers: hsa-miR-4783-3p and hsa-miR-4492);
(19-3) a combination of SEQ ID NOs: 237 and 62 (markers: hsa-miR-602 and hsa-miR-4492);

(19-4) a combination of SEQ ID NOs: 4 and 62 (markers: hsa-miR-4634 and hsa-miR-4492);
(19-5) a combination of SEQ ID NOs: 3 and 62 (markers: hsa-miR-1307-3p and hsa-miR-4492);
(20-1) a combination of SEQ ID NOs: 2 and 88 (markers: hsa-miR-4730 and hsa-miR-4484);
(20-2) a combination of SEQ ID NOs: 1 and 88 (markers: hsa-miR-4783-3p and hsa-miR-4484);
(20-3) a combination of SEQ ID NOs: 237 and 88 (markers: hsa-miR-602 and hsa-miR-4484);
(20-4) a combination of SEQ ID NOs: 4 and 88 (markers: hsa-miR-4634 and hsa-miR-4484);
(20-5) a combination of SEQ ID NOs: 3 and 88 (markers: hsa-miR-1307-3p and hsa-miR-4484);
(21-1) a combination of SEQ ID NOs: 2 and 52 (markers: hsa-miR-4730 and hsa-miR-4741);
(21-2) a combination of SEQ ID NOs: 1 and 52 (markers: hsa-miR-4783-3p and hsa-miR-4741);
(21-3) a combination of SEQ ID NOs: 237 and 52 (markers: hsa-miR-602 and hsa-miR-4741);
(21-4) a combination of SEQ ID NOs: 4 and 52 (markers: hsa-miR-4634 and hsa-miR-4741);
(21-5) a combination of SEQ ID NOs: 3 and 52 (markers: hsa-miR-1307-3p and hsa-miR-4741);
(22-1) a combination of SEQ ID NOs: 2 and 7 (markers: hsa-miR-4730 and hsa-miR-7704);
(22-2) a combination of SEQ ID NOs: 1 and 7 (markers: hsa-miR-4783-3p and hsa-miR-7704);
(22-3) a combination of SEQ ID NOs: 237 and 7 (markers: hsa-miR-602 and hsa-miR-7704);
(22-4) a combination of SEQ ID NOs: 4 and 7 (markers: hsa-miR-4634 and hsa-miR-7704);
(22-5) a combination of SEQ ID NOs: 3 and 7 (markers: hsa-miR-1307-3p and hsa-miR-7704);
(23-1) a combination of SEQ ID NOs: 2 and 26 (markers: hsa-miR-4730 and hsa-miR-6875-5p);
(23-2) a combination of SEQ ID NOs: 1 and 26 (markers: hsa-miR-4783-3p and hsa-miR-6875-5p);
(23-3) a combination of SEQ ID NOs: 237 and 26 (markers: hsa-miR-602 and hsa-miR-6875-5p);
(23-4) a combination of SEQ ID NOs: 4 and 26 (markers: hsa-miR-4634 and hsa-miR-6875-5p);
(23-5) a combination of SEQ ID NOs: 3 and 26 (markers: hsa-miR-1307-3p and hsa-miR-6875-5p);
(24-1) a combination of SEQ ID NOs: 2 and 25 (markers: hsa-miR-4730 and hsa-miR-8069);
(24-2) a combination of SEQ ID NOs: 1 and 25 (markers: hsa-miR-4783-3p and hsa-miR-8069);
(24-3) a combination of SEQ ID NOs: 237 and 25 (markers: hsa-miR-602 and hsa-miR-8069);
(24-4) a combination of SEQ ID NOs: 4 and 25 (markers: hsa-miR-4634 and hsa-miR-8069);
(24-5) a combination of SEQ ID NOs: 3 and 25 (markers: hsa-miR-1307-3p and hsa-miR-8069);
(25-1) a combination of SEQ ID NOs: 2 and 54 (markers: hsa-miR-4730 and hsa-miR-6869-5p);
(25-2) a combination of SEQ ID NOs: 1 and 54 (markers: hsa-miR-4783-3p and hsa-miR-6869-5p);
(25-3) a combination of SEQ ID NOs: 237 and 54 (markers: hsa-miR-602 and hsa-miR-6869-5p);
(25-4) a combination of SEQ ID NOs: 4 and 54 (markers: hsa-miR-4634 and hsa-miR-6869-5p);
(25-5) a combination of SEQ ID NOs: 3 and 54 (markers: hsa-miR-1307-3p and hsa-miR-6869-5p);
(26-1) a combination of SEQ ID NOs: 2 and 92 (markers: hsa-miR-4730 and hsa-miR-4725-3p);
(26-2) a combination of SEQ ID NOs: 1 and 92 (markers: hsa-miR-4783-3p and hsa-miR-4725-3p);
(26-3) a combination of SEQ ID NOs: 237 and 92 (markers: hsa-miR-602 and hsa-miR-4725-3p);
(26-4) a combination of SEQ ID NOs: 4 and 92 (markers: hsa-miR-4634 and hsa-miR-4725-3p);
(26-5) a combination of SEQ ID NOs: 3 and 92 (markers: hsa-miR-1307-3p and hsa-miR-4725-3p);
(27-1) a combination of SEQ ID NOs: 2 and 14 (markers: hsa-miR-4730 and hsa-miR-6088);
(27-2) a combination of SEQ ID NOs: 1 and 14 (markers: hsa-miR-4783-3p and hsa-miR-6088);
(27-3) a combination of SEQ ID NOs: 237 and 14 (markers: hsa-miR-602 and hsa-miR-6088);
(27-4) a combination of SEQ ID NOs: 4 and 14 (markers: hsa-miR-4634 and hsa-miR-6088);
(27-5) a combination of SEQ ID NOs: 3 and 14 (markers: hsa-miR-1307-3p and hsa-miR-6088);
(28-1) a combination of SEQ ID NOs: 2 and 242 (markers: hsa-miR-4730 and hsa-miR-135a-3p);
(28-2) a combination of SEQ ID NOs: 1 and 242 (markers: hsa-miR-4783-3p and hsa-miR-135a-3p);
(28-3) a combination of SEQ ID NOs: 237 and 242 (markers: hsa-miR-602 and hsa-miR-135a-3p);
(28-4) a combination of SEQ ID NOs: 4 and 242 (markers: hsa-miR-4634 and hsa-miR-135a-3p);
(28-5) a combination of SEQ ID NOs: 3 and 242 (markers: hsa-miR-1307-3p and hsa-miR-135a-3p);
(29-1) a combination of SEQ ID NOs: 2 and 47 (markers: hsa-miR-4730 and hsa-miR-1908-3p);
(29-2) a combination of SEQ ID NOs: 1 and 47 (markers: hsa-miR-4783-3p and hsa-miR-1908-3p);
(29-3) a combination of SEQ ID NOs: 237 and 47 (markers: hsa-miR-602 and hsa-miR-1908-3p);
(29-4) a combination of SEQ ID NOs: 4 and 47 (markers: hsa-miR-4634 and hsa-miR-1908-3p);
(29-5) a combination of SEQ ID NOs: 3 and 47 (markers: hsa-miR-1307-3p and hsa-miR-1908-3p);
(30-1) a combination of SEQ ID NOs: 2 and 45 (markers: hsa-miR-4730 and hsa-miR-6771-5p);
(30-2) a combination of SEQ ID NOs: 1 and 45 (markers: hsa-miR-4783-3p and hsa-miR-6771-5p);
(30-3) a combination of SEQ ID NOs: 237 and 45 (markers: hsa-miR-602 and hsa-miR-6771-5p);
(30-4) a combination of SEQ ID NOs: 4 and 45 (markers: hsa-miR-4634 and hsa-miR-6771-5p);
(30-5) a combination of SEQ ID NOs: 3 and 45 (markers: hsa-miR-1307-3p and hsa-miR-6771-5p);
(31-1) a combination of SEQ ID NOs: 2 and 39 (markers: hsa-miR-4730 and hsa-miR-6850-5p);
(31-2) a combination of SEQ ID NOs: 1 and 39 (markers: hsa-miR-4783-3p and hsa-miR-6850-5p);
(31-3) a combination of SEQ ID NOs: 237 and 39 (markers: hsa-miR-602 and hsa-miR-6850-5p);
(31-4) a combination of SEQ ID NOs: 4 and 39 (markers: hsa-miR-4634 and hsa-miR-6850-5p);
(31-5) a combination of SEQ ID NOs: 3 and 39 (markers: hsa-miR-1307-3p and hsa-miR-6850-5p);
(32-1) a combination of SEQ ID NOs: 2 and 21 (markers: hsa-miR-4730 and hsa-miR-885-3p);
(32-2) a combination of SEQ ID NOs: 1 and 21 (markers: hsa-miR-4783-3p and hsa-miR-885-3p);
(32-3) a combination of SEQ ID NOs: 237 and 21 (markers: hsa-miR-602 and hsa-miR-885-3p);
(32-4) a combination of SEQ ID NOs: 4 and 21 (markers: hsa-miR-4634 and hsa-miR-885-3p);

(32-5) a combination of SEQ ID NOs: 3 and 21 (markers: hsa-miR-1307-3p and hsa-miR-885-3p);
(33-1) a combination of SEQ ID NOs: 2 and 17 (markers: hsa-miR-4730 and hsa-miR-4787-5p);
(33-2) a combination of SEQ ID NOs: 1 and 17 (markers: hsa-miR-4783-3p and hsa-miR-4787-5p);
(33-3) a combination of SEQ ID NOs: 237 and 17 (markers: hsa-miR-602 and hsa-miR-4787-5p);
(33-4) a combination of SEQ ID NOs: 4 and 17 (markers: hsa-miR-4634 and hsa-miR-4787-5p);
(33-5) a combination of SEQ ID NOs: 3 and 17 (markers: hsa-miR-1307-3p and hsa-miR-4787-5p);
(34-1) a combination of SEQ ID NOs: 2 and 83 (markers: hsa-miR-4730 and hsa-miR-1909-3p);
(34-2) a combination of SEQ ID NOs: 1 and 83 (markers: hsa-miR-4783-3p and hsa-miR-1909-3p);
(34-3) a combination of SEQ ID NOs: 237 and 83 (markers: hsa-miR-602 and hsa-miR-1909-3p);
(34-4) a combination of SEQ ID NOs: 4 and 83 (markers: hsa-miR-4634 and hsa-miR-1909-3p);
(34-5) a combination of SEQ ID NOs: 3 and 83 (markers: hsa-miR-1307-3p and hsa-miR-1909-3p);
(35-1) a combination of SEQ ID NOs: 2 and 149 (markers: hsa-miR-4730 and hsa-miR-638);
(35-2) a combination of SEQ ID NOs: 1 and 149 (markers: hsa-miR-4783-3p and hsa-miR-638);
(35-3) a combination of SEQ ID NOs: 237 and 149 (markers: hsa-miR-602 and hsa-miR-638);
(35-4) a combination of SEQ ID NOs: 4 and 149 (markers: hsa-miR-4634 and hsa-miR-638);
(35-5) a combination of SEQ ID NOs: 3 and 149 (markers: hsa-miR-1307-3p and hsa-miR-638);
(36-1) a combination of SEQ ID NOs: 2 and 246 (markers: hsa-miR-4730 and hsa-miR-1915-3p);
(36-2) a combination of SEQ ID NOs: 1 and 246 (markers: hsa-miR-4783-3p and hsa-miR-1915-3p);
(36-3) a combination of SEQ ID NOs: 237 and 246 (markers: hsa-miR-602 and hsa-miR-1915-3p);
(36-4) a combination of SEQ ID NOs: 4 and 246 (markers: hsa-miR-4634 and hsa-miR-1915-3p);
(36-5) a combination of SEQ ID NOs: 3 and 246 (markers: hsa-miR-1307-3p and hsa-miR-1915-3p);
(37-1) a combination of SEQ ID NOs: 2 and 22 (markers: hsa-miR-4730 and hsa-miR-6802-5p);
(37-2) a combination of SEQ ID NOs: 1 and 22 (markers: hsa-miR-4783-3p and hsa-miR-6802-5p);
(37-3) a combination of SEQ ID NOs: 237 and 22 (markers: hsa-miR-602 and hsa-miR-6802-5p);
(37-4) a combination of SEQ ID NOs: 4 and 22 (markers: hsa-miR-4634 and hsa-miR-6802-5p);
(37-5) a combination of SEQ ID NOs: 3 and 22 (markers: hsa-miR-1307-3p and hsa-miR-6802-5p);
(38-1) a combination of SEQ ID NOs: 2 and 55 (markers: hsa-miR-4730 and hsa-miR-5090);
(38-2) a combination of SEQ ID NOs: 1 and 55 (markers: hsa-miR-4783-3p and hsa-miR-5090);
(38-3) a combination of SEQ ID NOs: 237 and 55 (markers: hsa-miR-602 and hsa-miR-5090);
(38-4) a combination of SEQ ID NOs: 4 and 55 (markers: hsa-miR-4634 and hsa-miR-5090);
(38-5) a combination of SEQ ID NOs: 3 and 55 (markers: hsa-miR-1307-3p and hsa-miR-5090);
(39-1) a combination of SEQ ID NOs: 2 and 182 (markers: hsa-miR-4730 and hsa-miR-3196);
(39-2) a combination of SEQ ID NOs: 1 and 182 (markers: hsa-miR-4783-3p and hsa-miR-3196);
(39-3) a combination of SEQ ID NOs: 237 and 182 (markers: hsa-miR-602 and hsa-miR-3196);
(39-4) a combination of SEQ ID NOs: 4 and 182 (markers: hsa-miR-4634 and hsa-miR-3196);
(39-5) a combination of SEQ ID NOs: 3 and 182 (markers: hsa-miR-1307-3p and hsa-miR-3196);
(40-1) a combination of SEQ ID NOs: 2 and 73 (markers: hsa-miR-4730 and hsa-miR-4707-3p);
(40-2) a combination of SEQ ID NOs: 1 and 73 (markers: hsa-miR-4783-3p and hsa-miR-4707-3p);
(40-3) a combination of SEQ ID NOs: 237 and 73 (markers: hsa-miR-602 and hsa-miR-4707-3p);
(40-4) a combination of SEQ ID NOs: 4 and 73 (markers: hsa-miR-4634 and hsa-miR-4707-3p);
(40-5) a combination of SEQ ID NOs: 3 and 73 (markers: hsa-miR-1307-3p and hsa-miR-4707-3p);
(41-1) a combination of SEQ ID NOs: 2 and 77 (markers: hsa-miR-4730 and hsa-miR-4651);
(41-2) a combination of SEQ ID NOs: 1 and 77 (markers: hsa-miR-4783-3p and hsa-miR-4651);
(41-3) a combination of SEQ ID NOs: 237 and 77 (markers: hsa-miR-602 and hsa-miR-4651);
(41-4) a combination of SEQ ID NOs: 4 and 77 (markers: hsa-miR-4634 and hsa-miR-4651);
(41-5) a combination of SEQ ID NOs: 3 and 77 (markers: hsa-miR-1307-3p and hsa-miR-4651);
(42-1) a combination of SEQ ID NOs: 2 and 24 (markers: hsa-miR-4730 and hsa-miR-6787-5p);
(42-2) a combination of SEQ ID NOs: 1 and 24 (markers: hsa-miR-4783-3p and hsa-miR-6787-5p);
(42-3) a combination of SEQ ID NOs: 237 and 24 (markers: hsa-miR-602 and hsa-miR-6787-5p);
(42-4) a combination of SEQ ID NOs: 4 and 24 (markers: hsa-miR-4634 and hsa-miR-6787-5p);
(42-5) a combination of SEQ ID NOs: 3 and 24 (markers: hsa-miR-1307-3p and hsa-miR-6787-5p);
(43-1) a combination of SEQ ID NOs: 2 and 103 (markers: hsa-miR-4730 and hsa-miR-3180-3p);
(43-2) a combination of SEQ ID NOs: 1 and 103 (markers: hsa-miR-4783-3p and hsa-miR-3180-3p);
(43-3) a combination of SEQ ID NOs: 237 and 103 (markers: hsa-miR-602 and hsa-miR-3180-3p);
(43-4) a combination of SEQ ID NOs: 4 and 103 (markers: hsa-miR-4634 and hsa-miR-3180-3p);
(43-5) a combination of SEQ ID NOs: 3 and 103 (markers: hsa-miR-1307-3p and hsa-miR-3180-3p);
(44-1) a combination of SEQ ID NOs: 2 and 49 (markers: hsa-miR-4730 and hsa-miR-3937);
(44-2) a combination of SEQ ID NOs: 1 and 49 (markers: hsa-miR-4783-3p and hsa-miR-3937);
(44-3) a combination of SEQ ID NOs: 237 and 49 (markers: hsa-miR-602 and hsa-miR-3937);
(44-4) a combination of SEQ ID NOs: 4 and 49 (markers: hsa-miR-4634 and hsa-miR-3937);
(44-5) a combination of SEQ ID NOs: 3 and 49 (markers: hsa-miR-1307-3p and hsa-miR-3937);
(45-1) a combination of SEQ ID NOs: 2 and 239 (markers: hsa-miR-4730 and hsa-miR-92a-2-5p);
(45-2) a combination of SEQ ID NOs: 1 and 239 (markers: hsa-miR-4783-3p and hsa-miR-92a-2-5p);
(45-3) a combination of SEQ ID NOs: 237 and 239 (markers: hsa-miR-602 and hsa-miR-92a-2-5p);
(45-4) a combination of SEQ ID NOs: 4 and 239 (markers: hsa-miR-4634 and hsa-miR-92a-2-5p);
(45-5) a combination of SEQ ID NOs: 3 and 239 (markers: hsa-miR-1307-3p and hsa-miR-92a-2-5p);

(46-1) a combination of SEQ ID NOs: 2 and 23 (markers: hsa-miR-4730 and hsa-miR-328-5p);
(46-2) a combination of SEQ ID NOs: 1 and 23 (markers: hsa-miR-4783-3p and hsa-miR-328-5p);
(46-3) a combination of SEQ ID NOs: 237 and 23 (markers: hsa-miR-602 and hsa-miR-328-5p);
(46-4) a combination of SEQ ID NOs: 4 and 23 (markers: hsa-miR-4634 and hsa-miR-328-5p);
(46-5) a combination of SEQ ID NOs: 3 and 23 (markers: hsa-miR-1307-3p and hsa-miR-328-5p);
(47-1) a combination of SEQ ID NOs: 2 and 58 (markers: hsa-miR-4730 and hsa-miR-128-1-5p);
(47-2) a combination of SEQ ID NOs: 1 and 58 (markers: hsa-miR-4783-3p and hsa-miR-128-1-5p);
(47-3) a combination of SEQ ID NOs: 237 and 58 (markers: hsa-miR-602 and hsa-miR-128-1-5p);
(47-4) a combination of SEQ ID NOs: 4 and 58 (markers: hsa-miR-4634 and hsa-miR-128-1-5p);
(47-5) a combination of SEQ ID NOs: 3 and 58 (markers: hsa-miR-1307-3p and hsa-miR-128-1-5p);
(48-1) a combination of SEQ ID NOs: 2 and 211 (markers: hsa-miR-4730 and hsa-miR-6765-5p);
(48-2) a combination of SEQ ID NOs: 1 and 211 (markers: hsa-miR-4783-3p and hsa-miR-6765-5p);
(48-3) a combination of SEQ ID NOs: 237 and 211 (markers: hsa-miR-602 and hsa-miR-6765-5p);
(48-4) a combination of SEQ ID NOs: 4 and 211 (markers: hsa-miR-4634 and hsa-miR-6765-5p);
(48-5) a combination of SEQ ID NOs: 3 and 211 (markers: hsa-miR-1307-3p and hsa-miR-6765-5p);
(49-1) a combination of SEQ ID NOs: 2 and 147 (markers: hsa-miR-4730 and hsa-miR-6786-5p);
(49-2) a combination of SEQ ID NOs: 1 and 147 (markers: hsa-miR-4783-3p and hsa-miR-6786-5p);
(49-3) a combination of SEQ ID NOs: 237 and 147 (markers: hsa-miR-602 and hsa-miR-6786-5p);
(49-4) a combination of SEQ ID NOs: 4 and 147 (markers: hsa-miR-4634 and hsa-miR-6786-5p);
(49-5) a combination of SEQ ID NOs: 3 and 147 (markers: hsa-miR-1307-3p and hsa-miR-6786-5p);
(50-1) a combination of SEQ ID NOs: 2 and 65 (markers: hsa-miR-4730 and hsa-miR-4525);
(50-2) a combination of SEQ ID NOs: 1 and 65 (markers: hsa-miR-4783-3p and hsa-miR-4525);
(50-3) a combination of SEQ ID NOs: 237 and 65 (markers: hsa-miR-602 and hsa-miR-4525);
(50-4) a combination of SEQ ID NOs: 4 and 65 (markers: hsa-miR-4634 and hsa-miR-4525);
(50-5) a combination of SEQ ID NOs: 3 and 65 (markers: hsa-miR-1307-3p and hsa-miR-4525);
(51-1) a combination of SEQ ID NOs: 2 and 31 (markers: hsa-miR-4730 and hsa-miR-3665);
(51-2) a combination of SEQ ID NOs: 1 and 31 (markers: hsa-miR-4783-3p and hsa-miR-3665);
(51-3) a combination of SEQ ID NOs: 237 and 31 (markers: hsa-miR-602 and hsa-miR-3665);
(51-4) a combination of SEQ ID NOs: 4 and 31 (markers: hsa-miR-4634 and hsa-miR-3665);
(51-5) a combination of SEQ ID NOs: 3 and 31 (markers: hsa-miR-1307-3p and hsa-miR-3665);
(52-1) a combination of SEQ ID NOs: 2 and 72 (markers: hsa-miR-4730 and hsa-miR-663b);
(52-2) a combination of SEQ ID NOs: 1 and 72 (markers: hsa-miR-4783-3p and hsa-miR-663b);
(52-3) a combination of SEQ ID NOs: 237 and 72 (markers: hsa-miR-602 and hsa-miR-663b);
(52-4) a combination of SEQ ID NOs: 4 and 72 (markers: hsa-miR-4634 and hsa-miR-663b);
(52-5) a combination of SEQ ID NOs: 3 and 72 (markers: hsa-miR-1307-3p and hsa-miR-663b);
(53-1) a combination of SEQ ID NOs: 2 and 63 (markers: hsa-miR-4730 and hsa-miR-6785-5p);
(53-2) a combination of SEQ ID NOs: 1 and 63 (markers: hsa-miR-4783-3p and hsa-miR-6785-5p);
(53-3) a combination of SEQ ID NOs: 237 and 63 (markers: hsa-miR-602 and hsa-miR-6785-5p);
(53-4) a combination of SEQ ID NOs: 4 and 63 (markers: hsa-miR-4634 and hsa-miR-6785-5p);
(53-5) a combination of SEQ ID NOs: 3 and 63 (markers: hsa-miR-1307-3p and hsa-miR-6785-5p);
(54-1) a combination of SEQ ID NOs: 2 and 80 (markers: hsa-miR-4730 and hsa-miR-4758-5p);
(54-2) a combination of SEQ ID NOs: 1 and 80 (markers: hsa-miR-4783-3p and hsa-miR-4758-5p);
(54-3) a combination of SEQ ID NOs: 237 and 80 (markers: hsa-miR-602 and hsa-miR-4758-5p);
(54-4) a combination of SEQ ID NOs: 4 and 80 (markers: hsa-miR-4634 and hsa-miR-4758-5p);
(54-5) a combination of SEQ ID NOs: 3 and 80 (markers: hsa-miR-1307-3p and hsa-miR-4758-5p);
(55-1) a combination of SEQ ID NOs: 2 and 37 (markers: hsa-miR-4730 and hsa-miR-197-5p);
(55-2) a combination of SEQ ID NOs: 1 and 37 (markers: hsa-miR-4783-3p and hsa-miR-197-5p);
(55-3) a combination of SEQ ID NOs: 237 and 37 (markers: hsa-miR-602 and hsa-miR-197-5p);
(55-4) a combination of SEQ ID NOs: 4 and 37 (markers: hsa-miR-4634 and hsa-miR-197-5p);
(55-5) a combination of SEQ ID NOs: 3 and 37 (markers: hsa-miR-1307-3p and hsa-miR-197-5p);
(56-1) a combination of SEQ ID NOs: 2 and 67 (markers: hsa-miR-4730 and hsa-miR-3180);
(56-2) a combination of SEQ ID NOs: 1 and 67 (markers: hsa-miR-4783-3p and hsa-miR-3180);
(56-3) a combination of SEQ ID NOs: 237 and 67 (markers: hsa-miR-602 and hsa-miR-3180);
(56-4) a combination of SEQ ID NOs: 4 and 67 (markers: hsa-miR-4634 and hsa-miR-3180);
(56-5) a combination of SEQ ID NOs: 3 and 67 (markers: hsa-miR-1307-3p and hsa-miR-3180);
(57-1) a combination of SEQ ID NOs: 2 and 232 (markers: hsa-miR-4730 and hsa-miR-6125);
(57-2) a combination of SEQ ID NOs: 1 and 232 (markers: hsa-miR-4783-3p and hsa-miR-6125);
(57-3) a combination of SEQ ID NOs: 237 and 232 (markers: hsa-miR-602 and hsa-miR-6125);
(57-4) a combination of SEQ ID NOs: 4 and 232 (markers: hsa-miR-4634 and hsa-miR-6125);
(57-5) a combination of SEQ ID NOs: 3 and 232 (markers: hsa-miR-1307-3p and hsa-miR-6125);
(58-1) a combination of SEQ ID NOs: 2 and 127 (markers: hsa-miR-4730 and hsa-miR-4446-3p);
(58-2) a combination of SEQ ID NOs: 1 and 127 (markers: hsa-miR-4783-3p and hsa-miR-4446-3p);
(58-3) a combination of SEQ ID NOs: 237 and 127 (markers: hsa-miR-602 and hsa-miR-4446-3p);
(58-4) a combination of SEQ ID NOs: 4 and 127 (markers: hsa-miR-4634 and hsa-miR-4446-3p);
(58-5) a combination of SEQ ID NOs: 3 and 127 (markers: hsa-miR-1307-3p and hsa-miR-4446-3p);
(59-1) a combination of SEQ ID NOs: 2 and 145 (markers: hsa-miR-4730 and hsa-miR-1268a);

(59-2) a combination of SEQ ID NOs: 1 and 145 (markers: hsa-miR-4783-3p and hsa-miR-1268a);
(59-3) a combination of SEQ ID NOs: 237 and 145 (markers: hsa-miR-602 and hsa-miR-1268a);
(59-4) a combination of SEQ ID NOs: 4 and 145 (markers: hsa-miR-4634 and hsa-miR-1268a);
(59-5) a combination of SEQ ID NOs: 3 and 145 (markers: hsa-miR-1307-3p and hsa-miR-1268a);
(60-1) a combination of SEQ ID NOs: 2 and 16 (markers: hsa-miR-4730 and hsa-miR-8073);
(60-2) a combination of SEQ ID NOs: 1 and 16 (markers: hsa-miR-4783-3p and hsa-miR-8073);
(60-3) a combination of SEQ ID NOs: 237 and 16 (markers: hsa-miR-602 and hsa-miR-8073);
(60-4) a combination of SEQ ID NOs: 4 and 16 (markers: hsa-miR-4634 and hsa-miR-8073);
(60-5) a combination of SEQ ID NOs: 3 and 16 (markers: hsa-miR-1307-3p and hsa-miR-8073);
(61-1) a combination of SEQ ID NOs: 2 and 11 (markers: hsa-miR-4730 and hsa-miR-4732-5p);
(61-2) a combination of SEQ ID NOs: 1 and 11 (markers: hsa-miR-4783-3p and hsa-miR-4732-5p);
(61-3) a combination of SEQ ID NOs: 237 and 11 (markers: hsa-miR-602 and hsa-miR-4732-5p);
(61-4) a combination of SEQ ID NOs: 4 and 11 (markers: hsa-miR-4634 and hsa-miR-4732-5p);
(61-5) a combination of SEQ ID NOs: 3 and 11 (markers: hsa-miR-1307-3p and hsa-miR-4732-5p);
(62-1) a combination of SEQ ID NOs: 2 and 186 (markers: hsa-miR-4730 and hsa-miR-6789-5p);
(62-2) a combination of SEQ ID NOs: 1 and 186 (markers: hsa-miR-4783-3p and hsa-miR-6789-5p);
(62-3) a combination of SEQ ID NOs: 237 and 186 (markers: hsa-miR-602 and hsa-miR-6789-5p);
(62-4) a combination of SEQ ID NOs: 4 and 186 (markers: hsa-miR-4634 and hsa-miR-6789-5p);
(62-5) a combination of SEQ ID NOs: 3 and 186 (markers: hsa-miR-1307-3p and hsa-miR-6789-5p);
(63-1) a combination of SEQ ID NOs: 2 and 50 (markers: hsa-miR-4730 and hsa-miR-887-3p);
(63-2) a combination of SEQ ID NOs: 1 and 50 (markers: hsa-miR-4783-3p and hsa-miR-887-3p);
(63-3) a combination of SEQ ID NOs: 237 and 50 (markers: hsa-miR-602 and hsa-miR-887-3p);
(63-4) a combination of SEQ ID NOs: 4 and 50 (markers: hsa-miR-4634 and hsa-miR-887-3p);
(63-5) a combination of SEQ ID NOs: 3 and 50 (markers: hsa-miR-1307-3p and hsa-miR-887-3p);
(64-1) a combination of SEQ ID NOs: 2 and 69 (markers: hsa-miR-4730 and hsa-miR-1199-5p);
(64-2) a combination of SEQ ID NOs: 1 and 69 (markers: hsa-miR-4783-3p and hsa-miR-1199-5p);
(64-3) a combination of SEQ ID NOs: 237 and 69 (markers: hsa-miR-602 and hsa-miR-1199-5p);
(64-4) a combination of SEQ ID NOs: 4 and 69 (markers: hsa-miR-4634 and hsa-miR-1199-5p);
(64-5) a combination of SEQ ID NOs: 3 and 69 (markers: hsa-miR-1307-3p and hsa-miR-1199-5p);
(65-1) a combination of SEQ ID NOs: 2 and 33 (markers: hsa-miR-4730 and hsa-miR-6821-5p);
(65-2) a combination of SEQ ID NOs: 1 and 33 (markers: hsa-miR-4783-3p and hsa-miR-6821-5p);
(65-3) a combination of SEQ ID NOs: 237 and 33 (markers: hsa-miR-602 and hsa-miR-6821-5p);
(65-4) a combination of SEQ ID NOs: 4 and 33 (markers: hsa-miR-4634 and hsa-miR-6821-5p);
(65-5) a combination of SEQ ID NOs: 3 and 33 (markers: hsa-miR-1307-3p and hsa-miR-6821-5p);
(66-1) a combination of SEQ ID NOs: 2 and 247 (markers: hsa-miR-4730 and hsa-miR-718);
(66-2) a combination of SEQ ID NOs: 1 and 247 (markers: hsa-miR-4783-3p and hsa-miR-718);
(66-3) a combination of SEQ ID NOs: 237 and 247 (markers: hsa-miR-602 and hsa-miR-718);
(66-4) a combination of SEQ ID NOs: 4 and 247 (markers: hsa-miR-4634 and hsa-miR-718);
(66-5) a combination of SEQ ID NOs: 3 and 247 (markers: hsa-miR-1307-3p and hsa-miR-718);
(67-1) a combination of SEQ ID NOs: 2 and 36 (markers: hsa-miR-4730 and hsa-miR-6726-5p);
(67-2) a combination of SEQ ID NOs: 1 and 36 (markers: hsa-miR-4783-3p and hsa-miR-6726-5p);
(67-3) a combination of SEQ ID NOs: 237 and 36 (markers: hsa-miR-602 and hsa-miR-6726-5p);
(67-4) a combination of SEQ ID NOs: 4 and 36 (markers: hsa-miR-4634 and hsa-miR-6726-5p);
(67-5) a combination of SEQ ID NOs: 3 and 36 (markers: hsa-miR-1307-3p and hsa-miR-6726-5p);
(68-1) a combination of SEQ ID NOs: 2 and 218 (markers: hsa-miR-4730 and hsa-miR-6784-5p);
(68-2) a combination of SEQ ID NOs: 1 and 218 (markers: hsa-miR-4783-3p and hsa-miR-6784-5p);
(68-3) a combination of SEQ ID NOs: 237 and 218 (markers: hsa-miR-602 and hsa-miR-6784-5p);
(68-4) a combination of SEQ ID NOs: 4 and 218 (markers: hsa-miR-4634 and hsa-miR-6784-5p);
(68-5) a combination of SEQ ID NOs: 3 and 218 (markers: hsa-miR-1307-3p and hsa-miR-6784-5p);
(69-1) a combination of SEQ ID NOs: 2 and 43 (markers: hsa-miR-4730 and hsa-miR-4763-3p);
(69-2) a combination of SEQ ID NOs: 1 and 43 (markers: hsa-miR-4783-3p and hsa-miR-4763-3p);
(69-3) a combination of SEQ ID NOs: 237 and 43 (markers: hsa-miR-602 and hsa-miR-4763-3p);
(69-4) a combination of SEQ ID NOs: 4 and 43 (markers: hsa-miR-4634 and hsa-miR-4763-3p);
(69-5) a combination of SEQ ID NOs: 3 and 43 (markers: hsa-miR-1307-3p and hsa-miR-4763-3p);
(70-1) a combination of SEQ ID NOs: 2 and 29 (markers: hsa-miR-4730 and hsa-miR-6757-5p);
(70-2) a combination of SEQ ID NOs: 1 and 29 (markers: hsa-miR-4783-3p and hsa-miR-6757-5p);
(70-3) a combination of SEQ ID NOs: 237 and 29 (markers: hsa-miR-602 and hsa-miR-6757-5p);
(70-4) a combination of SEQ ID NOs: 4 and 29 (markers: hsa-miR-4634 and hsa-miR-6757-5p);
(70-5) a combination of SEQ ID NOs: 3 and 29 (markers: hsa-miR-1307-3p and hsa-miR-6757-5p);
(71-1) a combination of SEQ ID NOs: 2 and 110 (markers: hsa-miR-4730 and hsa-miR-665);
(71-2) a combination of SEQ ID NOs: 1 and 110 (markers: hsa-miR-4783-3p and hsa-miR-665);
(71-3) a combination of SEQ ID NOs: 237 and 110 (markers: hsa-miR-602 and hsa-miR-665);
(71-4) a combination of SEQ ID NOs: 4 and 110 (markers: hsa-miR-4634 and hsa-miR-665);
(71-5) a combination of SEQ ID NOs: 3 and 110 (markers: hsa-miR-1307-3p and hsa-miR-665);
(72-1) a combination of SEQ ID NOs: 2 and 20 (markers: hsa-miR-4730 and hsa-miR-1233-5p);
(72-2) a combination of SEQ ID NOs: 1 and 20 (markers: hsa-miR-4783-3p and hsa-miR-1233-5p);

(72-3) a combination of SEQ ID NOs: 237 and 20 (markers: hsa-miR-602 and hsa-miR-1233-5p);
(72-4) a combination of SEQ ID NOs: 4 and 20 (markers: hsa-miR-4634 and hsa-miR-1233-5p);
(72-5) a combination of SEQ ID NOs: 3 and 20 (markers: hsa-miR-1307-3p and hsa-miR-1233-5p);
(73-1) a combination of SEQ ID NOs: 2 and 157 (markers: hsa-miR-4730 and hsa-miR-1268b);
(73-2) a combination of SEQ ID NOs: 1 and 157 (markers: hsa-miR-4783-3p and hsa-miR-1268b);
(73-3) a combination of SEQ ID NOs: 237 and 157 (markers: hsa-miR-602 and hsa-miR-1268b);
(73-4) a combination of SEQ ID NOs: 4 and 157 (markers: hsa-miR-4634 and hsa-miR-1268b);
(73-5) a combination of SEQ ID NOs: 3 and 157 (markers: hsa-miR-1307-3p and hsa-miR-1268b);
(74-1) a combination of SEQ ID NOs: 2 and 75 (markers: hsa-miR-4730 and hsa-miR-4675);
(74-2) a combination of SEQ ID NOs: 1 and 75 (markers: hsa-miR-4783-3p and hsa-miR-4675);
(74-3) a combination of SEQ ID NOs: 237 and 75 (markers: hsa-miR-602 and hsa-miR-4675);
(74-4) a combination of SEQ ID NOs: 4 and 75 (markers: hsa-miR-4634 and hsa-miR-4675);
(74-5) a combination of SEQ ID NOs: 3 and 75 (markers: hsa-miR-1307-3p and hsa-miR-4675);
(75-1) a combination of SEQ ID NOs: 2 and 82 (markers: hsa-miR-4730 and hsa-miR-3620-5p);
(75-2) a combination of SEQ ID NOs: 1 and 82 (markers: hsa-miR-4783-3p and hsa-miR-3620-5p);
(75-3) a combination of SEQ ID NOs: 237 and 82 (markers: hsa-miR-602 and hsa-miR-3620-5p);
(75-4) a combination of SEQ ID NOs: 4 and 82 (markers: hsa-miR-4634 and hsa-miR-3620-5p);
(75-5) a combination of SEQ ID NOs: 3 and 82 (markers: hsa-miR-1307-3p and hsa-miR-3620-5p);
(76-1) a combination of SEQ ID NOs: 2 and 106 (markers: hsa-miR-4730 and hsa-miR-6800-5p);
(76-2) a combination of SEQ ID NOs: 1 and 106 (markers: hsa-miR-4783-3p and hsa-miR-6800-5p);
(76-3) a combination of SEQ ID NOs: 237 and 106 (markers: hsa-miR-602 and hsa-miR-6800-5p);
(76-4) a combination of SEQ ID NOs: 4 and 106 (markers: hsa-miR-4634 and hsa-miR-6800-5p);
(76-5) a combination of SEQ ID NOs: 3 and 106 (markers: hsa-miR-1307-3p and hsa-miR-6800-5p);
(77-1) a combination of SEQ ID NOs: 2 and 111 (markers: hsa-miR-4730 and hsa-miR-6778-5p);
(77-2) a combination of SEQ ID NOs: 1 and 111 (markers: hsa-miR-4783-3p and hsa-miR-6778-5p);
(77-3) a combination of SEQ ID NOs: 237 and 111 (markers: hsa-miR-602 and hsa-miR-6778-5p);
(77-4) a combination of SEQ ID NOs: 4 and 111 (markers: hsa-miR-4634 and hsa-miR-6778-5p);
(77-5) a combination of SEQ ID NOs: 3 and 111 (markers: hsa-miR-1307-3p and hsa-miR-6778-5p);
(78-1) a combination of SEQ ID NOs: 2 and 96 (markers: hsa-miR-4730 and hsa-miR-8059);
(78-2) a combination of SEQ ID NOs: 1 and 96 (markers: hsa-miR-4783-3p and hsa-miR-8059);
(78-3) a combination of SEQ ID NOs: 237 and 96 (markers: hsa-miR-602 and hsa-miR-8059);
(78-4) a combination of SEQ ID NOs: 4 and 96 (markers: hsa-miR-4634 and hsa-miR-8059);
(78-5) a combination of SEQ ID NOs: 3 and 96 (markers: hsa-miR-1307-3p and hsa-miR-8059);
(79-1) a combination of SEQ ID NOs: 2 and 266 (markers: hsa-miR-4730 and hsa-miR-1908-5p);
(79-2) a combination of SEQ ID NOs: 1 and 266 (markers: hsa-miR-4783-3p and hsa-miR-1908-5p);
(79-3) a combination of SEQ ID NOs: 237 and 266 (markers: hsa-miR-602 and hsa-miR-1908-5p);
(79-4) a combination of SEQ ID NOs: 4 and 266 (markers: hsa-miR-4634 and hsa-miR-1908-5p);
(79-5) a combination of SEQ ID NOs: 3 and 266 (markers: hsa-miR-1307-3p and hsa-miR-1908-5p);
(80-1) a combination of SEQ ID NOs: 2 and 124 (markers: hsa-miR-4730 and hsa-miR-6798-5p);
(80-2) a combination of SEQ ID NOs: 1 and 124 (markers: hsa-miR-4783-3p and hsa-miR-6798-5p);
(80-3) a combination of SEQ ID NOs: 237 and 124 (markers: hsa-miR-602 and hsa-miR-6798-5p);
(80-4) a combination of SEQ ID NOs: 4 and 124 (markers: hsa-miR-4634 and hsa-miR-6798-5p);
(80-5) a combination of SEQ ID NOs: 3 and 124 (markers: hsa-miR-1307-3p and hsa-miR-6798-5p);
(81-1) a combination of SEQ ID NOs: 2 and 68 (markers: hsa-miR-4730 and hsa-miR-6879-5p);
(81-2) a combination of SEQ ID NOs: 1 and 68 (markers: hsa-miR-4783-3p and hsa-miR-6879-5p);
(81-3) a combination of SEQ ID NOs: 237 and 68 (markers: hsa-miR-602 and hsa-miR-6879-5p);
(81-4) a combination of SEQ ID NOs: 4 and 68 (markers: hsa-miR-4634 and hsa-miR-6879-5p);
(81-5) a combination of SEQ ID NOs: 3 and 68 (markers: hsa-miR-1307-3p and hsa-miR-6879-5p);
(82-1) a combination of SEQ ID NOs: 2 and 71 (markers: hsa-miR-4730 and hsa-miR-711);
(82-2) a combination of SEQ ID NOs: 1 and 71 (markers: hsa-miR-4783-3p and hsa-miR-711);
(82-3) a combination of SEQ ID NOs: 237 and 71 (markers: hsa-miR-602 and hsa-miR-711);
(82-4) a combination of SEQ ID NOs: 4 and 71 (markers: hsa-miR-4634 and hsa-miR-711);
(82-5) a combination of SEQ ID NOs: 3 and 71 (markers: hsa-miR-1307-3p and hsa-miR-711);
(83-1) a combination of SEQ ID NOs: 2 and 35 (markers: hsa-miR-4730 and hsa-miR-4728-5p);
(83-2) a combination of SEQ ID NOs: 1 and 35 (markers: hsa-miR-4783-3p and hsa-miR-4728-5p);
(83-3) a combination of SEQ ID NOs: 237 and 35 (markers: hsa-miR-602 and hsa-miR-4728-5p);
(83-4) a combination of SEQ ID NOs: 4 and 35 (markers: hsa-miR-4634 and hsa-miR-4728-5p);
(83-5) a combination of SEQ ID NOs: 3 and 35 (markers: hsa-miR-1307-3p and hsa-miR-4728-5p);
(84-1) a combination of SEQ ID NOs: 2 and 173 (markers: hsa-miR-4730 and hsa-miR-3195);
(84-2) a combination of SEQ ID NOs: 1 and 173 (markers: hsa-miR-4783-3p and hsa-miR-3195);
(84-3) a combination of SEQ ID NOs: 237 and 173 (markers: hsa-miR-602 and hsa-miR-3195);
(84-4) a combination of SEQ ID NOs: 4 and 173 (markers: hsa-miR-4634 and hsa-miR-3195);
(84-5) a combination of SEQ ID NOs: 3 and 173 (markers: hsa-miR-1307-3p and hsa-miR-3195);
(85-1) a combination of SEQ ID NOs: 2 and 5 (markers: hsa-miR-4730 and hsa-miR-663a);
(85-2) a combination of SEQ ID NOs: 1 and 5 (markers: hsa-miR-4783-3p and hsa-miR-663a);
(85-3) a combination of SEQ ID NOs: 237 and 5 (markers: hsa-miR-602 and hsa-miR-663a);

(85-4) a combination of SEQ ID NOs: 4 and 5 (markers: hsa-miR-4634 and hsa-miR-663a);
(85-5) a combination of SEQ ID NOs: 3 and 5 (markers: hsa-miR-1307-3p and hsa-miR-663a);
(86-1) a combination of SEQ ID NOs: 2 and 851 (markers: hsa-miR-4730 and hsa-miR-6089);
(86-2) a combination of SEQ ID NOs: 1 and 851 (markers: hsa-miR-4783-3p and hsa-miR-6089);
(86-3) a combination of SEQ ID NOs: 237 and 851 (markers: hsa-miR-602 and hsa-miR-6089);
(86-4) a combination of SEQ ID NOs: 4 and 851 (markers: hsa-miR-4634 and hsa-miR-6089);
(86-5) a combination of SEQ ID NOs: 3 and 851 (markers: hsa-miR-1307-3p and hsa-miR-6089);
(87-1) a combination of SEQ ID NOs: 2 and 852 (markers: hsa-miR-4730 and hsa-miR-6816-5p);
(87-2) a combination of SEQ ID NOs: 1 and 852 (markers: hsa-miR-4783-3p and hsa-miR-6816-5p);
(87-3) a combination of SEQ ID NOs: 237 and 852 (markers: hsa-miR-602 and hsa-miR-6816-5p);
(87-4) a combination of SEQ ID NOs: 4 and 852 (markers: hsa-miR-4634 and hsa-miR-6816-5p);
(87-5) a combination of SEQ ID NOs: 3 and 852 (markers: hsa-miR-1307-3p and hsa-miR-6816-5p);
(88-1) a combination of SEQ ID NOs: 2 and 30 (markers: hsa-miR-4730 and hsa-miR-6756-5p);
(88-2) a combination of SEQ ID NOs: 1 and 30 (markers: hsa-miR-4783-3p and hsa-miR-6756-5p);
(88-3) a combination of SEQ ID NOs: 237 and 30 (markers: hsa-miR-602 and hsa-miR-6756-5p);
(88-4) a combination of SEQ ID NOs: 4 and 30 (markers: hsa-miR-4634 and hsa-miR-6756-5p);
(88-5) a combination of SEQ ID NOs: 3 and 30 (markers: hsa-miR-1307-3p and hsa-miR-6756-5p);
(89-1) a combination of SEQ ID NOs: 2 and 93 (markers: hsa-miR-4730 and hsa-miR-6861-5p);
(89-2) a combination of SEQ ID NOs: 1 and 93 (markers: hsa-miR-4783-3p and hsa-miR-6861-5p);
(89-3) a combination of SEQ ID NOs: 237 and 93 (markers: hsa-miR-602 and hsa-miR-6861-5p);
(89-4) a combination of SEQ ID NOs: 4 and 93 (markers: hsa-miR-4634 and hsa-miR-6861-5p);
(89-5) a combination of SEQ ID NOs: 3 and 93 (markers: hsa-miR-1307-3p and hsa-miR-6861-5p);
(90-1) a combination of SEQ ID NOs: 2 and 27 (markers: hsa-miR-4730 and hsa-miR-1246);
(90-2) a combination of SEQ ID NOs: 1 and 27 (markers: hsa-miR-4783-3p and hsa-miR-1246);
(90-3) a combination of SEQ ID NOs: 237 and 27 (markers: hsa-miR-602 and hsa-miR-1246);
(90-4) a combination of SEQ ID NOs: 4 and 27 (markers: hsa-miR-4634 and hsa-miR-1246);
(90-5) a combination of SEQ ID NOs: 27 and 208 (markers: hsa-miR-1246 and hsa-miR-1343-5p);
(91-1) a combination of SEQ ID NOs: 2 and 853 (markers: hsa-miR-4730 and hsa-miR-4466);
(91-2) a combination of SEQ ID NOs: 1 and 853 (markers: hsa-miR-4783-3p and hsa-miR-4466);
(91-3) a combination of SEQ ID NOs: 237 and 853 (markers: hsa-miR-602 and hsa-miR-4466);
(91-4) a combination of SEQ ID NOs: 4 and 853 (markers: hsa-miR-4634 and hsa-miR-4466);
(91-5) a combination of SEQ ID NOs: 3 and 853 (markers: hsa-miR-1307-3p and hsa-miR-4466);
(92-1) a combination of SEQ ID NOs: 2 and 238 (markers: hsa-miR-4730 and hsa-miR-423-5p);
(92-2) a combination of SEQ ID NOs: 1 and 238 (markers: hsa-miR-4783-3p and hsa-miR-423-5p);
(92-3) a combination of SEQ ID NOs: 237 and 238 (markers: hsa-miR-602 and hsa-miR-423-5p);
(92-4) a combination of SEQ ID NOs: 4 and 238 (markers: hsa-miR-4634 and hsa-miR-423-5p);
(92-5) a combination of SEQ ID NOs: 3 and 238 (markers: hsa-miR-1307-3p and hsa-miR-423-5p);
(93-1) a combination of SEQ ID NOs: 2 and 130 (markers: hsa-miR-4730 and hsa-miR-6075);
(93-2) a combination of SEQ ID NOs: 1 and 130 (markers: hsa-miR-4783-3p and hsa-miR-6075);
(93-3) a combination of SEQ ID NOs: 237 and 130 (markers: hsa-miR-602 and hsa-miR-6075);
(93-4) a combination of SEQ ID NOs: 4 and 130 (markers: hsa-miR-4634 and hsa-miR-6075);
(93-5) a combination of SEQ ID NOs: 3 and 130 (markers: hsa-miR-1307-3p and hsa-miR-6075);
(94-1) a combination of SEQ ID NOs: 2 and 177 (markers: hsa-miR-4730 and hsa-miR-7108-5p);
(94-2) a combination of SEQ ID NOs: 1 and 177 (markers: hsa-miR-4783-3p and hsa-miR-7108-5p);
(94-3) a combination of SEQ ID NOs: 237 and 177 (markers: hsa-miR-602 and hsa-miR-7108-5p);
(94-4) a combination of SEQ ID NOs: 4 and 177 (markers: hsa-miR-4634 and hsa-miR-7108-5p);
(94-5) a combination of SEQ ID NOs: 3 and 177 (markers: hsa-miR-1307-3p and hsa-miR-7108-5p);
(95-1) a combination of SEQ ID NOs: 2 and 64 (markers: hsa-miR-4730 and hsa-miR-6511a-5p);
(95-2) a combination of SEQ ID NOs: 1 and 64 (markers: hsa-miR-4783-3p and hsa-miR-6511a-5p);
(95-3) a combination of SEQ ID NOs: 237 and 64 (markers: hsa-miR-602 and hsa-miR-6511a-5p);
(95-4) a combination of SEQ ID NOs: 4 and 64 (markers: hsa-miR-4634 and hsa-miR-6511a-5p);
(95-5) a combination of SEQ ID NOs: 3 and 64 (markers: hsa-miR-1307-3p and hsa-miR-6511a-5p);
(96-1) a combination of SEQ ID NOs: 2 and 114 (markers: hsa-miR-4730 and hsa-miR-211-3p);
(96-2) a combination of SEQ ID NOs: 1 and 114 (markers: hsa-miR-4783-3p and hsa-miR-211-3p);
(96-3) a combination of SEQ ID NOs: 237 and 114 (markers: hsa-miR-602 and hsa-miR-211-3p);
(96-4) a combination of SEQ ID NOs: 4 and 114 (markers: hsa-miR-4634 and hsa-miR-211-3p);
(96-5) a combination of SEQ ID NOs: 3 and 114 (markers: hsa-miR-1307-3p and hsa-miR-211-3p);
(97-1) a combination of SEQ ID NOs: 2 and 119 (markers: hsa-miR-4730 and hsa-miR-7110-5p);
(97-2) a combination of SEQ ID NOs: 1 and 119 (markers: hsa-miR-4783-3p and hsa-miR-7110-5p);
(97-3) a combination of SEQ ID NOs: 237 and 119 (markers: hsa-miR-602 and hsa-miR-7110-5p);
(97-4) a combination of SEQ ID NOs: 4 and 119 (markers: hsa-miR-4634 and hsa-miR-7110-5p);
(97-5) a combination of SEQ ID NOs: 3 and 119 (markers: hsa-miR-1307-3p and hsa-miR-7110-5p);
(98-1) a combination of SEQ ID NOs: 2 and 135 (markers: hsa-miR-4730 and hsa-miR-6870-5p);
(98-2) a combination of SEQ ID NOs: 1 and 135 (markers: hsa-miR-4783-3p and hsa-miR-6870-5p);
(98-3) a combination of SEQ ID NOs: 237 and 135 (markers: hsa-miR-602 and hsa-miR-6870-5p);
(98-4) a combination of SEQ ID NOs: 4 and 135 (markers: hsa-miR-4634 and hsa-miR-6870-5p);

(98-5) a combination of SEQ ID NOs: 3 and 135 (markers: hsa-miR-1307-3p and hsa-miR-6870-5p);
(99-1) a combination of SEQ ID NOs: 2 and 243 (markers: hsa-miR-4730 and hsa-miR-486-5p);
(99-2) a combination of SEQ ID NOs: 1 and 243 (markers: hsa-miR-4783-3p and hsa-miR-486-5p);
(99-3) a combination of SEQ ID NOs: 237 and 243 (markers: hsa-miR-602 and hsa-miR-486-5p);
(99-4) a combination of SEQ ID NOs: 4 and 243 (markers: hsa-miR-4634 and hsa-miR-486-5p);
(99-5) a combination of SEQ ID NOs: 3 and 243 (markers: hsa-miR-1307-3p and hsa-miR-486-5p);
(100-1) a combination of SEQ ID NOs: 2 and 122 (markers: hsa-miR-4730 and hsa-miR-4792);
(100-2) a combination of SEQ ID NOs: 1 and 122 (markers: hsa-miR-4783-3p and hsa-miR-4792);
(100-3) a combination of SEQ ID NOs: 237 and 122 (markers: hsa-miR-602 and hsa-miR-4792);
(100-4) a combination of SEQ ID NOs: 4 and 122 (markers: hsa-miR-4634 and hsa-miR-4792);
(100-5) a combination of SEQ ID NOs: 3 and 122 (markers: hsa-miR-1307-3p and hsa-miR-4792);
(101-1) a combination of SEQ ID NOs: 2 and 260 (markers: hsa-miR-4730 and hsa-miR-4687-3p);
(101-2) a combination of SEQ ID NOs: 1 and 260 (markers: hsa-miR-4783-3p and hsa-miR-4687-3p);
(101-3) a combination of SEQ ID NOs: 237 and 260 (markers: hsa-miR-602 and hsa-miR-4687-3p);
(101-4) a combination of SEQ ID NOs: 4 and 260 (markers: hsa-miR-4634 and hsa-miR-4687-3p);
(101-5) a combination of SEQ ID NOs: 3 and 260 (markers: hsa-miR-1307-3p and hsa-miR-4687-3p);
(102-1) a combination of SEQ ID NOs: 2 and 59 (markers: hsa-miR-4730 and hsa-miR-1238-5p);
(102-2) a combination of SEQ ID NOs: 1 and 59 (markers: hsa-miR-4783-3p and hsa-miR-1238-5p);
(102-3) a combination of SEQ ID NOs: 237 and 59 (markers: hsa-miR-602 and hsa-miR-1238-5p);
(102-4) a combination of SEQ ID NOs: 4 and 59 (markers: hsa-miR-4634 and hsa-miR-1238-5p);
(102-5) a combination of SEQ ID NOs: 3 and 59 (markers: hsa-miR-1307-3p and hsa-miR-1238-5p);
(103-1) a combination of SEQ ID NOs: 2 and 854 (markers: hsa-miR-4730 and hsa-miR-4488);
(103-2) a combination of SEQ ID NOs: 1 and 854 (markers: hsa-miR-4783-3p and hsa-miR-4488);
(103-3) a combination of SEQ ID NOs: 237 and 854 (markers: hsa-miR-602 and hsa-miR-4488);
(103-4) a combination of SEQ ID NOs: 4 and 854 (markers: hsa-miR-4634 and hsa-miR-4488);
(103-5) a combination of SEQ ID NOs: 3 and 854 (markers: hsa-miR-1307-3p and hsa-miR-4488);
(104-1) a combination of SEQ ID NOs: 2 and 132 (markers: hsa-miR-4730 and hsa-miR-6891-5p);
(104-2) a combination of SEQ ID NOs: 1 and 132 (markers: hsa-miR-4783-3p and hsa-miR-6891-5p);
(104-3) a combination of SEQ ID NOs: 237 and 132 (markers: hsa-miR-602 and hsa-miR-6891-5p);
(104-4) a combination of SEQ ID NOs: 4 and 132 (markers: hsa-miR-4634 and hsa-miR-6891-5p);
(104-5) a combination of SEQ ID NOs: 3 and 132 (markers: hsa-miR-1307-3p and hsa-miR-6891-5p);
(105-1) a combination of SEQ ID NOs: 2 and 181 (markers: hsa-miR-4730 and hsa-miR-2861);
(105-2) a combination of SEQ ID NOs: 1 and 181 (markers: hsa-miR-4783-3p and hsa-miR-2861);
(105-3) a combination of SEQ ID NOs: 237 and 181 (markers: hsa-miR-602 and hsa-miR-2861);
(105-4) a combination of SEQ ID NOs: 4 and 181 (markers: hsa-miR-4634 and hsa-miR-2861);
(105-5) a combination of SEQ ID NOs: 3 and 181 (markers: hsa-miR-1307-3p and hsa-miR-2861);
(106-1) a combination of SEQ ID NOs: 2 and 79 (markers: hsa-miR-4730 and hsa-miR-4665-5p);
(106-2) a combination of SEQ ID NOs: 1 and 79 (markers: hsa-miR-4783-3p and hsa-miR-4665-5p);
(106-3) a combination of SEQ ID NOs: 237 and 79 (markers: hsa-miR-602 and hsa-miR-4665-5p);
(106-4) a combination of SEQ ID NOs: 4 and 79 (markers: hsa-miR-4634 and hsa-miR-4665-5p);
(106-5) a combination of SEQ ID NOs: 3 and 79 (markers: hsa-miR-1307-3p and hsa-miR-4665-5p);
(107-1) a combination of SEQ ID NOs: 2 and 133 (markers: hsa-miR-4730 and hsa-miR-4745-5p);
(107-2) a combination of SEQ ID NOs: 1 and 133 (markers: hsa-miR-4783-3p and hsa-miR-4745-5p);
(107-3) a combination of SEQ ID NOs: 237 and 133 (markers: hsa-miR-602 and hsa-miR-4745-5p);
(107-4) a combination of SEQ ID NOs: 4 and 133 (markers: hsa-miR-4634 and hsa-miR-4745-5p);
(107-5) a combination of SEQ ID NOs: 3 and 133 (markers: hsa-miR-1307-3p and hsa-miR-4745-5p);
(108-1) a combination of SEQ ID NOs: 2 and 41 (markers: hsa-miR-4730 and hsa-miR-6858-5p);
(108-2) a combination of SEQ ID NOs: 1 and 41 (markers: hsa-miR-4783-3p and hsa-miR-6858-5p);
(108-3) a combination of SEQ ID NOs: 237 and 41 (markers: hsa-miR-602 and hsa-miR-6858-5p);
(108-4) a combination of SEQ ID NOs: 4 and 41 (markers: hsa-miR-4634 and hsa-miR-6858-5p);
(108-5) a combination of SEQ ID NOs: 3 and 41 (markers: hsa-miR-1307-3p and hsa-miR-6858-5p);
(109-1) a combination of SEQ ID NOs: 2 and 139 (markers: hsa-miR-4730 and hsa-miR-6825-5p);
(109-2) a combination of SEQ ID NOs: 1 and 139 (markers: hsa-miR-4783-3p and hsa-miR-6825-5p);
(109-3) a combination of SEQ ID NOs: 237 and 139 (markers: hsa-miR-602 and hsa-miR-6825-5p);
(109-4) a combination of SEQ ID NOs: 4 and 139 (markers: hsa-miR-4634 and hsa-miR-6825-5p);
(109-5) a combination of SEQ ID NOs: 3 and 139 (markers: hsa-miR-1307-3p and hsa-miR-6825-5p);
(110-1) a combination of SEQ ID NOs: 2 and 118 (markers: hsa-miR-4730 and hsa-miR-614);
(110-2) a combination of SEQ ID NOs: 1 and 118 (markers: hsa-miR-4783-3p and hsa-miR-614);
(110-3) a combination of SEQ ID NOs: 237 and 118 (markers: hsa-miR-602 and hsa-miR-614);
(110-4) a combination of SEQ ID NOs: 4 and 118 (markers: hsa-miR-4634 and hsa-miR-614);
(110-5) a combination of SEQ ID NOs: 3 and 118 (markers: hsa-miR-1307-3p and hsa-miR-614);
(111-1) a combination of SEQ ID NOs: 2 and 86 (markers: hsa-miR-4730 and hsa-miR-1343-3p);
(111-2) a combination of SEQ ID NOs: 1 and 86 (markers: hsa-miR-4783-3p and hsa-miR-1343-3p);
(111-3) a combination of SEQ ID NOs: 237 and 86 (markers: hsa-miR-602 and hsa-miR-1343-3p);
(111-4) a combination of SEQ ID NOs: 4 and 86 (markers: hsa-miR-4634 and hsa-miR-1343-3p);
(111-5) a combination of SEQ ID NOs: 3 and 86 (markers: hsa-miR-1307-3p and hsa-miR-1343-3p);

(112-1) a combination of SEQ ID NOs: 2 and 60 (markers: hsa-miR-4730 and hsa-miR-365a-5p);
(112-2) a combination of SEQ ID NOs: 1 and 60 (markers: hsa-miR-4783-3p and hsa-miR-365a-5p);
(112-3) a combination of SEQ ID NOs: 237 and 60 (markers: hsa-miR-602 and hsa-miR-365a-5p);
(112-4) a combination of SEQ ID NOs: 4 and 60 (markers: hsa-miR-4634 and hsa-miR-365a-5p);
(112-5) a combination of SEQ ID NOs: 3 and 60 (markers: hsa-miR-1307-3p and hsa-miR-365a-5p);
(113-1) a combination of SEQ ID NOs: 2 and 116 (markers: hsa-miR-4730 and hsa-miR-4750-5p);
(113-2) a combination of SEQ ID NOs: 1 and 116 (markers: hsa-miR-4783-3p and hsa-miR-4750-5p);
(113-3) a combination of SEQ ID NOs: 237 and 116 (markers: hsa-miR-602 and hsa-miR-4750-5p);
(113-4) a combination of SEQ ID NOs: 4 and 116 (markers: hsa-miR-4634 and hsa-miR-4750-5p);
(113-5) a combination of SEQ ID NOs: 3 and 116 (markers: hsa-miR-1307-3p and hsa-miR-4750-5p);
(114-1) a combination of SEQ ID NOs: 2 and 160 (markers: hsa-miR-4730 and hsa-miR-6732-5p);
(114-2) a combination of SEQ ID NOs: 1 and 160 (markers: hsa-miR-4783-3p and hsa-miR-6732-5p);
(114-3) a combination of SEQ ID NOs: 237 and 160 (markers: hsa-miR-602 and hsa-miR-6732-5p);
(114-4) a combination of SEQ ID NOs: 4 and 160 (markers: hsa-miR-4634 and hsa-miR-6732-5p);
(114-5) a combination of SEQ ID NOs: 3 and 160 (markers: hsa-miR-1307-3p and hsa-miR-6732-5p);
(115-1) a combination of SEQ ID NOs: 2 and 38 (markers: hsa-miR-4730 and hsa-miR-149-3p);
(115-2) a combination of SEQ ID NOs: 1 and 38 (markers: hsa-miR-4783-3p and hsa-miR-149-3p);
(115-3) a combination of SEQ ID NOs: 237 and 38 (markers: hsa-miR-602 and hsa-miR-149-3p);
(115-4) a combination of SEQ ID NOs: 4 and 38 (markers: hsa-miR-4634 and hsa-miR-149-3p);
(115-5) a combination of SEQ ID NOs: 3 and 38 (markers: hsa-miR-1307-3p and hsa-miR-149-3p);
(116-1) a combination of SEQ ID NOs: 2 and 99 (markers: hsa-miR-4730 and hsa-miR-4497);
(116-2) a combination of SEQ ID NOs: 1 and 99 (markers: hsa-miR-4783-3p and hsa-miR-4497);
(116-3) a combination of SEQ ID NOs: 237 and 99 (markers: hsa-miR-602 and hsa-miR-4497);
(116-4) a combination of SEQ ID NOs: 4 and 99 (markers: hsa-miR-4634 and hsa-miR-4497);
(116-5) a combination of SEQ ID NOs: 3 and 99 (markers: hsa-miR-1307-3p and hsa-miR-4497);
(117-1) a combination of SEQ ID NOs: 2 and 104 (markers: hsa-miR-4730 and hsa-miR-6848-5p);
(117-2) a combination of SEQ ID NOs: 1 and 104 (markers: hsa-miR-4783-3p and hsa-miR-6848-5p);
(117-3) a combination of SEQ ID NOs: 237 and 104 (markers: hsa-miR-602 and hsa-miR-6848-5p);
(117-4) a combination of SEQ ID NOs: 4 and 104 (markers: hsa-miR-4634 and hsa-miR-6848-5p); and
(117-5) a combination of SEQ ID NOs: 3 and 104 (markers: hsa-miR-1307-3p and hsa-miR-6848-5p).

The kit or the device of the present invention may also comprise a polynucleotide(s) that is/are already known or that will be found in the future, to enable detection of breast cancer, in addition to the polynucleotide(s) (which may include variant(s), fragment(s), or derivative(s)) according to the present invention The kit of the present invention may also comprise an antibody for measuring marker(s) for breast cancer examination known in the art, such as CEA, CA-15-3, and CA27-29, in addition to the polynucleotide(s) as described above.

The polynucleotides described above contained in the kit of the present invention may be packaged in different containers either individually or in any combination.

The kit of the present invention may comprise a kit for extracting nucleic acids (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above, variants thereof, derivatives thereof, or fragments thereof are bound or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves binding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group; a method of spraying the nucleic acids onto the solid phase using an inkjet which injects very small liquid droplets by a piezoelectric element or the like from a nozzle; or a method of sequentially synthesizing nucleotides on the solid phase] to prepare an array such as a chip and measuring a target nucleic acid through the use of hybridization using this array.

The kit or the device of the present invention comprises nucleic acids capable of specifically binding to the polynucleotides of at least one, preferably at least two, more preferably at least three, most preferably at least five to all of the breast cancer marker miRNAs, respectively, of the group 1 described above. The kit or the device of the present invention may optionally further comprise nucleic acids capable of specifically binding to the polynucleotides of at least one, preferably at least two, more preferably at least three, most preferably at least five to all of the breast cancer marker miRNAs, respectively, of the group 2 described above. The kit or the device of the present invention may optionally further comprise nucleic acids capable of specifically binding to the polynucleotides of at least one, preferably at least two, more preferably at least three, most preferably at least five to all of the breast cancer marker miRNAs, respectively, of the group 3 described above. The kit or the device of the present invention can be used for detecting breast cancer as described in Section 4 below.

4. Method for Detecting Breast Cancer

The present invention further provides a method for detecting breast cancer, comprising using the kit or the device of the present invention (comprising the aforementioned nucleic acid(s) that can be used in the present invention) as described in Section "3. Kit or device for detection of breast cancer" to measure an expression level of one or more breast cancer-derived genes represented by: expression level(s) of breast cancer-derived genes selected from the following group of miRNAs, i.e., miR-4783-3p, miR-4730, miR-1307-3p, miR-4634, miR-663a, miR-4532, miR-7704, miR-3178, miR-6729-5p, miR-6090, miR-4732-5p, miR-3184-5p, miR-6727-5p, miR-6088, miR-4674, miR-8073, miR-4787-5p, miR-1469, miR-125a-3p, miR-1233-5p, miR-885-3p, miR-6802-5p, miR-328-5p, miR-6787-5p, miR-8069, miR-6875-5p, miR-1246, miR-4734, miR-6757-5p, miR-6756-5p, miR-3665, miR-6836-3p, miR-6821-5p, miR-6805-5p, miR-4728-5p, miR-6726-5p, miR-197-5p, miR-149-3p, miR-6850-5p, miR-4476, miR-6858-5p, miR-564, miR-4763-3p, miR-575, miR-6771-5p, miR-1231, miR-1908-3p, miR-150-3p, miR-3937, miR-887-3p, miR-3940-5p, miR-4741, miR-6808-5p, miR-6869-5p, miR-5090, miR-615-5p, miR-8072, miR-128-1-5p, miR-1238-5p, miR-365a-5p, miR-204-3p, miR-4492, miR-6785-5p, miR-6511a-5p, miR-4525, miR-1915-5p, miR-3180, miR-6879-5p, miR-1199-5p, miR-6746-5p, miR-711, miR-663b, miR-4707-3p, miR-6893-5p, miR-4675, miR-4638-5p, miR-4651, miR-6087, miR-4665-5p, miR-4758-5p, miR-6887-5p, miR-3620-5p, miR-1909-3p, miR-7641, miR-6724-5p, miR-1343-3p, miR-6780b-5p, miR-4484, miR-4690-5p, miR-4429, miR-1227-5p, miR-4725-3p, miR-6861-5p, miR-6812-5p, miR-3197, miR-8059, miR-3185, miR-4706, miR-4497, miR-3131, miR-6806-5p, miR-187-5p, miR-3180-3p, miR-6848-5p, miR-6820-5p, miR-6800-5p, miR-6717-5p, miR-6795-5p, miR-4632-5p, miR-665, miR-6778-5p, miR-3663-3p, miR-4689, miR-211-3p, miR-6511b-5p, miR-4750-5p, miR-6126, miR-614, miR-7110-5p, miR-744-5p, miR-6769a-5p, miR-4792, miR-5787, miR-6798-5p, miR-6781-5p, miR-4419b, miR-4446-3p, miR-4259, miR-5572, miR-6075, miR-296-3p, miR-6891-5p, miR-4745-5p, miR-6775-5p, miR-6870-5p, miR-920, miR-4530, miR-6819-5p, miR-6825-5p, miR-7847-3p, miR-6131, miR-4433-3p, miR-1228-5p, miR-6743-5p, miR-1268a, miR-3917, miR-6786-5p, miR-3154, miR-638, miR-6741-5p, miR-6889-5p, miR-6840-3p, miR-6510-5p, miR-3188, miR-551b-5p, miR-5001-5p, miR-1268b, miR-7107-5p, miR-6824-5p, miR-6732-5p, miR-371a-5p, miR-6794-5p, miR-6779-5p, miR-4271, miR-5195-3p, miR-6762-5p, miR-939-5p, miR-1247-3p, miR-6777-5p, miR-6722-3p, miR-3656, miR-4688, miR-3195, miR-6766-5p, miR-4447, miR-4656, miR-7108-5p, miR-3191-3p, miR-1273g-3p, miR-4463, miR-2861, miR-3196, miR-6877-5p, miR-3679-5p, miR-4442, miR-6789-5p, miR-6782-5p, miR-486-3p, miR-6085, miR-4746-3p, miR-619-5p, miR-937-5p, miR-6803-5p, miR-4298, miR-4454, miR-4459, miR-7150, miR-6880-5p, miR-4449, miR-8063, miR-4695-5p, miR-6132, miR-6829-5p, miR-4486, miR-6805-3p, miR-6826-5p, miR-4508, miR-1343-5p, miR-7114-5p, miR-3622a-5p, miR-6765-5p, miR-7845-5p, miR-3960, miR-6749-5p, miR-1260b, miR-6799-5p, miR-4723-5p, miR-6784-5p, miR-5100, miR-6769b-5p, miR-1207-5p, miR-642a-3p, miR-4505, miR-4270, miR-6721-5p, miR-7111-5p, miR-6791-5p, miR-7109-5p, miR-4258, miR-6515-3p, miR-6851-5p, miR-6125, miR-4749-5p, miR-4726-5p, miR-4513, miR-6089, miR-6816-5p, miR-4466, miR-4488, miR-6752-5p and miR-4739; and optionally expression level(s) of breast cancer-derived gene(s) selected from the following group of miRNA: i.e., miR-760, miR-602, miR-423-5p, miR-92a-2-5p, miR-16-5p, miR-451a, miR-135a-3p, miR-486-5p, miR-4257, miR-92b-5p, miR-1915-3p, miR-718, miR-940, miR-296-5p, miR-23b-3p and miR-92a-3p, and optionally expression level(s) of breast cancer-derived gene(s) selected from the following group of miRNA: i.e., miR-658, miR-6842-5p, miR-6124, miR-6765-3p, miR-7106-5p, miR-4534, miR-92b-3p, miR-3135b, miR-4687-3p, miR-762, miR-3619-3p, miR-4467, miR-557, miR-1237-5p, miR-1908-5p, miR-4286, miR-6885-5p, and miR-6763-5p in a sample in vitro, further comparing, for example, the expression level(s) of the aforementioned gene(s) in the sample (e.g., blood, serum, or plasma) collected from a subject suspected of having breast cancer with a control expression level in the sample collected from a healthy subject (including a non-breast cancer patient(s)), and evaluating the subject as having breast cancer when the expression level(s) of the target nucleic acid(s) is different between the samples.

This method of the present invention enables limitedly-invasive early diagnosis of the breast cancer with high sensitivity and specificity and thereby brings about early treatment and improved prognosis. In addition, exacerbation of the disease or the effectiveness of surgical, radiotherapeutic, and chemotherapeutic treatments can be monitored.

The method for extracting the breast cancer-derived gene from the sample such as blood, serum, or plasma according to the present invention is particularly preferably a method in which the breast cancer-derived gene is prepared by the addition of a reagent for RNA extraction in 3D-Gene™ RNA extraction reagent from liquid sample kit (Toray Industries, Inc.). A general acidic phenol method (acid guanidinium-phenol-chloroform (AGPC)) may be used, or Trizol™ (Life Technologies Corp.) may be used. The breast cancer-derived gene(s) may be prepared by the addition of a reagent for RNA extraction containing acidic phenol, such as Trizol (Life Technologies Corp.) or Isogen (Nippon Gene Co., Ltd., Japan). Alternatively, a kit such as miRNeasy® Mini Kit (Qiagen N.V.) can be used, though the method is not limited thereto.

The present invention also provides use of the kit or the device of the present invention for detecting in vitro an expression product(s) of a breast cancer-derived miRNA gene in a sample derived from a subject.

In the method of the present invention, the used kit or the device comprises a single polynucleotide or any possible combination of polynucleotides that can be used in the present invention as described above.

In the detection or (genetic) diagnosis of breast cancer according to the present invention, each polynucleotide contained in the kit or the device of the present invention can be used as a probe or a primer. In the case of using the polynucleotide as a primer, TaqMan™ MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of breast or the detection of the presence or absence of breast cancer. Specifically, the detection of breast cancer using the kit or the device can be performed by detecting in vitro an expression level of a gene using the nucleic acid probe or the primer contained in the kit or the device in a sample such as blood, serum, plasma, or urine from a subject suspected of having breast cancer. The subject suspected of having breast cancer can be evaluated as having breast cancer when the expression level(s) of a target miRNA marker(s) measured using a polynucleotide(s) (including variant(s), fragment(s), or derivative(s) thereof) consisting of a nucleotide sequence(s) represented by at least one of SEQ ID NOs: 1 to 235, and 851 to 856 or a complementary sequence(s) thereof, and optionally a nucleotide sequence(s) represented by one or more of SEQ ID NOs: 236 to 251 or a complementary sequence(s) thereof, and optionally a nucleotide sequence(s) represented by one or more of SEQ ID NOs: 252 to 269 or a complementary sequence thereof in the sample such as blood, serum, plasma, or urine of the subject has a statistically significantly higher or lower than the expression level(s) thereof in the sample such as blood, serum, or plasma, or urine of a healthy subject.

The method of the present invention can be combined with a diagnostic imaging method such as mammography, ultrasonography (echo examination), CT, MRI, abdominal ultrasonography, bone scintigraphy, or PET, or pathological examination which involves analyzing a lesion tissue under a microscope. The method of the present invention is capable of specifically detecting breast cancer and can substantially discriminate breast cancer from the other cancers.

The method for detecting the absence of an expression product(s) of a breast cancer-derived gene(s) or the presence of the expression product(s) of a breast cancer-derived gene in a sample using the kit or the device of the present invention comprises; collecting a body fluid such as blood, serum, plasma, or urine of a subject; measuring the expression level(s) of the target gene(s) contained therein using one or more polynucleotides (including variant(s), fragment(s), or derivative(s)) selected from the polynucleotide group of the present invention; and evaluating the presence or absence of breast cancer or to detect breast cancer. The method for detecting breast cancer according to the present invention can also evaluate or diagnose, for example, the presence or absence of amelioration of the disease or the degree of amelioration thereof in a breast cancer patient in the case that a therapeutic drug is administered to the patient for amelioration of the disease.

The method of the present invention can comprise, for example, the following steps (a), (b), and (c):

(a) a step of contacting in vitro a sample from a subject with a polynucleotide(s) contained in the kit or the device of the present invention in vitro;

(b) a step of measuring an expression level(s) of the target nucleic acid(s) in the sample using the polynucleotide(s) as a nucleic acid probe(s) or a primer(s); and (c) a step of evaluating the presence or absence of breast cancer (cells) in the subject on the basis of the measurement results in the step (b).

Specifically, the present invention provides a method for detecting breast cancer, comprising measuring an expression level(s) of a target nucleic acid(s) in a sample of a subject using nucleic acid(s) capable of specifically binding to at least one (preferably at least two) polynucleotides selected from the group consisting of miR-4783-3p, miR-4730, miR-1307-3p, miR-4634, miR-663a, miR-4532, miR-7704, miR-3178, miR-6729-5p, miR-6090, miR-4732-5p, miR-3184-5p, miR-6727-5p, miR-6088, miR-4674, miR-8073, miR-4787-5p, miR-1469, miR-125a-3p, miR-1233-5p, miR-885-3p, miR-6802-5p, miR-328-5p, miR-6787-5p, miR-8069, miR-6875-5p, miR-1246, miR-4734, miR-6757-5p, miR-6756-5p, miR-3665, miR-6836-3p, miR-6821-5p, miR-6805-5p, miR-4728-5p, miR-6726-5p, miR-197-5p, miR-149-3p, miR-6850-5p, miR-4476, miR-6858-5p, miR-564, miR-4763-3p, miR-575, miR-6771-5p, miR-1231, miR-1908-3p, miR-150-3p, miR-3937, miR-887-3p, miR-3940-5p, miR-4741, miR-6808-5p, miR-6869-5p, miR-5090, miR-615-5p, miR-8072, miR-128-1-5p, miR-1238-5p, miR-365a-5p, miR-204-3p, miR-4492, miR-6785-5p, miR-6511a-5p, miR-4525, miR-1915-5p, miR-3180, miR-6879-5p, miR-1199-5p, miR-6746-5p, miR-711, miR-663b, miR-4707-3p, miR-6893-5p, miR-4675, miR-4638-5p, miR-4651, miR-6087, miR-4665-5p, miR-4758-5p, miR-6887-5p, miR-3620-5p, miR-1909-3p, miR-7641, miR-6724-5p, miR-1343-3p, miR-6780b-5p, miR-4484, miR-4690-5p, miR-4429, miR-1227-5p, miR-4725-3p, miR-6861-5p, miR-6812-5p, miR-3197, miR-8059, miR-3185, miR-4706, miR-4497, miR-3131, miR-6806-5p, miR-187-5p, miR-3180-3p, miR-6848-5p, miR-6820-5p, miR-6800-5p, miR-6717-5p, miR-6795-5p, miR-4632-5p, miR-665, miR-6778-5p, miR-3663-3p, miR-4689, miR-211-3p, miR-6511b-5p, miR-4750-5p, miR-6126, miR-614, miR-7110-5p, miR-744-5p, miR-6769a-5p, miR-4792, miR-5787, miR-6798-5p, miR-6781-5p, miR-4419b, miR-4446-3p, miR-4259, miR-5572, miR-6075, miR-296-3p, miR-6891-5p, miR-4745-5p, miR-6775-5p, miR-6870-5p, miR-920, miR-4530, miR-6819-5p, miR-6825-5p, miR-7847-3p, miR-6131, miR-4433-3p, miR-1228-5p, miR-6743-5p, miR-1268a, miR-3917, miR-6786-5p, miR-3154, miR-638, miR-6741-5p, miR-6889-5p, miR-6840-3p, miR-6510-5p, miR-3188, miR-551b-5p, miR-5001-5p, miR-1268b, miR-7107-5p, miR-6824-5p, miR-6732-5p, miR-371a-5p, miR-6794-5p, miR-6779-5p, miR-4271, miR-5195-3p, miR-6762-5p, miR-939-5p, miR-1247-3p, miR-6777-5p, miR-6722-3p, miR-3656, miR-4688, miR-3195, miR-6766-5p, miR-4447, miR-4656, miR-7108-5p, miR-3191-3p, miR-1273g-3p, miR-4463, miR-2861, miR-3196, miR-6877-5p, miR-3679-5p, miR-4442, miR-6789-5p, miR-6782-5p, miR-486-3p, miR-6085, miR-4746-3p, miR-619-5p, miR-937-5p, miR-6803-5p, miR-4298, miR-4454, miR-4459, miR-7150, miR-6880-5p, miR-4449, miR-8063, miR-4695-5p, miR-6132, miR-6829-5p, miR-4486, miR-6805-3p, miR-6826-5p, miR-4508, miR-1343-5p, miR-7114-5p, miR-3622a-5p, miR-6765-5p, miR-7845-5p, miR-3960, miR-6749-5p, miR-1260b, miR-6799-5p, miR-4723-5p, miR-6784-5p, miR-5100, miR-6769b-5p, miR-1207-5p, miR-642a-3p, miR-4505, miR-4270, miR-6721-5p, miR-7111-5p, miR-6791-5p, miR-7109-5p, miR-4258, miR-6515-3p, miR-6851-5p, miR-6125, miR-4749-5p, miR-4726-5p, miR-4513, miR-6089, miR-6816-5p, miR-4466, miR-4488, miR-6752-5p and miR-4739 and evaluating in vitro whether or not the subject has breast cancer in the subject using the above-measured expression levels and control expression levels of healthy subjects measured in the same way as above.

The term "evaluation" used herein is evaluation support based on results of in vitro examination, not physician's judgment.

As described above, in a preferred embodiment of the method of the present invention, specifically, miR-4783-3p is hsa-miR-4783-3p, miR-4730 is hsa-miR-4730, miR-1307-3p is hsa-miR-1307-3p, miR-4634 is hsa-miR-4634, miR-663a is hsa-miR-663a, miR-4532 is hsa-miR-4532, miR-7704 is hsa-miR-7704, miR-3178 is hsa-miR-3178, miR-6729-5p is hsa-miR-6729-5p, miR-6090 is hsa-miR-6090, miR-4732-5p is hsa-miR-4732-5p, miR-3184-5p is hsa-miR-3184-5p, miR-6727-5p is hsa-miR-6727-5p, miR-6088 is hsa-miR-6088, miR-4674 is hsa-miR-4674, miR-8073 is hsa-miR-8073, miR-4787-5p is hsa-miR-4787-5p, miR-1469 is hsa-miR-1469, miR-125a-3p is hsa-miR-125a-3p, miR-1233-5p is hsa-miR-1233-5p, miR-885-3p is hsa-miR-885-3p, miR-6802-5p is hsa-miR-6802-5p, miR-328-5p is hsa-miR-328-5p, miR-6787-5p is hsa-miR-6787-5p, miR-8069 is hsa-miR-8069, miR-6875-5p is hsa-miR-6875-5p, miR-1246 is hsa-miR-1246, miR-4734 is hsa-miR-4734, miR-6757-5p is hsa-miR-6757-5p, miR-6756-5p is hsa-miR-6756-5p, miR-3665 is hsa-miR-3665, miR-6836-3p is hsa-miR-6836-3p, miR-6821-5p is hsa-miR-6821-5p, miR-6805-5p is hsa-miR-6805-5p, miR-4728-5p is hsa-miR-4728-5p, miR-6726-5p is hsa-miR-6726-5p, miR-197-5p is hsa-miR-197-5p, miR-149-3p is hsa-miR-149-3p, miR-6850-5p is hsa-miR-6850-5p, miR-4476 is hsa-miR-4476, miR-6858-5p is hsa-miR-6858-5p, miR-564 is hsa-miR-564, miR-4763-3p is hsa-miR-4763-3p, miR-575 is hsa-miR-575, miR-6771-5p is hsa-miR-6771-5p, miR-1231 is hsa-miR-1231, miR-1908-3p is hsa-miR-1908-3p, miR-150-3p is hsa-miR-150-3p, miR-3937 is hsa-miR-3937, miR-887-3p is hsa-miR-887-3p, miR-3940-5p is hsa-miR-3940-5p, miR-4741 is hsa-miR-4741, miR-6808-5p is hsa-miR-6808-5p, miR-6869-5p is hsa-miR-6869-5p, miR-5090 is hsa-miR-5090, miR-615-5p is hsa-miR-615-5p, miR-8072 is hsa-miR-8072, miR-128-1-5p is hsa-miR-128-1-5p, miR-1238-5p is hsa-miR-1238-5p, miR-365a-5p is hsa-miR-365a-5p, miR-204-3p is hsa-miR-204-3p, miR-4492 is hsa-miR-4492, miR-6785-5p is hsa-miR-6785-5p, miR-6511a-5p is hsa-miR-6511a-5p, miR-4525 is hsa-miR-4525, miR-1915-5p is hsa-miR-1915-5p, miR-3180 is hsa-miR-3180, miR-6879-5p is hsa-miR-6879-5p, miR-1199-5p is hsa-miR-1199-5p, miR-6746-5p is hsa-miR-6746-5p, miR-711 is hsa-miR-711, miR-663b is hsa-miR-663b, miR-4707-3p is hsa-miR-4707-3p, miR-6893-5p is hsa-miR-6893-5p, miR-4675 is hsa-miR-4675, miR-4638-5p is hsa-miR-4638-5p, miR-4651 is hsa-miR-4651, miR-6087 is hsa-miR-6087, miR-4665-5p is hsa-miR-4665-5p, miR-4758-5p is hsa-miR-4758-5p, miR-6887-5p is hsa-miR-6887-5p, miR-3620-5p is hsa-miR-3620-5p, miR-1909-3p is hsa-miR-1909-3p, miR-7641 is hsa-miR-7641, miR-6724-5p is hsa-miR-6724-5p, miR-1343-3p is hsa-miR-1343-3p, miR-6780b-5p is hsa-miR-6780b-5p, miR-4484 is hsa-miR-4484, miR-4690-5p is hsa-miR-4690-5p, miR-4429 is hsa-miR-4429, miR-1227-5p is hsa-miR-1227-5p, miR-4725-3p is hsa-miR-4725-3p, miR-6861-5p is hsa-miR-6861-5p, miR-6812-5p is hsa-miR-6812-5p, miR-3197 is hsa-miR-3197, miR-8059 is hsa-miR-8059, miR-3185 is hsa-miR-3185, miR-4706 is hsa-miR-4706, miR-4497 is hsa-miR-4497, miR-3131 is hsa-miR-3131, miR-6806-5p is hsa-miR-6806-5p, miR-187-5p is hsa-miR-187-5p, miR-3180-3p is hsa-miR-3180-3p, miR-6848-5p is hsa-miR-6848-5p, miR-6820-5p is hsa-miR-6820-5p, miR-6800-5p is hsa-miR-6800-5p, miR-6717-5p is hsa-miR-6717-5p, miR-6795-5p is hsa-miR-6795-5p, miR-4632-5p is hsa-miR-4632-5p, miR-665 is hsa-miR-665, miR-6778-5p is hsa-miR-6778-5p, miR-3663-3p is hsa-miR-3663-3p, miR-4689 is hsa-miR-4689, miR-211-3p is hsa-miR-211-3p, miR-6511b-5p is hsa-miR-6511b-5p, miR-4750-5p is hsa-miR-4750-5p, miR-6126 is hsa-miR-6126, miR-614 is hsa-miR-614, miR-7110-5p is hsa-miR-7110-5p, miR-744-5p is hsa-miR-744-5p, miR-6769a-5p is hsa-miR-6769a-5p, miR-4792 is hsa-miR-4792, miR-5787 is hsa-miR-5787, miR-6798-5p is hsa-miR-6798-5p, miR-6781-5p is hsa-miR-6781-5p, miR-4419b is hsa-miR-4419b, miR-4446-3p is hsa-miR-4446-3p, miR-4259 is hsa-miR-4259, miR-5572 is hsa-miR-5572, miR-6075 is hsa-miR-6075, miR-296-3p is hsa-miR-296-3p, miR-6891-5p is hsa-miR-6891-5p, miR-4745-5p is hsa-miR-4745-5p, miR-6775-5p is hsa-miR-6775-5p, miR-6870-5p is hsa-miR-6870-5p, miR-920 is hsa-miR-920, miR-4530 is hsa-miR-4530, miR-6819-5p is hsa-miR-6819-5p, miR-6825-5p is hsa-miR-6825-5p, miR-7847-3p is hsa-miR-7847-3p, miR-6131 is hsa-miR-6131, miR-4433-3p is hsa-miR-4433-3p, miR-1228-5p is hsa-miR-1228-5p, miR-6743-5p is hsa-miR-6743-5p, miR-1268a is hsa-miR-1268a, miR-3917 is hsa-miR-3917, miR-6786-5p is hsa-miR-6786-5p, miR-3154 is hsa-miR-3154, miR-638 is hsa-miR-638, miR-6741-5p is hsa-miR-6741-5p, miR-6889-5p is hsa-miR-6889-5p, miR-6840-3p is hsa-miR-6840-3p, miR-6510-5p is hsa-miR-6510-5p, miR-3188 is hsa-miR-3188, miR-551b-5p is hsa-miR-551b-5p, miR-5001-5p is hsa-miR-5001-5p, miR-1268b is hsa-miR-1268b, miR-7107-5p is hsa-miR-7107-5p, miR-6824-5p is hsa-miR-6824-5p, miR-6732-5p is hsa-miR-6732-5p, miR-371a-5p is hsa-miR-371a-5p, miR-6794-5p is hsa-miR-6794-5p, miR-6779-5p is hsa-miR-6779-5p, miR-4271 is hsa-miR-4271, miR-5195-3p is hsa-miR-5195-3p, miR-6762-5p is hsa-miR-6762-5p, miR-939-5p is hsa-miR-939-5p, miR-1247-3p is hsa-miR-1247-3p, miR-6777-5p is hsa-miR-6777-5p, miR-6722-3p is hsa-miR-6722-3p, miR-3656 is hsa-miR-3656, miR-4688 is hsa-miR-4688, miR-3195 is hsa-miR-3195, miR-6766-5p is hsa-miR-6766-5p, miR-4447 is hsa-miR-4447, miR-4656 is hsa-miR-4656, miR-7108-5p is hsa-miR-7108-5p, miR-3191-3p is hsa-miR-3191-3p, miR-1273g-3p is hsa-miR-1273g-3p, miR-4463 is hsa-miR-4463, miR-2861 is hsa-miR-2861, miR-3196 is hsa-miR-3196, miR-6877-5p is hsa-miR-6877-5p, miR-3679-5p is hsa-miR-3679-5p, miR-4442 is hsa-miR-4442, miR-6789-5p is hsa-miR-6789-5p, miR-6782-5p is hsa-miR-6782-5p, miR-486-3p is hsa-miR-486-3p, miR-6085 is hsa-miR-6085, miR-4746-3p is hsa-miR-4746-3p, miR-619-5p is hsa-miR-619-5p, miR-937-5p is hsa-miR-937-5p, miR-6803-5p is hsa-miR-6803-5p, miR-4298 is hsa-miR-4298, miR-4454 is hsa-miR-4454, miR-4459 is hsa-miR-4459, miR-7150 is hsa-miR-7150, miR-6880-5p is hsa-miR-6880-5p, miR-4449 is hsa-miR-4449, miR-8063 is hsa-miR-8063, miR-4695-5p is hsa-miR-4695-5p, miR-6132 is hsa-miR-6132, miR-6829-5p is hsa-miR-6829-5p, miR-4486 is hsa-miR-4486, miR-6805-3p is hsa-miR-6805-3p, miR-6826-5p is hsa-miR-6826-5p, miR-4508 is hsa-miR-4508, miR-1343-5p is hsa-miR-1343-5p, miR-7114-5p is hsa-miR-7114-5p, miR-3622a-5p is hsa-miR-3622a-5p, miR-6765-5p is hsa-miR-6765-5p, miR-7845-5p is hsa-miR-7845-5p, miR-3960 is hsa-miR-3960, miR-6749-5p is hsa-miR-6749-5p, miR-1260b is hsa-miR-1260b, miR-6799-5p is hsa-miR-6799-5p, miR-4723-5p is hsa-miR-4723-5p, miR-6784-5p is hsa-miR-6784-5p, miR-5100 is hsa-miR-5100, miR-6769b-5p is hsa-miR-6769b-5p, miR-1207-5p is hsa-miR-1207-5p, miR-642a-3p is hsa-miR-642a-3p, miR-4505 is hsa-miR-4505, miR-4270 is hsa-miR-4270, miR-6721-5p is hsa-miR-6721-5p, miR-7111-5p is hsa-miR-7111-5p, miR-6791-5p is hsa-miR-6791-5p, miR-7109-5p is hsa-miR-7109-5p, miR-4258 is hsa-miR-4258, miR-6515-3p is hsa-miR-6515-3p, miR-6851-5p is hsa-miR-6851-5p, miR-6125 is hsa-miR-6125, miR-4749-5p is hsa-miR-4749-5p, miR-4726-5p is hsa-miR-4726-5p, miR-4513 is hsa-miR-4513, miR-6089 is hsa-miR-6089, miR-6816-5p is hsa-miR-6816-5p, miR-4466 is hsa-miR-4466, miR-4488 is hsa-miR-4488, miR-6752-5p is hsa-miR-6752-5p, and miR-4739 is hsa-miR-4739.

In a preferred embodiment of the method of the present invention, specifically, the nucleic acid (specifically, probe(s) or primer(s)) is selected from the group consisting of the following polynucleotides (a) to (e):

(a) a polynucleotide consisting of a nucleotide sequence represented by any of SEQ ID NOs: 1 to 235 and 851 to 856 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 235 and 851 to 856, (c) a polynucleotide consisting of a nucleotide sequence complementary to a nucleotide sequence represented by any of SEQ ID NOs: 1 to 235 and 851 to 856 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 235 and 851 to 856 or a nucleotide sequence derived from the nucleotide sequence by the replacement of u with t, and (e) a polynucleotide hybridizing under stringent conditions to any of the polynucleotides (a) to (d).

The method of the present invention can further employ nucleic acid(s) capable of specifically binding to at least one polynucleotide selected from the group consisting of miR-760, miR-602, miR-423-5p, miR-92a-2-5p, miR-16-5p, miR-451a, miR-135a-3p, miR-486-5p, miR-4257, miR-92b-5p, miR-1915-3p, miR-718, miR-940, miR-296-5p, miR-23b-3p and miR-92a-3p.

As for such a nucleic acid, specifically, miR-760 is hsa-miR-760, miR-602 is hsa-miR-602, miR-423-5p is hsa-miR-423-5p, miR-92a-2-5p is hsa-miR-92a-2-5p, miR-16-5p is hsa-miR-16-5p, miR-451a is hsa-miR-451a, miR-135a-3p is hsa-miR-135a-3p, miR-486-5p is hsa-miR-486-5p, miR-4257 is hsa-miR-4257, miR-92b-5p is hsa-miR-92b-5p, miR-1915-3p is hsa-miR-1915-3p, miR-718 is hsa-miR-718, miR-940 is hsa-miR-940, miR-296-5p is hsa-miR-296-5p, miR-23b-3p is hsa-miR-23b-3p, and miR-92a-3p is hsa-miR-92a-3p.

In a preferred embodiment, such a nucleic acid is specifically selected from the group consisting of the following polynucleotides (f) to (j):

(f) a polynucleotide consisting of a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 236 to 251, (h) a polynucleotide consisting of a nucleotide sequence complementary to a nucleotide sequence represented by any of SEQ ID NOs: 236 to 251 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 236 to 251 or a nucleotide sequence derived from the nucleotide sequence by the replacement of u with t, and (j) a polynucleotide hybridizing under stringent conditions to any of the polynucleotides (f) to (i).

The nucleic acid(s) further used in the method of the present invention can comprise nucleic acid(s) capable of specifically binding to at least one polynucleotide selected from the group consisting of miR-658, miR-6842-5p, miR-6124, miR-6765-3p, miR-7106-5p, miR-4534, miR-92b-3p, miR-3135b, miR-4687-3p, miR-762, miR-3619-3p, miR-4467, miR-557, miR-1237-5p, miR-1908-5p, miR-4286, miR-6885-5p and miR-6763-5p.

Specifically, miR-658 is hsa-miR-658, miR-6842-5p is hsa-miR-6842-5p, miR-6124 is hsa-miR-6124, miR-6765-3p is hsa-miR-6765-3p, miR-7106-5p is hsa-miR-7106-5p, miR-4534 is hsa-miR-4534, miR-92b-3p is hsa-miR-92b-3p, miR-3135b is hsa-miR-3135b, miR-4687-3p is hsa-miR-4687-3p, miR-762 is hsa-miR-762, miR-3619-3p is hsa-miR-3619-3p, miR-4467 is hsa-miR-4467, miR-557 is hsa-miR-557, miR-1237-5p is hsa-miR-1237-5p, miR-1908-5p is hsa-miR-1908-5p, miR-4286 is hsa-miR-4286, miR-6885-5p is hsa-miR-6885-5p, and miR-6763-5p is hsa-miR-6763-5p.

Further, in a preferred embodiment, such nucleic acid(s) is/are specifically a polynucleotide selected from the group consisting of the following polynucleotides (k) to (o):

(k) a polynucleotide consisting of a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 252 to 269, (m) a polynucleotide consisting of a nucleotide sequence complementary to a nucleotide sequence represented by any of SEQ ID NOs: 252 to 269 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 252 to 269 or a nucleotide sequence derived from the nucleotide sequence by the replacement of u with t, and (o) a polynucleotide hybridizing under stringent conditions to any of the polynucleotides (k) to (n).

Examples of the sample used in the method of the present invention can include samples prepared from living tissues (preferably breast tissues) or body fluids such as blood, serum, plasma, and urine from the subjects. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

The subject used herein refers to a mammal, for example, a human, a monkey, a mouse or a rat, and is preferably a human.

The steps of the method of the present invention can be changed according to the type of the sample to be assayed.

In the case of using RNA as an analyte, the detection of breast cancer (cells) can comprise, for example, the following steps (a), (b), and (c):

(a) a step of binding RNA prepared from a sample from a subject or complementary polynucleotides (cDNAs) transcribed from the RNA to a polynucleotide(s) in the kit or the device of the present invention;

(b) a step of measuring the sample-derived RNA or the cDNAs synthesized from the RNA, which is/are bound to the polynucleotide(s) by hybridization using the polynucleotide(s) as nucleic acid probe(s) or by quantitative RT-PCR using the polynucleotide(s) as primer(s); and (c) a step of evaluating the presence or absence of breast cancer (or breast cancer-derived gene expression) on the basis of the measurement results of the step (b).

For example, various hybridization methods can be used for detecting, examining, evaluating, or diagnosing breast cancer (or breast cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe(s) that can be used in the present invention. Specific examples thereof can include a method which comprises labeling the nucleic acid probe (or a complementary strand) with a radioisotope ($^{32}P$, $^{33}P$, $^{35}S$, etc.), a fluorescent material, or the like, that hybridizes the labeled product with the tissue-derived RNA from a subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which comprises; preparing cDNAs from the tissue-derived RNA of a subject according to a routine procedure; hybridizing a pair of primers (consisting of a plus strand and a reverse strand that bind to the cDNA) of the present invention with the cDNA such that the region of each target gene can be amplified with the cDNA as a template; and performing PCR according to a routine method to detect the obtained double-stranded DNA. The method for detecting the double-stranded DNA can include; a method of performing the PCR using the primers labeled in advance with a radioisotope or a fluorescent material; a method of electrophoresing the PCR product on an agarose gel and staining the double-stranded DNA with ethidium bromide or the like for detection; and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) are attached to a substrate (solid phase) is used. Regions having the attached nucleic acid probes are referred to as probe spots, and regions having no attached nucleic acid probe are referred to as blank spots. A gene group immobilized on a solid-phase substrate is generally called a nucleic acid chip, a nucleic acid array, a microarray, or the like. The DNA or RNA array includes a DNA or RNA macroarray and a DNA or RNA microarray. The term "chip" used herein includes all of these arrays. 3D-Gene™ Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label on the nucleic acid probe using an image detector (examples thereof can include Typhoon 9410 (GE Healthcare) and 3D-Gene™ scanner (Toray Industries, Inc.)).

The "stringent conditions" used herein are, as mentioned above, conditions under which a nucleic acid probe hybridizes to its target sequence to a larger extent (e.g., a measurement value equal to or larger than "(a mean of background measurement values)+(a standard deviation of the background measurement values)×2") than that for other sequences.

The stringent conditions are defined by hybridization and subsequent washing conditions. Examples of the hybridization conditions include, but not limited to 30° C. to 60° C. for 1 to 24 hours in a solution containing SSC, a surfactant, formamide, dextran sulfate, a blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3-10×SSC and 0.1-1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by the washing under such conditions. Specifically, examples of such a complementary strand can include a strand consisting of a nucleotide sequence in a completely complementary relationship with the nucleotide sequence of the target plus (+) strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using polynucleotide fragments contained in the kit of the present invention as primers include treatment for approximately 15 seconds to 1 minute at 5 to 10° C. plus a Tm value calculated from the sequences of the primers, using a PCR buffer having composition such as 10 mM Tris-HCL (pH 83), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan™ MicroRNA Assays (Life Technologies Corp.); LNA™-based MicroRNA PCR (Exiqon); or Ncode™ miRNA qRT-PCT kit (Invitrogen Corp.) may be used.

For the calculation of gene expression levels, statistical analysis described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene that shows a gene expression level of $2^6$, preferably $2^8$, more preferably $2^{10}$, or larger, in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring target genes or gene expression levels in a sample from a subject using the polynucleotide, the kit, or the device (e.g., chip) for detection of the present invention, or a combination thereof, preparing a discriminant (discriminant function) with gene expression levels in a sample from a breast cancer patient and a sample from a healthy subject as supervising samples, and determining or evaluating the presence and/or absence of the breast cancer-derived genes in the sample.

Specifically, the present invention further provides the method comprising: a first step of measuring in vitro expression levels of target genes in multiple samples known to determine or evaluate the presence and/or absence of the breast cancer-derived genes in the samples, using the polynucleotides, the kit, or the device (e.g., chip) for detection of the present invention, or a combination thereof; a second step of preparing a discriminant with the measurement values of the expression levels of the target genes (target nucleic acid) obtained in the first step as supervising samples; a third step of measuring in vitro expression levels of the target genes in a sample derived from a subject in the same way as in the first step; and a fourth step of assigning the measurement values of the expression levels of the target genes obtained in the third step to the discriminant obtained in the second step, and determining or evaluating the presence and/or absence of the breast cancer-derived gene in the sample on the basis of the results obtained from the discriminant, wherein the target genes can be detected using the polynucleotides or using polynucleotides for detection contained in the kit or the device (e.g., chip). In this context, the discriminant can be prepared by use of Fisher's discriminant analysis, nonlinear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In this formula, x represents an explanatory variable, w represents a coefficient of the explanatory variable, and $w_0$ represents a constant term.

$$f(x) = w_0 + \sum_{i=1}^{n} w_i x_i \quad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, one type of linear discriminant analysis, is a dimension reduction method for selecting a dimension suitable for classification, and constructs a highly discriminating synthetic variable by focusing on the variance of synthetic variables and minimizing the variance of data having the same label (Venables, W. N. et al., Modern Applied Statistics with S. Fourth edition. Springer., 2002). In the Fisher's discriminant analysis, direction w of projection is determined so as to maximize Formula 2. In this formula, μ represents an average input, ng represents the number of data associated to class g, and μg represents an average input of the data associated to class g. The numerator and the denominator are the interclass variance and the intraclass variance, respectively, when each data is projected in the direction of the vector w. Discriminant coefficient wi is determined by maximizing this ratio (Takafumi Kanamori et al., "Pattern Recognition", Kyoritsu Shuppan Co., Ltd. (2009); and Richard O. et al., Pattern Classification Second Edition., Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i: y_i = g} (w^T x_i - w^T \mu_g)(w^T x_i - w^T \mu_g)} \quad \text{Formula 2}$$

$$\text{subject to } \mu = \sum_{i=1}^{n} \frac{x_i}{n}, \mu_g = \sum_{i: u_i = g}^{n} \frac{x_i}{n_g}$$

The Mahalanobis' distance is calculated according to Formula 3 in consideration of data correlation and can be used as nonlinear discriminant analysis for determining a cluster to which a data point is associated, based on a short Mahalanobis' distance from the data point to that cluster. In this formula, μ represents a central vector of each cluster, and S-1 represents an inverse matrix of the variance-covariance matrix of the cluster. The central vector is calculated from explanatory variable x, and an average vector, a median value vector, or the like can be used.

$$D(x,\mu) = \{(x-\mu)^t S^{-1} (x-\mu)\}^{1/2} \quad \text{Formula 3}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the result of the discriminant analysis may be the associated class, may be a probability of being classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004); Nello Cristianini et al., Introduction to SVM, Kyoritsu Shuppan Co., Ltd. (2008)).

C-support vector classification (C-SVC), one type of SVM, comprises preparing a hyperplane by supervising a data set with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a breast cancer patient group and a healthy subject group. For example, breast tissue examination can be used for a reference under which each subject is confirmed either as a breast cancer patient or as a healthy subject.

Next, a data set consisting of comprehensive gene expression levels of serum-derived samples of the two divided groups (hereinafter, this data set is referred to as a training cohort) is prepared, and a C-SVC discriminant is determined by explanatory variables that are genes found to differ clearly in their gene expression levels between the two groups, and objective variables (e.g., −1 and +1) that are the grouping. An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_a \frac{1}{2} a^T Q a - e^T a$$

subject to $y^T = 0$, $0 \le a_i \le C$, $i = 1, \ldots, l$,

Formula 4

Formula 5 is a finally obtained discriminant, and a group to which the data point is associated can be determined on the basis of the sign of a value obtained according to the discriminant. In this formula, x represents a support vector, y represents a label indicating the association of a group, a represents the corresponding coefficient, b represents a constant term, and K represents a kernel function.

$$f(x) = \text{sgn}\left(\sum_{i=1}^{l} y_i a_i K(x_i, x) + b\right)$$

Formula 5

For example, a RBF kernel defined by Formula 6 can be used as the kernel function. In this formula, x represents a support vector, and γ represents a kernel parameter for adjusting the complexity of the hyperplane.

$$K(x_i, x_j) = \exp(-r\|x_i - x_j\|^2), r < 0$$

Formula 6

In addition, an approach such as neural network, k-nearest neighbor algorithms, decision trees, or logistic regression analysis can be selected as a method for determining or evaluating the presence and/or absence of expression of a breast cancer-derived target gene in a sample derived from a subject, or for evaluating the expression level thereof by comparison with a control derived from a healthy subject.

The method of the present invention can comprise, for example, the following steps (a), (b), and (c):

(a) a step of measuring expression level(s) of target gene(s) in tissues containing breast cancer-derived genes derived from breast cancer patients and/or samples already known to be tissues containing no breast cancer-derived gene(s) derived from healthy subjects, using the polynucleotide(s), the kit, or the device (e.g., DNA chip) for detection according to the present invention;

(b) a step of preparing the discriminants of Formulas 1 to 3, 5, and 6 described above from the measurement values of the expression level measured in the step (a); and (c) a step of measuring expression level(s) of the target gene(s) in a sample derived from a subject using the polynucleotide(s), the kit, or the device (e.g., DNA chip) for diagnosis (detection) according to the present invention, substituting the obtained measurement values into the discriminants prepared in the step (b), and determining or evaluating the presence and/or absence of the breast cancer-derived target gene in the sample, or evaluating the expression levels thereof by comparison with a healthy subject-derived control, on the basis of the obtained results. In this context, in the discriminants of Formulas 1 to 3, 5, and 6, x represents an explanatory variable and includes a value obtained by measuring polynucleotide(s) selected from the polynucleotides described in the Section 2 above, or any fragment thereof. Specifically, the explanatory variable for discriminating a breast cancer patient from a healthy subject according to the present invention is gene expression level(s) selected from, for example, the following expression levels (1) to (3):

(1) gene expression level(s) in the serum of a breast cancer patient or a healthy subject measured by any DNA comprising 15 or more consecutive nucleotides in a nucleotide sequence represented by any of SEQ ID NOs: 1 to 235 and 851 to 856 or a complementary sequence thereof, (2) gene expression level(s) in the serum of a breast cancer patient or a healthy subject measured by any DNA comprising 15 or more consecutive nucleotides in a nucleotide sequence represented by any of SEQ ID NOs: 236 to 251 or a complementary sequence thereof, (3) gene expression level(s) in the serum of a breast cancer patient or a healthy subject measured by any DNA comprising 15 or more consecutive nucleotides in a nucleotide sequence represented by any of SEQ ID NOs: 252 to 269 or a complementary sequence thereof.

As described above, for the method for determining or evaluating the presence and/or absence of breast cancer-derived gene(s) in a sample derived from a subject, the preparation of a discriminant requires a discriminant prepared from a training cohort. For enhancing the accuracy of the discriminant, it is necessary for the discriminant to use genes that show clear difference between two groups in the training cohort.

Each gene that is used for an explanatory variable in a discriminant is preferably determined as follows. First, comprehensive gene expression levels of a breast cancer patient group and comprehensive gene expression levels of a healthy subject group, both of which are in a training cohort, are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) of the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the statistical test, the absolute value (fold change) of an expression ratio of a median value of each gene expression level between gene expression levels of a breast cancer patient group and gene expression levels of a healthy subject group may be calculated to select a gene that is used for an explanatory variable in a discriminant. Alternatively, ROC curves may be prepared using gene expression levels of a breast cancer patient group and a healthy subject group, and a gene that is used for an explanatory variable in a discriminant can be selected on the basis of an AUROC value.

Next, a discriminant that can be calculated by various methods described above is prepared using any number of genes that show large difference in their gene expression levels determined here. Examples of the method for constructing a discriminant that produces the largest discriminant accuracy include a method of constructing a discriminant in every combination of genes that satisfy the significance level of P value, and a method of repetitively evaluating the genes for use in the construction of a discriminant while increasing the number of genes one by one in a descending order of the difference in gene expression level (Furey T S. et al., 2000, Bioinformatics., Vol. 16, p. 906-14). A gene expression level of another independent breast cancer patient or healthy subject is assigned as an explanatory variable to this discriminant to calculate discriminant results of the group to which this independent breast cancer patient or healthy subject is associated. Specifically, the found gene set for diagnosis and the discriminant constructed using the gene set for diagnosis can be evaluated in an independent sample cohort to find a more universal gene set for diagnosis capable of detecting breast cancer and a more universal method for discriminating breast cancer.

Split-sample method is preferably used for evaluating the performance (generality) of the discriminant. Specifically, a data set is divided into a training cohort and a validation cohort, and gene selection by a statistical test and discriminant construction are performed using the training cohort. Accuracy, sensitivity, and specificity are calculated using results of discriminant analysis in the validation cohort according to the discriminant constructed and a true group to which the validation cohort is associated, to evaluate the discriminant performance of the discriminant. On the other hand, instead of dividing a data set, gene selection by a statistical test and discriminant construction may be performed using all of samples, and accuracy, sensitivity, and specificity can be calculated by the discriminat analysis using a newly prepared cohorts for evaluation of the performance of the discriminant.

The present invention provides polynucleotides for detection and disease diagnosis useful in the diagnosis and treatment of breast cancer, a method for detecting breast cancer using the polynucleotide(s), and a kit and a device for the detection of breast cancer, comprising the polynucleotide(s). Particularly, in order to select gene(s) for diagnosis and prepare a discriminant so as to exhibit accuracy beyond the breast cancer diagnosis method using an existing tumor marker CEA, a gene set for diagnosis and a discriminant for the method of the present invention can be constructed, which exhibit accuracy beyond CEA, for example, by comparing expressed genes in serum from a patient confirmed to be negative using CEA but finally found to have breast cancer by detailed examination such as computed tomography using a contrast medium, with genes expressed in serum from a patient having no breast cancer.

For example, the gene set for diagnosis is set to any combination selected from one or two or more of the polynucleotides based on a nucleotide sequence represented by any of SEQ ID NOs: 1 to 235, and 851 to 856, or a complementary sequence thereof as described above; and optionally one or two or more of the polynucleotides based on a nucleotide sequence represented by any of SEQ ID NOs: 236 to 251, or a complementary sequence thereof; and optionally one or two or more of the polynucleotides based on a nucleotide sequence represented by any of SEQ ID NOs: 252 to 269, or a complementary sequence thereof. Further, a discriminant is constructed using expression levels of the gene set for diagnosis in samples from class I breast cancer patients as a result of tissue diagnosis and samples from class II healthy subjects as a result of tissue diagnosis. As a result, the presence or absence of breast cancer-derived genes in an unknown sample can be determined with 100% accuracy at the maximum by measuring expression levels of the gene set for diagnosis in an unknown sample.

EXAMPLES

Hereinafter, the present invention will be described further specifically with reference to Examples below. However, the scope of the present invention is not intended to be limited by these Examples.

Reference Example 1

<Collection of Samples from Breast Cancer Patients and Healthy Subjects>

Sera were collected using VENOJECT II vacuum blood collecting tube VP-AS109K60 (Terumo Corp.) from 100 healthy subjects (92 males and 8 females) and 62 breast cancer patients (20 cases with stage I, 24 cases with stage IIA, 7 cases with stage IIB, 2 cases with stage IIIA, 3 cases with stage IIIB, 1 case with stage IIIC, and 5 cases with stage IV) who were confirmed to have no primary cancer other than breast cancer after acquisition of informed consent, and used as a training cohort. Likewise, Sera were collected using VENOJECT II vacuum blood collecting tube VP-AS109K60 (Terumo Corp.) from 50 healthy subjects (44 males and 6 females) and 31 breast cancer patients (9 cases with stage I, 13 cases with stage IIA, 5 cases with stage IIB, 1 case with stage IIIA, 1 case with stage IIIB, 1 case with stage IIIC, and 1 case with stage IV) who were confirmed to have no primary cancer other than breast cancer after acquisition of informed consent, and used as a validation cohort.

<Extraction of Total RNA>

Total RNA was obtained from 300 µL of the serum sample obtained from each of 243 persons in total of 150 healthy subjects and 93 breast cancer patients included in the training cohort and the validation cohort, using a reagent for RNA extraction in 3D-Gene™ RNA extraction reagent from liquid sample kit (Toray Industries, Inc.) according to the protocol provided by the manufacturer.

<Measurement of Gene Expression Level> miRNAs in the total RNA obtained from the serum samples of each of 243 persons in total of 150 healthy subjects and 93 breast cancer patients included in the training cohort and the validation cohort were fluorescently labeled using 3D-Gene™ miRNA Labeling kit (Toray Industries, Inc.) according to the protocol (ver 2.20) provided by the manufacturer. The oligo DNA chip used was 3D-Gene™ Human miRNA Oligo chip (Toray Industries, Inc.) with attached probes having sequences complementary to 2,555 miRNAs among the miRNAs registered in miRBase Release 20. Hybridization between the miRNAs in the total RNA and the probes on the DNA chip under stringent conditions and washing following the hybridization were performed according to the protocol provided by the manufacturer. The DNA chip was scanned using 3D-Gene™ scanner (Toray Industries, Inc.) to obtain images. Fluorescence intensity was digitized using 3D-Gene™ Extraction (Toray Industries, Inc.). The digitized fluorescence intensity was converted to a logarithmic value with a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the sera were obtained for the 93 breast cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/) and MASS package 7.3-30 (Venables, W. N. & Ripley, B. D. (2002) Modern Applied Statistics with S. Fourth Edition. Springer, New York. ISBN 0-387-95457-0).

Reference Example 2

<Collection of Samples from Patients with Cancer Other than Breast Cancer>

Sera were collected using VENOJECT II vacuum blood collecting tube VP-AS109K60 (Terumo Corp.) from each of 33 prostate cancer patients confirmed to have no cancer in other organs after acquisition of informed consent, and used as a training cohort together with the samples of 62 breast cancer patients and 102 healthy subjects of Reference Example 1. Likewise, sera were collected using VENOJECT II vacuum blood collecting tube VP-AS109K60 (Terumo Corp.) from each of 19 prostate cancer patients confirmed to have no cancer in other organs after acquisition of informed consent, and used as a validation cohort together with the samples of 31 breast cancer patients confirmed to have no cancer in organs other than the breast and 48 healthy subjects of Reference Example 1. Subsequent operations were conducted in the same way as in Reference Example 1.

Example 1

<Selection of Gene Marker Using the Training Cohort, and Method for Evaluating Breast Cancer Discriminant Performance of the Single Gene Marker Using the Validation Cohort>

In this Example, a gene marker for discriminating a breast cancer patient from a healthy subject was selected from the training cohort and studied in the validation cohort independent of the training cohort, for a method for evaluating the breast cancer discriminant performance of each selected gene marker alone.

Specifically, first, the miRNA expression levels of the training cohort and the validation cohort obtained in the preceding Reference Examples were combined and normalized by quantile normalization.

Next, genes for diagnosis were selected using the training cohort. Here, in order to acquire diagnostic markers with higher reliability, only genes that show the gene expression level of $2^6$ or higher in 50% or more of the samples in either of the breast cancer patient group in the training cohort or the healthy subject group in the training cohort were selected. In order to further acquire statistically significant genes for discriminating a breast cancer patient group from a healthy subject group, the P value obtained by two-tailed t-test assuming equal variance as to each gene expression level was corrected by the Bonferroni method, and genes that satisfied p<0.01 were acquired as gene markers for use in explanatory variables of a discriminant. The obtained genes are described in Table 2.

In this way, hsa-miR-4783-3p, hsa-miR-4730, hsa-miR-1307-3p, hsa-miR-4634, hsa-miR-663a, hsa-miR-4532, hsa-miR-7704, hsa-miR-3178, hsa-miR-6729-5p, hsa-miR-6090, hsa-miR-4732-5p, hsa-miR-3184-5p, hsa-miR-6727-5p, hsa-miR-6088, hsa-miR-4674, hsa-miR-8073, hsa-miR-4787-5p, hsa-miR-1469, hsa-miR-125a-3p, hsa-miR-1233-5p, hsa-miR-885-3p, hsa-miR-6802-5p, hsa-miR-328-5p, hsa-miR-6787-5p, hsa-miR-8069, hsa-miR-6875-5p, hsa-miR-1246, hsa-miR-4734, hsa-miR-6757-5p, hsa-miR-6756-5p, hsa-miR-3665, hsa-miR-6836-3p, hsa-miR-6821-5p, hsa-miR-6805-5p, hsa-miR-4728-5p, hsa-miR-6726-5p, hsa-miR-197-5p, hsa-miR-149-3p, hsa-miR-6850-5p, hsa-miR-4476, hsa-miR-6858-5p, hsa-miR-564, hsa-miR-4763-3p, hsa-miR-575, hsa-miR-6771-5p, hsa-miR-1231, hsa-miR-1908-3p, hsa-miR-150-3p, hsa-miR-3937, hsa-miR-887-3p, hsa-miR-3940-5p, hsa-miR-4741, hsa-miR-6808-5p, hsa-miR-6869-5p, hsa-miR-5090, hsa-miR-615-5p, hsa-miR-8072, hsa-miR-128-1-5p, hsa-miR-1238-5p, hsa-miR-365a-5p, hsa-miR-204-3p, hsa-miR-4492, hsa-miR-6785-5p, hsa-miR-6511a-5p, hsa-miR-4525, hsa-miR-1915-5p, hsa-miR-3180, hsa-miR-6879-5p, hsa-miR-1199-5p, hsa-miR-6746-5p, hsa-miR-711, hsa-miR-663b, hsa-miR-4707-3p, hsa-miR-6893-5p, hsa-miR-4675, hsa-miR-4638-5p, hsa-miR-4651, hsa-miR-6087, hsa-miR-4665-5p, hsa-miR-4758-5p, hsa-miR-6887-5p, hsa-miR-3620-5p, hsa-miR-1909-3p, hsa-miR-7641, hsa-miR-6724-5p, hsa-miR-1343-3p, hsa-miR-6780b-5p, hsa-miR-4484, hsa-miR-4690-5p, hsa-miR-4429, hsa-miR-1227-5p, hsa-miR-4725-3p, hsa-miR-6861-5p, hsa-miR-6812-5p, hsa-miR-3197, hsa-miR-8059, hsa-miR-3185, hsa-miR-4706, hsa-miR-4497, hsa-miR-3131, hsa-miR-6806-5p, hsa-miR-187-5p, hsa-miR-3180-3p, hsa-miR-6848-5p, hsa-miR-6820-5p, hsa-miR-6800-5p, hsa-miR-6717-5p, hsa-miR-6795-5p, hsa-miR-4632-5p, hsa-miR-665, hsa-miR-6778-5p, hsa-miR-3663-

3p, hsa-miR-4689, hsa-miR-211-3p, hsa-miR-6511b-5p, hsa-miR-4750-5p, hsa-miR-6126, hsa-miR-614, hsa-miR-7110-5p, hsa-miR-744-5p, hsa-miR-6769a-5p, hsa-miR-4792, hsa-miR-5787, hsa-miR-6798-5p, hsa-miR-6781-5p, hsa-miR-4419b, hsa-miR-4446-3p, hsa-miR-4259, hsa-miR-5572, hsa-miR-6075, hsa-miR-296-3p, hsa-miR-6891-5p, hsa-miR-4745-5p, hsa-miR-6775-5p, hsa-miR-6870-5p, hsa-miR-920, hsa-miR-4530, hsa-miR-6819-5p, hsa-miR-6825-5p, hsa-miR-7847-3p, hsa-miR-6131, hsa-miR-4433-3p, hsa-miR-1228-5p, hsa-miR-6743-5p, hsa-miR-1268a, hsa-miR-3917, hsa-miR-6786-5p, hsa-miR-3154, hsa-miR-638, hsa-miR-6741-5p, hsa-miR-6889-5p, hsa-miR-6840-3p, hsa-miR-6510-5p, hsa-miR-3188, hsa-miR-551b-5p, hsa-miR-5001-5p, hsa-miR-1268b, hsa-miR-7107-5p, hsa-miR-6824-5p, hsa-miR-6732-5p, hsa-miR-371a-5p, hsa-miR-6794-5p, hsa-miR-6779-5p, hsa-miR-4271, hsa-miR-5195-3p, hsa-miR-6762-5p, hsa-miR-939-5p, hsa-miR-1247-3p, hsa-miR-6777-5p, hsa-miR-6722-3p, hsa-miR-3656, hsa-miR-4688, hsa-miR-3195, hsa-miR-6766-5p, hsa-miR-4447, hsa-miR-4656, hsa-miR-7108-5p, hsa-miR-3191-3p, hsa-miR-1273g-3p, hsa-miR-4463, hsa-miR-2861, hsa-miR-3196, hsa-miR-6877-5p, hsa-miR-3679-5p, hsa-miR-4442, hsa-miR-6789-5p, hsa-miR-6782-5p, hsa-miR-486-3p, hsa-miR-6085, hsa-miR-4746-3p, hsa-miR-619-5p, hsa-miR-937-5p, hsa-miR-6803-5p, hsa-miR-4298, hsa-miR-4454, hsa-miR-4459, hsa-miR-7150, hsa-miR-6880-5p, hsa-miR-4449, hsa-miR-8063, hsa-miR-4695-5p, hsa-miR-6132, hsa-miR-6829-5p, hsa-miR-4486, hsa-miR-6805-3p, hsa-miR-6826-5p, hsa-miR-4508, hsa-miR-1343-5p, hsa-miR-7114-5p, hsa-miR-3622a-5p, hsa-miR-6765-5p, hsa-miR-7845-5p, hsa-miR-3960, hsa-miR-6749-5p, hsa-miR-1260b, hsa-miR-6799-5p, hsa-miR-4723-5p, hsa-miR-6784-5p, hsa-miR-5100, hsa-miR-6769b-5p, hsa-miR-1207-5p, hsa-miR-642a-3p, hsa-miR-4505, hsa-miR-4270, hsa-miR-6721-5p, hsa-miR-7111-5p, hsa-miR-6791-5p, hsa-miR-7109-5p, hsa-miR-4258, hsa-miR-6515-3p, hsa-miR-6851-5p, hsa-miR-6125, hsa-miR-4749-5p, hsa-miR-4726-5p, hsa-miR-4513, hsa-miR-760, hsa-miR-602, hsa-miR-423-5p, hsa-miR-92a-2-5p, hsa-miR-16-5p, hsa-miR-451a, hsa-miR-135a-3p, hsa-miR-486-5p, hsa-miR-4257, hsa-miR-92b-5p, hsa-miR-1915-3p, hsa-miR-718, hsa-miR-940, hsa-miR-296-5p, hsa-miR-23b-3p and hsa-miR-92a-3p genes, and polynucleotides consisting of the nucleotide sequences of SEQ ID NOs: 1 to 251 related thereto were found.

Among them, genes newly found as markers for examining the presence or absence of breast cancer are polynucleotides consisting of the nucleotide sequences represented by SEQ ID NOs: 1 to 235.

A discriminant for determining the presence or absence of breast cancer was further prepared by Fisher's discriminant analysis with the expression levels of these genes as indicators. Specifically, any newly found polynucleotide consisting of a nucleotide sequence represented by any of SEQ ID NOs: 1 to 251 in the training cohort was applied for Formula 2 above to prepare a discriminant. Calculated accuracy, sensitivity, and specificity are shown in Table 3. In this respect, a discriminant coefficient and a constant term are shown in Table 4. Here, all of the polynucleotides consisting of the nucleotide sequences represented by SEQ ID NOs: 1 to 251 were selected as markers capable of determining not only invasive ductal breast cancer (56 cases), which is a main type of breast cancer, but also invasive lobular cancer (3 cases) and unusual metastatic carcinoma with poor prognosis (1 case).

Figure 2:
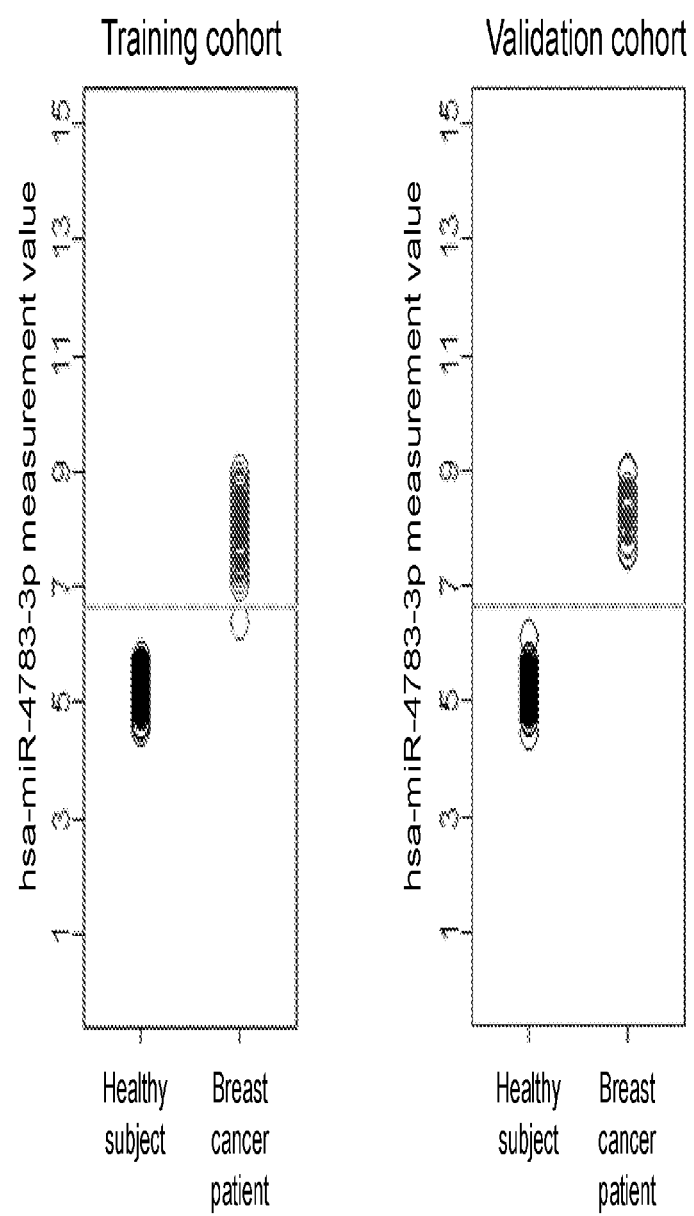
FIG. 2 Left diagram: the expression level measurement values of hsa-miR-4783-3p (SEQ ID NO: 1) in healthy subjects (100 persons) and breast cancer patients (62 persons) selected as a training cohort were each plotted on the ordinate. The horizontal line in the diagram depicts a threshold (6.63) that was optimized by Fisher's discriminant analysis and discriminated between the two groups. Right diagram: the expression level measurement values of hsa-miR-4783-3p (SEQ ID NO: 1) in healthy subjects (50 persons) and breast cancer patients (31 persons) selected as a validation cohort were each plotted on the ordinate. The horizontal line in the diagram depicts the threshold (6.63) that was set in the training cohort and discriminated between the two groups.

Accuracy, sensitivity, and specificity in the validation cohort were calculated using the discriminant thus prepared, and the discriminant performance of the selected polynucleotides was validated using the independent samples (Table 3). For example, the expression level measurement value of the gene that consists of the nucleotide sequence represented by SEQ ID NO: 1 was compared between the healthy subjects (100 persons) and the breast cancer patients (62 persons) in the training cohort. As a result, the expression level measurement values were found to be significantly lower in the breast cancer patient group than in the healthy subject group (see the left diagram of FIG. 2). These results were also reproducible for the healthy subjects (50 persons) and the breast cancer patients (31 persons) in the validation cohort (see the right diagram of FIG. 2). Likewise, the results obtained about the other polynucleotides shown in SEQ ID NOs: 2 to 251 showed that the expression level measurement values were significantly lower (−) or higher (+) in the breast cancer patient group than in the healthy subject group (Table 2). These results were able to be validated in the validation cohort. For example, as for this nucleotide sequence represented by SEQ ID NO: 1, the number of correctly or incorrectly identified samples in the detection of breast cancer was calculated using the threshold (6.63) that was set in the training cohort and discriminated between the two groups. As a result, 31 true positives, 50 true negatives, 0 false positives, and 0 false negatives were obtained. From these values, 100% accuracy, 100% sensitivity, and 100% specificity were obtained as the detection performance. In this way, the detection performance was calculated as to all of the polynucleotides shown in SEQ ID NOs: 1 to 251, and described in Table 3. Likewise, the polynucleotides consisting of the nucleotide sequences represented by SEQ ID NOs: 2 to 251 shown in Table 2 exhibited sensitivity of 100%, 100%, 90.3%, 96.8%, 100%, 100%, 96.8%, 96.8%, 100%, 100%, 100%, 100%, 96.8%, 96.8%, 100%, 100%, 96.8%, 100%, 93.5%, 96.8%, 96.8%, 100%, 96.8%, 96.8%, 93.5%, 96.8%, 93.5%, 87.1%, 83.9%, 96.8%, 96.8%, 96.8%, 100%, 80.6%, 87.1%, 87.1%, 100%, 90.3%, 90.3%, 90.3%, 100%, 96.8%, 100%, 87.1%, 87.1%, 96.8%, 96.8%, 90.3%, 96.8%, 83.9%, 77.4%, 90%, 83.9%, 96.8%, 93.5%, 80.6%, 96.8%, 90.3%, 93.5%, 90.3%, 87.1%, 87.1%, 96.8%, 83.9%, 87.1%, 77.4%, 90.3%, 77.4%, 90.3%, 83.9%, 74.2%, 93.5%, 87.1%, 93.5%, 93.5%, 77.4%, 90.3%, 87.1%, 87.1%, 83.9%, 87.1%, 93.5%, 77.4%, 93.5%, 74.2%, 83.9%, 100%, 90.3%, 74.2%, 83.9%, 80.6%, 87.1%, 77.4%, 83.9%, 71%, 96.8%, 77.4%, 87.1%, 77.4%, 71%, 90.3%, 80.6%, 67.7%, 77.4%, 87.1%, 74.2%, 83.9%, 77.4%, 71%, 87.1%, 74.2%, 90.3%, 80.6%, 74.2%, 83.9%, 83.9%, 71%, 87.1%, 61.3%, 61.3%, 83.9%, 61.3%, 90.3%, 80.6%, 61.3%, 64.5%, 80.6%, 74.2%, 80.6%, 71%, 71%, 77.4%, 64.5%, 71%, 71%, 83.9%, 74.2%, 83.9%, 63.3%, 64.5%, 71%, 67.7%, 71%, 71%, 74.2%, 71%, 64.5%, 83.9%, 71%, 83.9%, 61.3%, 61.3%, 67.7%, 64.5%, 64.5%, 54.8%, 64.5%, 74.2%, 58.1%, 58.1%, 58.1%, 58.1%, 61.3%, 67.7%, 61.3%, 67.7%, 58.1%, 58.1%, 54.8%, 67.7%, 58.1%, 64.5%, 61.3%, 67.7%, 58.1%, 58.1%, 48.4%, 61.3%, 54.8%, 38.7%, 35.5%, 64.5%, 54.8%, 64.5%, 54.8%, 61.3%, 35.5%, 48.4%, 61.3%, 61.3%, 54.8%, 71%, 61.3%, 45.2%, 48.4%, 29%, 54.8%, 41.9%, 671%, 29%, 29%, 53.3%, 51.6%, 45.2%, 35.5%, 41.9%, 41.9%, 48.4%, 41.9%, 35.5%, 41.9%, 35.5%, 48.4%, 32.3%, 41.9%, 41.9%, 41.9%, 35.5%, 35.5%, 41.9%, 61.3%, 32.3%, 45.2%, 38.7%, 51.6%, 29%, 35.5%, 381%, 54.8%, 58.1%, 51.6%, 29%, 41.9%, 38.7%, 96.8%, 96.8%, 96.8%, 100%, 96.8%, 87.1%, 80.6%, 100%, 87.1%, 93.5%, 671%, 67.7%, 61.3%, 67.7%, 38.7% and 54.8%, respectively, in the validation cohort (Table 3). As seen from Comparative Example mentioned later, the existing marker CEA had sensitivity of 19.4% in the validation cohort (Table 5-2), demonstrating that all of the polynucleotides consisting of the nucleotide sequences represented by SEQ ID Nos: 1 to 251 can discriminate, each alone, breast cancer in the validation cohort with sensitivity beyond CEA.

For example, the 83 polynucleotides consisting of the nucleotide sequences represented by SEQ ID NOs: 1, 2, 3, 4, 6, 7, 8, 9, 10, 11, 12, 13, 14, 15, 16, 17, 19, 20, 21, 22, 23, 24, 25, 26, 27, 28, 31, 32, 33, 34, 35, 36, 38, 40, 42, 44, 45, 47, 48, 49, 50, 55, 59, 64, 65, 66, 68, 70, 73, 75, 78, 79, 80, 81, 84, 88, 92, 93, 95, 97, 98, 99, 102, 109, 113, 119, 122, 124, 128, 130, 133, 145, 149, 169, 236, 237, 238, 239, 240, 241, 242, 243, 244 were able to correctly determine breast cancer in the 9 breast cancer samples of stage 1 contained in the validation cohort. Thus, these polynucleotides can detect even early breast cancer and contributes to the early diagnosis of breast cancer.

Example 2

<Method a for Evaluating Breast Cancer Discriminant Performance by Combination of Multiple Gene Markers Using the Samples in the Validation Cohort>

In this Example, a method for evaluating breast cancer discriminant performance by a combination of the gene markers selected in Example 1 was studied. Specifically, Fisher's discriminant analysis was conducted as to 31,255 polynucleotide combinations comprising at least one of the newly found polynucleotides consisting of the nucleotide sequences represented by SEQ ID NOs: 1 to 235 among the polynucleotides consisting of the nucleotide sequences represented by SEQ ID NOs: 1 to 251 selected in Example 1, to construct a discriminant for determining the presence or absence of breast cancer. Next, accuracy, sensitivity, and specificity in the validation cohort were calculated using the discriminant thus prepared, and the discriminant performance of the selected polynucleotides was validated using the independent samples.

Figure 3:
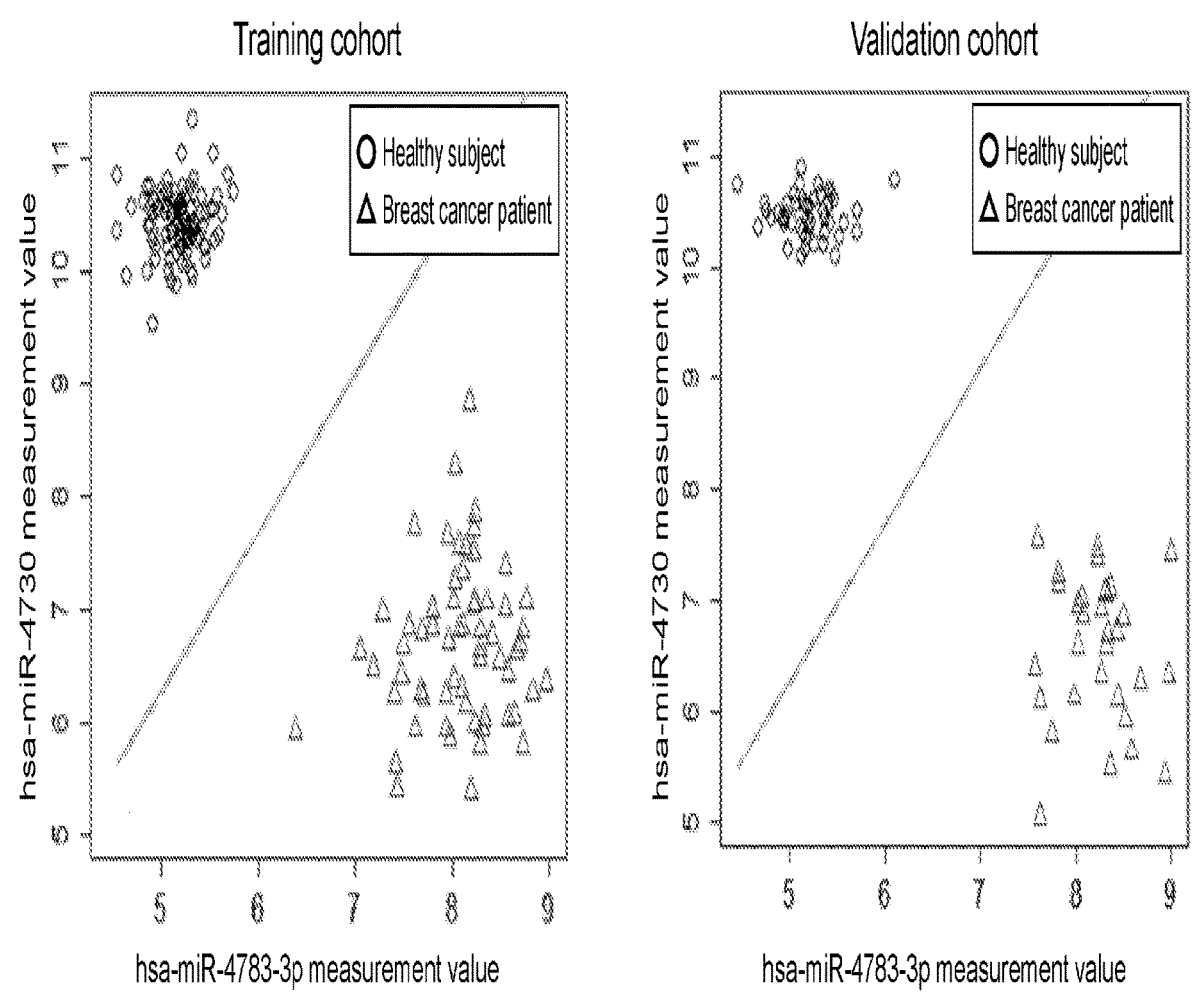
FIG. 3 Left diagram: the expression level measurement values of hsa-miR-4783-3p (SEQ ID NO: 1) in healthy subjects (100 persons, circles) and breast cancer patients (62 persons, triangles) selected as a training cohort were each plotted on the abscissa against their expression level measurement values of hsa-miR-4730 (SEQ ID NO: 2) on the ordinate. The line in the diagram depicts a discriminant function (0=1.41x+y+0.77) that was optimized by Fisher's discriminant analysis and discriminated between the two groups. Right diagram: the expression level measurement values of hsa-miR-4783-3p (SEQ ID NO: 1) in healthy subjects (50 persons, circles) and breast cancer patients (31 persons, triangles) selected as a validation cohort were each plotted on the abscissa against their expression level measurement values of hsa-miR-4730 (SEQ ID NO: 2) on the ordinate. The line in the diagram depicts the threshold (0=1.41x+y+0.77) that was set for the training cohort and discriminated between the two groups.

For example, the gene expression level measurement values of the nucleotide sequences represented by SEQ ID NO: 1 and SEQ ID NO: 2 were compared between the healthy subjects and the breast cancer patients. As a result, a scatter diagram that significantly separated the expression level measurement values of the breast cancer patient group from those of the healthy subject group was obtained (see the left diagram of FIG. 3). These results were also reproducible for the healthy subjects (50 persons) and the breast cancer patients (31 persons) in the validation cohort (see the right diagram of FIG. 3). Likewise, a scatter diagram that significantly separated the expression level measurement values of the breast cancer patient group from those of the healthy subject group was also obtained as to the other polynucleotide combinations comprising at least one of the newly found polynucleotides consisting of the nucleotide sequences represented by SEQ ID NOs: 1 to 235 among the polynucleotides consisting of the nucleotide sequences represented by SEQ ID NOs: 1 to 251. These results were able to be validated in the validation cohort. For example, as for these nucleotide sequences represented by SEQ ID NO: 1 and SEQ ID NO: 2, the number of samples that were correctly or incorrectly identified breast cancer was calculated using the discriminant function (0=1.41x+y+0.77) that was set in the training cohort and discriminated between the two groups. As a result, 31 true positives, 50 true negatives, 0 false positives, and 0 false negatives were obtained. From these values, 100% accuracy, 100% sensitivity, and 100% specificity were obtained as the detection performance. In this way, the detection performance was calculated as to all of the polynucleotide combinations comprising at least one of the newly found polynucleotides consisting of the nucleotide sequences represented by SEQ ID NOs: 1 to 235 among the polynucleotides consisting of the nucleotide sequences represented by SEQ ID NOs: 1 to 251. Among them, 250 combinations comprising the expression level measurement value of the polynucleotide consisting of the nucleotide sequence represented by SEQ ID NO: 1 and the detection performance thereof were described in Table 6 as an example. For example, all of the combinations of the expression level measurement values of the polynucleotides consisting of the nucleotide sequences represented by SEQ ID NOs: 1 and 2, SEQ ID NOs: 1 and 3, SEQ ID NOs: 1 and 4, and SEQ ID NOs: 1 and 5 exhibited sensitivity of 100% in the validation cohort. Likewise, all of the combinations of two polynucleotides consisting of the nucleotide sequence represented by SEQ ID NO: 1 and a nucleotide sequence represented by any of SEQ ID NOs: 6 to 251 also exhibited sensitivity of 100%. In addition, the combinations of two polynucleotides consisting of the nucleotide sequences except for SEQ ID NO: 1 were described in Table 7 as an example. As the specific combinations of two polynucleotides, for example, the combinations represented by SEQ ID NOs: 3 and 20, SEQ ID NOs: 6 and 20, SEQ ID NOs: 7 and 20, SEQ ID NOs: 10 and 20, SEQ ID NOs: 20 and 22, SEQ ID NOs: 20 and 238, SEQ ID NOs: 20 and 239, SEQ ID NOs: 12 and 24, SEQ ID NOs: 20 and 24, SEQ ID NOs: 24 and 27, SEQ ID NOs: 24 and 33, SEQ ID NOs: 24 and 236, SEQ ID NOs: 24 and 240, SEQ ID NOs: 3 and 26, SEQ ID NOs: 12 and 26, SEQ ID NOs: 13 and 26, SEQ ID NOs: 17 and 26, SEQ ID NOs: 19 and 26, SEQ ID NOs: 3 and 27, SEQ ID NOs: 5 and 27, SEQ ID NOs: 13 and 27, SEQ ID NOs: 20 and 27, SEQ ID NOs: 26 and 27, SEQ ID NOs: 27 and 120, SEQ ID NOs: 27 and 206, SEQ ID NOs: 27 and 237, SEQ ID NOs: 3 and 30, SEQ ID NOs: 17 and 30, SEQ ID NOs: 27 and 30, SEQ ID NOs: 27 and 33, SEQ ID NOs: 30 and 39, SEQ ID NOs: 30 and 117, SEQ ID NOs: 3 and 33, SEQ ID NOs: 7 and 33, SEQ ID NOs: 10 and 33, SEQ ID NOs: 11 and 33, SEQ ID NOs: 13 and 33, SEQ ID NOs: 25 and 33, SEQ ID NOs: 33 and 244, SEQ ID NOs: 3 and 182, SEQ ID NOs: 6 and 182, SEQ ID NOs: 7 and 182, SEQ ID NOs: 12 and 182, SEQ ID NOs: 27 and 182, SEQ ID NOs: 182 and 236, SEQ ID NOs: 2 and 194, SEQ ID NOs: 7 and 194, SEQ ID NOs: 27 and 194, SEQ ID NOs: 194 and 236, SEQ ID NOs: 2 and 206, SEQ ID NOs: 7 and 206, SEQ ID NOs: 206 and 236, SEQ ID NOs: 2 and 208, SEQ ID NOs: 7 and 208, SEQ ID NOs: 13 and 208, SEQ ID NOs: 20 and 208, and SEQ ID NOs: 27 and 208 exhibited accuracy of 96% or higher for discriminating the breast cancer patients from the healthy subjects in both of the training cohort and the validation cohort. Thus, the combinations of two of the polynucleotides consisting of the nucleotide sequences represented by SEQ ID NOs: 1 to 251 also produced excellent detection sensitivity for breast cancer.

Markers for the detection of breast cancer with better sensitivity are obtained by further combining 3, 4, 5, 6, 7, 8, 9, 10 or more of the measurement values of the polynucleotides consisting of the nucleotide sequences represented by SEQ ID NOs: 1 to 251. For example, the newly found polynucleotides consisting of the nucleotide sequences represented by SEQ ID NOs: 1 to 235 among the polynucleotides consisting of the nucleotide sequences represented by SEQ ID NOs: 1 to 251 selected in Example 1, were measured to obtain their expression levels between the healthy subject group and the breast cancer group in the validation cohort. All of the polynucleotides were ranked in the descending order of their P values based on the Student's t-test which indicates statistical significance of a difference between groups (i.e., one having the lowest P value was ranked in the first place), and breast cancer detection sensitivity was evaluated using combinations of one or more polynucleotides to which the polynucleotides were added one by one from the top to bottom according to the rank. In short, the order in which the polynucleotides were combined in this evaluation is in reverse in terms of SEQ ID NOs, such as SEQ ID NO: 235 to SEQ ID NOs: 234, 233, . . . shown in Table 2 in order. As a result, the sensitivity in the validation cohort was 38.7% for 1 polynucleotide (SEQ ID NO: 235), 48.4% for 2 polynucleotides (SEQ ID NOs: 234 and 235), 74.2% for 4 polynucleotides (SEQ ID NOs: 232 to 235), 87.1% for 6 polynucleotides (SEQ ID NOs: 230 to 235), 903% for 10 polynucleotides (SEQ ID NOs: 226 to 235), 93.5% for 13 polynucleotides (SEQ ID NOs: 223 to 235), 96.8% for 16 polynucleotides (SEQ ID NOs: 220 to 235), 100% for 20 polynucleotides (SEQ ID NOs: 216 to 235), 100% for 30 polynucleotides (SEQ ID NOs: 206 to 235), 100% for 50 polynucleotides (SEQ ID NOs: 186 to 235), 100% for 100 polynucleotides (SEQ ID NOs: 136 to 235), 100% for 200 polynucleotides (SEQ ID NOs: 36 to 235), and 100% for 235 polynucleotides (SEQ ID NOs: 1 to 235).

These results demonstrated that a combination of multiple polynucleotides can produce higher breast cancer discriminant performance than that of each polynucleotide alone or a combination of a fewer number of polynucleotides. In this context, the combinations of multiple polynucleotides are not limited to the combinations of the polynucleotides added in the order of statistically significant difference as described above, and any combination of multiple polynucleotides can be used in the detection of breast cancer.

From these results, it can be concluded that all of the polynucleotides consisting of the nucleotide sequences represented by SEQ ID NOs: 1 to 251 serve as excellent markers for breast cancer detection.

TABLE 2

| SEQ ID NO: | Gene name | P value after Bonferroni correction | Expression level in breast cancer patient with respect to healthy subject |
|---|---|---|---|
| 1 | hsa-miR-4783-3p | 1.88.E−98 | + |
| 2 | hsa-miR-4730 | 1.39.E−95 | − |
| 3 | hsa-miR-1307-3p | 9.90.E−81 | + |
| 4 | hsa-miR-4634 | 1.73.E−79 | − |
| 5 | hsa-miR-663a | 2.71.E−76 | + |
| 6 | hsa-miR-4532 | 2.24.E−75 | + |
| 7 | hsa-miR-7704 | 4.18.E−74 | − |
| 8 | hsa-miR-3178 | 2.19.E−71 | − |
| 9 | hsa-miR-6729-5p | 1.88.E−69 | − |
| 10 | hsa-miR-6090 | 2.55.E−68 | + |
| 11 | hsa-miR-4732-5p | 1.36.E−67 | + |
| 12 | hsa-miR-3184-5p | 8.11.E−67 | − |
| 13 | hsa-miR-6727-5p | 3.02.E−64 | − |
| 14 | hsa-miR-6088 | 3.54.E−64 | + |
| 15 | hsa-miR-4674 | 9.34.E−64 | − |
| 16 | hsa-miR-8073 | 1.47.E−63 | + |
| 17 | hsa-miR-4787-5p | 5.85.E−62 | − |
| 18 | hsa-miR-1469 | 2.97.E−61 | + |
| 19 | hsa-miR-125a-5p | 9.95.E−61 | − |
| 20 | hsa-miR-1233-5p | 2.94.E−60 | + |
| 21 | hsa-miR-885-3p | 6.54.E−60 | + |
| 22 | hsa-miR-6802-5p | 4.56.E−59 | + |
| 23 | hsa-miR-328-5p | 1.83.E−58 | + |
| 24 | hsa-miR-6787-5p | 5.55.E−58 | + |
| 25 | hsa-miR-8069 | 2.26.E−57 | − |
| 26 | hsa-miR-6875-5p | 2.72.E−53 | − |
| 27 | hsa-miR-1246 | 9.57.E−53 | + |
| 28 | hsa-miR-4734 | 2.06.E−52 | + |
| 29 | hsa-miR-6757-5p | 4.71.E−51 | + |
| 30 | hsa-miR-6756-5p | 5.35.E−51 | + |
| 31 | hsa-miR-3665 | 1.70.E−50 | − |
| 32 | hsa-miR-6836-3p | 8.38.E−50 | − |
| 33 | hsa-miR-6821-5p | 1.19.E−49 | + |
| 34 | hsa-miR-6805-5p | 3.17.E−49 | − |
| 35 | hsa-miR-4728-5p | 3.69.E−49 | + |
| 36 | hsa-miR-6726-5p | 5.62.E−49 | − |
| 37 | hsa-miR-197-5p | 1.43.E−46 | + |
| 38 | hsa-miR-149-3p | 3.23.E−46 | + |
| 39 | hsa-miR-6850-5p | 4.58.E−46 | − |
| 40 | hsa-miR-4476 | 5.54.E−46 | − |
| 41 | hsa-miR-6858-5p | 9.61.E−46 | + |
| 42 | hsa-miR-564 | 1.62.E−44 | − |
| 43 | hsa-miR-4763-3p | 2.01.E−44 | + |
| 44 | hsa-miR-575 | 3.61.E−44 | − |
| 45 | hsa-miR-6771-5p | 2.62.E−43 | − |
| 46 | hsa-miR-1231 | 7.46.E−43 | − |
| 47 | hsa-miR-1908-3p | 9.60.E−43 | − |
| 48 | hsa-miR-150-3p | 2.19.E−42 | − |
| 49 | hsa-miR-3937 | 9.92.E−42 | − |
| 50 | hsa-miR-887-3p | 2.38.E−41 | − |
| 51 | hsa-miR-3940-5p | 3.44.E−41 | − |
| 52 | hsa-miR-4741 | 4.16.E−41 | − |
| 53 | hsa-miR-6808-5p | 5.42.E−41 | + |
| 54 | hsa-miR-6869-5p | 1.03.E−40 | − |
| 55 | hsa-miR-5090 | 5.03.E−40 | − |
| 56 | hsa-miR-615-5p | 1.94.E−39 | − |
| 57 | hsa-miR-8072 | 2.71.E−39 | + |
| 58 | hsa-miR-128-1-5p | 2.72.E−39 | − |
| 59 | hsa-miR-1238-5p | 7.46.E−39 | + |
| 60 | hsa-miR-365a-5p | 9.50.E−39 | + |
| 61 | hsa-miR-204-3p | 1.32.E−38 | − |
| 62 | hsa-miR-4492 | 3.33.E−37 | − |
| 63 | hsa-miR-6785-5p | 4.21.E−37 | − |
| 64 | hsa-miR-6511a-5p | 7.68.E−37 | + |
| 65 | hsa-miR-4525 | 1.16.E−36 | − |
| 66 | hsa-miR-1915-5p | 1.34.E−36 | − |
| 67 | hsa-miR-3180 | 1.07.E−35 | − |
| 68 | hsa-miR-6879-5p | 1.56.E−35 | + |
| 69 | hsa-miR-1199-5p | 1.15.E−34 | − |
| 70 | hsa-miR-6746-5p | 5.65.E−34 | + |
| 71 | hsa-miR-711 | 5.82.E−34 | − |
| 72 | hsa-miR-663b | 1.42.E−33 | − |
| 73 | hsa-miR-4707-3p | 2.19.E−33 | − |
| 74 | hsa-miR-6893-5p | 6.31.E−33 | − |
| 75 | hsa-miR-4675 | 6.39.E−33 | + |
| 76 | hsa-miR-4638-5p | 6.40.E−33 | − |
| 77 | hsa-miR-4651 | 8.91.E−33 | − |
| 78 | hsa-miR-6087 | 1.91.E−32 | + |
| 79 | hsa-miR-4665-5p | 3.57.E−32 | − |
| 80 | hsa-miR-4758-5p | 4.55.E−32 | + |
| 81 | hsa-miR-6887-5p | 4.45.E−31 | + |
| 82 | hsa-miR-3620-5p | 4.64.E−31 | − |
| 83 | hsa-miR-1909-3p | 5.74.E−31 | − |
| 84 | hsa-miR-7641 | 8.30.E−31 | − |
| 85 | hsa-miR-6724-5p | 1.02.E−30 | + |
| 86 | hsa-miR-1343-3p | 1.19.E−30 | + |
| 87 | hsa-miR-6780b-5p | 1.22.E−30 | + |
| 88 | hsa-miR-4484 | 2.77.E−30 | − |
| 89 | hsa-miR-4690-5p | 3.50.E−30 | + |
| 90 | hsa-miR-4429 | 2.05.E−29 | + |
| 91 | hsa-miR-1227-5p | 3.84.E−29 | + |
| 92 | hsa-miR-4725-3p | 5.39.E−29 | − |
| 93 | hsa-miR-6861-5p | 5.43.E−29 | + |
| 94 | hsa-miR-6812-5p | 7.48.E−29 | + |
| 95 | hsa-miR-3197 | 8.20.E−29 | + |
| 96 | hsa-miR-8059 | 9.29.E−29 | + |
| 97 | hsa-miR-3185 | 9.34.E−29 | + |
| 98 | hsa-miR-4706 | 1.69.E−28 | + |
| 99 | hsa-miR-4497 | 2.22.E−28 | − |

TABLE 2-continued

| SEQ ID NO: | Gene name | P value after Bonferroni correction | Expression level in breast cancer patient with respect to healthy subject |
|---|---|---|---|
| 100 | hsa-miR-3131 | 3.64.E−28 | + |
| 101 | hsa-miR-6806-5p | 9.04.E−28 | − |
| 102 | hsa-miR-187-5p | 4.89.E−27 | − |
| 103 | hsa-miR-3180-3p | 7.10.E−27 | − |
| 104 | hsa-miR-6848-5p | 7.26.E−27 | − |
| 105 | hsa-miR-6820-5p | 7.77.E−27 | − |
| 106 | hsa-miR-6800-5p | 1.80.E−26 | − |
| 107 | hsa-miR-6717-5p | 1.97.E−26 | + |
| 108 | hsa-miR-6795-5p | 5.16.E−26 | + |
| 109 | hsa-miR-4632-5p | 8.43.E−26 | + |
| 110 | hsa-miR-665 | 2.56.E−25 | − |
| 111 | hsa-miR-6778-5p | 8.69.E−25 | − |
| 112 | hsa-miR-3663-3p | 1.09.E−24 | + |
| 113 | hsa-miR-4689 | 3.36.E−24 | + |
| 114 | hsa-miR-211-3p | 8.65.E−24 | + |
| 115 | hsa-miR-6511b-5p | 9.67.E−24 | + |
| 116 | hsa-miR-4750-5p | 1.07.E−23 | + |
| 117 | hsa-miR-6126 | 2.06.E−23 | + |
| 118 | hsa-miR-614 | 2.46.E−22 | + |
| 119 | hsa-miR-7110-5p | 3.56.E−22 | − |
| 120 | hsa-miR-744-5p | 5.83.E−22 | + |
| 121 | hsa-miR-6769a-5p | 1.44.E−21 | + |
| 122 | hsa-miR-4792 | 2.04.E−21 | − |
| 123 | hsa-miR-5787 | 3.93.E−21 | + |
| 124 | hsa-miR-6798-5p | 5.13.E−21 | − |
| 125 | hsa-miR-6781-5p | 2.43.E−20 | − |
| 126 | hsa-miR-4419b | 2.59.E−20 | + |
| 127 | hsa-miR-4446-3p | 7.52.E−20 | − |
| 128 | hsa-miR-4259 | 8.07.E−20 | + |
| 129 | hsa-miR-5572 | 1.06.E−19 | − |
| 130 | hsa-miR-6075 | 1.78.E−19 | − |
| 131 | hsa-miR-296-3p | 4.75.E−19 | + |
| 132 | hsa-miR-6891-5p | 8.62.E−19 | − |
| 133 | hsa-miR-4745-5p | 1.02.E−18 | − |
| 134 | hsa-miR-6775-5p | 1.17.E−18 | + |
| 135 | hsa-miR-6870-5p | 1.24.E−18 | − |
| 136 | hsa-miR-920 | 1.78.E−18 | + |
| 137 | hsa-miR-4530 | 3.26.E−18 | − |
| 138 | hsa-miR-6819-5p | 3.67.E−18 | + |
| 139 | hsa-miR-6825-5p | 5.28.E−18 | − |
| 140 | hsa-miR-7847-3p | 7.32.E−18 | + |
| 141 | hsa-miR-6131 | 1.09.E−17 | + |
| 142 | hsa-miR-4433-3p | 1.35.E−17 | + |
| 143 | hsa-miR-1228-5p | 9.82.E−17 | − |
| 144 | hsa-miR-6743-5p | 1.40.E−16 | + |
| 145 | hsa-miR-1268a | 2.20.E−16 | − |
| 146 | hsa-miR-3917 | 1.73.E−15 | + |
| 147 | hsa-miR-6786-5p | 1.89.E−15 | − |
| 148 | hsa-miR-3154 | 2.12.E−15 | + |
| 149 | hsa-miR-638 | 2.19.E−15 | − |
| 150 | hsa-miR-6741-5p | 5.44.E−15 | + |
| 151 | hsa-miR-6889-5p | 9.29.E−15 | − |
| 152 | hsa-miR-6840-3p | 1.61.E−14 | − |
| 153 | hsa-miR-6510-5p | 3.23.E−14 | − |
| 154 | hsa-miR-3188 | 4.44.E−14 | + |
| 155 | hsa-miR-551b-5p | 1.71.E−13 | + |
| 156 | hsa-miR-5001-5p | 2.07.E−13 | + |
| 157 | hsa-miR-1268b | 2.24.E−13 | − |
| 158 | hsa-miR-7107-5p | 2.31.E−13 | − |
| 159 | hsa-miR-6824-5p | 3.30.E−13 | + |
| 160 | hsa-miR-6732-5p | 3.62.E−13 | − |
| 161 | hsa-miR-371a-5p | 9.05.E−13 | + |
| 162 | hsa-miR-6794-5p | 9.74.E−13 | + |
| 163 | hsa-miR-6779-5p | 1.37.E−12 | − |
| 164 | hsa-miR-4271 | 1.69.E−12 | − |
| 165 | hsa-miR-5195-3p | 1.79.E−12 | + |
| 166 | hsa-miR-6762-5p | 3.61.E−12 | + |
| 167 | hsa-miR-939-5p | 4.78.E−12 | − |
| 168 | hsa-miR-1247-3p | 7.37.E−12 | + |
| 169 | hsa-miR-6777-5p | 9.79.E−12 | + |
| 170 | hsa-miR-6722-3p | 1.21.E−11 | + |
| 171 | hsa-miR-3656 | 1.27.E−11 | + |
| 172 | hsa-miR-4688 | 1.86.E−11 | + |
| 173 | hsa-miR-3195 | 2.02.E−11 | − |
| 174 | hsa-miR-6766-5p | 6.97.E−11 | + |
| 175 | hsa-miR-4447 | 1.08.E−10 | + |
| 176 | hsa-miR-4656 | 1.12.E−10 | − |
| 177 | hsa-miR-7108-5p | 1.51.E−10 | − |
| 178 | hsa-miR-3191-3p | 2.67.E−10 | + |
| 179 | hsa-miR-1273g-3p | 2.89.E−10 | − |
| 180 | hsa-miR-4463 | 4.62.E−10 | + |
| 181 | hsa-miR-2861 | 4.97.E−10 | + |
| 182 | hsa-miR-3196 | 5.22.E−10 | − |
| 183 | hsa-miR-6877-5p | 6.47.E−10 | − |
| 184 | hsa-miR-3679-5p | 1.33.E−09 | + |
| 185 | hsa-miR-4442 | 1.56.E−09 | − |
| 186 | hsa-miR-6789-5p | 1.93.E−09 | − |
| 187 | hsa-miR-6782-5p | 1.97.E−09 | + |
| 188 | hsa-miR-486-3p | 2.12.E−09 | − |
| 189 | hsa-miR-6085 | 4.04.E−09 | + |
| 190 | hsa-miR-4746-3p | 8.57.E−09 | − |
| 191 | hsa-miR-619-5p | 1.13.E−08 | − |
| 192 | hsa-miR-937-5p | 1.65.E−08 | + |
| 193 | hsa-miR-6803-5p | 2.32.E−08 | + |
| 194 | hsa-miR-4298 | 2.33.E−08 | + |
| 195 | hsa-miR-4454 | 2.63.E−08 | + |
| 196 | hsa-miR-4459 | 1.83.E−07 | + |
| 197 | hsa-miR-7150 | 2.60.E−07 | + |
| 198 | hsa-miR-6880-5p | 8.86.E−07 | − |
| 199 | hsa-miR-4449 | 9.44.E−07 | + |
| 200 | hsa-miR-8063 | 1.05.E−06 | + |
| 201 | hsa-miR-4695-5p | 1.65.E−06 | + |
| 202 | hsa-miR-6132 | 1.93.E−06 | + |
| 203 | hsa-miR-6829-5p | 2.66.E−06 | + |
| 204 | hsa-miR-4486 | 2.83.E−06 | − |
| 205 | hsa-miR-6805-3p | 3.24.E−06 | − |
| 206 | hsa-miR-6826-5p | 4.59.E−06 | + |
| 207 | hsa-miR-4508 | 6.28.E−06 | + |
| 208 | hsa-miR-1343-3p | 1.11.E−05 | − |
| 209 | hsa-miR-7114-5p | 1.35.E−05 | + |
| 210 | hsa-miR-3622a-5p | 1.53.E−05 | + |
| 211 | hsa-miR-6765-5p | 1.77.E−05 | − |
| 212 | hsa-miR-7845-5p | 2.11.E−05 | − |
| 213 | hsa-miR-3960 | 2.70.E−05 | − |
| 214 | hsa-miR-6749-5p | 4.51.E−05 | − |
| 215 | hsa-miR-1260b | 4.83.E−05 | + |
| 216 | hsa-miR-6799-5p | 5.38.E−05 | + |
| 217 | hsa-miR-4723-5p | 6.54.E−05 | + |
| 218 | hsa-miR-6784-5p | 7.88.E−05 | − |
| 219 | hsa-miR-5100 | 8.28.E−05 | + |
| 220 | hsa-miR-6769b-5p | 9.25.E−05 | + |
| 221 | hsa-miR-1207-5p | 1.25.E−04 | + |
| 222 | hsa-miR-642a-3p | 1.38.E−04 | − |
| 223 | hsa-miR-4505 | 1.49.E−04 | + |
| 224 | hsa-miR-4270 | 1.79.E−04 | − |
| 225 | hsa-miR-6721-5p | 3.50.E−04 | − |
| 226 | hsa-miR-7111-5p | 5.29.E−04 | − |
| 227 | hsa-miR-6791-5p | 8.34.E−04 | + |
| 228 | hsa-miR-7109-5p | 1.07.E−03 | + |
| 229 | hsa-miR-4258 | 1.55.E−03 | + |
| 230 | hsa-miR-6515-3p | 2.00.E−03 | + |
| 231 | hsa-miR-6851-5p | 2.15.E−03 | − |
| 232 | hsa-miR-6125 | 2.94.E−03 | − |
| 233 | hsa-miR-4749-5p | 3.39.E−03 | + |
| 234 | hsa-miR-4726-5p | 6.77.E−03 | + |
| 235 | hsa-miR-4513 | 9.77.E−03 | + |
| 236 | hsa-miR-760 | 5.40.E−76 | − |
| 237 | hsa-miR-602 | 3.27.E−58 | − |
| 238 | hsa-miR-423-5p | 4.16.E−57 | − |
| 239 | hsa-miR-92a-2-5p | 7.76.E−55 | − |
| 240 | hsa-miR-16-5p | 7.58.E−47 | − |
| 241 | hsa-miR-451a | 1.13.E−36 | − |
| 242 | hsa-miR-135a-3p | 1.83.E−35 | − |
| 243 | hsa-miR-486-5p | 8.56.E−34 | − |

TABLE 2-continued

| SEQ ID NO: | Gene name | P value after Bonferroni correction | Expression level in breast cancer patient with respect to healthy subject |
|---|---|---|---|
| 244 | hsa-miR-4257 | 4.39.E−31 | + |
| 245 | hsa-miR-92b-5p | 1.67.E−30 | + |
| 246 | hsa-miR-1915-3p | 3.95.E−18 | − |
| 247 | hsa-miR-718 | 1.38.E−15 | − |
| 248 | hsa-miR-940 | 4.63.E−15 | + |
| 249 | hsa-miR-296-5p | 2.67.E−10 | + |
| 250 | hsa-miR-23b-3p | 2.43.E−03 | + |
| 251 | hsa-miR-92a-3p | 3.86.E−03 | − |

TABLE 3

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 1 | 99.4 | 98.4 | 100 | 100 | 100 | 100 |
| 2 | 99.4 | 98.4 | 100 | 100 | 100 | 100 |
| 3 | 99.4 | 98.4 | 100 | 100 | 100 | 100 |
| 4 | 99.4 | 98.4 | 100 | 96.3 | 90.3 | 100 |
| 5 | 98.8 | 100 | 98 | 98.8 | 96.8 | 100 |
| 6 | 99.4 | 98.4 | 100 | 100 | 100 | 100 |
| 7 | 100 | 100 | 100 | 100 | 100 | 100 |
| 8 | 99.4 | 98.4 | 100 | 98.8 | 96.8 | 100 |
| 9 | 96.9 | 91.9 | 100 | 98.8 | 96.8 | 100 |
| 10 | 98.8 | 96.8 | 100 | 97.5 | 100 | 96 |
| 11 | 99.4 | 98.4 | 100 | 97.5 | 100 | 96 |
| 12 | 100 | 100 | 100 | 100 | 100 | 100 |
| 13 | 99.4 | 98.4 | 100 | 100 | 100 | 100 |
| 14 | 98.1 | 96.8 | 99 | 98.8 | 96.8 | 100 |
| 15 | 96.3 | 90.3 | 100 | 98.8 | 96.8 | 100 |
| 16 | 98.1 | 95.2 | 100 | 98.8 | 100 | 98 |
| 17 | 98.8 | 96.8 | 100 | 100 | 100 | 100 |
| 18 | 98.8 | 96.8 | 100 | 96.3 | 96.8 | 96 |
| 19 | 99.4 | 100 | 99 | 100 | 100 | 100 |
| 20 | 98.8 | 98.4 | 99 | 97.5 | 93.5 | 100 |
| 21 | 98.1 | 98.4 | 98 | 96.3 | 96.8 | 96 |
| 22 | 98.1 | 95.2 | 100 | 98.8 | 96.8 | 100 |
| 23 | 96.9 | 93.5 | 99 | 100 | 100 | 100 |
| 24 | 97.5 | 93.5 | 100 | 98.8 | 96.8 | 100 |
| 25 | 97.5 | 93.5 | 100 | 96.3 | 96.8 | 96 |
| 26 | 96.3 | 90.3 | 100 | 96.3 | 93.5 | 98 |
| 27 | 96.9 | 93.5 | 99 | 96.3 | 96.8 | 96 |
| 28 | 95.7 | 88.7 | 100 | 97.5 | 93.5 | 100 |
| 29 | 96.9 | 95.2 | 98 | 95.1 | 87.1 | 100 |
| 30 | 95.1 | 87.1 | 100 | 91.4 | 83.9 | 96 |
| 31 | 96.9 | 91.9 | 100 | 98.8 | 96.8 | 100 |
| 32 | 95.1 | 88.7 | 99 | 98.8 | 96.8 | 100 |
| 33 | 94.4 | 96.8 | 93 | 98.8 | 96.8 | 100 |
| 34 | 96.9 | 91.9 | 100 | 100 | 100 | 100 |
| 35 | 96.9 | 95.2 | 98 | 88.9 | 80.6 | 94 |
| 36 | 95.1 | 88.7 | 99 | 95.1 | 87.1 | 100 |
| 37 | 96.3 | 91.9 | 99 | 95.1 | 87.1 | 100 |
| 38 | 96.3 | 93.5 | 98 | 100 | 100 | 100 |
| 39 | 95.7 | 91.9 | 98 | 95.1 | 90.3 | 98 |
| 40 | 96.9 | 95.2 | 98 | 95.1 | 90.3 | 98 |
| 41 | 94.4 | 88.7 | 98 | 93.8 | 90.3 | 96 |
| 42 | 97.5 | 98.4 | 97 | 98.8 | 100 | 98 |
| 43 | 98.1 | 98.4 | 98 | 97.5 | 96.8 | 98 |
| 44 | 97.5 | 93.5 | 100 | 100 | 100 | 100 |
| 45 | 94.4 | 88.7 | 98 | 95.1 | 87.1 | 100 |
| 46 | 96.9 | 91.9 | 100 | 93.8 | 87.1 | 98 |
| 47 | 95.7 | 88.7 | 100 | 98.8 | 96.8 | 100 |
| 48 | 96.9 | 95.2 | 98 | 92.6 | 96.8 | 90 |
| 49 | 95.7 | 93.5 | 97 | 93.8 | 90.3 | 96 |
| 50 | 95.7 | 96.8 | 95 | 97.5 | 96.8 | 98 |
| 51 | 92.6 | 83.9 | 98 | 92.6 | 83.9 | 98 |
| 52 | 93.8 | 93.5 | 94 | 90.1 | 77.4 | 98 |
| 53 | 93.8 | 90.3 | 96 | 91.2 | 90 | 92 |
| 54 | 92.6 | 80.6 | 100 | 93.8 | 83.9 | 100 |
| 55 | 95.7 | 91.8 | 98 | 98.8 | 96.8 | 100 |
| 56 | 97.5 | 95.2 | 99 | 96.3 | 93.5 | 98 |
| 57 | 93.8 | 88.7 | 97 | 86.4 | 80.6 | 90 |
| 58 | 97.5 | 96.8 | 98 | 96.3 | 96.8 | 96 |
| 59 | 95.1 | 90.3 | 98 | 96.3 | 90.3 | 100 |
| 60 | 95.1 | 88.7 | 99 | 95.1 | 93.5 | 96 |

TABLE 3-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 61 | 93.8 | 90.3 | 96 | 84 | 90.3 | 80 |
| 62 | 91.3 | 80.3 | 98 | 95.1 | 87.1 | 100 |
| 63 | 93.2 | 95.2 | 92 | 88.9 | 87.1 | 90 |
| 64 | 92.6 | 85.5 | 97 | 98.8 | 96.8 | 100 |
| 65 | 93.2 | 87.1 | 97 | 93.8 | 83.9 | 100 |
| 66 | 93.8 | 87.1 | 98 | 92.6 | 87.1 | 96 |
| 67 | 87.7 | 79 | 93 | 88.9 | 77.4 | 96 |
| 68 | 92.6 | 83.9 | 98 | 96.3 | 90.3 | 100 |
| 69 | 91.4 | 82.3 | 97 | 90.1 | 77.4 | 98 |
| 70 | 93.2 | 87.1 | 97 | 91.4 | 90.3 | 92 |
| 71 | 92.6 | 87.1 | 96 | 93.8 | 83.9 | 100 |
| 72 | 93.8 | 83.9 | 100 | 90.1 | 74.2 | 100 |
| 73 | 95.7 | 91.9 | 98 | 97.5 | 93.5 | 100 |
| 74 | 92.6 | 90.3 | 94 | 87.7 | 87.1 | 88 |
| 75 | 90.1 | 79 | 97 | 96.3 | 93.5 | 98 |
| 76 | 93.8 | 91.9 | 95 | 93.8 | 93.5 | 94 |
| 77 | 93.8 | 87.1 | 98 | 90.1 | 77.4 | 98 |
| 78 | 92.6 | 82.3 | 99 | 91.4 | 90.3 | 92 |
| 79 | 90.7 | 80.6 | 97 | 90.1 | 87.1 | 92 |
| 80 | 90.7 | 75.8 | 100 | 95.1 | 87.1 | 100 |
| 81 | 91.4 | 85.5 | 95 | 87.7 | 83.9 | 90 |
| 82 | 90.7 | 88.7 | 92 | 91.4 | 87.1 | 94 |
| 83 | 93.2 | 83.9 | 99 | 96.3 | 93.5 | 98 |
| 84 | 89.5 | 90.3 | 89 | 84 | 77.4 | 88 |
| 85 | 90.1 | 82.3 | 95 | 93.8 | 93.5 | 94 |
| 86 | 92.6 | 83.9 | 98 | 87.7 | 74.2 | 96 |
| 87 | 88.9 | 79 | 95 | 93.8 | 83.9 | 100 |
| 88 | 92 | 88.7 | 94 | 92.6 | 100 | 88 |
| 89 | 90.7 | 85.5 | 94 | 91.4 | 90.3 | 92 |
| 90 | 92.6 | 90.3 | 94 | 90.1 | 74.2 | 100 |
| 91 | 89.5 | 74.2 | 99 | 92.6 | 83.9 | 98 |
| 92 | 89.5 | 82.3 | 94 | 90.1 | 80.6 | 96 |
| 93 | 89.5 | 79 | 96 | 90.1 | 87.1 | 92 |
| 94 | 89.5 | 80.6 | 95 | 84 | 77.4 | 88 |
| 95 | 89.5 | 91.9 | 88 | 86.4 | 83.9 | 88 |
| 96 | 87.7 | 79 | 93 | 88.9 | 71 | 100 |
| 97 | 90.1 | 88.7 | 91 | 91.4 | 96.8 | 88 |
| 98 | 90.1 | 83.9 | 94 | 86.4 | 77.4 | 92 |
| 99 | 87.6 | 83.6 | 90 | 82.7 | 87.1 | 80 |
| 100 | 88.3 | 80.6 | 93 | 88.9 | 77.4 | 96 |
| 101 | 93.2 | 85.5 | 98 | 88.9 | 71 | 100 |
| 102 | 88.3 | 74.2 | 97 | 95.1 | 90.3 | 98 |
| 103 | 87.7 | 80.6 | 92 | 90.1 | 80.6 | 96 |
| 104 | 87.7 | 77.4 | 94 | 80.2 | 67.7 | 88 |
| 105 | 92 | 88.7 | 94 | 82.7 | 77.4 | 86 |
| 106 | 86.4 | 77.4 | 92 | 93.8 | 87.1 | 98 |
| 107 | 89.5 | 85.5 | 92 | 86.4 | 74.2 | 94 |
| 108 | 88.9 | 80.6 | 94 | 81.5 | 83.9 | 80 |
| 109 | 91.4 | 87.1 | 94 | 87.7 | 77.4 | 94 |
| 110 | 88.3 | 75.8 | 96 | 86.4 | 71 | 96 |
| 111 | 86.4 | 82.3 | 89 | 90.1 | 87.1 | 92 |
| 112 | 86.4 | 67.7 | 98 | 86.4 | 74.2 | 94 |
| 113 | 85.8 | 74.2 | 93 | 95.1 | 90.3 | 98 |
| 114 | 95.1 | 88.7 | 99 | 92.6 | 80.6 | 100 |
| 115 | 90.1 | 82.3 | 95 | 87.7 | 74.2 | 96 |
| 116 | 90.1 | 82.3 | 95 | 88.9 | 83.9 | 92 |
| 117 | 83.3 | 72.6 | 90 | 88.9 | 83.9 | 92 |
| 118 | 86.4 | 83.9 | 88 | 80.2 | 71 | 86 |
| 119 | 86.4 | 80.6 | 90 | 88.9 | 87.1 | 90 |
| 120 | 88.3 | 79 | 94 | 84 | 61.3 | 98 |
| 121 | 84.6 | 72.6 | 92 | 75.3 | 61.3 | 84 |
| 122 | 84.6 | 74.2 | 91 | 85.2 | 83.9 | 86 |
| 123 | 82.7 | 79 | 85 | 77.8 | 61.3 | 88 |
| 124 | 84.6 | 80.6 | 87 | 85.2 | 90.3 | 82 |
| 125 | 92 | 82.3 | 98 | 91.4 | 80.6 | 98 |
| 126 | 82.7 | 69.4 | 91 | 84 | 61.3 | 98 |
| 127 | 88.9 | 72.6 | 99 | 86.4 | 64.5 | 100 |
| 128 | 88.9 | 83.9 | 92 | 91.4 | 80.6 | 98 |
| 129 | 87 | 82.3 | 90 | 84 | 74.2 | 90 |
| 130 | 84 | 66.1 | 95 | 86.4 | 80.6 | 90 |
| 131 | 79.6 | 69.4 | 86 | 80.2 | 71 | 86 |
| 132 | 84.6 | 71 | 93 | 84 | 71 | 92 |
| 133 | 81.5 | 71 | 88 | 85.2 | 77.4 | 90 |
| 134 | 81.5 | 61.3 | 94 | 81.5 | 64.5 | 92 |
| 135 | 82.1 | 66.1 | 92 | 82.7 | 71 | 90 |

TABLE 3-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 136 | 83.3 | 74.2 | 89 | 82.7 | 71 | 90 |
| 137 | 83.3 | 79 | 86 | 77.8 | 83.9 | 74 |
| 138 | 80.2 | 67.7 | 88 | 79 | 74.2 | 82 |
| 139 | 84 | 74.2 | 90 | 86.4 | 83.9 | 88 |
| 140 | 81.5 | 71 | 88 | 85 | 63.3 | 98 |
| 141 | 82.1 | 67.7 | 91 | 82.7 | 64.5 | 94 |
| 142 | 79.6 | 69.4 | 86 | 80.2 | 71 | 86 |
| 143 | 83.3 | 75.8 | 88 | 76.5 | 67.7 | 82 |
| 144 | 87.7 | 74.2 | 96 | 85.2 | 71 | 94 |
| 145 | 83.3 | 79 | 86 | 80.2 | 71 | 86 |
| 146 | 81.5 | 69.4 | 89 | 81.5 | 74.2 | 86 |
| 147 | 84.6 | 69.4 | 94 | 84 | 71 | 92 |
| 148 | 85.8 | 72.6 | 94 | 77.8 | 64.5 | 86 |
| 149 | 85.2 | 66.1 | 97 | 93.8 | 83.9 | 100 |
| 150 | 79.6 | 62.9 | 90 | 80.2 | 71 | 86 |
| 151 | 80.9 | 67.7 | 89 | 86.4 | 83.9 | 88 |
| 152 | 82.7 | 67.7 | 92 | 79 | 61.3 | 90 |
| 153 | 83.3 | 67.7 | 93 | 79 | 61.3 | 90 |
| 154 | 79.6 | 64.5 | 89 | 84 | 67.7 | 94 |
| 155 | 79.6 | 66.1 | 88 | 82.7 | 64.5 | 94 |
| 156 | 78.4 | 59.7 | 90 | 81.5 | 64.5 | 92 |
| 157 | 77.2 | 66.1 | 84 | 71.6 | 54.8 | 82 |
| 158 | 77.8 | 61.3 | 88 | 79 | 64.5 | 88 |
| 159 | 84 | 67.7 | 94 | 85.2 | 74.2 | 92 |
| 160 | 80.2 | 69.4 | 87 | 71.6 | 58.1 | 80 |
| 161 | 77.2 | 56.5 | 90 | 76.5 | 58.1 | 88 |
| 162 | 79 | 61.3 | 90 | 70.4 | 58.1 | 78 |
| 163 | 79.6 | 64.5 | 89 | 81.5 | 58.1 | 96 |
| 164 | 82.1 | 62.9 | 94 | 84 | 61.3 | 98 |
| 165 | 77.8 | 59.7 | 89 | 82.7 | 67.7 | 92 |
| 166 | 82.1 | 56.5 | 98 | 82.7 | 61.3 | 96 |
| 167 | 77.8 | 69.4 | 83 | 79 | 67.7 | 86 |
| 168 | 72.8 | 56.5 | 83 | 70.4 | 58.1 | 78 |
| 169 | 80.2 | 64.5 | 90 | 72.8 | 58.1 | 82 |
| 170 | 80.2 | 53.2 | 97 | 79 | 54.8 | 94 |
| 171 | 83.3 | 74.2 | 89 | 81.5 | 67.7 | 90 |
| 172 | 79 | 69.4 | 85 | 74.1 | 58.1 | 84 |
| 173 | 79.6 | 54.8 | 95 | 84 | 64.5 | 96 |
| 174 | 77.2 | 56.5 | 90 | 80.2 | 61.3 | 92 |
| 175 | 77.2 | 54.8 | 91 | 76.5 | 67.7 | 82 |
| 176 | 83.3 | 72.6 | 90 | 79 | 58.1 | 92 |
| 177 | 77.2 | 59.7 | 88 | 77.8 | 58.1 | 90 |
| 178 | 77.8 | 59.7 | 89 | 77.8 | 48.4 | 96 |
| 179 | 78.4 | 56.5 | 92 | 80.2 | 61.3 | 92 |
| 180 | 72.2 | 45.2 | 89 | 80.2 | 54.8 | 96 |
| 181 | 74.7 | 50 | 90 | 70.4 | 38.7 | 90 |
| 182 | 75.9 | 59.7 | 86 | 61.7 | 35.5 | 78 |
| 183 | 77.2 | 61.3 | 87 | 76.5 | 64.5 | 84 |
| 184 | 75.9 | 58.1 | 87 | 77.8 | 54.8 | 92 |
| 185 | 74.7 | 59.7 | 84 | 75.3 | 64.5 | 82 |
| 186 | 77.8 | 54.8 | 92 | 77.8 | 54.8 | 92 |
| 187 | 77.2 | 64.5 | 85 | 70.4 | 61.3 | 76 |
| 188 | 78.4 | 54.8 | 93 | 74.1 | 35.5 | 98 |
| 189 | 72.8 | 61.3 | 80 | 72.8 | 48.4 | 88 |
| 190 | 77.8 | 54.8 | 92 | 75.3 | 61.3 | 84 |
| 191 | 83.3 | 62.9 | 96 | 81.5 | 61.3 | 94 |
| 192 | 74.7 | 50 | 90 | 80.2 | 54.8 | 96 |
| 193 | 69.8 | 43.5 | 86 | 74.1 | 71 | 76 |
| 194 | 74.7 | 53.2 | 88 | 81.5 | 61.3 | 94 |
| 195 | 75.3 | 54.8 | 88 | 69.1 | 45.2 | 84 |
| 196 | 74.7 | 56.5 | 86 | 75.3 | 48.4 | 92 |
| 197 | 74.1 | 54.8 | 86 | 69.1 | 29 | 94 |
| 198 | 69.8 | 48.4 | 83 | 72.8 | 54.8 | 84 |
| 199 | 74.1 | 50 | 89 | 72.8 | 41.9 | 92 |
| 200 | 83.3 | 59.7 | 98 | 87.7 | 67.7 | 100 |
| 201 | 68.5 | 41.9 | 85 | 65.4 | 29 | 88 |
| 202 | 75.3 | 45.2 | 94 | 71.6 | 29 | 98 |
| 203 | 71.6 | 38.7 | 92 | 75 | 53.3 | 88 |
| 204 | 71.6 | 53.2 | 83 | 67.9 | 51.6 | 78 |
| 205 | 72.2 | 54.8 | 83 | 69.1 | 45.2 | 84 |
| 206 | 70.4 | 45.2 | 86 | 67.9 | 35.5 | 88 |
| 207 | 72.8 | 48.4 | 88 | 65.4 | 41.9 | 80 |
| 208 | 69.1 | 45.2 | 84 | 67.9 | 41.9 | 84 |
| 209 | 69.1 | 41.9 | 86 | 72.8 | 48.4 | 88 |
| 210 | 74.7 | 51.6 | 89 | 72.8 | 41.9 | 92 |

TABLE 3-continued

|  | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 211 | 71 | 53.2 | 82 | 61.7 | 35.5 | 78 |
| 212 | 71 | 45.2 | 87 | 61.7 | 41.9 | 74 |
| 213 | 71 | 24.2 | 100 | 75.3 | 35.5 | 100 |
| 214 | 71 | 45.2 | 87 | 76.5 | 48.4 | 94 |
| 215 | 75.3 | 53.2 | 89 | 65.4 | 32.3 | 86 |
| 216 | 71.6 | 50 | 85 | 71.6 | 41.9 | 90 |
| 217 | 69.8 | 43.5 | 86 | 67.9 | 41.9 | 84 |
| 218 | 71 | 40.3 | 90 | 71.6 | 41.9 | 90 |
| 219 | 71 | 40.3 | 90 | 70.4 | 35.5 | 92 |
| 220 | 73.5 | 45.2 | 91 | 66.7 | 35.5 | 86 |
| 221 | 71.6 | 43.5 | 89 | 72.8 | 41.9 | 92 |
| 222 | 70.4 | 46.8 | 85 | 76.5 | 61.3 | 86 |
| 223 | 77.8 | 46.8 | 97 | 72.8 | 32.3 | 98 |
| 224 | 70.4 | 43.5 | 87 | 72.8 | 45.2 | 90 |
| 225 | 67.3 | 37.1 | 86 | 74.1 | 38.7 | 96 |
| 226 | 67.9 | 37.1 | 87 | 75.3 | 51.6 | 90 |
| 227 | 71 | 41.9 | 89 | 66.7 | 29 | 90 |
| 228 | 69.1 | 40.3 | 87 | 65.4 | 35.5 | 84 |
| 229 | 71.6 | 46.8 | 87 | 65.4 | 38.7 | 82 |
| 230 | 69.1 | 40.3 | 87 | 71.6 | 54.8 | 82 |
| 231 | 71 | 41.9 | 89 | 72.8 | 58.1 | 82 |
| 232 | 71.6 | 41.9 | 90 | 76.5 | 51.6 | 92 |
| 233 | 75.3 | 38.7 | 98 | 72.8 | 29 | 100 |
| 234 | 66 | 33.9 | 86 | 64.2 | 41.9 | 78 |
| 235 | 69.8 | 37.1 | 90 | 67.9 | 38.7 | 86 |
| 236 | 100 | 100 | 100 | 98.8 | 96.8 | 100 |
| 237 | 96.9 | 93.5 | 99 | 98.8 | 96.8 | 100 |
| 238 | 98.8 | 98.4 | 99 | 98.8 | 96.8 | 100 |
| 239 | 96.9 | 95.2 | 98 | 98.8 | 100 | 98 |
| 240 | 95.1 | 93.5 | 96 | 96.3 | 96.8 | 96 |
| 241 | 95 | 91.8 | 97 | 91.4 | 87.1 | 94 |
| 242 | 90.7 | 85.5 | 94 | 91.4 | 80.6 | 98 |
| 243 | 91.4 | 85.5 | 95 | 96.3 | 100 | 94 |
| 244 | 88.9 | 80.6 | 94 | 90.1 | 87.1 | 92 |
| 245 | 94.4 | 87.1 | 99 | 95.1 | 93.5 | 96 |
| 246 | 83.3 | 69.4 | 92 | 81.5 | 67.7 | 90 |
| 247 | 83.3 | 61.3 | 97 | 84 | 67.7 | 94 |
| 248 | 79.6 | 64.5 | 89 | 81.5 | 61.3 | 94 |
| 249 | 75.9 | 56.5 | 88 | 77.8 | 67.7 | 84 |
| 250 | 72.2 | 41.9 | 91 | 70.4 | 38.7 | 90 |
| 251 | 69.1 | 41.9 | 86 | 77.8 | 54.8 | 92 |

TABLE 4

| SEQ ID NO: | Discriminant coefficient | Constant term |
|---|---|---|
| 1 | 2.857 | 18.934 |
| 2 | 2.104 | 18.009 |
| 3 | 2.003 | 12.711 |
| 4 | 3.992 | 34.175 |
| 5 | 3.801 | 39.484 |
| 6 | 2.447 | 30.974 |
| 7 | 4.663 | 59.811 |
| 8 | 5.763 | 63.889 |
| 9 | 5.239 | 59.962 |
| 10 | 6.627 | 84.995 |
| 11 | 1.955 | 14.548 |
| 12 | 2.330 | 14.910 |
| 13 | 4.150 | 48.634 |
| 14 | 3.013 | 32.040 |
| 15 | 2.055 | 18.255 |
| 16 | 2.774 | 19.077 |
| 17 | 5.084 | 64.746 |
| 18 | 4.563 | 46.280 |
| 19 | 1.821 | 9.652 |
| 20 | 2.266 | 26.872 |
| 21 | 2.626 | 14.611 |
| 22 | 3.963 | 34.565 |
| 23 | 4.250 | 47.336 |
| 24 | 3.079 | 27.833 |
| 25 | 6.783 | 80.858 |
| 26 | 3.237 | 25.431 |
| 27 | 1.634 | 14.286 |
| 28 | 2.807 | 33.656 |
| 29 | 2.658 | 20.910 |
| 30 | 4.607 | 39.043 |
| 31 | 5.299 | 67.817 |
| 32 | 2.652 | 19.984 |
| 33 | 4.337 | 38.009 |
| 34 | 4.682 | 48.862 |
| 35 | 5.352 | 38.578 |
| 36 | 2.977 | 26.855 |
| 37 | 2.882 | 21.114 |
| 38 | 5.933 | 55.485 |
| 39 | 5.346 | 55.986 |
| 40 | 1.915 | 11.901 |
| 41 | 4.597 | 34.155 |
| 42 | 2.048 | 10.706 |
| 43 | 4.172 | 34.713 |
| 44 | 1.763 | 9.076 |
| 45 | 5.446 | 45.658 |
| 46 | 2.725 | 15.338 |
| 47 | 1.886 | 10.786 |
| 48 | 2.535 | 15.378 |
| 49 | 4.415 | 34.502 |
| 50 | 2.583 | 15.891 |

TABLE 4-continued

| SEQ ID NO: | Discriminant coefficient | Constant term |
|---|---|---|
| 51 | 3.927 | 44.058 |
| 52 | 3.643 | 32.462 |
| 53 | 6.086 | 41.540 |
| 54 | 3.018 | 38.864 |
| 55 | 3.179 | 22.917 |
| 56 | 2.338 | 13.833 |
| 57 | 5.682 | 67.831 |
| 58 | 2.838 | 18.281 |
| 59 | 2.954 | 19.780 |
| 60 | 3.642 | 21.511 |
| 61 | 1.972 | 23.626 |
| 62 | 4.194 | 40.279 |
| 63 | 3.430 | 28.886 |
| 64 | 3.095 | 19.571 |
| 65 | 2.739 | 17.283 |
| 66 | 1.356 | 7.292 |
| 67 | 4.404 | 35.065 |
| 68 | 3.358 | 27.546 |
| 69 | 2.497 | 15.102 |
| 70 | 3.754 | 25.584 |
| 71 | 3.860 | 28.692 |
| 72 | 2.543 | 20.396 |
| 73 | 2.485 | 13.944 |
| 74 | 2.870 | 22.658 |
| 75 | 2.136 | 17.183 |
| 76 | 2.226 | 12.375 |
| 77 | 4.610 | 47.394 |
| 78 | 3.174 | 36.978 |
| 79 | 2.980 | 26.297 |
| 80 | 3.396 | 29.485 |
| 81 | 3.446 | 23.243 |
| 82 | 4.082 | 29.368 |
| 83 | 3.358 | 28.190 |
| 84 | 1.537 | 10.210 |
| 85 | 4.715 | 45.652 |
| 86 | 2.213 | 17.839 |
| 87 | 3.088 | 27.043 |
| 88 | 2.399 | 24.629 |
| 89 | 4.002 | 24.314 |
| 90 | 2.863 | 17.406 |
| 91 | 4.805 | 44.782 |
| 92 | 3.372 | 29.988 |
| 93 | 4.132 | 30.521 |
| 94 | 3.851 | 23.002 |
| 95 | 3.959 | 36.256 |
| 96 | 2.941 | 23.102 |
| 97 | 3.006 | 20.900 |
| 98 | 3.728 | 29.308 |
| 99 | 2.595 | 30.882 |
| 100 | 2.755 | 20.339 |
| 101 | 3.144 | 19.162 |
| 102 | 1.952 | 17.956 |
| 103 | 4.489 | 37.034 |
| 104 | 4.734 | 32.179 |
| 105 | 3.519 | 24.011 |
| 106 | 4.202 | 32.975 |
| 107 | 2.654 | 17.634 |
| 108 | 4.562 | 28.615 |
| 109 | 4.900 | 37.966 |
| 110 | 2.427 | 15.293 |
| 111 | 2.332 | 16.477 |
| 112 | 2.960 | 35.679 |
| 113 | 2.931 | 27.885 |
| 114 | 2.409 | 15.430 |
| 115 | 2.659 | 15.558 |
| 116 | 2.722 | 15.656 |
| 117 | 3.039 | 32.084 |
| 118 | 2.066 | 14.991 |
| 119 | 2.114 | 14.125 |
| 120 | 2.812 | 19.320 |
| 121 | 4.273 | 28.046 |
| 122 | 1.987 | 11.296 |
| 123 | 4.888 | 61.938 |
| 124 | 3.116 | 29.551 |
| 125 | 3.831 | 36.923 |
| 126 | 3.114 | 20.097 |
| 127 | 1.704 | 11.244 |
| 128 | 2.708 | 16.078 |
| 129 | 2.902 | 17.111 |
| 130 | 3.522 | 27.388 |
| 131 | 2.509 | 16.024 |
| 132 | 3.797 | 26.247 |
| 133 | 2.381 | 26.930 |
| 134 | 5.446 | 44.750 |
| 135 | 2.830 | 18.893 |
| 136 | 2.243 | 13.704 |
| 137 | 2.742 | 24.223 |
| 138 | 5.572 | 41.312 |
| 139 | 2.328 | 13.203 |
| 140 | 4.269 | 27.904 |
| 141 | 1.790 | 19.364 |
| 142 | 3.970 | 28.366 |
| 143 | 3.831 | 42.123 |
| 144 | 2.470 | 23.361 |
| 145 | 3.643 | 37.749 |
| 146 | 3.590 | 21.954 |
| 147 | 6.096 | 72.341 |
| 148 | 4.450 | 26.391 |
| 149 | 2.450 | 28.929 |
| 150 | 3.765 | 26.311 |
| 151 | 3.107 | 20.676 |
| 152 | 3.191 | 26.734 |
| 153 | 2.247 | 12.949 |
| 154 | 3.520 | 21.019 |
| 155 | 1.939 | 10.899 |
| 156 | 3.714 | 28.667 |
| 157 | 3.379 | 30.812 |
| 158 | 3.869 | 28.692 |
| 159 | 4.714 | 30.302 |
| 160 | 3.800 | 29.719 |
| 161 | 3.111 | 23.178 |
| 162 | 4.700 | 38.234 |
| 163 | 5.628 | 38.292 |
| 164 | 2.984 | 23.210 |
| 165 | 2.953 | 20.742 |
| 166 | 2.411 | 18.314 |
| 167 | 2.915 | 19.822 |
| 168 | 4.774 | 29.161 |
| 169 | 3.435 | 22.933 |
| 170 | 4.014 | 33.267 |
| 171 | 4.788 | 52.969 |
| 172 | 4.261 | 30.393 |
| 173 | 2.698 | 20.419 |
| 174 | 3.739 | 22.190 |
| 175 | 3.142 | 19.164 |
| 176 | 3.424 | 23.274 |
| 177 | 4.230 | 35.956 |
| 178 | 3.270 | 18.860 |
| 179 | 2.287 | 16.040 |
| 180 | 3.760 | 39.967 |
| 181 | 5.991 | 71.910 |
| 182 | 6.044 | 68.999 |
| 183 | 4.325 | 29.700 |
| 184 | 3.000 | 19.877 |
| 185 | 3.823 | 34.710 |
| 186 | 3.882 | 35.815 |
| 187 | 3.870 | 23.356 |
| 188 | 2.281 | 17.158 |
| 189 | 5.818 | 59.167 |
| 190 | 2.555 | 15.132 |
| 191 | 1.200 | 8.000 |
| 192 | 4.027 | 33.373 |
| 193 | 6.532 | 69.738 |
| 194 | 3.836 | 23.124 |
| 195 | 2.198 | 25.446 |
| 196 | 3.531 | 27.965 |
| 197 | 3.619 | 27.108 |
| 198 | 2.671 | 18.647 |
| 199 | 3.253 | 19.608 |
| 200 | 1.449 | 12.340 |
| 201 | 4.621 | 33.285 |
| 202 | 3.174 | 24.106 |
| 203 | 3.280 | 19.895 |
| 204 | 3.339 | 22.048 |

TABLE 4-continued

| SEQ ID NO: | Discriminant coefficient | Constant term |
|---|---|---|
| 205 | 2.930 | 20.016 |
| 206 | 2.705 | 17.147 |
| 207 | 5.111 | 63.738 |
| 208 | 4.111 | 39.848 |
| 209 | 4.418 | 30.103 |
| 210 | 3.749 | 22.673 |
| 211 | 4.949 | 48.983 |
| 212 | 3.159 | 19.444 |
| 213 | 3.351 | 49.006 |
| 214 | 4.185 | 40.143 |
| 215 | 2.257 | 19.312 |
| 216 | 4.261 | 34.145 |
| 217 | 2.984 | 26.230 |
| 218 | 3.064 | 35.877 |
| 219 | 2.311 | 23.637 |
| 220 | 4.200 | 26.644 |
| 221 | 3.404 | 21.751 |
| 222 | 3.076 | 22.488 |
| 223 | 3.273 | 26.709 |
| 224 | 5.275 | 40.615 |
| 225 | 3.461 | 24.300 |
| 226 | 5.789 | 41.289 |
| 227 | 4.602 | 40.407 |
| 228 | 5.697 | 41.534 |
| 229 | 2.323 | 20.843 |
| 230 | 3.839 | 25.014 |
| 231 | 3.506 | 21.544 |
| 232 | 4.082 | 45.878 |
| 233 | 3.909 | 30.033 |
| 234 | 4.028 | 26.498 |
| 235 | 4.173 | 25.119 |
| 236 | 3.887 | 30.454 |
| 237 | 2.014 | 10.053 |
| 238 | 2.607 | 16.589 |
| 239 | 1.925 | 14.853 |
| 240 | 1.301 | 6.443 |
| 241 | 1.152 | 8.583 |
| 242 | 1.774 | 11.079 |
| 243 | 2.154 | 13.220 |
| 244 | 3.309 | 23.530 |
| 245 | 3.226 | 25.503 |
| 246 | 3.387 | 34.563 |
| 247 | 2.652 | 16.404 |
| 248 | 3.534 | 22.326 |
| 249 | 3.779 | 28.687 |
| 250 | 1.490 | 9.528 |
| 251 | 2.072 | 13.756 |

TABLE 5-1

| Training cohort | | |
|---|---|---|
| Sample name | Cancer stage | CEA(ng/mL) |
| BB001 | IV | 1(−) |
| BB006 | IIIB | 14.4(+) |
| BB007 | IIA | 2.6(−) |
| BB009 | IIIC | 4.9(−) |
| BB010 | IIA | 1.2(−) |
| BB012 | I | 2.7(−) |
| BB013 | I | 1.4(−) |
| BB014 | IIA | 13.5(+) |
| BB015 | I | 3.5(−) |
| BB017 | IIA | 1.9(−) |
| BB018 | IIA | 2.1(−) |
| BB019 | I | 1.2(−) |
| BB023 | IIA | 2.8(−) |
| BB024 | I | 1.5(−) |
| BB026 | I | 3.8(−) |
| BB027 | IIB | 3.4(−) |
| BB028 | IV | 7.4(+) |
| BB032 | I | 1.7(−) |
| BB033 | IIB | 2.6(−) |
| BB035 | IIA | 2.7(−) |
| BB037 | IIB | 1.2(−) |
| BB038 | IV | 0.8(−) |
| BB039 | IIIA | 4.7(−) |
| BB041 | IIA | 2.1(−) |
| BB042 | IIIB | 1.3(−) |
| BB043 | IIIA | 1.2(−) |
| BB046 | I | 1.7(−) |
| BB047 | I | 1(−) |
| BB048 | I | 1.9(−) |
| BB049 | IIA | 0.6(−) |
| BB051 | IIA | 1(−) |
| BB052 | I | 2.4(−) |
| BB054 | IIA | 1.3(−) |
| BB056 | IIA | 1.9(−) |
| BB057 | IIIB | 3460(+) |
| BB058 | IIA | 0.8(−) |
| BB060 | I | 0.5(−) |
| BB061 | I | 1.4(−) |
| BB064 | IV | 2.4(−) |
| BB065 | IIB | 6.6(+) |
| BB068 | IIA | 0.6(−) |
| BB070 | IIB | 0.7(−) |
| BB071 | IIB | 1.8(−) |
| BB073 | I | 4.1(−) |
| BB076 | I | 2(−) |
| BB077 | IIA | 2.9(−) |
| BB078 | IIA | 2.3(−) |
| BB079 | IIA | 1.1(−) |
| BB082 | I | 1.5(−) |
| BB084 | IV | 435(+) |
| BB085 | IIA | 3.1(−) |
| BB086 | IIA | 1.5(−) |
| BB087 | IIA | 1.7(−) |
| BB089 | I | 2(−) |
| BB092 | I | 3.6(−) |
| BB093 | IIB | 3.7(−) |
| BB094 | I | 6(+) |
| BB095 | IIA | 2.4(−) |
| BB096 | I | 4.6(−) |
| BB097 | IIA | 1.8(−) |
| BB098 | IIA | 2.6(−) |
| BB099 | IIA | 4.2(−) |
| Sensitivity (%) | | 11.3 |

TABLE 5-2

| Validation cohort | | |
|---|---|---|
| Sample name | Cancer stage | CEA(ng/mL) |
| BB002 | IIIC | 1.3(−) |
| BB005 | IIA | 0.6(−) |
| BB008 | IIA | 0.7(−) |
| BB011 | IIB | 1.4(−) |
| BB016 | I | 2.9(−) |
| BB020 | IIB | 1.5(−) |
| BB021 | IIB | 1.5(−) |
| BB022 | IIA | 0.6(−) |
| BB025 | IIA | 4.1(−) |
| BB029 | IIIA | 2.7(−) |
| BB030 | IIA | 12.7(+) |
| BB031 | IIA | 1.4(−) |
| BB034 | IIB | 4.2(−) |
| BB036 | I | 3.5(−) |
| BB040 | IIB | 1.7(−) |
| BB050 | IIIB | 11.1(+) |
| BB053 | I | 0.8(−) |
| BB055 | IIA | 2.8(−) |
| BB059 | IIA | 10.2(+) |
| BB062 | IIA | 5.9(+) |
| BB063 | I | 0.7(−) |
| BB069 | IIA | 0.7(−) |
| BB072 | IIA | 1.1(−) |

TABLE 5-2-continued

| Validation cohort | | |
|---|---|---|
| Sample name | Cancer stage | CEA(ng/mL) |
| BB074 | IIA | 6.4(+) |
| BB075 | I | 0.5(−) |
| BB080 | IV | 6.6(+) |
| BB081 | I | 0.8(−) |
| BB083 | I | 0.7(−) |
| BB088 | I | 1(−) |
| BB090 | I | 5.4(+) |
| BB091 | IIA | 1.2(−) |
| | Sensitivity (%) | 19.4 |

For CEA, 5 ng/ml or lower was indicated by as"−", while values exceeding these were indicated as "+".

TABLE 6

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 1_2 | 100 | 100 | 100 | 100 | 100 | 100 |
| 1_3 | 99.4 | 98.4 | 100 | 100 | 100 | 100 |
| 1_4 | 100 | 100 | 100 | 100 | 100 | 100 |
| 1_5 | 99.4 | 98.4 | 100 | 100 | 100 | 100 |
| 1_6 | 100 | 100 | 100 | 100 | 100 | 100 |
| 1_7 | 100 | 100 | 100 | 100 | 100 | 100 |
| 1_8 | 100 | 100 | 100 | 100 | 100 | 100 |
| 1_9 | 99.4 | 98.4 | 100 | 100 | 100 | 100 |
| 1_10 | 100 | 100 | 100 | 100 | 100 | 100 |
| 1_11 | 100 | 100 | 100 | 100 | 100 | 100 |
| 1_12 | 100 | 100 | 100 | 100 | 100 | 100 |
| 1_13 | 100 | 100 | 100 | 100 | 100 | 100 |
| 1_14 | 100 | 100 | 100 | 100 | 100 | 100 |
| 1_15 | 100 | 100 | 100 | 100 | 100 | 100 |
| 1_16 | 100 | 100 | 100 | 100 | 100 | 100 |
| 1_17 | 100 | 100 | 100 | 100 | 100 | 100 |
| 1_18 | 99.4 | 98.4 | 100 | 100 | 100 | 100 |
| 1_19 | 100 | 100 | 100 | 100 | 100 | 100 |
| 1_20 | 100 | 100 | 100 | 100 | 100 | 100 |
| 1_21 | 99.4 | 98.4 | 100 | 100 | 100 | 100 |
| 1_22 | 100 | 100 | 100 | 100 | 100 | 100 |
| 1_23 | 100 | 100 | 100 | 100 | 100 | 100 |
| 1_24 | 100 | 100 | 100 | 100 | 100 | 100 |
| 1_25 | 100 | 100 | 100 | 98.8 | 100 | 98 |
| 1_26 | 100 | 100 | 100 | 100 | 100 | 100 |
| 1_27 | 100 | 100 | 100 | 100 | 100 | 100 |
| 1_28 | 99.4 | 98.4 | 100 | 100 | 100 | 100 |
| 1_29 | 100 | 100 | 100 | 100 | 100 | 100 |
| 1_30 | 100 | 100 | 100 | 100 | 100 | 100 |
| 1_31 | 100 | 100 | 100 | 100 | 100 | 100 |
| 1_32 | 100 | 100 | 100 | 100 | 100 | 100 |
| 1_33 | 99.4 | 98.4 | 100 | 100 | 100 | 100 |
| 1_34 | 100 | 100 | 100 | 100 | 100 | 100 |
| 1_35 | 100 | 100 | 100 | 100 | 100 | 100 |
| 1_36 | 100 | 100 | 100 | 100 | 100 | 100 |
| 1_37 | 100 | 100 | 100 | 100 | 100 | 100 |
| 1_38 | 99.4 | 98.4 | 100 | 100 | 100 | 100 |
| 1_39 | 100 | 100 | 100 | 100 | 100 | 100 |
| 1_40 | 100 | 100 | 100 | 100 | 100 | 100 |
| 1_41 | 100 | 100 | 100 | 100 | 100 | 100 |
| 1_42 | 100 | 100 | 100 | 100 | 100 | 100 |
| 1_43 | 99.4 | 98.4 | 100 | 100 | 100 | 100 |
| 1_44 | 100 | 100 | 100 | 100 | 100 | 100 |
| 1_45 | 100 | 100 | 100 | 100 | 100 | 100 |
| 1_46 | 99.4 | 98.4 | 100 | 100 | 100 | 100 |
| 1_47 | 100 | 100 | 100 | 100 | 100 | 100 |
| 1_48 | 99.4 | 98.4 | 100 | 100 | 100 | 100 |
| 1_49 | 99.4 | 98.4 | 100 | 100 | 100 | 100 |
| 1_50 | 99.4 | 98.4 | 100 | 100 | 100 | 100 |
| 1_51 | 100 | 100 | 100 | 100 | 100 | 100 |
| 1_52 | 100 | 100 | 100 | 100 | 100 | 100 |
| 1_53 | 99.4 | 98.4 | 100 | 100 | 100 | 100 |
| 1_54 | 99.4 | 98.4 | 100 | 100 | 100 | 100 |
| 1_55 | 100 | 100 | 100 | 100 | 100 | 100 |
| 1_56 | 99.4 | 98.4 | 100 | 100 | 100 | 100 |
| 1_57 | 100 | 100 | 100 | 100 | 100 | 100 |
| 1_58 | 100 | 100 | 100 | 100 | 100 | 100 |
| 1_59 | 100 | 100 | 100 | 100 | 100 | 100 |
| 1_60 | 99.4 | 98.4 | 100 | 100 | 100 | 100 |
| 1_61 | 99.4 | 98.4 | 100 | 100 | 100 | 100 |

TABLE 6-continued

| SEQ ID NO: | Training cohort ||| Validation cohort |||
|---|---|---|---|---|---|---|
| | Accuracy (%) | Sensitivity (%) | Specificity (%) | Accuracy (%) | Sensitivity (%) | Specificity (%) |
| 1_62 | 100 | 100 | 100 | 100 | 100 | 100 |
| 1_63 | 99.4 | 98.4 | 100 | 100 | 100 | 100 |
| 1_64 | 100 | 100 | 100 | 100 | 100 | 100 |
| 1_65 | 99.4 | 98.4 | 100 | 100 | 100 | 100 |
| 1_66 | 99.4 | 98.4 | 100 | 100 | 100 | 100 |
| 1_67 | 100 | 100 | 100 | 100 | 100 | 100 |
| 1_68 | 100 | 100 | 100 | 100 | 100 | 100 |
| 1_69 | 100 | 100 | 100 | 100 | 100 | 100 |
| 1_70 | 100 | 100 | 100 | 100 | 100 | 100 |
| 1_71 | 99.4 | 98.4 | 100 | 100 | 100 | 100 |
| 1_72 | 100 | 100 | 100 | 100 | 100 | 100 |
| 1_73 | 99.4 | 98.4 | 100 | 100 | 100 | 100 |
| 1_74 | 99.4 | 98.4 | 100 | 100 | 100 | 100 |
| 1_75 | 99.4 | 98.4 | 100 | 100 | 100 | 100 |
| 1_76 | 100 | 100 | 100 | 100 | 100 | 100 |
| 1_77 | 100 | 100 | 100 | 100 | 100 | 100 |
| 1_78 | 100 | 100 | 100 | 100 | 100 | 100 |
| 1_79 | 99.4 | 98.4 | 100 | 100 | 100 | 100 |
| 1_80 | 100 | 100 | 100 | 100 | 100 | 100 |
| 1_81 | 100 | 100 | 100 | 100 | 100 | 100 |
| 1_82 | 99.4 | 98.4 | 100 | 100 | 100 | 100 |
| 1_83 | 99.4 | 98.4 | 100 | 100 | 100 | 100 |
| 1_84 | 99.4 | 98.4 | 100 | 100 | 100 | 100 |
| 1_85 | 99.4 | 98.4 | 100 | 100 | 100 | 100 |
| 1_86 | 100 | 100 | 100 | 100 | 100 | 100 |
| 1_87 | 99.4 | 98.4 | 100 | 100 | 100 | 100 |
| 1_88 | 99.4 | 98.4 | 100 | 100 | 100 | 100 |
| 1_89 | 99.4 | 98.4 | 100 | 100 | 100 | 100 |
| 1_90 | 100 | 100 | 100 | 100 | 100 | 100 |
| 1_91 | 99.4 | 98.4 | 100 | 100 | 100 | 100 |
| 1_92 | 99.4 | 98.4 | 100 | 100 | 100 | 100 |
| 1_93 | 99.4 | 98.4 | 100 | 100 | 100 | 100 |
| 1_94 | 100 | 100 | 100 | 100 | 100 | 100 |
| 1_95 | 99.4 | 98.4 | 100 | 100 | 100 | 100 |
| 1_96 | 100 | 100 | 100 | 100 | 100 | 100 |
| 1_97 | 99.4 | 98.4 | 100 | 100 | 100 | 100 |
| 1_98 | 99.4 | 98.4 | 100 | 100 | 100 | 100 |
| 1_99 | 99.4 | 98.4 | 100 | 100 | 100 | 100 |
| 1_100 | 100 | 100 | 100 | 100 | 100 | 100 |
| 1_101 | 99.4 | 98.4 | 100 | 100 | 100 | 100 |
| 1_102 | 100 | 100 | 100 | 100 | 100 | 100 |
| 1_103 | 99.4 | 98.4 | 100 | 100 | 100 | 100 |
| 1_104 | 100 | 100 | 100 | 100 | 100 | 100 |
| 1_105 | 99.4 | 98.4 | 100 | 100 | 100 | 100 |
| 1_106 | 100 | 100 | 100 | 100 | 100 | 100 |
| 1_107 | 100 | 100 | 100 | 100 | 100 | 100 |
| 1_108 | 99.4 | 98.4 | 100 | 100 | 100 | 100 |
| 1_109 | 100 | 100 | 100 | 100 | 100 | 100 |
| 1_110 | 99.4 | 98.4 | 100 | 100 | 100 | 100 |
| 1_111 | 99.4 | 98.4 | 100 | 100 | 100 | 100 |
| 1_112 | 100 | 100 | 100 | 100 | 100 | 100 |
| 1_113 | 100 | 100 | 100 | 100 | 100 | 100 |
| 1_114 | 99.4 | 98.4 | 100 | 100 | 100 | 100 |
| 1_115 | 99.4 | 98.4 | 100 | 100 | 100 | 100 |
| 1_116 | 99.4 | 98.4 | 100 | 100 | 100 | 100 |
| 1_117 | 99.4 | 98.4 | 100 | 100 | 100 | 100 |
| 1_118 | 99.4 | 98.4 | 100 | 100 | 100 | 100 |
| 1_119 | 99.4 | 98.4 | 100 | 100 | 100 | 100 |
| 1_120 | 99.4 | 98.4 | 100 | 100 | 100 | 100 |
| 1_121 | 100 | 100 | 100 | 100 | 100 | 100 |
| 1_122 | 99.4 | 98.4 | 100 | 100 | 100 | 100 |
| 1_123 | 99.4 | 98.4 | 100 | 100 | 100 | 100 |
| 1_124 | 99.4 | 98.4 | 100 | 100 | 100 | 100 |
| 1_125 | 100 | 100 | 100 | 100 | 100 | 100 |
| 1_126 | 99.4 | 98.4 | 100 | 100 | 100 | 100 |
| 1_127 | 100 | 100 | 100 | 100 | 100 | 100 |
| 1_128 | 99.4 | 98.4 | 100 | 100 | 100 | 100 |
| 1_129 | 99.4 | 98.4 | 100 | 100 | 100 | 100 |
| 1_130 | 99.4 | 98.4 | 100 | 100 | 100 | 100 |
| 1_131 | 99.4 | 98.4 | 100 | 100 | 100 | 100 |
| 1_132 | 99.4 | 98.4 | 100 | 100 | 100 | 100 |
| 1_133 | 99.4 | 98.4 | 100 | 100 | 100 | 100 |
| 1_134 | 99.4 | 98.4 | 100 | 100 | 100 | 100 |
| 1_135 | 99.4 | 98.4 | 100 | 100 | 100 | 100 |
| 1_136 | 99.4 | 98.4 | 100 | 100 | 100 | 100 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_137 | 99.4 | 98.4 | 100 | 100 | 100 | 100 |
| 1_138 | 99.4 | 98.4 | 100 | 100 | 100 | 100 |
| 1_139 | 99.4 | 98.4 | 100 | 100 | 100 | 100 |
| 1_140 | 99.4 | 98.4 | 100 | 100 | 100 | 100 |
| 1_141 | 99.4 | 98.4 | 100 | 100 | 100 | 100 |
| 1_142 | 99.4 | 98.4 | 100 | 100 | 100 | 100 |
| 1_143 | 100 | 100 | 100 | 100 | 100 | 100 |
| 1_144 | 99.4 | 98.4 | 100 | 100 | 100 | 100 |
| 1_145 | 99.4 | 98.4 | 100 | 100 | 100 | 100 |
| 1_146 | 99.4 | 98.4 | 100 | 100 | 100 | 100 |
| 1_147 | 99.4 | 98.4 | 100 | 100 | 100 | 100 |
| 1_148 | 100 | 100 | 100 | 100 | 100 | 100 |
| 1_149 | 99.4 | 98.4 | 100 | 100 | 100 | 100 |
| 1_150 | 99.4 | 98.4 | 100 | 100 | 100 | 100 |
| 1_151 | 99.4 | 98.4 | 100 | 100 | 100 | 100 |
| 1_152 | 100 | 100 | 100 | 100 | 100 | 100 |
| 1_153 | 99.4 | 98.4 | 100 | 100 | 100 | 100 |
| 1_154 | 99.4 | 98.4 | 100 | 100 | 100 | 100 |
| 1_155 | 99.4 | 98.4 | 100 | 100 | 100 | 100 |
| 1_156 | 99.4 | 98.4 | 100 | 100 | 100 | 100 |
| 1_157 | 100 | 100 | 100 | 100 | 100 | 100 |
| 1_158 | 99.4 | 98.4 | 100 | 100 | 100 | 100 |
| 1_159 | 99.4 | 98.4 | 100 | 100 | 100 | 100 |
| 1_160 | 99.4 | 98.4 | 100 | 100 | 100 | 100 |
| 1_161 | 100 | 100 | 100 | 100 | 100 | 100 |
| 1_162 | 100 | 100 | 100 | 100 | 100 | 100 |
| 1_163 | 99.4 | 98.4 | 100 | 100 | 100 | 100 |
| 1_164 | 99.4 | 98.4 | 100 | 100 | 100 | 100 |
| 1_165 | 99.4 | 98.4 | 100 | 100 | 100 | 100 |
| 1_166 | 99.4 | 98.4 | 100 | 100 | 100 | 100 |
| 1_167 | 99.4 | 98.4 | 100 | 100 | 100 | 100 |
| 1_168 | 99.4 | 98.4 | 100 | 100 | 100 | 100 |
| 1_169 | 100 | 100 | 100 | 100 | 100 | 100 |
| 1_170 | 99.4 | 98.4 | 100 | 100 | 100 | 100 |
| 1_171 | 99.4 | 98.4 | 100 | 100 | 100 | 100 |
| 1_172 | 99.4 | 98.4 | 100 | 100 | 100 | 100 |
| 1_173 | 99.4 | 98.4 | 100 | 100 | 100 | 100 |
| 1_174 | 99.4 | 98.4 | 100 | 100 | 100 | 100 |
| 1_175 | 99.4 | 98.4 | 100 | 100 | 100 | 100 |
| 1_176 | 99.4 | 98.4 | 100 | 100 | 100 | 100 |
| 1_177 | 99.4 | 98.4 | 100 | 100 | 100 | 100 |
| 1_178 | 99.4 | 98.4 | 100 | 100 | 100 | 100 |
| 1_179 | 99.4 | 98.4 | 100 | 100 | 100 | 100 |
| 1_180 | 99.4 | 98.4 | 100 | 100 | 100 | 100 |
| 1_181 | 99.4 | 98.4 | 100 | 100 | 100 | 100 |
| 1_182 | 99.4 | 98.4 | 100 | 100 | 100 | 100 |
| 1_183 | 99.4 | 98.4 | 100 | 100 | 100 | 100 |
| 1_184 | 99.4 | 98.4 | 100 | 100 | 100 | 100 |
| 1_185 | 99.4 | 98.4 | 100 | 100 | 100 | 100 |
| 1_186 | 100 | 100 | 100 | 100 | 100 | 100 |
| 1_187 | 99.4 | 98.4 | 100 | 100 | 100 | 100 |
| 1_188 | 100 | 100 | 100 | 100 | 100 | 100 |
| 1_189 | 99.4 | 98.4 | 100 | 100 | 100 | 100 |
| 1_190 | 99.4 | 98.4 | 100 | 100 | 100 | 100 |
| 1_191 | 99.4 | 98.4 | 100 | 100 | 100 | 100 |
| 1_192 | 99.4 | 98.4 | 100 | 100 | 100 | 100 |
| 1_193 | 99.4 | 98.4 | 100 | 100 | 100 | 100 |
| 1_194 | 99.4 | 98.4 | 100 | 100 | 100 | 100 |
| 1_195 | 100 | 100 | 100 | 100 | 100 | 100 |
| 1_196 | 99.4 | 98.4 | 100 | 100 | 100 | 100 |
| 1_197 | 99.4 | 98.4 | 100 | 100 | 100 | 100 |
| 1_198 | 99.4 | 98.4 | 100 | 100 | 100 | 100 |
| 1_199 | 99.4 | 98.4 | 100 | 100 | 100 | 100 |
| 1_200 | 99.4 | 98.4 | 100 | 100 | 100 | 100 |
| 1_201 | 99.4 | 98.4 | 100 | 100 | 100 | 100 |
| 1_202 | 99.4 | 98.4 | 100 | 100 | 100 | 100 |
| 1_203 | 99.4 | 98.4 | 100 | 100 | 100 | 100 |
| 1_204 | 99.4 | 98.4 | 100 | 100 | 100 | 100 |
| 1_205 | 99.4 | 98.4 | 100 | 100 | 100 | 100 |
| 1_206 | 99.4 | 98.4 | 100 | 100 | 100 | 100 |
| 1_207 | 99.4 | 98.4 | 100 | 100 | 100 | 100 |
| 1_208 | 99.4 | 98.4 | 100 | 100 | 100 | 100 |
| 1_209 | 99.4 | 98.4 | 100 | 100 | 100 | 100 |
| 1_210 | 99.4 | 98.4 | 100 | 100 | 100 | 100 |
| 1_211 | 99.4 | 98.4 | 100 | 100 | 100 | 100 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 1_212 | 99.4 | 98.4 | 100 | 100 | 100 | 100 |
| 1_213 | 99.4 | 98.4 | 100 | 100 | 100 | 100 |
| 1_214 | 100 | 100 | 100 | 100 | 100 | 100 |
| 1_215 | 100 | 100 | 100 | 100 | 100 | 100 |
| 1_216 | 99.4 | 98.4 | 100 | 100 | 100 | 100 |
| 1_217 | 99.4 | 98.4 | 100 | 100 | 100 | 100 |
| 1_218 | 99.4 | 98.4 | 100 | 100 | 100 | 100 |
| 1_219 | 100 | 100 | 100 | 100 | 100 | 100 |
| 1_220 | 100 | 100 | 100 | 100 | 100 | 100 |
| 1_221 | 99.4 | 98.4 | 100 | 100 | 100 | 100 |
| 1_222 | 99.4 | 98.4 | 100 | 100 | 100 | 100 |
| 1_223 | 99.4 | 98.4 | 100 | 100 | 100 | 100 |
| 1_224 | 99.4 | 98.4 | 100 | 100 | 100 | 100 |
| 1_225 | 100 | 100 | 100 | 100 | 100 | 100 |
| 1_226 | 99.4 | 98.4 | 100 | 100 | 100 | 100 |
| 1_227 | 99.4 | 98.4 | 100 | 100 | 100 | 100 |
| 1_228 | 99.4 | 98.4 | 100 | 100 | 100 | 100 |
| 1_229 | 99.4 | 98.4 | 100 | 100 | 100 | 100 |
| 1_230 | 99.4 | 98.4 | 100 | 100 | 100 | 100 |
| 1_231 | 99.4 | 98.4 | 100 | 100 | 100 | 100 |
| 1_232 | 99.4 | 98.4 | 100 | 100 | 100 | 100 |
| 1_233 | 99.4 | 98.4 | 100 | 100 | 100 | 100 |
| 1_234 | 99.4 | 98.4 | 100 | 100 | 100 | 100 |
| 1_235 | 99.4 | 98.4 | 100 | 100 | 100 | 100 |
| 1_236 | 100 | 100 | 100 | 100 | 100 | 100 |
| 1_237 | 100 | 100 | 100 | 100 | 100 | 100 |
| 1_238 | 100 | 100 | 100 | 100 | 100 | 100 |
| 1_239 | 100 | 100 | 100 | 100 | 100 | 100 |
| 1_240 | 100 | 100 | 100 | 100 | 100 | 100 |
| 1_241 | 100 | 100 | 100 | 100 | 100 | 100 |
| 1_242 | 100 | 100 | 100 | 100 | 100 | 100 |
| 1_243 | 100 | 100 | 100 | 100 | 100 | 100 |
| 1_244 | 100 | 100 | 100 | 100 | 100 | 100 |
| 1_245 | 99.4 | 98.4 | 100 | 100 | 100 | 100 |
| 1_246 | 99.4 | 98.4 | 100 | 100 | 100 | 100 |
| 1_247 | 99.4 | 98.4 | 100 | 100 | 100 | 100 |
| 1_248 | 99.4 | 98.4 | 100 | 100 | 100 | 100 |
| 1_249 | 99.4 | 98.4 | 100 | 100 | 100 | 100 |
| 1_250 | 99.4 | 98.4 | 100 | 100 | 100 | 100 |
| 1_251 | 99.4 | 98.4 | 100 | 100 | 100 | 100 |

TABLE 7

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 3_20 | 100 | 100 | 100 | 100 | 100 | 100 |
| 6_20 | 100 | 100 | 100 | 100 | 100 | 100 |
| 7_20 | 100 | 100 | 100 | 100 | 100 | 100 |
| 10_20 | 100 | 100 | 100 | 100 | 100 | 100 |
| 20_22 | 98.8 | 96.7 | 100 | 98.8 | 96.8 | 100 |
| 20_238 | 98.8 | 96.7 | 100 | 98.8 | 96.8 | 100 |
| 20_239 | 100 | 100 | 100 | 100 | 100 | 100 |
| 12_24 | 100 | 100 | 100 | 98.8 | 96.8 | 100 |
| 20_24 | 100 | 100 | 100 | 98.8 | 96.8 | 100 |
| 24_27 | 98.8 | 96.8 | 100 | 98.8 | 96.8 | 100 |
| 24_33 | 100 | 100 | 100 | 100 | 100 | 100 |
| 24_236 | 100 | 100 | 100 | 98.8 | 96.8 | 100 |
| 24_240 | 100 | 100 | 100 | 100 | 100 | 100 |
| 3_26 | 100 | 100 | 100 | 100 | 100 | 100 |
| 12_26 | 100 | 100 | 100 | 98.8 | 96.8 | 100 |
| 13_26 | 100 | 100 | 100 | 98.8 | 96.8 | 100 |
| 17_26 | 100 | 100 | 100 | 98.8 | 100 | 98 |
| 19_26 | 100 | 100 | 100 | 98.8 | 100 | 98 |
| 3_27 | 100 | 100 | 100 | 100 | 100 | 100 |
| 5_27 | 100 | 100 | 100 | 100 | 100 | 100 |
| 13_27 | 99.4 | 98.4 | 100 | 100 | 100 | 100 |
| 20_27 | 98.1 | 96.7 | 99 | 100 | 100 | 100 |
| 26_27 | 99.4 | 98.4 | 100 | 96.3 | 93.5 | 98 |
| 27_120 | 98.8 | 98.4 | 99 | 100 | 100 | 100 |

TABLE 7-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 27_206 | 98.1 | 95.2 | 100 | 97.5 | 96.8 | 98 |
| 27_237 | 99.4 | 98.4 | 100 | 100 | 100 | 100 |
| 3_30 | 100 | 100 | 100 | 100 | 100 | 100 |
| 17_30 | 99.4 | 98.4 | 100 | 100 | 100 | 100 |
| 27_30 | 100 | 100 | 100 | 98.8 | 96.8 | 100 |
| 27_33 | 98.8 | 98.4 | 99 | 100 | 100 | 100 |
| 30_39 | 99.4 | 98.4 | 100 | 100 | 100 | 100 |
| 30_117 | 99.4 | 98.4 | 100 | 98.8 | 96.8 | 100 |
| 3_33 | 99.4 | 98.4 | 100 | 100 | 100 | 100 |
| 7_33 | 100 | 100 | 100 | 100 | 100 | 100 |
| 10_33 | 100 | 100 | 100 | 100 | 100 | 100 |
| 11_33 | 100 | 100 | 100 | 98.8 | 100 | 98 |
| 13_33 | 100 | 100 | 100 | 100 | 100 | 100 |
| 25_33 | 100 | 100 | 100 | 98.8 | 100 | 98 |
| 33_244 | 100 | 100 | 100 | 100 | 100 | 100 |
| 3_182 | 99.4 | 98.4 | 100 | 100 | 100 | 100 |
| 6_182 | 99.4 | 98.4 | 100 | 100 | 100 | 100 |
| 7_182 | 100 | 100 | 100 | 100 | 100 | 100 |
| 12_182 | 100 | 100 | 100 | 100 | 100 | 100 |
| 27_182 | 98.1 | 96.8 | 99 | 97.5 | 96.8 | 98 |
| 182_236 | 100 | 100 | 100 | 98.8 | 96.8 | 100 |
| 2_194 | 99.4 | 98.4 | 100 | 100 | 100 | 100 |
| 7_194 | 100 | 100 | 100 | 100 | 100 | 100 |
| 27_194 | 98.1 | 95.2 | 100 | 97.5 | 96.8 | 98 |
| 194_236 | 100 | 100 | 100 | 98.8 | 96.8 | 100 |
| 2_206 | 99.4 | 98.4 | 100 | 100 | 100 | 100 |
| 7_206 | 100 | 100 | 100 | 100 | 100 | 100 |
| 206_236 | 100 | 100 | 100 | 98.8 | 96.8 | 100 |
| 2_208 | 99.4 | 98.4 | 100 | 100 | 100 | 100 |
| 7_208 | 100 | 100 | 100 | 100 | 100 | 100 |
| 13_208 | 99.4 | 98.4 | 100 | 100 | 100 | 100 |
| 20_208 | 98.1 | 96.7 | 99 | 97.5 | 93.5 | 100 |
| 27_208 | 98.1 | 95.2 | 100 | 98.8 | 96.8 | 100 |

Example 3

<Selection of Gene Markers Using all Samples and Method for Evaluating Breast Cancer Discriminant Performance of Acquired Gene Markers>

In this Example, the samples of the training cohort and the validation cohort used in Examples 1 and 2 were integrated, and selection of a gene marker and evaluation of its breast cancer discriminant performance were conducted using all of the samples.

Specifically, the miRNA expression levels in the sera of the 93 breast cancer patients and the 150 healthy subjects obtained in the preceding Reference Examples were normalized by quantile normalization. In order to acquire diagnostic markers with higher reliability, only genes having a gene expression level of $2^6$ or higher in 50% or more of the samples in either of the breast cancer patient group or the healthy subject group, were selected in the gene marker selection. In order to further acquire statistical significance for discriminating a breast cancer patient group from a healthy subject group, the P value obtained by two-tailed t-test assuming equal variance as to each gene expression level was corrected by the Bonferroni method, and genes that satisfied p<0.01 were selected as gene markers for use in explanatory variables of a discriminant. The obtained genes are described in Table 7. In this way, hsa-miR-658, hsa-miR-6842-5p, hsa-miR-6124, hsa-miR-6765-3p, hsa-miR-7106-5p, hsa-miR-4534, hsa-miR-92b-3p, hsa-miR-3135b, hsa-miR-4687-3p, hsa-miR-762, hsa-miR-3619-3p, hsa-miR-4467, hsa-miR-557, hsa-miR-1237-5p, hsa-miR-1908-5p, hsa-miR-4286, hsa-miR-6885-5ph and hsa-miR-6763-5p genes, and the nucleotide sequences of SEQ ID NOs: 252 to 269 related thereto were found in addition to the genes described in Table 2. As with the nucleotide sequences of SEQ ID NOs: 1 to 251, the results obtained about the polynucleotides represented by the nucleotide sequences of SEQ ID NOs: 252 to 269 also showed that the measurement values were significantly lower (−) or higher (+) in the breast cancer patient group than in the healthy subject group (Table 8). These results were able to be validated in the validation cohort. Thus, the presence or absence of breast cancer in the newly obtained samples can be determined by the methods described in Examples 1 and 2 by using the gene expression level measurement values described in Table 8 either alone or in combination with the gene expression level measurement values described in Table 2

TABLE 8

| SEQ ID NO: | Gene name | P value after Bonferroni correction | Expression level in breast cancer patient with respect to healthy subject |
|---|---|---|---|
| 1 | hsa-miR-4783-3p | 1.81.E−151 | + |
| 2 | hsa-miR-4730 | 1.00.E−148 | − |
| 3 | hsa-miR-1307-3p | 5.85.E−126 | + |
| 4 | hsa-miR-4634 | 9.92.E−114 | − |
| 5 | hsa-miR-663a | 2.55.E−112 | − |
| 6 | hsa-miR-4532 | 8.96.E−113 | + |
| 7 | hsa-miR-7704 | 4.82.E−114 | + |
| 8 | hsa-miR-3178 | 5.69.E−112 | − |
| 9 | hsa-miR-6729-5p | 3.52.E−112 | − |
| 10 | hsa-miR-6090 | 1.64.E−100 | − |
| 11 | hsa-miR-4732-5p | 7.04.E−96 | − |
| 12 | hsa-miR-3184-5p | 2.08.E−103 | + |
| 13 | hsa-miR-6727-5p | 3.11.E−99 | + |

TABLE 8-continued

| SEQ ID NO: | Gene name | P value after Bonferroni correction | Expression level in breast cancer patient with respect to healthy subject |
|---|---|---|---|
| 14 | hsa-miR-6088 | 4.52.E−100 | − |
| 15 | hsa-miR-4674 | 2.03.E−94 | + |
| 16 | hsa-miR-8073 | 5.49.E−98 | − |
| 17 | hsa-miR-4787-5p | 1.53.E−96 | + |
| 18 | hsa-miR-1469 | 3.95.E−87 | + |
| 19 | hsa-miR-125a-3p | 3.12.E−91 | − |
| 20 | hsa-miR-1233-5p | 2.43.E−93 | + |
| 21 | hsa-miR-885-3p | 4.92.E−87 | − |
| 22 | hsa-miR-6802-5p | 5.06.E−87 | − |
| 23 | hsa-miR-328-5p | 6.06.E−96 | + |
| 24 | hsa-miR-6787-5p | 2.26.E−85 | + |
| 25 | hsa-miR-8069 | 5.26.E−78 | + |
| 26 | hsa-miR-6875-5p | 2.38.E−74 | + |
| 27 | hsa-miR-1246 | 1.05.E−75 | + |
| 28 | hsa-miR-4734 | 6.82.E−87 | − |
| 29 | hsa-miR-6757-5p | 9.57.E−75 | + |
| 30 | hsa-miR-6756-5p | 4.28.E−70 | − |
| 31 | hsa-miR-3665 | 5.78.E−78 | − |
| 32 | hsa-miR-6836-3p | 7.87.E−76 | − |
| 33 | hsa-miR-6821 | 1.18.E−80 | − |
| 34 | hsa-miR-6805-5p | 3.26.E−79 | − |
| 35 | hsa-miR-4728-5p | 9.76.E−65 | + |
| 36 | hsa-miR-6726-5p | 4.07.E−72 | + |
| 37 | hsa-miR-197-5p | 5.63.E−71 | − |
| 38 | hsa-miR-149-3p | 3.94.E−70 | + |
| 39 | hsa-miR-6850-5p | 2.45.E−70 | − |
| 40 | hsa-miR-4476 | 8.32.E−64 | + |
| 41 | hsa-miR-6858-5p | 4.09.E−67 | − |
| 42 | hsa-miR-564 | 5.81.E−69 | + |
| 43 | hsa-miR-4763-3p | 2.83.E−72 | + |
| 44 | hsa-miR-575 | 1.96.E−69 | − |
| 45 | hsa-miR-6771-5p | 1.90.E−65 | − |
| 46 | hsa-miR-1231 | 8.50.E−61 | − |
| 47 | hsa-miR-1908-3p | 3.70.E−64 | + |
| 48 | hsa-miR-150-3p | 2.41.E−58 | − |
| 49 | hsa-miR-3937 | 5.29.E−66 | − |
| 50 | hsa-miR-887-3p | 1.78.E−64 | − |
| 51 | hsa-miR-3940-5p | 2.92.E−65 | − |
| 52 | hsa-miR-4741 | 1.21.E−57 | + |
| 53 | hsa-miR-6808-5p | 5.95.E−62 | − |
| 54 | hsa-miR-6869-5p | 9.36.E−66 | − |
| 55 | hsa-miR-5090 | 2.20.E−62 | − |
| 56 | hsa-miR-615-5p | 1.59.E−59 | − |
| 57 | hsa-miR-8072 | 1.93.E−53 | + |
| 58 | hsa-miR-128-1-5p | 2.45.E−57 | + |
| 59 | hsa-miR-1238-5p | 3.00.E−60 | − |
| 60 | hsa-miR-365a-5p | 5.03.E−59 | + |
| 61 | hsa-miR-204-3p | 1.93.E−49 | − |
| 62 | hsa-miR-4492 | 6.71.E−60 | − |
| 63 | hsa-miR-6785-5p | 3.81.E−56 | + |
| 64 | hsa-miR-6511a-5p | 6.21.E−62 | + |
| 65 | hsa-miR-4525 | 2.38.E−55 | − |
| 66 | hsa-miR-1915-5p | 8.81.E−57 | − |
| 67 | hsa-miR-3180 | 1.19.E−50 | − |
| 68 | hsa-miR-6879-5p | 2.38.E−58 | − |
| 69 | hsa-miR-1199-5p | 7.83.E−51 | − |
| 70 | hsa-miR-6746-5p | 9.76.E−50 | − |
| 71 | hsa-miR-711 | 1.44.E−49 | + |
| 72 | hsa-miR-663b | 4.49.E−49 | − |
| 73 | hsa-miR-4707-3p | 2.18.E−52 | + |
| 74 | hsa-miR-6893-5p | 2.49.E−43 | − |
| 75 | hsa-miR-4675 | 5.39.E−56 | + |
| 76 | hsa-miR-4638-5p | 1.64.E−51 | + |
| 77 | hsa-miR-4651 | 6.25.E−50 | − |
| 78 | hsa-miR-6087 | 6.15.E−53 | − |
| 79 | hsa-miR-4665-5p | 3.35.E−48 | − |
| 80 | hsa-miR-4758-5p | 1.52.E−54 | − |
| 81 | hsa-miR-6887-5p | 8.54.E−46 | − |
| 82 | hsa-miR-3620-5p | 4.32.E−42 | − |
| 83 | hsa-miR-1909-3p | 6.17.E−53 | + |
| 84 | hsa-miR-7641 | 2.63.E−43 | − |
| 85 | hsa-miR-6724-5p | 3.58.E−49 | + |
| 86 | hsa-miR-1343-3p | 1.04.E−45 | − |
| 87 | hsa-miR-6780b-5p | 5.24.E−50 | − |
| 88 | hsa-miR-4484 | 5.63.E−49 | + |
| 89 | hsa-miR-4690-5p | 2.68.E−43 | − |
| 90 | hsa-miR-4429 | 7.93.E−44 | − |
| 91 | hsa-miR-1227-5p | 1.26.E−46 | − |
| 92 | hsa-miR-4725-3p | 3.25.E−44 | + |
| 93 | hsa-miR-6861-5p | 2.28.E−46 | + |
| 94 | hsa-miR-6812-5p | 3.34.E−37 | + |
| 95 | hsa-miR-3197 | 8.32.E−45 | + |
| 96 | hsa-miR-8059 | 6.38.E−41 | + |
| 97 | hsa-miR-3185 | 7.20.E−46 | + |
| 98 | hsa-miR-4706 | 4.07.E−39 | + |
| 99 | hsa-miR-4497 | 7.65.E−39 | + |
| 100 | hsa-miR-3131 | 4.60.E−42 | − |
| 101 | hsa-miR-6806-5p | 8.93.E−34 | + |
| 102 | hsa-miR-187-5p | 5.69.E−42 | + |
| 103 | hsa-miR-3180-3p | 1.37.E−41 | − |
| 104 | hsa-miR-6848-5p | 9.99.E−33 | − |
| 105 | hsa-miR-6820-5p | 2.48.E−37 | + |
| 106 | hsa-miR-6800-5p | 2.58.E−42 | + |
| 107 | hsa-miR-6717-5p | 2.75.E−37 | − |
| 108 | hsa-miR-6795-5p | 2.83.E−36 | − |
| 109 | hsa-miR-4632-5p | 1.50.E−40 | + |
| 110 | hsa-miR-665 | 3.04.E−37 | − |
| 111 | hsa-miR-6778-5p | 3.57.E−36 | − |
| 112 | hsa-miR-3663-3p | 2.48.E−39 | + |
| 113 | hsa-miR-4689 | 1.46.E−43 | + |
| 114 | hsa-miR-211-3p | 1.36.E−39 | + |
| 115 | hsa-miR-6511b-5p | 4.55.E−39 | + |
| 116 | hsa-miR-4750-5p | 1.70.E−32 | + |
| 117 | hsa-miR-6126 | 6.52.E−41 | + |
| 118 | hsa-miR-614 | 1.36.E−31 | + |
| 119 | hsa-miR-7110-5p | 2.57.E−36 | − |
| 120 | hsa-miR-744-5p | 1.36.E−32 | − |
| 121 | hsa-miR-6769a-5p | 2.68.E−28 | + |
| 122 | hsa-miR-4792 | 3.78.E−29 | − |
| 123 | hsa-miR-5787 | 5.62.E−30 | + |
| 124 | hsa-miR-6798-5p | 8.69.E−34 | − |
| 125 | hsa-miR-6781-5p | 1.34.E−35 | + |
| 126 | hsa-miR-4419b | 3.49.E−28 | − |
| 127 | hsa-miR-4446-3p | 2.83.E−32 | − |
| 128 | hsa-miR-4259 | 9.25.E−30 | − |
| 129 | hsa-miR-5572 | 7.92.E−32 | − |
| 130 | hsa-miR-6075 | 1.06.E−34 | − |
| 131 | hsa-miR-296-3p | 7.28.E−27 | − |
| 132 | hsa-miR-6891-5p | 1.19.E−28 | + |
| 133 | hsa-miR-4745-5p | 1.47.E−30 | + |
| 134 | hsa-miR-6775-5p | 1.24.E−28 | − |
| 135 | hsa-miR-6870-5p | 1.50.E−29 | − |
| 136 | hsa-miR-920 | 2.07.E−27 | + |
| 137 | hsa-miR-4530 | 4.79.E−26 | + |
| 138 | hsa-miR-6819-5p | 4.33.E−27 | − |
| 139 | hsa-miR-6825-5p | 3.99.E−29 | + |
| 140 | hsa-miR-7847-3p | 1.49.E−26 | + |
| 141 | hsa-miR-6131 | 3.83.E−28 | − |
| 142 | hsa-miR-4433-3p | 8.75.E−27 | − |
| 143 | hsa-miR-1228-5p | 4.12.E−20 | − |
| 144 | hsa-miR-6743-5p | 4.05.E−31 | − |
| 145 | hsa-miR-1268a | 1.93.E−25 | + |
| 146 | hsa-miR-3917 | 3.71.E−24 | − |
| 147 | hsa-miR-6786-5p | 3.71.E−27 | + |
| 148 | hsa-miR-3154 | 1.49.E−21 | + |
| 149 | hsa-miR-638 | 2.61.E−28 | + |
| 150 | hsa-miR-6741-5p | 2.54.E−24 | − |
| 151 | hsa-miR-6889-5p | 3.14.E−26 | + |
| 152 | hsa-miR-6840-3p | 4.16.E−20 | − |
| 153 | hsa-miR-6510-5p | 2.15.E−19 | + |
| 154 | hsa-miR-3188 | 3.01.E−21 | + |
| 156 | hsa-miR-5001-5p | 1.47.E−22 | + |
| 157 | hsa-miR-1268b | 1.93.E−20 | + |
| 158 | hsa-miR-7107-5p | 6.37.E−21 | − |
| 159 | hsa-miR-6824-5p | 9.39.E−21 | − |
| 160 | hsa-miR-6732-5p | 3.49.E−17 | − |
| 161 | hsa-miR-371a-5p | 1.21.E−19 | − |
| 162 | hsa-miR-6794-5p | 1.02.E−15 | + |
| 163 | hsa-miR-6779-5p | 6.91.E−17 | + |
| 164 | hsa-miR-4271 | 2.14.E−22 | + |

TABLE 8-continued

| SEQ ID NO: | Gene name | P value after Bonferroni correction | Expression level in breast cancer patient with respect to healthy subject |
|---|---|---|---|
| 165 | hsa-miR-5195-3p | 1.17.E-19 | − |
| 166 | hsa-miR-6762-5p | 5.65.E-18 | + |
| 167 | hsa-miR-939-5p | 4.70.E-21 | + |
| 168 | hsa-miR-1247-3p | 4.05.E-14 | + |
| 169 | hsa-miR-6777-5p | 4.37.E-16 | − |
| 170 | hsa-miR-6722-3p | 9.50.E-18 | − |
| 171 | hsa-miR-3656 | 1.77.E-21 | + |
| 172 | hsa-miR-4688 | 4.75.E-17 | − |
| 173 | hsa-miR-3195 | 3.33.E-18 | − |
| 174 | hsa-miR-6766-5p | 1.29.E-18 | − |
| 175 | hsa-miR-4447 | 1.50.E-14 | + |
| 176 | hsa-miR-4656 | 7.31.E-14 | + |
| 177 | hsa-miR-7108-5p | 1.06.E-16 | − |
| 179 | hsa-miR-1273g-3p | 3.79.E-17 | + |
| 180 | hsa-miR-4463 | 4.63.E-18 | − |
| 181 | hsa-miR-2861 | 2.60.E-15 | + |
| 182 | hsa-miR-3196 | 6.55.E-12 | + |
| 183 | hsa-miR-6877-5p | 2.44.E-17 | + |
| 184 | hsa-miR-3679-5p | 6.45.E-18 | + |
| 185 | hsa-miR-4442 | 3.11.E-15 | − |
| 186 | hsa-miR-6789-5p | 1.50.E-14 | − |
| 187 | hsa-miR-6782-5p | 1.14.E-13 | − |
| 188 | hsa-miR-486-3p | 8.80.E-15 | + |
| 189 | hsa-miR-6085 | 3.88.E-15 | + |
| 190 | hsa-miR-4746-3p | 2.87.E-13 | − |
| 191 | hsa-miR-619-5p | 2.89.E-12 | − |
| 192 | hsa-miR-937-5p | 2.36.E-13 | + |
| 193 | hsa-miR-6803-5p | 2.14.E-12 | + |
| 194 | hsa-miR-4298 | 1.25.E-14 | + |
| 195 | hsa-miR-4454 | 9.63.E-11 | + |
| 196 | hsa-miR-4459 | 3.66.E-13 | − |
| 197 | hsa-miR-7150 | 1.76.E-10 | + |
| 198 | hsa-miR-6880-5p | 3.57.E-11 | − |
| 199 | hsa-miR-4449 | 4.62.E-11 | + |
| 200 | hsa-miR-8063 | 4.89.E-13 | + |
| 201 | hsa-miR-4695-5p | 5.30.E-09 | − |
| 202 | hsa-miR-6132 | 2.15.E-10 | + |
| 203 | hsa-miR-6829-5p | 3.96.E-09 | − |
| 204 | hsa-miR-4486 | 2.13.E-07 | + |
| 205 | hsa-miR-6805-3p | 8.96.E-10 | + |
| 206 | hsa-miR-6826-5p | 7.62.E-08 | − |
| 207 | hsa-miR-4508 | 6.79.E-08 | + |
| 208 | hsa-miR-1343-5p | 8.96.E-07 | + |
| 209 | hsa-miR-7114-5p | 1.55.E-09 | + |
| 210 | hsa-miR-3622a-5p | 2.52.E-08 | − |
| 211 | hsa-miR-6765-5p | 6.46.E-07 | + |
| 212 | hsa-miR-7845-5p | 1.78.E-04 | − |
| 213 | hsa-miR-3960 | 2.10.E-10 | − |
| 214 | hsa-miR-6749-5p | 1.32.E-07 | − |
| 215 | hsa-miR-1260b | 1.44.E-04 | + |
| 216 | hsa-miR-6799-5p | 1.14.E-07 | + |
| 217 | hsa-miR-4723-5p | 6.30.E-07 | − |
| 218 | hsa-miR-6784-5p | 4.08.E-08 | + |
| 219 | hsa-miR-5100 | 1.78.E-06 | − |
| 220 | hsa-miR-6769b-5p | 6.44.E-06 | + |
| 221 | hsa-miR-1207-5p | 8.21.E-07 | − |
| 222 | hsa-miR-642a-3p | 2.06.E-09 | − |
| 223 | hsa-miR-4505 | 3.06.E-06 | + |
| 224 | hsa-miR-4270 | 9.73.E-07 | − |
| 225 | hsa-miR-6721-5p | 1.84.E-08 | − |
| 226 | hsa-miR-7111-5p | 3.24.E-09 | + |
| 227 | hsa-miR-6791-5p | 2.88.E-06 | − |
| 228 | hsa-miR-7109-5p | 7.96.E-05 | + |
| 229 | hsa-miR-4258 | 1.36.E-05 | + |
| 230 | hsa-miR-6515-3p | 3.81.E-03 | + |
| 231 | hsa-miR-6851-5p | 1.63.E-06 | − |
| 232 | hsa-miR-6125 | 1.36.E-05 | − |
| 233 | hsa-miR-4749-5p | 7.65.E-05 | − |
| 234 | hsa-miR-4726-5p | 5.88.E-04 | + |
| 235 | hsa-miR-4513 | 4.79.E-06 | − |
| 236 | hsa-miR-760 | 1.45.E-111 | + |
| 237 | hsa-miR-602 | 1.06.E-88 | − |
| 238 | hsa-miR-423-5p | 9.24.E-79 | − |
| 239 | hsa-miR-92a-2-5p | 2.54.E-85 | − |
| 240 | hsa-miR-16-5p | 1.34.E-69 | + |
| 241 | hsa-miR-451a | 5.22.E-54 | + |
| 242 | hsa-miR-135a-3p | 8.02.E-58 | + |
| 243 | hsa-miR-486-5p | 8.22.E-52 | + |
| 244 | hsa-miR-4257 | 4.02.E-46 | + |
| 245 | hsa-miR-92b-5p | 1.86.E-45 | − |
| 246 | hsa-miR-1915-3p | 4.13.E-28 | − |
| 247 | hsa-miR-718 | 1.29.E-25 | + |
| 248 | hsa-miR-940 | 5.23.E-17 | − |
| 249 | hsa-miR-296-5p | 3.77.E-16 | − |
| 250 | hsa-miR-23b-3p | 1.91.E-04 | + |
| 251 | hsa-miR-92a-3p | 3.74.E-07 | + |
| 252 | hsa-miR-658 | 4.76.E-43 | + |
| 253 | hsa-miR-6842-5p | 3.63.E-12 | − |
| 254 | hsa-miR-6124 | 8.99.E-06 | + |
| 255 | hsa-miR-6765-3p | 2.30.E-05 | − |
| 256 | hsa-miR-7106-5p | 4.48.E-05 | − |
| 257 | hsa-miR-4534 | 2.10.E-04 | − |
| 258 | hsa-miR-92b-3p | 2.53.E-04 | − |
| 259 | hsa-miR-3135b | 3.35.E-04 | + |
| 260 | hsa-miR-4687-3p | 3.90.E-04 | + |
| 261 | hsa-miR-762 | 4.64.E-04 | − |
| 262 | hsa-miR-3619-3p | 1.13.E-03 | + |
| 263 | hsa-miR-4467 | 1.30.E-03 | − |
| 264 | hsa-miR-557 | 1.49.E-03 | + |
| 265 | hsa-miR-1237-5p | 1.57.E-03 | + |
| 266 | hsa-miR-1908-5p | 4.45.E-03 | − |
| 267 | hsa-miR-4286 | 5.37.E-03 | − |
| 268 | hsa-miR-6885-5p | 7.57.E-03 | + |
| 269 | hsa-miR-6763-5p | 9.02.E-03 | + |

Example 4

<Method for Evaluating Breast Cancer-Specific Discriminant Performance by Combination of Multiple Gene Markers Using Samples in the Validation Cohort>

In this Example, gene expression levels of miRNAs in sera were compared between breast cancer patients and a control group consisting of healthy subjects and prostate cancer patients in the same way as the method described in Example 1 using the gene markers selected in Example 1 with respect to the training cohort described in Reference Example 2, to select a gene marker for diagnosis. The polynucleotides consisting of the nucleotide sequences represented by SEQ ID NOs: 851 to 856 thus newly selected were further combined with the polynucleotides consisting of the nucleotide sequences represented by SEQ ID NOs: 1 to 269 to study a method for evaluating breast cancer-specific discriminant performance.

Specifically, first, the miRNA expression levels in the training cohort and the validation cohort obtained in Reference Example 2 mentioned above were combined and normalized by quantile normalization. Next, Fisher's discriminant analysis was conducted as to combinations of 1 to 2 measurement values that comprise at least one of the measurement values of the polynucleotides consisting of the nucleotide sequences represented by SEQ ID NOs: 1 to 269, and 851 to 856 to construct a discriminant for determining the presence or absence of breast cancer. Next, accuracy, sensitivity, and specificity in the validation cohort were calculated using the discriminant thus prepared, with a positive sample group that is the breast cancer patient group and a negative sample group that is a combination of the healthy subject group and the prostate cancer patient group. The discriminant performance of the selected polynucleotides was validated using independent samples.

Most of polynucleotides consisting of the nucleotide sequences represented by these SEQ ID NOs (SEQ ID NOs: 1 to 269, and 851 to 856 corresponding to the miRNA markers of Table 1) or complementary sequences thereof mentioned above were able to provide relatively high accuracy, sensitivity, and specificity in the determination of the presence or absence of breast cancer, and furthermore, were able to specifically discriminate breast cancer from the other cancers.

At least one polynucleotide selected from the group consisting of polynucleotides consisting of the nucleotide sequences represented by SEQ ID NOs: 1, 2, 3, 4, 5, 6, 7, 8, 9, 11, 12, 13, 14, 15, 16, 17, 20, 21, 22, 23, 24, 25, 26, 27, 29, 30, 31, 32, 33, 34, 35, 36, 37, 38, 39, 41, 43, 45, 46, 47, 49, 50, 51, 52, 53, 54, 55, 58, 59, 60, 62, 63, 64, 65, 67, 68, 69, 70, 71, 72, 73, 75, 77, 79, 80, 81, 82, 83, 86, 88, 89, 90, 92, 93, 94, 96, 98, 99, 100, 103, 104, 106, 107, 108, 110, 111, 113, 114, 115, 116, 118, 119, 121, 122, 124, 125, 126, 127, 128, 129, 130, 131, 132, 133, 135, 136, 139, 140, 143, 145, 146, 147, 149, 150, 155, 157, 160, 161, 165, 167, 171, 173, 174, 175, 177, 178, 181, 182, 186, 190, 193, 194, 199, 204, 205, 206, 208, 211, 218, 225, 232, 236, 237, 238, 239, 242, 243, 244, 246, 247, 252, 260, 265, 266, 851, 852, 853, 854, 855 and 856, or complementary sequences thereof (the cancer type-specific polynucleotide group 1) was capable of specifically binding to the target marker. Among the combinations of multiple polynucleotides selected from the cancer type-specific polynucleotide group 1, particularly, combinations comprising at least one polynucleotide selected from the group consisting of polynucleotides consisting of the nucleotide sequences represented by SEQ ID NOs: 1, 2, 3, 4, 5, 6, 7, 8, 9, 11, 12, 13, 14, 15, 16, 17, 20, 21, 22, 23, 24, 25, 26, 27, 29, 30, 31, 32, 33, 34, 35, 36, 37, 38, 39, 41, 43, 45, 46, 47, 49, 50, 51, 52, 54, 55, 58, 59, 60, 62, 63, 64, 65, 67, 68, 69, 71, 72, 73, 75, 77, 79, 80, 82, 83, 86, 88, 92, 93, 96, 99, 103, 104, 106, 110, 111, 114, 116, 118, 119, 122, 124, 125, 127, 130, 132, 133, 135, 139, 143, 145, 147, 149, 157, 160, 173, 177, 181, 182, 186, 211, 218, 232, 236, 237, 238, 239, 242, 243, 246, 247, 260, 266, 851, 852, 853 and 854, or complementary sequences thereof (the cancer type-specific polynucleotide group 2) were able to specifically discriminate breast cancer from the other cancer with high accuracy.

The number of the polynucleotides with cancer type specificity in the combination mentioned above can be 1, 2, 3, 4, 5, 6, 7, 8, 9, 10 or more for the combination. The combinations of 2 or more of these polynucleotides were able to exhibit discriminant accuracy of 95% or higher.

Specifically, the discriminant accuracy of the measurement using combinations of one or two polynucleotide(s) that consists of a nucleotide sequence represented by any of SEQ ID NOs: 1 to 269 and 851 to 856 or a complementary sequence thereof is shown in Table 9.

For example, the combinations of SEQ ID NOs: 2 and 1, SEQ ID NOs: 2 and 237, SEQ ID NOs: 2 and 4, SEQ ID NOs: 2 and 3, SEQ ID NOs: 2 and 51, SEQ ID NOs: 1 and 237, SEQ ID NOs: 1 and 4, SEQ ID NOs: 1 and 3, SEQ ID NOs: 1 and 51, SEQ ID NOs: 1 and 6, SEQ ID NOs: 4 and 237, SEQ ID NOs: 3 and 237, SEQ ID NOs: 51 and 237, SEQ ID NOs: 237 and 6, SEQ ID NOs: 237 and 12, SEQ ID NOs: 3 and 4, SEQ ID NOs: 4 and 51, SEQ ID NOs: 4 and 6, SEQ ID NOs: 4 and 12, SEQ ID NOs: 4 and 15, SEQ ID NOs: 3 and 51, SEQ ID NOs: 3 and 6, SEQ ID NOs: 3 and 12, SEQ ID NOs: 3 and 15, SEQ ID NOs: 3 and 8, SEQ ID NOs: 51 and 6, SEQ ID NOs: 51 and 12, SEQ ID NOs: 51 and 15, SEQ ID NOs: 51 and 8, SEQ ID NOs: 51 and 34, SEQ ID NOs: 2 and 6, SEQ ID NOs: 12 and 6, SEQ ID NOs: 15 and 6, SEQ ID NOs: 8 and 6, SEQ ID NOs: 6 and 34, SEQ ID NOs: 2 and 12, SEQ ID NOs: 1 and 12, SEQ ID NOs: 12 and 15, SEQ ID NOs: 8 and 12, SEQ ID NOs: 12 and 34, SEQ ID NOs: 2 and 15, SEQ ID NOs: 1 and 15, SEQ ID NOs: 237 and 15, SEQ ID NOs: 8 and 15, SEQ ID NOs: 15 and 34, SEQ ID NOs: 2 and 8, SEQ ID NOs: 1 and 8, SEQ ID NOs: 237 and 8, SEQ ID NOs: 4 and 8, SEQ ID NOs: 8 and 34, SEQ ID NOs: 2 and 34, SEQ ID NOs: 1 and 34, SEQ ID NOs: 237 and 34, SEQ ID NOs: 4 and 34, SEQ ID NOs: 3 and 34, SEQ ID NOs: 2 and 9, SEQ ID NOs: 1 and 9, SEQ ID NOs: 9 and 237, SEQ ID NOs: 4 and 9, SEQ ID NOs: 3 and 9, SEQ ID NOs: 2 and 143, SEQ ID NOs: 1 and 143, SEQ ID NOs: 237 and 143, SEQ ID NOs: 4 and 143, SEQ ID NOs: 3 and 143, SEQ ID NOs: 2 and 13, SEQ ID NOs: 1 and 13, SEQ ID NOs: 237 and 13, SEQ ID NOs: 4 and 13, SEQ ID NOs: 3 and 13, SEQ ID NOs: 2 and 125, SEQ ID NOs: 1 and 125, SEQ ID NOs: 237 and 125, SEQ ID NOs: 4 and 125, SEQ ID NOs: 3 and 125, SEQ ID NOs: 2 and 236, SEQ ID NOs: 1 and 236, SEQ ID NOs: 237 and 236, SEQ ID NOs: 4 and 236, SEQ ID NOs: 3 and 236, SEQ ID NOs: 2 and 46, SEQ ID NOs: 1 and 46, SEQ ID NOs: 237 and 46, SEQ ID NOs: 4 and 46, SEQ ID NOs: 3 and 46, SEQ ID NOs: 2 and 32, SEQ ID NOs: 1 and 32, SEQ ID NOs: 237 and 32, SEQ ID NOs: 4 and 32, SEQ ID NOs: 3 and 32, SEQ ID NOs: 2 and 62, SEQ ID NOs: 1 and 62, SEQ ID NOs: 237 and 62, SEQ ID NOs: 4 and 62, SEQ ID NOs: 3 and 62, SEQ ID NOs: 2 and 88, SEQ ID NOs: 1 and 88, SEQ ID NOs: 237 and 88, SEQ ID NOs: 4 and 88, SEQ ID NOs: 3 and 88, SEQ ID NOs: 2 and 52, SEQ ID NOs: 1 and 52, SEQ ID NOs: 237 and 52, SEQ ID NOs: 4 and 52, SEQ ID NOs: 3 and 52, SEQ ID NOs: 2 and 7, SEQ ID NOs: 1 and 7, SEQ ID NOs: 237 and 7, SEQ ID NOs: 4 and 7, SEQ ID NOs: 3 and 7, SEQ ID NOs: 2 and 26, SEQ ID NOs: 1 and 26, SEQ ID NOs: 237 and 26, SEQ ID NOs: 4 and 26, SEQ ID NOs: 3 and 26, SEQ ID NOs: 2 and 25, SEQ ID NOs: 1 and 25, SEQ ID NOs: 237 and 25, SEQ ID NOs: 4 and 25, SEQ ID NOs: 3 and 25, SEQ ID NOs: 2 and 54, SEQ ID NOs: 1 and 54, SEQ ID NOs: 237 and 54, SEQ ID NOs: 4 and 54, SEQ ID NOs: 3 and 54, SEQ ID NOs: 2 and 92, SEQ ID NOs: 1 and 92, SEQ ID NOs: 237 and 92, SEQ ID NOs: 4 and 92, SEQ ID NOs: 3 and 92, SEQ ID NOs: 2 and 14, SEQ ID NOs: 1 and 14, SEQ ID NOs: 237 and 14, SEQ ID NOs: 4 and 14, SEQ ID NOs: 3 and 14, SEQ ID NOs: 2 and 242, SEQ ID NOs: 1 and 242, SEQ ID NOs: 237 and 242, SEQ ID NOs: 4 and 242, SEQ ID NOs: 3 and 242, SEQ ID NOs: 2 and 47, SEQ ID NOs: 1 and 47, SEQ ID NOs: 237 and 47, SEQ ID NOs: 4 and 47, SEQ ID NOs: 3 and 47, SEQ ID NOs: 2 and 45, SEQ ID NOs: 1 and 45, SEQ ID NOs: 237 and 45, SEQ ID NOs: 4 and 45, SEQ ID NOs: 3 and 45, SEQ ID NOs: 2 and 39, SEQ ID NOs: 1 and 39, SEQ ID NOs: 237 and 39, SEQ ID NOs: 4 and 39, SEQ ID NOs: 3 and 39, SEQ ID NOs: 2 and 21, SEQ ID NOs: 1 and 21, SEQ ID NOs: 237 and 21, SEQ ID NOs: 4 and 21, SEQ ID NOs: 3 and 21, SEQ ID NOs: 2 and 17, SEQ ID NOs: 1 and 17, SEQ ID NOs: 237 and 17, SEQ ID NOs: 4 and 17, SEQ ID NOs: 3 and 17, SEQ ID NOs: 2 and 83, SEQ ID NOs: 1 and 83, SEQ ID NOs: 237 and 83, SEQ ID NOs: 4 and 83, SEQ ID NOs: 3 and 83, SEQ ID NOs: 2 and 149, SEQ ID NOs: 1 and 149, SEQ ID NOs: 237 and 149, SEQ ID NOs: 4 and 149, SEQ ID NOs: 3 and 149, SEQ ID NOs: 2 and 246, SEQ ID NOs: 1 and 246, SEQ ID NOs: 237 and 246, SEQ ID NOs: 4 and 246, SEQ ID NOs: 3 and 246, SEQ ID NOs: 2 and 22, SEQ ID NOs: 1 and 22, SEQ ID NOs: 237 and 22, SEQ ID NOs: 4 and 22, SEQ ID NOs: 3 and 22, SEQ ID NOs: 2 and 55, SEQ ID NOs: 1 and 55, SEQ ID NOs: 237 and 55, SEQ ID NOs: 4 and 55, SEQ ID NOs: 3 and 55, SEQ ID NOs: 2 and 182, SEQ ID NOs: 1 and 182, SEQ ID NOs: 237 and 182, SEQ ID NOs: 4 and 182, SEQ ID NOs: 3 and 182, SEQ ID NOs: 2 and 73, SEQ ID NOs: 1 and 73, SEQ ID NOs: 237 and 73, SEQ ID NOs: 4 and 73, SEQ ID NOs: 3 and 73, SEQ ID NOs: 2 and 77, SEQ ID NOs: 1 and 77, SEQ ID NOs: 237 and 77, SEQ ID NOs: 4 and 77, SEQ ID NOs: 3 and 77, SEQ ID NOs: 2 and 24, SEQ ID NOs: 1 and 24, SEQ ID NOs: 237 and 24, SEQ ID NOs: 4 and 24, SEQ ID NOs: 3 and 24, SEQ ID NOs: 2 and 103, SEQ ID NOs: 1 and 103, SEQ ID NOs: 237 and 103, SEQ ID NOs: 4 and 103, SEQ ID NOs: 3 and 103, SEQ ID NOs: 2 and 49, SEQ ID NOs: 1 and 49, SEQ ID NOs: 237 and 49, SEQ ID NOs: 4 and 49, SEQ ID NOs: 3 and 49, SEQ ID NOs: 2 and 239, SEQ ID NOs: 1 and 239, SEQ ID NOs: 237 and 239, SEQ ID NOs: 4 and 239, SEQ ID NOs: 3 and 239, SEQ ID NOs: 2 and 23, SEQ ID NOs: 1 and 23, SEQ ID NOs: 237 and 23, SEQ ID NOs: 4 and 23, SEQ ID NOs: 3 and 23, SEQ ID NOs: 2 and 58, SEQ ID NOs: 1 and 58, SEQ ID NOs: 237 and 58, SEQ ID NOs: 4 and 58, SEQ ID NOs: 3 and 58, SEQ ID NOs: 2 and 211, SEQ ID NOs: 1 and 211, SEQ ID NOs: 237 and 211, SEQ ID NOs: 4 and 211, SEQ ID NOs: 3 and 211, SEQ ID NOs: 2 and 147, SEQ ID NOs: 1 and 147, SEQ ID NOs: 237 and 147, SEQ ID NOs: 4 and 147, SEQ ID NOs: 3 and 147, SEQ ID NOs: 2 and 65, SEQ ID NOs: 1 and 65, SEQ ID NOs: 237 and 65, SEQ ID NOs: 4 and 65, SEQ ID NOs: 3 and 65, SEQ ID NOs: 2 and 31, SEQ ID NOs: 1 and 31, SEQ ID NOs: 237 and 31, SEQ ID NOs: 4 and 31, SEQ ID NOs: 3 and 31, SEQ ID NOs: 2 and 72, SEQ ID NOs: 1 and 72, SEQ ID NOs: 237 and 72, SEQ ID NOs: 4 and 72, SEQ ID NOs: 3 and 72, SEQ ID NOs: 2 and 63, SEQ ID NOs: 1 and 63, SEQ ID NOs: 237 and 63, SEQ ID NOs: 4 and 63, SEQ ID NOs: 3 and 63, SEQ ID NOs: 2 and 80, SEQ ID NOs: 1 and 80, SEQ ID NOs: 237 and 80, SEQ ID NOs: 4 and 80, SEQ ID NOs: 3 and 80, SEQ ID NOs: 2 and 37, SEQ ID NOs: 1 and 37, SEQ ID NOs: 237 and 37, SEQ ID NOs: 4 and 37, SEQ ID NOs: 3 and 37, SEQ ID NOs: 2 and 67, SEQ ID NOs: 1 and 67, SEQ ID NOs: 237 and 67, SEQ ID NOs: 4 and 67, SEQ ID NOs: 3 and 67, SEQ ID NOs: 2 and 232, SEQ ID NOs: 1 and 232, SEQ ID NOs: 237 and 232, SEQ ID NOs: 4 and 232, SEQ ID NOs: 3 and 232, SEQ ID NOs: 2 and 127, SEQ ID NOs: 1 and 127, SEQ ID NOs: 237 and 127, SEQ ID NOs: 4 and 127, SEQ ID NOs: 3 and 127, SEQ ID NOs: 2 and 145, SEQ ID NOs: 1 and 145, SEQ ID NOs: 237 and 145, SEQ ID NOs: 4 and 145, SEQ ID NOs: 3 and 145, SEQ ID NOs: 2 and 16, SEQ ID NOs: 1 and 16, SEQ ID NOs: 237 and 16, SEQ ID NOs: 4 and 16, SEQ ID NOs: 3 and 16, SEQ ID NOs: 2 and 11, SEQ ID NOs: 1 and 11, SEQ ID NOs: 237 and 11, SEQ ID NOs: 4 and 11, SEQ ID NOs: 3 and 11, SEQ ID NOs: 2 and 186, SEQ ID NOs: 1 and 186, SEQ ID NOs: 237 and 186, SEQ ID NOs: 4 and 186, SEQ ID NOs: 3 and 186, SEQ ID NOs: 2 and 50, SEQ ID NOs: 1 and 50, SEQ ID NOs: 237 and 50, SEQ ID NOs: 4 and 50, SEQ ID NOs: 3 and 50, SEQ ID NOs: 2 and 69, SEQ ID NOs: 1 and 69, SEQ ID NOs: 237 and 69, SEQ ID NOs: 4 and 69, SEQ ID NOs: 3 and 69, SEQ ID NOs: 2 and 33, SEQ ID NOs: 1 and 33, SEQ ID NOs: 237 and 33, SEQ ID NOs: 4 and 33, SEQ ID NOs: 3 and 33, SEQ ID NOs: 2 and 247, SEQ ID NOs: 1 and 247, SEQ ID NOs: 237 and 247, SEQ ID NOs: 4 and 247, SEQ ID NOs: 3 and 247, SEQ ID NOs: 2 and 36, SEQ ID NOs: 1 and 36, SEQ ID NOs: 237 and 36, SEQ ID NOs: 4 and 36, SEQ ID NOs: 3 and 36, SEQ ID NOs: 2 and 218, SEQ ID NOs: 1 and 218, SEQ ID NOs: 237 and 218, SEQ ID NOs: 4 and 218, SEQ ID NOs: 3 and 218, SEQ ID NOs: 2 and 43, SEQ ID NOs: 1 and 43, SEQ ID NOs: 237 and 43, SEQ ID NOs: 4 and 43, SEQ ID NOs: 3 and 43, SEQ ID NOs: 2 and 29, SEQ ID NOs: 1 and 29, SEQ ID NOs: 237 and 29, SEQ ID NOs: 4 and 29, SEQ ID NOs: 3 and 29, SEQ ID NOs: 2 and 110, SEQ ID NOs: 1 and 110, SEQ ID NOs: 237 and 110, SEQ ID NOs: 4 and 110, SEQ ID NOs: 3 and 110, SEQ ID NOs: 2 and 20, SEQ ID NOs: 1 and 20, SEQ ID NOs: 237 and 20, SEQ ID NOs: 4 and 20, SEQ ID NOs: 3 and 20, SEQ ID NOs: 2 and 157, SEQ ID NOs: 1 and 157, SEQ ID NOs: 237 and 157, SEQ ID NOs: 4 and 157, SEQ ID NOs: 3 and 157, SEQ ID NOs: 2 and 75, SEQ ID NOs: 1 and 75, SEQ ID NOs: 237 and 75, SEQ ID NOs: 4 and 75, SEQ ID NOs: 3 and 75, SEQ ID NOs: 2 and 82, SEQ ID NOs: 1 and 82, SEQ ID NOs: 237 and 82, SEQ ID NOs: 4 and 82, SEQ ID NOs: 3 and 82, SEQ ID NOs: 2 and 106, SEQ ID NOs: 1 and 106, SEQ ID NOs: 237 and 106, SEQ ID NOs: 4 and 106, SEQ ID NOs: 3 and 106, SEQ ID NOs: 2 and 111, SEQ ID NOs: 1 and 111, SEQ ID NOs: 237 and 111, SEQ ID NOs: 4 and 111, SEQ ID NOs: 3 and 111, SEQ ID NOs: 2 and 96, SEQ ID NOs: 1 and 96, SEQ ID NOs: 237 and 96, SEQ ID NOs: 4 and 96, SEQ ID NOs: 3 and 96, SEQ ID NOs: 2 and 266, SEQ ID NOs: 1 and 266, SEQ ID NOs: 237 and 266, SEQ ID NOs: 4 and 266, SEQ ID NOs: 3 and 266, SEQ ID NOs: 2 and 124, SEQ ID NOs: 1 and 124, SEQ ID NOs: 237 and 124, SEQ ID NOs: 4 and 124, SEQ ID NOs: 3 and 124, SEQ ID NOs: 2 and 68, SEQ ID NOs: 1 and 68, SEQ ID NOs: 237 and 68, SEQ ID NOs: 4 and 68, SEQ ID NOs: 3 and 68, SEQ ID NOs: 2 and 71, SEQ ID NOs: 1 and 71, SEQ ID NOs: 237 and 71, SEQ ID NOs: 4 and 71, SEQ ID NOs: 3 and 71, SEQ ID NOs: 2 and 35, SEQ ID NOs: 1 and 35, SEQ ID NOs: 237 and 35, SEQ ID NOs: 4 and 35, SEQ ID NOs: 3 and 35, SEQ ID NOs: 2 and 173, SEQ ID NOs: 1 and 173, SEQ ID NOs: 237 and 173, SEQ ID NOs: 4 and 173, SEQ ID NOs: 3 and 173, SEQ ID NOs: 2 and 5, SEQ ID NOs: 1 and 5, SEQ ID NOs: 237 and 5, SEQ ID NOs: 4 and 5, SEQ ID NOs: 3 and 5, SEQ ID NOs: 2 and 851, SEQ ID NOs: 1 and 851, SEQ ID NOs: 237 and 851, SEQ ID NOs: 4 and 851, SEQ ID NOs: 3 and 851, SEQ ID NOs: 2 and 852, SEQ ID NOs: 1 and 852, SEQ ID NOs: 237 and 852, SEQ ID NOs: 4 and 852, SEQ ID NOs: 3 and 852, SEQ ID NOs: 2 and 30, SEQ ID NOs: 1 and 30, SEQ ID NOs: 237 and 30, SEQ ID NOs: 4 and 30, SEQ ID NOs: 3 and 30, SEQ ID NOs: 2 and 93, SEQ ID NOs: 1 and 93, SEQ ID NOs: 237 and 93, SEQ ID NOs: 4 and 93, SEQ ID NOs: 3 and 93, SEQ ID NOs: 2 and 27, SEQ ID NOs: 1 and 27, SEQ ID NOs: 237 and 27, SEQ ID NOs: 4 and 27, SEQ ID NOs: 3 and 27, SEQ ID NOs: 2 and 853, SEQ ID NOs: 1 and 853, SEQ ID NOs: 237 and 853, SEQ ID NOs: 4 and 853, SEQ ID NOs: 3 and 853, SEQ ID NOs: 2 and 238, SEQ ID NOs: 1 and 238, SEQ ID NOs: 237 and 238, SEQ ID NOs: 4 and 238, SEQ ID NOs: 3 and 238, SEQ ID NOs: 2 and 130, SEQ ID NOs: 1 and 130, SEQ ID NOs: 237 and 130, SEQ ID NOs: 4 and 130, SEQ ID NOs: 3 and 130, SEQ ID NOs: 2 and 177, SEQ ID NOs: 1 and 177, SEQ ID NOs: 237 and 177, SEQ ID NOs: 4 and 177, SEQ ID NOs: 3 and 177, SEQ ID NOs: 2 and 64, SEQ ID NOs: 1 and 64, SEQ ID NOs: 237 and 64, SEQ ID NOs: 4 and 64, SEQ ID NOs: 3 and 64, SEQ ID NOs: 2 and 114, SEQ ID NOs: 1 and 114, SEQ ID NOs: 237 and 114, SEQ ID NOs: 4 and 114, SEQ ID NOs: 3 and 114, SEQ ID NOs: 2 and 119, SEQ ID NOs: 1 and 119, SEQ ID NOs: 237 and 119, SEQ ID NOs: 4 and 119, SEQ ID NOs: 3 and 119, SEQ ID NOs: 2 and 135, SEQ ID NOs: 1 and 135, SEQ ID NOs: 237 and 135, SEQ ID NOs: 4 and 135, SEQ ID NOs: 3 and 135, SEQ ID NOs: 2 and 243, SEQ ID NOs: 1 and 243, SEQ ID NOs: 237 and 243, SEQ ID NOs: 4 and 243, SEQ ID NOs: 3 and 243, SEQ ID NOs: 2 and 122, SEQ ID NOs: 1 and 122, SEQ ID NOs: 237 and 122, SEQ ID NOs: 4 and 122, SEQ ID NOs: 3 and 122, SEQ ID NOs: 2 and 260, SEQ ID NOs: 1 and 260, SEQ ID NOs: 237 and 260, SEQ ID NOs: 4 and 260, SEQ ID NOs: 3 and 260, SEQ ID NOs: 2 and 59, SEQ ID NOs: 1 and 59, SEQ ID NOs: 237 and 59, SEQ ID NOs: 4 and 59, SEQ ID NOs: 3 and 59, SEQ ID NOs: 2 and 854, SEQ ID NOs: 1 and 854, SEQ ID NOs: 237 and 854, SEQ ID NOs: 4 and 854, SEQ ID NOs: 3 and 854, SEQ ID NOs: 2 and 132, SEQ ID NOs: 1 and 132, SEQ ID NOs: 237 and 132, SEQ ID NOs: 4 and 132, SEQ ID NOs: 3 and 132, SEQ ID NOs: 2 and 181, SEQ ID NOs: 1 and 181, SEQ ID NOs: 237 and 181, SEQ ID NOs: 4 and 181, SEQ ID NOs: 3 and 181, SEQ ID NOs: 2 and 79, SEQ ID NOs: 1 and 79, SEQ ID NOs: 237 and 79, SEQ ID NOs: 4 and 79, SEQ ID NOs: 3 and 79, SEQ ID NOs: 2 and 133, SEQ ID NOs: 1 and 133, SEQ ID NOs: 237 and 133, SEQ ID NOs: 4 and 133, SEQ ID NOs: 3 and 133, SEQ ID NOs: 2 and 41, SEQ ID NOs: 1 and 41, SEQ ID NOs: 237 and 41, SEQ ID NOs: 4 and 41, SEQ ID NOs: 3 and 41, SEQ ID NOs: 2 and 139, SEQ ID NOs: 1 and 139, SEQ ID NOs: 237 and 139, SEQ ID NOs: 4 and 139, SEQ ID NOs: 3 and 139, SEQ ID NOs: 2 and 118, SEQ ID NOs: 1 and 118, SEQ ID NOs: 237 and 118, SEQ ID NOs: 4 and 118, SEQ ID NOs: 3 and 118, SEQ ID NOs: 2 and 86, SEQ ID NOs: 1 and 86, SEQ ID NOs: 237 and 86, SEQ ID NOs: 4 and 86, SEQ ID NOs: 3 and 86, SEQ ID NOs: 2 and 60, SEQ ID NOs: 1 and 60, SEQ ID NOs: 237 and 60, SEQ ID NOs: 4 and 60, SEQ ID NOs: 3 and 60, SEQ ID NOs: 2 and 116, SEQ ID NOs: 1 and 116, SEQ ID NOs: 237 and 116, SEQ ID NOs: 4 and 116, SEQ ID NOs: 3 and 116, SEQ ID NOs: 2 and 160, SEQ ID NOs: 1 and 160, SEQ ID NOs: 237 and 160, SEQ ID NOs: 4 and 160, SEQ ID NOs: 3 and 160, SEQ ID NOs: 2 and 38, SEQ ID NOs: 1 and 38, SEQ ID NOs: 237 and 38, SEQ ID NOs: 4 and 38, SEQ ID NOs: 3 and 38, SEQ ID NOs: 2 and 99, SEQ ID NOs: 1 and 99, SEQ ID NOs: 237 and 99, SEQ ID NOs: 4 and 99, SEQ ID NOs: 3 and 99, SEQ ID NOs: 2 and 104, SEQ ID NOs: 1 and 104, SEQ ID NOs: 237 and 104, SEQ ID NOs: 4 and 104, and SEQ ID NOs: 3 and 104 were able to produce breast cancer discriminant accuracy of 95% or higher.

Figure 4:
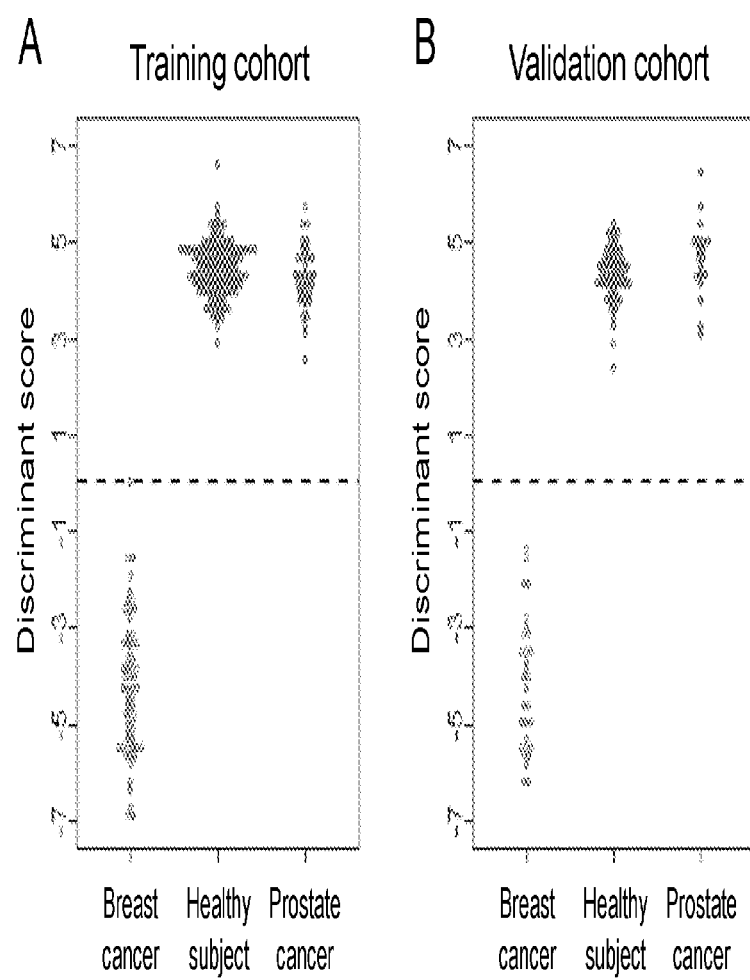
FIG. 4 Upper diagram: a discriminant (1.87× hsa-miR-4730+0.42×hsa-miR-602-18.58) was prepared by use of Fisher's discriminant analysis from the expression level measurement values of hsa-miR-602 (SEQ ID NO: 237) and hsa-miR-4730 (SEQ ID NO: 2) in 62 breast cancer patients, 102 healthy subjects, and 33 prostate cancer patients selected as a training cohort, and discriminant scores obtained from the discriminant were plotted on the ordinate against the sample groups on the abscissa. The dotted line in the diagram depicts a discriminant boundary that offered a discriminant score of 0 and discriminated between the groups. Lower diagram: discriminant scores obtained from the discriminant prepared for the training cohort as to the expression level measurement values of hsa-miR-602 (SEQ ID NO: 237) and hsa-miR-4730 (SEQ ID NO: 2) in 31 breast cancer patients, 48 healthy subjects, and 19 prostate cancer patients selected as a validation cohort were plotted on the ordinate against the sample groups on the abscissa. The dotted line in the diagram depicts the discriminant boundary that offered a discriminant score of 0 and discriminated between the two groups.

The measurement values of the nucleotide sequences represented by SEQ ID NOs: 2 and 237 were further compared among 62 breast cancer patients, 102 healthy subjects, and 33 prostate cancer patients in the training cohort. As a result, a scatter diagram that significantly separated the discriminant scores of the breast cancer patient group from those of the other groups was obtained in the training cohort (see FIG. 4A). These results were also reproducible for the validation cohort (see FIG. 4B).

TABLE 9

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 2 | 99.5 | 99.5 | 99.5 | 99.5 | 99.5 | 99.5 |
| 2_1 | 100 | 100 | 100 | 100 | 100 | 100 |
| 2_237 | 99.5 | 98.4 | 100 | 100 | 100 | 100 |
| 2_4 | 99.5 | 98.4 | 100 | 100 | 100 | 100 |
| 2_3 | 100 | 100 | 100 | 100 | 100 | 100 |
| 2_51 | 99.5 | 98.4 | 100 | 100 | 100 | 100 |
| 1 | 99.5 | 99.5 | 99.5 | 99.5 | 99.5 | 99.5 |
| 1_237 | 100 | 100 | 100 | 100 | 100 | 100 |
| 1_4 | 100 | 100 | 100 | 100 | 100 | 100 |
| 1_3 | 99.5 | 98.4 | 100 | 100 | 100 | 100 |
| 1_51 | 100 | 100 | 100 | 100 | 100 | 100 |
| 1_6 | 99.5 | 98.4 | 100 | 100 | 100 | 100 |
| 237 | 98.5 | 98.5 | 98.5 | 98.5 | 98.5 | 98.5 |
| 4_237 | 99.5 | 98.4 | 100 | 99 | 96.8 | 100 |
| 3_237 | 100 | 100 | 100 | 100 | 100 | 100 |
| 51_237 | 99 | 96.8 | 100 | 100 | 100 | 100 |
| 237_6 | 100 | 100 | 100 | 100 | 100 | 100 |
| 237_12 | 100 | 100 | 100 | 99 | 96.8 | 100 |
| 4 | 99 | 99 | 99 | 99 | 99 | 99 |
| 3_4 | 100 | 100 | 100 | 100 | 100 | 100 |
| 4_51 | 99.5 | 98.4 | 100 | 100 | 100 | 100 |
| 4_6 | 100 | 100 | 100 | 100 | 100 | 100 |
| 4_12 | 100 | 100 | 100 | 99 | 96.8 | 100 |
| 4_15 | 99.5 | 98.4 | 100 | 99 | 96.8 | 100 |
| 3 | 99.5 | 99.5 | 99.5 | 99.5 | 99.5 | 99.5 |
| 3_51 | 100 | 100 | 100 | 100 | 100 | 100 |
| 3_6 | 99 | 96.8 | 100 | 100 | 100 | 100 |
| 3_12 | 100 | 100 | 100 | 100 | 100 | 100 |
| 3_15 | 100 | 100 | 100 | 100 | 100 | 100 |
| 3_8 | 100 | 100 | 100 | 100 | 100 | 100 |
| 51 | 99 | 99 | 99 | 99 | 99 | 99 |
| 51_6 | 99.5 | 100 | 99.3 | 100 | 100 | 100 |
| 51_12 | 100 | 100 | 100 | 100 | 100 | 100 |
| 51_15 | 99.5 | 98.4 | 100 | 100 | 100 | 100 |
| 51_8 | 100 | 100 | 100 | 100 | 100 | 100 |
| 51_34 | 99.5 | 98.4 | 100 | 100 | 100 | 100 |
| 6 | 98.5 | 98.5 | 98.5 | 98.5 | 98.5 | 98.5 |
| 2_6 | 100 | 100 | 100 | 100 | 100 | 100 |
| 12_6 | 100 | 100 | 100 | 100 | 100 | 100 |
| 15_6 | 100 | 100 | 100 | 100 | 100 | 100 |
| 8_6 | 100 | 100 | 100 | 100 | 100 | 100 |
| 6_34 | 100 | 100 | 100 | 100 | 100 | 100 |
| 12 | 100 | 100 | 100 | 100 | 100 | 100 |
| 2_12 | 100 | 100 | 100 | 100 | 100 | 100 |
| 1_12 | 100 | 100 | 100 | 100 | 100 | 100 |
| 12_15 | 100 | 100 | 100 | 99 | 96.8 | 100 |
| 8_12 | 100 | 100 | 100 | 100 | 100 | 100 |

TABLE 9-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 12_34 | 100 | 100 | 100 | 100 | 100 | 100 |
| 15 | 98.5 | 98.5 | 98.5 | 98.5 | 98.5 | 98.5 |
| 2_15 | 99.5 | 98.4 | 100 | 100 | 100 | 100 |
| 1_15 | 100 | 100 | 100 | 100 | 100 | 100 |
| 237_15 | 99 | 96.8 | 100 | 99 | 96.8 | 100 |
| 8_15 | 99.5 | 98.4 | 100 | 100 | 100 | 100 |
| 15_34 | 99 | 96.8 | 100 | 100 | 100 | 100 |
| 8 | 99.5 | 99.5 | 99.5 | 99.5 | 99.5 | 99.5 |
| 2_8 | 99.5 | 98.4 | 100 | 100 | 100 | 100 |
| 1_8 | 100 | 100 | 100 | 100 | 100 | 100 |
| 237_8 | 100 | 100 | 100 | 100 | 100 | 100 |
| 4_8 | 100 | 100 | 100 | 100 | 100 | 100 |
| 8_34 | 99.5 | 98.4 | 100 | 99 | 100 | 98.5 |
| 34 | 99 | 99 | 99 | 99 | 99 | 99 |
| 2_34 | 99.5 | 98.4 | 100 | 100 | 100 | 100 |
| 1_34 | 100 | 100 | 100 | 100 | 100 | 100 |
| 237_34 | 100 | 100 | 100 | 99 | 96.8 | 100 |
| 4_34 | 100 | 100 | 100 | 100 | 100 | 100 |
| 3_34 | 100 | 100 | 100 | 100 | 100 | 100 |
| 9 | 99.5 | 99.5 | 99.5 | 99.5 | 99.5 | 99.5 |
| 2_9 | 100 | 100 | 100 | 100 | 100 | 100 |
| 1_9 | 99.5 | 98.4 | 100 | 100 | 100 | 100 |
| 9_237 | 100 | 100 | 100 | 100 | 100 | 100 |
| 4_9 | 100 | 100 | 100 | 100 | 100 | 100 |
| 3_9 | 100 | 100 | 100 | 100 | 100 | 100 |
| 143 | 98 | 98 | 98 | 98 | 98 | 98 |
| 2_143 | 100 | 100 | 100 | 100 | 100 | 100 |
| 1_143 | 100 | 100 | 100 | 100 | 100 | 100 |
| 237_143 | 100 | 100 | 100 | 99 | 96.8 | 100 |
| 4_143 | 100 | 100 | 100 | 100 | 100 | 100 |
| 3_143 | 100 | 100 | 100 | 100 | 100 | 100 |
| 13 | 99 | 99 | 99 | 99 | 99 | 99 |
| 2_13 | 99.5 | 98.4 | 100 | 100 | 100 | 100 |
| 1_13 | 99.5 | 98.4 | 100 | 100 | 100 | 100 |
| 237_13 | 100 | 100 | 100 | 100 | 100 | 100 |
| 4_13 | 99.5 | 98.4 | 100 | 100 | 100 | 100 |
| 3_13 | 100 | 100 | 100 | 100 | 100 | 100 |
| 125 | 98 | 98 | 98 | 98 | 98 | 98 |
| 2_125 | 99.5 | 98.4 | 100 | 100 | 100 | 100 |
| 1_125 | 100 | 100 | 100 | 100 | 100 | 100 |
| 237_125 | 99 | 96.8 | 100 | 99 | 96.8 | 100 |
| 4_125 | 99.5 | 98.4 | 100 | 99 | 96.8 | 100 |
| 3_125 | 99.5 | 98.4 | 100 | 100 | 100 | 100 |
| 236 | 100 | 100 | 100 | 100 | 100 | 100 |
| 2_236 | 100 | 100 | 100 | 100 | 100 | 100 |
| 1_236 | 100 | 100 | 100 | 100 | 100 | 100 |
| 237_236 | 99.5 | 98.4 | 100 | 99 | 96.8 | 100 |
| 4_236 | 100 | 100 | 100 | 99 | 96.8 | 100 |
| 3_236 | 100 | 100 | 100 | 100 | 100 | 100 |
| 46 | 95.4 | 95.4 | 95.4 | 95.4 | 95.4 | 95.4 |
| 2_46 | 99.5 | 98.4 | 100 | 100 | 100 | 100 |
| 1_46 | 99.5 | 98.4 | 100 | 100 | 100 | 100 |
| 237_46 | 99.5 | 98.4 | 100 | 98 | 93.5 | 100 |
| 4_46 | 100 | 100 | 100 | 99 | 96.8 | 100 |
| 3_46 | 100 | 100 | 100 | 100 | 100 | 100 |
| 32 | 97.5 | 97.5 | 97.5 | 97.5 | 97.5 | 97.5 |
| 2_32 | 99.5 | 98.4 | 100 | 100 | 100 | 100 |
| 1_32 | 100 | 100 | 100 | 100 | 100 | 100 |
| 237_32 | 99 | 96.8 | 100 | 99 | 96.8 | 100 |
| 4_32 | 99 | 96.8 | 100 | 98 | 93.5 | 100 |
| 3_32 | 100 | 100 | 100 | 100 | 100 | 100 |
| 62 | 95.4 | 95.4 | 95.4 | 95.4 | 95.4 | 95.4 |
| 2_62 | 99.5 | 98.4 | 100 | 100 | 100 | 100 |
| 1_62 | 99.5 | 98.4 | 100 | 100 | 100 | 100 |
| 237_62 | 99 | 96.7 | 100 | 99 | 96.8 | 100 |
| 4_62 | 99 | 96.7 | 100 | 98 | 93.5 | 100 |
| 3_62 | 100 | 100 | 100 | 99 | 96.8 | 100 |
| 88 | 94.9 | 94.9 | 94.9 | 94.9 | 94.9 | 94.9 |
| 2_88 | 100 | 100 | 100 | 100 | 100 | 100 |
| 1_88 | 99.5 | 98.4 | 100 | 100 | 100 | 100 |
| 237_88 | 100 | 100 | 100 | 99 | 96.8 | 100 |
| 4_88 | 100 | 100 | 100 | 100 | 100 | 100 |
| 3_88 | 100 | 100 | 100 | 100 | 100 | 100 |
| 52 | 95.4 | 95.4 | 95.4 | 95.4 | 95.4 | 95.4 |
| 2_52 | 100 | 100 | 100 | 100 | 100 | 100 |

TABLE 9-continued

| SEQ ID NO: | Training cohort ||| Validation cohort |||
|---|---|---|---|---|---|---|
| | Accuracy (%) | Sensitivity (%) | Specificity (%) | Accuracy (%) | Sensitivity (%) | Specificity (%) |
| 1_52 | 100 | 100 | 100 | 100 | 100 | 100 |
| 237_52 | 100 | 100 | 100 | 99 | 96.8 | 100 |
| 4_52 | 99 | 96.8 | 100 | 99 | 96.8 | 100 |
| 3_52 | 100 | 100 | 100 | 100 | 100 | 100 |
| 7 | 98.5 | 98.5 | 98.5 | 98.5 | 98.5 | 98.5 |
| 2_7 | 99.5 | 98.4 | 100 | 100 | 100 | 100 |
| 1_7 | 99.5 | 98.4 | 100 | 100 | 100 | 100 |
| 237_7 | 99.5 | 98.4 | 100 | 100 | 100 | 100 |
| 4_7 | 99.5 | 98.4 | 100 | 99 | 96.8 | 100 |
| 3_7 | 100 | 100 | 100 | 100 | 100 | 100 |
| 26 | 94.4 | 94.4 | 94.4 | 94.4 | 94.4 | 94.4 |
| 2_26 | 99.5 | 98.4 | 100 | 100 | 100 | 100 |
| 1_26 | 100 | 100 | 100 | 100 | 100 | 100 |
| 237_26 | 99.5 | 98.4 | 100 | 99 | 96.8 | 100 |
| 4_26 | 100 | 100 | 100 | 99 | 96.8 | 100 |
| 3_26 | 100 | 100 | 100 | 100 | 100 | 100 |
| 25 | 99 | 99 | 99 | 99 | 99 | 99 |
| 2_25 | 99.5 | 98.4 | 100 | 100 | 100 | 100 |
| 1_25 | 100 | 100 | 100 | 100 | 100 | 100 |
| 237_25 | 99.5 | 98.4 | 100 | 100 | 100 | 100 |
| 4_25 | 100 | 100 | 100 | 100 | 100 | 100 |
| 3_25 | 100 | 100 | 100 | 100 | 100 | 100 |
| 54 | 95.9 | 95.9 | 95.9 | 95.9 | 95.9 | 95.9 |
| 2_54 | 100 | 100 | 100 | 100 | 100 | 100 |
| 1_54 | 99.5 | 98.4 | 100 | 100 | 100 | 100 |
| 237_54 | 99 | 96.8 | 100 | 99 | 96.8 | 100 |
| 4_54 | 99.5 | 98.4 | 100 | 99 | 96.8 | 100 |
| 3_54 | 99.5 | 98.4 | 100 | 100 | 100 | 100 |
| 92 | 94.4 | 94.4 | 94.4 | 94.4 | 94.4 | 94.4 |
| 2_92 | 100 | 100 | 100 | 100 | 100 | 100 |
| 1_92 | 99.5 | 98.4 | 100 | 100 | 100 | 100 |
| 237_92 | 99.5 | 98.4 | 100 | 98 | 93.5 | 100 |
| 4_92 | 99 | 96.8 | 100 | 99 | 96.8 | 100 |
| 3_92 | 99.5 | 98.4 | 100 | 100 | 100 | 100 |
| 14 | 96.4 | 96.4 | 96.4 | 96.4 | 96.4 | 96.4 |
| 2_14 | 100 | 100 | 100 | 100 | 100 | 100 |
| 1_14 | 100 | 100 | 100 | 100 | 100 | 100 |
| 237_14 | 100 | 100 | 100 | 100 | 100 | 100 |
| 4_14 | 100 | 100 | 100 | 100 | 100 | 100 |
| 3_14 | 100 | 100 | 100 | 100 | 100 | 100 |
| 242 | 95.4 | 95.4 | 95.4 | 95.4 | 95.4 | 95.4 |
| 2_242 | 99.5 | 98.4 | 100 | 100 | 100 | 100 |
| 1_242 | 100 | 100 | 100 | 100 | 100 | 100 |
| 237_242 | 98.5 | 95.2 | 100 | 99 | 96.8 | 100 |
| 4_242 | 99.5 | 98.4 | 100 | 99 | 96.8 | 100 |
| 3_242 | 99.5 | 98.4 | 100 | 100 | 100 | 100 |
| 47 | 97 | 97 | 97 | 97 | 97 | 97 |
| 2_47 | 99.5 | 98.4 | 100 | 100 | 100 | 100 |
| 1_47 | 100 | 100 | 100 | 100 | 100 | 100 |
| 237_47 | 98.5 | 95.2 | 100 | 98 | 93.5 | 100 |
| 4_47 | 99 | 96.8 | 100 | 98 | 93.5 | 100 |
| 3_47 | 100 | 100 | 100 | 100 | 100 | 100 |
| 45 | 95.9 | 95.9 | 95.9 | 95.9 | 95.9 | 95.9 |
| 2_45 | 100 | 100 | 100 | 100 | 100 | 100 |
| 1_45 | 100 | 100 | 100 | 100 | 100 | 100 |
| 237_45 | 99 | 96.8 | 100 | 98 | 93.5 | 100 |
| 4_45 | 100 | 100 | 100 | 99 | 96.8 | 100 |
| 3_45 | 100 | 100 | 100 | 100 | 100 | 100 |
| 39 | 98.5 | 98.5 | 98.5 | 98.5 | 98.5 | 98.5 |
| 2_39 | 99.5 | 98.4 | 100 | 100 | 100 | 100 |
| 1_39 | 99.5 | 98.4 | 100 | 100 | 100 | 100 |
| 237_39 | 99 | 96.8 | 100 | 100 | 100 | 100 |
| 4_39 | 99 | 96.8 | 100 | 100 | 100 | 100 |
| 3_39 | 100 | 100 | 100 | 100 | 100 | 100 |
| 21 | 95.9 | 95.9 | 95.9 | 95.9 | 95.9 | 95.9 |
| 2_21 | 100 | 100 | 100 | 100 | 100 | 100 |
| 1_21 | 99.5 | 98.4 | 100 | 100 | 100 | 100 |
| 237_21 | 99.5 | 100 | 99.3 | 100 | 100 | 100 |
| 4_21 | 99.5 | 100 | 99.3 | 100 | 100 | 100 |
| 3_21 | 99.5 | 98.4 | 100 | 100 | 100 | 100 |
| 17 | 98 | 98 | 98 | 98 | 98 | 98 |
| 2_17 | 99.5 | 98.4 | 100 | 100 | 100 | 100 |
| 1_17 | 99.5 | 98.4 | 100 | 100 | 100 | 100 |
| 237_17 | 99.5 | 98.4 | 100 | 100 | 100 | 100 |
| 4_17 | 99.5 | 98.4 | 100 | 100 | 100 | 100 |

TABLE 9-continued

| SEQ ID NO: | Training cohort ||| Validation cohort |||
|---|---|---|---|---|---|---|
| | Accuracy (%) | Sensitivity (%) | Specificity (%) | Accuracy (%) | Sensitivity (%) | Specificity (%) |
| 3_17 | 99.5 | 98.4 | 100 | 100 | 100 | 100 |
| 83 | 96.4 | 96.4 | 96.4 | 96.4 | 96.4 | 96.4 |
| 2_83 | 99.5 | 98.4 | 100 | 100 | 100 | 100 |
| 1_83 | 99.5 | 98.4 | 100 | 100 | 100 | 100 |
| 237_83 | 99.5 | 98.4 | 100 | 99 | 96.8 | 100 |
| 4_83 | 100 | 100 | 100 | 100 | 100 | 100 |
| 3_83 | 99.5 | 98.4 | 100 | 100 | 100 | 100 |
| 149 | 94.9 | 94.9 | 94.9 | 94.9 | 94.9 | 94.9 |
| 2_149 | 99.5 | 98.4 | 100 | 100 | 100 | 100 |
| 1_149 | 99.5 | 98.4 | 100 | 100 | 100 | 100 |
| 237_149 | 99.5 | 98.4 | 100 | 99 | 96.8 | 100 |
| 4_149 | 99.5 | 98.4 | 100 | 99 | 96.8 | 100 |
| 3_149 | 99.5 | 98.4 | 100 | 100 | 100 | 100 |
| 246 | 94.4 | 94.4 | 94.4 | 94.4 | 94.4 | 94.4 |
| 2_246 | 99.5 | 98.4 | 100 | 100 | 100 | 100 |
| 1_246 | 99.5 | 98.4 | 100 | 100 | 100 | 100 |
| 237_246 | 98.5 | 95.2 | 100 | 98 | 93.5 | 100 |
| 4_246 | 99 | 96.8 | 100 | 98 | 93.5 | 100 |
| 3_246 | 100 | 100 | 100 | 100 | 100 | 100 |
| 22 | 94.9 | 94.9 | 94.9 | 94.9 | 94.9 | 94.9 |
| 2_22 | 100 | 100 | 100 | 100 | 100 | 100 |
| 1_22 | 99.5 | 98.4 | 100 | 100 | 100 | 100 |
| 237_22 | 99.5 | 98.4 | 100 | 100 | 100 | 100 |
| 4_22 | 99.5 | 98.4 | 100 | 99 | 96.8 | 100 |
| 3_22 | 100 | 100 | 100 | 100 | 100 | 100 |
| 55 | 98.5 | 98.5 | 98.5 | 98.5 | 98.5 | 98.5 |
| 2_55 | 99.5 | 98.4 | 100 | 100 | 100 | 100 |
| 1_55 | 100 | 100 | 100 | 100 | 100 | 100 |
| 237_55 | 99 | 96.8 | 100 | 100 | 100 | 100 |
| 4_55 | 99 | 96.8 | 100 | 100 | 100 | 100 |
| 3_55 | 100 | 100 | 100 | 100 | 100 | 100 |
| 182 | 97 | 97 | 97 | 97 | 97 | 97 |
| 2_182 | 99.5 | 98.4 | 100 | 100 | 100 | 100 |
| 1_182 | 99.5 | 98.4 | 100 | 100 | 100 | 100 |
| 237_182 | 100 | 100 | 100 | 100 | 100 | 100 |
| 4_182 | 100 | 100 | 100 | 100 | 100 | 100 |
| 3_182 | 100 | 100 | 100 | 100 | 100 | 100 |
| 73 | 98 | 98 | 98 | 98 | 98 | 98 |
| 2_73 | 99.5 | 98.4 | 100 | 100 | 100 | 100 |
| 1_73 | 100 | 100 | 100 | 100 | 100 | 100 |
| 237_73 | 99 | 96.8 | 100 | 99 | 96.8 | 100 |
| 4_73 | 99.5 | 98.4 | 100 | 99 | 96.8 | 100 |
| 3_73 | 100 | 100 | 100 | 100 | 100 | 100 |
| 77 | 93.9 | 93.9 | 93.9 | 93.9 | 93.9 | 93.9 |
| 2_77 | 99.5 | 98.4 | 100 | 100 | 100 | 100 |
| 1_77 | 99.5 | 98.4 | 100 | 100 | 100 | 100 |
| 237_77 | 99.5 | 98.4 | 100 | 99 | 96.8 | 100 |
| 4_77 | 99 | 96.8 | 100 | 98 | 93.5 | 100 |
| 3_77 | 100 | 100 | 100 | 100 | 100 | 100 |
| 24 | 94.4 | 94.4 | 94.4 | 94.4 | 94.4 | 94.4 |
| 2_24 | 100 | 100 | 100 | 100 | 100 | 100 |
| 1_24 | 99.5 | 98.4 | 100 | 100 | 100 | 100 |
| 237_24 | 100 | 100 | 100 | 100 | 100 | 100 |
| 4_24 | 100 | 100 | 100 | 100 | 100 | 100 |
| 3_24 | 99.5 | 98.4 | 100 | 99 | 96.8 | 100 |
| 103 | 92.4 | 92.4 | 92.4 | 92.4 | 92.4 | 92.4 |
| 2_103 | 100 | 100 | 100 | 100 | 100 | 100 |
| 1_103 | 100 | 100 | 100 | 100 | 100 | 100 |
| 237_103 | 99 | 96.8 | 100 | 98 | 93.5 | 100 |
| 4_103 | 99 | 96.8 | 100 | 99 | 96.8 | 100 |
| 3_103 | 100 | 100 | 100 | 100 | 100 | 100 |
| 49 | 94.4 | 94.4 | 94.4 | 94.4 | 94.4 | 94.4 |
| 2_49 | 100 | 100 | 100 | 100 | 100 | 100 |
| 1_49 | 100 | 100 | 100 | 100 | 100 | 100 |
| 237_49 | 99.5 | 98.4 | 100 | 98 | 93.5 | 100 |
| 4_49 | 100 | 100 | 100 | 99 | 96.8 | 100 |
| 3_49 | 100 | 100 | 100 | 100 | 100 | 100 |
| 239 | 98 | 98 | 98 | 98 | 98 | 98 |
| 2_239 | 100 | 100 | 100 | 100 | 100 | 100 |
| 1_239 | 100 | 100 | 100 | 100 | 100 | 100 |
| 237_239 | 100 | 100 | 100 | 100 | 100 | 100 |
| 4_239 | 100 | 100 | 100 | 100 | 100 | 100 |
| 3_239 | 100 | 100 | 100 | 100 | 100 | 100 |
| 23 | 89.3 | 89.3 | 89.3 | 89.3 | 89.3 | 89.3 |
| 2_23 | 100 | 100 | 100 | 100 | 100 | 100 |

TABLE 9-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_23 | 100 | 100 | 100 | 100 | 100 | 100 |
| 237_23 | 99.5 | 98.4 | 100 | 100 | 100 | 100 |
| 4_23 | 100 | 100 | 100 | 100 | 100 | 100 |
| 3_23 | 100 | 100 | 100 | 100 | 100 | 100 |
| 58 | 94.4 | 94.4 | 94.4 | 94.4 | 94.4 | 94.4 |
| 2_58 | 99.5 | 98.4 | 100 | 100 | 100 | 100 |
| 1_58 | 100 | 100 | 100 | 100 | 100 | 100 |
| 237_58 | 100 | 100 | 100 | 99 | 96.8 | 100 |
| 4_58 | 100 | 100 | 100 | 99 | 96.8 | 100 |
| 3_58 | 100 | 100 | 100 | 100 | 100 | 100 |
| 211 | 93.4 | 93.4 | 93.4 | 93.4 | 93.4 | 93.4 |
| 2_211 | 99.5 | 98.4 | 100 | 100 | 100 | 100 |
| 1_211 | 99.5 | 98.4 | 100 | 100 | 100 | 100 |
| 237_211 | 100 | 100 | 100 | 96.9 | 90.3 | 100 |
| 4_211 | 99.5 | 98.4 | 100 | 99 | 96.8 | 100 |
| 3_211 | 99.5 | 98.4 | 100 | 100 | 100 | 100 |
| 147 | 93.4 | 93.4 | 93.4 | 93.4 | 93.4 | 93.4 |
| 2_147 | 100 | 100 | 100 | 100 | 100 | 100 |
| 1_147 | 99.5 | 98.4 | 100 | 100 | 100 | 100 |
| 237_147 | 100 | 100 | 100 | 100 | 100 | 100 |
| 4_147 | 99.5 | 98.4 | 100 | 100 | 100 | 100 |
| 3_147 | 99.5 | 98.4 | 100 | 100 | 100 | 100 |
| 65 | 90.9 | 90.9 | 90.9 | 90.9 | 90.9 | 90.9 |
| 2_65 | 99.5 | 98.4 | 100 | 100 | 100 | 100 |
| 1_65 | 99.5 | 98.4 | 100 | 100 | 100 | 100 |
| 237_65 | 99 | 96.8 | 100 | 98 | 93.5 | 100 |
| 4_65 | 99 | 96.8 | 100 | 98 | 93.5 | 100 |
| 3_65 | 99.5 | 98.4 | 100 | 100 | 100 | 100 |
| 31 | 91.9 | 91.9 | 91.9 | 91.9 | 91.9 | 91.9 |
| 2_31 | 99.5 | 98.4 | 100 | 100 | 100 | 100 |
| 1_31 | 99.5 | 98.4 | 100 | 100 | 100 | 100 |
| 237_31 | 99.5 | 98.4 | 100 | 99 | 96.8 | 100 |
| 4_31 | 99 | 96.8 | 100 | 99 | 96.8 | 100 |
| 3_31 | 99.5 | 98.4 | 100 | 100 | 100 | 100 |
| 72 | 90.4 | 90.4 | 90.4 | 90.4 | 90.4 | 90.4 |
| 2_72 | 99.5 | 98.4 | 100 | 100 | 100 | 100 |
| 1_72 | 100 | 100 | 100 | 100 | 100 | 100 |
| 237_72 | 98.5 | 95.2 | 100 | 100 | 100 | 100 |
| 4_72 | 99.5 | 98.4 | 100 | 100 | 100 | 100 |
| 3_72 | 100 | 100 | 100 | 100 | 100 | 100 |
| 63 | 87.8 | 87.8 | 87.8 | 87.8 | 87.8 | 87.8 |
| 2_63 | 100 | 100 | 100 | 100 | 100 | 100 |
| 1_63 | 99.5 | 98.4 | 100 | 100 | 100 | 100 |
| 237_63 | 99.5 | 98.4 | 100 | 98 | 93.5 | 100 |
| 4_63 | 99.5 | 98.4 | 100 | 99 | 96.8 | 100 |
| 3_63 | 99.5 | 98.4 | 100 | 100 | 100 | 100 |
| 80 | 88.3 | 88.3 | 88.3 | 88.3 | 88.3 | 88.3 |
| 2_80 | 100 | 100 | 100 | 100 | 100 | 100 |
| 1_80 | 99.5 | 98.4 | 100 | 100 | 100 | 100 |
| 237_80 | 100 | 100 | 100 | 100 | 100 | 100 |
| 4_80 | 100 | 100 | 100 | 99 | 96.8 | 100 |
| 3_80 | 99.5 | 98.4 | 100 | 100 | 100 | 100 |
| 37 | 97 | 97 | 97 | 97 | 97 | 97 |
| 2_37 | 99.5 | 98.4 | 100 | 100 | 100 | 100 |
| 1_37 | 99.5 | 98.4 | 100 | 100 | 100 | 100 |
| 237_37 | 99.5 | 98.4 | 100 | 100 | 100 | 100 |
| 4_37 | 99.5 | 98.4 | 100 | 99 | 96.8 | 100 |
| 3_37 | 100 | 100 | 100 | 100 | 100 | 100 |
| 67 | 92.4 | 92.4 | 92.4 | 92.4 | 92.4 | 92.4 |
| 2_67 | 99.5 | 98.4 | 100 | 100 | 100 | 100 |
| 1_67 | 100 | 100 | 100 | 100 | 100 | 100 |
| 237_67 | 98.5 | 95.2 | 100 | 99 | 96.8 | 100 |
| 4_67 | 99 | 96.8 | 100 | 99 | 96.8 | 100 |
| 3_67 | 100 | 100 | 100 | 100 | 100 | 100 |
| 232 | 90.9 | 90.9 | 90.9 | 90.9 | 90.9 | 90.9 |
| 2_232 | 99.5 | 98.4 | 100 | 100 | 100 | 100 |
| 1_232 | 99.5 | 98.4 | 100 | 100 | 100 | 100 |
| 237_232 | 99.5 | 98.4 | 100 | 98 | 93.5 | 100 |
| 4_232 | 99 | 96.8 | 100 | 99 | 96.8 | 100 |
| 3_232 | 99.5 | 98.4 | 100 | 100 | 100 | 100 |
| 127 | 83.8 | 83.8 | 83.8 | 83.8 | 83.8 | 83.8 |
| 2_127 | 99.5 | 98.4 | 100 | 100 | 100 | 100 |
| 1_127 | 100 | 100 | 100 | 100 | 100 | 100 |
| 237_127 | 98.5 | 95.2 | 100 | 98 | 93.5 | 100 |
| 4_127 | 99 | 96.8 | 100 | 98 | 93.5 | 100 |

TABLE 9-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 3_127 | 100 | 100 | 100 | 99 | 96.8 | 100 |
| 145 | 91.9 | 91.9 | 91.9 | 91.9 | 91.9 | 91.9 |
| 2_145 | 100 | 100 | 100 | 100 | 100 | 100 |
| 1_145 | 99.5 | 98.4 | 100 | 100 | 100 | 100 |
| 237_145 | 100 | 100 | 100 | 99 | 96.8 | 100 |
| 4_145 | 99.5 | 98.4 | 100 | 100 | 100 | 100 |
| 3_145 | 100 | 100 | 100 | 100 | 100 | 100 |
| 16 | 98.5 | 98.5 | 98.5 | 98.5 | 98.5 | 98.5 |
| 2_16 | 100 | 100 | 100 | 100 | 100 | 100 |
| 1_16 | 99.5 | 98.4 | 100 | 100 | 100 | 100 |
| 237_16 | 100 | 100 | 100 | 100 | 100 | 100 |
| 4_16 | 100 | 100 | 100 | 99 | 96.8 | 100 |
| 3_16 | 99.5 | 98.4 | 100 | 99 | 96.8 | 100 |
| 11 | 99.5 | 99.5 | 99.5 | 99.5 | 99.5 | 99.5 |
| 2_11 | 100 | 100 | 100 | 100 | 100 | 100 |
| 1_11 | 99.5 | 98.4 | 100 | 100 | 100 | 100 |
| 237_11 | 100 | 100 | 100 | 100 | 100 | 100 |
| 4_11 | 100 | 100 | 100 | 100 | 100 | 100 |
| 3_11 | 100 | 100 | 100 | 100 | 100 | 100 |
| 186 | 87.3 | 87.3 | 87.3 | 87.3 | 87.3 | 87.3 |
| 2_186 | 99.5 | 98.4 | 100 | 100 | 100 | 100 |
| 1_186 | 99.5 | 98.4 | 100 | 100 | 100 | 100 |
| 237_186 | 98.5 | 95.2 | 100 | 96.9 | 90.3 | 100 |
| 4_186 | 99.5 | 98.4 | 100 | 99 | 96.8 | 100 |
| 3_186 | 100 | 100 | 100 | 100 | 100 | 100 |
| 50 | 98.5 | 98.5 | 98.5 | 98.5 | 98.5 | 98.5 |
| 2_50 | 100 | 100 | 100 | 100 | 100 | 100 |
| 1_50 | 99.5 | 98.4 | 100 | 100 | 100 | 100 |
| 237_50 | 100 | 100 | 100 | 100 | 100 | 100 |
| 4_50 | 100 | 100 | 100 | 100 | 100 | 100 |
| 3_50 | 100 | 100 | 100 | 100 | 100 | 100 |
| 69 | 90.9 | 90.9 | 90.9 | 90.9 | 90.9 | 90.9 |
| 2_69 | 99.5 | 98.4 | 100 | 100 | 100 | 100 |
| 1_69 | 99.5 | 98.4 | 100 | 100 | 100 | 100 |
| 237_69 | 98.5 | 95.2 | 100 | 98 | 93.5 | 100 |
| 4_69 | 99 | 96.8 | 100 | 98 | 93.5 | 100 |
| 3_69 | 100 | 100 | 100 | 100 | 100 | 100 |
| 33 | 81.2 | 81.2 | 81.2 | 81.2 | 81.2 | 81.2 |
| 2_33 | 100 | 100 | 100 | 100 | 100 | 100 |
| 1_33 | 99.5 | 98.4 | 100 | 100 | 100 | 100 |
| 237_33 | 100 | 100 | 100 | 100 | 100 | 100 |
| 4_33 | 100 | 100 | 100 | 100 | 100 | 100 |
| 3_33 | 99.5 | 98.4 | 100 | 100 | 100 | 100 |
| 247 | 89.3 | 89.3 | 89.3 | 89.3 | 89.3 | 89.3 |
| 2_247 | 100 | 100 | 100 | 100 | 100 | 100 |
| 1_247 | 100 | 100 | 100 | 100 | 100 | 100 |
| 237_247 | 98.5 | 95.2 | 100 | 98 | 93.5 | 100 |
| 4_247 | 99 | 96.8 | 100 | 99 | 96.8 | 100 |
| 3_247 | 100 | 100 | 100 | 100 | 100 | 100 |
| 36 | 93.9 | 93.9 | 93.9 | 93.9 | 93.9 | 93.9 |
| 2_36 | 99.5 | 98.4 | 100 | 100 | 100 | 100 |
| 1_36 | 99.5 | 98.4 | 100 | 100 | 100 | 100 |
| 237_36 | 100 | 100 | 100 | 99 | 96.8 | 100 |
| 4_36 | 99 | 96.8 | 100 | 98 | 93.5 | 100 |
| 3_36 | 100 | 100 | 100 | 100 | 100 | 100 |
| 218 | 89.3 | 89.3 | 89.3 | 89.3 | 89.3 | 89.3 |
| 2_218 | 99.5 | 98.4 | 100 | 100 | 100 | 100 |
| 1_218 | 99.5 | 98.4 | 100 | 100 | 100 | 100 |
| 237_218 | 99 | 96.8 | 100 | 100 | 100 | 100 |
| 4_218 | 99 | 96.8 | 100 | 99 | 96.8 | 100 |
| 3_218 | 100 | 100 | 100 | 100 | 100 | 100 |
| 43 | 82.7 | 82.7 | 82.7 | 82.7 | 82.7 | 82.7 |
| 2_43 | 99.5 | 98.4 | 100 | 100 | 100 | 100 |
| 1_43 | 99.5 | 98.4 | 100 | 100 | 100 | 100 |
| 237_43 | 100 | 100 | 100 | 99 | 96.8 | 100 |
| 4_43 | 99.5 | 98.4 | 100 | 99 | 96.8 | 100 |
| 3_43 | 99.5 | 98.4 | 100 | 100 | 100 | 100 |
| 29 | 96.4 | 96.4 | 96.4 | 96.4 | 96.4 | 96.4 |
| 2_29 | 99.5 | 98.4 | 100 | 100 | 100 | 100 |
| 1_29 | 99.5 | 98.4 | 100 | 100 | 100 | 100 |
| 237_29 | 98.5 | 95.2 | 100 | 100 | 100 | 100 |
| 4_29 | 99.5 | 98.4 | 100 | 100 | 100 | 100 |
| 3_29 | 100 | 100 | 100 | 100 | 100 | 100 |
| 110 | 83.8 | 83.8 | 83.8 | 83.8 | 83.8 | 83.8 |
| 2_110 | 99.5 | 98.4 | 100 | 100 | 100 | 100 |

TABLE 9-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_110 | 99.5 | 98.4 | 100 | 100 | 100 | 100 |
| 237_110 | 99 | 96.8 | 100 | 96.9 | 90.3 | 100 |
| 4_110 | 99 | 96.8 | 100 | 99 | 96.8 | 100 |
| 3_110 | 99.5 | 98.4 | 100 | 99 | 96.8 | 100 |
| 20 | 95.9 | 95.9 | 95.9 | 95.9 | 95.9 | 95.9 |
| 2_20 | 100 | 100 | 100 | 100 | 100 | 100 |
| 1_20 | 100 | 100 | 100 | 100 | 100 | 100 |
| 237_20 | 99 | 96.7 | 100 | 99 | 96.8 | 100 |
| 4_20 | 99.5 | 98.4 | 100 | 98 | 93.5 | 100 |
| 3_20 | 100 | 100 | 100 | 100 | 100 | 100 |
| 157 | 89.3 | 89.3 | 89.3 | 89.3 | 89.3 | 89.3 |
| 2_157 | 100 | 100 | 100 | 100 | 100 | 100 |
| 1_157 | 99.5 | 98.4 | 100 | 100 | 100 | 100 |
| 237_157 | 100 | 100 | 100 | 98 | 93.5 | 100 |
| 4_157 | 99 | 96.8 | 100 | 99 | 96.8 | 100 |
| 3_157 | 100 | 100 | 100 | 100 | 100 | 100 |
| 75 | 90.9 | 90.9 | 90.9 | 90.9 | 90.9 | 90.9 |
| 2_75 | 100 | 100 | 100 | 100 | 100 | 100 |
| 1_75 | 99.5 | 98.4 | 100 | 100 | 100 | 100 |
| 237_75 | 99.5 | 98.4 | 100 | 100 | 100 | 100 |
| 4_75 | 100 | 100 | 100 | 100 | 100 | 100 |
| 3_75 | 99.5 | 98.4 | 100 | 100 | 100 | 100 |
| 82 | 89.3 | 89.3 | 89.3 | 89.3 | 89.3 | 89.3 |
| 2_82 | 100 | 100 | 100 | 100 | 100 | 100 |
| 1_82 | 99.5 | 98.4 | 100 | 100 | 100 | 100 |
| 237_82 | 99 | 96.8 | 100 | 98 | 93.5 | 100 |
| 4_82 | 100 | 100 | 100 | 99 | 96.8 | 100 |
| 3_82 | 100 | 100 | 100 | 100 | 100 | 100 |
| 106 | 89.3 | 89.3 | 89.3 | 89.3 | 89.3 | 89.3 |
| 2_106 | 99.5 | 98.4 | 100 | 100 | 100 | 100 |
| 1_106 | 100 | 100 | 100 | 100 | 100 | 100 |
| 237_106 | 99 | 96.8 | 100 | 99 | 96.8 | 100 |
| 4_106 | 99.5 | 98.4 | 100 | 100 | 100 | 100 |
| 3_106 | 100 | 100 | 100 | 100 | 100 | 100 |
| 111 | 81.7 | 81.7 | 81.7 | 81.7 | 81.7 | 81.7 |
| 2_111 | 99.5 | 98.4 | 100 | 100 | 100 | 100 |
| 1_111 | 99.5 | 98.4 | 100 | 100 | 100 | 100 |
| 237_111 | 98.5 | 95.2 | 100 | 98 | 93.5 | 100 |
| 4_111 | 99 | 96.8 | 100 | 99 | 96.8 | 100 |
| 3_111 | 99.5 | 98.4 | 100 | 100 | 100 | 100 |
| 96 | 86.3 | 86.3 | 86.3 | 86.3 | 86.3 | 86.3 |
| 2_96 | 99.5 | 98.4 | 100 | 100 | 100 | 100 |
| 1_96 | 99.5 | 98.4 | 100 | 100 | 100 | 100 |
| 237_96 | 99 | 96.8 | 100 | 99 | 96.8 | 100 |
| 4_96 | 99 | 96.8 | 100 | 99 | 96.8 | 100 |
| 3_96 | 99.5 | 98.4 | 100 | 100 | 100 | 100 |
| 266 | 87.8 | 87.8 | 87.8 | 87.8 | 87.8 | 87.8 |
| 2_266 | 99.5 | 98.4 | 100 | 100 | 100 | 100 |
| 1_266 | 99.5 | 98.4 | 100 | 100 | 100 | 100 |
| 237_266 | 99 | 96.8 | 100 | 98 | 93.5 | 100 |
| 4_266 | 99.5 | 98.4 | 100 | 99 | 96.8 | 100 |
| 3_266 | 99.5 | 98.4 | 100 | 99 | 96.8 | 100 |
| 124 | 91.9 | 91.9 | 91.9 | 91.9 | 91.9 | 91.9 |
| 2_124 | 100 | 100 | 100 | 100 | 100 | 100 |
| 1_124 | 99.5 | 98.4 | 100 | 100 | 100 | 100 |
| 237_124 | 100 | 100 | 100 | 100 | 100 | 100 |
| 4_124 | 100 | 100 | 100 | 100 | 100 | 100 |
| 3_124 | 99.5 | 98.4 | 100 | 100 | 100 | 100 |
| 68 | 81.2 | 81.2 | 81.2 | 81.2 | 81.2 | 81.2 |
| 2_68 | 99.5 | 98.4 | 100 | 100 | 100 | 100 |
| 1_68 | 99.5 | 98.4 | 100 | 100 | 100 | 100 |
| 237_68 | 99 | 96.8 | 100 | 99 | 96.8 | 100 |
| 4_68 | 99 | 96.8 | 100 | 99 | 96.8 | 100 |
| 3_68 | 99.5 | 98.4 | 100 | 100 | 100 | 100 |
| 71 | 86.8 | 86.8 | 86.8 | 86.8 | 86.8 | 86.8 |
| 2_71 | 100 | 100 | 100 | 100 | 100 | 100 |
| 1_71 | 99.5 | 98.4 | 100 | 100 | 100 | 100 |
| 237_71 | 99 | 96.8 | 100 | 96.9 | 90.3 | 100 |
| 4_71 | 99 | 96.8 | 100 | 99 | 96.8 | 100 |
| 3_71 | 100 | 100 | 100 | 99 | 96.8 | 100 |
| 35 | 90.4 | 90.4 | 90.4 | 90.4 | 90.4 | 90.4 |
| 2_35 | 99.5 | 98.4 | 100 | 100 | 100 | 100 |
| 1_35 | 99.5 | 98.4 | 100 | 100 | 100 | 100 |
| 237_35 | 99.5 | 98.4 | 100 | 100 | 100 | 100 |
| 4_35 | 99.5 | 98.4 | 100 | 100 | 100 | 100 |

TABLE 9-continued

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 3_35 | 99.5 | 98.4 | 100 | 100 | 100 | 100 |
| 173 | 82.2 | 82.2 | 82.2 | 82.2 | 82.2 | 82.2 |
| 2_173 | 99.5 | 98.4 | 100 | 100 | 100 | 100 |
| 1_173 | 99.5 | 98.4 | 100 | 100 | 100 | 100 |
| 237_173 | 98.5 | 95.2 | 100 | 98 | 93.5 | 100 |
| 4_173 | 99 | 96.8 | 100 | 98 | 93.5 | 100 |
| 3_173 | 99.5 | 98.4 | 100 | 100 | 100 | 100 |
| 5 | 94.4 | 94.4 | 94.4 | 94.4 | 94.4 | 94.4 |
| 2_5 | 100 | 100 | 100 | 100 | 100 | 100 |
| 1_5 | 99.5 | 98.4 | 100 | 100 | 100 | 100 |
| 237_5 | 100 | 100 | 100 | 100 | 100 | 100 |
| 4_5 | 100 | 100 | 100 | 100 | 100 | 100 |
| 3_5 | 99.5 | 98.4 | 100 | 100 | 100 | 100 |
| 851 | 81.7 | 81.7 | 81.7 | 81.7 | 81.7 | 81.7 |
| 2_851 | 99.5 | 98.4 | 100 | 100 | 100 | 100 |
| 1_851 | 99.5 | 98.4 | 100 | 100 | 100 | 100 |
| 237_851 | 99 | 96.8 | 100 | 98 | 93.5 | 100 |
| 4_851 | 99 | 96.8 | 100 | 99 | 96.8 | 100 |
| 3_851 | 99.5 | 98.4 | 100 | 100 | 100 | 100 |
| 852 | 85.8 | 85.8 | 85.8 | 85.8 | 85.8 | 85.8 |
| 2_852 | 100 | 100 | 100 | 100 | 100 | 100 |
| 1_852 | 99.5 | 98.4 | 100 | 100 | 100 | 100 |
| 237_852 | 99 | 96.8 | 100 | 98 | 93.5 | 100 |
| 4_852 | 99 | 96.8 | 100 | 99 | 96.8 | 100 |
| 3_852 | 100 | 100 | 100 | 100 | 100 | 100 |
| 30 | 93.4 | 93.4 | 93.4 | 93.4 | 93.4 | 93.4 |
| 2_30 | 100 | 100 | 100 | 100 | 100 | 100 |
| 1_30 | 99.5 | 98.4 | 100 | 100 | 100 | 100 |
| 237_30 | 99 | 96.8 | 100 | 100 | 100 | 100 |
| 4_30 | 99.5 | 98.4 | 100 | 99 | 96.8 | 100 |
| 3_30 | 99.5 | 98.4 | 100 | 100 | 100 | 100 |
| 93 | 88.8 | 88.8 | 88.8 | 88.8 | 88.8 | 88.8 |
| 2_93 | 99.5 | 98.4 | 100 | 100 | 100 | 100 |
| 1_93 | 99.5 | 98.4 | 100 | 100 | 100 | 100 |
| 237_93 | 99.5 | 98.4 | 100 | 100 | 100 | 100 |
| 4_93 | 100 | 100 | 100 | 100 | 100 | 100 |
| 3_93 | 99.5 | 98.4 | 100 | 100 | 100 | 100 |
| 27 | 98.5 | 98.5 | 98.5 | 98.5 | 98.5 | 98.5 |
| 2_27 | 100 | 100 | 100 | 100 | 100 | 100 |
| 1_27 | 99.5 | 98.4 | 100 | 100 | 100 | 100 |
| 237_27 | 100 | 100 | 100 | 100 | 100 | 100 |
| 4_27 | 99.5 | 98.4 | 100 | 99 | 96.8 | 100 |
| 27_208 | 99 | 98.4 | 99.3 | 98 | 96.8 | 98.5 |
| 853 | 79.2 | 79.2 | 79.2 | 79.2 | 79.2 | 79.2 |
| 2_853 | 99.5 | 98.4 | 100 | 100 | 100 | 100 |
| 1_853 | 99.5 | 98.4 | 100 | 100 | 100 | 100 |
| 237_853 | 98.5 | 95.2 | 100 | 98 | 93.5 | 100 |
| 4_853 | 99 | 96.8 | 100 | 99 | 96.8 | 100 |
| 3_853 | 99.5 | 98.4 | 100 | 100 | 100 | 100 |
| 238 | 97.5 | 97.5 | 97.5 | 97.5 | 97.5 | 97.5 |
| 2_238 | 100 | 100 | 100 | 100 | 100 | 100 |
| 1_238 | 100 | 100 | 100 | 100 | 100 | 100 |
| 237_238 | 99 | 96.8 | 100 | 99 | 96.8 | 100 |
| 4_238 | 99 | 96.8 | 100 | 99 | 96.8 | 100 |
| 3_238 | 100 | 100 | 100 | 100 | 100 | 100 |
| 130 | 80.7 | 80.7 | 80.7 | 80.7 | 80.7 | 80.7 |
| 2_130 | 100 | 100 | 100 | 100 | 100 | 100 |
| 1_130 | 99.5 | 98.4 | 100 | 100 | 100 | 100 |
| 237_130 | 99 | 96.8 | 100 | 99 | 96.8 | 100 |
| 4_130 | 99 | 96.8 | 100 | 99 | 96.8 | 100 |
| 3_130 | 99.5 | 98.4 | 100 | 100 | 100 | 100 |
| 177 | 81.7 | 81.7 | 81.7 | 81.7 | 81.7 | 81.7 |
| 2_177 | 100 | 100 | 100 | 100 | 100 | 100 |
| 1_177 | 99.5 | 98.4 | 100 | 100 | 100 | 100 |
| 237_177 | 99 | 96.8 | 100 | 99 | 96.8 | 100 |
| 4_177 | 99.5 | 98.4 | 100 | 99 | 96.8 | 100 |
| 3_177 | 99.5 | 98.4 | 100 | 99 | 96.8 | 100 |
| 64 | 87.3 | 87.3 | 87.3 | 87.3 | 87.3 | 87.3 |
| 2_64 | 99.5 | 98.4 | 100 | 100 | 100 | 100 |
| 1_64 | 99.5 | 98.4 | 100 | 100 | 100 | 100 |
| 237_64 | 99.5 | 98.4 | 100 | 100 | 100 | 100 |
| 4_64 | 99.5 | 98.4 | 100 | 100 | 100 | 100 |
| 3_64 | 99.5 | 98.4 | 100 | 100 | 100 | 100 |
| 114 | 95.4 | 95.4 | 95.4 | 95.4 | 95.4 | 95.4 |
| 2_114 | 100 | 100 | 100 | 99 | 100 | 98.5 |

TABLE 9-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_114 | 99.5 | 98.4 | 100 | 99 | 100 | 98.5 |
| 237_114 | 99.5 | 98.4 | 100 | 99 | 100 | 98.5 |
| 4_114 | 100 | 100 | 100 | 99 | 100 | 98.5 |
| 3_114 | 99.5 | 98.4 | 100 | 99 | 100 | 98.5 |
| 119 | 92.4 | 92.4 | 92.4 | 92.4 | 92.4 | 92.4 |
| 2_119 | 100 | 100 | 100 | 100 | 100 | 100 |
| 1_119 | 99.5 | 98.4 | 100 | 100 | 100 | 100 |
| 237_119 | 100 | 100 | 100 | 99 | 96.8 | 100 |
| 4_119 | 100 | 100 | 100 | 100 | 100 | 100 |
| 3_119 | 99.5 | 98.4 | 100 | 100 | 100 | 100 |
| 135 | 87.8 | 87.8 | 87.8 | 87.8 | 87.8 | 87.8 |
| 2_135 | 99.5 | 98.4 | 100 | 100 | 100 | 100 |
| 1_135 | 99.5 | 98.4 | 100 | 100 | 100 | 100 |
| 237_135 | 99.5 | 98.4 | 100 | 96.9 | 90.3 | 100 |
| 4_135 | 99.5 | 98.4 | 100 | 99 | 96.8 | 100 |
| 3_135 | 99.5 | 98.4 | 100 | 99 | 96.8 | 100 |
| 243 | 93.9 | 93.9 | 93.9 | 93.9 | 93.9 | 93.9 |
| 2_243 | 99.5 | 98.4 | 100 | 100 | 100 | 100 |
| 1_243 | 99.5 | 98.4 | 100 | 100 | 100 | 100 |
| 237_243 | 99.5 | 98.4 | 100 | 99 | 96.8 | 100 |
| 4_243 | 99.5 | 98.4 | 100 | 100 | 100 | 100 |
| 3_243 | 100 | 100 | 100 | 100 | 100 | 100 |
| 122 | 87.8 | 87.8 | 87.8 | 87.8 | 87.8 | 87.8 |
| 2_122 | 99.5 | 98.4 | 100 | 100 | 100 | 100 |
| 1_122 | 99.5 | 98.4 | 100 | 100 | 100 | 100 |
| 237_122 | 98.5 | 95.2 | 100 | 96.9 | 90.3 | 100 |
| 4_122 | 99 | 96.8 | 100 | 99 | 96.8 | 100 |
| 3_122 | 100 | 100 | 100 | 100 | 100 | 100 |
| 260 | 90.9 | 90.9 | 90.9 | 90.9 | 90.9 | 90.9 |
| 2_260 | 99.5 | 98.4 | 100 | 100 | 100 | 100 |
| 1_260 | 99.5 | 98.4 | 100 | 100 | 100 | 100 |
| 237_260 | 99.5 | 98.4 | 100 | 96.9 | 90.3 | 100 |
| 4_260 | 99.5 | 98.4 | 100 | 99 | 96.8 | 100 |
| 3_260 | 99.5 | 98.4 | 100 | 99 | 96.8 | 100 |
| 59 | 91.9 | 91.9 | 91.9 | 91.9 | 91.9 | 91.9 |
| 2_59 | 99.5 | 98.4 | 100 | 100 | 100 | 100 |
| 1_59 | 99.5 | 98.4 | 100 | 100 | 100 | 100 |
| 237_59 | 99.5 | 98.4 | 100 | 100 | 100 | 100 |
| 4_59 | 99 | 96.8 | 100 | 99 | 96.8 | 100 |
| 3_59 | 99.5 | 98.4 | 100 | 100 | 100 | 100 |
| 854 | 77.7 | 77.7 | 77.7 | 77.7 | 77.7 | 77.7 |
| 2_854 | 99.5 | 98.4 | 100 | 100 | 100 | 100 |
| 1_854 | 99.5 | 98.4 | 100 | 100 | 100 | 100 |
| 237_854 | 99.5 | 98.4 | 100 | 99 | 96.8 | 100 |
| 4_854 | 99 | 96.8 | 100 | 99 | 96.8 | 100 |
| 3_854 | 99.5 | 98.4 | 100 | 100 | 100 | 100 |
| 132 | 91.4 | 91.4 | 91.4 | 91.4 | 91.4 | 91.4 |
| 2_132 | 100 | 100 | 100 | 100 | 100 | 100 |
| 1_132 | 99.5 | 98.4 | 100 | 100 | 100 | 100 |
| 237_132 | 99.5 | 98.4 | 100 | 98 | 93.5 | 100 |
| 4_132 | 99.5 | 98.4 | 100 | 99 | 96.8 | 100 |
| 3_132 | 99.5 | 98.4 | 100 | 99 | 96.8 | 100 |
| 181 | 79.2 | 79.2 | 79.2 | 79.2 | 79.2 | 79.2 |
| 2_181 | 99.5 | 98.4 | 100 | 100 | 100 | 100 |
| 1_181 | 99.5 | 98.4 | 100 | 100 | 100 | 100 |
| 237_181 | 99 | 96.8 | 100 | 99 | 96.8 | 100 |
| 4_181 | 99 | 96.8 | 100 | 98 | 93.5 | 100 |
| 3_181 | 99.5 | 98.4 | 100 | 100 | 100 | 100 |
| 79 | 92.4 | 92.4 | 92.4 | 92.4 | 92.4 | 92.4 |
| 2_79 | 100 | 100 | 100 | 100 | 100 | 100 |
| 1_79 | 99.5 | 98.4 | 100 | 100 | 100 | 100 |
| 237_79 | 99.5 | 98.4 | 100 | 98 | 93.5 | 100 |
| 4_79 | 99.5 | 98.4 | 100 | 99 | 96.8 | 100 |
| 3_79 | 99.5 | 98.4 | 100 | 100 | 100 | 100 |
| 133 | 79.7 | 79.7 | 79.7 | 79.7 | 79.7 | 79.7 |
| 2_133 | 99.5 | 98.4 | 100 | 100 | 100 | 100 |
| 1_133 | 99.5 | 98.4 | 100 | 100 | 100 | 100 |
| 237_133 | 98.5 | 95.2 | 100 | 99 | 96.8 | 100 |
| 4_133 | 99 | 96.8 | 100 | 99 | 96.8 | 100 |
| 3_133 | 99.5 | 98.4 | 100 | 100 | 100 | 100 |
| 41 | 91.4 | 91.4 | 91.4 | 91.4 | 91.4 | 91.4 |
| 2_41 | 99.5 | 98.4 | 100 | 100 | 100 | 100 |
| 1_41 | 99.5 | 98.4 | 100 | 100 | 100 | 100 |
| 237_41 | 99 | 96.8 | 100 | 99 | 96.8 | 100 |
| 4_41 | 99.5 | 98.4 | 100 | 99 | 96.8 | 100 |

TABLE 9-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 3_41 | 99.5 | 98.4 | 100 | 100 | 100 | 100 |
| 139 | 88.3 | 88.3 | 88.3 | 88.3 | 88.3 | 88.3 |
| 2_139 | 100 | 100 | 100 | 100 | 100 | 100 |
| 1_139 | 99.5 | 98.4 | 100 | 100 | 100 | 100 |
| 237_139 | 100 | 100 | 100 | 98 | 93.5 | 100 |
| 4_139 | 100 | 100 | 100 | 99 | 96.8 | 100 |
| 3_139 | 99.5 | 98.4 | 100 | 100 | 100 | 100 |
| 118 | 87.8 | 87.8 | 87.8 | 87.8 | 87.8 | 87.8 |
| 2_118 | 99.5 | 98.4 | 100 | 100 | 100 | 100 |
| 1_118 | 99.5 | 98.4 | 100 | 100 | 100 | 100 |
| 237_118 | 99 | 96.8 | 100 | 100 | 100 | 100 |
| 4_118 | 99.5 | 98.4 | 100 | 100 | 100 | 100 |
| 3_118 | 99.5 | 98.4 | 100 | 100 | 100 | 100 |
| 86 | 85.3 | 85.3 | 85.3 | 85.3 | 85.3 | 85.3 |
| 2_86 | 99.5 | 98.4 | 100 | 100 | 100 | 100 |
| 1_86 | 99.5 | 98.4 | 100 | 100 | 100 | 100 |
| 237_86 | 99 | 96.8 | 100 | 100 | 100 | 100 |
| 4_86 | 99 | 96.8 | 100 | 100 | 100 | 100 |
| 3_86 | 99.5 | 98.4 | 100 | 99 | 96.8 | 100 |
| 60 | 84.8 | 84.8 | 84.8 | 84.8 | 84.8 | 84.8 |
| 2_60 | 99.5 | 98.4 | 100 | 100 | 100 | 100 |
| 1_60 | 99.5 | 98.4 | 100 | 100 | 100 | 100 |
| 237_60 | 99 | 96.8 | 100 | 99 | 96.8 | 100 |
| 4_60 | 99.5 | 98.4 | 100 | 99 | 96.8 | 100 |
| 3_60 | 99.5 | 98.4 | 100 | 100 | 100 | 100 |
| 116 | 80.2 | 80.2 | 80.2 | 80.2 | 80.2 | 80.2 |
| 2_116 | 100 | 100 | 100 | 100 | 100 | 100 |
| 1_116 | 99.5 | 98.4 | 100 | 100 | 100 | 100 |
| 237_116 | 99.5 | 98.4 | 100 | 100 | 100 | 100 |
| 4_116 | 99.5 | 98.4 | 100 | 99 | 96.8 | 100 |
| 3_116 | 99.5 | 98.4 | 100 | 100 | 100 | 100 |
| 160 | 80.2 | 80.2 | 80.2 | 80.2 | 80.2 | 80.2 |
| 2_160 | 99.5 | 98.4 | 100 | 100 | 100 | 100 |
| 1_160 | 99.5 | 98.4 | 100 | 100 | 100 | 100 |
| 237_160 | 99.5 | 98.4 | 100 | 98 | 93.5 | 100 |
| 4_160 | 99 | 96.8 | 100 | 99 | 96.8 | 100 |
| 3_160 | 99.5 | 98.4 | 100 | 100 | 100 | 100 |
| 38 | 79.2 | 79.2 | 79.2 | 79.2 | 79.2 | 79.2 |
| 2_38 | 99.5 | 98.4 | 100 | 100 | 100 | 100 |
| 1_38 | 99.5 | 98.4 | 100 | 100 | 100 | 100 |
| 237_38 | 98.5 | 95.2 | 100 | 100 | 100 | 100 |
| 4_38 | 99 | 96.8 | 100 | 99 | 96.8 | 100 |
| 3_38 | 99.5 | 98.4 | 100 | 99 | 96.8 | 100 |
| 99 | 86.2 | 86.2 | 86.2 | 86.2 | 86.2 | 86.2 |
| 2_99 | 99.5 | 98.4 | 100 | 100 | 100 | 100 |
| 1_99 | 99.5 | 98.4 | 100 | 100 | 100 | 100 |
| 237_99 | 99 | 96.7 | 100 | 99 | 96.8 | 100 |
| 4_99 | 99 | 96.7 | 100 | 98 | 93.5 | 100 |
| 3_99 | 99.5 | 98.4 | 100 | 100 | 100 | 100 |
| 104 | 86.3 | 86.3 | 86.3 | 86.3 | 86.3 | 86.3 |
| 2_104 | 99.5 | 98.4 | 100 | 100 | 100 | 100 |
| 1_104 | 100 | 100 | 100 | 100 | 100 | 100 |
| 237_104 | 98.5 | 95.2 | 100 | 98 | 93.5 | 100 |
| 4_104 | 99 | 96.8 | 100 | 99 | 96.8 | 100 |
| 3_104 | 100 | 100 | 100 | 100 | 100 | 100 |

Comparative Example 1

<Breast Cancer Discriminant Performance of an Existing Tumor Marker in Blood>

The concentrations of the existing tumor marker CEA in blood were measured in the training cohort and the validation cohort obtained in the preceding Reference Examples. When the concentrations of these tumor markers in blood are higher than the reference values described in Non-Patent Literature 3 above (CEA: 5 ng/mL), subjects are usually suspected of having cancer. Thus, whether or not the concentration of CEA in blood exceeded its reference value was confirmed for each sample, and the results were assessed for the ability of the tumor marker to detect cancer in breast cancer patients. The sensitivity of the existing marker in the training cohort and the validation cohort was calculated. The results are shown in Table 5. The sensitivity of CEA was as low as 113% in the training cohort and 19.4% in the validation cohort, demonstrating that the marker is not useful in the detection of breast cancer (Table 5).

On the other hand, as shown above in Tables 3 and 6 of Examples 1 and 2, it can be concluded that in all of the polynucleotides consisting of the nucleotide sequences represented by SEQ ID NOs: 1 to 251, combinations of 1 or 2 polynucleotides exhibiting sensitivity beyond the existing breast cancer markers are present, and thus such polynucleotides serve as excellent diagnosis markers.

As shown in these Examples and Comparative Example, the kit, etc., and the method of the present invention can detect breast cancer with higher sensitivity than the existing tumor marker and therefore permit early detection and treatment of breast cancer. As a result, improvement in the survival rate because of the reduced risk of recurrence, and breast conservation therapy as a therapeutic option can also be provided.

INDUSTRIAL APPLICABILITY

According to the present invention, breast cancer can be effectively detected by a simple and inexpensive method. This enables early detection, diagnosis and treatment of breast cancer. The method of the present invention can detect breast cancer with limited invasiveness using the blood of a patient and therefore allows breast cancer to be detected conveniently and rapidly. All publications, patents, and patent applications cited herein are incorporated herein by reference in their entirety.

The invention claimed is:

1. A method for detecting breast cancer in a human subject, comprising:
    measuring an expression level of hsa-miR-1233-5p in a blood, serum or plasma sample from the subject,
    comparing the measured expression level of hsa-miR-1233-5p to a control expression level for a healthy subject;
    detecting an increased level of hsa-miR-1233-5p in the sample from the subject as compared to the control expression level from the sample from the healthy subject;
    wherein the increased level of hsa-miR-1233-5p indicates that the subject has breast cancer; and
    wherein the method further comprises treating the subject for the breast cancer or performing a diagnostic procedure on the subject with the breast cancer;
    wherein the treating comprises surgery, radiotherapy, chemotherapy, or a combination thereof; and
    wherein the diagnostic procedure comprises mammography, ultrasonography (echo examination), CT, MRI, abdominal ultrasonography, bone scintigraphy, PET, pathological examination which involves analyzing a lesion tissue under a microscope, or a combination thereof.

2. The method according to claim 1, comprising performing the diagnostic procedure on the subject.

3. The method according to claim 1, wherein the expression level of hsa-miR-1233-5p in the sample is measured by using a device comprising a nucleic acid(s) that specifically binds to hsa-miR-1233-5p.

4. The method according to claim 3, wherein the device further comprises at least one nucleic acid capable of specifically binding to at least one polynucleotide selected from the group consisting of other breast cancer markers: miR-4730, miR-1307-3p, miR-4634, miR-663a, miR-4532, miR-7704, miR-3178, miR-6729-5p, miR-6090, miR-4732-5p, miR-3184-5p, miR-6727-5p, miR-6088, miR-4674, miR-8073, miR-4787-5p, miR-1469, miR-125a-3p, miR-885-3p, miR-6802-5p, miR-328-5p, miR-6787-5p, miR-8069, miR-6875-5p, miR-1246, miR-4734, miR-6757-5p, miR-6756-5p, miR-3665, miR-6836-3p, miR-6821-5p, miR-6805-5p, miR-4728-5p, miR-6726-5p, miR-197-5p, miR-149-3p, miR-6850-5p, miR-4476, miR-6858-5p, miR-564, miR-4763-3p, miR-575, miR-6771-5p, miR-1231, miR-1908-3p, miR-150-3p, miR-3937, miR-887-3p, miR-3940-5p, miR-4741, miR-6808-5p, miR-6869-5p, miR-5090, miR-615-5p, miR-8072, miR-128-1-5p, miR-1238-5p, miR-365a-5p, miR-204-3p, miR-4492, miR-6785-5p, miR-6511a-5p, miR-4525, miR-1915-5p, miR-3180, miR-6879-5p, miR-1199-5p, miR-6746-5p, miR-711, miR-663b, miR-4707-3p, miR-6893-5p, miR-4675, miR-4638-5p, miR-4651, miR-6087, miR-4665-5p, miR-4758-5p, miR-6887-5p, miR-3620-5p, miR-1909-3p, miR-7641, miR-6724-5p, miR-1343-3p, miR-6780b-5p, miR-4484, miR-4690-5p, miR-4429, miR-1227-5p, miR-4725-3p, miR-6861-5p, miR-6812-5p, miR-3197, miR-8059, miR-3185, miR-4706, miR-4497, miR-3131, miR-6806-5p, miR-187-5p, miR-3180-3p, miR-6848-5p, miR-6820-5p, miR-6800-5p, miR-6717-5p, miR-6795-5p, miR-4632-5p, miR-665, miR-6778-5p, miR-3663-3p, miR-4689, miR-211-3p, miR-6511b-5p, miR-4750-5p, miR-6126, miR-614, miR-7110-5p, miR-744-5p, miR-6769a-5p, miR-4792, miR-5787, miR-6798-5p, miR-6781-5p, miR-4419b, miR-4446-3p, miR-4259, miR-5572, miR-6075, miR-296-3p, miR-6891-5p, miR-4745-5p, miR-6775-5p, miR-6870-5p, miR-920, miR-4530, miR-6819-5p, miR-6825-5p, miR-7847-3p, miR-6131, miR-4433-3p, miR-1228-5p, miR-6743-5p, miR-1268a, miR-3917, miR-6786-5p, miR-3154, miR-638, miR-6741-5p, miR-6889-5p, miR-6840-3p, miR-6510-5p, miR-3188, miR-551b-5p, miR-5001-5p, miR-1268b, miR-7107-5p, miR-6824-5p, miR-6732-5p, miR-371a-5p, miR-6794-5p, miR-6779-5p, miR-4271, miR-5195-3p, miR-6762-5p, miR-939-5p, miR-1247-3p, miR-6777-5p, miR-6722-3p, miR-3656, miR-4688, miR-3195, miR-6766-5p, miR-4447, miR-4656, miR-7108-5p, miR-3191-3p, miR-1273g-3p, miR-4463, miR-2861, miR-3196, miR-6877-5p, miR-3679-5p, miR-4442, miR-6789-5p, miR-6782-5p, miR-486-3p, miR-6085, miR-4746-3p, miR-619-5p, miR-937-5p, miR-6803-5p, miR-4298, miR-4454, miR-4459, miR-7150, miR-6880-5p, miR-4449, miR-8063, miR-4695-5p, miR-6132, miR-6829-5p, miR-4486, miR-6805-3p, miR-6826-5p, miR-4508, miR-1343-5p, miR-7114-5p, miR-3622a-5p, miR-6765-5p, miR-7845-5p, miR-3960, miR-6749-5p, miR-1260b, miR-6799-5p, miR-4723-5p, miR-6784-5p, miR-5100, miR-6769b-5p, miR-1207-5p, miR-642a-3p, miR-4505, miR-4270, miR-6721-5p, miR-7111-5p, miR-6791-5p, miR-7109-5p, miR-4258, miR-6515-3p, miR-6851-5p, miR-6125, miR-4749-

5p, miR-4726-5p, miR-4513, miR-6089, miR-6816-5p, miR-4466, miR-4488, miR-6752-5p and miR-4739, and/or miR-760, miR-602, miR-423-5p, miR-92a-2-5p, miR-16-5p, miR-451a, miR-135a-3p, miR-486-5p, miR-4257, miR-92b-5p, miR-1915-3p, miR-718, miR-940, miR-296-5p, miR-23b-3p, miR-92a-3p, miR-658, miR-6842-5p, miR-6124, miR-6765-3p, miR-7106-5p, miR-4534, miR-92b-3p, miR-3135b, miR-4687-3p, miR-762, miR-3619-3p, miR-4467, miR-557, miR-1237-5p, miR-1908-5p, miR-4286, miR-6885-5p and miR-6763-5p.

5. The method according to claim 1, wherein the expression level of hsa-miR-1233-5p in the sample is measured by using a kit comprising a nucleic acid(s) that specifically binds to hsa-miR-1233-5p.

6. The method according to claim 5, wherein the kit further comprises at least one nucleic acid capable of specifically binding to at least one polynucleotide selected from the group consisting of other breast cancer markers: miR-4730, miR-1307-3p, miR-4634, miR-663a, miR-4532, miR-7704, miR-3178, miR-6729-5p, miR-6090, miR-4732-5p, miR-3184-5p, miR-6727-5p, miR-6088, miR-4674, miR-8073, miR-4787-5p, miR-1469, miR-125a-3p, miR-885-3p, miR-6802-5p, miR-328-5p, miR-6787-5p, miR-8069, miR-6875-5p, miR-1246, miR-4734, miR-6757-5p, miR-6756-5p, miR-3665, miR-6836-3p, miR-6821-5p, miR-6805-5p, miR-4728-5p, miR-6726-5p, miR-197-5p, miR-149-3p, miR-6850-5p, miR-4476, miR-6858-5p, miR-564, miR-4763-3p, miR-575, miR-6771-5p, miR-1231, miR-1908-3p, miR-150-3p, miR-3937, miR-887-3p, miR-3940-5p, miR-4741, miR-6808-5p, miR-6869-5p, miR-5090, miR-615-5p, miR-8072, miR-128-1-5p, miR-1238-5p, miR-365a-5p, miR-204-3p, miR-4492, miR-6785-5p, miR-6511a-5p, miR-4525, miR-1915-5p, miR-3180, miR-6879-5p, miR-1199-5p, miR-6746-5p, miR-711, miR-663b, miR-4707-3p, miR-6893-5p, miR-4675, miR-4638-5p, miR-4651, miR-6087, miR-4665-5p, miR-4758-5p, miR-6887-5p, miR-3620-5p, miR-1909-3p, miR-7641, miR-6724-5p, miR-1343-3p, miR-6780b-5p, miR-4484, miR-4690-5p, miR-4429, miR-1227-5p, miR-4725-3p, miR-6861-5p, miR-6812-5p, miR-3197, miR-8059, miR-3185, miR-4706, miR-4497, miR-3131, miR-6806-5p, miR-187-5p, miR-3180-3p, miR-6848-5p, miR-6820-5p, miR-6800-5p, miR-6717-5p, miR-6795-5p, miR-4632-5p, miR-665, miR-6778-5p, miR-3663-3p, miR-4689, miR-211-3p, miR-6511b-5p, miR-4750-5p, miR-6126, miR-614, miR-7110-5p, miR-744-5p, miR-6769a-5p, miR-4792, miR-5787, miR-6798-5p, miR-6781-5p, miR-4419b, miR-4446-3p, miR-4259, miR-5572, miR-6075, miR-296-3p, miR-6891-5p, miR-4745-5p, miR-6775-5p, miR-6870-5p, miR-920, miR-4530, miR-6819-5p, miR-6825-5p, miR-7847-3p, miR-6131, miR-4433-3p, miR-1228-5p, miR-6743-5p, miR-1268a, miR-3917, miR-6786-5p, miR-3154, miR-638, miR-6741-5p, miR-6889-5p, miR-6840-3p, miR-6510-5p, miR-3188, miR-551b-5p, miR-5001-5p, miR-1268b, miR-7107-5p, miR-6824-5p, miR-6732-5p, miR-371a-5p, miR-6794-5p, miR-6779-5p, miR-4271, miR-5195-3p, miR-6762-5p, miR-939-5p, miR-1247-3p, miR-6777-5p, miR-6722-3p, miR-3656, miR-4688, miR-3195, miR-6766-5p, miR-4447, miR-4656, miR-7108-5p, miR-3191-3p, miR-1273g-3p, miR-4463, miR-2861, miR-3196, miR-6877-5p, miR-3679-5p, miR-4442, miR-6789-5p, miR-6782-5p, miR-486-3p, miR-6085, miR-4746-3p, miR-619-5p, miR-937-5p, miR-6803-5p, miR-4298, miR-4454, miR-4459, miR-7150, miR-6880-5p, miR-4449, miR-8063, miR-4695-5p, miR-6132, miR-6829-5p, miR-4486, miR-6805-3p, miR-6826-5p, miR-4508, miR-1343-5p, miR-7114-5p, miR-3622a-5p, miR-6765-5p, miR-7845-5p, miR-3960, miR-6749-5p, miR-1260b, miR-6799-5p, miR-4723-5p, miR-6784-5p, miR-5100, miR-6769b-5p, miR-1207-5p, miR-642a-3p, miR-4505, miR-4270, miR-6721-5p, miR-7111-5p, miR-6791-5p, miR-7109-5p, miR-4258, miR-6515-3p, miR-6851-5p, miR-6125, miR-4749-5p, miR-4726-5p, miR-4513, miR-6089, miR-6816-5p, miR-4466, miR-4488, miR-6752-5p and miR-4739, and/or miR-760, miR-602, miR-423-5p, miR-92a-2-5p, miR-16-5p, miR-451a, miR-135a-3p, miR-486-5p, miR-4257, miR-92b-5p, miR-1915-3p, miR-718, miR-940, miR-296-5p, miR-23b-3p, miR-92a-3p, miR-658, miR-6842-5p, miR-6124, miR-6765-3p, miR-7106-5p, miR-4534, miR-92b-3p, miR-3135b, miR-4687-3p, miR-762, miR-3619-3p, miR-4467, miR-557, miR-1237-5p, miR-1908-5p, miR-4286, miR-6885-5p and miR-6763-5p.

* * * * *

SEQUENCE LISTING

```
<160> NUMBER OF SEQ ID NOS: 871

<210> SEQ ID NO 1
<211> LENGTH: 23
<212> TYPE: RNA
<213> ORGANISM: Homo sapiens

<400> SEQUENCE: 1 ccccguguu ggggcgcguc ugc                                             23

<210> SEQ ID NO 2
<211> LENGTH: 23
<212> TYPE: RNA
<213> ORGANISM: Homo sapiens

<400> SEQUENCE: 2
cuggcggagc ccauuccaug cca                                            23

<210> SEQ ID NO 3
<211> LENGTH: 22
<212> TYPE: RNA
<213> ORGANISM: Homo sapiens

<400> SEQUENCE: 3
acucggcgug gcgucggucg ug                                             22

<210> SEQ ID NO 4
<211> LENGTH: 19
<212> TYPE: RNA
<213> ORGANISM: Homo sapiens

<400> SEQUENCE: 4
cggcgcgacc ggcccgggg                                                 19

<210> SEQ ID NO 5
<211> LENGTH: 22
<212> TYPE: RNA
<213> ORGANISM: Homo sapiens
```

```
<400> SEQUENCE: 5
aggcggggcg ccgcgggacc gc                                              22

<210> SEQ ID NO 6
<211> LENGTH: 17
<212> TYPE: RNA
<213> ORGANISM: Homo sapiens

<400> SEQUENCE: 6
ccccggggag cccggcg                                                    17

<210> SEQ ID NO 7
<211> LENGTH: 19
<212> TYPE: RNA
<213> ORGANISM: Homo sapiens

<400> SEQUENCE: 7
cggggucggc ggcgacgug                                                  19

<210> SEQ ID NO 8
<211> LENGTH: 17
<212> TYPE: RNA
<213> ORGANISM: Homo sapiens

<400> SEQUENCE: 8
ggggcgcggc cggaucg                                                    17

<210> SEQ ID NO 9
<211> LENGTH: 22
<212> TYPE: RNA
<213> ORGANISM: Homo sapiens

<400> SEQUENCE: 9
ugggcgaggg cggcugagcg gc                                              22

<210> SEQ ID NO 10
<211> LENGTH: 19
<212> TYPE: RNA
<213> ORGANISM: Homo sapiens

<400> SEQUENCE: 10
ggggagcgag gggcggggc                                                  19

<210> SEQ ID NO 11
<211> LENGTH: 23
<212> TYPE: RNA
<213> ORGANISM: Homo sapiens

<400> SEQUENCE: 11
uguagagcag ggagcaggaa gcu                                             23

<210> SEQ ID NO 12
<211> LENGTH: 24
<212> TYPE: RNA
<213> ORGANISM: Homo sapiens

<400> SEQUENCE: 12
ugaggggccu cagaccgagc uuuu                                            24

<210> SEQ ID NO 13
<211> LENGTH: 23
<212> TYPE: RNA
<213> ORGANISM: Homo sapiens
```

```
<400> SEQUENCE: 13
cucggggcag gcggcuggga gcg                                          23

<210> SEQ ID NO 14
<211> LENGTH: 20
<212> TYPE: RNA
<213> ORGANISM: Homo sapiens

<400> SEQUENCE: 14
agagaugaag cgggggggcg                                              20

<210> SEQ ID NO 15
<211> LENGTH: 21
<212> TYPE: RNA
<213> ORGANISM: Homo sapiens

<400> SEQUENCE: 15
cugggcucgg gacgcgcggc u                                            21

<210> SEQ ID NO 16
<211> LENGTH: 22
<212> TYPE: RNA
<213> ORGANISM: Homo sapiens

<400> SEQUENCE: 16
accuggcagc agggagcguc gu                                           22

<210> SEQ ID NO 17
<211> LENGTH: 22
<212> TYPE: RNA
<213> ORGANISM: Homo sapiens

<400> SEQUENCE: 17 gcggggugg cggcggcauc cc                                            22

<210> SEQ ID NO 18
<211> LENGTH: 22
<212> TYPE: RNA
<213> ORGANISM: Homo sapiens

<400> SEQUENCE: 18
cucggcgcgg ggcgcgggcu cc                                           22

<210> SEQ ID NO 19
<211> LENGTH: 22
<212> TYPE: RNA
<213> ORGANISM: Homo sapiens

<400> SEQUENCE: 19
acaggugagg uucuugggag cc                                           22

<210> SEQ ID NO 20
<211> LENGTH: 22
<212> TYPE: RNA
<213> ORGANISM: Homo sapiens

<400> SEQUENCE: 20
agugggaggc cagggcacgg ca                                           22

<210> SEQ ID NO 21
<211> LENGTH: 22
<212> TYPE: RNA
```

<213> ORGANISM: Homo sapiens

<400> SEQUENCE: 21
aggcagcggg guguagugga ua                                          22

<210> SEQ ID NO 22
<211> LENGTH: 20
<212> TYPE: RNA
<213> ORGANISM: Homo sapiens

<400> SEQUENCE: 22
cuaggugggg ggcuugaagc                                             20

<210> SEQ ID NO 23
<211> LENGTH: 23
<212> TYPE: RNA
<213> ORGANISM: Homo sapiens

<400> SEQUENCE: 23
gggggggcag gaggggcuca ggg                                         23

<210> SEQ ID NO 24
<211> LENGTH: 22
<212> TYPE: RNA
<213> ORGANISM: Homo sapiens

<400> SEQUENCE: 24
uggcgggggu agagcuggcu gc                                          22

<210> SEQ ID NO 25
<211> LENGTH: 23
<212> TYPE: RNA
<213> ORGANISM: Homo sapiens

<400> SEQUENCE: 25
ggaugguugg gggcggucgg cgu                                         23

<210> SEQ ID NO 26
<211> LENGTH: 21
<212> TYPE: RNA
<213> ORGANISM: Homo sapiens

<400> SEQUENCE: 26
ugagggaccc aggacaggag a                                           21

<210> SEQ ID NO 27
<211> LENGTH: 19
<212> TYPE: RNA
<213> ORGANISM: Homo sapiens

<400> SEQUENCE: 27
aauggauuuu uggagcagg                                              19

<210> SEQ ID NO 28
<211> LENGTH: 22
<212> TYPE: RNA
<213> ORGANISM: Homo sapiens

<400> SEQUENCE: 28
gcugcgggcu gcggucaggg cg                                          22

<210> SEQ ID NO 29
<211> LENGTH: 22

<212> TYPE: RNA
<213> ORGANISM: Homo sapiens

<400> SEQUENCE: 29
uagggauggg aggccaggau ga    22

<210> SEQ ID NO 30
<211> LENGTH: 23
<212> TYPE: RNA
<213> ORGANISM: Homo sapiens

<400> SEQUENCE: 30 agggugggggc uggaggugggg gcu    23

<210> SEQ ID NO 31
<211> LENGTH: 18
<212> TYPE: RNA
<213> ORGANISM: Homo sapiens

<400> SEQUENCE: 31
agcaggugcg gggcggcg    18

<210> SEQ ID NO 32
<211> LENGTH: 21
<212> TYPE: RNA
<213> ORGANISM: Homo sapiens

<400> SEQUENCE: 32
augccucccc cggccccgca g    21

<210> SEQ ID NO 33
<211> LENGTH: 23
<212> TYPE: RNA
<213> ORGANISM: Homo sapiens

<400> SEQUENCE: 33
gugcguggug gcucgaggcg ggg    23

<210> SEQ ID NO 34
<211> LENGTH: 22
<212> TYPE: RNA
<213> ORGANISM: Homo sapiens

<400> SEQUENCE: 34 uaggggggcgg cuuguggagu gu    22

<210> SEQ ID NO 35
<211> LENGTH: 23
<212> TYPE: RNA
<213> ORGANISM: Homo sapiens

<400> SEQUENCE: 35
ugggagggga gaggcagcaa gca    23

<210> SEQ ID NO 36
<211> LENGTH: 21
<212> TYPE: RNA
<213> ORGANISM: Homo sapiens

<400> SEQUENCE: 36
cgggagcugg ggucugcagg u    21

<210> SEQ ID NO 37

```
<211> LENGTH: 23
<212> TYPE: RNA
<213> ORGANISM: Homo sapiens

<400> SEQUENCE: 37
cggguagaga gggcagugggg agg                                          23

<210> SEQ ID NO 38
<211> LENGTH: 21
<212> TYPE: RNA
<213> ORGANISM: Homo sapiens

<400> SEQUENCE: 38
agggagggac gggggcugug c                                             21

<210> SEQ ID NO 39
<211> LENGTH: 22
<212> TYPE: RNA
<213> ORGANISM: Homo sapiens

<400> SEQUENCE: 39
gugcggaacg cuggccgggg cg                                            22

<210> SEQ ID NO 40
<211> LENGTH: 22
<212> TYPE: RNA
<213> ORGANISM: Homo sapiens

<400> SEQUENCE: 40
caggaaggau uuagggacag gc                                            22

<210> SEQ ID NO 41
<211> LENGTH: 22
<212> TYPE: RNA
<213> ORGANISM: Homo sapiens

<400> SEQUENCE: 41
gugaggaggg gcuggcaggg ac                                            22

<210> SEQ ID NO 42
<211> LENGTH: 19
<212> TYPE: RNA
<213> ORGANISM: Homo sapiens

<400> SEQUENCE: 42
aggcacgguc ucagcaggc                                                19

<210> SEQ ID NO 43
<211> LENGTH: 24
<212> TYPE: RNA
<213> ORGANISM: Homo sapiens

<400> SEQUENCE: 43
aggcaggggc uggugcuggg cggg                                          24

<210> SEQ ID NO 44
<211> LENGTH: 19
<212> TYPE: RNA
<213> ORGANISM: Homo sapiens

<400> SEQUENCE: 44
gagccaguug gacaggagc                                                19
```

```
<210> SEQ ID NO 45
<211> LENGTH: 22
<212> TYPE: RNA
<213> ORGANISM: Homo sapiens

<400> SEQUENCE: 45
cucgggaggg caugggccag gc                                              22

<210> SEQ ID NO 46
<211> LENGTH: 20
<212> TYPE: RNA
<213> ORGANISM: Homo sapiens

<400> SEQUENCE: 46
gugucugggc ggacagcugc                                                 20

<210> SEQ ID NO 47
<211> LENGTH: 21
<212> TYPE: RNA
<213> ORGANISM: Homo sapiens

<400> SEQUENCE: 47
ccggccgccg gcuccgcccc g                                               21

<210> SEQ ID NO 48
<211> LENGTH: 22
<212> TYPE: RNA
<213> ORGANISM: Homo sapiens

<400> SEQUENCE: 48
cugguacagg ccuggggac ag                                               22

<210> SEQ ID NO 49
<211> LENGTH: 23
<212> TYPE: RNA
<213> ORGANISM: Homo sapiens

<400> SEQUENCE: 49
acaggcggcu guagcaaugg ggg                                             23

<210> SEQ ID NO 50
<211> LENGTH: 22
<212> TYPE: RNA
<213> ORGANISM: Homo sapiens

<400> SEQUENCE: 50
gugaacgggc gccaucccga gg                                              22

<210> SEQ ID NO 51
<211> LENGTH: 20
<212> TYPE: RNA
<213> ORGANISM: Homo sapiens

<400> SEQUENCE: 51
guggguuggg gcgggcucug                                                 20

<210> SEQ ID NO 52
<211> LENGTH: 23
<212> TYPE: RNA
<213> ORGANISM: Homo sapiens

<400> SEQUENCE: 52
cgggcugucc ggaggggucg gcu                                             23
```

```
<210> SEQ ID NO 53
<211> LENGTH: 22
<212> TYPE: RNA
<213> ORGANISM: Homo sapiens

<400> SEQUENCE: 53
caggcaggga ggugggacca ug                                              22

<210> SEQ ID NO 54
<211> LENGTH: 22
<212> TYPE: RNA
<213> ORGANISM: Homo sapiens

<400> SEQUENCE: 54
gugaguagug gcgcgcggcg gc                                              22

<210> SEQ ID NO 55
<211> LENGTH: 23
<212> TYPE: RNA
<213> ORGANISM: Homo sapiens

<400> SEQUENCE: 55
ccggggcaga uugguguagg gug                                             23

<210> SEQ ID NO 56
<211> LENGTH: 22
<212> TYPE: RNA
<213> ORGANISM: Homo sapiens

<400> SEQUENCE: 56
gggggucccc ggugcucgga uc                                              22

<210> SEQ ID NO 57
<211> LENGTH: 20
<212> TYPE: RNA
<213> ORGANISM: Homo sapiens

<400> SEQUENCE: 57
ggcggcgggg agguaggcag                                                 20

<210> SEQ ID NO 58
<211> LENGTH: 23
<212> TYPE: RNA
<213> ORGANISM: Homo sapiens

<400> SEQUENCE: 58
cggggccgua gcacugucug aga                                             23

<210> SEQ ID NO 59
<211> LENGTH: 23
<212> TYPE: RNA
<213> ORGANISM: Homo sapiens

<400> SEQUENCE: 59
gugaguggga gccccagugu gug                                             23

<210> SEQ ID NO 60
<211> LENGTH: 23
<212> TYPE: RNA
<213> ORGANISM: Homo sapiens

<400> SEQUENCE: 60
agggacuuuu gggggcagau gug                                             23
```

```
<210> SEQ ID NO 61
<211> LENGTH: 21
<212> TYPE: RNA
<213> ORGANISM: Homo sapiens

<400> SEQUENCE: 61
gcugggaagg caaagggacg u                                          21

<210> SEQ ID NO 62
<211> LENGTH: 17
<212> TYPE: RNA
<213> ORGANISM: Homo sapiens

<400> SEQUENCE: 62
ggggcugggc gcgcgcc                                               17

<210> SEQ ID NO 63
<211> LENGTH: 22
<212> TYPE: RNA
<213> ORGANISM: Homo sapiens

<400> SEQUENCE: 63
ugggagggcg uggaugaugg ug                                         22

<210> SEQ ID NO 64
<211> LENGTH: 23
<212> TYPE: RNA
<213> ORGANISM: Homo sapiens

<400> SEQUENCE: 64
caggcagaag ugggcugac agg                                         23

<210> SEQ ID NO 65
<211> LENGTH: 21
<212> TYPE: RNA
<213> ORGANISM: Homo sapiens

<400> SEQUENCE: 65 gggggaugu gcaugcuggu u                                           21

<210> SEQ ID NO 66
<211> LENGTH: 22
<212> TYPE: RNA
<213> ORGANISM: Homo sapiens

<400> SEQUENCE: 66
accuugccuu gcugcccggg cc                                         22

<210> SEQ ID NO 67
<211> LENGTH: 19
<212> TYPE: RNA
<213> ORGANISM: Homo sapiens

<400> SEQUENCE: 67
uggggcggag cuuccggag                                             19

<210> SEQ ID NO 68
<211> LENGTH: 22
<212> TYPE: RNA
<213> ORGANISM: Homo sapiens

<400> SEQUENCE: 68
```
cagggcaggg aaggugggag ag                                              22

<210> SEQ ID NO 69
<211> LENGTH: 20
<212> TYPE: RNA
<213> ORGANISM: Homo sapiens

<400> SEQUENCE: 69
ccugagcccg ggccgcgcag                                                 20

<210> SEQ ID NO 70
<211> LENGTH: 22
<212> TYPE: RNA
<213> ORGANISM: Homo sapiens

<400> SEQUENCE: 70
ccgggagaag gagguggccu gg                                              22

<210> SEQ ID NO 71
<211> LENGTH: 22
<212> TYPE: RNA
<213> ORGANISM: Homo sapiens

<400> SEQUENCE: 71
gggacccagg gagagacgua ag                                              22

<210> SEQ ID NO 72
<211> LENGTH: 22
<212> TYPE: RNA
<213> ORGANISM: Homo sapiens

<400> SEQUENCE: 72
gguggcccgg ccgugccuga gg                                              22

<210> SEQ ID NO 73
<211> LENGTH: 22
<212> TYPE: RNA
<213> ORGANISM: Homo sapiens

<400> SEQUENCE: 73
agcccgcccc agccgagguu cu                                              22

<210> SEQ ID NO 74
<211> LENGTH: 21
<212> TYPE: RNA
<213> ORGANISM: Homo sapiens

<400> SEQUENCE: 74
caggcaggug uaggguggag c                                               21

<210> SEQ ID NO 75
<211> LENGTH: 22
<212> TYPE: RNA
<213> ORGANISM: Homo sapiens

<400> SEQUENCE: 75
ggggcuguga uugaccagca gg                                              22

<210> SEQ ID NO 76
<211> LENGTH: 21
<212> TYPE: RNA
<213> ORGANISM: Homo sapiens

<400> SEQUENCE: 76

```
acucggcugc gguggacaag u                                              21

<210> SEQ ID NO 77
<211> LENGTH: 20
<212> TYPE: RNA
<213> ORGANISM: Homo sapiens

<400> SEQUENCE: 77
cggggugggu gaggucgggc                                                20

<210> SEQ ID NO 78
<211> LENGTH: 18
<212> TYPE: RNA
<213> ORGANISM: Homo sapiens

<400> SEQUENCE: 78
ugaggcgggg gggcgagc                                                  18

<210> SEQ ID NO 79
<211> LENGTH: 23
<212> TYPE: RNA
<213> ORGANISM: Homo sapiens

<400> SEQUENCE: 79 cuggggacg cgugagcgcg agc                                             23

<210> SEQ ID NO 80
<211> LENGTH: 23
<212> TYPE: RNA
<213> ORGANISM: Homo sapiens

<400> SEQUENCE: 80
gugaguggga gccgguggggg cug                                           23

<210> SEQ ID NO 81
<211> LENGTH: 23
<212> TYPE: RNA
<213> ORGANISM: Homo sapiens

<400> SEQUENCE: 81
uggggggaca gauggagagg aca                                            23

<210> SEQ ID NO 82
<211> LENGTH: 22
<212> TYPE: RNA
<213> ORGANISM: Homo sapiens

<400> SEQUENCE: 82
gugggcuggg cugggcuggg cc                                             22

<210> SEQ ID NO 83
<211> LENGTH: 22
<212> TYPE: RNA
<213> ORGANISM: Homo sapiens

<400> SEQUENCE: 83
cgcaggggcc gggugcucac cg                                             22

<210> SEQ ID NO 84
<211> LENGTH: 19
<212> TYPE: RNA
<213> ORGANISM: Homo sapiens
```

```
<400> SEQUENCE: 84
uugaucucgg aagcuaagc                                                  19

<210> SEQ ID NO 85
<211> LENGTH: 23
<212> TYPE: RNA
<213> ORGANISM: Homo sapiens

<400> SEQUENCE: 85
cugggcccgc ggcgggcgug ggg                                             23

<210> SEQ ID NO 86
<211> LENGTH: 22
<212> TYPE: RNA
<213> ORGANISM: Homo sapiens

<400> SEQUENCE: 86
cuccuggggc ccgcacucuc gc                                              22

<210> SEQ ID NO 87
<211> LENGTH: 23
<212> TYPE: RNA
<213> ORGANISM: Homo sapiens

<400> SEQUENCE: 87
uggggaaggc uuggcaggga aga                                             23

<210> SEQ ID NO 88
<211> LENGTH: 20
<212> TYPE: RNA
<213> ORGANISM: Homo sapiens

<400> SEQUENCE: 88
aaaaggcggg agaagcccca                                                 20

<210> SEQ ID NO 89
<211> LENGTH: 22
<212> TYPE: RNA
<213> ORGANISM: Homo sapiens

<400> SEQUENCE: 89
gagcaggcga ggcugggcug aa                                              22

<210> SEQ ID NO 90
<211> LENGTH: 20
<212> TYPE: RNA
<213> ORGANISM: Homo sapiens

<400> SEQUENCE: 90
aaaagcuggg cugagaggcg                                                 20

<210> SEQ ID NO 91
<211> LENGTH: 17
<212> TYPE: RNA
<213> ORGANISM: Homo sapiens

<400> SEQUENCE: 91 gugggggccag gcggugg                                                   17

<210> SEQ ID NO 92
<211> LENGTH: 22
<212> TYPE: RNA
<213> ORGANISM: Homo sapiens
```

```
<400> SEQUENCE: 92 ugggggaaggc gucagugucg gg                                          22

<210> SEQ ID NO 93
<211> LENGTH: 22
<212> TYPE: RNA
<213> ORGANISM: Homo sapiens

<400> SEQUENCE: 93 acugguagg uggggcucca gg                                            22

<210> SEQ ID NO 94
<211> LENGTH: 25
<212> TYPE: RNA
<213> ORGANISM: Homo sapiens

<400> SEQUENCE: 94
auggggugag auggggagga gcagc                                        25

<210> SEQ ID NO 95
<211> LENGTH: 23
<212> TYPE: RNA
<213> ORGANISM: Homo sapiens

<400> SEQUENCE: 95
ggaggcgcag gcucggaaag gcg                                          23

<210> SEQ ID NO 96
<211> LENGTH: 22
<212> TYPE: RNA
<213> ORGANISM: Homo sapiens

<400> SEQUENCE: 96
ggggaacugu agaugaaaag gc                                           22

<210> SEQ ID NO 97
<211> LENGTH: 23
<212> TYPE: RNA
<213> ORGANISM: Homo sapiens

<400> SEQUENCE: 97
agaagaaggc ggucggucug cgg                                          23

<210> SEQ ID NO 98
<211> LENGTH: 25
<212> TYPE: RNA
<213> ORGANISM: Homo sapiens

<400> SEQUENCE: 98
agcggggagg aagugggcgc ugcuu                                        25

<210> SEQ ID NO 99
<211> LENGTH: 17
<212> TYPE: RNA
<213> ORGANISM: Homo sapiens

<400> SEQUENCE: 99
cuccgggacg gcugggc                                                 17

<210> SEQ ID NO 100
<211> LENGTH: 23
<212> TYPE: RNA
```

```
<213> ORGANISM: Homo sapiens

<400> SEQUENCE: 100
ucgaggacug guggaagggc cuu                                              23

<210> SEQ ID NO 101
<211> LENGTH: 24
<212> TYPE: RNA
<213> ORGANISM: Homo sapiens

<400> SEQUENCE: 101
uguaggcaug aggcagggcc cagg                                             24

<210> SEQ ID NO 102
<211> LENGTH: 22
<212> TYPE: RNA
<213> ORGANISM: Homo sapiens

<400> SEQUENCE: 102
ggcuacaaca caggacccgg gc                                               22

<210> SEQ ID NO 103
<211> LENGTH: 22
<212> TYPE: RNA
<213> ORGANISM: Homo sapiens

<400> SEQUENCE: 103
uggggcggag cuuccggagg cc                                               22

<210> SEQ ID NO 104
<211> LENGTH: 23
<212> TYPE: RNA
<213> ORGANISM: Homo sapiens

<400> SEQUENCE: 104 uggggggcugg gaugggccau ggu                                             23

<210> SEQ ID NO 105
<211> LENGTH: 19
<212> TYPE: RNA
<213> ORGANISM: Homo sapiens

<400> SEQUENCE: 105
ugcggcagag cuggguca                                                    19

<210> SEQ ID NO 106
<211> LENGTH: 21
<212> TYPE: RNA
<213> ORGANISM: Homo sapiens

<400> SEQUENCE: 106
guaggugaca gucaggggcg g                                                21

<210> SEQ ID NO 107
<211> LENGTH: 22
<212> TYPE: RNA
<213> ORGANISM: Homo sapiens

<400> SEQUENCE: 107
aggcgaugug gggauguaga ga                                               22

<210> SEQ ID NO 108
<211> LENGTH: 24
```

<212> TYPE: RNA
<213> ORGANISM: Homo sapiens

<400> SEQUENCE: 108 ugggggggaca ggaugagagg cugu                                         24

<210> SEQ ID NO 109
<211> LENGTH: 23
<212> TYPE: RNA
<213> ORGANISM: Homo sapiens

<400> SEQUENCE: 109
gagggcagcg uggugugggc gga                                           23

<210> SEQ ID NO 110
<211> LENGTH: 20
<212> TYPE: RNA
<213> ORGANISM: Homo sapiens

<400> SEQUENCE: 110
accaggaggc ugaggccccu                                               20

<210> SEQ ID NO 111
<211> LENGTH: 22
<212> TYPE: RNA
<213> ORGANISM: Homo sapiens

<400> SEQUENCE: 111
agugggagga caggaggcag gu                                            22

<210> SEQ ID NO 112
<211> LENGTH: 23
<212> TYPE: RNA
<213> ORGANISM: Homo sapiens

<400> SEQUENCE: 112
ugagcaccac acaggccggg cgc                                           23

<210> SEQ ID NO 113
<211> LENGTH: 22
<212> TYPE: RNA
<213> ORGANISM: Homo sapiens

<400> SEQUENCE: 113
uugaggagac auggugggggg cc                                           22

<210> SEQ ID NO 114
<211> LENGTH: 21
<212> TYPE: RNA
<213> ORGANISM: Homo sapiens

<400> SEQUENCE: 114
gcagggacag caaaggggug c                                             21

<210> SEQ ID NO 115
<211> LENGTH: 24
<212> TYPE: RNA
<213> ORGANISM: Homo sapiens

<400> SEQUENCE: 115
cugcaggcag aagugggggcu gaca                                         24

<210> SEQ ID NO 116

```
<211> LENGTH: 22
<212> TYPE: RNA
<213> ORGANISM: Homo sapiens

<400> SEQUENCE: 116
cucgggcgga ggugguugag ug                                          22

<210> SEQ ID NO 117
<211> LENGTH: 18
<212> TYPE: RNA
<213> ORGANISM: Homo sapiens

<400> SEQUENCE: 117
gugaaggccc ggcggaga                                               18

<210> SEQ ID NO 118
<211> LENGTH: 23
<212> TYPE: RNA
<213> ORGANISM: Homo sapiens

<400> SEQUENCE: 118
gaacgccugu ucuugccagg ugg                                         23

<210> SEQ ID NO 119
<211> LENGTH: 21
<212> TYPE: RNA
<213> ORGANISM: Homo sapiens

<400> SEQUENCE: 119 uggggugug gggagagaga g                                            21

<210> SEQ ID NO 120
<211> LENGTH: 22
<212> TYPE: RNA
<213> ORGANISM: Homo sapiens

<400> SEQUENCE: 120
ugcggggcua gggcuaacag ca                                          22

<210> SEQ ID NO 121
<211> LENGTH: 21
<212> TYPE: RNA
<213> ORGANISM: Homo sapiens

<400> SEQUENCE: 121
agguggguau ggaggagccc u                                           21

<210> SEQ ID NO 122
<211> LENGTH: 18
<212> TYPE: RNA
<213> ORGANISM: Homo sapiens

<400> SEQUENCE: 122
cggugagcgc ucgcuggc                                               18

<210> SEQ ID NO 123
<211> LENGTH: 20
<212> TYPE: RNA
<213> ORGANISM: Homo sapiens

<400> SEQUENCE: 123
gggcuggggc gcggggaggu                                             20
```

```
<210> SEQ ID NO 124
<211> LENGTH: 23
<212> TYPE: RNA
<213> ORGANISM: Homo sapiens

<400> SEQUENCE: 124 ccaggggau gggcgagcuu ggg                                              23

<210> SEQ ID NO 125
<211> LENGTH: 21
<212> TYPE: RNA
<213> ORGANISM: Homo sapiens

<400> SEQUENCE: 125
cgggccggag gucaagggcg u                                               21

<210> SEQ ID NO 126
<211> LENGTH: 18
<212> TYPE: RNA
<213> ORGANISM: Homo sapiens

<400> SEQUENCE: 126
gaggcugaag gaagaugg                                                   18

<210> SEQ ID NO 127
<211> LENGTH: 22
<212> TYPE: RNA
<213> ORGANISM: Homo sapiens

<400> SEQUENCE: 127
cagggcuggc agugacaugg gu                                              22

<210> SEQ ID NO 128
<211> LENGTH: 22
<212> TYPE: RNA
<213> ORGANISM: Homo sapiens

<400> SEQUENCE: 128
caguuggguc uaggggucag ga                                              22

<210> SEQ ID NO 129
<211> LENGTH: 21
<212> TYPE: RNA
<213> ORGANISM: Homo sapiens

<400> SEQUENCE: 129
guuggggugc agggucugc u                                                21

<210> SEQ ID NO 130
<211> LENGTH: 21
<212> TYPE: RNA
<213> ORGANISM: Homo sapiens

<400> SEQUENCE: 130
acggcccagg cggcauuggu g                                               21

<210> SEQ ID NO 131
<211> LENGTH: 22
<212> TYPE: RNA
<213> ORGANISM: Homo sapiens

<400> SEQUENCE: 131 gagguuggg uggaggcucu cc                                               22
```

```
<210> SEQ ID NO 132
<211> LENGTH: 19
<212> TYPE: RNA
<213> ORGANISM: Homo sapiens

<400> SEQUENCE: 132
uaaggagggg gaugagggg                                                  19

<210> SEQ ID NO 133
<211> LENGTH: 23
<212> TYPE: RNA
<213> ORGANISM: Homo sapiens

<400> SEQUENCE: 133 ugagugggc ucccgggacg gcg                                              23

<210> SEQ ID NO 134
<211> LENGTH: 25
<212> TYPE: RNA
<213> ORGANISM: Homo sapiens

<400> SEQUENCE: 134
ucggggcaug ggggagggag gcugg                                           25

<210> SEQ ID NO 135
<211> LENGTH: 19
<212> TYPE: RNA
<213> ORGANISM: Homo sapiens

<400> SEQUENCE: 135 uggggagau gggggluuga                                                  19

<210> SEQ ID NO 136
<211> LENGTH: 20
<212> TYPE: RNA
<213> ORGANISM: Homo sapiens

<400> SEQUENCE: 136
ggggagcugu ggaagcagua                                                 20

<210> SEQ ID NO 137
<211> LENGTH: 18
<212> TYPE: RNA
<213> ORGANISM: Homo sapiens

<400> SEQUENCE: 137
cccagcagga cgggagcg                                                   18

<210> SEQ ID NO 138
<211> LENGTH: 22
<212> TYPE: RNA
<213> ORGANISM: Homo sapiens

<400> SEQUENCE: 138
uuggggugga gggccaagga gc                                              22

<210> SEQ ID NO 139
<211> LENGTH: 22
<212> TYPE: RNA
<213> ORGANISM: Homo sapiens

<400> SEQUENCE: 139
uggggaggug uggagucagc au                                              22
```

<210> SEQ ID NO 140
<211> LENGTH: 21
<212> TYPE: RNA
<213> ORGANISM: Homo sapiens

<400> SEQUENCE: 140
cguggaggac gaggaggagg c                                          21

<210> SEQ ID NO 141
<211> LENGTH: 19
<212> TYPE: RNA
<213> ORGANISM: Homo sapiens

<400> SEQUENCE: 141
ggcuggucag augggagug                                             19

<210> SEQ ID NO 142
<211> LENGTH: 21
<212> TYPE: RNA
<213> ORGANISM: Homo sapiens

<400> SEQUENCE: 142
acaggagugg ggugggaca u                                           21

<210> SEQ ID NO 143
<211> LENGTH: 21
<212> TYPE: RNA
<213> ORGANISM: Homo sapiens

<400> SEQUENCE: 143
gugggcgggg gcaggugugu g                                          21

<210> SEQ ID NO 144
<211> LENGTH: 22
<212> TYPE: RNA
<213> ORGANISM: Homo sapiens

<400> SEQUENCE: 144
aaggggcagg gacggguggc cc                                         22

<210> SEQ ID NO 145
<211> LENGTH: 18
<212> TYPE: RNA
<213> ORGANISM: Homo sapiens

<400> SEQUENCE: 145
cgggcguggu ggugggg                                               18

<210> SEQ ID NO 146
<211> LENGTH: 20
<212> TYPE: RNA
<213> ORGANISM: Homo sapiens

<400> SEQUENCE: 146
gcucggacug agcagguggg                                            20

<210> SEQ ID NO 147
<211> LENGTH: 21
<212> TYPE: RNA
<213> ORGANISM: Homo sapiens

<400> SEQUENCE: 147

```
gcggugggc cggaggggcg u                                              21

<210> SEQ ID NO 148
<211> LENGTH: 22
<212> TYPE: RNA
<213> ORGANISM: Homo sapiens

<400> SEQUENCE: 148
cagaagggga guugggagca ga                                            22

<210> SEQ ID NO 149
<211> LENGTH: 25
<212> TYPE: RNA
<213> ORGANISM: Homo sapiens

<400> SEQUENCE: 149
agggaucgcg ggcggguggc ggccu                                         25

<210> SEQ ID NO 150
<211> LENGTH: 22
<212> TYPE: RNA
<213> ORGANISM: Homo sapiens

<400> SEQUENCE: 150
gugggugcug gugggagccg ug                                            22

<210> SEQ ID NO 151
<211> LENGTH: 23
<212> TYPE: RNA
<213> ORGANISM: Homo sapiens

<400> SEQUENCE: 151
ucggggaguc uggggguccgg aau                                          23

<210> SEQ ID NO 152
<211> LENGTH: 22
<212> TYPE: RNA
<213> ORGANISM: Homo sapiens

<400> SEQUENCE: 152
gcccaggacu uugugcgggg ug                                            22

<210> SEQ ID NO 153
<211> LENGTH: 22
<212> TYPE: RNA
<213> ORGANISM: Homo sapiens

<400> SEQUENCE: 153
cagcagggga gagagaggag uc                                            22

<210> SEQ ID NO 154
<211> LENGTH: 23
<212> TYPE: RNA
<213> ORGANISM: Homo sapiens

<400> SEQUENCE: 154
agaggcuuug ugcggauacg ggg                                           23

<210> SEQ ID NO 155
<211> LENGTH: 22
<212> TYPE: RNA
<213> ORGANISM: Homo sapiens

<400> SEQUENCE: 155
```
gaaaucaagc gugggugaga cc                                          22

<210> SEQ ID NO 156
<211> LENGTH: 24
<212> TYPE: RNA
<213> ORGANISM: Homo sapiens

<400> SEQUENCE: 156
agggcuggac ucagcggcgg agcu                                        24

<210> SEQ ID NO 157
<211> LENGTH: 20
<212> TYPE: RNA
<213> ORGANISM: Homo sapiens

<400> SEQUENCE: 157
cgggcguggu gguggggug                                              20

<210> SEQ ID NO 158
<211> LENGTH: 22
<212> TYPE: RNA
<213> ORGANISM: Homo sapiens

<400> SEQUENCE: 158
ucggccuggg gaggaggaag gg                                          22

<210> SEQ ID NO 159
<211> LENGTH: 22
<212> TYPE: RNA
<213> ORGANISM: Homo sapiens

<400> SEQUENCE: 159
guaggggagg uugggccagg ga                                          22

<210> SEQ ID NO 160
<211> LENGTH: 20
<212> TYPE: RNA
<213> ORGANISM: Homo sapiens

<400> SEQUENCE: 160 uaggggugg caggcuggcc                                              20

<210> SEQ ID NO 161
<211> LENGTH: 20
<212> TYPE: RNA
<213> ORGANISM: Homo sapiens

<400> SEQUENCE: 161
acucaaacug uggggcacu                                              20

<210> SEQ ID NO 162
<211> LENGTH: 20
<212> TYPE: RNA
<213> ORGANISM: Homo sapiens

<400> SEQUENCE: 162 caggggacu gggggugagc                                              20

<210> SEQ ID NO 163
<211> LENGTH: 21
<212> TYPE: RNA
<213> ORGANISM: Homo sapiens

<400> SEQUENCE: 163
cugggagggg cuggguuugg c                                          21

<210> SEQ ID NO 164
<211> LENGTH: 19
<212> TYPE: RNA
<213> ORGANISM: Homo sapiens

<400> SEQUENCE: 164
gggggaagaa aaggugggg                                             19

<210> SEQ ID NO 165
<211> LENGTH: 21
<212> TYPE: RNA
<213> ORGANISM: Homo sapiens

<400> SEQUENCE: 165
auccaguucu cugagggggc u                                          21

<210> SEQ ID NO 166
<211> LENGTH: 23
<212> TYPE: RNA
<213> ORGANISM: Homo sapiens

<400> SEQUENCE: 166
cggggccaug gagcagccug ugu                                        23

<210> SEQ ID NO 167
<211> LENGTH: 24
<212> TYPE: RNA
<213> ORGANISM: Homo sapiens

<400> SEQUENCE: 167
uggggagcug aggcucuggg ggug                                       24

<210> SEQ ID NO 168
<211> LENGTH: 24
<212> TYPE: RNA
<213> ORGANISM: Homo sapiens

<400> SEQUENCE: 168
ccccgggaac gucgagacug gagc                                       24

<210> SEQ ID NO 169
<211> LENGTH: 23
<212> TYPE: RNA
<213> ORGANISM: Homo sapiens

<400> SEQUENCE: 169
acggggaguc aggcaguggu gga                                        23

<210> SEQ ID NO 170
<211> LENGTH: 22
<212> TYPE: RNA
<213> ORGANISM: Homo sapiens

<400> SEQUENCE: 170 ugcaggggguc gggugggcca gg                                        22

<210> SEQ ID NO 171
<211> LENGTH: 17
<212> TYPE: RNA
<213> ORGANISM: Homo sapiens

```
<400> SEQUENCE: 171
ggcgggugcg ggggugg                                                    17

<210> SEQ ID NO 172
<211> LENGTH: 22
<212> TYPE: RNA
<213> ORGANISM: Homo sapiens

<400> SEQUENCE: 172 uagggggcagc agaggaccug gg                                             22

<210> SEQ ID NO 173
<211> LENGTH: 17
<212> TYPE: RNA
<213> ORGANISM: Homo sapiens

<400> SEQUENCE: 173
cgcgccgggc ccggguu                                                    17

<210> SEQ ID NO 174
<211> LENGTH: 24
<212> TYPE: RNA
<213> ORGANISM: Homo sapiens

<400> SEQUENCE: 174
cgggugggag cagaucuuau ugag                                            24

<210> SEQ ID NO 175
<211> LENGTH: 17
<212> TYPE: RNA
<213> ORGANISM: Homo sapiens

<400> SEQUENCE: 175 gguggggcu guuguuu                                                     17

<210> SEQ ID NO 176
<211> LENGTH: 23
<212> TYPE: RNA
<213> ORGANISM: Homo sapiens

<400> SEQUENCE: 176
ugggcugagg gcaggaggcc ugu                                             23

<210> SEQ ID NO 177
<211> LENGTH: 21
<212> TYPE: RNA
<213> ORGANISM: Homo sapiens

<400> SEQUENCE: 177
guguggccgg caggcgggug g                                               21

<210> SEQ ID NO 178
<211> LENGTH: 23
<212> TYPE: RNA
<213> ORGANISM: Homo sapiens

<400> SEQUENCE: 178
uggggacgua gcuggccaga cag                                             23

<210> SEQ ID NO 179
<211> LENGTH: 21
<212> TYPE: RNA
```

```
<213> ORGANISM: Homo sapiens

<400> SEQUENCE: 179
accacugcac uccagccuga g                                          21

<210> SEQ ID NO 180
<211> LENGTH: 17
<212> TYPE: RNA
<213> ORGANISM: Homo sapiens

<400> SEQUENCE: 180
gagacugggg ugggggcc                                              17

<210> SEQ ID NO 181
<211> LENGTH: 19
<212> TYPE: RNA
<213> ORGANISM: Homo sapiens

<400> SEQUENCE: 181
ggggccuggc gguggggcgg                                            19

<210> SEQ ID NO 182
<211> LENGTH: 18
<212> TYPE: RNA
<213> ORGANISM: Homo sapiens

<400> SEQUENCE: 182
cggggcggca ggggccuc                                              18

<210> SEQ ID NO 183
<211> LENGTH: 22
<212> TYPE: RNA
<213> ORGANISM: Homo sapiens

<400> SEQUENCE: 183
agggccgaag gguggaagcu gc                                         22

<210> SEQ ID NO 184
<211> LENGTH: 23
<212> TYPE: RNA
<213> ORGANISM: Homo sapiens

<400> SEQUENCE: 184
ugaggauaug gcagggaagg gga                                        23

<210> SEQ ID NO 185
<211> LENGTH: 17
<212> TYPE: RNA
<213> ORGANISM: Homo sapiens

<400> SEQUENCE: 185
gccggacaag agggagg                                               17

<210> SEQ ID NO 186
<211> LENGTH: 24
<212> TYPE: RNA
<213> ORGANISM: Homo sapiens

<400> SEQUENCE: 186 guagggggcgu cccgggcgcg cggg                                      24

<210> SEQ ID NO 187
<211> LENGTH: 25
```

<212> TYPE: RNA
<213> ORGANISM: Homo sapiens

<400> SEQUENCE: 187
uagggguggg ggaauucagg ggugu                                         25

<210> SEQ ID NO 188
<211> LENGTH: 21
<212> TYPE: RNA
<213> ORGANISM: Homo sapiens

<400> SEQUENCE: 188 cgggcagcu caguacagga u                                              21

<210> SEQ ID NO 189
<211> LENGTH: 19
<212> TYPE: RNA
<213> ORGANISM: Homo sapiens

<400> SEQUENCE: 189
aaggggcugg gggagcaca                                                19

<210> SEQ ID NO 190
<211> LENGTH: 21
<212> TYPE: RNA
<213> ORGANISM: Homo sapiens

<400> SEQUENCE: 190
agcggugcuc cugcgggccg a                                             21

<210> SEQ ID NO 191
<211> LENGTH: 22
<212> TYPE: RNA
<213> ORGANISM: Homo sapiens

<400> SEQUENCE: 191
gcugggauua caggcaugag cc                                            22

<210> SEQ ID NO 192
<211> LENGTH: 20
<212> TYPE: RNA
<213> ORGANISM: Homo sapiens

<400> SEQUENCE: 192
gugagucagg guggggcugg                                               20

<210> SEQ ID NO 193
<211> LENGTH: 22
<212> TYPE: RNA
<213> ORGANISM: Homo sapiens

<400> SEQUENCE: 193
cugggggugg ggggcugggc gu                                            22

<210> SEQ ID NO 194
<211> LENGTH: 22
<212> TYPE: RNA
<213> ORGANISM: Homo sapiens

<400> SEQUENCE: 194
cugggacagg aggaggaggc ag                                            22

<210> SEQ ID NO 195

```
<211> LENGTH: 20
<212> TYPE: RNA
<213> ORGANISM: Homo sapiens

<400> SEQUENCE: 195
ggauccgagu cacggcacca                                               20

<210> SEQ ID NO 196
<211> LENGTH: 22
<212> TYPE: RNA
<213> ORGANISM: Homo sapiens

<400> SEQUENCE: 196
ccaggaggcg gaggaggugg ag                                            22

<210> SEQ ID NO 197
<211> LENGTH: 18
<212> TYPE: RNA
<213> ORGANISM: Homo sapiens

<400> SEQUENCE: 197
cuggcagggg gagaggua                                                 18

<210> SEQ ID NO 198
<211> LENGTH: 22
<212> TYPE: RNA
<213> ORGANISM: Homo sapiens

<400> SEQUENCE: 198
ugguggagga agagggcagc uc                                            22

<210> SEQ ID NO 199
<211> LENGTH: 22
<212> TYPE: RNA
<213> ORGANISM: Homo sapiens

<400> SEQUENCE: 199
cgucccgggg cugcgcgagg ca                                            22

<210> SEQ ID NO 200
<211> LENGTH: 22
<212> TYPE: RNA
<213> ORGANISM: Homo sapiens

<400> SEQUENCE: 200
ucaaaaucag gagucggggc uu                                            22

<210> SEQ ID NO 201
<211> LENGTH: 22
<212> TYPE: RNA
<213> ORGANISM: Homo sapiens

<400> SEQUENCE: 201
caggaggcag ugggcgagca gg                                            22

<210> SEQ ID NO 202
<211> LENGTH: 19
<212> TYPE: RNA
<213> ORGANISM: Homo sapiens

<400> SEQUENCE: 202
agcagggcug gggauugca                                                19
```

```
<210> SEQ ID NO 203
<211> LENGTH: 20
<212> TYPE: RNA
<213> ORGANISM: Homo sapiens

<400> SEQUENCE: 203
ugggcugcug agaaggggca                                              20

<210> SEQ ID NO 204
<211> LENGTH: 17
<212> TYPE: RNA
<213> ORGANISM: Homo sapiens

<400> SEQUENCE: 204
gcugggcgag gcuggca                                                 17

<210> SEQ ID NO 205
<211> LENGTH: 23
<212> TYPE: RNA
<213> ORGANISM: Homo sapiens

<400> SEQUENCE: 205
uugcucugcu cccccgcccc cag                                          23

<210> SEQ ID NO 206
<211> LENGTH: 23
<212> TYPE: RNA
<213> ORGANISM: Homo sapiens

<400> SEQUENCE: 206
ucaauaggaa agagguggga ccu                                          23

<210> SEQ ID NO 207
<211> LENGTH: 17
<212> TYPE: RNA
<213> ORGANISM: Homo sapiens

<400> SEQUENCE: 207
gcggggcugg gcgcgcg                                                 17

<210> SEQ ID NO 208
<211> LENGTH: 22
<212> TYPE: RNA
<213> ORGANISM: Homo sapiens

<400> SEQUENCE: 208
uggggagcgg cccccggugu gg                                           22

<210> SEQ ID NO 209
<211> LENGTH: 21
<212> TYPE: RNA
<213> ORGANISM: Homo sapiens

<400> SEQUENCE: 209
ucuguggagu ggggugccug u                                            21

<210> SEQ ID NO 210
<211> LENGTH: 22
<212> TYPE: RNA
<213> ORGANISM: Homo sapiens

<400> SEQUENCE: 210
caggcacggg agcucaggug ag                                           22
```

```
<210> SEQ ID NO 211
<211> LENGTH: 25
<212> TYPE: RNA
<213> ORGANISM: Homo sapiens

<400> SEQUENCE: 211
gugaggcggg gccaggaggg ugugu                                           25

<210> SEQ ID NO 212
<211> LENGTH: 21
<212> TYPE: RNA
<213> ORGANISM: Homo sapiens

<400> SEQUENCE: 212
aagggacagg gagggucgug g                                               21

<210> SEQ ID NO 213
<211> LENGTH: 20
<212> TYPE: RNA
<213> ORGANISM: Homo sapiens

<400> SEQUENCE: 213
ggcggcggcg gaggcggggg                                                 20

<210> SEQ ID NO 214
<211> LENGTH: 22
<212> TYPE: RNA
<213> ORGANISM: Homo sapiens

<400> SEQUENCE: 214
ucgggccugg gguugggga gc                                               22

<210> SEQ ID NO 215
<211> LENGTH: 19
<212> TYPE: RNA
<213> ORGANISM: Homo sapiens

<400> SEQUENCE: 215
aucccaccac ugccaccau                                                  19

<210> SEQ ID NO 216
<211> LENGTH: 20
<212> TYPE: RNA
<213> ORGANISM: Homo sapiens

<400> SEQUENCE: 216
ggggaggugu gcagggcugg                                                 20

<210> SEQ ID NO 217
<211> LENGTH: 24
<212> TYPE: RNA
<213> ORGANISM: Homo sapiens

<400> SEQUENCE: 217 uggggagcc augagauaag agca                                             24

<210> SEQ ID NO 218
<211> LENGTH: 20
<212> TYPE: RNA
<213> ORGANISM: Homo sapiens

<400> SEQUENCE: 218
gccggggcuu ugggugaggg                                                 20
```

```
<210> SEQ ID NO 219
<211> LENGTH: 22
<212> TYPE: RNA
<213> ORGANISM: Homo sapiens

<400> SEQUENCE: 219
uucagauccc agcggugccu cu                                              22

<210> SEQ ID NO 220
<211> LENGTH: 23
<212> TYPE: RNA
<213> ORGANISM: Homo sapiens

<400> SEQUENCE: 220 ugguggugg ggaggagaaag ugc                                             23

<210> SEQ ID NO 221
<211> LENGTH: 21
<212> TYPE: RNA
<213> ORGANISM: Homo sapiens

<400> SEQUENCE: 221
uggcagggag gcugggaggg g                                               21

<210> SEQ ID NO 222
<211> LENGTH: 22
<212> TYPE: RNA
<213> ORGANISM: Homo sapiens

<400> SEQUENCE: 222
agacacauuu ggagagggaa cc                                              22

<210> SEQ ID NO 223
<211> LENGTH: 18
<212> TYPE: RNA
<213> ORGANISM: Homo sapiens

<400> SEQUENCE: 223
aggcugggcu gggacgga                                                   18

<210> SEQ ID NO 224
<211> LENGTH: 20
<212> TYPE: RNA
<213> ORGANISM: Homo sapiens

<400> SEQUENCE: 224
ucagggaguc aggggagggc                                                 20

<210> SEQ ID NO 225
<211> LENGTH: 23
<212> TYPE: RNA
<213> ORGANISM: Homo sapiens

<400> SEQUENCE: 225
ugggcagggg cuuauuguag gag                                             23

<210> SEQ ID NO 226
<211> LENGTH: 22
<212> TYPE: RNA
<213> ORGANISM: Homo sapiens

<400> SEQUENCE: 226
```

```
ugggggagga aggacaggcc au                                        22

<210> SEQ ID NO 227
<211> LENGTH: 22
<212> TYPE: RNA
<213> ORGANISM: Homo sapiens

<400> SEQUENCE: 227
ccccuggggc ugggcaggcg ga                                        22

<210> SEQ ID NO 228
<211> LENGTH: 21
<212> TYPE: RNA
<213> ORGANISM: Homo sapiens

<400> SEQUENCE: 228
cuggggggag gagacccugc u                                         21

<210> SEQ ID NO 229
<211> LENGTH: 17
<212> TYPE: RNA
<213> ORGANISM: Homo sapiens

<400> SEQUENCE: 229
ccccgccacc gccuugg                                              17

<210> SEQ ID NO 230
<211> LENGTH: 20
<212> TYPE: RNA
<213> ORGANISM: Homo sapiens

<400> SEQUENCE: 230
ucucuucauc uaccccccag                                           20

<210> SEQ ID NO 231
<211> LENGTH: 23
<212> TYPE: RNA
<213> ORGANISM: Homo sapiens

<400> SEQUENCE: 231
aggagguggu acuaggggcc agc                                       23

<210> SEQ ID NO 232
<211> LENGTH: 20
<212> TYPE: RNA
<213> ORGANISM: Homo sapiens

<400> SEQUENCE: 232
gcggaaggcg gagcggcgga                                           20

<210> SEQ ID NO 233
<211> LENGTH: 22
<212> TYPE: RNA
<213> ORGANISM: Homo sapiens

<400> SEQUENCE: 233
ugcggggaca ggccagggca uc                                        22

<210> SEQ ID NO 234
<211> LENGTH: 23
<212> TYPE: RNA
<213> ORGANISM: Homo sapiens

<400> SEQUENCE: 234
```
agggccagag gagccuggag ugg                                          23

<210> SEQ ID NO 235
<211> LENGTH: 22
<212> TYPE: RNA
<213> ORGANISM: Homo sapiens

<400> SEQUENCE: 235
agacugacgg cuggaggccc au                                           22

<210> SEQ ID NO 236
<211> LENGTH: 20
<212> TYPE: RNA
<213> ORGANISM: Homo sapiens

<400> SEQUENCE: 236
cggcucuggg ucugugggga                                              20

<210> SEQ ID NO 237
<211> LENGTH: 23
<212> TYPE: RNA
<213> ORGANISM: Homo sapiens

<400> SEQUENCE: 237
gacacgggcg acagcugcgg ccc                                          23

<210> SEQ ID NO 238
<211> LENGTH: 23
<212> TYPE: RNA
<213> ORGANISM: Homo sapiens

<400> SEQUENCE: 238
ugaggggcag agagcgagac uuu                                          23

<210> SEQ ID NO 239
<211> LENGTH: 22
<212> TYPE: RNA
<213> ORGANISM: Homo sapiens

<400> SEQUENCE: 239 gggugggggau uuguugcauu ac                                          22

<210> SEQ ID NO 240
<211> LENGTH: 22
<212> TYPE: RNA
<213> ORGANISM: Homo sapiens

<400> SEQUENCE: 240
uagcagcacg uaaauauugg cg                                           22

<210> SEQ ID NO 241
<211> LENGTH: 22
<212> TYPE: RNA
<213> ORGANISM: Homo sapiens

<400> SEQUENCE: 241
aaaccguuac cauuacugag uu                                           22

<210> SEQ ID NO 242
<211> LENGTH: 22
<212> TYPE: RNA
<213> ORGANISM: Homo sapiens

```
<400> SEQUENCE: 242
uauagggauu ggagccgugg cg                                              22

<210> SEQ ID NO 243
<211> LENGTH: 22
<212> TYPE: RNA
<213> ORGANISM: Homo sapiens

<400> SEQUENCE: 243
uccuguacug agcugccccg ag                                              22

<210> SEQ ID NO 244
<211> LENGTH: 18
<212> TYPE: RNA
<213> ORGANISM: Homo sapiens

<400> SEQUENCE: 244
ccagaggugg ggacugag                                                   18

<210> SEQ ID NO 245
<211> LENGTH: 22
<212> TYPE: RNA
<213> ORGANISM: Homo sapiens

<400> SEQUENCE: 245
agggacggga cgcggugcag ug                                              22

<210> SEQ ID NO 246
<211> LENGTH: 20
<212> TYPE: RNA
<213> ORGANISM: Homo sapiens

<400> SEQUENCE: 246
ccccagggcg acgcggcggg                                                 20

<210> SEQ ID NO 247
<211> LENGTH: 21
<212> TYPE: RNA
<213> ORGANISM: Homo sapiens

<400> SEQUENCE: 247
cuuccgcccc gccgggcguc g                                               21

<210> SEQ ID NO 248
<211> LENGTH: 21
<212> TYPE: RNA
<213> ORGANISM: Homo sapiens

<400> SEQUENCE: 248
aaggcagggc ccccgcuccc c                                               21

<210> SEQ ID NO 249
<211> LENGTH: 21
<212> TYPE: RNA
<213> ORGANISM: Homo sapiens

<400> SEQUENCE: 249
agggcccccc cucaauccug u                                               21

<210> SEQ ID NO 250
<211> LENGTH: 21
<212> TYPE: RNA
<213> ORGANISM: Homo sapiens
```

<400> SEQUENCE: 250
aucacauugc cagggauuac c                                      21

<210> SEQ ID NO 251
<211> LENGTH: 22
<212> TYPE: RNA
<213> ORGANISM: Homo sapiens

<400> SEQUENCE: 251
uauugcacuu gucccggccu gu                                     22

<210> SEQ ID NO 252
<211> LENGTH: 25
<212> TYPE: RNA
<213> ORGANISM: Homo sapiens

<400> SEQUENCE: 252
ggcggaggga aguagguccg uuggu                                  25

<210> SEQ ID NO 253
<211> LENGTH: 22
<212> TYPE: RNA
<213> ORGANISM: Homo sapiens

<400> SEQUENCE: 253
uggggguggu cucuagccaa gg                                     22

<210> SEQ ID NO 254
<211> LENGTH: 20
<212> TYPE: RNA
<213> ORGANISM: Homo sapiens

<400> SEQUENCE: 254
gggaaaagga aggggagga                                         20

<210> SEQ ID NO 255
<211> LENGTH: 21
<212> TYPE: RNA
<213> ORGANISM: Homo sapiens

<400> SEQUENCE: 255
ucaccuggcu ggcccgccca g                                      21

<210> SEQ ID NO 256
<211> LENGTH: 20
<212> TYPE: RNA
<213> ORGANISM: Homo sapiens

<400> SEQUENCE: 256
ugggaggagg ggaucuuggg                                        20

<210> SEQ ID NO 257
<211> LENGTH: 17
<212> TYPE: RNA
<213> ORGANISM: Homo sapiens

<400> SEQUENCE: 257
ggauggagga gggucu                                            17

<210> SEQ ID NO 258
<211> LENGTH: 22
<212> TYPE: RNA

```
<213> ORGANISM: Homo sapiens

<400> SEQUENCE: 258
uauugcacuc gucccggccu cc                                              22

<210> SEQ ID NO 259
<211> LENGTH: 22
<212> TYPE: RNA
<213> ORGANISM: Homo sapiens

<400> SEQUENCE: 259
ggcuggagcg agugcagugg ug                                              22

<210> SEQ ID NO 260
<211> LENGTH: 21
<212> TYPE: RNA
<213> ORGANISM: Homo sapiens

<400> SEQUENCE: 260
uggcuguugg aggggggcagg c                                              21

<210> SEQ ID NO 261
<211> LENGTH: 22
<212> TYPE: RNA
<213> ORGANISM: Homo sapiens

<400> SEQUENCE: 261
ggggcugggg ccggggccga gc                                              22

<210> SEQ ID NO 262
<211> LENGTH: 22
<212> TYPE: RNA
<213> ORGANISM: Homo sapiens

<400> SEQUENCE: 262
gggaccaucc ugccugcugu gg                                              22

<210> SEQ ID NO 263
<211> LENGTH: 22
<212> TYPE: RNA
<213> ORGANISM: Homo sapiens

<400> SEQUENCE: 263
uggcggcggu aguuaugggc uu                                              22

<210> SEQ ID NO 264
<211> LENGTH: 23
<212> TYPE: RNA
<213> ORGANISM: Homo sapiens

<400> SEQUENCE: 264
guuugcacgg gugggccuug ucu                                             23

<210> SEQ ID NO 265
<211> LENGTH: 21
<212> TYPE: RNA
<213> ORGANISM: Homo sapiens

<400> SEQUENCE: 265
cgggggcggg gccgaagcgc g                                               21

<210> SEQ ID NO 266
<211> LENGTH: 21
```

-continued

<212> TYPE: RNA
<213> ORGANISM: Homo sapiens

<400> SEQUENCE: 266
cggcggggac ggcgauuggu c                                              21

<210> SEQ ID NO 267
<211> LENGTH: 17
<212> TYPE: RNA
<213> ORGANISM: Homo sapiens

<400> SEQUENCE: 267
accccacucc ugguacc                                                   17

<210> SEQ ID NO 268
<211> LENGTH: 25
<212> TYPE: RNA
<213> ORGANISM: Homo sapiens

<400> SEQUENCE: 268 agggggcac ugcgcaagca aagcc                                           25

<210> SEQ ID NO 269
<211> LENGTH: 19
<212> TYPE: RNA
<213> ORGANISM: Homo sapiens

<400> SEQUENCE: 269
cuggggagug gcuggggag                                                 19

<210> SEQ ID NO 270
<211> LENGTH: 82
<212> TYPE: RNA
<213> ORGANISM: Homo sapiens

<400> SEQUENCE: 270
gggaaagcgg agggcgcgcc cagcucccgg gcugauugcg cuaacagugg ccccggguguu   60 ggggcgcguc ugccgcugcc cc                                             82

<210> SEQ ID NO 271
<211> LENGTH: 76
<212> TYPE: RNA
<213> ORGANISM: Homo sapiens

<400> SEQUENCE: 271
cgcaggccuc uggcggagcc cauuccaugc cagaugcuga gcgauggcug gugugugcug   60
cuccacaggc cuggug                                                    76

<210> SEQ ID NO 272
<211> LENGTH: 149
<212> TYPE: RNA
<213> ORGANISM: Homo sapiens

<400> SEQUENCE: 272
caucaagacc cagcugaguc acugucacug ccuaccaauc ucgaccggac cucgaccggc   60
ucgucugugu ugccaaucga cucggcgugg cgucggucgu gguagauagg cggucaugca  120
uacgaauuuu cagcucuugu ucuggugac                                    149

<210> SEQ ID NO 273
<211> LENGTH: 54
<212> TYPE: RNA

<213> ORGANISM: Homo sapiens

<400> SEQUENCE: 273
ggacaagggc ggcgcgaccg gcccggggcu cuugggcggc cgcguuuccc cucc        54

<210> SEQ ID NO 274
<211> LENGTH: 93
<212> TYPE: RNA
<213> ORGANISM: Homo sapiens

<400> SEQUENCE: 274
ccuuccggcg ucccaggcgg ggcgccgcgg gaccgcccuc gugucugugg cgguggqauc  60 ccgcggccgu guuuuccugg uggcccggcc aug                                93

<210> SEQ ID NO 275
<211> LENGTH: 51
<212> TYPE: RNA
<213> ORGANISM: Homo sapiens

<400> SEQUENCE: 275
acagaccccg gggagcccgg cggugaagcu ccugguaucc uggguqucug a            51

<210> SEQ ID NO 276
<211> LENGTH: 59
<212> TYPE: RNA
<213> ORGANISM: Homo sapiens

<400> SEQUENCE: 276
cggggucggc ggcgacgugc ucagcuuggc acccaaguuc ugccgcuccg acgcccggc   59

<210> SEQ ID NO 277
<211> LENGTH: 84
<212> TYPE: RNA
<213> ORGANISM: Homo sapiens

<400> SEQUENCE: 277
gaggcugggc ggggcgcggc cggaucgguc gagagcgucc uggcugauga cggucucccg  60
ugcccacgcc ccaaacgcag ucuc                                          84

<210> SEQ ID NO 278
<211> LENGTH: 65
<212> TYPE: RNA
<213> ORGANISM: Homo sapiens

<400> SEQUENCE: 278
gagggugggc gagggcggcu gagcggcucc aucccccggc cugcucaucc cccucgcccu  60
cucag                                                               65

<210> SEQ ID NO 279
<211> LENGTH: 60
<212> TYPE: RNA
<213> ORGANISM: Homo sapiens

<400> SEQUENCE: 279
cgcugggucc gcgcgcccug ggccgggcga uguccgcuug ggggagcgag gggcggggcg  60

<210> SEQ ID NO 280
<211> LENGTH: 76
<212> TYPE: RNA
<213> ORGANISM: Homo sapiens

<400> SEQUENCE: 280

```
gagggagcug uagagcaggg agcaggaagc ugugugaguc cagcccugac cuguccuguu    60
cugcccccag ccccuc                                                    76

<210> SEQ ID NO 281
<211> LENGTH: 75
<212> TYPE: RNA
<213> ORGANISM: Homo sapiens

<400> SEQUENCE: 281
aagcaagacu gagggggccuc agaccgagcu uuuggaaaau agaaaagucu cgcucucugc    60
cccucagccu aacuu                                                     75

<210> SEQ ID NO 282
<211> LENGTH: 65
<212> TYPE: RNA
<213> ORGANISM: Homo sapiens

<400> SEQUENCE: 282
gggugcucgg ggcaggcggc ugggagcggc ccucacauug auggcuccug ccaccuccuc    60
cgcag                                                                65

<210> SEQ ID NO 283
<211> LENGTH: 51
<212> TYPE: RNA
<213> ORGANISM: Homo sapiens

<400> SEQUENCE: 283
agagaugaag cggggggggcg gggucuugcu cuauugccua cgcugaucuc a             51

<210> SEQ ID NO 284
<211> LENGTH: 87
<212> TYPE: RNA
<213> ORGANISM: Homo sapiens

<400> SEQUENCE: 284
cccaggcgcc cgcucccgac ccacgccgcg ccgccgggguc ccuccucccc ggagaggcug    60
ggcucgggac gcgcggcuca gcucggg                                        87

<210> SEQ ID NO 285
<211> LENGTH: 72
<212> TYPE: RNA
<213> ORGANISM: Homo sapiens

<400> SEQUENCE: 285
gauuucagug accuggcagc agggagcguc gucaguguuu gacuguuuau gguaugucag    60
ggagcugguu cc                                                        72

<210> SEQ ID NO 286
<211> LENGTH: 84
<212> TYPE: RNA
<213> ORGANISM: Homo sapiens

<400> SEQUENCE: 286
cgguccagac guggcggggg uggcggcggc aucccggacg gccugugagg gaugcgccgc    60
ccacugcccc gcgccgccug accg                                           84

<210> SEQ ID NO 287
<211> LENGTH: 47
<212> TYPE: RNA
```

```
<213> ORGANISM: Homo sapiens

<400> SEQUENCE: 287
cucggcgcgg ggcgcgggcu ccggguuggg gcgagccaac gccgggg            47

<210> SEQ ID NO 288
<211> LENGTH: 86
<212> TYPE: RNA
<213> ORGANISM: Homo sapiens

<400> SEQUENCE: 288
ugccagucuc uaggucccug agacccuuua accugugagg acauccaggg ucacagguga   60
gguucuuggg agccuggcgu cuggcc                                       86

<210> SEQ ID NO 289
<211> LENGTH: 82
<212> TYPE: RNA
<213> ORGANISM: Homo sapiens

<400> SEQUENCE: 289
gugaguggga ggccagggca cggcaggggg agcugcaggg cuagggagg ggccccagcg   60 ucugagcccu guccucccgc ag                                           82

<210> SEQ ID NO 290
<211> LENGTH: 82
<212> TYPE: RNA
<213> ORGANISM: Homo sapiens

<400> SEQUENCE: 290
gugaguggga ggccagggca cggcaggggg agcugcaggg cuagggagg ggccccagcg   60 ucugagcccu guccucccgc ag                                           82

<210> SEQ ID NO 291
<211> LENGTH: 74
<212> TYPE: RNA
<213> ORGANISM: Homo sapiens

<400> SEQUENCE: 291
ccgcacucuc uccauuacac uacccugccu cuucuccaug agaggcagcg ggguguagug   60
gauagagcac gggu                                                    74

<210> SEQ ID NO 292
<211> LENGTH: 65
<212> TYPE: RNA
<213> ORGANISM: Homo sapiens

<400> SEQUENCE: 292
gagggcuagg uggggggcuu gaagcccga gaugccucac gucuucaccc cucucaccua   60
agcag                                                              65

<210> SEQ ID NO 293
<211> LENGTH: 75
<212> TYPE: RNA
<213> ORGANISM: Homo sapiens

<400> SEQUENCE: 293
uggagugggg gggcaggagg ggcucaggga gaaagugcau acagcccug gcccucucug    60 cccuuccguc cccug                                                   75
```

-continued

```
<210> SEQ ID NO 294
<211> LENGTH: 61
<212> TYPE: RNA
<213> ORGANISM: Homo sapiens

<400> SEQUENCE: 294
ucggcuggcg gggguagagc uggcugcagg cccggccccu cucagcugcu gcccucucca     60
g                                                                    61

<210> SEQ ID NO 295
<211> LENGTH: 86
<212> TYPE: RNA
<213> ORGANISM: Homo sapiens

<400> SEQUENCE: 295
cgccugagcg ugcagcagga caucuuccug accugguaau aauuagguga gaaggauggu     60 uggggcggu cggcguaacu caggga                                           86

<210> SEQ ID NO 296
<211> LENGTH: 72
<212> TYPE: RNA
<213> ORGANISM: Homo sapiens

<400> SEQUENCE: 296
gagucugagg gacccaggac aggagaaggc cuauggugau uugcauucuu ccugcccugg     60
cuccauccuc ag                                                        72

<210> SEQ ID NO 297
<211> LENGTH: 73
<212> TYPE: RNA
<213> ORGANISM: Homo sapiens

<400> SEQUENCE: 297
uguauccuug aauggauuuu uggagcagga guggacaccu gacccaaagg aaaucaaucc     60
auaggcuagc aau                                                       73

<210> SEQ ID NO 298
<211> LENGTH: 70
<212> TYPE: RNA
<213> ORGANISM: Homo sapiens

<400> SEQUENCE: 298
cucgggcccg accgcgccgg cccgcaccuc ccggcccgga gcugcgggcu gcggucaggg     60
cgaucccggg                                                           70

<210> SEQ ID NO 299
<211> LENGTH: 69
<212> TYPE: RNA
<213> ORGANISM: Homo sapiens

<400> SEQUENCE: 299
gggcuuaggg augggaggcc aggaugaaga uuaaucccua auccccaaca cuggccuugc     60
uauccccag                                                            69

<210> SEQ ID NO 300
<211> LENGTH: 63
<212> TYPE: RNA
<213> ORGANISM: Homo sapiens

<400> SEQUENCE: 300
```

```
acccuagggu ggggcuggag gugggggcuga ggcugagucu uccucccuu ccucccugcc    60
cag                                                                 63

<210> SEQ ID NO 301
<211> LENGTH: 105
<212> TYPE: RNA
<213> ORGANISM: Homo sapiens

<400> SEQUENCE: 301
gcgggcggcg gcggcggcag cagcagcagg ugcggggcgg cggccgcgcu ggccgcucga    60
cuccgcagcc gcucguucug cuucuccagc uugcgcacca gcucc                  105

<210> SEQ ID NO 302
<211> LENGTH: 63
<212> TYPE: RNA
<213> ORGANISM: Homo sapiens

<400> SEQUENCE: 302
ggcuccgcag ggcccuggcg caggcaucca gacagcgggc gaaugccucc cccggccccg    60
cag                                                                 63

<210> SEQ ID NO 303
<211> LENGTH: 74
<212> TYPE: RNA
<213> ORGANISM: Homo sapiens

<400> SEQUENCE: 303
gugcguggug gcucgaggcg gggguggggg ccucgcccug cuugggcccu cccugaccuc    60
uccgcuccgc acag                                                     74

<210> SEQ ID NO 304
<211> LENGTH: 62
<212> TYPE: RNA
<213> ORGANISM: Homo sapiens

<400> SEQUENCE: 304
uggccuaggg ggcggcuugu ggaguguaug ggcugagccu ugcucugcuc cccgccccc     60
ag                                                                  62

<210> SEQ ID NO 305
<211> LENGTH: 67
<212> TYPE: RNA
<213> ORGANISM: Homo sapiens

<400> SEQUENCE: 305
gugggagggg agaggcagca agcacacagg gccugggacu agcaugcuga ccuccuccu    60
gccccag                                                             67

<210> SEQ ID NO 306
<211> LENGTH: 61
<212> TYPE: RNA
<213> ORGANISM: Homo sapiens

<400> SEQUENCE: 306
gggggcggga gcuggggucu gcagguucgc acugaugccu gcucgcccug ucccgcua     60
g                                                                   61

<210> SEQ ID NO 307
<211> LENGTH: 75
```

<212> TYPE: RNA
<213> ORGANISM: Homo sapiens

<400> SEQUENCE: 307
ggcugugccg gguagagagg gcagugggag guaagagcuc uucacccuuc accaccuucu    60
ccacccagca uggcc    75

<210> SEQ ID NO 308
<211> LENGTH: 89
<212> TYPE: RNA
<213> ORGANISM: Homo sapiens

<400> SEQUENCE: 308
gccggcgccc gagcucuggc uccgugucuu cacucccgug cuuguccgag gagggaggga    60
gggacggggg cugugcuggg gcagcugga    89

<210> SEQ ID NO 309
<211> LENGTH: 61
<212> TYPE: RNA
<213> ORGANISM: Homo sapiens

<400> SEQUENCE: 309
gugcggaacg cuggccgggg cgggagggga agggacgccc ggccggaacg ccgcacucac    60
g    61

<210> SEQ ID NO 310
<211> LENGTH: 70
<212> TYPE: RNA
<213> ORGANISM: Homo sapiens

<400> SEQUENCE: 310
aaaagccugu cccuaagucc cucccagccu uccagaguug gugccaggaa ggauuuaggg    60
acaggcuuug    70

<210> SEQ ID NO 311
<211> LENGTH: 67
<212> TYPE: RNA
<213> ORGANISM: Homo sapiens

<400> SEQUENCE: 311
gugaggaggg gcuggcaggg accccuccaa guuggggacg gcagccagcc ccugcucacc    60
ccucgcc    67

<210> SEQ ID NO 312
<211> LENGTH: 94
<212> TYPE: RNA
<213> ORGANISM: Homo sapiens

<400> SEQUENCE: 312
cgggcagcgg gugccaggca cggugucagc aggcaacaug gccgagaggc cggggccucc    60
gggcggcgcc guguccgcga ccgcguaccc ugac    94

<210> SEQ ID NO 313
<211> LENGTH: 92
<212> TYPE: RNA
<213> ORGANISM: Homo sapiens

<400> SEQUENCE: 313 ccuguccuc cugccugcg ccugcccagc ccuccugcuc uggugacuga ggaccgccag    60

```
gcaggggcug gugcugggcg gggggcggcg gg                                  92
```

<210> SEQ ID NO 314
<211> LENGTH: 94
<212> TYPE: RNA
<213> ORGANISM: Homo sapiens

<400> SEQUENCE: 314

```
aauucagccc ugccacuggc uuaugucaug accuugggcu acucaggcug ucugcacaau   60
gagccaguug gacaggagca gugccacuca acuc                               94
```

<210> SEQ ID NO 315
<211> LENGTH: 60
<212> TYPE: RNA
<213> ORGANISM: Homo sapiens

<400> SEQUENCE: 315

```
ggugccucgg gagggcaugg gccaggccac auaaugagcc aaaccccugu cuacccgcag   60
```

<210> SEQ ID NO 316
<211> LENGTH: 92
<212> TYPE: RNA
<213> ORGANISM: Homo sapiens

<400> SEQUENCE: 316

```
gucagugucu gggcggacag cugcaggaaa gggaagacca aggcuugcug ucguccagu    60 cugccacccu acccugucug uucuugccac ag                                 92
```

<210> SEQ ID NO 317
<211> LENGTH: 80
<212> TYPE: RNA
<213> ORGANISM: Homo sapiens

<400> SEQUENCE: 317

```
cgggaaugcc gcggcgggga cggcgauugg uccguaugug uggugccacc ggccgccggc   60
uccgccccgg cccccgcccc                                               80
```

<210> SEQ ID NO 318
<211> LENGTH: 84
<212> TYPE: RNA
<213> ORGANISM: Homo sapiens

<400> SEQUENCE: 318

```
cuccccaugg cccugucucc caacccuugu accagugcug ggcucagacc cugguacagg   60 ccuggggac agggaccugg ggac                                           84
```

<210> SEQ ID NO 319
<211> LENGTH: 106
<212> TYPE: RNA
<213> ORGANISM: Homo sapiens

<400> SEQUENCE: 319

```
agaagaaugc ccaaccagcc cucaguugcu acaguucccu guuguuucag cucgacaaca   60
acaggcggcu guagcaaugg ggggcuggau gggcaucuca augugc                 106
```

<210> SEQ ID NO 320
<211> LENGTH: 79
<212> TYPE: RNA
<213> ORGANISM: Homo sapiens

<400> SEQUENCE: 320

```
gugcagaucc uugggagccc uguuagacuc uggauuuuac acuuggagug aacgggcgcc    60
aucccgaggc uuugcacag                                                 79

<210> SEQ ID NO 321
<211> LENGTH: 102
<212> TYPE: RNA
<213> ORGANISM: Homo sapiens

<400> SEQUENCE: 321
gcuuaucgag gaaaagaucg agguggguug gggcgggcuc uggggauuug gucucacagc    60
ccggauccca gcccacuuac cuugguuacu cuccuuccuu cu                      102

<210> SEQ ID NO 322
<211> LENGTH: 90
<212> TYPE: RNA
<213> ORGANISM: Homo sapiens

<400> SEQUENCE: 322
cgggcggggc ggguccggcc gccuccgagc ccggccggca gccccggcc uuaaagcgcg     60 ggcuguccgg aggggucggc uuucccaccg                                     90

<210> SEQ ID NO 323
<211> LENGTH: 59
<212> TYPE: RNA
<213> ORGANISM: Homo sapiens

<400> SEQUENCE: 323
ggggccaggc agggaggugg gaccaugggg gccuugcugu gugaccaccg uuccugcag     59

<210> SEQ ID NO 324
<211> LENGTH: 62
<212> TYPE: RNA
<213> ORGANISM: Homo sapiens

<400> SEQUENCE: 324
gugaguagug gcgcgcggcg gcucggagua ccucugccgc cgcgcgcauc ggcucagcau    60
gc                                                                   62

<210> SEQ ID NO 325
<211> LENGTH: 85
<212> TYPE: RNA
<213> ORGANISM: Homo sapiens

<400> SEQUENCE: 325
ucugagguac ccggggcaga uugguguagg gugcaaagcc ugcccgcccc cuaagccuuc    60 ugccccaac uccagccugu cagga                                           85

<210> SEQ ID NO 326
<211> LENGTH: 96
<212> TYPE: RNA
<213> ORGANISM: Homo sapiens

<400> SEQUENCE: 326
cucgggaggg gcgggagggg ggucccggu gcucggaucu cgagggugcu uauuguucgg     60
uccgagccug ggucucccuc uucccccaa cccccc                               96

<210> SEQ ID NO 327
<211> LENGTH: 80
<212> TYPE: RNA
```

```
<213> ORGANISM: Homo sapiens

<400> SEQUENCE: 327
gcgucaagau ggcggcgggg agguaggcag agcaggacgc cgcugcugcc gccgccaccg    60
ccgccuccgc uccagucgcc                                                80

<210> SEQ ID NO 328
<211> LENGTH: 82
<212> TYPE: RNA
<213> ORGANISM: Homo sapiens

<400> SEQUENCE: 328
ugagcuguug gauucggggc cguagcacug ucugagaggu uuacauuucu cacagugaac    60
cggucucuuu uucagcugcu uc                                             82

<210> SEQ ID NO 329
<211> LENGTH: 83
<212> TYPE: RNA
<213> ORGANISM: Homo sapiens

<400> SEQUENCE: 329
gugaguggga gccccagugu gugguuggg ccauggcggg ugggcagccc agccucugag     60
ccuuccucgu cugucugccc cag                                            83

<210> SEQ ID NO 330
<211> LENGTH: 87
<212> TYPE: RNA
<213> ORGANISM: Homo sapiens

<400> SEQUENCE: 330
accgcaggga aaugaggga cuuuggggg cagaugguguu ccauccac uaucauaaug       60 ccccuaaaaa uccuuauugc ucuugca                                        87

<210> SEQ ID NO 331
<211> LENGTH: 110
<212> TYPE: RNA
<213> ORGANISM: Homo sapiens

<400> SEQUENCE: 331
ggcuacaguc uuucuucaug ugacucgugg acuucccuuu gucauccuau gccugagaau    60
auaugaagga ggcugggaag gcaaagggac guucaauugu caucacuggc              110

<210> SEQ ID NO 332
<211> LENGTH: 80
<212> TYPE: RNA
<213> ORGANISM: Homo sapiens

<400> SEQUENCE: 332
cugcagcgug cuucuccagg cccccgcgcgc ggacagacac acggacaagu cccgccaggg   60
gcugggcgcg cgccagccgg                                                80

<210> SEQ ID NO 333
<211> LENGTH: 81
<212> TYPE: RNA
<213> ORGANISM: Homo sapiens

<400> SEQUENCE: 333
cucccuggga gggcguggau gauggugga gaggagcccc acuguggaag ucugaccccc     60
acaucgcccc accuuccca g                                               81
```

<210> SEQ ID NO 334
<211> LENGTH: 67
<212> TYPE: RNA
<213> ORGANISM: Homo sapiens

<400> SEQUENCE: 334
ccugcaggca aagugggggc ugacagggca gaggguugcg cccccucacc aucccuucug    60
ccugcag                                                             67

<210> SEQ ID NO 335
<211> LENGTH: 67
<212> TYPE: RNA
<213> ORGANISM: Homo sapiens

<400> SEQUENCE: 335
ccugcaggca aagugggggc ugacagggca gaggguugcg cccccucacc aucccuucug    60
ccugcag                                                             67

<210> SEQ ID NO 336
<211> LENGTH: 67
<212> TYPE: RNA
<213> ORGANISM: Homo sapiens

<400> SEQUENCE: 336
ccugcaggca aagugggggc ugacagggca gaggguugcg cccccucacc aucccuucug    60
ccugcag                                                             67

<210> SEQ ID NO 337
<211> LENGTH: 67
<212> TYPE: RNA
<213> ORGANISM: Homo sapiens

<400> SEQUENCE: 337
ccugcaggca aagugggggc ugacagggca gaggguugcg cccccucacc aucccuucug    60
ccugcag                                                             67

<210> SEQ ID NO 338
<211> LENGTH: 75
<212> TYPE: RNA
<213> ORGANISM: Homo sapiens

<400> SEQUENCE: 338
gucagagggg ggaugugcau gcugguuggg gugggcugcc uguggaccaa ucagcgugca    60
cuuccccacc cugaa                                                    75

<210> SEQ ID NO 339
<211> LENGTH: 80
<212> TYPE: RNA
<213> ORGANISM: Homo sapiens

<400> SEQUENCE: 339
ugagaggccg caccuugccu ugcugcccgg gccgugcacc cgugggcccc agggcgacgc    60
ggcgggggcg gcccuagcga                                               80

<210> SEQ ID NO 340
<211> LENGTH: 153
<212> TYPE: RNA
<213> ORGANISM: Homo sapiens

```
<400> SEQUENCE: 340
gcuccgcccc acgucgcaug cgccccggga acgcgugggg cggagcuucc ggaggcccg      60 cucugcugcc gacccugugg agcggagggu gaagccuccg gaugccaguc ccucaucgcu    120
ggccuggucg cgcuguggcg aaggggggcgg agc                                 153

<210> SEQ ID NO 341
<211> LENGTH: 153
<212> TYPE: RNA
<213> ORGANISM: Homo sapiens

<400> SEQUENCE: 341
gcuccgcccc acgucgcaug cgccccggga acgcgugggg cggagcuucc ggaggcccg      60 cccugcugcc gacccugugg agcggagggu gaagccuccg gaugccaguc ccucaucgcu    120
ggcccggucg cgcuguggcg aaggggggcgg agc                                 153

<210> SEQ ID NO 342
<211> LENGTH: 66
<212> TYPE: RNA
<213> ORGANISM: Homo sapiens

<400> SEQUENCE: 342
cagagcaggg cagggaaggu gggagagggg cccagcugac ccuccuguca cccgcuccuu     60
gcccag                                                                66

<210> SEQ ID NO 343
<211> LENGTH: 119
<212> TYPE: RNA
<213> ORGANISM: Homo sapiens

<400> SEQUENCE: 343
agccugcgcc ggagccgggg ccugagcccg ggccgcgcag gccgugaacu cgucgagcug     60
cgcgugcggc cggugcucaa ccugccgggu ccuggccccg cgcucccgcg cgcccugga    119

<210> SEQ ID NO 344
<211> LENGTH: 63
<212> TYPE: RNA
<213> ORGANISM: Homo sapiens

<400> SEQUENCE: 344
cuugcccggg agaaggaggu ggccuggaga gcugcugucu ccagccgccg ccugucucca     60
cag                                                                   63

<210> SEQ ID NO 345
<211> LENGTH: 76
<212> TYPE: RNA
<213> ORGANISM: Homo sapiens

<400> SEQUENCE: 345
acugacuuug agucucuccu cagggugcug caggcaaagc uggggaccca gggagagacg     60
uaagugaggg gagaug                                                     76

<210> SEQ ID NO 346
<211> LENGTH: 115
<212> TYPE: RNA
<213> ORGANISM: Homo sapiens

<400> SEQUENCE: 346
ggugccgagg gccguccggc auccuaggcg ggucgcugcg guaccucccu ccugucugug     60
```

```
gcgguggau cccguggccg uguuuccug guggcccggc cgugccugag guuuc      115
```

<210> SEQ ID NO 347
<211> LENGTH: 80
<212> TYPE: RNA
<213> ORGANISM: Homo sapiens

<400> SEQUENCE: 347

```
gguuccggag ccccggcgcg ggcggguucu gggguguaga cgcugcuggc cagcccgccc   60
cagccgaggu ucucggcacc                                              80
```

<210> SEQ ID NO 348
<211> LENGTH: 69
<212> TYPE: RNA
<213> ORGANISM: Homo sapiens

<400> SEQUENCE: 348

```
ccgggcaggc agguguaggg uggagcccac guggcuccu gacucagccc ugcugccuuc   60
accugccag                                                          69
```

<210> SEQ ID NO 349
<211> LENGTH: 77
<212> TYPE: RNA
<213> ORGANISM: Homo sapiens

<400> SEQUENCE: 349

```
caugagaaau ccugcugguc aaccauagcc cuggucagac ucuccggggc ugugauugac   60
cagcaggacu ucucaug                                                 77
```

<210> SEQ ID NO 350
<211> LENGTH: 68
<212> TYPE: RNA
<213> ORGANISM: Homo sapiens

<400> SEQUENCE: 350

```
gacucggcug cgguggacaa guccggcucc agaaccugga caccgcucag ccggccgcgg   60
caggggguc                                                          68
```

<210> SEQ ID NO 351
<211> LENGTH: 73
<212> TYPE: RNA
<213> ORGANISM: Homo sapiens

<400> SEQUENCE: 351

```
cggcgacggc ggggugggug aggucgggcc ccaagacucg gggguugccg ggcgccucag   60
uucaccgcgg ccg                                                     73
```

<210> SEQ ID NO 352
<211> LENGTH: 49
<212> TYPE: RNA
<213> ORGANISM: Homo sapiens

<400> SEQUENCE: 352

```
ggugaggcgg gggggcgagc ccugaggggc ucucgcuucu ggcgccaag              49
```

<210> SEQ ID NO 353
<211> LENGTH: 79
<212> TYPE: RNA
<213> ORGANISM: Homo sapiens

```
<400> SEQUENCE: 353
cucgaggugc uggggacgc gugagcgcga gccgcuuccu cacggcucgg ccgcggcgcg    60
uagcccccgc cacaucggg                                                79

<210> SEQ ID NO 354
<211> LENGTH: 71
<212> TYPE: RNA
<213> ORGANISM: Homo sapiens

<400> SEQUENCE: 354 ggugagugg agccgguggg gcuggaguaa gggcacgccc ggggcugccc caccugcuga    60 ccaccccuccc c                                                       71

<210> SEQ ID NO 355
<211> LENGTH: 65
<212> TYPE: RNA
<213> ORGANISM: Homo sapiens

<400> SEQUENCE: 355
gagaaugggg ggacagaugg agaggacaca ggcuggcacu gagguccccu ccacuuccu    60 ccuag                                                               65

<210> SEQ ID NO 356
<211> LENGTH: 79
<212> TYPE: RNA
<213> ORGANISM: Homo sapiens

<400> SEQUENCE: 356 gugaggugg ggccagcagg gagugggcug ggcugggcug ggccaaggua caaggccuca    60
cccugcaucc cgcacccag                                                79

<210> SEQ ID NO 357
<211> LENGTH: 80
<212> TYPE: RNA
<213> ORGANISM: Homo sapiens

<400> SEQUENCE: 357
cauccaggac aauggugagu gccggugccu gcccuggggc cgucccugcg caggggccgg    60
gugcucaccg caucugcccc                                               80

<210> SEQ ID NO 358
<211> LENGTH: 61
<212> TYPE: RNA
<213> ORGANISM: Homo sapiens

<400> SEQUENCE: 358
ucucguuuga ucucggaagc uaagcagggu ugggccuggu uaguacuugg augggaaacu    60
u                                                                   61

<210> SEQ ID NO 359
<211> LENGTH: 53
<212> TYPE: RNA
<213> ORGANISM: Homo sapiens

<400> SEQUENCE: 359
guuugaucuc ggaagcuaag cagggucggg ccugguuagu acuuggaugg gag          53

<210> SEQ ID NO 360
<211> LENGTH: 92
```

```
<212> TYPE: RNA
<213> ORGANISM: Homo sapiens

<400> SEQUENCE: 360
cgcugcgcuu cugggcccgc ggcgggcgug ggcugcccg ggccggucga ccagcgcgcc    60
guagcucccg aggcccgagc cgcgacccgc gg                                 92

<210> SEQ ID NO 361
<211> LENGTH: 84
<212> TYPE: RNA
<213> ORGANISM: Homo sapiens

<400> SEQUENCE: 361
gcuggcgucg gugcugggga gcggcccccg ggugggccuc ugcucuggcc ccuccugggg    60
cccgcacucu cgcucugggc ccgc                                          84

<210> SEQ ID NO 362
<211> LENGTH: 79
<212> TYPE: RNA
<213> ORGANISM: Homo sapiens

<400> SEQUENCE: 362
cagccugggg aaggcuuggc agggaagaca caugagcagu gccuccacuu cacgccucuc    60
ccuugucucc uuucccuag                                                79

<210> SEQ ID NO 363
<211> LENGTH: 83
<212> TYPE: RNA
<213> ORGANISM: Homo sapiens

<400> SEQUENCE: 363
ggguuuccuc ugccuuuuuu uccaaugaaa auaacgaaac cguuauuuc ccauugaggg    60 ggaaaaaggc gggagaagcc cca                                           83

<210> SEQ ID NO 364
<211> LENGTH: 60
<212> TYPE: RNA
<213> ORGANISM: Homo sapiens

<400> SEQUENCE: 364
gagcaggcga ggcugggcug aacccguggg ugaggagugc agcccagcug aggccucugc    60

<210> SEQ ID NO 365
<211> LENGTH: 73
<212> TYPE: RNA
<213> ORGANISM: Homo sapiens

<400> SEQUENCE: 365
agggagaaaa gcugggcuga gaggcgacug gugucuaauu uguuugucuc uccaacucag    60
acugccuggc cca                                                      73

<210> SEQ ID NO 366
<211> LENGTH: 88
<212> TYPE: RNA
<213> ORGANISM: Homo sapiens

<400> SEQUENCE: 366
guggggccag gcgguggugg gcacugcugg gguggcaca gcagccaugc agagcgggca    60
uuugaccccg ugccacccuu uucccag                                       88
```

```
<210> SEQ ID NO 367
<211> LENGTH: 90
<212> TYPE: RNA
<213> ORGANISM: Homo sapiens

<400> SEQUENCE: 367
gugucucucu ggagacccug cagccuuccc acccaccagg gagcuuucca ugggcugugg    60
ggaaggcguc agugucgggu gagggaacac                                    90

<210> SEQ ID NO 368
<211> LENGTH: 64
<212> TYPE: RNA
<213> ORGANISM: Homo sapiens

<400> SEQUENCE: 368
gaggcacugg guaggugggg cuccagggcu ccugacaccu ggaccucucc ucccaggcc    60 caca                                                                64

<210> SEQ ID NO 369
<211> LENGTH: 64
<212> TYPE: RNA
<213> ORGANISM: Homo sapiens

<400> SEQUENCE: 369
ugaggauggg gugagauggg gaggagcagc caguccuguc ucaccgcucu uccccugacc    60
ccag                                                                64

<210> SEQ ID NO 370
<211> LENGTH: 73
<212> TYPE: RNA
<213> ORGANISM: Homo sapiens

<400> SEQUENCE: 370
ggcgagggga ggcgcaggcu cggaaaggcg cgcgaggcuc caggcuccuu cccgauccac    60
cgcucuccuc gcu                                                      73

<210> SEQ ID NO 371
<211> LENGTH: 81
<212> TYPE: RNA
<213> ORGANISM: Homo sapiens

<400> SEQUENCE: 371
uacaggugca ggggaacugu agaugaaaag gcuuggcacu ugagggaaag ccucaguuca    60
uucucauuuu gcucaccugu u                                             81

<210> SEQ ID NO 372
<211> LENGTH: 68
<212> TYPE: RNA
<213> ORGANISM: Homo sapiens

<400> SEQUENCE: 372
gaauggaaga agaaggcggu cggucugcgg gagccaggcc gcagagccau ccgccuucug    60
uccauguc                                                            68

<210> SEQ ID NO 373
<211> LENGTH: 82
<212> TYPE: RNA
<213> ORGANISM: Homo sapiens

<400> SEQUENCE: 373
```

```
gcuacgggga gcggggagga agugggcgcu gcuucugcgu uaucuggaag gagcagccca    60
cuccuguccu gggcucugug gu                                             82

<210> SEQ ID NO 374
<211> LENGTH: 89
<212> TYPE: RNA
<213> ORGANISM: Homo sapiens

<400> SEQUENCE: 374
accuccggga cggcugggcg ccggcggccg ggagauccgc gcuuccugaa ucccggccgg    60
cccgcccggc gcccguccgc ccgcggguc                                      89

<210> SEQ ID NO 375
<211> LENGTH: 63
<212> TYPE: RNA
<213> ORGANISM: Homo sapiens

<400> SEQUENCE: 375
gagucgagga cugguggaag ggccuuuccc cucagaccaa ggcccuggcc ccagcuucuu    60
cuc                                                                  63

<210> SEQ ID NO 376
<211> LENGTH: 64
<212> TYPE: RNA
<213> ORGANISM: Homo sapiens

<400> SEQUENCE: 376
ugcucuguag gcaugaggca gggcccaggu uccaugugau gcugaagcuc ugacauuccu    60
gcag                                                                 64

<210> SEQ ID NO 377
<211> LENGTH: 109
<212> TYPE: RNA
<213> ORGANISM: Homo sapiens

<400> SEQUENCE: 377
ggucgggcuc accaugacac agugugagac cucgggcuac aacacaggac ccgggcgcug    60
cucugacccc ucgugucuug uguugcagcc ggagggacgc aggaccgca               109

<210> SEQ ID NO 378
<211> LENGTH: 94
<212> TYPE: RNA
<213> ORGANISM: Homo sapiens

<400> SEQUENCE: 378
cagugcgacg ggcggagcuu ccagacgcuc cgcccacgu cgcaugcgcc ccgggaaagc     60
guggggcgga gcuuccggag gccccgcccu gcug                                94

<210> SEQ ID NO 379
<211> LENGTH: 88
<212> TYPE: RNA
<213> ORGANISM: Homo sapiens

<400> SEQUENCE: 379
gcgacgggcg gagcuuccag acgcuccgcc ccacgucgca ugcgcccgg gaaagcgugg     60 ggcggagcuu ccggaggccc cgcccugc                                       88

<210> SEQ ID NO 380
```

```
<211> LENGTH: 94
<212> TYPE: RNA
<213> ORGANISM: Homo sapiens

<400> SEQUENCE: 380
cagugcgacg ggcggagcuu ccagacgcuc cgccccacgu cgcaugcgcc ccgggaaagc    60 gugggggcgga gcuuccggag gccccgcccu gcug                              94

<210> SEQ ID NO 381
<211> LENGTH: 70
<212> TYPE: RNA
<213> ORGANISM: Homo sapiens

<400> SEQUENCE: 381
gucccugggg gcugggaugg gccauggugu gcucugaucc cccugugguc ucuuggcccc    60
caggaacucc                                                          70

<210> SEQ ID NO 382
<211> LENGTH: 62
<212> TYPE: RNA
<213> ORGANISM: Homo sapiens

<400> SEQUENCE: 382
ccuucugcgg cagagcuggg gucaccagcc cucauguacu ugugacuucu ccccugccac    60
ag                                                                  62

<210> SEQ ID NO 383
<211> LENGTH: 82
<212> TYPE: RNA
<213> ORGANISM: Homo sapiens

<400> SEQUENCE: 383
accuguaggu gacagucagg ggcggggugu gguggggcug ggcuggccc ccuccucaca    60 ccucuccugg caucgccccc ag                                            82

<210> SEQ ID NO 384
<211> LENGTH: 73
<212> TYPE: RNA
<213> ORGANISM: Homo sapiens

<400> SEQUENCE: 384
cugguguuug aggcgaugug gggauguaga gacaacuucc cagucucauu uccucauccu    60
gccaggccac cau                                                      73

<210> SEQ ID NO 385
<211> LENGTH: 68
<212> TYPE: RNA
<213> ORGANISM: Homo sapiens

<400> SEQUENCE: 385
aggguugggg ggacaggaug agaggcuguc uucauucccu cuugaccacc ccucguuucu    60
ucccccag                                                            68

<210> SEQ ID NO 386
<211> LENGTH: 61
<212> TYPE: RNA
<213> ORGANISM: Homo sapiens

<400> SEQUENCE: 386
gagggcagcg uggguguggc ggaggcaggc gugaccguuu gccgcccucu cgcugcucua    60
``` g                                                               61

<210> SEQ ID NO 387
<211> LENGTH: 72
<212> TYPE: RNA
<213> ORGANISM: Homo sapiens

<400> SEQUENCE: 387
ucuccucgag gggucucugc cucuacccag gacucuuuca ugaccaggag gcugaggccc    60
cucacaggcg gc                                                      72

<210> SEQ ID NO 388
<211> LENGTH: 73
<212> TYPE: RNA
<213> ORGANISM: Homo sapiens

<400> SEQUENCE: 388
guucaagugg gaggacagga ggcaggugug guuggaggaa gcagccugaa ccugccuccc    60
ugacauucca cag                                                     73

<210> SEQ ID NO 389
<211> LENGTH: 97
<212> TYPE: RNA
<213> ORGANISM: Homo sapiens

<400> SEQUENCE: 389
cccgggaccu ugguccaggc gcuggucugc guggugcucg gguggauaag ucugaucuga    60
gcaccacaca ggccgggcgc cgggaccaag ggggcuc                            97

<210> SEQ ID NO 390
<211> LENGTH: 70
<212> TYPE: RNA
<213> ORGANISM: Homo sapiens

<400> SEQUENCE: 390
gguuucuccu ugaggagaca uggugggggc cggucaggca gcccaugcca uguguccuca    60
uggagaggcc                                                         70

<210> SEQ ID NO 391
<211> LENGTH: 110
<212> TYPE: RNA
<213> ORGANISM: Homo sapiens

<400> SEQUENCE: 391
ucaccuggcc augugacuug ugggcuuccc uuugucaucc uucgccuagg gcucugagca    60
gggcagggac agcaaagggg ugcucaguug ucacuuccca cagcacggag              110

<210> SEQ ID NO 392
<211> LENGTH: 85
<212> TYPE: RNA
<213> ORGANISM: Homo sapiens

<400> SEQUENCE: 392
gggacggggc cugcaggcag aaguggggcu gacagggcag agggurgcgc ccccucacca    60 cccccuucugc cugcagcggu gggcu                                       85

<210> SEQ ID NO 393
<211> LENGTH: 71
<212> TYPE: RNA

```
<213> ORGANISM: Homo sapiens

<400> SEQUENCE: 393
ggggccugca ggcagaagug gggcugacag ggcagagggu ugcgccccu caccacccu      60 ucugccugca g                                                         71

<210> SEQ ID NO 394
<211> LENGTH: 56
<212> TYPE: RNA
<213> ORGANISM: Homo sapiens

<400> SEQUENCE: 394
cgcucgggcg gagguggnug agugccgacu ggcgccugac ccacccccuc ccgcag        56

<210> SEQ ID NO 395
<211> LENGTH: 89
<212> TYPE: RNA
<213> ORGANISM: Homo sapiens

<400> SEQUENCE: 395
agccuguggg aaagagaaga gcagggcagg gugaaggccc ggcggagaca cucugcccac    60
cccacacccu gccuauggc cacacagcu                                       89

<210> SEQ ID NO 396
<211> LENGTH: 90
<212> TYPE: RNA
<213> ORGANISM: Homo sapiens

<400> SEQUENCE: 396
ucuaagaaac gcagugguucu cugaagccug caggggcagg ccagcccugc acugaacgcc   60
uguucuugcc agguggcaga agguugcugc                                     90

<210> SEQ ID NO 397
<211> LENGTH: 86
<212> TYPE: RNA
<213> ORGANISM: Homo sapiens

<400> SEQUENCE: 397
ggggcugggg gugugggggag agagagugca cagccagcuc agggauuaaa gcucuuucuc   60
ucucucucuc ucccacuucc cugcag                                         86

<210> SEQ ID NO 398
<211> LENGTH: 98
<212> TYPE: RNA
<213> ORGANISM: Homo sapiens

<400> SEQUENCE: 398
uugggcaagg ucgggggcua gggcuaacag cagucuuacu gaagguuucc uggaaaccac    60
gcacaugcug uugccacuaa ccucaaccuu acucgguc                            98

<210> SEQ ID NO 399
<211> LENGTH: 73
<212> TYPE: RNA
<213> ORGANISM: Homo sapiens

<400> SEQUENCE: 399
aggccaggug gguauggagg agcccucaua uggcaguugg cgagggccca gugagcccu     60 cucugcucuc cag                                                       73
```

```
<210> SEQ ID NO 400
<211> LENGTH: 74
<212> TYPE: RNA
<213> ORGANISM: Homo sapiens

<400> SEQUENCE: 400
gcagcccggu gagcgcucgc uggccuggca gugcgucgga agaacagggc ggguggggcc    60
gcgcacaucu cugc                                                     74

<210> SEQ ID NO 401
<211> LENGTH: 55
<212> TYPE: RNA
<213> ORGANISM: Homo sapiens

<400> SEQUENCE: 401
gggggcuggg gcgcggggag gugcuagguc ggccucggcu cccgcgccgc acccc         55

<210> SEQ ID NO 402
<211> LENGTH: 67
<212> TYPE: RNA
<213> ORGANISM: Homo sapiens

<400> SEQUENCE: 402
ggcagccagg gggaugggcg agcuuugggcc cauuccuuuc cuuacccuac ccccauccc    60 ccuguag                                                             67

<210> SEQ ID NO 403
<211> LENGTH: 64
<212> TYPE: RNA
<213> ORGANISM: Homo sapiens

<400> SEQUENCE: 403
aaccccgggc cggaggucaa gggcgucgcu ucucccuaau guugccucuu uccacggcc    60 ucag                                                                64

<210> SEQ ID NO 404
<211> LENGTH: 68
<212> TYPE: RNA
<213> ORGANISM: Homo sapiens

<400> SEQUENCE: 404
cucaggcuca guggugcaug cuuauagucc cagccacucu ggaggcugaa ggaagauggc    60
uugagccu                                                            68

<210> SEQ ID NO 405
<211> LENGTH: 67
<212> TYPE: RNA
<213> ORGANISM: Homo sapiens

<400> SEQUENCE: 405
cugguccauu ucccugccau ucccuuggcu ucaauuuacu cccagggcug gcagugacau    60
gggucaa                                                             67

<210> SEQ ID NO 406
<211> LENGTH: 101
<212> TYPE: RNA
<213> ORGANISM: Homo sapiens

<400> SEQUENCE: 406
gaugggcccc uuguguccug aauugggugg gggcucugag uggggaaagu gggggccuag    60
```

```
gggaggucac aguugggucu aggggucagg agggcccagg a                 101
```

<210> SEQ ID NO 407
<211> LENGTH: 137
<212> TYPE: RNA
<213> ORGANISM: Homo sapiens

<400> SEQUENCE: 407

```
agccagacaa gagggucaug gggagucacu gucaacccag agcaggcacu gccccugcga   60
ccagccuggg gcaucgguug gggugcaggg gucugcuggu gaugcuuucc aucucuuugc  120
uuuguccuga uuguagc                                                 137
```

<210> SEQ ID NO 408
<211> LENGTH: 95
<212> TYPE: RNA
<213> ORGANISM: Homo sapiens

<400> SEQUENCE: 408

```
gacaccacau gcuccuccag gccugccugc ccuccagguc auguccagu gucccacaga    60 ugcagcacca cggcccaggc ggcauuggug ucacc                              95
```

<210> SEQ ID NO 409
<211> LENGTH: 80
<212> TYPE: RNA
<213> ORGANISM: Homo sapiens

<400> SEQUENCE: 409

```
aggacccuuc cagagggccc ccccucaauc cuguugugcc uaauucagag gguuggugg    60 aggcucuccu gaagggcucu                                              80
```

<210> SEQ ID NO 410
<211> LENGTH: 93
<212> TYPE: RNA
<213> ORGANISM: Homo sapiens

<400> SEQUENCE: 410

```
guaaggaggg ggaugagggg ucauaucucu ucucagggaa agcaggagcc cuucagcagg   60
gucagggccc cucaucuucc ccuccuuucc cag                                93
```

<210> SEQ ID NO 411
<211> LENGTH: 62
<212> TYPE: RNA
<213> ORGANISM: Homo sapiens

<400> SEQUENCE: 411

```
gugagugggg cucccgggac ggcgcccgcc cuggcccugg cccggcgacg ucucacgguc   60
cc                                                                  62
```

<210> SEQ ID NO 412
<211> LENGTH: 69
<212> TYPE: RNA
<213> ORGANISM: Homo sapiens

<400> SEQUENCE: 412

```
gaaccucggg gcauggggga gggaggcugg acaggagagg gcucacccag gcccuguccu   60
cugccccag                                                           69
```

<210> SEQ ID NO 413
<211> LENGTH: 60
```

-continued

```
<212> TYPE: RNA
<213> ORGANISM: Homo sapiens

<400> SEQUENCE: 413
caaggugggg gagauggggg uugaacuuca uuucucaugc ucauccccau cuccuuucag      60

<210> SEQ ID NO 414
<211> LENGTH: 75
<212> TYPE: RNA
<213> ORGANISM: Homo sapiens

<400> SEQUENCE: 414
guaguuguuc uacagaagac cuggaugugu aggagcuaag acacacucca ggggagcugu      60
ggaagcagua acacg                                                      75

<210> SEQ ID NO 415
<211> LENGTH: 56
<212> TYPE: RNA
<213> ORGANISM: Homo sapiens

<400> SEQUENCE: 415
cgaccgcacc cgcccgaagc uggucaagg agcccagcag acgggagcg cggcgc           56

<210> SEQ ID NO 416
<211> LENGTH: 61
<212> TYPE: RNA
<213> ORGANISM: Homo sapiens

<400> SEQUENCE: 416 gagguuggg guggagggcc aaggagcugg guggggugcc aagccucugu ccccacccca      60
g                                                                     61

<210> SEQ ID NO 417
<211> LENGTH: 66
<212> TYPE: RNA
<213> ORGANISM: Homo sapiens

<400> SEQUENCE: 417
gggcaugggg aggguggag ucagcauggg gcuaggaggc cccgcgcuga cccgccuucu      60
ccgcag                                                                66

<210> SEQ ID NO 418
<211> LENGTH: 103
<212> TYPE: RNA
<213> ORGANISM: Homo sapiens

<400> SEQUENCE: 418
gugucggcug uggcgugacu gucccucugu gucccccacu aggcccacug cucaguggag     60
cguggaggac gaggaggagg ccguccacga gcaaugccag cau                       103

<210> SEQ ID NO 419
<211> LENGTH: 109
<212> TYPE: RNA
<213> ORGANISM: Homo sapiens

<400> SEQUENCE: 419
ucccgcauuc ccucugcuuu ggucaggugg ugcccuccuu ccaugggguag agccagagau    60 ggugggucu ggcuggucag augggagugg acagagaccc ggggguccuc                 109

<210> SEQ ID NO 420
```

```
<211> LENGTH: 81
<212> TYPE: RNA
<213> ORGANISM: Homo sapiens

<400> SEQUENCE: 420
cauccuccuu acgucccacc ccccacuccu guuucggug aaauauucaa acaggagugg    60 ggugggaca uaaggaggau a                                              81

<210> SEQ ID NO 421
<211> LENGTH: 73
<212> TYPE: RNA
<213> ORGANISM: Homo sapiens

<400> SEQUENCE: 421
gugggcgggg gcaggugugu ggugggggu ggccugcggu gagcagggcc cucacaccug    60
ccucgccccc cag                                                      73

<210> SEQ ID NO 422
<211> LENGTH: 71
<212> TYPE: RNA
<213> ORGANISM: Homo sapiens

<400> SEQUENCE: 422
ggguaaaggg gcagggacgg guggcccag gaagaagggc cuggggagc cgcucuucuc     60 ccugcccaca g                                                        71

<210> SEQ ID NO 423
<211> LENGTH: 52
<212> TYPE: RNA
<213> ORGANISM: Homo sapiens

<400> SEQUENCE: 423
uagccgggcg ugguggugg gccuguggu cccagcuacu uuggaggcug ag             52

<210> SEQ ID NO 424
<211> LENGTH: 93
<212> TYPE: RNA
<213> ORGANISM: Homo sapiens

<400> SEQUENCE: 424
ggcgcuuuug ugcgcgcccg ggucuguugg ugcucagagu guggucaggc ggcucggacu    60
gagcaggugg gugcggggcu cggaggaggc ggc                                 93

<210> SEQ ID NO 425
<211> LENGTH: 113
<212> TYPE: RNA
<213> ORGANISM: Homo sapiens

<400> SEQUENCE: 425 gccgggugg gcggggcggc cucaggaggg gcccagcucc ccuggaugug cugcgguggg    60
gccggagggg cgucacgugc acccaaguga cgcccccuucu gauucugccu cag         113

<210> SEQ ID NO 426
<211> LENGTH: 84
<212> TYPE: RNA
<213> ORGANISM: Homo sapiens

<400> SEQUENCE: 426
ggccccuccu ucucagcccc agcucccgcu caccccugcc acgucaaagg aggcagaagg    60
ggaguuggga gcagagaggg gacc                                          84
```

```
<210> SEQ ID NO 427
<211> LENGTH: 100
<212> TYPE: RNA
<213> ORGANISM: Homo sapiens

<400> SEQUENCE: 427
gugagcgggc gcggcaggga ucgcgggcgg guggcggccu agggcgcgga gggcggaccg    60
ggaauggcgc gccgugcgcc gccggcguaa cugcggcgcu                         100

<210> SEQ ID NO 428
<211> LENGTH: 63
<212> TYPE: RNA
<213> ORGANISM: Homo sapiens

<400> SEQUENCE: 428 aaugggugggg ugcuggugggg agccgugccc uggccacuca uucggcucuc ucccucaccc   60
uag                                                                 63

<210> SEQ ID NO 429
<211> LENGTH: 59
<212> TYPE: RNA
<213> ORGANISM: Homo sapiens

<400> SEQUENCE: 429
cugugucggg gagucugggg uccggaauuc uccagagccu cugugccccu acuucccag     59

<210> SEQ ID NO 430
<211> LENGTH: 71
<212> TYPE: RNA
<213> ORGANISM: Homo sapiens

<400> SEQUENCE: 430
ugaccacccc cgggcaaaga ccugcagauc cccuguuaga gacgggccca ggacuuugug    60
cggggugccc a                                                        71

<210> SEQ ID NO 431
<211> LENGTH: 54
<212> TYPE: RNA
<213> ORGANISM: Homo sapiens

<400> SEQUENCE: 431
agcagcaggg gagagagagg aguccucuag acaccgacuc ugucuccugc agau          54

<210> SEQ ID NO 432
<211> LENGTH: 85
<212> TYPE: RNA
<213> ORGANISM: Homo sapiens

<400> SEQUENCE: 432
ggcgccuccu gcucugcugu gccgccaggg ccuccccuag cgcgccuucu ggagaggcuu    60
ugugcggaua cggggcugga ggccu                                         85

<210> SEQ ID NO 433
<211> LENGTH: 96
<212> TYPE: RNA
<213> ORGANISM: Homo sapiens

<400> SEQUENCE: 433
agaugugcuc uccuggccca ugaaaucaag cgugggugag accugugca gaacgggaag    60
```

```
gcgacccaua cuugguuuca gaggcuguga gaauaa                              96

<210> SEQ ID NO 434
<211> LENGTH: 100
<212> TYPE: RNA
<213> ORGANISM: Homo sapiens

<400> SEQUENCE: 434
agcucagggc ggcugcgcag agggcuggac ucagcggcgg agcuggcugc uggccucagu    60
ucugccucug uccagguccu ugugacccgc ccgcucuccu                         100

<210> SEQ ID NO 435
<211> LENGTH: 50
<212> TYPE: RNA
<213> ORGANISM: Homo sapiens

<400> SEQUENCE: 435
acccgggcgu ggguggggg gugggugccu guaauuccag cuaguuggga               50

<210> SEQ ID NO 436
<211> LENGTH: 80
<212> TYPE: RNA
<213> ORGANISM: Homo sapiens

<400> SEQUENCE: 436
ugccgucggc cugggagga ggaagggcaa guccaaaggu auacaguugg ucguucauu      60 cucucuuuuu ggccuacaag                                                80

<210> SEQ ID NO 437
<211> LENGTH: 63
<212> TYPE: RNA
<213> ORGANISM: Homo sapiens

<400> SEQUENCE: 437
gagguguagg ggagguuggg ccagggaugc cuucacugug ucucucuggu cuugccaccc    60
cag                                                                  63

<210> SEQ ID NO 438
<211> LENGTH: 60
<212> TYPE: RNA
<213> ORGANISM: Homo sapiens

<400> SEQUENCE: 438
aggccuaggg gguggcaggc uggccaucag ugugggcuaa cccugucCuc ucccucccag    60

<210> SEQ ID NO 439
<211> LENGTH: 67
<212> TYPE: RNA
<213> ORGANISM: Homo sapiens

<400> SEQUENCE: 439
guggcacuca aacugugggg gcacuuucug cucucuggug aaagugccgc caucuuuuga    60
guguuac                                                              67

<210> SEQ ID NO 440
<211> LENGTH: 68
<212> TYPE: RNA
<213> ORGANISM: Homo sapiens

<400> SEQUENCE: 440
gggcgcaggg ggacuggggg ugagcaggcc cagaacccag cucgugcuca cucucaguCc    60
```

-continued

```
cuccccuag                                                             68

<210> SEQ ID NO 441
<211> LENGTH: 64
<212> TYPE: RNA
<213> ORGANISM: Homo sapiens

<400> SEQUENCE: 441
gagcucuggg aggggcuggg uuuggcagga caguuuccaa gcccugucuc cucccaucuu     60
ccag                                                                  64

<210> SEQ ID NO 442
<211> LENGTH: 67
<212> TYPE: RNA
<213> ORGANISM: Homo sapiens

<400> SEQUENCE: 442
aaaucucucu ccauaucuuu ccugcagccc ccaggugggg gggaagaaaa ggugggaau      60 uagauuc                                                               67

<210> SEQ ID NO 443
<211> LENGTH: 115
<212> TYPE: RNA
<213> ORGANISM: Homo sapiens

<400> SEQUENCE: 443
gagcaaaaac cagagaacaa caugggagcg uuccuaaccc cuaaggcaac uggaugggag     60
accugaccca uccaguucuc ugagggggcu cuugugguu cuacaagguu guuca          115

<210> SEQ ID NO 444
<211> LENGTH: 86
<212> TYPE: RNA
<213> ORGANISM: Homo sapiens

<400> SEQUENCE: 444
agagccgggg ccauggagca gccuguguag acggggaccu gcccugcaug ggcaccccu      60 cacuggcugc uucccuuggu cuccag                                          86

<210> SEQ ID NO 445
<211> LENGTH: 82
<212> TYPE: RNA
<213> ORGANISM: Homo sapiens

<400> SEQUENCE: 445
ugugggcagg gcccugggga gcugaggcuc uggggguggc cggggcugac ccugggccuc     60 ugcucccag ugucugaccg cg                                               82

<210> SEQ ID NO 446
<211> LENGTH: 136
<212> TYPE: RNA
<213> ORGANISM: Homo sapiens

<400> SEQUENCE: 446
ccgcuugccu cgcccagcgc agcccggcc gcugggcgca cccgucccgu ucgucccgg       60 acguugcucu cuaccccggg aacgucgaga cuggagcgcc cgaacugagc caccuucgcg    120
gaccccgaga gcggcg                                                    136

<210> SEQ ID NO 447
```

```
<211> LENGTH: 66
<212> TYPE: RNA
<213> ORGANISM: Homo sapiens

<400> SEQUENCE: 447
ucaagacggg gagucaggca guggguggaga uggagagccc ugagccucca cucuccuggc    60
ccccag                                                                66

<210> SEQ ID NO 448
<211> LENGTH: 78
<212> TYPE: RNA
<213> ORGANISM: Homo sapiens

<400> SEQUENCE: 448
ggccucaggc aggcgcaccc gaccacaugc auggcuggug gcggcgugca ggggucgggu    60
gggccaggcu gugggcg                                                   78

<210> SEQ ID NO 449
<211> LENGTH: 69
<212> TYPE: RNA
<213> ORGANISM: Homo sapiens

<400> SEQUENCE: 449
cuuucggcca gcgggacggc auccgaggug ggcuaggcuc gggcccgugg cgggugcggg    60
ggugggagg                                                            69

<210> SEQ ID NO 450
<211> LENGTH: 83
<212> TYPE: RNA
<213> ORGANISM: Homo sapiens

<400> SEQUENCE: 450
gucuacuccc agggugccaa gcuguuucgu guucccuccc uaggggaucc cagguagggg    60
cagcagagga ccugggccug gac                                            83

<210> SEQ ID NO 451
<211> LENGTH: 84
<212> TYPE: RNA
<213> ORGANISM: Homo sapiens

<400> SEQUENCE: 451
ccgcagccgc cgcgccgggc ccggguuggc cgcugacccc cgcggggccc ccggcggccg    60 gggcggggc ggggcugcc ccgg                                             84

<210> SEQ ID NO 452
<211> LENGTH: 72
<212> TYPE: RNA
<213> ORGANISM: Homo sapiens

<400> SEQUENCE: 452
augagcgggu gggagcagau cuuauugaga guuccuucuc cugcuccuga uugucuuccc    60
ccacccucac ag                                                        72

<210> SEQ ID NO 453
<211> LENGTH: 91
<212> TYPE: RNA
<213> ORGANISM: Homo sapiens

<400> SEQUENCE: 453
guucuagagc augguuucuc aucauuugca cuacugauac uuggggucag auaauuguuu    60
```
gugguggggg cuguuguuug cauuguagga u    91

<210> SEQ ID NO 454
<211> LENGTH: 75
<212> TYPE: RNA
<213> ORGANISM: Homo sapiens

<400> SEQUENCE: 454
aggcuggcgu gggcugaggg caggaggccu guggccgguc ccaggccucc ugcuuccugg    60
gcucaggcuc gguuu    75

<210> SEQ ID NO 455
<211> LENGTH: 87
<212> TYPE: RNA
<213> ORGANISM: Homo sapiens

<400> SEQUENCE: 455
guguggccgg caggcgggug ggcggggcg gccgguggga accccgcccc gccccgcgcc    60
cgcacucacc cgcccgucuc cccacag    87

<210> SEQ ID NO 456
<211> LENGTH: 76
<212> TYPE: RNA
<213> ORGANISM: Homo sapiens

<400> SEQUENCE: 456
ggggucaccu cucuggccgu cuaccuucca cacugacaag ggccgugggg acguagcugg    60
ccagacaggu gaccc    76

<210> SEQ ID NO 457
<211> LENGTH: 100
<212> TYPE: RNA
<213> ORGANISM: Homo sapiens

<400> SEQUENCE: 457
gaggugggag gauugcuuga gucaggugg uugaggcugc aguaaguugu gaucauacca    60
cugcacucca gccugaguga cagagcaaga ccuugucuca    100

<210> SEQ ID NO 458
<211> LENGTH: 67
<212> TYPE: RNA
<213> ORGANISM: Homo sapiens

<400> SEQUENCE: 458
aauagauuau uggucaccac cuccaguuuc ugaauugug agacugggu ggggccugag    60 aauuugc    67

<210> SEQ ID NO 459
<211> LENGTH: 90
<212> TYPE: RNA
<213> ORGANISM: Homo sapiens

<400> SEQUENCE: 459
ggcgccucug cagcuccggc uccccuggc cucucgggaa cuacaagucc caggggccu    60 ggcggugggc ggcgggcgga agaggcgggg    90

<210> SEQ ID NO 460
<211> LENGTH: 64
<212> TYPE: RNA

```
<213> ORGANISM: Homo sapiens

<400> SEQUENCE: 460 ggguggggc gggggcggcag gggccucccc cagugccagg ccccauucug cuucucuccc    60
agcu                                                                 64

<210> SEQ ID NO 461
<211> LENGTH: 64
<212> TYPE: RNA
<213> ORGANISM: Homo sapiens

<400> SEQUENCE: 461
aguucagggc cgaagggugg aagcugcugg ugcucaucuc agccucugcc cuuggccucc    60
ccag                                                                 64

<210> SEQ ID NO 462
<211> LENGTH: 68
<212> TYPE: RNA
<213> ORGANISM: Homo sapiens

<400> SEQUENCE: 462
cguggugagg auauggcagg aaggggagu ucccucuau cccuucccc ccaguaaucu       60 ucaucaug                                                             68

<210> SEQ ID NO 463
<211> LENGTH: 67
<212> TYPE: RNA
<213> ORGANISM: Homo sapiens

<400> SEQUENCE: 463
gcgcccuccc ucucccccg gugugcaaau gugugugugc ggguuaugc cggacaagag      60 ggaggug                                                              67

<210> SEQ ID NO 464
<211> LENGTH: 98
<212> TYPE: RNA
<213> ORGANISM: Homo sapiens

<400> SEQUENCE: 464
cgagguaggg gcguccccggg cgcgcggggcg ggucccaggc ugggcccuc ggaggccggg   60 ugcucacugc cccgucccgg cgcccguguc uccuccag                            98

<210> SEQ ID NO 465
<211> LENGTH: 69
<212> TYPE: RNA
<213> ORGANISM: Homo sapiens

<400> SEQUENCE: 465 uggguaggg gugggggaau ucaggggugu cgaacucaug gcugccaccu uugugucccc     60
auccugcag                                                            69

<210> SEQ ID NO 466
<211> LENGTH: 68
<212> TYPE: RNA
<213> ORGANISM: Homo sapiens

<400> SEQUENCE: 466
gcauccugua cugagcugcc ccgaggcccu ucaugcugcc cagcucgggg cagcucagua    60
caggauac                                                             68
```

<210> SEQ ID NO 467
<211> LENGTH: 64
<212> TYPE: RNA
<213> ORGANISM: Homo sapiens

<400> SEQUENCE: 467
uccuguacug agcugccccg agcugggcag caugaagggc cucggggcag cucaguacag    60
gaug    64

<210> SEQ ID NO 468
<211> LENGTH: 110
<212> TYPE: RNA
<213> ORGANISM: Homo sapiens

<400> SEQUENCE: 468
gucuaccagg ugugggccca gcuuuacaua guucaugcug aggccgggau uucaugcaga    60
aaacugguug caaaaggugc ugaaggggcu gggggagcac aagggagaag    110

<210> SEQ ID NO 469
<211> LENGTH: 71
<212> TYPE: RNA
<213> ORGANISM: Homo sapiens

<400> SEQUENCE: 469
gugucugugc cggucccagg agaaccugca gaggcaucgg gucagcggug cuccugcggg    60
ccgacacuca c    71

<210> SEQ ID NO 470
<211> LENGTH: 99
<212> TYPE: RNA
<213> ORGANISM: Homo sapiens

<400> SEQUENCE: 470
cgcccaccuc agccucccaa aaugcuggga uuacaggcau gagccacugc ggucgaccau    60
gaccuggaca uguuugugcc caguacuguc aguuugcag    99

<210> SEQ ID NO 471
<211> LENGTH: 86
<212> TYPE: RNA
<213> ORGANISM: Homo sapiens

<400> SEQUENCE: 471
agcacugccc ccggugaguc agggugggge uggcccccug cuucgugccc auccgcgcuc    60
ugacucucug cccaccugca ggagcu    86

<210> SEQ ID NO 472
<211> LENGTH: 65
<212> TYPE: RNA
<213> ORGANISM: Homo sapiens

<400> SEQUENCE: 472
cucccucugg gggugggggc ugggcguggu ggacagcgau gcaucccucg ccuucucacc    60
cucag    65

<210> SEQ ID NO 473
<211> LENGTH: 73
<212> TYPE: RNA
<213> ORGANISM: Homo sapiens

<400> SEQUENCE: 473
ggggagguac cugggacagg aggaggaggc agccuugccu cagaaaccaa acugucaaaa    60
guguagguuc cac    73

<210> SEQ ID NO 474
<211> LENGTH: 55
<212> TYPE: RNA
<213> ORGANISM: Homo sapiens

<400> SEQUENCE: 474
ccggauccga gucacggcac caaauuucau gcguguccgu gugaagagac cacca    55

<210> SEQ ID NO 475
<211> LENGTH: 66
<212> TYPE: RNA
<213> ORGANISM: Homo sapiens

<400> SEQUENCE: 475
acccaggagg cggaggaggu ggagguugca gugagccaag aucguggcac ugacuccagc    60
cuggggg    66

<210> SEQ ID NO 476
<211> LENGTH: 94
<212> TYPE: RNA
<213> ORGANISM: Homo sapiens

<400> SEQUENCE: 476 cacgguqucc ccuggqugqaa ccuggcaggg ggagagguaa ggucuuucag ccucuccaaa    60
gcccaugguc agguacucag guggqgqgqagc ccug    94

<210> SEQ ID NO 477
<211> LENGTH: 62
<212> TYPE: RNA
<213> ORGANISM: Homo sapiens

<400> SEQUENCE: 477 gagggugguq gaggaagagg gcagcuccca ugacugccug accgccuucu cuccucccccc    60 ag    62

<210> SEQ ID NO 478
<211> LENGTH: 66
<212> TYPE: RNA
<213> ORGANISM: Homo sapiens

<400> SEQUENCE: 478
agcagcccuc ggcggcccgg ggggcgggcg gcggugcccg ucccggggcu gcgcgaggca    60
caggcg    66

<210> SEQ ID NO 479
<211> LENGTH: 81
<212> TYPE: RNA
<213> ORGANISM: Homo sapiens

<400> SEQUENCE: 479
uagaggcagu uucaacagau guguagacuu uugauaugag aaauugguuu caaaaucagg    60
agucggggcu uuacugcuuu u    81

<210> SEQ ID NO 480
<211> LENGTH: 74

-continued

```
<212> TYPE: RNA
<213> ORGANISM: Homo sapiens

<400> SEQUENCE: 480
ccugcaggag gcagugggcg agcaggcggg gcagcccaau gccaugggcc ugaucucacc    60
gcugccuccu uccc                                                     74

<210> SEQ ID NO 481
<211> LENGTH: 109
<212> TYPE: RNA
<213> ORGANISM: Homo sapiens

<400> SEQUENCE: 481
ugcuauuguc uuacugcuac agcagggcug gggauugcag uauccgcugu ugcugcugcu    60
cccaguccug ccccugcugc uaccuagucc agccucaccg caucccaga              109

<210> SEQ ID NO 482
<211> LENGTH: 67
<212> TYPE: RNA
<213> ORGANISM: Homo sapiens

<400> SEQUENCE: 482
cagcgugggc ugcugagaag gggcagggguc cuccagcuca uuccuccugc cuccuccgug    60
gccucag                                                             67

<210> SEQ ID NO 483
<211> LENGTH: 63
<212> TYPE: RNA
<213> ORGANISM: Homo sapiens

<400> SEQUENCE: 483
gcaugcuggg cgaggcuggc aucuagcaca ggcgguagau gcuugcucuu gccauugcaa    60
uga                                                                 63

<210> SEQ ID NO 484
<211> LENGTH: 98
<212> TYPE: RNA
<213> ORGANISM: Homo sapiens

<400> SEQUENCE: 484
cuuggucaau aggaaagagg ugggaccucc uggcuuuucc ucugcagcau ggcucggacc    60
uagugcaaug uuuaagcucc ccucucuuuc cuguucag                           98

<210> SEQ ID NO 485
<211> LENGTH: 70
<212> TYPE: RNA
<213> ORGANISM: Homo sapiens

<400> SEQUENCE: 485
aggacccagc ggggcugggc gcgcggagca gcgcuggggug cagcgccugc gccggcagcu    60
gcaagggccg                                                          70

<210> SEQ ID NO 486
<211> LENGTH: 61
<212> TYPE: RNA
<213> ORGANISM: Homo sapiens

<400> SEQUENCE: 486
uccgcucugu ggaguggggu gccugucccc ugccacuggg ugacccaccc cucuccacca    60
```

```
g                                                              61

<210> SEQ ID NO 487
<211> LENGTH: 83
<212> TYPE: RNA
<213> ORGANISM: Homo sapiens

<400> SEQUENCE: 487
aauagagggu gcacaggcac gggagcucag gugaggcagg gagcugagcu caccugaccu    60
cccaugccug ugcacccucu auu                                           83

<210> SEQ ID NO 488
<211> LENGTH: 87
<212> TYPE: RNA
<213> ORGANISM: Homo sapiens

<400> SEQUENCE: 488
gugaggcggg gccaggaggg uguguggcgu gggugcugcg gggccgucag ggugccugcg    60
ggacgcucac cuggcuggcc cgcccag                                       87

<210> SEQ ID NO 489
<211> LENGTH: 99
<212> TYPE: RNA
<213> ORGANISM: Homo sapiens

<400> SEQUENCE: 489
gcaagggaca gggagggucg uggcgacacu cgcgccagcu cccgggacgg cugggcucgg    60
gcuggucgcc gaccuccgac ccuccacuag augccuggc                          99

<210> SEQ ID NO 490
<211> LENGTH: 91
<212> TYPE: RNA
<213> ORGANISM: Homo sapiens

<400> SEQUENCE: 490
ggcgccccgg cuccccgcgc ccccgaucgg ggccgccgcu aguaguggcg gcggcggagg    60
cgggggcagc ggcggcggcg gcggaggcgc c                                  91

<210> SEQ ID NO 491
<211> LENGTH: 69
<212> TYPE: RNA
<213> ORGANISM: Homo sapiens

<400> SEQUENCE: 491
ggcccucggg ccuggggüug ggggagcucu guccugucuc acucauugcu ccuccccugc    60
cuggcccag                                                           69

<210> SEQ ID NO 492
<211> LENGTH: 89
<212> TYPE: RNA
<213> ORGANISM: Homo sapiens

<400> SEQUENCE: 492
ucuccguuua ucccaccacu gccaccauua uugcuacugu ucagcaggug cugcuggugg    60
ugauggugau agucuggugg gggcggugg                                     89

<210> SEQ ID NO 493
<211> LENGTH: 69
<212> TYPE: RNA
<213> ORGANISM: Homo sapiens
```

```
<400> SEQUENCE: 493
gaggagggga ggugugcagg gcugggguca cugacucugc uuccccugcc cugcauggug    60
uccccacag                                                            69

<210> SEQ ID NO 494
<211> LENGTH: 81
<212> TYPE: RNA
<213> ORGANISM: Homo sapiens

<400> SEQUENCE: 494 aguuggugg ggagccauga gauaagagca ccuccuagag aauguugaac uaaaggugcc    60
cucucuggcu ccuccccaaa g                                              81

<210> SEQ ID NO 495
<211> LENGTH: 67
<212> TYPE: RNA
<213> ORGANISM: Homo sapiens

<400> SEQUENCE: 495
uacaggccgg ggcuuugggu gagggacccc cggagucugu cacggucuca ccccaacucu    60
gccccag                                                              67

<210> SEQ ID NO 496
<211> LENGTH: 119
<212> TYPE: RNA
<213> ORGANISM: Homo sapiens

<400> SEQUENCE: 496
ccaugaggag cuggcagugg gauggccugg ggguaggagc guggcuucug gagcuagacc    60 acaugggguuc agaucccagc ggugcccuca acuggccaca ggaccuuggg cagucagcu   119

<210> SEQ ID NO 497
<211> LENGTH: 62
<212> TYPE: RNA
<213> ORGANISM: Homo sapiens

<400> SEQUENCE: 497
cuuccuggug ggugggagg agaagugccg uccucaugag ccccucucug ucccacccau    60
ag                                                                   62

<210> SEQ ID NO 498
<211> LENGTH: 87
<212> TYPE: RNA
<213> ORGANISM: Homo sapiens

<400> SEQUENCE: 498
gcagggcugg cagggaggcu gggaggggcu ggcuggguu ggaguggggc aucagcuggc    60
ccucauuucu uaagacagca cuucugu                                        87

<210> SEQ ID NO 499
<211> LENGTH: 97
<212> TYPE: RNA
<213> ORGANISM: Homo sapiens

<400> SEQUENCE: 499
aucugaguug ggagggucc ucuccaaaug ugucuugggg uggggaucaa agacacauuu    60
ggagagggaa ccucccaacu cggccucugc caucauu                             97
```

```
<210> SEQ ID NO 500
<211> LENGTH: 73
<212> TYPE: RNA
<213> ORGANISM: Homo sapiens

<400> SEQUENCE: 500
ggaggcuggg cuggacgga cacccggccu ccacuuucug uggcagguac cuccuccaug    60
ucggcccgcc uug                                                      73

<210> SEQ ID NO 501
<211> LENGTH: 70
<212> TYPE: RNA
<213> ORGANISM: Homo sapiens

<400> SEQUENCE: 501
acaaauagcu ucagggaguc aggggagggc agaaauagau ggccuucccc ugcugggaag   60
aaaguggguc                                                          70

<210> SEQ ID NO 502
<211> LENGTH: 87
<212> TYPE: RNA
<213> ORGANISM: Homo sapiens

<400> SEQUENCE: 502
cccucaucuc ugggcagggg cuuauuguag gagucucuga agagagcugu ggacugaccu   60
gcuuuaaccc uuccccaggu ucccauu                                       87

<210> SEQ ID NO 503
<211> LENGTH: 72
<212> TYPE: RNA
<213> ORGANISM: Homo sapiens

<400> SEQUENCE: 503 cuggggagg aaggacaggc caucugcuau ucguccacca accugacuug auccucucuu    60
cccuccuccc ag                                                       72

<210> SEQ ID NO 504
<211> LENGTH: 67
<212> TYPE: RNA
<213> ORGANISM: Homo sapiens

<400> SEQUENCE: 504 ccagacccu gggcugggc aggcggaaag aggucugaac ugccucugcc uccuuggucu    60
ccggcag                                                             67

<210> SEQ ID NO 505
<211> LENGTH: 65
<212> TYPE: RNA
<213> ORGANISM: Homo sapiens

<400> SEQUENCE: 505
gucuccuggg gggaggagac ccugcucucc cuggcagcaa gccucuccug cccuuccaga   60
uuagc                                                               65

<210> SEQ ID NO 506
<211> LENGTH: 91
<212> TYPE: RNA
<213> ORGANISM: Homo sapiens

<400> SEQUENCE: 506
```

```
acgcccccg ccccgccacc gccuuggagg cugaccucuu acuuucgguc ggucuucuuc    60
ccugggcuug guuuggggc ggggagugu c                                    91

<210> SEQ ID NO 507
<211> LENGTH: 57
<212> TYPE: RNA
<213> ORGANISM: Homo sapiens

<400> SEQUENCE: 507
cauuggaggg uguggaagac aucugggcca acucugaucu cuucaucuac cccccag      57

<210> SEQ ID NO 508
<211> LENGTH: 67
<212> TYPE: RNA
<213> ORGANISM: Homo sapiens

<400> SEQUENCE: 508
cagggaggag gugguacuag gggccagcaa ccugauuacc ccucuuuggc ccuuuguacc   60
ccuccag                                                             67

<210> SEQ ID NO 509
<211> LENGTH: 96
<212> TYPE: RNA
<213> ORGANISM: Homo sapiens

<400> SEQUENCE: 509
gcucuggggc gugccgccgc cgucgcugcc accucccccua ccgcuagugg aagaagaugg  60
cggaaggcgg agcggcggau cuggacaccc agcggu                             96

<210> SEQ ID NO 510
<211> LENGTH: 61
<212> TYPE: RNA
<213> ORGANISM: Homo sapiens

<400> SEQUENCE: 510
ccugcgggga caggccaggg caucuaggcu gugcacagug acgcccccucc ugcccccaca  60 g                                                                   61

<210> SEQ ID NO 511
<211> LENGTH: 58
<212> TYPE: RNA
<213> ORGANISM: Homo sapiens

<400> SEQUENCE: 511
agggccagag gagccuggag ggucgdgguc gacugaaccc agguucccuc uggccgca     58

<210> SEQ ID NO 512
<211> LENGTH: 86
<212> TYPE: RNA
<213> ORGANISM: Homo sapiens

<400> SEQUENCE: 512
auucuaggug gggagacuga cggcuggagg cccauaagcu gucuaaaacu ucggccccca   60
gauuucuggu cucccacuu cagaac                                         86

<210> SEQ ID NO 513
<211> LENGTH: 80
<212> TYPE: RNA
<213> ORGANISM: Homo sapiens
```

<400> SEQUENCE: 513
ggcgcgucgc cccccucagu ccaccagagc ccggauaccu cagaaauucg gcucuggguc    60 ugugggagc gaaaugcaac                                                 80

<210> SEQ ID NO 514
<211> LENGTH: 98
<212> TYPE: RNA
<213> ORGANISM: Homo sapiens

<400> SEQUENCE: 514
uucucacccc cgccugacac gggcgacagc ugcggcccgc uguuucacu cgggccgagu    60 gcgucuccug ucaggcaagg gagagcagag ccccccug                           98

<210> SEQ ID NO 515
<211> LENGTH: 94
<212> TYPE: RNA
<213> ORGANISM: Homo sapiens

<400> SEQUENCE: 515
auaaaggaag uuaggcugag gggcagagag cgagacuuuu cuauuuucca aaagcucggu    60
cugaggcccc ucagucuugc uuccuaaccc gcgc                               94

<210> SEQ ID NO 516
<211> LENGTH: 75
<212> TYPE: RNA
<213> ORGANISM: Homo sapiens

<400> SEQUENCE: 516
ucaucccugg gugggauuu guugcauuac uuguguucua uauaaaguau ugcacuugc    60 ccggccugug gaaga                                                    75

<210> SEQ ID NO 517
<211> LENGTH: 89
<212> TYPE: RNA
<213> ORGANISM: Homo sapiens

<400> SEQUENCE: 517
gucagcagug ccuuagcagc acguaaauau uggcguuaag auucuaaaau uaucccagu    60 auuaacugug cugcugaagu aagguugac                                     89

<210> SEQ ID NO 518
<211> LENGTH: 81
<212> TYPE: RNA
<213> ORGANISM: Homo sapiens

<400> SEQUENCE: 518
guuccacucu agcagcacgu aaauauuggc guagugaaau auauauuaaa caccaauauu    60
acugugcugc uuuaguguga c                                             81

<210> SEQ ID NO 519
<211> LENGTH: 72
<212> TYPE: RNA
<213> ORGANISM: Homo sapiens

<400> SEQUENCE: 519
cuugggaaug gcaaggaaac cguuaccauu acugaguuua guaaugguaa ugguucucuu    60
gcuauaccca ga                                                       72

```
<210> SEQ ID NO 520
<211> LENGTH: 90
<212> TYPE: RNA
<213> ORGANISM: Homo sapiens

<400> SEQUENCE: 520
aggccucgcu guucucuaug gcuuuuuauu ccuaugugau ucuacugcuc acucauauag    60
ggauuggagc cguggcgcac ggcggggaca                                    90

<210> SEQ ID NO 521
<211> LENGTH: 86
<212> TYPE: RNA
<213> ORGANISM: Homo sapiens

<400> SEQUENCE: 521
ggcuuagaaa cagucccuag guaggauuug gggaggagcu aagaagcccc uacagggccc    60
agaggugggg acugagccuu aguugg                                        86

<210> SEQ ID NO 522
<211> LENGTH: 96
<212> TYPE: RNA
<213> ORGANISM: Homo sapiens

<400> SEQUENCE: 522
cgggccccgg gcgggcggga gggacgggac gcggugcagu guuguuuuuu ccccgccaa    60 uauugcacuc gucccggccu ccggccccc cggccc                              96

<210> SEQ ID NO 523
<211> LENGTH: 70
<212> TYPE: RNA
<213> ORGANISM: Homo sapiens

<400> SEQUENCE: 523
ggccgcggcg cgcaagaugg cggcgggccc gggcaccgcc ccuuccgccc cgccgggcgu    60
cgcacgaggc                                                          70

<210> SEQ ID NO 524
<211> LENGTH: 94
<212> TYPE: RNA
<213> ORGANISM: Homo sapiens

<400> SEQUENCE: 524
gugaggugug ggcccggccc caggagcggg gccugggcag cccgugugu ugaggaagga     60 aggcagggcc cccgcucccc gggccugacc ccac                               94

<210> SEQ ID NO 525
<211> LENGTH: 97
<212> TYPE: RNA
<213> ORGANISM: Homo sapiens

<400> SEQUENCE: 525
cucaggugcu cuggcugcuu ggguuccugg caugcugauu ugugacuuaa gauuaaaauc    60
acauugccag ggauuaccac gcaaccacga ccuuggc                            97

<210> SEQ ID NO 526
<211> LENGTH: 78
<212> TYPE: RNA
<213> ORGANISM: Homo sapiens

<400> SEQUENCE: 526
```

```
cuuucuacac agguugggau cgguugcaau gcuguguuuc uguaugguau ugcacuuguc    60
ccggccuguu gaguuugg                                                 78

<210> SEQ ID NO 527
<211> LENGTH: 75
<212> TYPE: RNA
<213> ORGANISM: Homo sapiens

<400> SEQUENCE: 527
ucaucccugg gugggauuu guugcauuac uuguguucua uauaaaguau ugcacuuguc    60
ccggccugug gaaga                                                   75

<210> SEQ ID NO 528
<211> LENGTH: 100
<212> TYPE: RNA
<213> ORGANISM: Homo sapiens

<400> SEQUENCE: 528
gcucgguugc cgugguugcg ggcccugccc gcccgccagc ucgcugacag cacgacucag   60
ggcggaggga aguagguccg uuggucgguc gggaacgagg                        100

<210> SEQ ID NO 529
<211> LENGTH: 65
<212> TYPE: RNA
<213> ORGANISM: Homo sapiens

<400> SEQUENCE: 529
agcccugggg guggucucua gccaaggcuc uggggucuca cccuuggcug gucucugcuc   60
cgcag                                                              65

<210> SEQ ID NO 530
<211> LENGTH: 85
<212> TYPE: RNA
<213> ORGANISM: Homo sapiens

<400> SEQUENCE: 530
ggggaggusg ggaaaaggaa gggggaggag aaggugagac caauguccug ggugccacuc   60
cugcccagug ccucccuucc ucguu                                        85

<210> SEQ ID NO 531
<211> LENGTH: 87
<212> TYPE: RNA
<213> ORGANISM: Homo sapiens

<400> SEQUENCE: 531
gugaggcggg gccaggaggg uguguggcgu gggugcugcg gggccgucag ggugccugcg   60
ggacgcucac cuggcuggcc cgcccag                                      87

<210> SEQ ID NO 532
<211> LENGTH: 65
<212> TYPE: RNA
<213> ORGANISM: Homo sapiens

<400> SEQUENCE: 532
gcuucuggga ggagggauc uugggaguga ucccaacagc ugagcucccu gaaucccugu    60
cccag                                                              65

<210> SEQ ID NO 533
<211> LENGTH: 60
```

```
<212> TYPE: RNA
<213> ORGANISM: Homo sapiens

<400> SEQUENCE: 533
ugugaaugac ccccuuccag agccaaaauc accagggaug gaggaggggu cuugggacu      60

<210> SEQ ID NO 534
<211> LENGTH: 68
<212> TYPE: RNA
<213> ORGANISM: Homo sapiens

<400> SEQUENCE: 534
ugcccaggcu ggagcgagug cagguggcua gucaguccua gcucacugca gccucgaacu     60
ccugggcu                                                             68

<210> SEQ ID NO 535
<211> LENGTH: 80
<212> TYPE: RNA
<213> ORGANISM: Homo sapiens

<400> SEQUENCE: 535
accugaggag ccagcccucc ucccgcaccc aaacuuggag cacuugaccu uuggcuguug     60 gaggggcag gcucgcgggu                                                 80

<210> SEQ ID NO 536
<211> LENGTH: 83
<212> TYPE: RNA
<213> ORGANISM: Homo sapiens

<400> SEQUENCE: 536
ggcccggcuc cgggucucgg cccguacagu ccggccggcc augcuggcgg ggcuggggcc    60
ggggccgagc ccgcggcggg gcc                                            83

<210> SEQ ID NO 537
<211> LENGTH: 83
<212> TYPE: RNA
<213> ORGANISM: Homo sapiens

<400> SEQUENCE: 537
acggcaucuu ugcacucagc aggcaggcug gugcagcccg ugguggggga ccauccugcc    60 ugcuguggg uaaggacggc ugu                                             83

<210> SEQ ID NO 538
<211> LENGTH: 63
<212> TYPE: RNA
<213> ORGANISM: Homo sapiens

<400> SEQUENCE: 538 uggugcggc gguaguuaug ggcuucucuu ucucaccagc agccccuggg ccgccgccuc     60
ccu                                                                  63

<210> SEQ ID NO 539
<211> LENGTH: 98
<212> TYPE: RNA
<213> ORGANISM: Homo sapiens

<400> SEQUENCE: 539
agaaugggca aaugaacagu aaauuuggag gccuggggcc cucccugcug cuggagaagu    60
guuugcacgg gugggccuug ucuuugaaag gaggugga                            98
```

```
<210> SEQ ID NO 540
<211> LENGTH: 102
<212> TYPE: RNA
<213> ORGANISM: Homo sapiens

<400> SEQUENCE: 540
gugggagggc ccaggcgcgg gcagggguggg ggguggcaga gcgcuguccc gggggcgggg      60
ccgaagcgcg gcgaccguaa cuccuucugc uccgucccc ag                          102

<210> SEQ ID NO 541
<211> LENGTH: 80
<212> TYPE: RNA
<213> ORGANISM: Homo sapiens

<400> SEQUENCE: 541
cgggaaugcc gcggcgggga cggcgauugg uccguaugug uggugccacc ggccgccggc      60
uccgccccgg cccccgcccc                                                  80

<210> SEQ ID NO 542
<211> LENGTH: 93
<212> TYPE: RNA
<213> ORGANISM: Homo sapiens

<400> SEQUENCE: 542
uacuuauggc accccacucc ugguaccaua gucauaaguu aggagauguu agagcuguga      60
guaccaugac uuaagugugg uggcuuaaac aug                                   93

<210> SEQ ID NO 543
<211> LENGTH: 66
<212> TYPE: RNA
<213> ORGANISM: Homo sapiens

<400> SEQUENCE: 543
ccuggagggg ggcacugcgc aagcaaagcc agggacccug agaggcuuug cuuccugcuc      60
cccuag                                                                 66

<210> SEQ ID NO 544
<211> LENGTH: 65
<212> TYPE: RNA
<213> ORGANISM: Homo sapiens

<400> SEQUENCE: 544
uucuccuggg gaguggcugg ggagcagaca gacccaaccu caugcucccc ggccucugcc      60
cccag                                                                  65

<210> SEQ ID NO 545
<211> LENGTH: 22
<212> TYPE: RNA
<213> ORGANISM: Homo sapiens

<400> SEQUENCE: 545
ccccgguguu ggggcgcguc ug                                               22

<210> SEQ ID NO 546
<211> LENGTH: 21
<212> TYPE: RNA
<213> ORGANISM: Homo sapiens

<400> SEQUENCE: 546
cccgguguug gggcgcgucu g                                                21
```

<210> SEQ ID NO 547
<211> LENGTH: 22
<212> TYPE: RNA
<213> ORGANISM: Homo sapiens

<400> SEQUENCE: 547
uggcggagcc cauuccaugc ca                                               22

<210> SEQ ID NO 548
<211> LENGTH: 21
<212> TYPE: RNA
<213> ORGANISM: Homo sapiens

<400> SEQUENCE: 548
cuggcggagc ccauuccaug c                                                21

<210> SEQ ID NO 549
<211> LENGTH: 25
<212> TYPE: RNA
<213> ORGANISM: Homo sapiens

<400> SEQUENCE: 549
acucggcgug gcgucggucg uggua                                            25

<210> SEQ ID NO 550
<211> LENGTH: 15
<212> TYPE: RNA
<213> ORGANISM: Homo sapiens

<400> SEQUENCE: 550
acucggcgug gcguc                                                       15

<210> SEQ ID NO 551
<211> LENGTH: 19
<212> TYPE: RNA
<213> ORGANISM: Homo sapiens

<400> SEQUENCE: 551
cggcgcgacc ggcccgggg                                                   19

<210> SEQ ID NO 552
<211> LENGTH: 19
<212> TYPE: RNA
<213> ORGANISM: Homo sapiens

<400> SEQUENCE: 552
cggcgcgacc ggcccgggg                                                   19

<210> SEQ ID NO 553
<211> LENGTH: 26
<212> TYPE: RNA
<213> ORGANISM: Homo sapiens

<400> SEQUENCE: 553 cgguggfauc ccgcggccgu guuuuc                                           26

<210> SEQ ID NO 554
<211> LENGTH: 15
<212> TYPE: RNA
<213> ORGANISM: Homo sapiens

<400> SEQUENCE: 554
ggggcgccgc gggac        15

<210> SEQ ID NO 555
<211> LENGTH: 20
<212> TYPE: RNA
<213> ORGANISM: Homo sapiens

<400> SEQUENCE: 555
ccccggggag cccggcggug        20

<210> SEQ ID NO 556
<211> LENGTH: 15
<212> TYPE: RNA
<213> ORGANISM: Homo sapiens

<400> SEQUENCE: 556
accccgggga gcccg        15

<210> SEQ ID NO 557
<211> LENGTH: 24
<212> TYPE: RNA
<213> ORGANISM: Homo sapiens

<400> SEQUENCE: 557
gaucggucga gagcguccug gcug        24

<210> SEQ ID NO 558
<211> LENGTH: 15
<212> TYPE: RNA
<213> ORGANISM: Homo sapiens

<400> SEQUENCE: 558
gcugggcggg gcgcg        15

<210> SEQ ID NO 559
<211> LENGTH: 23
<212> TYPE: RNA
<213> ORGANISM: Homo sapiens

<400> SEQUENCE: 559
uguagagcag ggagcaggaa gcu        23

<210> SEQ ID NO 560
<211> LENGTH: 15
<212> TYPE: RNA
<213> ORGANISM: Homo sapiens

<400> SEQUENCE: 560
cagggagcag gaagc        15

<210> SEQ ID NO 561
<211> LENGTH: 15
<212> TYPE: RNA
<213> ORGANISM: Homo sapiens

<400> SEQUENCE: 561
ugaagcgggg gggcg        15

<210> SEQ ID NO 562
<211> LENGTH: 15
<212> TYPE: RNA
<213> ORGANISM: Homo sapiens

<400> SEQUENCE: 562

```
ugaagcgggg gggcg                                                    15

<210> SEQ ID NO 563
<211> LENGTH: 22
<212> TYPE: RNA
<213> ORGANISM: Homo sapiens

<400> SEQUENCE: 563
cugggcucgg gacgcgcggc uc                                            22

<210> SEQ ID NO 564
<211> LENGTH: 19
<212> TYPE: RNA
<213> ORGANISM: Homo sapiens

<400> SEQUENCE: 564
cugggcucgg gacgcgcgg                                                19

<210> SEQ ID NO 565
<211> LENGTH: 23
<212> TYPE: RNA
<213> ORGANISM: Homo sapiens

<400> SEQUENCE: 565
cacaggugag guucuuggga gcc                                           23

<210> SEQ ID NO 566
<211> LENGTH: 15
<212> TYPE: RNA
<213> ORGANISM: Homo sapiens

<400> SEQUENCE: 566
acaggugagg uucuu                                                    15

<210> SEQ ID NO 567
<211> LENGTH: 19
<212> TYPE: RNA
<213> ORGANISM: Homo sapiens

<400> SEQUENCE: 567
agugggaggc cagggcacg                                                19

<210> SEQ ID NO 568
<211> LENGTH: 15
<212> TYPE: RNA
<213> ORGANISM: Homo sapiens

<400> SEQUENCE: 568 aggggagcu gcagg                                                     15

<210> SEQ ID NO 569
<211> LENGTH: 22
<212> TYPE: RNA
<213> ORGANISM: Homo sapiens

<400> SEQUENCE: 569
aggcagcggg guguagugga ua                                            22

<210> SEQ ID NO 570
<211> LENGTH: 21
<212> TYPE: RNA
<213> ORGANISM: Homo sapiens
```

```
<400> SEQUENCE: 570
aggcagcggg guguagugga u                                          21

<210> SEQ ID NO 571
<211> LENGTH: 22
<212> TYPE: RNA
<213> ORGANISM: Homo sapiens

<400> SEQUENCE: 571 gggggcagg aggggcucag gg                                          22

<210> SEQ ID NO 572
<211> LENGTH: 16
<212> TYPE: RNA
<213> ORGANISM: Homo sapiens

<400> SEQUENCE: 572 guggggggc aggagg                                                 16

<210> SEQ ID NO 573
<211> LENGTH: 21
<212> TYPE: RNA
<213> ORGANISM: Homo sapiens

<400> SEQUENCE: 573
gaauggauuu uuggagcagg a                                          21

<210> SEQ ID NO 574
<211> LENGTH: 15
<212> TYPE: RNA
<213> ORGANISM: Homo sapiens

<400> SEQUENCE: 574
gaauggauuu uugga                                                 15

<210> SEQ ID NO 575
<211> LENGTH: 24
<212> TYPE: RNA
<213> ORGANISM: Homo sapiens

<400> SEQUENCE: 575
gcugcgggcu gcggucaggg cgau                                       24

<210> SEQ ID NO 576
<211> LENGTH: 20
<212> TYPE: RNA
<213> ORGANISM: Homo sapiens

<400> SEQUENCE: 576
gcugcgggcu gcggucaggg                                            20

<210> SEQ ID NO 577
<211> LENGTH: 18
<212> TYPE: RNA
<213> ORGANISM: Homo sapiens

<400> SEQUENCE: 577
gcggcggcgg cggcagca                                              18

<210> SEQ ID NO 578
<211> LENGTH: 15
<212> TYPE: RNA
<213> ORGANISM: Homo sapiens
```

-continued

```
<400> SEQUENCE: 578
gcgggcggcg gcggc                                                       15

<210> SEQ ID NO 579
<211> LENGTH: 22
<212> TYPE: RNA
<213> ORGANISM: Homo sapiens

<400> SEQUENCE: 579
ugggagggga gaggcagcaa gc                                               22

<210> SEQ ID NO 580
<211> LENGTH: 22
<212> TYPE: RNA
<213> ORGANISM: Homo sapiens

<400> SEQUENCE: 580
ugggagggga gaggcagcaa gc                                               22

<210> SEQ ID NO 581
<211> LENGTH: 26
<212> TYPE: RNA
<213> ORGANISM: Homo sapiens

<400> SEQUENCE: 581
cggguagaga gggcaguggg agguaa                                           26

<210> SEQ ID NO 582
<211> LENGTH: 15
<212> TYPE: RNA
<213> ORGANISM: Homo sapiens

<400> SEQUENCE: 582
cggguagaga gggca                                                       15

<210> SEQ ID NO 583
<211> LENGTH: 23
<212> TYPE: RNA
<213> ORGANISM: Homo sapiens

<400> SEQUENCE: 583
gagggaggga cggggcugu gcu                                               23

<210> SEQ ID NO 584
<211> LENGTH: 15
<212> TYPE: RNA
<213> ORGANISM: Homo sapiens

<400> SEQUENCE: 584
gaggagggag ggagg                                                       15

<210> SEQ ID NO 585
<211> LENGTH: 25
<212> TYPE: RNA
<213> ORGANISM: Homo sapiens

<400> SEQUENCE: 585
caggaaggau uuagggacag gcuuu                                            25

<210> SEQ ID NO 586
<211> LENGTH: 19
<212> TYPE: RNA
```

```
<213> ORGANISM: Homo sapiens

<400> SEQUENCE: 586
caggaaggau uuagggaca                                          19

<210> SEQ ID NO 587
<211> LENGTH: 18
<212> TYPE: RNA
<213> ORGANISM: Homo sapiens

<400> SEQUENCE: 587
cuccgggcgg cgccgugu                                           18

<210> SEQ ID NO 588
<211> LENGTH: 18
<212> TYPE: RNA
<213> ORGANISM: Homo sapiens

<400> SEQUENCE: 588 cuccggcgg cgccgugu                                            18

<210> SEQ ID NO 589
<211> LENGTH: 24
<212> TYPE: RNA
<213> ORGANISM: Homo sapiens

<400> SEQUENCE: 589
aggcaggggc uggugcuggg cggg                                    24

<210> SEQ ID NO 590
<211> LENGTH: 15
<212> TYPE: RNA
<213> ORGANISM: Homo sapiens

<400> SEQUENCE: 590 gggcggggggg cggcg                                             15

<210> SEQ ID NO 591
<211> LENGTH: 21
<212> TYPE: RNA
<213> ORGANISM: Homo sapiens

<400> SEQUENCE: 591
ccggccgccg gcuccgcccc g                                       21

<210> SEQ ID NO 592
<211> LENGTH: 17
<212> TYPE: RNA
<213> ORGANISM: Homo sapiens

<400> SEQUENCE: 592
ccggccgccg gcuccgc                                            17

<210> SEQ ID NO 593
<211> LENGTH: 24
<212> TYPE: RNA
<213> ORGANISM: Homo sapiens

<400> SEQUENCE: 593
cugguacagg ccuggggac aggg                                     24

<210> SEQ ID NO 594
<211> LENGTH: 18
```

<212> TYPE: RNA
<213> ORGANISM: Homo sapiens

<400> SEQUENCE: 594
cugguacagg ccuggggg                                                    18

<210> SEQ ID NO 595
<211> LENGTH: 27
<212> TYPE: RNA
<213> ORGANISM: Homo sapiens

<400> SEQUENCE: 595
gugaacgggc gccaucccga ggcuuug                                          27

<210> SEQ ID NO 596
<211> LENGTH: 16
<212> TYPE: RNA
<213> ORGANISM: Homo sapiens

<400> SEQUENCE: 596
gugaacgggc gccauc                                                      16

<210> SEQ ID NO 597
<211> LENGTH: 19
<212> TYPE: RNA
<213> ORGANISM: Homo sapiens

<400> SEQUENCE: 597
gugguugggg gcgggcucu                                                   19

<210> SEQ ID NO 598
<211> LENGTH: 19
<212> TYPE: RNA
<213> ORGANISM: Homo sapiens

<400> SEQUENCE: 598
gugguugggg gcgggcucu                                                   19

<210> SEQ ID NO 599
<211> LENGTH: 26
<212> TYPE: RNA
<213> ORGANISM: Homo sapiens

<400> SEQUENCE: 599
gcgggcuguc cggagggguc ggcuuu                                           26

<210> SEQ ID NO 600
<211> LENGTH: 16
<212> TYPE: RNA
<213> ORGANISM: Homo sapiens

<400> SEQUENCE: 600
gcuguccgga gggguc                                                      16

<210> SEQ ID NO 601
<211> LENGTH: 24
<212> TYPE: RNA
<213> ORGANISM: Homo sapiens

<400> SEQUENCE: 601
cccggggcag auugguguag ggug                                             24

<210> SEQ ID NO 602

```
<211> LENGTH: 17
<212> TYPE: RNA
<213> ORGANISM: Homo sapiens

<400> SEQUENCE: 602
cggggcagau uggugua                                                      17

<210> SEQ ID NO 603
<211> LENGTH: 23
<212> TYPE: RNA
<213> ORGANISM: Homo sapiens

<400> SEQUENCE: 603
gggggucccc ggugucgga ucu                                                23

<210> SEQ ID NO 604
<211> LENGTH: 16
<212> TYPE: RNA
<213> ORGANISM: Homo sapiens

<400> SEQUENCE: 604
ucgggagggg cgggag                                                       16

<210> SEQ ID NO 605
<211> LENGTH: 23
<212> TYPE: RNA
<213> ORGANISM: Homo sapiens

<400> SEQUENCE: 605
cggggccgua gcacugucug aga                                               23

<210> SEQ ID NO 606
<211> LENGTH: 20
<212> TYPE: RNA
<213> ORGANISM: Homo sapiens

<400> SEQUENCE: 606
cggggccgua gcacugucug                                                   20

<210> SEQ ID NO 607
<211> LENGTH: 27
<212> TYPE: RNA
<213> ORGANISM: Homo sapiens

<400> SEQUENCE: 607
ugagggacuu uuggggcag auguguu                                            27

<210> SEQ ID NO 608
<211> LENGTH: 17
<212> TYPE: RNA
<213> ORGANISM: Homo sapiens

<400> SEQUENCE: 608
ggacuuuugg gggcaga                                                      17

<210> SEQ ID NO 609
<211> LENGTH: 24
<212> TYPE: RNA
<213> ORGANISM: Homo sapiens

<400> SEQUENCE: 609
gaggcuggga aggcaaaggg acgu                                              24
```

```
<210> SEQ ID NO 610
<211> LENGTH: 15
<212> TYPE: RNA
<213> ORGANISM: Homo sapiens

<400> SEQUENCE: 610
gaaggaggcu gggaa                                               15

<210> SEQ ID NO 611
<211> LENGTH: 17
<212> TYPE: RNA
<213> ORGANISM: Homo sapiens

<400> SEQUENCE: 611
aggggcuggg cgcgcgc                                             17

<210> SEQ ID NO 612
<211> LENGTH: 15
<212> TYPE: RNA
<213> ORGANISM: Homo sapiens

<400> SEQUENCE: 612
caggggcugg gcgcg                                               15

<210> SEQ ID NO 613
<211> LENGTH: 25
<212> TYPE: RNA
<213> ORGANISM: Homo sapiens

<400> SEQUENCE: 613
ugcaggcaga agugggcug acagg                                     25

<210> SEQ ID NO 614
<211> LENGTH: 20
<212> TYPE: RNA
<213> ORGANISM: Homo sapiens

<400> SEQUENCE: 614
cugcaggcag aagugggcu                                           20

<210> SEQ ID NO 615
<211> LENGTH: 23
<212> TYPE: RNA
<213> ORGANISM: Homo sapiens

<400> SEQUENCE: 615 gggggaugu gcaugcuggu ugg                                       23

<210> SEQ ID NO 616
<211> LENGTH: 15
<212> TYPE: RNA
<213> ORGANISM: Homo sapiens

<400> SEQUENCE: 616
aucagcgugc acuuc                                               15

<210> SEQ ID NO 617
<211> LENGTH: 23
<212> TYPE: RNA
<213> ORGANISM: Homo sapiens

<400> SEQUENCE: 617
caccuugccu ugcugcccgg gcc                                      23
```

-continued

```
<210> SEQ ID NO 618
<211> LENGTH: 22
<212> TYPE: RNA
<213> ORGANISM: Homo sapiens

<400> SEQUENCE: 618
caccuugccu ugcugcccgg gc                                              22

<210> SEQ ID NO 619
<211> LENGTH: 23
<212> TYPE: RNA
<213> ORGANISM: Homo sapiens

<400> SEQUENCE: 619
uggggcggag cuuccggagg ccc                                             23

<210> SEQ ID NO 620
<211> LENGTH: 17
<212> TYPE: RNA
<213> ORGANISM: Homo sapiens

<400> SEQUENCE: 620
uggggcggag cuuccgg                                                    17

<210> SEQ ID NO 621
<211> LENGTH: 16
<212> TYPE: RNA
<213> ORGANISM: Homo sapiens

<400> SEQUENCE: 621
ggacccaggg agagac                                                     16

<210> SEQ ID NO 622
<211> LENGTH: 16
<212> TYPE: RNA
<213> ORGANISM: Homo sapiens

<400> SEQUENCE: 622
ggacccaggg agagac                                                     16

<210> SEQ ID NO 623
<211> LENGTH: 23
<212> TYPE: RNA
<213> ORGANISM: Homo sapiens

<400> SEQUENCE: 623
ggcccggccg ugccugaggu uuc                                             23

<210> SEQ ID NO 624
<211> LENGTH: 15
<212> TYPE: RNA
<213> ORGANISM: Homo sapiens

<400> SEQUENCE: 624
ggcgguggga ucccg                                                      15

<210> SEQ ID NO 625
<211> LENGTH: 23
<212> TYPE: RNA
<213> ORGANISM: Homo sapiens

<400> SEQUENCE: 625
cagcccgccc cagccgaggu ucu                                             23
```

```
<210> SEQ ID NO 626
<211> LENGTH: 17
<212> TYPE: RNA
<213> ORGANISM: Homo sapiens

<400> SEQUENCE: 626
agcccgcccc agccgag                                                    17

<210> SEQ ID NO 627
<211> LENGTH: 22
<212> TYPE: RNA
<213> ORGANISM: Homo sapiens

<400> SEQUENCE: 627
acucggcugc gguggacaag uc                                              22

<210> SEQ ID NO 628
<211> LENGTH: 20
<212> TYPE: RNA
<213> ORGANISM: Homo sapiens

<400> SEQUENCE: 628
acucggcugc gguggacaag                                                 20

<210> SEQ ID NO 629
<211> LENGTH: 23
<212> TYPE: RNA
<213> ORGANISM: Homo sapiens

<400> SEQUENCE: 629
ggugggugag gucgggcccc aag                                             23

<210> SEQ ID NO 630
<211> LENGTH: 20
<212> TYPE: RNA
<213> ORGANISM: Homo sapiens

<400> SEQUENCE: 630
cggggugggu gaggucgggc                                                 20

<210> SEQ ID NO 631
<211> LENGTH: 26
<212> TYPE: RNA
<213> ORGANISM: Homo sapiens

<400> SEQUENCE: 631
gaggggcucu cgcuucuggc gccaag                                          26

<210> SEQ ID NO 632
<211> LENGTH: 15
<212> TYPE: RNA
<213> ORGANISM: Homo sapiens

<400> SEQUENCE: 632
ggugaggcgg ggggg                                                      15

<210> SEQ ID NO 633
<211> LENGTH: 23
<212> TYPE: RNA
<213> ORGANISM: Homo sapiens

<400> SEQUENCE: 633
```

```
cuggggacg cgugagcgcg agc                                               23

<210> SEQ ID NO 634
<211> LENGTH: 21
<212> TYPE: RNA
<213> ORGANISM: Homo sapiens

<400> SEQUENCE: 634 cuggggacg cgugagcgcg a                                                 21

<210> SEQ ID NO 635
<211> LENGTH: 24
<212> TYPE: RNA
<213> ORGANISM: Homo sapiens

<400> SEQUENCE: 635 gugagugga gccgguggg cugg                                               24

<210> SEQ ID NO 636
<211> LENGTH: 15
<212> TYPE: RNA
<213> ORGANISM: Homo sapiens

<400> SEQUENCE: 636
ggggcuggag uaagg                                                       15

<210> SEQ ID NO 637
<211> LENGTH: 23
<212> TYPE: RNA
<213> ORGANISM: Homo sapiens

<400> SEQUENCE: 637
gugggcuggg cugggcuggg cca                                              23

<210> SEQ ID NO 638
<211> LENGTH: 15
<212> TYPE: RNA
<213> ORGANISM: Homo sapiens

<400> SEQUENCE: 638
gggcugggcu gggcu                                                       15

<210> SEQ ID NO 639
<211> LENGTH: 23
<212> TYPE: RNA
<213> ORGANISM: Homo sapiens

<400> SEQUENCE: 639
ugcgcagggg ccggugcuc acc                                               23

<210> SEQ ID NO 640
<211> LENGTH: 19
<212> TYPE: RNA
<213> ORGANISM: Homo sapiens

<400> SEQUENCE: 640
cgcaggggcc gggugcuca                                                   19

<210> SEQ ID NO 641
<211> LENGTH: 25
<212> TYPE: RNA
<213> ORGANISM: Homo sapiens

<400> SEQUENCE: 641
```

```
uucugggccc gcggcgggcg ugggg                                      25

<210> SEQ ID NO 642
<211> LENGTH: 15
<212> TYPE: RNA
<213> ORGANISM: Homo sapiens

<400> SEQUENCE: 642
cgcggcgggc guggg                                                 15

<210> SEQ ID NO 643
<211> LENGTH: 23
<212> TYPE: RNA
<213> ORGANISM: Homo sapiens

<400> SEQUENCE: 643
cuccuggggc ccgcacucuc gcu                                        23

<210> SEQ ID NO 644
<211> LENGTH: 18
<212> TYPE: RNA
<213> ORGANISM: Homo sapiens

<400> SEQUENCE: 644
cuccuggggc ccgcacuc                                              18

<210> SEQ ID NO 645
<211> LENGTH: 22
<212> TYPE: RNA
<213> ORGANISM: Homo sapiens

<400> SEQUENCE: 645
gaaaaaggcg ggagaagccc ca                                         22

<210> SEQ ID NO 646
<211> LENGTH: 15
<212> TYPE: RNA
<213> ORGANISM: Homo sapiens

<400> SEQUENCE: 646
gaaaaaggcg ggaga                                                 15

<210> SEQ ID NO 647
<211> LENGTH: 19
<212> TYPE: RNA
<213> ORGANISM: Homo sapiens

<400> SEQUENCE: 647
gcaggcgagg cugggcuga                                             19

<210> SEQ ID NO 648
<211> LENGTH: 16
<212> TYPE: RNA
<213> ORGANISM: Homo sapiens

<400> SEQUENCE: 648
aggcgaggcu gggcug                                                16

<210> SEQ ID NO 649
<211> LENGTH: 22
<212> TYPE: RNA
<213> ORGANISM: Homo sapiens
```

```
<400> SEQUENCE: 649
aaaagcuggg cugagaggcg ac                                              22

<210> SEQ ID NO 650
<211> LENGTH: 15
<212> TYPE: RNA
<213> ORGANISM: Homo sapiens

<400> SEQUENCE: 650
aaagcugggc ugaga                                                      15

<210> SEQ ID NO 651
<211> LENGTH: 23
<212> TYPE: RNA
<213> ORGANISM: Homo sapiens

<400> SEQUENCE: 651 ugggggaaggc gucagugucg ggu                                            23

<210> SEQ ID NO 652
<211> LENGTH: 16
<212> TYPE: RNA
<213> ORGANISM: Homo sapiens

<400> SEQUENCE: 652
uggggaaggc gucagu                                                     16

<210> SEQ ID NO 653
<211> LENGTH: 23
<212> TYPE: RNA
<213> ORGANISM: Homo sapiens

<400> SEQUENCE: 653
ggaggcgcag gcucggaaag gcg                                             23

<210> SEQ ID NO 654
<211> LENGTH: 15
<212> TYPE: RNA
<213> ORGANISM: Homo sapiens

<400> SEQUENCE: 654
gcaggcucgg aaagg                                                      15

<210> SEQ ID NO 655
<211> LENGTH: 23
<212> TYPE: RNA
<213> ORGANISM: Homo sapiens

<400> SEQUENCE: 655
agaagaaggc ggucggucug cgg                                             23

<210> SEQ ID NO 656
<211> LENGTH: 21
<212> TYPE: RNA
<213> ORGANISM: Homo sapiens

<400> SEQUENCE: 656
aagaaggcgg ucggucugcg g                                               21

<210> SEQ ID NO 657
<211> LENGTH: 25
<212> TYPE: RNA
<213> ORGANISM: Homo sapiens
```

```
<400> SEQUENCE: 657
agcggggagg aagugggcgc ugcuu                                          25

<210> SEQ ID NO 658
<211> LENGTH: 21
<212> TYPE: RNA
<213> ORGANISM: Homo sapiens

<400> SEQUENCE: 658
agcggggagg aagugggcgc u                                              21

<210> SEQ ID NO 659
<211> LENGTH: 17
<212> TYPE: RNA
<213> ORGANISM: Homo sapiens

<400> SEQUENCE: 659
ccuccgggac ggcuggg                                                   17

<210> SEQ ID NO 660
<211> LENGTH: 15
<212> TYPE: RNA
<213> ORGANISM: Homo sapiens

<400> SEQUENCE: 660
cuccgggacg gcugg                                                     15

<210> SEQ ID NO 661
<211> LENGTH: 24
<212> TYPE: RNA
<213> ORGANISM: Homo sapiens

<400> SEQUENCE: 661
ucgaggacug guggaagggc cuuu                                           24

<210> SEQ ID NO 662
<211> LENGTH: 16
<212> TYPE: RNA
<213> ORGANISM: Homo sapiens

<400> SEQUENCE: 662
ucgaggacug guggaa                                                    16

<210> SEQ ID NO 663
<211> LENGTH: 23
<212> TYPE: RNA
<213> ORGANISM: Homo sapiens

<400> SEQUENCE: 663
ggcuacaaca caggacccgg gcg                                            23

<210> SEQ ID NO 664
<211> LENGTH: 21
<212> TYPE: RNA
<213> ORGANISM: Homo sapiens

<400> SEQUENCE: 664
ggcuacaaca caggacccgg g                                              21

<210> SEQ ID NO 665
<211> LENGTH: 23
<212> TYPE: RNA
```

```
<213> ORGANISM: Homo sapiens

<400> SEQUENCE: 665 ugggggcggag cuuccggagg ccc                                          23

<210> SEQ ID NO 666
<211> LENGTH: 15
<212> TYPE: RNA
<213> ORGANISM: Homo sapiens

<400> SEQUENCE: 666
gccccgggaa agcgu                                                    15

<210> SEQ ID NO 667
<211> LENGTH: 21
<212> TYPE: RNA
<213> ORGANISM: Homo sapiens

<400> SEQUENCE: 667
gaggcgaugu ggggauguag a                                             21

<210> SEQ ID NO 668
<211> LENGTH: 20
<212> TYPE: RNA
<213> ORGANISM: Homo sapiens

<400> SEQUENCE: 668
cccagucuca uuuccucauc                                               20

<210> SEQ ID NO 669
<211> LENGTH: 21
<212> TYPE: RNA
<213> ORGANISM: Homo sapiens

<400> SEQUENCE: 669
gagggcagcg ugggugugge g                                             21

<210> SEQ ID NO 670
<211> LENGTH: 21
<212> TYPE: RNA
<213> ORGANISM: Homo sapiens

<400> SEQUENCE: 670
gagggcagcg ugggugugge g                                             21

<210> SEQ ID NO 671
<211> LENGTH: 22
<212> TYPE: RNA
<213> ORGANISM: Homo sapiens

<400> SEQUENCE: 671
accaggaggc ugaggccccu ca                                            22

<210> SEQ ID NO 672
<211> LENGTH: 15
<212> TYPE: RNA
<213> ORGANISM: Homo sapiens

<400> SEQUENCE: 672
accaggaggc ugagg                                                    15

<210> SEQ ID NO 673
<211> LENGTH: 21
```

```
<212> TYPE: RNA
<213> ORGANISM: Homo sapiens

<400> SEQUENCE: 673
uugaggagac auggugggggg c                                        21

<210> SEQ ID NO 674
<211> LENGTH: 15
<212> TYPE: RNA
<213> ORGANISM: Homo sapiens

<400> SEQUENCE: 674
uugaggagac auggu                                                15

<210> SEQ ID NO 675
<211> LENGTH: 22
<212> TYPE: RNA
<213> ORGANISM: Homo sapiens

<400> SEQUENCE: 675
ggcagggaca gcaaaggggu gc                                        22

<210> SEQ ID NO 676
<211> LENGTH: 18
<212> TYPE: RNA
<213> ORGANISM: Homo sapiens

<400> SEQUENCE: 676
gcagggacag caaagggg                                             18

<210> SEQ ID NO 677
<211> LENGTH: 25
<212> TYPE: RNA
<213> ORGANISM: Homo sapiens

<400> SEQUENCE: 677
cugcaggcag aagugggggcu gacag                                    25

<210> SEQ ID NO 678
<211> LENGTH: 19
<212> TYPE: RNA
<213> ORGANISM: Homo sapiens

<400> SEQUENCE: 678
caggcagaag uggggcuga                                            19

<210> SEQ ID NO 679
<211> LENGTH: 24
<212> TYPE: RNA
<213> ORGANISM: Homo sapiens

<400> SEQUENCE: 679
cgcucgggcg gaggugguug agug                                      24

<210> SEQ ID NO 680
<211> LENGTH: 17
<212> TYPE: RNA
<213> ORGANISM: Homo sapiens

<400> SEQUENCE: 680
ucgggcggag gugguug                                              17

<210> SEQ ID NO 681
```

```
<211> LENGTH: 16
<212> TYPE: RNA
<213> ORGANISM: Homo sapiens

<400> SEQUENCE: 681
gugaaggccc ggcgga                                                        16

<210> SEQ ID NO 682
<211> LENGTH: 15
<212> TYPE: RNA
<213> ORGANISM: Homo sapiens

<400> SEQUENCE: 682
gugaaggccc ggcgg                                                         15

<210> SEQ ID NO 683
<211> LENGTH: 17
<212> TYPE: RNA
<213> ORGANISM: Homo sapiens

<400> SEQUENCE: 683
ugcaggggca ggccagc                                                       17

<210> SEQ ID NO 684
<211> LENGTH: 17
<212> TYPE: RNA
<213> ORGANISM: Homo sapiens

<400> SEQUENCE: 684
ugcaggggca ggccagc                                                       17

<210> SEQ ID NO 685
<211> LENGTH: 25
<212> TYPE: RNA
<213> ORGANISM: Homo sapiens

<400> SEQUENCE: 685
ugcggggcua gggcuaacag caguc                                              25

<210> SEQ ID NO 686
<211> LENGTH: 15
<212> TYPE: RNA
<213> ORGANISM: Homo sapiens

<400> SEQUENCE: 686
ugcggggcua gggcu                                                         15

<210> SEQ ID NO 687
<211> LENGTH: 17
<212> TYPE: RNA
<213> ORGANISM: Homo sapiens

<400> SEQUENCE: 687
ggugagcgcu cgcuggc                                                       17

<210> SEQ ID NO 688
<211> LENGTH: 15
<212> TYPE: RNA
<213> ORGANISM: Homo sapiens

<400> SEQUENCE: 688
cggugagcgc ucgcu                                                         15
```

```
<210> SEQ ID NO 689
<211> LENGTH: 15
<212> TYPE: RNA
<213> ORGANISM: Homo sapiens

<400> SEQUENCE: 689
ggcgcgggga ggugc                                                    15

<210> SEQ ID NO 690
<211> LENGTH: 15
<212> TYPE: RNA
<213> ORGANISM: Homo sapiens

<400> SEQUENCE: 690
ggcgcgggga ggugc                                                    15

<210> SEQ ID NO 691
<211> LENGTH: 18
<212> TYPE: RNA
<213> ORGANISM: Homo sapiens

<400> SEQUENCE: 691
gaggcugaag gaagaugg                                                 18

<210> SEQ ID NO 692
<211> LENGTH: 15
<212> TYPE: RNA
<213> ORGANISM: Homo sapiens

<400> SEQUENCE: 692
gaggcugaag gaaga                                                    15

<210> SEQ ID NO 693
<211> LENGTH: 23
<212> TYPE: RNA
<213> ORGANISM: Homo sapiens

<400> SEQUENCE: 693
ccagggcugg cagugacaug ggu                                           23

<210> SEQ ID NO 694
<211> LENGTH: 19
<212> TYPE: RNA
<213> ORGANISM: Homo sapiens

<400> SEQUENCE: 694
cagggcuggc agugacaug                                                19

<210> SEQ ID NO 695
<211> LENGTH: 16
<212> TYPE: RNA
<213> ORGANISM: Homo sapiens

<400> SEQUENCE: 695
ugcuggugau gcuuuc                                                   16

<210> SEQ ID NO 696
<211> LENGTH: 16
<212> TYPE: RNA
<213> ORGANISM: Homo sapiens

<400> SEQUENCE: 696
ugcuggugau gcuuuc                                                   16
```

```
<210> SEQ ID NO 697
<211> LENGTH: 22
<212> TYPE: RNA
<213> ORGANISM: Homo sapiens

<400> SEQUENCE: 697
gaggguuggg uggaggcucu cc                                              22

<210> SEQ ID NO 698
<211> LENGTH: 15
<212> TYPE: RNA
<213> ORGANISM: Homo sapiens

<400> SEQUENCE: 698
gaggguuggg uggag                                                      15

<210> SEQ ID NO 699
<211> LENGTH: 20
<212> TYPE: RNA
<213> ORGANISM: Homo sapiens

<400> SEQUENCE: 699 ugagugggc ucccgggacg                                                  20

<210> SEQ ID NO 700
<211> LENGTH: 20
<212> TYPE: RNA
<213> ORGANISM: Homo sapiens

<400> SEQUENCE: 700
ugaguggggc ucccgggacg                                                 20

<210> SEQ ID NO 701
<211> LENGTH: 21
<212> TYPE: RNA
<213> ORGANISM: Homo sapiens

<400> SEQUENCE: 701
cccagcagga cgggagcgcg g                                               21

<210> SEQ ID NO 702
<211> LENGTH: 16
<212> TYPE: RNA
<213> ORGANISM: Homo sapiens

<400> SEQUENCE: 702
aagcuggguc aaggag                                                     16

<210> SEQ ID NO 703
<211> LENGTH: 20
<212> TYPE: RNA
<213> ORGANISM: Homo sapiens

<400> SEQUENCE: 703
ggcuggucag augggagugg                                                 20

<210> SEQ ID NO 704
<211> LENGTH: 20
<212> TYPE: RNA
<213> ORGANISM: Homo sapiens

<400> SEQUENCE: 704
ggcuggucag augggagugg                                                 20
```

<210> SEQ ID NO 705
<211> LENGTH: 23
<212> TYPE: RNA
<213> ORGANISM: Homo sapiens

<400> SEQUENCE: 705
acaggagugg ggugggaca uaa         23

<210> SEQ ID NO 706
<211> LENGTH: 20
<212> TYPE: RNA
<213> ORGANISM: Homo sapiens

<400> SEQUENCE: 706
acaggagugg ggugggaca            20

<210> SEQ ID NO 707
<211> LENGTH: 22
<212> TYPE: RNA
<213> ORGANISM: Homo sapiens

<400> SEQUENCE: 707
gugggcgggg gcaggugugu gg         22

<210> SEQ ID NO 708
<211> LENGTH: 15
<212> TYPE: RNA
<213> ORGANISM: Homo sapiens

<400> SEQUENCE: 708
cgggggcagg ugugu               15

<210> SEQ ID NO 709
<211> LENGTH: 21
<212> TYPE: RNA
<213> ORGANISM: Homo sapiens

<400> SEQUENCE: 709
gccgggcgug guggugggg c          21

<210> SEQ ID NO 710
<211> LENGTH: 15
<212> TYPE: RNA
<213> ORGANISM: Homo sapiens

<400> SEQUENCE: 710
uagccgggcg uggug               15

<210> SEQ ID NO 711
<211> LENGTH: 29
<212> TYPE: RNA
<213> ORGANISM: Homo sapiens

<400> SEQUENCE: 711
ggucaggcgg cucggacuga gcagguggg  29

<210> SEQ ID NO 712
<211> LENGTH: 15
<212> TYPE: RNA
<213> ORGANISM: Homo sapiens

<400> SEQUENCE: 712

```
agaguguggu caggc                                                15

<210> SEQ ID NO 713
<211> LENGTH: 22
<212> TYPE: RNA
<213> ORGANISM: Homo sapiens

<400> SEQUENCE: 713
cagaagggga guuggagcca ga                                        22

<210> SEQ ID NO 714
<211> LENGTH: 16
<212> TYPE: RNA
<213> ORGANISM: Homo sapiens

<400> SEQUENCE: 714 gaagggagu ugggag                                                16

<210> SEQ ID NO 715
<211> LENGTH: 16
<212> TYPE: RNA
<213> ORGANISM: Homo sapiens

<400> SEQUENCE: 715
ggcgcggagg gcggac                                               16

<210> SEQ ID NO 716
<211> LENGTH: 15
<212> TYPE: RNA
<213> ORGANISM: Homo sapiens

<400> SEQUENCE: 716
ggcgcggagg gcgga                                                15

<210> SEQ ID NO 717
<211> LENGTH: 21
<212> TYPE: RNA
<213> ORGANISM: Homo sapiens

<400> SEQUENCE: 717
cagcagggga gagagaggag u                                         21

<210> SEQ ID NO 718
<211> LENGTH: 20
<212> TYPE: RNA
<213> ORGANISM: Homo sapiens

<400> SEQUENCE: 718
cagcagggga gagagaggag                                           20

<210> SEQ ID NO 719
<211> LENGTH: 26
<212> TYPE: RNA
<213> ORGANISM: Homo sapiens

<400> SEQUENCE: 719
ccuucuggag aggcuuugug cggaua                                    26

<210> SEQ ID NO 720
<211> LENGTH: 15
<212> TYPE: RNA
<213> ORGANISM: Homo sapiens

<400> SEQUENCE: 720
```
ccuucuggag aggcu 15

<210> SEQ ID NO 721
<211> LENGTH: 23
<212> TYPE: RNA
<213> ORGANISM: Homo sapiens

<400> SEQUENCE: 721
gaaaucaagc gugggugaga ccu 23

<210> SEQ ID NO 722
<211> LENGTH: 20
<212> TYPE: RNA
<213> ORGANISM: Homo sapiens

<400> SEQUENCE: 722
gaaaucaagc gugggugaga 20

<210> SEQ ID NO 723
<211> LENGTH: 26
<212> TYPE: RNA
<213> ORGANISM: Homo sapiens

<400> SEQUENCE: 723
agggcuggac ucagcggcgg agcugg 26

<210> SEQ ID NO 724
<211> LENGTH: 17
<212> TYPE: RNA
<213> ORGANISM: Homo sapiens

<400> SEQUENCE: 724
gcggcggagc uggcugc 17

<210> SEQ ID NO 725
<211> LENGTH: 24
<212> TYPE: RNA
<213> ORGANISM: Homo sapiens

<400> SEQUENCE: 725
cgggcguggu ggugggggug ggug 24

<210> SEQ ID NO 726
<211> LENGTH: 15
<212> TYPE: RNA
<213> ORGANISM: Homo sapiens

<400> SEQUENCE: 726
cgggcguggu ggugg 15

<210> SEQ ID NO 727
<211> LENGTH: 22
<212> TYPE: RNA
<213> ORGANISM: Homo sapiens

<400> SEQUENCE: 727
acucaaacug uggggcacu uu 22

<210> SEQ ID NO 728
<211> LENGTH: 19
<212> TYPE: RNA
<213> ORGANISM: Homo sapiens

<400> SEQUENCE: 728
acucaaacug uggggggcac                                                    19

<210> SEQ ID NO 729
<211> LENGTH: 16
<212> TYPE: RNA
<213> ORGANISM: Homo sapiens

<400> SEQUENCE: 729 uggggggaa gaaaag                                                         16

<210> SEQ ID NO 730
<211> LENGTH: 16
<212> TYPE: RNA
<213> ORGANISM: Homo sapiens

<400> SEQUENCE: 730 uggggggaa gaaaag                                                         16

<210> SEQ ID NO 731
<211> LENGTH: 21
<212> TYPE: RNA
<213> ORGANISM: Homo sapiens

<400> SEQUENCE: 731
auccaguucu cugaggggc u                                                   21

<210> SEQ ID NO 732
<211> LENGTH: 21
<212> TYPE: RNA
<213> ORGANISM: Homo sapiens

<400> SEQUENCE: 732
auccaguucu cugaggggc u                                                   21

<210> SEQ ID NO 733
<211> LENGTH: 24
<212> TYPE: RNA
<213> ORGANISM: Homo sapiens

<400> SEQUENCE: 733 ugggagcug aggcucuggg ggug                                                24

<210> SEQ ID NO 734
<211> LENGTH: 15
<212> TYPE: RNA
<213> ORGANISM: Homo sapiens

<400> SEQUENCE: 734
ggcccugggg agcug                                                         15

<210> SEQ ID NO 735
<211> LENGTH: 22
<212> TYPE: RNA
<213> ORGANISM: Homo sapiens

<400> SEQUENCE: 735
ccgggaacgu cgagacugga gc                                                 22

<210> SEQ ID NO 736
<211> LENGTH: 15
<212> TYPE: RNA
<213> ORGANISM: Homo sapiens

```
<400> SEQUENCE: 736
cgggaacguc gagac                                                     15

<210> SEQ ID NO 737
<211> LENGTH: 19
<212> TYPE: RNA
<213> ORGANISM: Homo sapiens

<400> SEQUENCE: 737
uggcgggugc ggggguggg                                                 19

<210> SEQ ID NO 738
<211> LENGTH: 15
<212> TYPE: RNA
<213> ORGANISM: Homo sapiens

<400> SEQUENCE: 738
uggcgggugc ggggg                                                     15

<210> SEQ ID NO 739
<211> LENGTH: 23
<212> TYPE: RNA
<213> ORGANISM: Homo sapiens

<400> SEQUENCE: 739
uaggggcagc agaggaccug ggc                                            23

<210> SEQ ID NO 740
<211> LENGTH: 20
<212> TYPE: RNA
<213> ORGANISM: Homo sapiens

<400> SEQUENCE: 740
uaggggcagc agaggaccug                                                20

<210> SEQ ID NO 741
<211> LENGTH: 17
<212> TYPE: RNA
<213> ORGANISM: Homo sapiens

<400> SEQUENCE: 741
ggggcggggg cgggggc                                                   17

<210> SEQ ID NO 742
<211> LENGTH: 15
<212> TYPE: RNA
<213> ORGANISM: Homo sapiens

<400> SEQUENCE: 742
cgcgccgggc ccggg                                                     15

<210> SEQ ID NO 743
<211> LENGTH: 23
<212> TYPE: RNA
<213> ORGANISM: Homo sapiens

<400> SEQUENCE: 743
uggggacgua gcuggccaga cag                                            23

<210> SEQ ID NO 744
<211> LENGTH: 20
<212> TYPE: RNA
```

<213> ORGANISM: Homo sapiens

<400> SEQUENCE: 744 ugggggacgua gcuggccaga                                    20

<210> SEQ ID NO 745
<211> LENGTH: 21
<212> TYPE: RNA
<213> ORGANISM: Homo sapiens

<400> SEQUENCE: 745
cagccugagu gacagagcaa g                                   21

<210> SEQ ID NO 746
<211> LENGTH: 15
<212> TYPE: RNA
<213> ORGANISM: Homo sapiens

<400> SEQUENCE: 746
acugcacucc agccu                                          15

<210> SEQ ID NO 747
<211> LENGTH: 18
<212> TYPE: RNA
<213> ORGANISM: Homo sapiens

<400> SEQUENCE: 747
gagacugggg uggggccu                                       18

<210> SEQ ID NO 748
<211> LENGTH: 16
<212> TYPE: RNA
<213> ORGANISM: Homo sapiens

<400> SEQUENCE: 748
agacuggggu ggggcc                                         16

<210> SEQ ID NO 749
<211> LENGTH: 16
<212> TYPE: RNA
<213> ORGANISM: Homo sapiens

<400> SEQUENCE: 749
ggcggugggc ggcggg                                         16

<210> SEQ ID NO 750
<211> LENGTH: 15
<212> TYPE: RNA
<213> ORGANISM: Homo sapiens

<400> SEQUENCE: 750
ggccucucgg gaacu                                          15

<210> SEQ ID NO 751
<211> LENGTH: 17
<212> TYPE: RNA
<213> ORGANISM: Homo sapiens

<400> SEQUENCE: 751
gcggggcggc aggggcc                                        17

<210> SEQ ID NO 752
<211> LENGTH: 15

<212> TYPE: RNA
<213> ORGANISM: Homo sapiens

<400> SEQUENCE: 752
gggggcgggg cggca                                                        15

<210> SEQ ID NO 753
<211> LENGTH: 23
<212> TYPE: RNA
<213> ORGANISM: Homo sapiens

<400> SEQUENCE: 753
ugaggauaug gcagggaagg gga                                               23

<210> SEQ ID NO 754
<211> LENGTH: 19
<212> TYPE: RNA
<213> ORGANISM: Homo sapiens

<400> SEQUENCE: 754
ugaggauaug gcagggaag                                                    19

<210> SEQ ID NO 755
<211> LENGTH: 20
<212> TYPE: RNA
<213> ORGANISM: Homo sapiens

<400> SEQUENCE: 755
cuccccggug ugcaaaugug                                                   20

<210> SEQ ID NO 756
<211> LENGTH: 15
<212> TYPE: RNA
<213> ORGANISM: Homo sapiens

<400> SEQUENCE: 756
gugugcggug uuaug                                                        15

<210> SEQ ID NO 757
<211> LENGTH: 23
<212> TYPE: RNA
<213> ORGANISM: Homo sapiens

<400> SEQUENCE: 757
cggggcagcu caguacagga uac                                               23

<210> SEQ ID NO 758
<211> LENGTH: 15
<212> TYPE: RNA
<213> ORGANISM: Homo sapiens

<400> SEQUENCE: 758
agcucaguac aggau                                                        15

<210> SEQ ID NO 759
<211> LENGTH: 24
<212> TYPE: RNA
<213> ORGANISM: Homo sapiens

<400> SEQUENCE: 759
cccaaaaugc ugggauuaca ggca                                              24

<210> SEQ ID NO 760

```
<211> LENGTH: 15
<212> TYPE: RNA
<213> ORGANISM: Homo sapiens

<400> SEQUENCE: 760
gcccaccuca gccuc                                                         15

<210> SEQ ID NO 761
<211> LENGTH: 21
<212> TYPE: RNA
<213> ORGANISM: Homo sapiens

<400> SEQUENCE: 761
gugagucagg gugggcugg c                                                   21

<210> SEQ ID NO 762
<211> LENGTH: 21
<212> TYPE: RNA
<213> ORGANISM: Homo sapiens

<400> SEQUENCE: 762
gugagucagg gugggcugg c                                                   21

<210> SEQ ID NO 763
<211> LENGTH: 15
<212> TYPE: RNA
<213> ORGANISM: Homo sapiens

<400> SEQUENCE: 763
aggaggagga ggcag                                                         15

<210> SEQ ID NO 764
<211> LENGTH: 15
<212> TYPE: RNA
<213> ORGANISM: Homo sapiens

<400> SEQUENCE: 764
aggaggagga ggcag                                                         15

<210> SEQ ID NO 765
<211> LENGTH: 21
<212> TYPE: RNA
<213> ORGANISM: Homo sapiens

<400> SEQUENCE: 765
cggauccgag ucacggcacc a                                                  21

<210> SEQ ID NO 766
<211> LENGTH: 15
<212> TYPE: RNA
<213> ORGANISM: Homo sapiens

<400> SEQUENCE: 766
ggauccgagu cacgg                                                         15

<210> SEQ ID NO 767
<211> LENGTH: 23
<212> TYPE: RNA
<213> ORGANISM: Homo sapiens

<400> SEQUENCE: 767
ccaggaggcg gaggaggugg agg                                                23
```

```
<210> SEQ ID NO 768
<211> LENGTH: 15
<212> TYPE: RNA
<213> ORGANISM: Homo sapiens

<400> SEQUENCE: 768
acccaggagg cggag                                                    15

<210> SEQ ID NO 769
<211> LENGTH: 26
<212> TYPE: RNA
<213> ORGANISM: Homo sapiens

<400> SEQUENCE: 769
gucccggggc ugcgcgaggc acaggc                                        26

<210> SEQ ID NO 770
<211> LENGTH: 15
<212> TYPE: RNA
<213> ORGANISM: Homo sapiens

<400> SEQUENCE: 770
ggcccggggg gcggg                                                    15

<210> SEQ ID NO 771
<211> LENGTH: 21
<212> TYPE: RNA
<213> ORGANISM: Homo sapiens

<400> SEQUENCE: 771
aggaggcagu gggcgagcag g                                             21

<210> SEQ ID NO 772
<211> LENGTH: 21
<212> TYPE: RNA
<213> ORGANISM: Homo sapiens

<400> SEQUENCE: 772
aggaggcagu gggcgagcag g                                             21

<210> SEQ ID NO 773
<211> LENGTH: 23
<212> TYPE: RNA
<213> ORGANISM: Homo sapiens

<400> SEQUENCE: 773
acagcagggc ugggauugc agu                                            23

<210> SEQ ID NO 774
<211> LENGTH: 19
<212> TYPE: RNA
<213> ORGANISM: Homo sapiens

<400> SEQUENCE: 774
ugcugcuccc aguccugcc                                                19

<210> SEQ ID NO 775
<211> LENGTH: 19
<212> TYPE: RNA
<213> ORGANISM: Homo sapiens

<400> SEQUENCE: 775
gcugggcgag gcuggcauc                                                19
```

```
<210> SEQ ID NO 776
<211> LENGTH: 17
<212> TYPE: RNA
<213> ORGANISM: Homo sapiens

<400> SEQUENCE: 776
gcugggcgag gcuggca                                                    17

<210> SEQ ID NO 777
<211> LENGTH: 18
<212> TYPE: RNA
<213> ORGANISM: Homo sapiens

<400> SEQUENCE: 777
cagcggggcu gggcgcgc                                                   18

<210> SEQ ID NO 778
<211> LENGTH: 15
<212> TYPE: RNA
<213> ORGANISM: Homo sapiens

<400> SEQUENCE: 778
cagcggggcu gggcg                                                      15

<210> SEQ ID NO 779
<211> LENGTH: 22
<212> TYPE: RNA
<213> ORGANISM: Homo sapiens

<400> SEQUENCE: 779
caggcacggg agcucaggug ag                                              22

<210> SEQ ID NO 780
<211> LENGTH: 17
<212> TYPE: RNA
<213> ORGANISM: Homo sapiens

<400> SEQUENCE: 780
caggcacggg agcucag                                                    17

<210> SEQ ID NO 781
<211> LENGTH: 18
<212> TYPE: RNA
<213> ORGANISM: Homo sapiens

<400> SEQUENCE: 781
ggcagcggcg gcggcggc                                                   18

<210> SEQ ID NO 782
<211> LENGTH: 15
<212> TYPE: RNA
<213> ORGANISM: Homo sapiens

<400> SEQUENCE: 782
gcuccccgcg ccccc                                                      15

<210> SEQ ID NO 783
<211> LENGTH: 20
<212> TYPE: RNA
<213> ORGANISM: Homo sapiens

<400> SEQUENCE: 783
aucccaccac ugccaccauu                                                 20
```

```
<210> SEQ ID NO 784
<211> LENGTH: 15
<212> TYPE: RNA
<213> ORGANISM: Homo sapiens

<400> SEQUENCE: 784
aucccaccac ugcca                                                   15

<210> SEQ ID NO 785
<211> LENGTH: 25
<212> TYPE: RNA
<213> ORGANISM: Homo sapiens

<400> SEQUENCE: 785
gggggagcca ugagauaaga gcacc                                        25

<210> SEQ ID NO 786
<211> LENGTH: 20
<212> TYPE: RNA
<213> ORGANISM: Homo sapiens

<400> SEQUENCE: 786 uggggagcc augagauaag                                               20

<210> SEQ ID NO 787
<211> LENGTH: 17
<212> TYPE: RNA
<213> ORGANISM: Homo sapiens

<400> SEQUENCE: 787
gaucccagcg gugccuc                                                 17

<210> SEQ ID NO 788
<211> LENGTH: 15
<212> TYPE: RNA
<213> ORGANISM: Homo sapiens

<400> SEQUENCE: 788
gaucccagcg gugcc                                                   15

<210> SEQ ID NO 789
<211> LENGTH: 24
<212> TYPE: RNA
<213> ORGANISM: Homo sapiens

<400> SEQUENCE: 789
agacacauuu ggagagggaa ccuc                                         24

<210> SEQ ID NO 790
<211> LENGTH: 16
<212> TYPE: RNA
<213> ORGANISM: Homo sapiens

<400> SEQUENCE: 790
agacacauuu ggagag                                                  16

<210> SEQ ID NO 791
<211> LENGTH: 30
<212> TYPE: RNA
<213> ORGANISM: Homo sapiens

<400> SEQUENCE: 791
```

-continued gcugggcugg gacggacacc cggccuccac                           30

<210> SEQ ID NO 792
<211> LENGTH: 19
<212> TYPE: RNA
<213> ORGANISM: Homo sapiens

<400> SEQUENCE: 792
gaggcugggc ugggacgga                                       19

<210> SEQ ID NO 793
<211> LENGTH: 25
<212> TYPE: RNA
<213> ORGANISM: Homo sapiens

<400> SEQUENCE: 793
ugggcagggg cuuauuguag gaguc                                25

<210> SEQ ID NO 794
<211> LENGTH: 19
<212> TYPE: RNA
<213> ORGANISM: Homo sapiens

<400> SEQUENCE: 794
ugggcagggg cuuauugua                                       19

<210> SEQ ID NO 795
<211> LENGTH: 21
<212> TYPE: RNA
<213> ORGANISM: Homo sapiens

<400> SEQUENCE: 795
caacucugau cucuucaucu a                                    21

<210> SEQ ID NO 796
<211> LENGTH: 20
<212> TYPE: RNA
<213> ORGANISM: Homo sapiens

<400> SEQUENCE: 796
ucucuucauc uaccccccag                                      20

<210> SEQ ID NO 797
<211> LENGTH: 23
<212> TYPE: RNA
<213> ORGANISM: Homo sapiens

<400> SEQUENCE: 797
cuaguggaag aagauggcgg aag                                  23

<210> SEQ ID NO 798
<211> LENGTH: 15
<212> TYPE: RNA
<213> ORGANISM: Homo sapiens

<400> SEQUENCE: 798
uaguggaaga agaug                                           15

<210> SEQ ID NO 799
<211> LENGTH: 24
<212> TYPE: RNA
<213> ORGANISM: Homo sapiens

<400> SEQUENCE: 799
cugcggggac aggccagggc aucu                                                    24

<210> SEQ ID NO 800
<211> LENGTH: 20
<212> TYPE: RNA
<213> ORGANISM: Homo sapiens

<400> SEQUENCE: 800
cugcggggac aggccagggc                                                         20

<210> SEQ ID NO 801
<211> LENGTH: 27
<212> TYPE: RNA
<213> ORGANISM: Homo sapiens

<400> SEQUENCE: 801
agggccagag gagccuggag uggucgg                                                 27

<210> SEQ ID NO 802
<211> LENGTH: 23
<212> TYPE: RNA
<213> ORGANISM: Homo sapiens

<400> SEQUENCE: 802
agggccagag gagccuggag ugg                                                     23

<210> SEQ ID NO 803
<211> LENGTH: 18
<212> TYPE: RNA
<213> ORGANISM: Homo sapiens

<400> SEQUENCE: 803
ucuagguggg gagacuga                                                           18

<210> SEQ ID NO 804
<211> LENGTH: 16
<212> TYPE: RNA
<213> ORGANISM: Homo sapiens

<400> SEQUENCE: 804 gugggagac ugacgg                                                              16

<210> SEQ ID NO 805
<211> LENGTH: 23
<212> TYPE: RNA
<213> ORGANISM: Homo sapiens

<400> SEQUENCE: 805
ucggcucugg gucuguggg agc                                                      23

<210> SEQ ID NO 806
<211> LENGTH: 15
<212> TYPE: RNA
<213> ORGANISM: Homo sapiens

<400> SEQUENCE: 806
gcccggauac cucag                                                              15

<210> SEQ ID NO 807
<211> LENGTH: 30
<212> TYPE: RNA
<213> ORGANISM: Homo sapiens

```
<400> SEQUENCE: 807
ugaggggcag agagcgagac uuuucuauuu                                30

<210> SEQ ID NO 808
<211> LENGTH: 15
<212> TYPE: RNA
<213> ORGANISM: Homo sapiens

<400> SEQUENCE: 808
ugaggggcag agagc                                                15

<210> SEQ ID NO 809
<211> LENGTH: 25
<212> TYPE: RNA
<213> ORGANISM: Homo sapiens

<400> SEQUENCE: 809 gggugggggau uguugcauu acuug                                     25

<210> SEQ ID NO 810
<211> LENGTH: 20
<212> TYPE: RNA
<213> ORGANISM: Homo sapiens

<400> SEQUENCE: 810 gggugggggau uguugcauu                                           20

<210> SEQ ID NO 811
<211> LENGTH: 27
<212> TYPE: RNA
<213> ORGANISM: Homo sapiens

<400> SEQUENCE: 811
uagcagcacg uaaauauugg cguuaag                                   27

<210> SEQ ID NO 812
<211> LENGTH: 15
<212> TYPE: RNA
<213> ORGANISM: Homo sapiens

<400> SEQUENCE: 812
uagcagcacg uaaau                                                15

<210> SEQ ID NO 813
<211> LENGTH: 27
<212> TYPE: RNA
<213> ORGANISM: Homo sapiens

<400> SEQUENCE: 813
aaaccguuac cauuacugag uuuagua                                   27

<210> SEQ ID NO 814
<211> LENGTH: 15
<212> TYPE: RNA
<213> ORGANISM: Homo sapiens

<400> SEQUENCE: 814
gaaaccguua ccauu                                                15

<210> SEQ ID NO 815
<211> LENGTH: 22
<212> TYPE: RNA
<213> ORGANISM: Homo sapiens
```

```
<400> SEQUENCE: 815
auauagggau uggagccgug gc                                    22

<210> SEQ ID NO 816
<211> LENGTH: 20
<212> TYPE: RNA
<213> ORGANISM: Homo sapiens

<400> SEQUENCE: 816
auauagggau uggagccgug                                       20

<210> SEQ ID NO 817
<211> LENGTH: 25
<212> TYPE: RNA
<213> ORGANISM: Homo sapiens

<400> SEQUENCE: 817
uccuguacug agcugccccg aggcc                                 25

<210> SEQ ID NO 818
<211> LENGTH: 15
<212> TYPE: RNA
<213> ORGANISM: Homo sapiens

<400> SEQUENCE: 818
uccuguacug agcug                                            15

<210> SEQ ID NO 819
<211> LENGTH: 26
<212> TYPE: RNA
<213> ORGANISM: Homo sapiens

<400> SEQUENCE: 819
agggacggga cgcggugcag uguugu                                26

<210> SEQ ID NO 820
<211> LENGTH: 15
<212> TYPE: RNA
<213> ORGANISM: Homo sapiens

<400> SEQUENCE: 820
ggcgggcggg aggga                                            15

<210> SEQ ID NO 821
<211> LENGTH: 20
<212> TYPE: RNA
<213> ORGANISM: Homo sapiens

<400> SEQUENCE: 821
ccccagggcg acgcggcggg                                       20

<210> SEQ ID NO 822
<211> LENGTH: 15
<212> TYPE: RNA
<213> ORGANISM: Homo sapiens

<400> SEQUENCE: 822
cgcggcgggg gcggc                                            15

<210> SEQ ID NO 823
<211> LENGTH: 15
<212> TYPE: RNA
```

-continued

<213> ORGANISM: Homo sapiens

<400> SEQUENCE: 823
ggcggcgggc ccggg                                            15

<210> SEQ ID NO 824
<211> LENGTH: 15
<212> TYPE: RNA
<213> ORGANISM: Homo sapiens

<400> SEQUENCE: 824
ggcggcgggc ccggg                                            15

<210> SEQ ID NO 825
<211> LENGTH: 25
<212> TYPE: RNA
<213> ORGANISM: Homo sapiens

<400> SEQUENCE: 825
aaggcagggc ccccgcuccc cgggc                                 25

<210> SEQ ID NO 826
<211> LENGTH: 15
<212> TYPE: RNA
<213> ORGANISM: Homo sapiens

<400> SEQUENCE: 826
guguguugag gaagg                                            15

<210> SEQ ID NO 827
<211> LENGTH: 23
<212> TYPE: RNA
<213> ORGANISM: Homo sapiens

<400> SEQUENCE: 827
gagggccccc ccucaauccu guu                                   23

<210> SEQ ID NO 828
<211> LENGTH: 16
<212> TYPE: RNA
<213> ORGANISM: Homo sapiens

<400> SEQUENCE: 828
agggcccccc cucaau                                           16

<210> SEQ ID NO 829
<211> LENGTH: 26
<212> TYPE: RNA
<213> ORGANISM: Homo sapiens

<400> SEQUENCE: 829
aaaaucacau ugccagggau uaccac                                26

<210> SEQ ID NO 830
<211> LENGTH: 15
<212> TYPE: RNA
<213> ORGANISM: Homo sapiens

<400> SEQUENCE: 830
aaucacauug ccagg                                            15

<210> SEQ ID NO 831
<211> LENGTH: 28

```
<212> TYPE: RNA
<213> ORGANISM: Homo sapiens

<400> SEQUENCE: 831
guaugguauu gcacuugucc cggccugu                28

<210> SEQ ID NO 832
<211> LENGTH: 15
<212> TYPE: RNA
<213> ORGANISM: Homo sapiens

<400> SEQUENCE: 832
uauugcacuu guccc                              15

<210> SEQ ID NO 833
<211> LENGTH: 22
<212> TYPE: RNA
<213> ORGANISM: Homo sapiens

<400> SEQUENCE: 833
gcacgacuca gggcggaggg aa                      22

<210> SEQ ID NO 834
<211> LENGTH: 15
<212> TYPE: RNA
<213> ORGANISM: Homo sapiens

<400> SEQUENCE: 834
agggcggagg gaagu                              15

<210> SEQ ID NO 835
<211> LENGTH: 18
<212> TYPE: RNA
<213> ORGANISM: Homo sapiens

<400> SEQUENCE: 835
aaaaggaagg gggaggag                           18

<210> SEQ ID NO 836
<211> LENGTH: 16
<212> TYPE: RNA
<213> ORGANISM: Homo sapiens

<400> SEQUENCE: 836
aaggaagggg gaggag                             16

<210> SEQ ID NO 837
<211> LENGTH: 24
<212> TYPE: RNA
<213> ORGANISM: Homo sapiens

<400> SEQUENCE: 837
aauauugcac ucgucccggc cucc                    24

<210> SEQ ID NO 838
<211> LENGTH: 15
<212> TYPE: RNA
<213> ORGANISM: Homo sapiens

<400> SEQUENCE: 838
uauugcacuc guccc                              15

<210> SEQ ID NO 839
```

```
<211> LENGTH: 21
<212> TYPE: RNA
<213> ORGANISM: Homo sapiens

<400> SEQUENCE: 839
cccaggcugg agcgagugca g                                              21

<210> SEQ ID NO 840
<211> LENGTH: 15
<212> TYPE: RNA
<213> ORGANISM: Homo sapiens

<400> SEQUENCE: 840
agcucacugc agccu                                                     15

<210> SEQ ID NO 841
<211> LENGTH: 20
<212> TYPE: RNA
<213> ORGANISM: Homo sapiens

<400> SEQUENCE: 841
uggcuguugg aggggggcagg                                               20

<210> SEQ ID NO 842
<211> LENGTH: 15
<212> TYPE: RNA
<213> ORGANISM: Homo sapiens

<400> SEQUENCE: 842 ggaggggggca ggcuc                                                    15

<210> SEQ ID NO 843
<211> LENGTH: 25
<212> TYPE: RNA
<213> ORGANISM: Homo sapiens

<400> SEQUENCE: 843
uggcggcggu aguuaugggc uucuc                                          25

<210> SEQ ID NO 844
<211> LENGTH: 25
<212> TYPE: RNA
<213> ORGANISM: Homo sapiens

<400> SEQUENCE: 844
uggcggcggu aguuaugggc uucuc                                          25

<210> SEQ ID NO 845
<211> LENGTH: 15
<212> TYPE: RNA
<213> ORGANISM: Homo sapiens

<400> SEQUENCE: 845
uggcagagcg cuguc                                                     15

<210> SEQ ID NO 846
<211> LENGTH: 15
<212> TYPE: RNA
<213> ORGANISM: Homo sapiens

<400> SEQUENCE: 846
uggcagagcg cuguc                                                     15
```

```
<210> SEQ ID NO 847
<211> LENGTH: 22
<212> TYPE: RNA
<213> ORGANISM: Homo sapiens

<400> SEQUENCE: 847
cgcggcgggg acggcgauug gu                                           22

<210> SEQ ID NO 848
<211> LENGTH: 17
<212> TYPE: RNA
<213> ORGANISM: Homo sapiens

<400> SEQUENCE: 848
cggcggggac ggcgauu                                                 17

<210> SEQ ID NO 849
<211> LENGTH: 22
<212> TYPE: RNA
<213> ORGANISM: Homo sapiens

<400> SEQUENCE: 849
accccacucc ugguaccaua gu                                           22

<210> SEQ ID NO 850
<211> LENGTH: 15
<212> TYPE: RNA
<213> ORGANISM: Homo sapiens

<400> SEQUENCE: 850
accccacucc uggua                                                   15

<210> SEQ ID NO 851
<211> LENGTH: 24
<212> TYPE: RNA
<213> ORGANISM: Homo sapiens

<400> SEQUENCE: 851
ggaggccggg gugggcggg gcgg                                          24

<210> SEQ ID NO 852
<211> LENGTH: 21
<212> TYPE: RNA
<213> ORGANISM: Homo sapiens

<400> SEQUENCE: 852
uggggcgggg caggucccug c                                            21

<210> SEQ ID NO 853
<211> LENGTH: 18
<212> TYPE: RNA
<213> ORGANISM: Homo sapiens

<400> SEQUENCE: 853
gggugcgggc cggcgggg                                                18

<210> SEQ ID NO 854
<211> LENGTH: 18
<212> TYPE: RNA
<213> ORGANISM: Homo sapiens

<400> SEQUENCE: 854 aggggcggg cuccggcg                                                 18
```

<210> SEQ ID NO 855
<211> LENGTH: 22
<212> TYPE: RNA
<213> ORGANISM: Homo sapiens

<400> SEQUENCE: 855 gggggguguq gagccagggg gc                                              22

<210> SEQ ID NO 856
<211> LENGTH: 25
<212> TYPE: RNA
<213> ORGANISM: Homo sapiens

<400> SEQUENCE: 856
aagggaggag gagcggaggg gcccu                                           25

<210> SEQ ID NO 857
<211> LENGTH: 64
<212> TYPE: RNA
<213> ORGANISM: Homo sapiens

<400> SEQUENCE: 857
ccccgggccc ggcguucccu ccccuuccgu gcgccagugg aggccggggu ggggcggggc     60
gggg                                                                  64

<210> SEQ ID NO 858
<211> LENGTH: 64
<212> TYPE: RNA
<213> ORGANISM: Homo sapiens

<400> SEQUENCE: 858
ccccgggccc ggcguucccu ccccuuccgu gcgccagugg aggccggggu ggggcggggc     60
gggg                                                                  64

<210> SEQ ID NO 859
<211> LENGTH: 66
<212> TYPE: RNA
<213> ORGANISM: Homo sapiens

<400> SEQUENCE: 859 ccgaguggg cggggcaggu cccugcaggg acugugacac ugaaggaccu gcaccuucgc      60
ccacag                                                                66

<210> SEQ ID NO 860
<211> LENGTH: 54
<212> TYPE: RNA
<213> ORGANISM: Homo sapiens

<400> SEQUENCE: 860
acgcgggugc gggccggcgg gguagaagcc acccggcccg gcccggcccg gcga           54

<210> SEQ ID NO 861
<211> LENGTH: 62
<212> TYPE: RNA
<213> ORGANISM: Homo sapiens

<400> SEQUENCE: 861 gguaggggc gggcuccggc gcugggaccc cacuagggug gcgccuuggc cccgcccgc       60 cc                                                                    62

```
<210> SEQ ID NO 862
<211> LENGTH: 71
<212> TYPE: RNA
<213> ORGANISM: Homo sapiens

<400> SEQUENCE: 862
auggaggggg guguggagcc aggggggccca ggucuacagc uucccccgc ucccugcccc    60 cauacuccca g                                                        71

<210> SEQ ID NO 863
<211> LENGTH: 74
<212> TYPE: RNA
<213> ORGANISM: Homo sapiens

<400> SEQUENCE: 863
gggaggaaga agggaggagg agcggagggg cccuugucuu cccagagccu cucccuuccu    60
ccccuccccc uccc                                                     74

<210> SEQ ID NO 864
<211> LENGTH: 16
<212> TYPE: RNA
<213> ORGANISM: Homo sapiens

<400> SEQUENCE: 864
cgggcccggc guuccc                                                   16

<210> SEQ ID NO 865
<211> LENGTH: 15
<212> TYPE: RNA
<213> ORGANISM: Homo sapiens

<400> SEQUENCE: 865
ccgggcccgg cguuc                                                    15

<210> SEQ ID NO 866
<211> LENGTH: 19
<212> TYPE: RNA
<213> ORGANISM: Homo sapiens

<400> SEQUENCE: 866
gggugcgggc cggcggggu                                                19

<210> SEQ ID NO 867
<211> LENGTH: 15
<212> TYPE: RNA
<213> ORGANISM: Homo sapiens

<400> SEQUENCE: 867
ugcgggccgg cgggg                                                    15

<210> SEQ ID NO 868
<211> LENGTH: 19
<212> TYPE: RNA
<213> ORGANISM: Homo sapiens

<400> SEQUENCE: 868 aggggggcggg cuccggcgc                                               19

<210> SEQ ID NO 869
<211> LENGTH: 15
<212> TYPE: RNA
```

```
<400> SEQUENCE: 869
guagggggcg ggcuc                                                    15

<210> SEQ ID NO 870
<211> LENGTH: 23
<212> TYPE: RNA
<213> ORGANISM: Homo sapiens

<400> SEQUENCE: 870
aagggaggag gagcggaggg gcc                                           23

<210> SEQ ID NO 871
<211> LENGTH: 15
<212> TYPE: RNA
<213> ORGANISM: Homo sapiens

<400> SEQUENCE: 871
gggaggagga gcgga                                                    15
```